US007211572B2

(12) United States Patent
Miyazaki et al.

(10) Patent No.: US 7,211,572 B2
(45) Date of Patent: May 1, 2007

(54) NITROGEN-CONTAINING FUSED RING COMPOUND AND USE THEREOF AS HIV INTEGRASE INHIBITOR

(75) Inventors: Susumu Miyazaki, Osaka (JP); Susumu Katoh, Osaka (JP); Kaoru Adachi, Osaka (JP); Hirotaka Isoshima, Osaka (JP); Satoru Kobayashi, Osaka (JP); Yuji Matsuzaki, Osaka (JP); Wataru Watanabe, Osaka (JP); Kazunobu Yamataka, Osaka (JP); Shinichi Kiyonari, Osaka (JP); Shuichi Wamaki, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 95 days.

(21) Appl. No.: 11/255,605

(22) Filed: Oct. 13, 2005

(65) Prior Publication Data

US 2006/0052361 A1 Mar. 9, 2006

Related U.S. Application Data

(63) Continuation of application No. 10/958,225, filed on Oct. 5, 2004, now abandoned, which is a continuation of application No. PCT/JP04/11869, filed on Aug. 12, 2004.

(30) Foreign Application Priority Data

Aug. 13, 2003 (JP) ............................ 2003-293117
Apr. 28, 2004 (JP) ............................ 2004-134896

(51) Int. Cl.
*A01N 43/00* (2006.01)
*A01N 43/58* (2006.01)
*A61K 31/55* (2006.01)
*A61K 31/553* (2006.01)
*A61K 31/554* (2006.01)

(52) U.S. Cl. ................ 514/211.04; 514/248; 514/249; 514/259.1; 514/291; 514/300; 540/460; 540/461; 544/236; 544/278; 544/281; 544/282; 544/349; 546/86; 546/113

(58) Field of Classification Search .................... None
See application file for complete search history.

(56) References Cited

U.S. PATENT DOCUMENTS

| | | | | |
|---|---|---|---|---|
| 5,519,016 | A | 5/1996 | Kimura et al. | |
| 5,688,791 | A | 11/1997 | Kimura et al. | |
| 2004/0039060 | A1 | 2/2004 | Kiyama et al. | |
| 2005/0119482 | A1* | 6/2005 | Egbertson et al. | .......... 544/125 |

FOREIGN PATENT DOCUMENTS

| | | | |
|---|---|---|---|
| JP | A 2 502281 | | 7/1990 |
| JP | 6-116241 | A | 4/1994 |
| JP | 2000-502722 | A | 3/2000 |
| JP | 2002-155084 | A | 5/2002 |
| JP | 2002-293745 | | 10/2002 |
| WO | WO 88/06588 | | 9/1988 |
| WO | WO 98/08846 | | 3/1998 |
| WO | WO 2001/95905 | A1 | 12/2001 |
| WO | WO 2001/96283 | A2 | 12/2001 |
| WO | WO 2002/22574 | A1 | 3/2002 |
| WO | WO 2002/30426 | A1 | 4/2002 |
| WO | WO 2002/30930 | A2 | 4/2002 |
| WO | WO 2002/30931 | A2 | 4/2002 |
| WO | WO 2002/36734 | A2 | 5/2002 |
| WO | WO 2002/055079 | A2 | 7/2002 |
| WO | WO 2003/016266 | A1 | 2/2003 |
| WO | WO 2003/016275 | A1 | 2/2003 |
| WO | WO 2003/031413 | A1 | 4/2003 |
| WO | WO 2003/035076 | A1 | 5/2003 |
| WO | WO 2003/035077 | A1 | 5/2003 |
| WO | WO 2003/047564 | A1 | 6/2003 |
| WO | WO 2004/024078 | A2 | 3/2004 |

(Continued)

OTHER PUBLICATIONS

Mekouar et al, "Stryrylquinoline Derivatives: A New Class of Potent HIV-1 Integrase Inhibitors That Block HIV-1 Replication in CEM Cells" Journal of Medicinal Chemistry, vol. 41(15), pp. 2546-2857 (1998).*

(Continued)

*Primary Examiner*—Zachary C. Tucker
(74) *Attorney, Agent, or Firm*—Finnegan, Henderson, Farabow, Garrett & Dunner LLP

(57) ABSTRACT

The present invention relates to a nitrogen-containing fused ring compound represented by the following formula [I]

[I]

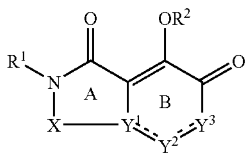

wherein each symbol is as defined in the specification, or a pharmaceutically acceptable salt thereof, and an anti-HIV agent containing such compound. The compound of the present invention has an HIV integrase inhibitory activity, and is useful as an agent for the prophylaxis or treatment of AIDS, or as an anti-HIV agent. In addition, by the combined use with other anti-HIV agents such as a protease inhibitor, a reverse transcriptase inhibitor and the like, it can be a more effective anti-HIV agent. Because it shows integrase-specific high inhibitory activity, the compound can be a pharmaceutical agent safe on human body, which causes only a fewer side effects.

2 Claims, No Drawings

FOREIGN PATENT DOCUMENTS

| | | | |
|---|---|---|---|
| WO | WO2005/086700 | A2 | 9/2005 |
| WO | WO2005/087766 | A1 | 9/2005 |
| WO | WO2005/087767 | A1 | 9/2005 |
| WO | WO2005/087768 | A1 | 9/2005 |
| WO | WO2005/092099 | A1 | 10/2005 |
| WO | WO 2006/066414 | A1 | 6/2006 |

OTHER PUBLICATIONS

Zouhiri et al, "Structure-Activity Relationships and Binding Mode of Styrylquinolines as Potent Inhibitors of HIV-1 Integrase and Replication of HIV-1 in Cell Culture" Journal of Medicinal Chemistry, 43(8), pp. 1533-1540 (2000).*

U.S. Appl. No. 60/349,775, filed Jun. 2005, Egbertson et al.*

Guidelines for the Use of Antiretroviral Agents in HIV-Infected Adults and Adolescents. (Aug. 13, 2001).

Folia Pharmacologica Japonica, 118, pp. 131-134 (2001).

Breslow, D.S. et al., "The Synthesis of Certain 4-Aminoquinoline Derivatives" J. Am. Chem. Soc., 68, p. 1232 (1946).

Li et al., Palladium in Heterocyclic Chemistry: A Guide for the Synthetic Chemist (Tetrahedron Organic Chemistry Series, V. 20) (2000) Elsevier Science Ltd.

Lui et al., "Synthesis, Physicochemical Characterization and Biological Evaluation of 2-(1'-Hydroxyalkyl)-3-hydroxypyridin-4-one: Novel Iron Chelators with Enhanced $pFe^{3+}$Values." J. Med. Chem., 42, pp. 4818-4823 (1999).

Malleron et al., Handbook of Palladium-Catalysed Organic Reactions: Synthetic Aspects and Catalytic Cycles, (1997) Academic Press.

Mekouar et al., "Stryrylquinoline Derivatives: A New Class of Potent HIV-1 Integrase Inhibitors That Block HIV-1 Replication in CEM Cells" Journal of Medicinal Chemistry, vol. 41(15), pp. 2546-2587 (1998).

Micovic, I.V. et al., J. Chem. Soc., Perkin Trans. 16, p. 2041 (1996).

Zouhiri et al., "Structure-Activity Relationships and Binding Mode of Styrylquinolines as Potent Inhibitors of HIV-1 Integrase and Replication of HIV-1 in Cell Culture" Journal of Medicinal Chemistry, vol. 43(8), pp. 1533-1540 (2000).

* cited by examiner

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

-continued acccttttag tcagtgtgga aaatctctag ca 32

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
actgctagag attttccaca ctgactaaaa g 31

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
tgaccaaggg ctaattcact 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
agtgaattag cccttggtca 20

NITROGEN-CONTAINING FUSED RING COMPOUND AND USE THEREOF AS HIV INTEGRASE INHIBITOR

CROSS REFERENCE TO RELATED APPLICATIONS

This is a continuation of application Ser. No. 10/958,225, filed Oct. 5, 2004, now abandoned, which is a continuation of International Application No. PCT/JP04/011869, filed Aug. 12, 2004, which claims the priority of Japanese Patent Application Nos. 2003-293117, filed Aug. 13, 2003, and 2004-134896, filed Apr. 28, 2004, all of which are incorporated herein by reference.

TECHNICAL FIELD

The present invention relates to a novel nitrogen-containing fused ring compound or a pharmaceutically acceptable salt thereof useful as an anti-HIV agent. Moreover, the present invention relates to novel use of a certain kind of nitrogen-containing fused ring compound or a pharmaceutically acceptable salt thereof as an anti-HIV agent. More specifically, the present invention relates to an anti-HIV agent containing a nitrogen-containing fused ring compound or a pharmaceutically acceptable salt thereof showing an anti-HIV action particularly based on an integrase inhibitory activity.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a pharmaceutical agent that eradicates HIV in a living organism or suppresses its growth is effective for the treatment or prophylaxis of AIDS.

HIV possesses a bimolecular RNA gene in a shell, and which is covered with an envelope protein. The RNA codes for several enzymes (protease, reverse transcriptase, integrase etc.) characteristic of the virus and the like, and has translated reverse transcriptase and integrase in the core, as well as protease inside and outside the core.

HIV contacts and invades a host cell, causes uncoating, and releases a complex of RNA and integrase, and the like into the cytoplasm. From the RNA, DNA is transcribed by reverse transcriptase, and a full length double stranded DNA is produced. The DNA moves into the core of the host cell and is incorporated by integrase into the DNA of the host cell. The incorporated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine and the like have been already on the market as reverse transcriptase inhibitors, and indinavir, nelfinavir and the like as protease inhibitors.

In addition, a multiple drug combination therapy concurrently using these pharmaceutical agents has been employed. For example, a combined use of two reverse transcriptase inhibitors (zidovudine and didanosine), and a combined use of three agents of reverse transcriptase inhibitors (zidovudine and lamivudine) and a protease inhibitor (nelfinavir) have been clinically applied. Such multiple drug combination therapy is becoming a mainstream of AIDS therapy (Folia Pharmacologica Japonica, 118, 131–134, 2001).

However, some of these pharmaceutical agents are known to HIV cause side effects such as liver function failure, central nervous disorders (e.g., vertigo), and the like. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired, wherein a development of an anti-HIV agent having an integrase inhibitory activity is-expected, because an integrase characteristic of retrovirus is an essential enzyme for the growth of HIV.

Nevertheless, an effective integrase inhibitor has not been found as yet.

Known compounds comparatively similar to the anti-HIV agent of the present invention are described in the following.

WO01/96283 describes, as an anti-HIV agent having an integrase inhibitory activity, the following compound [A] (see WO01/96283, p. 176, compound 70).

Compound [A]

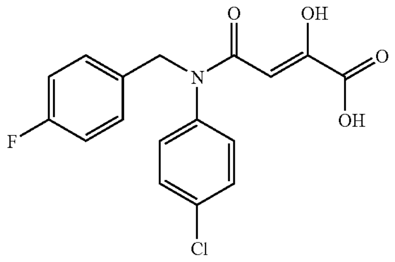

(Compound 70)

WO03/016266 describes the following compound [B] and the like having an integrase inhibitory activity (see WO03/016266, p. 159, Example Nos. 3–17).

Compound [B]

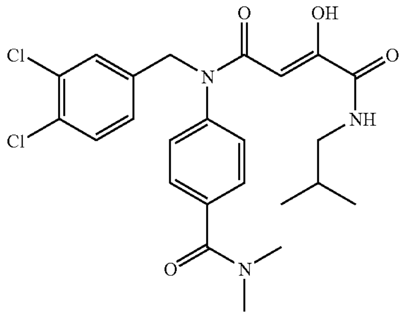

(Example No. 3-17)

WO01/95905 describes the following compound [C] and the like, as an anti-HIV agent having an integrase inhibitory activity (see WO01/95905, p. 109, Example E-2).

Compound [C]

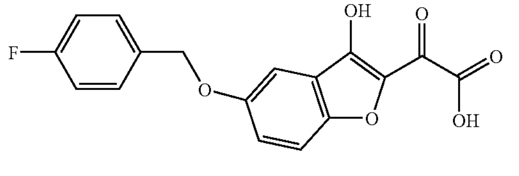

(Example E-2)

In addition, WO03/047564 describes the following compound [D] and the like, as an anti-HIV agent having an integrase inhibitory activity (see WO03/047564, p. 73, Example 11).

Compound [D]

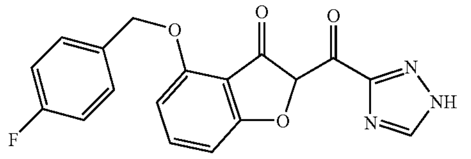

(Example 11)

Moreover, WO02/30930 and WO02/55079 describe, as an anti-HIV agent having an integrase inhibitory activity, the following compounds [E], [F] and the like, respectively (see WO02/30930, p. 171, Example 1; WO02/55079, p. 79, Example 1). WO02/30426, WO02/30931 and WO02/36734 also disclose similar compounds.

Compound [E]

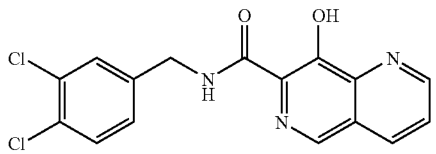

(Ex. 1)

Compound [F]

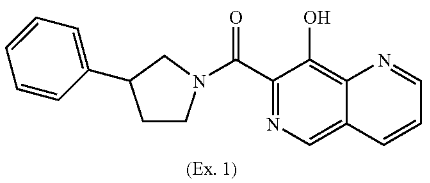

(Ex. 1)

In addition, WO03/031413 describes, as an anti-HIV agent having an integrase inhibitory activity, the following compound [G] and the like (see WO03/031413, p. 21, compound 8).

Compound [G]

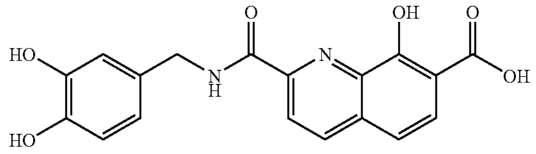

(Ex. 8)

Moreover, WO03/035076 and WO03/035077 describe, as an anti-HIV agent having an integrase inhibitory activity, the following compounds [H], [i] and the like (WO03/035076, p. 188, Example 1; WO03/035077, p. 146, Example 22).

Compound [H]

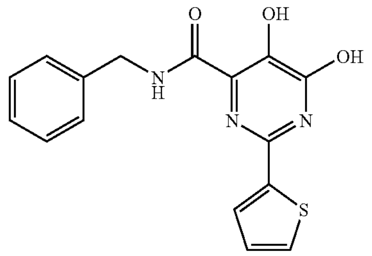

(Ex. 1)

Compound [i]

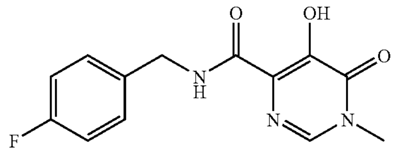

(Exp. 22)

However, these publications do not disclose nitrogen-containing fused ring compound encompassed in the present invention, or a description suggestive thereof.

Furthermore, WO2004/24078 describe, as an anti-HIV agent having an integrase inhibitory activity, the following compound [J] and the like.

Compound [J]

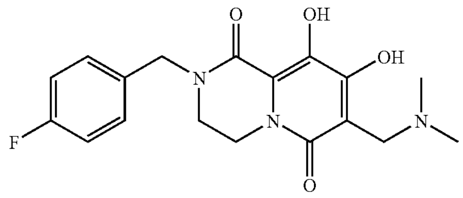

(Ex. 13)

This publication describes the following formula as the formula (I) of claim 1 and a tautomer thereof. However, the compound described in this publication is clearly different from the compound of the present invention in that a hydroxyl group or a carbonyl group is essential at a position corresponding to the position of $R^{y1}$ for $y^2$ in the formula [I] of the nitrogen-containing fused ring compound of the present invention. In addition, this publication does not suggest a compound free of a hydroxyl group or a carbonyl group at said position.

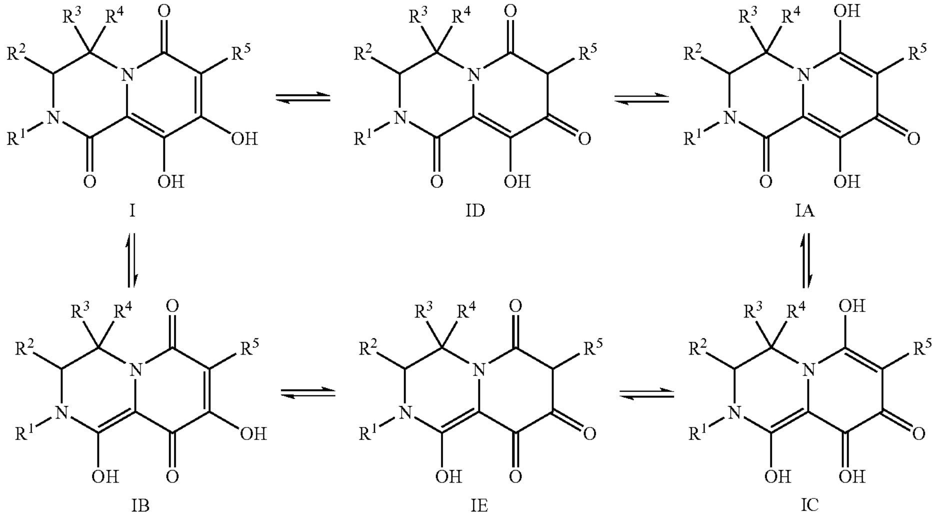

I ID IA IB IE IC

A production method of the compound of the formula (I) is disclosed in this publication from page 46 to page 113, but the production method concretely disclosed here cannot produce a nitrogen-containing fused ring compound encompassed in the present invention, and a concrete production method of this compound is not referred to at all.

DISCLOSURE OF THE INVENTION

From the findings based on the researches and clinical results obtained so far, an anti-HIV agent is effective for the prophylaxis of the onset of AIDS and the treatment thereof, and particularly a-compound having an integrase inhibitory action can provide an effective anti-HIV agent.

It is therefore an object of the present invention to provide a pharmaceutical agent having an anti-HIV action, particularly a pharmaceutical agent having an integrase inhibitory action.

The present inventors have conducted intensive studies in an attempt to find a compound having an anti-HIV action, particularly a compound having an integrase inhibitory action, and completed the present invention.

More particularly, the present invention is as shown in the following [1] to [38].

[1] A nitrogen-containing fused ring compound represented by the following formula [I] or a pharmaceutically acceptable salt thereof:

[I]

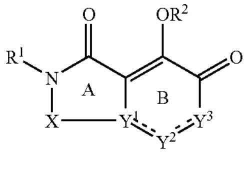

wherein $R^1$ is (1) a C1–6 alkyl group optionally substituted by 1 to 3 substituent(s) selected from the following group A, (2) a C2–6 alkenyl group optionally substituted by 1 to 3 substituent(s) selected from the following group A or (3) a group represented by the formula

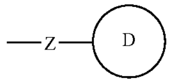

wherein Z is (1') a bond, (2') a C1–6 alkylene, (3') a C2–6 alkenylene or (4') $*—(CH_2)_m\text{-}Q\text{-}(CH_2)_n—$ wherein Q is (1") —O—, (2") $—NR^5—$ wherein $R^5$ is a hydrogen atom or a C1–6 alkyl group, (3") —CO—, (4") —SO—, (5") $—SO_2—$ or (6") $**—CO—NR^6—$ wherein $R^6$ is a hydrogen atom or a C1–6 alkyl group and

** shows the side to be bonded to $(CH_2)_m$, m is 0 or an integer of 1 to 4, n is 0 or an integer of 1 to 4 and

* shows the side to be bonded to a nitrogen atom of ring A, and ring D is (1') a C3–10 carbon ring group optionally substituted by 1 to 3 substituent(s) selected from the following group B or (2') a heterocyclic group optionally substituted by 1 to 3 substituent(s) selected from the following group B wherein the heterocyclic group contains at least one hetero atom selected from nitrogen atom, oxygen atom and sulfur atom;

X is (1) $—C(R^{x1})(R^{x2})\text{-}\#$, (2) $—C(R^{x1})(R^{x2})—C(R^{x3})(R^{x4})\text{-}\#$, (3) $—C(R^{x1})(R^{x2})—C(R^{x3})(R^{x4})—C(R^{x5})(R^{x6})\text{-}\#$, (4) $—C(R^{x7})=C(R^{x8})\text{-}\#$, (5) —$C(R^{x1})(R^{x2})$—$C(R^{x7})$=$C(R^{x8})$-#, (6) —$C(R^{x7})$=$C(R^{x8})$—$C(R^{x1})(R^{x2})$-#, (7) —N=$C(R^{x9})$-# or (8) —$C(R^{x10})$=N-# wherein # shows the side to be bonded to $Y^1$ of ring B, $R^{x1}$ to $R^{x10}$ are each independently selected from the following group C, $R^{x1}$ and $R^{x2}$, $R^{x3}$ and $R^{x4}$, and $R^{x5}$ and $R^{x6}$ each independently optionally form a C3–8 cycloalkyl together with the adjacent carbon atom;

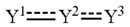

of ring B is (1) C=C $(R^{y1})$—$N(R^{y2})$, (2) N—$C(R^{y1})$=N, (3) N—$C(R^{y1})$=C $(R^{y2})$, (4) C=N—$N(R^{y2})$ or (5) N—N=$C(R^{y3})$ wherein $R^{y1}$ to $R^{y3}$ are each independently selected from the following group C, when

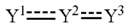

is N—$C(R^{y1})$=$C(R^{y2})$, ring B is optionally condensed with a benzene ring to form a fused ring represented by

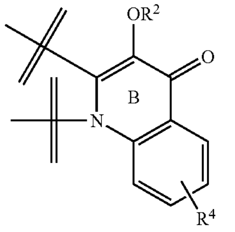

wherein $R^4$ is selected from the following group C; and $R^2$ is (1) a hydrogen atom, (2) a C1–6 alkyl group, (3) a C6–14 aryl C1–6 alkyl group or (4) —$SO_2R^{d1}$ wherein $R^{d1}$ is a hydrogen atom, a C1–7 alkyl group optionally substituted by 1 to 3 substituent(s) selected from the following group A or a C6–14 aryl group:

group A:

(1) a halogen atom, (2) a cyano group, (3) —$OR^{a1}$, (4) —$SR^{a1}$, (5) —$CO_2R^{a1}$, (6) —$CONR^{a2}R^{a3}$, (7) —$COR^{a4}$, (8) —$SO_2NR^{a2}R^{a3}$, (9) —$SO_2R^{a4}$,

(10) a C6–14 aryloxy group,

(11) a C6–14 aryl C1–6 alkyloxycarbonyl group,

(12) a C1–6 alkylcarbonyloxy group optionally substituted by halogen atom(s),

(13) a C6–14 aryl group optionally substituted by 1 to 3 substituent(s) selected from the group consisting of a halogen atom, a C1–6 alkyl group, a C1–6 alkylsulfonyl group, a di(C1–6 alkyl)amino group and a C1–6 alkylcarbonylamino group and

(14) a heterocyclic group optionally substituted by a C1–6 alkyloxy group, wherein $R^{a1}$, $R^{a2}$, $R^{a3}$ and $R^{a4}$ are each independently a hydrogen atom or a C1–6 alkyl group;

group B:

(1) a halogen atom, (2) a cyano group, (3) a C1–6 alkyl group, (4) a halo C1–6 alkyl group, (5) —$OR^{b1}$, (6) —$SR^{b1}$, (7) —$CO_2R^{b1}$, (8) —$CONR^{b2}R^{b3}$, (9) —$COR^{b4}$,

(10) —$SO_2NR^{b2}R^{b3}$,

(11) —$SO_2R^{b4}$,

(12) a C6–14 aryloxy group,

(13) a C6–14 aryl C1–6 alkyloxycarbonyl group,

(14) a C6–14 aryl C1–6 alkyloxy group and

(15) —$NR^{b5}COR^{b6}$, wherein $R^{b1}$, $R^{b2}$, $R^{b3}$, $R^{b4}$, $R^{b5}$ and $R^{b6}$ are each independently a hydrogen atom or a C1–6 alkyl group;

group C:

(1) a hydrogen atom, (2) a C3–8 cycloalkyl C1–6 alkyl group, (3) a cyano group, (4) a halogen atom, (5) a C1–7 alkyl group, (6) a C2–6 alkenyl group, (7) a C2–6 alkynyl group, (8) a C6–14 aryl group, (9) a heterocyclic group wherein said heterocyclic group is a saturated or unsaturated 5-membered or 6-membered heteromonocycle containing at least one hetero atom selected from nitrogen atom, oxygen atom and sulfur atom, or a fused ring of such heterocycles, or a fused ring of a carbon ring selected from benzene, cyclopentane and cyclohexane and the above-defined heterocycle,

(10) a C1–6 alkyloxy group,

(11) a C6–14 aryl C1–6 alkyl group,

(12) a C6–14 aryl C1–6 alkyloxy group,

(13) —$CO_2R^{c1}$,

(14) —$CONR^{c2}R^{c3}$,

(15) —$COR^{c4}$,

(16) —$SO_2NR^{c2}R^{c3}$,

(17) a C6–14 arylcarbonyl group,

(18) —$NR^{c4}R^{c5}$,

(19) —$NR^{c6}COR^{c7}$,

(20) —$NR^{c8}SO_2R^{c9}$,

(21) —$SR^{c10}$,

(22) —$SOR^{c11}$,

(23) —$SO_2R^{c12}$,

(24) —$NR^{c13}CONR^{c14}R^{c15}$,

(25) —$NR^{c16}CO_2R^{c17}$, and,

(26) —$NR^{c18}COCOR^{c19}$, $R^{c1}$, $R^{c2}$, $R^{c3}$, $R^{c4}$, $R^{c5}$, $R^{c6}$, $R^{c7}$, $R^{c8}$, $R^{c9}$, $R^{c10}$, $R^{c11}$, $R^{c12}$, $R^{c13}$, $R^{14c}$, $R^{c15}$, $R^{c16}$, $R^{c17}$, $R^{c18}$ and $R^{c19}$ are each independently (1') a hydrogen atom, (2') a C1–7 alkyl group optionally substituted by 1 to 3 substituent(s) selected from the above-mentioned group A, (3') a C6–14 aryl group optionally substituted by 1 to 3 substituent(s) selected from the above-mentioned group B, (4') a heterocyclic group optionally substituted by 1 to 3 substituent(s) selected from the above-mentioned group B or (5') a C3–8 cycloalkyl group, wherein $R^{c2}$ and $R^{c3}$ optionally form, together with the adjacent nitrogen atom, a nitrogen-containing heterocycle optionally substituted by 1 to 3 substituent(s) selected from the above-mentioned group B;

the C1–7 alkyl group, C1–6 alkyl moiety, C2–6 alkenyl group and C2–6 alkynyl group of the above-mentioned group C are optionally substituted by 1 to 3 substituent(s) selected from the above-mentioned group A, or a heterocyclic group; and the C6–14 aryl group, C6–14 aryl moiety and heterocyclic group of the above-mentioned group C are optionally substituted by 1 to 3 substituent(s) selected from the above-mentioned group B.

[2] The nitrogen-containing fused ring compound of [1], wherein $Y^1$----$Y^2$----$Y^3$ of ring B is C═C($R^{y1}$)—N($R^{y2}$), N—C($R^{y1}$)═N, N—C($R^{y1}$)═C($R^{y2}$) or C═N—N($R^{y2}$), wherein each symbol is as defined in [1], or a pharmaceutically acceptable salt thereof.

[3] The nitrogen-containing fused ring compound of [2] represented by the following formula [I]-1, or a pharmaceutically acceptable salt thereof:

[I]-1

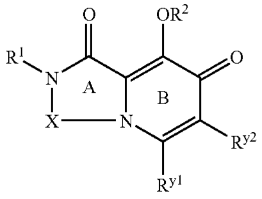

wherein each symbol is as defined in [1].

[4] The nitrogen-containing fused ring compound of [2] represented by the following formula [I]-2, or a pharmaceutically acceptable salt thereof:

[I]-2

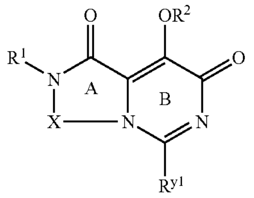

wherein each symbol is as defined in [1].

[5] The nitrogen-containing fused ring compound of [2] represented by the following formula [I]-3, or a pharmaceutically acceptable salt thereof:

[I]-3

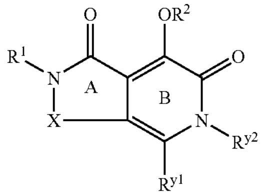

wherein each symbol is as defined in [1].

[6] The nitrogen-containing fused ring compound of [2] represented by the following formula [T]-4, or a pharmaceutically acceptable salt thereof:

[I]-4

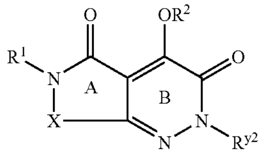

wherein each symbol is as defined in [1].

[7] The nitrogen-containing fused ring compound of any of [1]–[6], wherein X is —C($R^{x1}$) ($R^{x2}$)—C($R^{x3}$)($R^{x4}$)-#, —C($R^{x1}$) ($R^{x2}$)—C($R^{x3}$)($R^{x4}$)—C($R^{x5}$)($R^{x6}$)#, —C($R^{x7}$)═C($R^{x8}$)-#, —N═C($R^{x9}$)# or —C($R^{x10}$)═N-# wherein each symbol is as defined in [1], or a pharmaceutically acceptable salt thereof.

[8] The nitrogen-containing fused ring compound of [7], wherein X is —C($R^{x1}$)($R^{x2}$)—C($R^{x3}$)($R^{x4}$)-# or —C($R^{x7}$)═C($R^{x8}$)-# wherein each symbol is as defined in [1], or a pharmaceutically acceptable salt thereof.

[9] The nitrogen-containing fused ring compound of [8], wherein X is —C($R^{x1}$) ($R^{x2}$)—C($R^{x3}$)($R^{x4}$)-# wherein each symbol is as defined in [1], or a pharmaceutically acceptable salt thereof.

[10] The nitrogen-containing fused ring compound of [8], wherein X is —C($R^{x7}$)═C($R^{x8}$)-# wherein each symbol is as defined in [1], or a pharmaceutically acceptable salt thereof.

[11] The nitrogen-containing fused ring compound of any of [1]–[6], wherein $R^1$ is a group represented by the formula

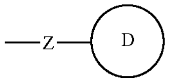

wherein Z is C1–6 alkylene or *—$(CH_2)_m$-Q-$(CH_2)_n$—, and other symbols are as defined in [1], or a pharmaceutically acceptable salt thereof.

[12] The nitrogen-containing fused ring compound of [11], wherein Z is a C1–6 alkylene, or a pharmaceutically acceptable salt thereof.

[13] The nitrogen-containing fused ring compound of [11], wherein ring D is a C3–10 carbon ring group optionally substituted by 1 to 3 substituent(s) selected from group B, or a pharmaceutically acceptable salt thereof.

[14] The nitrogen-containing fused ring compound of any of [1]–[6], wherein $R^{x1}$ to $R^{x10}$ are each independently selected from the following groups and $R^{x1}$ and $R^{x2}$, $R^{x3}$ and $R^{x4}$, and $R^{x5}$ and $R^{x6}$ each independently optionally form, together with the adjacent carbon atom, a C3–8 cycloalkyl, or a pharmaceutically acceptable salt thereof:

a hydrogen atom,
a C3–8 cycloalkyl C1–6 alkyl group,
a cyano group,
a C1–7 alkyl group,
a C6–14 aryl group,
a C6–14 aryl C1–6 alkyl group,
—$CO_2R^{c1}$,
—$CONR^{c2}R^{c3}$ and,
—$COR^{c4}$ wherein the above-mentioned C1–7 alkyl group and C1–6 alkyl moiety are optionally substituted by 1 to 3 substituent(s) selected from group A or a heterocyclic group, and other symbols are as defined in [1].

[15] The nitrogen-containing fused ring compound of [14], wherein $R^{x1}$ to $R^{x10}$ are each a hydrogen atom, or a pharmaceutically acceptable salt thereof.

[16] The nitrogen-containing fused ring compound of any of [1]–[6], wherein $R^{y1}$ is selected from the following groups, or a pharmaceutically acceptable salt thereof:

a hydrogen atom,
a C1–7 alkyl group,
a C6–14 aryl group,
—$CO_2R^{c1}$,
—$CONR^{c2}R^{c3}$,
—$COR^{c4}$ and,
a C6–14 arylcarbonyl group wherein the above-mentioned C1–7 alkyl group is optionally substituted by 1 to 3 substituent(s) selected from group A or a heterocyclic group, the above-mentioned C6–14 aryl group is optionally substituted by 1 to 3 substituent(s) selected from group B, and other symbols are as defined in [1].

[17] The nitrogen-containing fused ring compound of [16], wherein $R^{y1}$ is a hydrogen atom, or a pharmaceutically acceptable salt thereof.

[18] The nitrogen-containing fused ring compound of any of [1]–[6], wherein $R^{y2}$ is selected from the following groups, or a pharmaceutically acceptable salt thereof:

a hydrogen, atom,
a halogen atom,
a C1–7 alkyl group
a C6–14 aryl group,
a heterocyclic group,
—$CO_2R^{c1}$,
—$CONR^{c2}R^{c3}$,
—$COR^{c4}$, ——$NR^{c4}R^{c5}$,
—$NR^{c6}COR^{c7}$,
—$SR^{c10}$,
—$SO_2R^{c12}$, —$NR^{c13}CONR^{c14}R^{c15}$,
—$NR^{c16}CO_2R^{c17}$, and, —$NR^{c18}COCOR^{c19}$ wherein the above-mentioned C1–7 alkyl group is optionally substituted by 1 to 3 substituent(s) selected from group A or a heterocyclic group, the above-mentioned C6–14 aryl group and heterocyclic group are optionally substituted by 1 to 3 substituent(s) selected from group B, and other symbols are as defined in [1].

[19] The nitrogen-containing fused ring compound of [18], wherein $R^{y2}$ is a heterocyclic group optionally substituted by 1 to 3 substituent(s) selected from group B, or a pharmaceutically acceptable salt thereof.

[20] The nitrogen-containing fused ring compound of [19], wherein $R^{y2}$ is a heterocyclic group optionally substituted by 1 to 3 substituent(s) selected from group B, which is bonded to $Y^3$ via a carbon atom, wherein at least one α-position of the carbon atom is a hetero atom selected from the group consisting of nitrogen atom, oxygen atom and sulfur atom, or a pharmaceutically acceptable salt thereof.

[21] The nitrogen-containing fused ring compound of [18], wherein $R^{y2}$ is selected from —$CO_2R^{c1}$, —$CONR^{c2}R^{c3}$ and —$COR^{c4}$ wherein each symbol is as defined in [1], or a pharmaceutically acceptable salt thereof.

[22] The nitrogen-containing fused ring compound of [18], wherein $R^{y2}$ is selected from —$NR^{c4}R^{c5}$, —$NR^{c6}COR^{c7}$, —$NR^{c8}SO_2R^{c9}$, —$NR^{c13}CONR^{c14}R^{c15}$, —$NR^{c16}CO_2R^{c17}$ and —$NR^{c18}COCOR^{c19}$ wherein each symbol is as defined in [1], or a pharmaceutically acceptable salt thereof.

[23] The nitrogen-containing fused ring compound of [22], wherein $R^{y2}$ is selected from —$NR^{c6}COR^{c7}$, —$NR^{c8}SO_2R^{c9}$, —$NR^{c13}CONR^{c14}R^{c15}$, —$NR^{c16}CO_2R^{c17}$ and —$NRC^{c18}COCOR^{c19}$ wherein each symbol is as defined in [1], or a pharmaceutically acceptable salt thereof.

[24] The nitrogen-containing fused ring compound of any of [1]–[6], wherein $R^2$ is a hydrogen atom, or a pharmaceutically acceptable salt thereof.

[25] The nitrogen-containing fused ring compound of [1], which is selected from the group consisting of 2-(3,4-dichlorobenzyl)-9-hydroxy-3,4-dihydro-2H-pyrido[1,2-a]pyrazine-1,8-dione hydrochloride (Example 1), 2-(3,4-dichlorobenzyl)-10-hydroxy-2,3,4,5-tetrahydropyrido[1,2-a][1,4]diazepine-1,9-dione (Example 2), 2-(3,4-dichlorobenzyl)-9-hydroxy-3-methyl-3,4-dihydro-2H-pyrido[1,2-a]pyrazine-1,8-dione (Example 3), 2-(3,4-dichlorobenzyl)-9-hydroxy-4,4-dimethyl-3,4-dihydro-2H-pyrido[1,2-a]pyrazine-1,8-dione (Example 4), 2-(3,4-dichlorobenzyl)-9-hydroxy-6-hydroxymethyl-3,4-dihydro-2H-pyrido[1,2-a]pyrazine-1,8-dione (Example 5), 2-(3,4-dichlorobenzyl)-9-hydroxy-1,8-dioxo-1,3,4,8-tetrahydro-2H-pyrido[1,2-a]pyrazine-6-carboxylic acid (Example 6), 2-(3,4-dichlorobenzyl)-6-(2,2-dimethylpropionyl)-9-hydroxy-3,4-dihydro-2H-pyrido[1,2-a]pyrazine-1,8-dione (Example 7), 2-(3,4-dichlorobenzyl)-9-hydroxy-2H-pyrido[1,2-a]pyrazine-1,8-dione (Example 8), 2-(3,4-dichlorobenzyl)-9-hydroxy-3-methyl-2H-pyrido[1,2-a]pyrazine-1,8-dione (Example 9), 2-(3-chlorobenzyl)-9-hydroxy-4-isopropyl-2H-pyrido[1,2-a]pyrazine-1,8-dione hydrochloride (Example 10), 2-[3-(2,6-dichlorophenyl)propyl]-9-hydroxy-2H-pyrido[1,2-a]pyrazine-1,8-dione (Example 11), 2-(3,4-dichlorobenzyl)-9-hydroxy-2H-pyrazino[1,2-c]pyrimidine-1,8-dione hydrochloride (Example 12), 2-(3,4-dichlorobenzyl)-9-hydroxy-4-methyl-3,4-dihydro-2H-pyrido[1,2-a]pyrazine-1,8-dione (Example 13), 4-benzyl-2-(3,4-dichlorobenzyl)-9-hydroxy-3,4-dihydro-2H-pyrido[1,2-a]pyrazine-1,8-dione (Example 14), 2-(3,4-dichlorobenzyl)-9-hydroxy-4-phenyl-3,4-dihydro-2H-pyrido[1,2-a]pyrazine-1,8-dione (Example 15), 4-butyl-2-(3,4-dichlorobenzyl)-9-hydroxy-3,4-dihydro-2H-pyrido[1,2-a]pyrazine-1,8-dione (Example 16), 2-(3,4-dichlorobenzyl)-9-hydroxy-4-isopropyl-3,4-dihydro-2H-pyrido[1,2-a]pyrazine-1,8-dione (Example 17), 2-(3,4-dichlorobenzyl)-9-hydroxy-3,3-dimethyl-3,4-dihydro-2H-pyrido[1,2-a]pyrazine-1,8-dione (Example 18), 2-(3,4-dichlorobenzyl)-9-hydroxy-3,4-dihydro-2H-pyrido[1,2-a]pyrazine-4-spiro-1'-cyclopentane-1,8-dione (Example 19), 2-(3,4-dichlorobenzyl)-9-hydroxy-3,4-dihydro-2H-pyrido[1,2-a]pyrazine-4-spiro-1'-cyclohexane-1,8-dione (Example 20), methyl 2-(3,4-dichlorobenzyl)-9-hydroxy-1,8-dioxo-1,3,4,8-tetrahydro-2H-pyrido[1,2-a]pyrazine-4-carboxylate (Example 21), 2-(3,4-dichlorobenzyl)-9-hydroxy-1,8-dioxo-1,3,4,8-tetrahydro-2H-pyrido[1,2-a]pyrazine-4-carboxylic acid (Example 22), 2-(3,4-dichlorobenzyl)-9-hydroxy-6-methoxymethyl-3,4-dihydro-2H-pyrido[1,2-a]pyrazine-1,8-dione (Example 23), N,N-dimethyl-2-(3,4-dichlorobenzyl)-9-hydroxy-1,8-dioxo-1,3,4,8-tetrahydro-2H-pyrido[1,2-a]pyrazine-6-carboxamide (Example 24), 3-benzyl-2-(3,4-dichlorobenzyl)-9-hydroxy-3,4-dihydro-2H-pyrido[1,2-a]pyrazine-1,8-dione (Example 25), 3-butyl-2-(3,4-dichlorobenzyl)-9-hydroxy-3,4-dihydro-2H-pyrido[1,2-a]pyrazine-1,8-dione (Example 26), N,N-dimethyl-2-(3,4-dichlorobenzyl)-9-hydroxy-1,8-dioxo-1,3,4,8-tetrahydro-2H-pyrido[1,2-a]pyrazine-4-carboxamide (Example 27), 2-(3,4-dichlorobenzyl)-9-hydroxy-4-hydroxymethyl-3,4-dihydro-2H-pyrido[1,2-a]pyrazine-1,8-dione (Example 28), 2-(3,4-dichlorobenzyl)-9-hydroxy-4-methoxymethyl-3,4-dihydro-2H-pyrido[1,2-a]pyrazine-1,8-dione (Example 29), 2-(3,4-dichlorobenzyl)-9-hydroxy-6-methylsulfanylmethyl-3,4-dihydro-2H-pyrido[1,2-a]pyrazine-1,8-dione (Example 30), 2-(3,4-dichlorobenzyl)-9-hydroxy-6-methanesulfonylmethyl-3,4-dihydro-2H-pyrido[1,2-a]pyrazine-1,8-dione (Example 31), 2-(3,4-dichlorobenzyl)-9-hydroxy-4-(2-methanesulfonylethyl)-3,4-dihydro-2H-pyrido[1,2-a]pyrazine-1,8-dione (Example 32), 2-(3,4-dichlorobenzyl)-9-hydroxy-4-(2-methylsulfanylethyl)-3,4-dihydro-2H-pyrido[1,2-a]pyrazine-1,8-dione (Example 33), methyl 2-(3,4-dichlorobenzyl)-9-hydroxy-1,8-dioxo-1,3,4,8-tetrahydro-2H-pyrido[1,2-a]pyrazine-6-carboxylate (Example 34), 6-acetyl-2-(3,4-dichlorobenzyl)-9-hydroxy-3,4-dihydro-2H-pyrido[1,2-a]pyrazine-1,8-dione (Example 35), 2-(3,4-dichlorobenzyl)-9-hydroxy-6-isopropylsulfanylmethyl-3,4-dihydro-2H-pyrido[1,2-a]pyrazine-1,8-dione (Example 36), 2-(3,4-dichlorobenzyl)-9-hydroxy-6-isopropylsulfonylmethyl-3,4-dihydro-2H-pyrido[1,2-a]pyrazine-1,8-dione (Example 37), 2-(3,4-dichlorobenzyl)-9-hydroxy-6-isopropoxymethyl-3,4-dihydro-2H-pyrido[1,2-a]pyrazine-1,8-dione (Example 38), 2-(3,4-dichlorobenzyl)-9-hydroxy-6-isobutoxymethyl-3,4-dihydro-2H-pyrido[1,2-a]pyrazine-1,8-dione (Example 39), 2-(3,4-dichlorobenzyl)-9-hydroxy-6-(1-hydroxyethyl)-3,4-dihydro-2H-pyrido[1,2-a]pyrazine-1,8-dione (Example 40), 2-(3,4-dichlorobenzyl)-9-hydroxy-6-phenoxymethyl-3,4-dihydro-2H-pyrido[1,2-a]pyrazine-1,8-dione (Example 41), 2-(4-fluorobenzyl)-9-hydroxy-3,4-dihydro-2H-pyrido[1,2-a]pyrazine-1,8-dione (Example 42), 2-(3-chlorobenzyl)-9-hydroxy-3,4-dihydro-2H-pyrido[1,2-a]pyrazine-1,8-dione (Example 43), 2-benzyl-9-hydroxy-3,4-dihydro-2H-pyrido[1,2-a]pyrazine-1,8-dione (Example 44), 2-(4-chlorobenzyl)-9-hydroxy-3,4-dihydro-2H-pyrido[1,2-a]pyrazine-1,8-dione (Example 45), 2-(3,4-dichlorobenzyl)-9-hydroxy-6-isopropyl-3,4-dihydro-2H-pyrido[1,2-a]pyrazine-1,8-dione (Example 46), 2-(3,4-dichlorobenzyl)-9-hydroxy-6-isobutyryl-3,4-dihydro-2H-pyrido[1,2-a]pyrazine-1,8-dione (Example 47), 2-(3,4-dichlorobenzyl)-9-hydroxy-1,8-dioxo-1,3,4,8-tetrahydro-2H-pyrido[1,2-a]pyrazine-6-carbaldehyde (Example 48), 2-(3,4-dichlorobenzyl)-9-hydroxy-6-phenyl-3,4-dihydro-2H-pyrido[1,2-a]pyrazine-1,8-dione (Example 49), 9-hydroxy-2-(3-phenylpropyl)-3,4-dihydro-2H-pyrido[1,2-a]pyrazine-1,8-dione (Example 50), 2-(3-chloro-2-fluorobenzyl)-9-hydroxy-3,4-dihydro-2H-pyrido[1,2-a]pyrazine-1,8-dione (Example 51), 9-hydroxy-2-phenethyl-3,4-dihydro-2H-pyrido[1,2-a]pyrazine-1,8-dione (Example 52), 2-(3,4-dichlorobenzyl)-9-hydroxy-6-(1-hydroxy-2-methylpropyl)-3,4-dihydro-2H-pyrido[1,2-a]pyrazine-1,8-dione (Example 53), 2-(3,4-dichlorobenzyl)-9-hydroxy-6-isobutyl-3,4-dihydro-2H-pyrido[1,2-a]pyrazine-1,8-dione (Example 54), 2-(3,4-dichlorobenzyl)-9-hydroxy-1,8-dioxo-1,3,4,8-tetrahydro-2H-pyrido[1,2-a]pyrazine-6-carboxamide (Example 55), N-methyl-2-(3,4-dichlorobenzyl)-9-hydroxy-1,8-dioxo-1,3,4,8-tetrahydro-2H-pyrido[1,2-a]pyrazine-6-carboxamide (Example 56), 2-(4-chloro-3-fluorobenzyl)-9-hydroxy-3,4-dihydro-2H-pyrido[1,2-a]pyrazine-1,8-dione (Example 57), 6-benzoyl-2-(3,4-dichlorobenzyl)-9-hydroxy-3,4-dihydro-2H-pyrido[1,2-a]pyrazine-1,8-dione (Example 58), 2-(3,4-dichlorobenzyl)-9-hydroxy-6-propionyl-3,4-dihydro-2H-pyrido[1,2-a]pyrazine-1,8-dione (Example 59), 2-(3,4-dichlorobenzyl)-9-hydroxy-6-methyl-3,4-dihydro-2H-pyrido[1,2-a]pyrazine-1,8-dione (Example 60), N,N-diethyl-2-(3,4-dichlorobenzyl)-9-hydroxy-1,8-dioxo-1,3,4,8-tetrahydro-2H-pyrido[1,2-a]pyrazine-6-carboxamide (Example 61), N-isopropyl-N-methyl-2-(3,4-dichlorobenzyl)-9-hydroxy-1,8-dioxo-1,3,4,8-tetrahydro-2H-pyrido[1,2-a]pyrazine-6-carboxamide (Example 62), N-ethyl-N-methyl-2-(3,4-dichlorobenzyl)-9-hydroxy-1,8-dioxo-1,3,4,8-tetrahydro-2H-pyrido[1,2-a]pyrazine-6-carboxamide (Example 63)

2-(3-chloro-4-fluorobenzyl)-9-hydroxy-3,4-dihydro-2H-pyrido[1,2-a]pyrazine-1,8-dione (Example 64), 2-(2-chlorobenzyl)-9-hydroxy-3,4-dihydro-2H-pyrido[1,2-a]pyrazine-1,8-dione (Example 65), 2-(3,5-dichlorobenzyl)-9-hydroxy-3,4-dihydro-2H-pyrido[1,2-a]pyrazine-1,8-dione (Example 66), 6-tert-butyl-2-(3,4-dichlorobenzyl)-9-hydroxy-3,4-dihydro-2H-pyrido[1,2-a]pyrazine-1,8-dione (Example 67), 2-(3,4-dichlorobenzyl)-9-hydroxy-6-(1-hydroxy-2,2-dimethylpropyl)-3,4-dihydro-2H-pyrido[1,2-a]pyrazine-1,8-dione (Example 68), 3-benzyl-9-hydroxy-2-methyl-2H-pyrido[1,2-a]pyrazine-1,8-dione (Example 69), 2-[3-(4-chlorophenyl)propyl]-9-hydroxy-2H-pyrido[1,2-a]pyrazine-1,8-dione (Example 70), 2-[3-(2-chlorophenyl)propyl]-9-hydroxy-2H-pyrido[1,2-a]pyrazine-1,8-dione (Example 71), 2-(3,4-dichlorobenzyl)-9-hydroxy-4-methyl-2H-pyrido[1,2-a]pyrazine-1,8-dione hydrochloride (Example 72), 2-(3-chloro-4-methoxybenzyl)-9-hydroxy-3,4-dihydro-2H-pyrido[1,2-a]pyrazine-1,8-dione (Example 73), 9-hydroxy-2-methyl-3-phenethyl-2H-pyrido[1,2-a]pyrazine-1,8-dione (Example 74),

[2-(3,4-dichlorobenzyl)-9-hydroxy-1,8-dioxo-1,3,4,8-tetrahydro-2H-pyrido[1,2-a]pyrazin-6-yl]acetonitrile (Example 75), 2-[3-(3-chlorophenyl)propyl]-9-hydroxy-2H-pyrido[1,2-a]pyrazine-1,8-dione (Example 76), 9-hydroxy-2-methyl-3-(3-phenylpropyl)-2H-pyrido[1,2-a]pyrazine-1,8-dione (Example 77), 2-(3,4-dichlorobenzyl)-9-hydroxy-4-isopropyl-2H-pyrido[1,2-a]pyrazine-1,8-dione (Example 78), 2-[3-(3,4-dichlorophenyl)propyl]-9-hydroxy-2H-pyrido[1,2-a]pyrazine-1,8-dione (Example 79), 2-[3-(3,5-dichlorophenyl)propyl]-9-hydroxy-2H-pyrido[1,2-a]pyrazine-1,8-dione (Example 80), benzyl[2-(3,4-dichlorobenzyl)-9-hydroxy-1,8-dioxo-1,3,4,8-tetrahydro-2H-pyrido[1,2-a]pyrazin-6-yl]acetate (Example 81), benzyl 2-[2-(3,4-dichlorobenzyl)-9-hydroxy-1,8-dioxo-1,3,4,8-tetrahydro-2H-pyrido[1,2-a]pyrazin-6-yl]-3-phenylpropionate (Example 82), 2-(3,4-dichlorobenzyl)-9-hydroxy-6-(2-hydroxyethyl)-3,4-dihydro-2H-pyrido[1,2-a]pyrazine-1,8-dione (Example 83), 2-(3,4-dichlorobenzyl)-9-hydroxy-4-propyl-2H-pyrido[1,2-a]pyrazine-1,8-dione (Example 84), 2-(3,4-dichlorobenzyl)-4-ethyl-9-hydroxy-2H-pyrido[1,2-a]pyrazine-1,8-dione (Example 85), 2-(3,4-dichlorobenzyl)-9-hydroxy-4-hydroxymethyl-2H-pyrido[1,2-a]pyrazine-1,8-dione (Example 86), 2-(3,4-dichlorobenzyl)-9-hydroxy-4-isobutyl-2H-pyrido[1,2-a]pyrazine-1,8-dione (Example 87), 2-(3-chlorobenzyl)-9-hydroxy-2H-pyrido[1,2-a]pyrazine-1,8-dione hydrochloride (Example 88), methyl 2-(3,4-dichlorobenzyl)-9-hydroxy-1,8-dioxo-1,8-dihydro-2H-pyrido[1,2-a]pyrazine-4-carboxylate (Example 89), 2-(3-chloro-4-fluorobenzyl)-9-hydroxy-2H-pyrido[1,2-a]pyrazine-1,8-dione hydrochloride (Example 90), 2-[3-(2,3-dichlorophenyl)propyl]-9-hydroxy-2H-pyrido[1,2-a]pyrazine-1,8-dione hydrochloride (Example 91), 2-(3-chloro-4-fluorobenzyl)-9-hydroxy-4-isopropyl-2H-pyrido[1,2-a]pyrazine-1,8-dione hydrochloride (Example 92), methyl 2-(3-chlorobenzyl)-9-hydroxy-1,8-dioxo-1,8-dihydro-2H-pyrido[1,2-a]pyrazine-4-carboxylate (Example 93), 7-bromo-2-(3-chlorobenzyl)-9-hydroxy-2H-pyrido[1,2-a]pyrazine-1,8-dione hydrochloride (Example 94), 2-[3-(2-chloro-6-fluorophenyl)propyl]-9-hydroxy-2H-pyrido[1,2-a]pyrazine-1,8-dione hydrochloride (Example 95), 2-(3-chlorobenzyl)-9-hydroxy-7-phenyl-2H-pyrido[1,2-a]pyrazine-1,8-dione hydrochloride (Example 96), N,N-dimethyl-2-(3-chlorobenzyl)-9-hydroxy-1,8-dioxo-1,8-dihydro-2H-pyrido[1,2-a]pyrazine-4-carboxamide (Example 97), 2-(3-chlorobenzyl)-9-hydroxy-1,8-dioxo-1,8-dihydro-2H-pyrido[1,2-a]pyrazine-4-carboxylic acid (Example 98), 3-(3-chlorobenzyl)-5-hydroxy-3H-pyrazino[1,2-a]quinoline-4,6-dione hydrochloride (Example 99), 2-(3-chlorobenzyl)-9-hydroxy-2H-pyrazino[1,2-c]pyrimidine-1,8-dione hydrochloride (Example 100), 2-(3-chlorobenzyl)-9-hydroxy-1,8-dioxo-1,8-dihydro-2H-pyrido[1,2-a]pyrazine-4-carbaldehyde (Example 101), 2-(3-chlorobenzyl)-9-hydroxy-4-hydroxymethyl-2H-pyrido[1,2-a]pyrazine-1,8-dione (Example 102), 2-(3-chlorobenzyl)-9-hydroxy-4-(1-hydroxyethyl)-2H-pyrido[1,2-a]pyrazine-1,8-dione (Example 103), 2-(3-chlorobenzyl)-9-hydroxy-7-isopropyl-2H-pyrido[1,2-a]pyrazine-1,8-dione hydrochloride (Example 104), 4-acetyl-2-(3-chlorobenzyl)-9-hydroxy-2H-pyrido[1,2-a]pyrazine-1,8-dione (Example 105), 2-(3-chlorobenzyl)-8-hydroxy-6-methyl-2,3,4,6-tetrahydro-2,6-naphthyridine-1,7-dione (Example 106), 2-(3-chlorobenzyl)-9-hydroxy-1,8-dioxo-1,8-dihydro-2H-pyrido[1,2-a]pyrazine-4-carbonitrile (Example 107), 2-(3-chlorobenzyl)-9-hydroxy-3,4-dihydro-2H-pyrazino[1,2-c]pyrimidine-1,8-dione (Example 108), 7-bromo-2-(3-chlorobenzyl)-1,8-dioxo-1,8-dihydro-2H-pyrido[1,2-a]pyrazin-9-yl methanesulfonate (Example 109), 7-bromo-2-(3-chlorobenzyl)-3,9-dihydroxy-3,4-dihydro-2H-pyrido[1,2-a]pyrazine-1,8-dione hydrochloride (Example 110), 3-(3-chlorobenzyl)-5-hydroxy-2,3-dihydro-1H-pyrazino[1,2-a]quinoline-4,6-dione (Example 111), 2-(3-chlorobenzyl)-7-(3-chlorophenyl)-9-hydroxy-2H-pyrido[1,2-a]pyrazine-1,8-dione hydrochloride (Example 112), 2-(3-chlorobenzyl)-7-(4-chlorophenyl)-9-hydroxy-2H-pyrido[1,2-a]pyrazine-1,8-dione hydrochloride (Example 113), 2-(3-chlorobenzyl)-7-(2-chlorophenyl)-9-hydroxy-2H-pyrido[1,2-a]pyrazine-1,8-dione hydrochloride (Example 114), 2-(3-chlorobenzyl)-9-hydroxy-7-(pyridin-3-yl)-2H-pyrido[1,2-a]pyrazine-1,8-dione hydrochloride (Example 115), 2-(3-chlorobenzyl)-9-hydroxy-7-(pyridin-4-yl)-2H-pyrido[1,2-a]pyrazine-1,8-dione hydrochloride (Example 116), 2-(3-chlorobenzyl)-9-hydroxy-7-(pyridin-2-yl)-2H-pyrido[1,2-a]pyrazine-1,8-dione hydrochloride (Example 117), 2-(3-chlorobenzyl)-9-hydroxy-7-(1-hydroxy-2,2-dimethylpropyl)-2H-pyrido[1,2-a]pyrazine-1,8-dione hydrochloride (Example 118), 2-(3-chlorobenzyl)-4-cyclohexylmethyl-9-hydroxy-7-phenyl-2H-pyrido[1,2-a]pyrazine-1,8-dione hydrochloride (Example 119), 2-(3-chlorobenzyl)-7-(furan-2-yl)-9-hydroxy-2H-pyrido[1,2-a]pyrazine-1,8-dione hydrochloride (Example 120), 2-(3,4-dichlorobenzyl)-8-hydroxy-6-methyl-2,3,4,6-tetrahydro-2,6-naphthyridine-1,7-dione (Example 121), 2-[3-(2-chloro-6-fluorophenyl)propyl]-8-hydroxy-6-methyl-2,3,4,6-tetrahydro-2,6-naphthyridine-1,7-dione (Example 122), 6-(3-chlorobenzyl)-4-hydroxy-2-methyl-2,6,7,8-tetrahydropyrido[4,3-c]pyridazine-3,5-dione (Example 123), 7-(benzofuran-2-yl)-2-(3-chlorobenzyl)-9-hydroxy-2H-pyrido[1,2-a]pyrazine-1,8-dione hydrochloride (Example 124), 2-(3-chlorobenzyl)-7-(2,2-dimethylpropionyl)-9-hydroxy-2H-pyrido[1,2-a]pyrazine-1,8-dione hydrochloride (Example 125), 2-(3-chlorobenzyl)-7-(2,2-dimethylpropyl)-9-hydroxy-2H-pyrido[1,2-a]pyrazine-1,8-dione hydrochloride (Example 126), 2-(3-chlorobenzyl)-9-hydroxy-7-(2-trifluoromethylphenyl)-2H-pyrido[1,2-a]pyrazine-1,8-dione hydrochloride (Example 127), 2-(3-chlorobenzyl)-9-hydroxy-7-(3-methoxyphenyl)-2H-pyrido[1,2-a]pyrazine-1,8-dione hydrochloride (Example 128), 7-bromo-2-(3-chlorobenzyl)-9-hydroxy-4-isopropyl-2H-pyrido[1,2-a]pyrazine-1,8-dione hydrochloride (Example 129), 2-(3-chlorobenzyl)-7-(2-fluorophenyl)-9-hydroxy-2H-pyrido[1,2-a]pyrazine-1,8-dione hydrochloride (Example 130), 2-(3-chlorobenzyl)-9-hydroxy-4-isopropyl-7-phenyl-2H-pyrido[1,2-a]pyrazine-1,8-dione hydrochloride (Example 131), 2-(3-chlorobenzyl)-9-hydroxy-7-(2-methoxyphenyl)-2H-pyrido[1,2-a]pyrazine-1,8-dione hydrochloride. (Example 132), 2-(3-chlorobenzyl)-9-hydroxy-7-(4-methoxyphenyl)-2H-pyrido[1,2-a]pyrazine-1,8-dione hydrochloride (Example 133), 2-(3-chlorobenzyl)-7-ethyl-9-hydroxy-2H-pyrido[1,2-a]pyrazine-1,8-dione hydrochloride. (Example 134), 2-(3-chlorobenzyl)-7-(2,6-dimethylphenyl)-9-hydroxy-2H-pyrido[1,2-a]pyrazine-1,8-dione hydrochloride (Example 135), 2-(3-chlorobenzyl)-9-hydroxy-7-(3-hydroxyphenyl)-2H-pyrido[1,2-a]pyrazine-1,8-dione (Example 136), 7-benzoyl-2-(3-chlorobenzyl)-9-hydroxy-2H-pyrido[1,2-a]pyrazine-1,8-dione hydrochloride (Example 137), 2-(3-chlorobenzyl)-7-(2-ethylphenyl)-9-hydroxy-2H-pyrido[1,2-a]pyrazine-1,8-dione hydrochloride (Example 138), 2-(3-chlorobenzyl)-7-(3-chlorophenyl)-9-hydroxy-4-isopropyl-2H-pyrido[1,2-a]pyrazine-1,8-dione (Example 139), 7-benzyl-2-(3-chlorobenzyl)-9-hydroxy-2H-pyrido[1,2-a]pyrazine-1,8-dione hydrochloride (Example 140), 2-(3-chlorobenzyl)-9-hydroxy-7-(2-hydroxyphenyl)-2H-pyrido[1,2-a]pyrazine-1,8-dione (Example 141), 2-(3-chlorobenzyl)-9-hydroxy-7-(4-hydroxyphenyl)-2H-pyrido[1,2-a]pyrazine-1,8-dione (Example 142), 8-hydroxy-6-methyl-2-(3-trifluoromethylbenzyl)-2,3,4,6-tetrahydro-2,6-naphthyridine-1,7-dione (Example 143), 8-hydroxy-2-(3-methoxybenzyl)-6-methyl-2,3,4,6-tetrahydro-2,6-naphthyridine-1,7-dione (Example 144), 6-(3-chlorobenzyl)-4-hydroxy-2-methyl-2,6-dihydropyrido[4,3-c]pyridazine-3,5-dione (Example 145), 3-(3-chlorobenzyl)-5-hydroxy-3H-pyrido[2,1-f][1,2,4]triazine-4,6-dione (Example 146), methyl 2-(3-chlorobenzyl)-9-hydroxy-1,8-dioxo-1,8-dihydro-2H-pyrido[1,2-a]pyrazine-7-carboxylate hydrochloride (Example 147), 2-(3-chlorobenzyl)-9-hydroxy-7-(1-methyl-1H-imidazol-2-yl)-2H-pyrido[1,2-a]pyrazine-1,8-dione hydrochloride (Example 148), 2-(3-chlorobenzyl)-9-hydroxy-7-isobutyryl-2H-pyrido[1,2-a]pyrazine-1,8-dione hydrochloride (Example 149), isopropyl 2-(3-chlorobenzyl)-9-hydroxy-1,8-dioxo-1,8-dihydro-2H-pyrido[1,2-a]pyrazine-7-carboxylate (Example 150), 2-(4-chlorobenzyl)-9-hydroxy-2H-pyrido[1,2-a]pyrazine-1,8-dione hydrochloride (Example 151), 2-(3-chlorobenzyl)-9-hydroxy-1,8-dioxo-1,8-dihydro-2H-pyrido[1,2-a]pyrazine-7-carboxylic acid hydrochloride (Example 152), N,N-dimethyl-2-(3-chlorobenzyl)-9-hydroxy-1,8-dioxo-1,8-dihydro-2H-pyrido[1,2-a]pyrazine-7-carboxamide (Example 153), 2-(3-chlorobenzyl)-9-hydroxy-1,8-dioxo-1,8-dihydro-2H-pyrido[1,2-a]pyrazine-7-carboxylic acid isopropylamide (Example 154), N-methyl-2-(3-chlorobenzyl)-9-hydroxy-1,8-dioxo-1,8-dihydro-2H-pyrido[1,2-a]pyrazine-7-carboxamide (Example 155), N,N-diethyl-2-(3-chlorobenzyl)-9-hydroxy-1,8-dioxo-1,8-dihydro-2H-pyrido[1,2-a]pyrazine-7-carboxamide (Example 156), 2-(4-bromobenzyl)-9-hydroxy-2H-pyrido[1,2-a]pyrazine-1,8-dione hydrochloride (Example 157), 2-(3-bromobenzyl)-9-hydroxy-2H-pyrido[1,2-a]pyrazine-1,8-dione hydrochloride (Example 158), 2,2-dimethylpropyl 2-(3-chlorobenzyl)-9-hydroxy-1,8-dioxo-1,8-dihydro-2H-pyrido[1,2-a]pyrazine-7-carboxylate (Example 159), cyclohexyl 2-(3-chlorobenzyl)-9-hydroxy-1,8-dioxo-1,8-dihydro-2H-pyrido[1,2-a]pyrazine-7-carboxylate (Example 160), 7-amino-2-(3-chlorobenzyl)-9-hydroxy-2H-pyrido[1,2-a]pyrazine-1,8-dione hydrochloride (Example 161), 2-(3-chlorobenzyl)-9-hydroxy-4-methyl-2H-pyrido[1,2-d][1,2,4]triazine-1,8-dione hydrochloride (Example 162), 2-(3-chlorobenzyl)-9-hydroxy-7-(thiazol-2-yl)-2H-pyrido[1,2-a]pyrazine-1,8-dione hydrochloride (Example 163), 2-(3-chlorobenzyl)-9-hydroxy-7-(4H-1,2,4-triazol-3-yl)-2H-pyrido[1,2-a]pyrazine-1,8-dione hydrochloride (Example 164), N-[2-(3-chlorobenzyl)-9-hydroxy-1,8-dioxo-1,8-dihydro-2H-pyrido[1,2-a]pyrazin-7-yl]acetamide (Example 165), 2-(4-chloro-2-methoxybenzyl)-9-hydroxy-2H-pyrido[1,2-a]pyrazine-1,8-dione hydrochloride (Example 166), 2-(3-chlorobenzyl)-9-hydroxy-1,8-dioxo-1,8-dihydro-2H-pyrido[1,2-a]pyrazine-7-carboxamide (Example 167), 2-(3-chloro-2-methoxybenzyl)-9-hydroxy-2H-pyrido[1,2-a]pyrazine-1,8-dione hydrochloride (Example 168), 2-[2-(2-chlorophenoxy)ethyl]-9-hydroxy-2H-pyrido[1,2-a]pyrazine-1,8-dione hydrochloride (Example 169), 2-(3-chlorobenzyl)-9-hydroxy-7-(pyrimidin-2-yl)-2H-pyrido[1,2-a]pyrazine-1,8-dione hydrochloride (Example 170), N-propyl-2-(3-chlorobenzyl)-9-hydroxy-1,8-dioxo-1,8-dihydro-2H-pyrido[1,2-a]pyrazine-7-carboxamide (Example 171), N-butyl-2-(3-chlorobenzyl)-9-hydroxy-1,8-dioxo-1,8-dihydro-2H-pyrido[1,2-a]pyrazine-7-carboxamide (Example 172), N-isobutyl-2-(3-chlorobenzyl)-9-hydroxy-1,8-dioxo-1,8-dihydro-2H-pyrido[1,2-a]pyrazine-7-carboxamide (Example 173), methyl{[2-(3-chlorobenzyl)-9-hydroxy-1,8-dioxo-1,8-dihydro-2H-pyrido[1,2-a]pyrazine-7-carbonyl]amino}acetate (Example 174), N-ethyl-2-(3-chlorobenzyl)-9-hydroxy-1,8-dioxo-1,8-dihydro-2H-pyrido[1,2-a]pyrazine-7-carboxamide (Example 175), N-(2-methoxyethyl)-2-(3-chlorobenzyl)-9-hydroxy-1,8-dioxo-1,8-dihydro-2H-pyrido[1,2-a]pyrazine-7-carboxamide (Example 176), 2-{[2-(3-chlorobenzyl)-9-hydroxy-1,8-dioxo-1,8-dihydro-2H-pyrido[1,2-a]pyrazine-7-carbonyl]amino}ethyl trifluoroacetate (Example 177), N-(2-hydroxyethyl)-2-(3-chlorobenzyl)-9-hydroxy-1,8-dioxo-1,8-dihydro-2H-pyrido[1,2-a]pyrazine-7-carboxamide (Example 178), 2-(3-chloro-2-hydroxybenzyl)-9-hydroxy-2H-pyrido[1,2-a]pyrazine-1,8-dione hydrochloride (Example 179), N-benzyl-2-(3-chlorobenzyl)-9-hydroxy-1,8-dioxo-1,8-dihydro-2H-pyrido[1,2-a]pyrazine-7-carboxamide (Example 180), N-(2,2,2-trifluoroethyl)-2-(3-chlorobenzyl)-9-hydroxy-1,8-dioxo-1,8-dihydro-2H-pyrido[1,2-a]pyrazine-7-carboxamide (Example 181), N-butyl-N-methyl-2-(3-chlorobenzyl)-9-hydroxy-1,8-dioxo-1,8-dihydro-2H-pyrido[1,2-a]pyrazine-7-carboxamide (Example 182), N-(2-methoxyethyl)-N-methyl-2-(3-chlorobenzyl)-9-hydroxy-1,8-dioxo-1,8-dihydro-2H-pyrido[1,2-a]pyrazine-7-carboxamide (Example 183), 2-(3-chlorobenzyl)-9-hydroxy-7-(pyrrolidine-1-carbonyl)-2H-pyrido[1,2-a]pyrazine-1,8-dione (Example 184), 2-(3-chlorobenzyl)-9-hydroxy-7-(morpholine-4-carbonyl)-2H-pyrido[1,2-a]pyrazine-1,8-dione (Example 185), 2-(4-chloro-3-methoxybenzyl)-9-hydroxy-2H-pyrido[1,2-a]pyrazine-1,8-dione hydrochloride (Example 186), methyl[2-(3-chlorobenzyl)-9-hydroxy-1,8-dioxo-1,8-dihydro-2H-pyrido[1,2-a]pyrazin-7-yl]acetate (Example 187), 2-(3-chlorobenzyl)-9-hydroxy-7-(1H-tetrazol-5-yl)-2H-pyrido[1,2-a]pyrazine-1,8-dione hydrochloride (Example 188), 2-[2-(3-chlorobenzyl)-9-hydroxy-1,8-dioxo-1,8-dihydro-2H-pyrido[1,2-a]pyrazin-7-yl]-N-methylacetamide (Example 189), 2-[2-(3-chlorobenzyl)-9-hydroxy-1,8-dioxo-1,8-dihydro-2H-pyrido[1,2-a]pyrazin-7-yl]-N,N-dimethylacetamide (Example 190),

[2-(3-chlorobenzyl)-9-hydroxy-1,8-dioxo-1,8-dihydro-2H-pyrido[1,2-a]pyrazin-7-yl]acetic acid (Example 191), N-(2-hydroxypropyl)-2-(3-chlorobenzyl)-9-hydroxy-1,8-dioxo-1,8-dihydro-2H-pyrido[1,2-a]pyrazine-7-carboxamide hydrochloride (Example 192), {[2-(3-chlorobenzyl)-9-hydroxy-1,8-dioxo-1,8-dihydro-2H-pyrido[1,2-a]pyrazine-7-carbonyl]amino}acetic acid (Example 193), N-dimethylcarbamoylmethyl-2-(3-chlorobenzyl)-9-hydroxy-1,8-dioxo-1,8-dihydro-2H-pyrido[1,2-a]pyrazine-7-carboxamide (Example 194)

N-methylcarbamoylmethyl-2-(3-chlorobenzyl)-9-hydroxy-1,8-dioxo-1,8-dihydro-2H-pyrido[1,2-a]pyrazine-7-carboxamide (Example 195), N-phenyl-2-(3-chlorobenzyl)-9-hydroxy-1,8-dioxo-1,8-dihydro-2H-pyrido[1,2-a]pyrazine-7-carboxamide hydrochloride (Example 196), 2-(3-chlorobenzyl)-9-hydroxy-7-(oxazol-2-yl)-2H-pyrido[1,2-a]pyrazine-1,8-dione hydrochloride (Example 197), 2-(3-chlorobenzyl)-9-hydroxy-7-(3-hydroxypyrrolidine-1-carbonyl)-2H-pyrido[1,2-a]pyrazine-1,8-dione hydrochloride (Example 198), N-(2-oxopropyl)-2-(3-chlorobenzyl)-9-hydroxy-1,8-dioxo-1,8-dihydro-2H-pyrido[1,2-a]pyrazine-7-carboxamide (Example 199), 2-(9-hydroxy-1,8-dioxo-1,8-dihydro-pyrido[1,2-a]pyrazin-2-yl)-N-phenylacetamide hydrochloride (Example 200), 2-(3-chlorobenzyl)-9-hydroxy-7-(3-oxopyrrolidine-1-carbonyl)-2H-pyrido[1,2-a]pyrazine-1,8-dione (Example 201), 2-(5-chloro-2-methoxybenzyl)-9-hydroxy-2H-pyrido[1,2-a]pyrazine-1,8-dione hydrochloride (Example 202), N-[2-(3-chlorobenzyl)-9-hydroxy-1,8-dioxo-1,8-dihydro-2H-pyrido[1,2-a]pyrazin-7-yl]methanesulfonamide (Example 203), 7-acetyl-2-(3-chlorobenzyl)-9-hydroxy-2H-pyrido[1,2-a]pyrazine-1,8-dione hydrochloride (Example 204), 2-(3-chlorobenzyl)-9-hydroxy-7-propionyl-2H-pyrido[1,2-a]pyrazine-1,8-dione hydrochloride (Example 205), 9-hydroxy-2-(3-phenylallyl)-2H-pyrido[1,2-a]pyrazine-1,8-dione (Example 206), N-methyl-2-(3-chloro-4-fluorobenzyl)-9-hydroxy-1,8-dioxo-1,8-dihydro-2H-pyrido[1,2-a]pyrazine-7-carboxamide (Example 207), N,N-dimethyl-2-(3-chloro-4-fluorobenzyl)-9-hydroxy-1,8-dioxo-1,8-dihydro-2H-pyrido[1,2-a]pyrazine-7-carboxamide (Example 208), N-(2-methanesulfonylethyl)-2-(3-chlorobenzyl)-9-hydroxy-1,8-dioxo-1,8-dihydro-2H-pyrido[1,2-a]pyrazine-7-carboxamide (Example 209), N-[2-(2-oxopyrrolidin-1-yl)ethyl)-2-(3-chlorobenzyl)-9-hydroxy-1,8-dioxo-1,8-dihydro-2H-pyrido[1,2-a]pyrazine-7-carboxamide (Example 210), N-[2-(3-chlorobenzyl)-9-hydroxy-1,8-dioxo-1,8-dihydro-2H-pyrido[1,2-a]pyrazin-7-yl]-N-methylmethanesulfonamide (Example 211), 2-(3-chloro-5-methoxybenzyl)-9-hydroxy-2H-pyrido[1,2-a]pyrazine-1,8-dione hydrochloride (Example 212), N-(pyridin-4-ylmethyl)-2-(3-chlorobenzyl)-9-hydroxy-1,8-dioxo-1,8-dihydro-2H-pyrido[1,2-a]pyrazine-7-carboxamide-(Example 213), N-(4-fluorobenzyl)-2-(3-chlorobenzyl)-9-hydroxy-1,8-dioxo-1,8-dihydro-2H-pyrido[1,2-a]pyrazine-7-carboxamide (Example 214), 2-(3-chlorobenzyl)-9-hydroxy-7-(thiazol-2-yl)-3,4-dihydro-2H-pyrido[1,2-a]pyrazine-1,8-dione (Example 215), 2-(3-chlorobenzyl)-9-hydroxy-7-hydroxymethyl-2H-pyrido[1,2-a]pyrazine-1,8-dione hydrochloride (Example 216), 2-(3-chloro-4-fluorobenzyl)-7-(2,2-dimethylpropionyl)-9-hydroxy-2H-pyrido[1,2-a]pyrazine-1,8-dione hydrochloride (Example 217), 2-(3-chlorobenzyl)-9-hydroxy-7-(thiazol-5-yl)-2H-pyrido[1,2-a]pyrazine-1,8-dione hydrochloride (Example 218), 2-(3-chlorobenzyl)-9-hydroxy-1,8-dioxo-1,3,4,8-tetrahydro-2H-pyrido[1,2-a]pyrazine-7-carboxylic acid methylamide (Example 219), N,N-dimethyl-2-(3-chlorobenzyl)-9-hydroxy-1,8-dioxo-1,3,4,8-tetrahydro-2H-pyrido[1,2-a]pyrazine-7-carboxamide (Example 220), 2-(3-chloro-4-fluorobenzyl)-7-(2,2-dimethylpropionyl)-9-hydroxy-3,4-dihydro-2H-pyrido[1,2-a]pyrazine-1,8-dione hydrochloride (Example 221), 2-(3-chloro-4-fluorobenzyl)-9-hydroxy-4-hydroxymethyl-1,8-dioxo-1,8-dihydro-2H-pyrido[1,2-a]pyrazine-7-carboxylic acid methylamide hydrochloride (Example 222), 2-(3-chlorobenzyl)-7-(2,2-dimethylpropionyl)-9-hydroxy-3,4-dihydro-2H-pyrido[1,2-a]pyrazine-1,8-dione hydrochloride (Example 223), 2-(4-chloro-2-hydroxybenzyl)-9-hydroxy-2H-pyrido[1,2-a]pyrazine-1,8-dione hydrochloride (Example 224), 2-(3-chloro-4-fluorobenzyl)-9-hydroxy-7-(thiazol-2-yl)-3,4-dihydro-2H-pyrido[1,2-a]pyrazine-1,8-dione (Example 225), 2-(9-hydroxy-1,8-dioxo-1,8-dihydro-pyrido[1,2-a]pyrazin-2-yl)-N-methyl-N-phenylacetamide hydrochloride (Example 226), N-methyl-2-(3-chloro-4-fluorobenzyl)-9-hydroxy-1,8-dioxo-1,3,4,8-tetrahydro-2H-pyrido[1,2-a]pyrazine-7-carboxamide (Example 227)

N,N-dimethyl-2-(3-chloro-4-fluorobenzyl)-9-hydroxy-1,8-dioxo-1,3,4,8-tetrahydro-2H-pyrido[1,2-a]pyrazine-7-carboxamide (Example 228), 3-[2-(3-chlorobenzyl)-9-hydroxy-1,8-dioxo-1,8-dihydro-2H-pyrido[1,2-a]pyrazin-7-yl]-2,2-dimethyl-3-oxopropyl acetate hydrochloride (Example 229), 2-(3-chlorobenzyl)-9-hydroxy-7-(3-hydroxy-2,2-dimethylpropionyl)-2H-pyrido[1,2-a]pyrazine-1,8-dione hydrochloride (Example 230), 2-(3-chlorobenzyl)-9-hydroxy-7-(pyrazin-2-yl)-2H-pyrido[1,2-a]pyrazine-1,8-dione hydrochloride (Example 231), 2-(3-chlorobenzyl)-9-hydroxy-7-(2-methyl-2H-1,2,4-triazol-3-yl)-2H-pyrido[1,2-a]pyrazine-1,8-dione hydrochloride (Example 232), N-(2-fluoroethyl)-2-(3-chlorobenzyl)-9-hydroxy-1,8-dioxo-1,8-dihydro-2H-pyrido[1,2-a]pyrazine-7-carboxamide (Example 233), N-benzyl-N-methyl-2-(3-chlorobenzyl)-9-hydroxy-1,8-dioxo-1,8-dihydro-2H-pyrido[1,2-a]pyrazine-7-carboxamide (Example 234), 2-(3-chlorobenzyl)-9-hydroxy-7-phenylsulfanyl-2H-pyrido[1,2-a]pyrazine-1,8-dione (Example 235), 7-benzenesulfinyl-2-(3-chlorobenzyl)-9-hydroxy-2H-pyrido[1,2-a]pyrazine-1,8-dione (Example 236), 7-benzenesulfonyl-2-(3-chlorobenzyl)-9-hydroxy-2H-pyrido [1,2-a]pyrazine-1,8-dione (Example 237), 2-(3,4-dichlorobenzyl)-7-(2,2-dimethylpropionyl)-9-hydroxy-3,4-dihydro-2H-pyrido[1,2-a]pyrazine-1,8-dione (Example 238), N-[2-(3-chlorobenzyl)-9-hydroxy-1,8-dioxo-1,8-dihydro-2H-pyrido[1,2-a]pyrazin-7-yl]isobutyramide (Example 239), N-[2-(3-chloro-4-fluorobenzyl)-9-hydroxy-1,8-dioxo-1,8-dihydro-2H-pyrido[1,2-a]pyrazin-7-yl]acetamide (Example 240), 2-(3-chloro-4-fluorobenzyl)-7-(2,2-dimethylpropionyl)-9-hydroxy-4-hydroxymethyl-2H-pyrido[1,2-a]pyrazine-1,8-dione hydrochloride (Example 241), N-[2-(3-chlorobenzyl)-9-hydroxy-1,8-dioxo-1,8-dihydro-2H-pyrido[1,2-a]pyrazin-7-yl]propionamide (Example 242), N-[2-(3-chlorobenzyl)-9-hydroxy-1,8-dioxo-1,8-dihydro-2H-pyrido[1,2-a]pyrazin-7-yl]-2-phenylacetamide (Example 243), 7-acetyl-2-(3-chloro-4-fluorobenzyl)-9-hydroxy-2H-pyrido[1,2-a]pyrazine-1,8-dione hydrochloride (Example 244), 2-(3-chlorobenzyl)-9-hydroxy-7-methylsulfanyl-2H-pyrido[1,2-a]pyrazine-1,8-dione (Example 245), 2-(3-chlorobenzyl)-9-hydroxy-7-methanesulfonyl-2H-pyrido[1,2-a]pyrazine-1,8-dione (Example 246), 2-(3-chlorobenzyl)-9-hydroxy-7-methanesulfinyl-2H-pyrido[1,2-a]pyrazine-1,8-dione (Example 247), 2-(3-chlorobenzyl)-9-hydroxy-7-(5-methylthiazol-2-yl)-3,4-dihydro-2H-pyrido[1,2-a]pyrazine-1,8-dione (Example 248), 2-(3,4-dichlorobenzyl)-9-hydroxy-7-(thiazol-2-yl)-3,4-dihydro-2H-pyrido[1,2-a]pyrazine-1,8-dione (Example 249), 2-(4-fluorobenzyl)-9-hydroxy-2H-pyrido[1,2-a]pyrazine-1,8-dione hydrochloride (Example 250), 7-(2,2-dimethylpropionyl)-2-(4-fluorobenzyl)-9-hydroxy-2H-pyrido[1,2-a]pyrazine-1,8-dione hydrochloride (Example 251), 2-(4-fluorobenzyl)-9-hydroxy-7-(thiazol-2-yl)-2H-pyrido [1,2-a]pyrazine-1,8-dione hydrochloride (Example 252), N-methyl-2-(4-fluorobenzyl)-9-hydroxy-1,8-dioxo-1,8-dihydro-2H-pyrido[1,2-a]pyrazine-7-carboxamide (Example 253), 2-[3-(2-chloro-6-fluorophenyl)propyl]-7-(2,2-dimethylpropionyl)-9-hydroxy-2H-pyrido[1,2-a]pyrazine-1,8-dione hydrochloride (Example 254), 2-(3-chlorobenzyl)-9-hydroxy-7-(4-methylthiazol-2-yl)-3,4-dihydro-2H-pyrido[1,2-a]pyrazine-1,8-dione (Example 255), N-[2-(3-chlorobenzyl)-9-hydroxy-1,8-dioxo-1,8-dihydro-2H-pyrido[1,2-a]pyrazin-7-yl]butyramide (Example 256), N-[2-(3-chlorobenzyl)-9-hydroxy-1,8-dioxo-1,8-dihydro-2H-pyrido[1,2-a]pyrazin-7-yl]benzamide (Example 257), N-[2-(3-chlorobenzyl)-9-hydroxy-1,8-dioxo-1,8-dihydro-2H-pyrido[1,2-a]pyrazin-7-yl]-3-phenylpropionamide (Example 258), N-[2-(3-chlorobenzyl)-9-hydroxy-1,8-dioxo-1,8-dihydro-2H-pyrido[1,2-a]pyrazin-7-yl]-N-methylacetamide (Example 259), N-[2-(3-chlorobenzyl)-9-hydroxy-1,8-dioxo-1,8-dihydro-2H-pyrido[1,2-a]pyrazin-7-yl]-2-methoxyacetamide (Example 260), methyl 2-(3-chlorobenzyl)-9-hydroxy-1,8-dioxo-1,3,4,8-tetrahydro-2H-pyrido[1,2-a]pyrazine-7-carboxylate (Example 261), 3-[2-(3-chlorobenzyl)-9-hydroxy-1,8-dioxo-1,8-dihydro-2H-pyrido[1,2-a]pyrazin-7-yl]-1,1-dimethylurea (Example 262), methyl[2-(3-chlorobenzyl)-9-hydroxy-1,8-dioxo-1,8-dihydro-2H-pyrido[1,2-a]pyrazin-7-yl]carbamate (Example 263), 2-[3-(2-chloro-6-fluorophenyl)propyl]-9-hydroxy-7-(thiazol-2-yl)-3,4-dihydro-2H-pyrido[1,2-a]pyrazine-1,8-dione (Example 264), N-[2-(3-chlorobenzyl)-9-hydroxy-1,8-dioxo-1,8-dihydro-2H-pyrido[1,2-a]pyrazin-7-yl]-2-oxopropionamide (Example 265), N-benzyl-2-(3-chlorobenzyl)-9-hydroxy-1,8-dioxo-1,3,4,8-tetrahydro-2H-pyrido[1,2-a]pyrazine-7-carboxamide (Example 266), 2-(3-chlorobenzyl)-9-hydroxy-7-(1H-pyrazol-3-yl)-3,4-dihydro-2H-pyrido[1,2-a]pyrazine-1,8-dione (Example 267), 2-(3-chlorobenzyl)-9-hydroxy-7-(pyrimidin-4-yl)-3,4-dihydro-2H-pyrido[1,2-a]pyrazine-1,8-dione (Example 268), N-(naphthalen-1-ylmethyl)-2-(3-chlorobenzyl)-9-hydroxy-1,8-dioxo-1,3,4,8-tetrahydro-2H-pyrido [1,2-a]pyrazine-7-carboxamide (Example 269)

N-benzhydryl-2-(3-chlorobenzyl)-9-hydroxy-1,8-dioxo-1,3,4,8-tetrahydro-2H-pyrido[1,2-a]pyrazine-7-carboxamide (Example 270), 2-(3-chlorobenzyl)-9-hydroxy-7-(pyrimidin-2-yl)-3,4-dihydro-2H-pyrido[1,2-a]pyrazine-1,8-dione hydrochloride (Example 271), 2-(3-chlorobenzyl)-9-hydroxy-7-(2-methyl-2-phenylpropionyl)-3,4-dihydro-2H-pyrido[1,2-a]pyrazine-1,8-dione (Example 272), N-(4-tert-butylbenzyl)-2-(3-chlorobenzyl)-9-hydroxy-1,8-dioxo-1,3,4,8-tetrahydro-2H-pyrido [1,2-a] pyrazine-7-carboxamide (Example 273), N-[2-(3-chlorobenzyl)-9-hydroxy-1,8-dioxo-1,8-dihydro-2H-pyrido[1,2-a]pyrazin-7-yl)cyclopentanecarboxamide (Example 274), N-[2-(3-chlorobenzyl)-9-hydroxy-1,8-dioxo-1,8-dihydro-2H-pyrido[1,2-a]pyrazin-7-yl]-2-(4-fluorophenyl)acetamide (Example 275), N-[2-(3-chlorobenzyl)-9-hydroxy-1,8-dioxo-1,8-dihydro-2H-pyrido[1,2-a]pyrazin-7-yl]-2,2-dimethylpropionamide (Example 276), N-[2-(3-chlorobenzyl)-9-hydroxy-1,8-dioxo-1,8-dihydro-2H-pyrido[1,2-a]pyrazin-7-yl]-2-phenylisobutyramide (Example 277), N-[2-(3-chlorobenzyl)-9-hydroxy-1,8-dioxo-1,8-dihydro-2H-pyrido[1,2-a]pyrazin-7-yl]-4-fluorobenzamide (Example 278), N-[2-(3-chlorobenzyl)-9-hydroxy-1,8-dioxo-1,8-dihydro-2H-pyrido[1,2-a]pyrazin-7-yl]pyridine-2-carboxamide trifluoroacetate (Example 279), 2-(3-chlorobenzyl)-9-hydroxy-7-isopropylamino-2H-pyrido [1,2-a]pyrazine-1,8-dione hydrochloride (Example 280), 2-(3-chlorobenzyl)-7-diethylamino-9-hydroxy-2H-pyrido [1,2-a]pyrazine-1,8-dione hydrochloride (Example 281), 2-(3-chlorobenzyl)-9-hydroxy-7-(pyridin-2-yl)-3,4-dihydro-2H-pyrido[1,2-a]pyrazine-1,8-dione hydrochloride (Example 282), 2-(3-chlorobenzyl)-9-hydroxy-7-isobutylamino-2H-pyrido [1,2-a]pyrazine-1,8-dione hydrochloride (Example 283), N-[2-(3-chlorobenzyl)-9-hydroxy-1,8-dioxo-1,8-dihydro-2H-pyrido[1,2-a] pyrazin-7-yl] -2-isopropyl-3-methylbutyramide (Example 284)

2-(3-chlorobenzyl)-7-ethylamino-9-hydroxy-2H-pyrido[1,2-a]pyrazine-1,8-dione hydrochloride (Example 285), N-[2-(3-chlorobenzyl)-9-hydroxy-1,8-dioxo-1,8-dihydro-2H-pyrido[1,2-a]pyrazin-7-yl]nicotinamide trifluoroacetate (Example 286)

N-[2-(3-chlorobenzyl)-9-hydroxy-1,8-dioxo-1,8-dihydro-2H-pyrido[1,2-a]pyrazin-7-yl]isonicotinamide trifluoroacetate (Example 287), N-[2-(3-chlorobenzyl)-9-hydroxy-1,8-dioxo-1,8-dihydro-2H-pyrido[1,2-a]pyrazin-7-yl]furan-2-carboxamide (Example 288), N-[2-(3-chlorobenzyl)-9-hydroxy-1,8-dioxo-1,8-dihydro-2H-pyrido[1,2-a]pyrazin-7-yl]thiophene-2-carboxamide (Example 289), 2-(3-chlorobenzyl)-9-hydroxy-7-(pyridazin-3-yl)-3,4-dihydro-2H-pyrido[1,2-a]pyrazine-1,8-dione hydrochloride (Example 290), 2-(3,4-difluorobenzyl)-9-hydroxy-7-(thiazol-2-yl)-3,4-dihydro-2H-pyrido[1,2-a]pyrazine-1,8-dione (Example 291), 2-(3-chloro-2-fluorobenzyl)-9-hydroxy-7-(thiazol-2-yl)-3,4-dihydro-2H-pyrido[1,2-a]pyrazine-1,8-dione (Example 292), 2-(4-chlorobenzyl)-9-hydroxy-7-(thiazol-2-yl)-3,4-dihydro-2H-pyrido[1,2-a]pyrazine-1,8-dione (Example 293), 2-(4-chloro-3-fluorobenzyl)-9-hydroxy-7-(thiazol-2-yl)-3,4-dihydro-2H-pyrido[1,2-a]pyrazine-1,8-dione (Example 294), 2-(4-chloro-2-methoxybenzyl)-9-hydroxy-7-(thiazol-2-yl)-3,4-dihydro-2H-pyrido[1,2-a]pyrazine-1,8-dione (Example 295), N-[2-(3-chlorobenzyl)-9-hydroxy-1,8-dioxo-1,8-dihydro-2H-pyrido[1,2-a]pyrazin-7-yl]-1-methyl-1H-pyrrole-2-carboxamide (Example 296), 2-[3-(4-chlorophenyl)propyl]-9-hydroxy-7-(thiazol-2-yl)-3,4-dihydro-2H-pyrido[1,2-a]pyrazine-1,8-dione hydrochloride (Example 297)

2-[3-(2-chlorophenyl)propyl]-9-hydroxy-7-(thiazol-2-yl)-3,4-dihydro-2H-pyrido[1,2-a]pyrazine-1,8-dione hydrochloride (Example 298), 2-[3-(3-chlorophenyl)propyl]-9-hydroxy-7-(thiazol-2-yl)-3,4-dihydro-2H-pyrido[1,2-a]pyrazine-1,8-dione hydrochloride (Example 299), 2-(3-chlorobenzyl)-9-hydroxy-7-(3-methyl-1,2,4-thiadiazol-5-yl)-3,4-dihydro-2H-pyrido[1,2-a]pyrazine-1,8-dione hydrochloride (Example 300), 5-fluoro-2-[9-hydroxy-1,8-dioxo-7-(thiazol-2-yl)-1,3,4,8-tetrahydro-pyrido[1,2-a]pyrazin-2-ylmethyl]-N-methylbenzamide (Example 301), N-[2-(3-chlorobenzyl)-9-hydroxy-1,8-dioxo-1,8-dihydro-2H-pyrido[1,2-a]pyrazin-7-yl]-N-isobutylacetamide (Example 302), N-[2-(4-fluorobenzyl)-9-hydroxy-1,8-dioxo-1,8-dihydro-2H-pyrido[1,2-a]pyrazin-7-yl]acetamide (Example 303), N-[2-(4-fluorobenzyl)-9-hydroxy-1,8-dioxo-1,8-dihydro-2H-pyrido[1,2-a]pyrazin-7-yl]benzamide (Example 304), N-[2-(4-fluorobenzyl)-9-hydroxy-1,8-dioxo-1,8-dihydro-2H-pyrido[1,2-a]pyrazin-7-yl]methanesulfonamide (Example 305), 2-(4-fluorobenzyl)-9-hydroxy-7-(pyridin-2-yl)-2H-pyrido [1,2-a]pyrazine-1,8-dione trifluoroacetate (Example 306), 2-(2-fluorobenzyl)-9-hydroxy-7-(thiazol-2-yl)-3,4-dihydro-2H-pyrido[1,2-a]pyrazine-1,8-dione (Example 307), 2-(3-fluorobenzyl)-9-hydroxy-7-(thiazol-2-yl)-3,4-dihydro-2H-pyrido[1,2-a]pyrazine-1,8-dione (Example 308), 2-(4-fluorobenzyl)-9-hydroxy-7-(thiazol-2-yl)-3,4-dihydro-2H-pyrido[1,2-a]pyrazine-1,8-dione (Example 309), 2-(2-chlorobenzyl)-9-hydroxy-7-(thiazol-2-yl)-3,4-dihydro-2H-pyrido[1,2-a]pyrazine-1,8-dione (Example 310), 9-hydroxy-2-(naphthalen-2-ylmethyl)-7-(thiazol-2-yl)-3,4-dihydro-2H-pyrido[1,2-a]pyrazine-1,8-dione (Example 311), 2-[3-(3-chloro-2-fluorophenyl)propyl]-9-hydroxy-7-(thiazol-2-yl)-3,4-dihydro-2H-pyrido[1,2-a]pyrazine-1,8-dione (Example 312), 2-[3-(4-chloro-3-fluorophenyl)propyl]-9-hydroxy-7-(thiazol-2-yl)-3,4-dihydro-2H-pyrido[1,2-a]pyrazine-1,8-dione (Example 313), 2-[3-(4-fluorophenyl)propyl]-9-hydroxy-7-(thiazol-2-yl)-3,4-dihydro-2H-pyrido[1,2-a]pyrazine-1,8-dione (Example 314), 2-[3-(3-fluorophenyl)propyl]-9-hydroxy-7-(thiazol-2-yl)-3,4-dihydro-2H-pyrido[1,2-a]pyrazine-1,8-dione (Example 315), 9-hydroxy-2-(3-phenylpropyl)-7-(thiazol-2-yl)-3,4-dihydro-2H-pyrido[1,2-a]pyrazine-1,8-dione hydrochloride (Example 316), 2-(3-chloro-2-fluorobenzyl)-9-hydroxy-7-(pyridin-2-yl)-3,4-dihydro-2H-pyrido[1,2-a]pyrazine-1,8-dione hydrochloride (Example 317)

N-[2-(4-fluorobenzyl)-9-hydroxy-1,8-dioxo-1,8-dihydro-2H-pyrido[1,2-a]pyrazin-7-yl]-2-methoxyacetamide (Example 318), N-[2-(4-fluorobenzyl)-9-hydroxy-1,8-dioxo-1,8-dihydro-2H-pyrido[1,2-a]pyrazin-7-yl]-2-propanesulfonamide (Example 319), N-[2-(4-fluorobenzyl)-9-hydroxy-1,8-dioxo-1,8-dihydro-2H-pyrido[1,2-a]pyrazin-7-yl]nicotinamide trifluoroacetate (Example 320), N-[2-(4-fluorobenzyl)-9-hydroxy-1,8-dioxo-1,8-dihydro-2H-pyrido[1,2-a]pyrazin-7-yl]isobutyramide (Example 321), N-(2-methoxyethyl)-2-(4-fluorobenzyl)-9-hydroxy-1,8-dioxo-1,8-dihydro-2H-pyrido[1,2-a]pyrazine-7-carboxamide (Example 322), N-ethyl-2-(4-fluorobenzyl)-9-hydroxy-1,8-dioxo-1,8-dihydro-2H-pyrido[1,2-a]pyrazine-7-carboxamide (Example 323), N-{2-[3-(2-chloro-6-fluorophenyl)propyl]-9-hydroxy-1,8-dioxo-1,8-dihydro-2H-pyrido[1,2-a]pyrazin-7-yl]acetamide (Example 324), N-[2-(3-chloro-2-fluorobenzyl)-9-hydroxy-1,8-dioxo-1,8-dihydro-2H-pyrido[1,2-a]pyrazin-7-yl]acetamide hydrochloride (Example 325), methyl 5-fluoro-2-[9-hydroxy-1,8-dioxo-7-(thiazol-2-yl)-1,3,4,8-tetrahydro-pyrido[1,2-a]pyrazin-2-ylmethyl]benzoate (Example 326), 2-(3-chloro-4-fluorobenzyl)-9-hydroxy-7-(pyridin-2-yl)-3,4-dihydro-2H-pyrido[1,2-a]pyrazine-1,8-dione hydrochloride (Example 327), 2-(3-chloro-2-fluorobenzyl)-9-hydroxy-7-(pyridin-3-yl)-3,4-dihydro-2H-pyrido[1,2-a]pyrazine-1,8-dione hydrochloride (Example 328), 2-[3-(2-chloro-6-fluorophenyl)propyl]-9-hydroxy-7-(pyridin-2-yl)-3,4-dihydro-2H-pyrido[1,2-a]pyrazine-1,8-dione hydrochloride (Example 329), 2-(benzofuran-2-ylmethyl)-9-hydroxy-7-(thiazol-2-yl)-3,4-dihydro-2H-pyrido[1,2-a]pyrazine-1,8-dione (Example 330), N-(1,2-diphenylethyl)-2-(3-chlorobenzyl)-9-hydroxy-1,8-dioxo-1,3,4,8-tetrahydro-2H-pyrido[1,2-a]pyrazine-7-carboxamide (Example 331)

N-[2-(3-chloro-2-fluorobenzyl)-9-hydroxy-1,8-dioxo-1,3,4,8-tetrahydro-2H-pyrido[1,2-a]pyrazin-7-yl]acetamide (Example 332), 2-[3-(2-fluorophenyl)propyl)-9-hydroxy-7-(thiazol-2-yl)-3,4-dihydro-2H-pyrido[1,2-a]pyrazine-1,8-dione (Example 333), N-(1,3-diphenylpropyl)-2-(3-chlorobenzyl)-9-hydroxy-1,8-dioxo-1,3,4,8-tetrahydro-2H-pyrido[1,2-a]pyrazine-7-carboxamide (Example 334), 5-fluoro-2-{3-[9-hydroxy-1,8-dioxo-7-(thiazol-2-yl)-1,3,4,8-tetrahydro-pyrido[1,2-a]pyrazin-2-yl]propyl)-N-methylbenzamide (Example 335), 2-[3-(2-chloro-6-fluorophenyl)propyl]-7-(2,2-dimethylpropionyl)-9-hydroxy-3,4-dihydro-2H-pyrido[1,2-a]pyrazine-1,8-dione (Example 336), 2-(3-chlorobenzyl)-9-hydroxy-7-isobutyryl-3,4-dihydro-2H-pyrido[1,2-a]pyrazine-1,8-dione (Example 337), 9-hydroxy-2-(4-phenylbutyl)-7-(thiazol-2-yl)-3,4-dihydro-2H-pyrido[1,2-a]pyrazine-1,8-dione hydrochloride (Example 338), 9-hydroxy-2-pentyl-7-(thiazol-2-yl)-3,4-dihydro-2H-pyrido[1,2-a]pyrazine-1,8-dione hydrochloride (Example 339), 2-(3-chloro-2-fluorobenzyl)-9-hydroxy-7-(pyridin-4-yl)-3,4-dihydro-2H-pyrido[1,2-a]pyrazine-1,8-dione hydrochloride (Example 340), 2-(4-fluorobenzyl)-9-hydroxy-7-(pyridin-4-yl)-2H-pyrido[1,2-a]pyrazine-1,8-dione hydrochloride (Example 341), 2-(3-chloro-2-fluorobenzyl)-9-hydroxy-7-(pyrimidin-4-yl)-2H-pyrido[1,2-a]pyrazine-1,8-dione trifluoroacetate. (Example 342), 2-(3-chloro-4-fluorobenzyl)-9-hydroxy-7-(2-methyl-2H-1,2,4-triazol-3-yl)-3,4-dihydro-2H-pyrido[1,2-a]pyrazine-1,8-dione (Example 343), 7-acetyl-2-(4-fluorobenzyl)-9-hydroxy-2H-pyrido [1,2-a]pyrazine-1,8-dione (Example 344), 2-(4-fluorobenzyl)-9-hydroxy-7-isobutyryl-2H-pyrido[1,2-a]pyrazine-1,8-dione hydrochloride (Example 345), N-[2-(3-chlorobenzyl)-9-hydroxy-1,8-dioxo-1,3,4,8-tetrahydro-2H-pyrido[1,2-a]pyrazin-7-yl]isonicotinamide hydrochloride (Example 346)

2-(4-fluorobenzyl)-9-hydroxy-7-(pyrimidin-4-yl)-2H-pyrido[1,2-a]pyrazine-1,8-dione (Example 347), 2-(3-chloro-4-fluorobenzyl)-9-hydroxy-7-(pyrazin-2-yl)-3,4-dihydro-2H-pyrido[1,2-a]pyrazine-1,8-dione (Example 348), N-[2-(3-chloro-4-fluorobenzyl)-9-hydroxy-1,8-dioxo-1,3,4,8-tetrahydro-2H-pyrido[1,2-a]pyrazin-7-yl]isobutyramide (Example 349), 2-(4-chloro-2-hydroxybenzyl)-9-hydroxy-7-(thiazol-2-yl)-3,4-dihydro-2H-pyrido[1,2-a]pyrazine-1,8-dione hydrochloride (Example 350), 9-hydroxy-2-(3-phenylbutyl)-7-(thiazol-2-yl)-3,4-dihydro-2H-pyrido[1,2-a]pyrazine-1,8-dione hydrochloride (Example 351), N-[2-(3-chloro-2-fluorobenzyl)-9-hydroxy-1,8-dioxo-1,3,4,8-tetrahydro-2H-pyrido[1,2-a]pyrazin-7-yl)nicotinamide hydrochloride (Example 352), N-[2-(3-chloro-4-fluorobenzyl)-9-hydroxy-1,8-dioxo-1,3,4,8-tetrahydro-2H-pyrido[1,2-a]pyrazin-7-yl]methanesulfonamide (Example 353), 2-(3-chloro-4-propoxybenzyl)-9-hydroxy-7-(thiazol-2-yl)-3,4-dihydro-2H-pyrido[1,2-a]pyrazine-1,8-dione hydrochloride (Example 354), 2-(3-chloro-4-isopropoxybenzyl)-9-hydroxy-7-(thiazol-2-yl)-3,4-dihydro-2H-pyrido[1,2-a]pyrazine-1,8-dione hydrochloride (Example 355), 2-(4-benzyloxy-3-chlorobenzyl)-9-hydroxy-7-(thiazol-2-yl)-3,4-dihydro-2H-pyrido[1,2-a]pyrazine-1,8-dione hydrochloride (Example 356), 2-(4-chloro-2-propoxybenzyl)-9-hydroxy-7-(thiazol-2-yl)-3,4-dihydro-2H-pyrido[1,2-a]pyrazine-1,8-dione hydrochloride (Example 357), 2-(4-chloro-2-isopropoxybenzyl)-9-hydroxy-7-(thiazol-2-yl)-3,4-dihydro-2H-pyrido[1,2-a]pyrazine-1,8-dione hydrochloride (Example 358), 2-(2-benzyloxy-4-chlorobenzyl)-9-hydroxy-7-(thiazol-2-yl)-3,4-dihydro-2H-pyrido[1,2-a]pyrazine-1,8-dione hydrochloride (Example 359), 2-(4-fluorobenzyl)-9-hydroxy-7-(2-methyl-2H-1,2,4-triazol-3-yl)-2H-pyrido[1,2-a]pyrazine-1,8-dione hydrochloride (Example 360), N-methyl-2-(3-chloro-2-fluorobenzyl)-9-hydroxy-1,8-dioxo-1,3,4,8-tetrahydro-2H-pyrido[1,2-a]pyrazine-7-carboxamide (Example 361), 2-(3-chlorobenzyl)-7-(2,2-dimethylbutyryl)-9-hydroxy-3,4-dihydro-2H-pyrido[1,2-a]pyrazine-1,8-dione (Example 362), 2-(4-fluorobenzyl)-9-hydroxy-7-(pyridin-2-yl)-3,4-dihydro-2H-pyrido[1,2-a]pyrazine-1,8-dione hydrochloride (Example 363), 2-(3-chloro-2-fluorobenzyl)-9-hydroxy-7-(pyridin-2-yl)-2H-pyrido[1,2-a]pyrazine-1,8-dione hydrochloride (Example 364), 2-(3-fluorobenzyl)-9-hydroxy-7-(pyridin-2-yl)-2H-pyrido[1,2-a]pyrazine-1,8-dione hydrochloride (Example 365), N-{5-fluoro-2-[9-hydroxy-1,8-dioxo-7-(thiazol-2-yl)-1,3,4,8-tetrahydro-pyrido[1,2-a]pyrazin-2-ylmethyl]phenyl}acetamide hydrochloride (Example 366), 2-(3-chloro-2-fluorobenzyl)-7-(2,2-dimethylpropionyl)-9-hydroxy-3,4-dihydro-2H-pyrido[1,2-a]pyrazine-1,8-dione hydrochloride (Example 367), 5-fluoro-2-[9-hydroxy-1,8-dioxo-7-(thiazol-2-yl)-1,3,4,8-tetrahydro-pyrido[1,2-a]pyrazin-2-ylmethyl]benzoic acid hydrochloride (Example 368), 2-(3,4-difluorobenzyl)-9-hydroxy-7-(pyridin-2-yl)-2H-pyrido[1,2-a]pyrazine-1,8-dione hydrochloride (Example 369), N-benzyl-N-methyl-2-(3-chlorobenzyl)-9-hydroxy-1,8-dioxo-1,3,4,8-tetrahydro-2H-pyrido[1,2-a]pyrazine-7-carboxamide hydrochloride (Example 370), N-(pyridin-3-ylmethyl)-2-(3-chlorobenzyl)-9-hydroxy-1,8-dioxo-1,3,4,8-tetrahydro-2H-pyrido[1,2-a]pyrazine-7-carboxamide hydrochloride (Example 371), N-(pyridin-2-ylmethyl)-2-(3-chlorobenzyl)-9-hydroxy-1,8-dioxo-1,3,4,8-tetrahydro-2H-pyrido[1,2-a]pyrazine-7-carboxamide hydrochloride (Example 372), 2-(3,4-dichlorobenzyl)-9-hydroxy-7-(pyridin-2-yl)-3,4-dihydro-2H-pyrido[1,2-a]pyrazine-1,8-dione trifluoroacetate (Example 373), N-(2-oxopropyl)-2-(3-chlorobenzyl)-9-hydroxy-1,8-dioxo-1,3,4,8-tetrahydro-2H-pyrido[1,2-a]pyrazine-7-carboxamide hydrochloride (Example 374), 2-(3-fluorobenzyl)-9-hydroxy-7-(pyridin-4-yl)-2H-pyrido[1,2-a]pyrazine-1,8-dione hydrochloride (Example 375), 7-(2,2-dimethylpropionyl)-2-(3-fluorobenzyl)-9-hydroxy-2H-pyrido[1,2-a]pyrazine-1,8-dione hydrochloride (Example 376), N-(2-fluorobenzyl)-2-(4-fluorobenzyl)-9-hydroxy-1,8-dioxo-1,3,4,8-tetrahydro-2H-pyrido[1,2-a]pyrazine-7-carboxamide (Example 377), N-(4-fluorobenzyl)-2-(4-fluorobenzyl)-9-hydroxy-1,8-dioxo-1,3,4,8-tetrahydro-2H-pyrido[1,2-a]pyrazine-7-carboxamide (Example 378), N-methyl-2-(4-fluorobenzyl)-9-hydroxy-1,8-dioxo-1,3,4,8-tetrahydro-2H-pyrido1,2-a]pyrazine-7-carboxamide (Example 379), N-benzyl-2-(4-fluorobenzyl)-9-hydroxy-1,8-dioxo-1,3,4,8-tetrahydro-2H-pyrido[1,2-a]pyrazine-7-carboxamide (Example 380), N-methyl-2-(4-chlorobenzyl)-9-hydroxy-1,8-dioxo-1,3,4,8-tetrahydro-2H-pyrido[1,2-a]pyrazine-7-carboxamide (Example 381), 7-(2,2-dimethylbutyryl)-2-(4-fluorobenzyl)-9-hydroxy-2H-pyrido[1,2-a]pyrazine-1,8-dione hydrochloride (Example 382), 2-(3,4-dichlorobenzyl)-9-hydroxy-7-(pyrazin-2-yl)-3,4-dihydro-2H-pyrido[1,2-a]pyrazine-1,8-dione hydrochloride (Example 383), 2-(3,4-dichlorobenzyl)-9-hydroxy-7-isobutyryl-3,4-dihydro-2H-pyrido[1,2-a]pyrazine-1,8-dione (Example 384), 2-(4-fluorobenzyl)-9-hydroxy-7-isobutyryl-3,4-dihydro-2H-pyrido[1,2-a]pyrazine-1,8-dione (Example 385), 7-(2,2-dimethylpropionyl)-2-(4-fluorobenzyl)-9-hydroxy-3,4-dihydro-2H-pyrido[1,2-a]pyrazine-1,8-dione (Example 386), 2-(4-fluorobenzyl)-9-hydroxy-7-(3-methylbutyryl)-2H-pyrido[1,2-a]pyrazine-1,8-dione hydrochloride (Example 387), N-methyl-2-(3,4-difluorobenzyl)-9-hydroxy-1,8-dioxo-1,3,4,8-tetrahydro-2H-pyrido[1,2-a]pyrazine-7-carboxamide (Example 388), 2-(4-fluorobenzyl)-9-hydroxy-7-(3-methoxy-2,2-dimethylpropionyl)-3,4-dihydro-2H-pyrido[1,2-a]pyrazine-1,8-dione (Example 389), 9-benzyloxy-7-bromo-2-(3-chlorobenzyl)-3,4-dihydro-2H-pyrido[1,2-a]pyrazine-1,8-dione (Example 390), 2-(3-chlorobenzyl)-9-hydroxy-7-(pyrimidin-4-yl)-2H-pyrido[1,2-a]pyrazine-1,8-dione hydrochloride (Example 391), 2-(4-fluorobenzyl)-9-hydroxy-7-(pyrimidin-4-yl)-3,4-dihydro-2H-pyrido[1,2-a]pyrazine-1,8-dione hydrochloride (Example 392), 2-(4-chlorobenzyl)-9-hydroxy-7-(pyrimidin-4-yl)-3,4-dihydro-2H-pyrido[1,2-a]pyrazine-1,8-dione hydrochloride (Example 393), 2-(3-chloro-4-fluorobenzyl)-9-hydroxy-7-(pyrimidin-4-yl)-3,4-dihydro-2H-pyrido[1,2-a]pyrazine-1,8-dione hydrochloride (Example 394)

2-(3-chloro-4-fluorobenzyl)-9-hydroxy-7-(pyrimidin-4-yl)-2H-pyrido[1,2-a]pyrazine-1,8-dione hydrochloride (Example 395), 2-(3-chloro-5-propoxybenzyl)-9-hydroxy-7-(thiazol-2-yl)-3,4-dihydro-2H-pyrido[1,2-a]pyrazine-1,8-dione hydrochloride (Example 396), 2-(3-chloro-5-isopropoxybenzyl)-9-hydroxy-7-(thiazol-2-yl)-3,4-dihydro-2H-pyrido[1,2-a]pyrazine-1,8-dione hydrochloride (Example 397), 2-(3-benzyloxy-5-chlorobenzyl)-9-hydroxy-7-(thiazol-2-yl)-3,4-dihydro-2H-pyrido[1,2-a]pyrazine-1,8-dione hydrochloride (Example 398), 2-(4-chlorobenzyl)-9-hydroxy-7-(pyrimidin-4-yl)-2H-pyrido[1,2-a]pyrazine-1,8-dione hydrochloride (Example 399), N-[2-(3-chlorobenzyl)-9-hydroxy-1,8-dioxo-1,8-dihydro-2H-pyrido[1,2-a]pyrazin-7-yl]-2-(pyridin-3-yl)acetamide hydrochloride (Example 400), N-[2-(3-chlorobenzyl)-9-hydroxy-1,8-dioxo-1,8-dihydro-2H-pyrido[1,2-a]pyrazin-7-yl]-2-(pyridin-4-yl)acetamide hydrochloride (Example 401), N-[2-(3-chlorobenzyl)-9-hydroxy-1,8-dioxo-1,8-dihydro-2H-pyrido[1,2-a]pyrazin-7-yl]-2-(pyridin-2-yl)acetamide hydrochloride (Example 402), 2-(3-fluorobenzyl)-9-hydroxy-7-(pyrimidin-4-yl)-2H-pyrido[1,2-a]pyrazine-1,8-dione hydrochloride (Example 403), 2-(3-fluorobenzyl)-9-hydroxy-7-(pyrazin-2-yl)-2H-pyrido[1,2-a]pyrazine-1,8-dione hydrochloride (Example 404), 2-(3-chloro-4-fluorobenzyl)-9-hydroxy-7-(2-methyl-2H-1,2,4-triazol-3-yl)-2H-pyrido[1,2-a]pyrazine-1,8-dione hydrochloride (Example 405), N-[2-(3-chloro-4-fluorobenzyl)-9-hydroxy-1,8-dioxo-1,3,4,8-tetrahydro-2H-pyrido[1,2-a]pyrazin-7-yl]-3,3-dimethylbutyramide (Example 406), 2-(3-fluorobenzyl)-9-hydroxy-4-methyl-7-(pyridin-2-yl)-2H-pyrido[1,2-a]pyrazine-1,8-dione hydrochloride (Example 407), 7-(2,2-dimethylpropionyl)-2-(4-fluorobenzyl)-9-hydroxy-4-methyl-2H-pyrido[1,2-a]pyrazine-1,8-dione hydrochloride (Example 408), 7-(2,2-dimethylpropionyl)-2-(4-fluorobenzyl)-9-hydroxy-6-methoxymethyl-3,4-dihydro-2H-pyrido[1,2-a]pyrazine-1,8-dione hydrochloride (Example 409), N-(pyridin-2-ylmethyl)-2-(4-fluorobenzyl)-9-hydroxy-1,8-dioxo-1,3,4,8-tetrahydro-2H-pyrido[1,2-a]pyrazine-7-carboxamide hydrochloride (Example 410), N-(furan-2-ylmethyl)-2-(4-fluorobenzyl)-9-hydroxy-1,8-dioxo-1,3,4,8-tetrahydro-2H-pyrido[1,2-a]pyrazine-7-carboxamide hydrochloride (Example 411), 7-(2,2-dimethylpropionyl)-2-(4-fluorobenzyl)-9-hydroxy-4,4-dimethyl-3,4-dihydro-2H-pyrido[1,2-a]pyrazine-1,8-dione hydrochloride (Example 412), 7-bromo-2-(4-fluorobenzyl)-9-hydroxy-4,4-dimethyl-3,4-dihydro-2H-pyrido[1,2-a]pyrazine-1,8-dione hydrochloride (Example 413), 2-(4-fluorobenzyl)-9-hydroxy-4,47dimethyl-7-(pyridin-2-yl)-3,4-dihydro-2H-pyrido[1,2-a]pyrazine-1,8-dione hydrochloride (Example 414), N-(4-dimethylaminobenzyl)-2-(4-fluorobenzyl)-9-hydroxy.-1,8-dioxo-1,3,4,8-tetrahydro-2H-pyrido[1,2-a]pyrazine-7-carboxamide hydrochloride (Example 415), 2-(3-chlorobenzyl)-9-hydroxy-7-(pyrazin-2-yl)-3,4-dihydro-2H-pyrido[1,2-a]pyrazine-1,8-dione hydrochloride (Example 416), 2-(4-fluorobenzyl)-9-hydroxy-7-(pyrazin-2-yl)-3,4-dihydro-2H-pyrido[1,2-a]pyrazine-1,8-dione hydrochloride (Example 417), N-[2-(3-chloro-4-fluorobenzyl)-9-hydroxy-1,8-dioxo-1,3,4,8-tetrahydro-2H-pyrido[1,2-a]pyrazin-7-yl]benzenesulfonamide (Example 418), N-[2-(3-chloro-4-fluorobenzyl)-9-hydroxy-1,8-dioxo-1,3,4,8-tetrahydro-2H-pyrido[1,2-a]pyrazin-7-yl]benzylsulfonamide (Example 419), N-[2-(3-chloro-4-fluorobenzyl)-9-hydroxy-1,8-dioxo-1,3,4,8-tetrahydro-2H-pyrido[1,2-a]pyrazin-7-yl]-2-thiophenesulfonamide (Example 420), N-(4-methanesulfonylbenzyl)-2-(4-fluorobenzyl)-9-hydroxy-1,8-dioxo-1,3,4,8-tetrahydro-2H-pyrido[1,2-a]pyrazine-7-carboxamide hydrochloride (Example 421), 2-(4-fluorobenzyl)-9-hydroxy-6-(2-hydroxy-3,3-dimethylbutyl)-3,4-dihydro-2H-pyrido[1,2-a]pyrazine-1,8-dione hydrochloride (Example 422), N-[2-(3-chlorobenzyl)-9-hydroxy-4-methyl-1,8-dioxo-1,8-dihydro-2H-pyrido[1,2-a]pyrazin-7-yl]acetamide (Example 423), 2-(4-fluorobenzyl)-9-hydroxy-6-methoxymethyl-7-(pyridin-2-yl)-3,4-dihydro-2H-pyrido[1,2-a]pyrazine-1,8-dione hydrochloride (Example 424), 2-(4-fluorobenzyl)-9-hydroxy-7-(3-methoxy-2,2-dimethylpropionyl)-2H-pyrido[1,2-a]pyrazine-1,8-dione hydrochloride (Example 425), N-(4-methoxypyrimidin-2-ylmethyl)-2-(4-fluorobenzyl)-9-hydroxy-1,8-dioxo-1,3,4,8-tetrahydro-2H-pyrido[1,2-a]pyrazine-7-carboxamide hydrochloride (Example 426), 6-(3,3-dimethyl-2-oxobutyl)-7-(2,2-dimethylpropionyl)-2-(4-fluorobenzyl)-9-hydroxy-3,4-dihydro-2H-pyrido [1,2-a]pyrazine-1,8-dione hydrochloride (Example 427), N-(4-acetylaminobenzyl)-2-(4-fluorobenzyl)-9-hydroxy-1,8-dioxo-1,3,4,8-tetrahydro-2H-pyrido[1,2-a]pyrazine-7-carboxamide (Example 428), 2-(3,4-dichlorobenzyl)-9-hydroxy-4-(2-hydroxyethyl)-2H-pyrido[1,2-a]pyrazine-1,8-dione hydrochloride (Example 429), 2-(3,4-dichlorobenzyl)-9-hydroxy-4-(1-hydroxypropyl)-2H-pyrido[1,2-a]pyrazine-1,8-dione (Example 430), 2-(3,4-dichlorobenzyl)-9-hydroxy-4-(3-hydroxypropyl)-2H-pyrido[1,2-a]pyrazine-1,8-dione (Example 431), 2-(3,4-dichlorobenzyl)-9-hydroxy-4-(1-hydroxy-2-methylpropyl)-2H-pyrido[1,2-a]pyrazine-1,8-dione (Example 432), 2-(3,4-dichlorobenzyl)-9-hydroxy-4-phenethyl-2H-pyrido [1,2-a]pyrazine-1,8-dione (Example 433), 2-(4-fluorobenzyl)-9-hydroxy-2H-pyrazino[1,2-c]pyrimidine-1,8-dione hydrochloride (Example 434), 2-(3,4-dichlorobenzyl)-9-hydroxy-4-isopropyl-2H-pyrido [1,2-a]pyrazine-1,8-dione hydrochloride (Example 435), 2-(3-chlorobenzyl)-9-hydroxy-4-methyl-2H-pyrido[1,2-d] [1,2,4]triazine-1,8-dione (Example 436), 2-(3-chlorobenzyl)-7-(2,2-dimethylpropionyl)-9-hydroxy-3,4-dihydro-2H-pyrido[1,2-a]pyrazine-1,8-dione (Example 437), 7-(2,2-dimethylpropionyl)-2-(4-fluorobenzyl)-9-hydroxy-2H-pyrido[1,2-a]pyrazine-1,8-dione (Example 438), 7-(2,2-dimethylpropionyl)-2-(4-fluorobenzyl)-9-hydroxy-2H-pyrido[1,2-a]pyrazine-1,8-dione sodium salt (Example 439), N-[2-(3-chlorobenzyl)-9-hydroxy-1,8-dioxo-1,8-dihydro-2H-pyrido[1,2-a]pyrazin-7-yl]acetamide sodium salt (Example 440), and 2-(3-chlorobenzyl)-7-(2,2-dimethylpropionyl)-9-hydroxy-3,4-dihydro-2H-pyrido[1,2-a]pyrazine-1,8-dione sodium salt (Example 441), or a pharmaceutically acceptable salt thereof.

[26] A pharmaceutical composition comprising a nitrogen-containing fused ring compound of any of [1] to [25], or a pharmaceutically acceptable salt thereof, and a pharmaceutically acceptable carrier.

[27] An anti-HIV agent comprising a nitrogen-containing fused ring compound of any of [1] to [25] or a pharmaceutically acceptable salt thereof as an active ingredient.

[28] An integrase inhibitor comprising a nitrogen-containing fused ring compound of any of [1] to [25] or a pharmaceutically acceptable salt thereof as an active ingredient.

[29] An antivirus agent comprising a nitrogen-containing fused ring compound of any of [1] to [25] or a pharmaceutically acceptable salt thereof as an active ingredient.

[30] An anti-HIV composition comprising a nitrogen-containing fused ring compound of any of [1] to [25] or a pharmaceutically acceptable salt thereof and one or more other kinds of anti-HIV active substances as active ingredients.

[31] An anti-HIV agent comprising a nitrogen-containing fused ring compound of any of [1] to [25] or a pharmaceutically acceptable salt thereof as an active ingredient, which is used for a multiple drug therapy with other anti-HIV agents.

[32] Use of a nitrogen-containing fused ring compound of any of [1] to [25] or a pharmaceutically acceptable salt thereof for the production of an anti-HIV agent.

[33] Use of a nitrogen-containing fused ring compound of any of [1] to [25] or a pharmaceutically acceptable salt thereof for the production of an integrase inhibitor.

[34] Use of a nitrogen-containing fused ring compound of any of [1] to [25] or a pharmaceutically acceptable salt thereof for the production of an antivirus agent.

[35] A method for the prophylaxis or treatment of an HIV infectious disease, which comprises administering an effective amount of a nitrogen-containing fused ring compound of any of [1] to [25] or a pharmaceutically acceptable salt thereof to a mammal.

[36] The method of [35], further comprising administering an effective amount of at least one kind of other anti-HIV active substance to the mammal.

[37] A method of inhibiting integrase, which comprises administering an effective amount of a nitrogen-containing fused ring compound of any of [1] to [25] or a pharmaceutically acceptable salt thereof to a mammal.

[38] A method for the prophylaxis or treatment of a viral infectious disease, which comprises administering an effective amount of a nitrogen-containing fused ring compound of any of [1] to [25] or a pharmaceutically acceptable salt thereof to a mammal.

The compound of the present invention can be a pharmaceutical agent effective for the prophylaxis or treatment of AIDS, as an anti-HIV agent having an HIV integrase inhibitory activity. In addition, by a combined use with other anti-HIV agents such as protease inhibitors, reverse transcriptase inhibitors and the like, the compound can be a more effective anti-HIV agent. Moreover, since the compound has an integrase-specific high inhibitory activity, it can be a pharmaceutical agent safe on the human body, which is associated with a fewer side effects.

BEST MODE FOR EMBODYING THE INVENTION

The "bond" means a direct connection and in the case of N-Z-Ph, for example, when Z is a "bond", it means N-Ph.

The "halogen atom" is a fluorine atom, a chlorine atom, a bromine atom or an iodine atom, and is preferably a fluorine atom, a chlorine atom or a bromine atom.

For group A, it is more preferably a fluorine atom, for group B, it is more preferably a fluorine atom or a chlorine atom, and for group C, it is more preferably a bromine atom.

The "C1–6 alkyl group" is a linear or branched chain alkyl group having 1 to 6 carbon atoms, and preferably a linear or branched chain alkyl group having 1 to 4 carbon atoms. Specifically, methyl group, ethyl group, propyl group, isopropyl group, butyl group, isobutyl group, sec-butyl group, tert-butyl group, pentyl group, isopentyl group, tert-pentyl group, hexyl group and the like can be mentioned.

It is preferably a methyl group for $R^6$, $R^{b2}$, $R^{b3}$, $R^{b4}$, $R^{b5}$ or $R^{b6}$, preferably a methyl group, a propyl group or an isopropyl group for $R^{b1}$, and preferably a methyl group, an ethyl group or a tert-butyl group for group B.

The "C1–7 alkyl group" is a linear or branched chain alkyl group having 1 to 7 carbon atoms, and is preferably a linear or branched chain alkyl group having 1 to 4 carbon atoms. Specifically, methyl group, ethyl group, propyl group, isopropyl group, butyl group, isobutyl group, sec-butyl group, tert-butyl group, pentyl group, isopentyl group, tert-pentyl group, hexyl group, 1-isopropyl-2-methylpropyl group and the like can be mentioned.

The "C2–6 alkenyl group" is a linear or branched chain alkenyl group having 2 to 6 carbon atoms. Specifically, vinyl group, allyl group, 1-propenyl group, isopropenyl group, 2-methyl-1-propenyl group, 1-butenyl group, 2-butenyl group, 1,3-butadienyl group, 3-methyl-2-butenyl group, 4-methyl-2-pentenyl group, 4-methyl-3-pentenyl group, 1-methyl-2-butenyl group and the like can be mentioned.

The "C2–6 alkynyl group" is a linear or branched chain alkynyl group having 2 to 6 carbon atoms. Specifically, ethynyl group, 1-propynyl group, 2-propynyl group, 3-butynyl group and the like can be mentioned.

The "C1–6 alkylene" is a linear or branched chain alkylene. having 1 to 6 carbon atoms and methylene, ethylene, trimethylene, tetramethylene, pentamethylene, hexamethylene, propylene, $—CH(CH_3)—$, $C(CH_3)_2—$, $—CH(CH_3)—(CH_2)_2—$ and the like can be mentioned.

Preferably, it is methylene, ethylene, trimethylene or tetramethylene, and more preferably methylene.

The "C2–6 alkenylene" is a linear or branched chain alkenylene having 2 to 6 carbon atoms and vinylene, propenylene, 1-butenylene, 1,3-butadienylene, $—CH(CH_3)—CH{=}CH—$ and the like can be mentioned. Preferably, it is propenylene.

The "haloC1–6 alkyl group" is the above-defined "C1–6 alkyl group" substituted by the above-defined "halogen atom", and preferably it is a haloalkyl group wherein its alkyl moiety is a linear or branched chain alkyl group having 1 to 4 carbon atoms. Specifically, fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like can be mentioned. Preferably, it is trifluoromethyl group.

The "C1–6 alkyloxy group" is an alkyl-oxy group wherein its alkyl moiety is the above-defined "C1–6 alkyl group", and preferably an alkyl-oxy group wherein its alkyl moiety is a linear or branched chain alkyl group having 1 to 4 carbon atoms. Specifically, methoxy group, ethoxy group, propoxy group, isopropyloxy group, butoxy group, isobutyloxy group, tert-butyloxy group, pentyloxy group, hexyloxy group and the like can be mentioned.

The "C6–14 aryl group" is an aromatic hydrocarbon group having 6 to 14 carbon atoms. Specifically, phenyl group, naphthyl group, anthryl group, indenyl group, azulenyl group, fluorenyl group, phenanthryl group and the like can be mentioned, with preference given to phenyl group.

The "C6–14 aryloxy group" is an aryl-oxy group wherein its aryl moiety is the above-defined "C6–14 aryl group". Specifically, phenoxy group, naphthyloxy group, anthryloxy group, indenyloxy group, azulenyloxy group, fluorenyloxy group, phenanthryloxy group and the like can be mentioned, with preference given to phenoxy group.

The "C6–14 aryl C1–6 alkyl group" is an aryl-alkyl group wherein its alkyl moiety is the above-defined "C1–6 alkyl group" and its aryl moiety is the above-defined "C6–14 aryl group". Preferably, it is an aryl-alkyl group wherein its alkyl moiety is a linear or branched chain alkyl group having 1 to 4 carbon atoms and its aryl moiety is phenyl group. Specifically, benzyl group, phenethyl group, 3-phenylpropyl group, 2-phenylpropyl group, 4-phenylbutyl group and the like can be mentioned.

It is particularly preferably benzyl group for $R^2$.

The "C6–14 aryl C1–6 alkyloxy group" is an aryl-alkyloxy group wherein its C6–14 aryl C1–6 alkyl moiety is the above-defined "C6–14 aryl C1–6 alkyl group". Preferably, it is an aryl-alkyl-oxy group wherein its alkyl moiety is a linear or branched chain alkyl group having 1 to 4 carbon atoms and its aryl moiety is phenyl group. Specifically, benzyloxy group, phenethyloxy group, 3-phenylpropyloxy group, 2-phenylpropyloxy group, 4-phenylbutyloxy group and the like can be mentioned.

The "C6–14 aryl C1–6 alkyloxycarbonyl group" is an aryl-alkyl-oxy-carbonyl group wherein its C6–14 aryl C1–6 alkyl moiety is the above-defined "C6–14 aryl C1–6 alkyl group". Preferably, it is an aryl-alkyl-oxy-carbonyl group wherein its alkyl moiety is a linear or branched chain alkyl group having 1 to 4 carbon atoms and its aryl moiety is phenyl group. Specifically, benzyloxycarbonyl group, phenethyloxycarbonyl group, 3-phenylpropyloxycarbonyl group, 2-phenylpropyloxycarbonyl group, 4-phenylbutyloxycarbonyl group and the like can be mentioned.

It is preferably benzyloxycarbonyl group.

The "C6–14 arylcarbonyl group" is an aryl-carbonyl group wherein its aryl moiety is the above-defined "C6–14 aryl group". Specifically, benzoyl group, 1-naphthoyl group, 2-naphthoyl group, anthrylcarbonyl group, indenylcarbonyl group, azulenylcarbonyl group, fluorenylcarbonyl group, phenanthrylcarbonyl group and the like can be mentioned, with preference given to benzoyl group.

The "C3–10 carbon ring group" is a saturated or unsaturated cyclic hydrocarbon group having 3 to 10 carbon atoms and means aryl group, cycloalkyl group, cycloalkenyl group, or a fused ring thereof.

As the "aryl group", phenyl group, naphthyl group, pentalenyl group, azulenyl group and the like can be specifically mentioned. It is preferably phenyl group or naphthyl group, and more preferably phenyl group.

As the "cycloalkyl group", cyclopropyl group, cyclobutyl group, cyclopentyl group, cyclohexyl group, cycloheptyl group, cyclooctyl group, adamantyl group, norbornanyl group and the like can be specifically mentioned. It preferably includes cyclopentyl group, cyclohexyl group and cycloheptyl group, and particularly preferably includes cyclopentyl group and cyclohexyl group.

The "cycloalkenyl group" contains at least one, preferably 1 or 2, double bonds. Specifically, cyclopropenyl group, cyclobutenyl group, cyclopentenyl group, cyclopentadienyl group, cyclohexenyl group (2,4-cyclohexadien-1-yl group, 2,5-cyclohexadien-1-yl group etc.), cycloheptenyl group and cyclooctenyl group and the like can be mentioned.

As a fused ring of these "aryl group", "cycloalkyl group" and "cycloalkenyl group", indenyl group, indanyl group, 1,4-dihydronaphthyl group, 1,2,3,4-tetrahydronaphthyl group (1,2,3,4-tetrahydro-2-naphthyl group, 5,6,7,8-tetrahydro-2-napthyl group etc.), perhydronaphthyl group and the like can be specifically mentioned. Preferably, it is a fused ring of phenyl group and other ring, such as indenyl group, indanyl group, 1,4-dihydronaphthyl group, 1,2,3,4-tetrahydronaphthyl group and the like.

The "heteroaryl group" is a 5 or 6-membered heteroaryl group containing, as a ring-constituting atom, besides the carbon atom, at least one hetero atom selected from nitrogen atom, oxygen atom and sulfur atom.

Specifically, pyridyl group, pyrazinyl group, pyrimidinyl group, pyridazinyl group, 1,3,5-triazinyl group, pyrrolyl group, pyrazolyl group, imidazolyl group, triazolyl group (1,2,3-triazolyl group, 1,2,4-triazolyl group), tetrazolyl group, thienyl group, furyl group, oxazolyl group, isoxazolyl group, thiazolyl group, isothiazolyl group, oxadiazolyl group (1,2,4-oxadiazolyl group, 1,3,4-oxadiazolyl group, 1,2,5-oxadiazolyl group), thiadiazolyl group (1,2,4-thiadiazolyl group, 1,3,4-thiadiazolyl group, 1,2,5-thiadiazolyl group) and the like can be mentioned.

The "heterocyclic group" is a saturated or unsaturated (including partially unsaturated and completely unsaturated) monocyclic 5-membered or 6-membered heterocycle containing, besides carbon atom, at least 1, preferably 1 to 4, hetero atoms selected from nitrogen atom, oxygen atom and sulfur atom, or a fused ring of such heterocycles, or a fused ring of a carbon ring selected from benzene, cyclopentane and cyclohexane and the above-defined heterocycle.

As the "saturated monocyclic heterocyclic group", pyrrolidinyl group, tetrahydrofuryl group, tetrahydrothienyl group, imidazolidinyl group, pyrazolidinyl group, 1,3-dioxolanyl group, 1,3-oxathiolanyl group, oxazolidinyl group, thiazolidinyl group, piperidinyl group, piperazinyl group, tetrahydropyranyl group, tetrahydrothiopyranyl group, dioxanyl group, morpholinyl group, thiomorpholinyl group, 3-hydroxypyrrolidinyl group, 2-oxopyrrolidinyl group, 3-oxopyrrolidinyl group, 2-oxopiperidinyl group, 4-oxopiperidinyl group, 2,6-dioxopiperidinyl group and the like can be mentioned. Preferably, it is pyrrolidinyl group, piperidinyl group or morpholinyl group.

As the "unsaturated monocyclic heterocyclic group", pyrrolyl group, furyl group, thienyl group, imidazolyl group, 1,2-dihydro-2-oxoimidazolyl group, pyrazolyl group, oxazolyl group, isoxazolyl group, thiazolyl group, isothiazolyl group, 1,2,4-triazolyl group, 1,2,3-triazolyl group, tetrazolyl group, 1,3,4-oxadiazolyl group, 1,2,4-oxadiazolyl group, 1,3,4-thiadiazolyl group, 1,2,4-thiadiazolyl group, furazanyl group, pyridyl group, pyrimidinyl group, 3,4-dihydro-4-oxopyrimidinyl group, pyridazinyl group, pyrazinyl group, 1,3,5-triazinyl group, imidazolinyl group, pyrazolinyl group, oxazolinyl group (2-oxazolinyl group, 3-oxazolinyl group, 4-oxazolinyl group), isoxazolinyl group, thiazolinyl group, isothiazolinyl group, pyranyl group, 2-oxopyranyl group and the like can be mentioned. It is preferably imidazolyl group, pyrazolyl group, isoxazolyl group, thiazolyl group, 1,2,4-triazolyl group, tetrazolyl group, 1,3,4-oxadiazolyl group, pyridyl group, pyrimidinyl group, pyridazinyl group, pyrazinyl group or oxazolinyl group.

As the "fused heterocyclic group", indolyl group, isoindolyl group, 1,3-dihydro-1,3-dioxoisoindolyl group, benzimidazolyl group, indazolyl group, benzothiazolyl group, benzofuranyl group, isobenzofuranyl group, indolizinyl group, quinolyl group, isoquinolyl group, 1,2-dihydro-2-oxoquinolyl group, quinazolinyl group, quinoxalinyl group, cinnolinyl group, phthalazinyl group, quinolizinyl group, pyrinyl group, pteridinyl group, indolinyl group, isoindolinyl group, 5,6,7,8-tetrahydroquinolyl group, 1,2,3,4-tetrahydroquinolyl group, 2-oxo-1,2,3,4-tetrahydroquinolyl group, 1,3-benzodioxolyl group, 3,4-methylenedioxypyridyl group, 4,5-ethylenedioxypyrimidinyl group, chromenyl group, chromanyl group, isochromanyl group, 1,2,4-benzotriazinyl group and the like can be mentioned. Preferably, it is indolyl group, benzofuranyl group, quinolyl group, benzothiazolyl group, 1,2,3,4-tetrahydroquinolyl group, 1,3-benzodioxolyl group or 1,2,4-benzotriazinyl group.

The "heterocyclic group" that substitutes C1–7 alkyl group, C1–6 alkyl moiety, C2–6 alkenyl group and C2–6 alkynyl group of group C is preferably a 2-oxopyrrolidin-1-yl group.

The "C3–8 cycloalkyl group" is a cycloalkyl group having 3 to 8 carbon atoms, and is specifically cyclopropyl group, cyclobutyl group, cyclopentyl group, cyclohexyl group, cycloheptyl group or cyclooctyl group.

As $R^{c7}$ in group C, preferred is a cyclopentyl group.

The "C3–8 cycloalkyl C1–6 alkyl group" is a cycloalkyl-alkyl group wherein the above-defined "C1–6 alkyl group" is substituted by the above-defined "C3–8 cycloalkyl group". The C1–6 alkyl moiety is preferably a linear alkyl group having 1 to 4 carbon atoms, and as C3–8 cycloalkyl, preferred are cyclopropyl group, cyclobutyl group, cyclopentyl group and cyclohexyl group.

As the "C3–8 cycloalkyl C1–6 alkyl group", cyclopropylmethyl group, cyclobutylmethyl group, cyclopentylmethyl group, cyclohexylmethyl group, 2-cyclohexylethyl group, 3-cyclohexylpropyl group and the like can be specifically mentioned.

It is preferably a cyclohexylmethyl group for group C.

The "C1–6 alkylsulfonyl group" is an alkyl-sulfonyl group wherein its C1–6 alkyl moiety is the above-defined "C1–6 alkyl group", preferably a linear or branched chain alkyl group having 1 to 4 carbon atoms.

Specifically, methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group, isopentylsulfonyl group, tert-pentylsulfonyl group, hexylsulfonyl group and the like can be mentioned.

It is preferably a methylsulfonyl group for group A.

The "di(C1–6 alkyl)amino group" is a di(alkyl)-amino group wherein its C1–6 alkyl moiety is the above-defined "C1–6 alkyl group", preferably a linear or branched chain alkyl group having 1 to 4 carbon atoms.

Specifically, dimethylamino group, diethylamino group, dipropylamino group, diisopropylamino group, N-ethyl-N-methylamino group, N-isopropyl-N-methylamino group and the like can be mentioned.

It is preferably a dimethylamino group for group A.

The "C1–6 alkylcarbonylamino group" is an alkyl-carbonyl-amino group wherein its C1–6 alkyl moiety is the above-defined "C1–6 alkyl group", and preferably a linear or branched chain alkyl group having 1 to 4 carbon atoms.

Specifically, acetylamino group, propionylamino group, butyrylamino group, isobutyrylamino group, pivaloylamino group and the like can be mentioned.

It is preferably an acetylamino group for group A.

The "C1–6 alkylcarbonyloxy group optionally substituted by halogen atom(s)" is an alkyl-carbonyl-oxy group wherein its C1–6 alkyl moiety is the above-defined "C1–6 alkyl group", which is optionally substituted by the above-defined "halogen atom". It includes unsubstituted C1–6 alkylcarbonyloxy group, and is preferably one wherein its alkyl moiety is a linear or branched chain alkyl group having 1 to 4 carbon atoms. Here, the halogen atom is preferably a fluorine atom.

Specifically, acetyloxy group, propionyloxy group, butyryloxy group, isobutyryloxy group, pivaloyloxy group, fluoromethylcarbonyloxy group, trifluoromethylcarbonyloxy group, 2,2,2-trifluoroethylcarbonyloxy group can be mentioned.

It is preferably an acetyloxy group or a trifluoromethylcarbonyloxy group for group A.

The "C6–14 aryl group optionally substituted by 1 to 3 substituent(s) selected from the group consisting of halogen atom, C1–6 alkyl group, C1–6 alkylsulfonyl group, di(C1–6 alkyl)amino group and C1–6 alkylcarbonylamino group" is the above-defined "C6–14 aryl group", preferably a phenyl group, which is optionally substituted by 1 to 3 substituent(s) selected from the group consisting of the above-defined "halogen atom", the above-defined "C1–6 alkyl group", the above-defined "C1–6 alkylsulfonyl group", the above-defined "di(C1–6 alkyl)amino group" and the above-defined "C1–6 alkylcarbonylamino group", and includes unsubstituted aryl group.

As the "C6–14 aryl group optionally substituted by 1 to 3 substituent(s) selected from the group consisting of halogen atom, C1–6 alkyl group, C1–6 alkylsulfonyl group, di(C1–6 alkyl)amino group and C1–6 alkylcarbonylamino group", phenyl group, 2-fluorophenyl group, 3-fluorophenyl group, 4-fluorophenyl group, 4-chlorophenyl group, 4-bromophenyl group, 2,4-difluorophenyl group, 3,5-dichlorophenyl group, 4-methylphenyl group, 4-isopropylphenyl group, 4-tert-butylphenyl group, 4-dimethylaminophenyl group, 4-methylsulfonylphenyl group, 4-acetylaminophenyl group and the like can be specifically mentioned.

It is preferably phenyl group, 2-fluorophenyl group, 4-fluorophenyl group, 4-tert-butylphenyl group, 4-dimethylaminophenyl group, 4-methylsulfonylphenyl group or 4-acetylaminophenyl group for group A.

The "heterocyclic group optionally substituted by C1–6 alkyloxy group" is the above-defined "heterocyclic group", which is optionally substituted by the above-defined "C1–6 alkyloxy group", and includes unsubstituted heterocyclic group.

It is preferably a 5-membered or 6-membered monocyclic heterocyclic group.

As the "heterocyclic group optionally substituted by C1–6 alkyloxy group", pyrrolidinyl group, piperidinyl group, piperazinyl group, morpholinyl group, pyrrolyl group, furyl group, imidazolyl group, pyrazolyl group, 1,2,4-triazolyl group, tetrazolyl group, pyridyl group, pyrimidinyl group, pyrazinyl group, pyridazinyl group, 3-methoxypyridin-2-yl group, 6-methoxypyridin-2-yl group, 5-isopropyloxypyridin-3-yl group and 4-methoxypyrimidin-2-yl group and the like can be specifically mentioned.

It is preferably 2-pyridyl group, 3-pyridyl group, 2-furyl group, 6-methoxypyridin-2-yl group or 4-methoxypyrimidin-2-yl group for group A.

The "group A" is the following substituent group, in which $R^{a1}$, $R^{a2}$, $R^{a3}$ and $R^{a4}$ are each independently a hydrogen atom or the above-defined "C1–6 alkyl group":

the above-defined "halogen atom", cyano group,

—$OR^{a1}$ (e.g., hydroxyl group, methoxy group, ethoxy group, propoxy group, isopropyloxy group, butoxy group, isobutyloxy group, tert-butyloxy group etc.), —$SR^{a1}$ (e.g., mercapto group, methylsulfanyl group, ethylsulfanyl group, isopropylsulfanyl group etc.), —$CO_2R^{a1}$ (e.g., carboxyl group, methoxycarbonyl group, ethoxycarbonyl group, isopropyloxycarbonyl group, tert-butoxycarbonyl group etc.)

—$CONR^{a2}R^{a3}$ (e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group, N-isopropyl-N-methylcarbamoyl group etc.), —$COR^{a4}$ (e.g., formyl group, acetyl group, propionyl group, butyryl group, isobutyryl group, pivaloyl group etc.), —$SO_2NR^{a2}R^{a3}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group, N-isopropyl-N-methylsulfamoyl group etc.), —$SO_2R^{a4}$ (e.g., methylsulfonyl group, ethylsulfonyl group, isopropylsulfonyl group, tert-butylsulfonyl group etc.), the above-defined "C6–14 aryloxy group", the above-defined "C6–14 aryl C1–6 alkyloxycarbonyl group", the above-defined "C1–6 alkylcarbonyloxy group optionally substituted by halogen atom", the above-defined "C6–14 aryl group optionally substituted by 1 to 3 substituent(s) selected from the group consisting of halogen atom, C1–6 alkyl group, C1–6 alkylsulfonyl group, di(C1–6 alkyl)amino group and C1–6 alkylcarbonylamino group" and the above-defined "heterocyclic group optionally substituted by C1–6 alkyloxy group".

The "C1–6 alkyl group optionally substituted by 1 to 3 substituent(s) selected from group A" is the above-defined "C1–6 alkyl group", which is optionally substituted by 1 to 3 substituent(s) selected from the above-defined "group A", and includes unsubstituted alkyl group.

Specifically, methyl group, ethyl group, propyl group, isopropyl group, butyl group, isobutyl group, sec-butyl group, tert-butyl group, pentyl group, isopentyl group, tert-pentyl group, neopentyl group, 1-ethylpropyl group, hexyl group, trifluoromethyl group, cyanomethyl group, 2-cyanoethyl group, hydroxymethyl group, 1-hydroxyethyl group, 2-hydroxyethyl group, 3-hydroxypropyl group, 4-hydroxybutyl group, 1-hydroxy-1-methylethyl group, 1-hydroxypropane-2-yl group, 1,3-dihydroxypropane-2-yl group, 1-hydroxy-2-methylpropane-2-yl group, 1-hydroxy-2-methylpropyl group, 1-hydroxy-2,2-dimethylpropyl group, methoxymethyl group, 2-methoxyethyl group, isopropyloxymethyl group, isobutyloxymethyl group, mercaptomethyl group, methylsulfanylmethyl group, isopropylsulfanylmethyl group, 2-methylsulfanylethyl group, carboxymethyl group, ethoxycarbonylmethyl group, 2-carboxyethyl group, 2-ethoxycarbonylethyl group, carbamoylmethyl group, methylcarbamoylmethyl group, formylmethyl group, acetylmethyl group, isobutyrylmethyl group, pivaloylmethyl group, sulfamoylmethyl group, 2-sulfamoylethyl group, methylsulfamoylmethyl group, methylsulfonylmethyl group, isopropylsulfonylmethyl group, 2-methylsulfonylethyl group, phenoxymethyl group, benzyloxycarbonylmethyl group and the like can be mentioned.

It is preferably methyl group, ethyl group, propyl group or pentyl group, particularly preferably methyl group or pentyl group, for $R^1$.

The "C1–7 alkyl group optionally substituted by 1 to 3 substituent(s) selected from group A" is the above-defined "C1–7 alkyl group", which is optionally substituted by 1 to 3 substituent(s) selected from "group A", and includes unsubstituted alkyl group.

Specifically, the substituents for the "C1–6 alkyl group optionally substituted by 1 to 3 substituent(s) selected from group A" can be mentioned.

It is preferably a methyl group for $R^2$. As group C, preferred are methyl group, ethyl group, propyl group, isobutyl group, isopropyl group, butyl group, isobutyl group, tert-butyl group, cyanomethyl group, hydroxymethyl group, 2-hydroxyethyl group, 1-hydroxyethyl group, 3-hydroxypropyl group, 1-hydroxypropyl group, 1-hydroxy-2-methylpropyl group, methoxymethyl group, isopropyloxymethyl group, isobutyloxymethyl group, 2,2-dimethylpropyl group, 2,2-dimethyl-1-hydroxypropyl group, 3,3-dimethyl-2-hydroxybutyl group, carboxymethyl group, methoxycarbonylmethyl group, methylcarbamoylmethyl group, dimethylcarbamoylmethyl group, methylsulfanylmethyl group, 2-(methylsulfanyl)ethyl group, methylsulfonylmethyl group, isopropylsulfonylmethyl group, 2-(methylsulfonyl)ethyl group, isopropylsulfanylmethyl group, pivaloylmethyl group, benzyl group, phenethyl group, 3-phenylpropyl group, phenoxymethyl group and benzyloxycarbonylmethyl group.

The "C2–6 alkenyl group optionally substituted by 1 to 3 substituent(s) selected from group A" is the above-defined "C2–6 alkenyl group", which is optionally substituted by 1 to 3 substituent(s) selected from "group A", and includes unsubstituted alkenyl group.

Specifically, vinyl group, allyl group, 1-propenyl group, isopropenyl group, 2-methyl-1-propenyl group, 1-butenyl group, 2-butenyl group, 1,3-butadienyl group, 3-methyl-2-butenyl group, 4-methyl-2-pentenyl group, 4-methyl-3-pentenyl group, 1-methyl-2-butenyl group, carboxyvinyl group, carbamoylvinyl group and the like can be mentioned.

The "C2–6 alkynyl group optionally substituted by 1 to 3 substituent(s) selected from group A" is the above-defined "C2–6 alkynyl group", which is optionally substituted by 1 to 3 substituent(s) selected from "group A", and includes unsubstituted alkynyl group.

Specifically, ethynyl group, 1-propynyl group, 2-propynyl group, 3-butynyl group, carboxyethynyl group, carbamoylethynyl group and the like can be mentioned.

The "group B" is a group selected from the following substituent group, in which $R^{b1}$, $R^{b2}$, $R^{b3}$, $R^{b4}$, $R^{b5}$ and $R^{b6}$ are each independently a hydrogen atom or the above-defined "C1–6 alkyl group":

the above-defined "halogen atom", cyano group, the above-defined "C1–6 alkyl group", the above-defined "haloC1–6 alkyl group", —$OR^{b1}$ (e.g., hydroxyl group, methoxy group, ethoxy group, propoxy group, isopropyloxy group, butoxy group, isobutyloxy group, tert-butyloxy group etc.), —$SR^{b1}$ (e.g., mercapto group, methylsulfanyl group, ethylsulfanyl group, isopropylsulfanyl group etc.), —$CO_2R^{b1}$ (e.g., carboxyl group, methoxycarbonyl group, ethoxycarbonyl group, isopropyloxycarbonyl group, tert-butoxycarbonyl group etc.), —$CONR^{b2}R^{b3}$ (e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group, N-isopropyl-N-methylcarbamoyl group etc.), —$COR^{b4}$ (e.g., formyl group, acetyl group, propionyl group, butyryl group, isobutyryl group, pivaloyl group etc.), —$SO_2NR^{b2}R^{b3}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group, N-isopropyl-N-methylsulfamoyl group etc.), —$SO_2R^{b4}$ (e.g., methylsulfonyl group, ethylsulfonyl group, isopropylsulfonyl group, tert-butylsulfonyl group etc.), the above-defined "C6–14 aryloxy group" and the above-defined "C6–14 aryl C1–6 alkyloxycarbonyl group"

—$NR^{b5}COR^{b6}$ (e.g., acetylamino group, propionylamino group, butyrylamino group, isobutyrylamino group, pivaloylamino group and the like.

The "C3–10 carbon ring group optionally substituted by 1 to 3 substituent(s) selected from group B" is the above-defined "C3–10 carbon ring group", preferably a phenyl group, which is optionally substituted by 1 to 3 substituent(s) selected from the above-defined "group C", and includes unsubstituted C3–10 carbon ring group.

Specifically, phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 2-bromophenyl group, 3-bromophenyl group, 4-bromophenyl group, 2,3-dichlorophenyl group, 2,4-dichlorophenyl group, 2,6-dichlorophenyl group, 3,4-dichlorophenyl group, 3,5-dichlorophenyl group, 3,4-dibromophenyl group, 3-chloro-2-fluorophenyl group, 2-chloro-3-fluorophenyl group, 4-chloro-3-fluorophenyl group, 3-chloro-4-fluorophenyl group, 2-chloro-6-fluorophenyl group, 2-methylphenyl group, 3-methylphenyl group, 4-methylphenyl group, 4-ethylphenyl group, 4-propylphenyl group, 3-isopropylphenyl group, 4-isopropylphenyl group, 3-butylphenyl group, 3-isobutylphenyl group, 4-isobutylphenyl group, 3-(2-methyl-1-propenyl)phenyl group, 2-trifluoromethylphenyl group, 3-trifluoromethylphenyl group, 4-trifluoromethylphenyl group, 3,5-bistrifluoromethylphenyl group, 2-methoxyphenyl group, 3-methoxyphenyl group, 4-methoxyphenyl group, 2-ethoxyphenyl group, 3-ethoxyphenyl group, 4-ethoxyphenyl group, 2-isopropyloxyphenyl group, 3-isopropyloxyphenyl group, 4-isopropyloxyphenyl group, 3-phenoxyphenyl group, 4-phenoxyphenyl group, 3-methylthiophenyl group, 4-methylthiophenyl group, 3-carboxyphenyl group, 4-carboxyphenyl group, 3-cyanophenyl group, 4-cyanophenyl group, 3-acetylphenyl group, 4-acetylphenyl group, 3-isobutyrylphenyl group, 4-isobutyrylphenyl group, 3-carbamoylphenyl group, 4-carbamoylphenyl group, 3-(methylcarbamoyl)phenyl group, 4-(methylcarbamoyl)phenyl group, 3-(isopropylcarbamoyl) phenyl group, 4-(isopropylcarbamoyl)phenyl group, 3-(butylcarbamoyl)phenyl group, 3-(N-ethyl-N-methylcarbamoyl)phenyl group, 3-(dimethylcarbamoyl)phenyl group, 4-(dimethylcarbamoyl)phenyl group, 3-(diethylcarbamoyl) phenyl group, 4-(diethylcarbamoyl)phenyl group, 3-(N-methyl-N-(3-methylbutyl)carbamoyl}phenyl group, 4-{N-methyl-N-(3-methylbutyl)carbamoyl}phenyl group, 3-sulfamoylphenyl group, 4-sulfamoylphenyl group, 3-(methylsulfamoyl)phenyl group, 4-(methylsulfamoyl)phenyl group, 3-(ethylsulfamoyl)phenyl group, 4-(ethylsulfamoyl) phenyl group, 3-(isopropylsulfamoyl)phenyl group, 3-(butylsulfamoyl)phenyl group, 3-(dimethylsulfamoyl)phenyl group, 4-(dimethylsulfamoyl)phenyl group, 3-(diethylsulfamoyl)phenyl group, 4-(diethylsulfamoyl)phenyl group, 3-(N-ethyl-N-methylsulfamoyl)phenyl group, 3-(methylsulfonyl)phenyl group, 4-(methylsulfonyl)phenyl group, 3-(ethylsulfonyl)phenyl group, 4-(ethylsulfonyl)phenyl group, 3-(isopropylsulfonyl)phenyl group, 4-(isopropylsulfonyl)phenyl group, 4-chloro-3-carboxyphenyl group, 4-chloro-3-dimethylcarbamoylphenyl group, 3-chloro-4-methylphenyl group, 3-chloro-2-hydroxyphenyl group, 3-chloro-4-hydroxyphenyl group, 3-chloro-2-methoxyphenyl group, 3-chloro-4-methoxyphenyl group, 3-chloro-4-propyloxyphenyl group, 3-chloro-4-isopropyloxyphenyl group, 3-chloro-4-benzyloxyphenyl group, 3-chloro-5-methoxyphenyl group, 3-chloro-6-methoxyphenyl group, 3-chloro-4-ethoxyphenyl group, 3-chloro-4-isopropyloxyphenyl group, 4-chloro-2-methoxyphenyl group, 4-chloro-3-methoxyphenyl group, 4-chloro-2-hydroxyphenyl group, 4-chloro-2-isopropyloxyphenyl group, 4-chloro-2-propyloxyphenyl group, 4-chloro-2-benzyloxyphenyl group, 3-carboxy-5-trifluoromethylphenyl group, 3-dimethylcarbamoyl-5-trifluoromethylphenyl group, 4-dimethylcarbamoyl-2-fluorophenyl group, 4-carboxy-3-chlorophenyl group, 3-chloro-4-methylcarbamoylphenyl group, 3-chloro-4-dimethylcarbamoylphenyl group, 3-chloro-4-diethylcarbamoylphenyl group, 4-carbamoyl-3-chlorophenyl group, 3-chloro-4-acetylphenyl group, 3-chloro-4-pivaloylphenyl group, 3-chloro-5-dimethylcarbamoylphenyl group, 3-hydroxy-4-dimethylcarbamoylphenyl group, 3-hydroxy-5-dimethylcarbamoylphenyl group, 3-cyano-5-dimethylcarbamoylphenyl group, 3-carboxy-5-methoxyphenyl group, 3-carboxy-5-ethoxyphenyl group, 3-carboxy-5-isopropyloxyphenyl group, 3-carboxy-5-cyanophenyl group, 3,5-dicarboxyphenyl group, 3,4-dicarboxyphenyl group, 3-carboxy-5-dimethylcarbamoylphenyl group, 3-carboxy-4-methoxyphenyl group, 3-carboxy-4-ethoxyphenyl group, 3-carboxy-4-isopropyloxyphenyl group, 3-carboxy-4-cyanophenyl group, 3-carbamoyl-5-dimethylcarbamoylphenyl group, 3-dimethylcarbamoyl-5-methylcarbamoylphenyl group, 4-carboxy-3-methoxyphenyl group, 4-carboxy-2-methoxyphenyl group, 4-carboxy-3-ethoxyphenyl group, 4-carboxy-3-isopropyloxyphenyl group, 4-carboxy-3-cyanophenyl group, 4-carbamoyl-2-methoxyphenyl group, 4-methylcarbamoyl-3-methoxyphenyl group, 4-dimethylcarbamoyl-3-methoxyphenyl group, 3,5-bis(dimethylcarbamoyl)phenyl group, 3-carbamoyl-5-cyanophenyl group, 3-carboxy-4-methylphenyl group, 3-dimethylcarbamoyl-4-methylphenyl group, 4-methyl-3-methylcarbamoylphenyl group, 3-dimethylsulfamoyl-4-methylphenyl group, 4-fluoro-3-chlorophenyl group, 4-fluoro-2-carboxyphenyl group, 4-fluoro-2-methoxycarbonylphenyl group, 4-fluoro-2-methylcarbamoylphenyl group, 4-fluoro-2-acetylaminophenyl group, 3,5-dichloro-4-hydroxyphenyl group, 3,5-dichloro-4-methoxyphenyl group, 1-naphthyl group, 2-naphthyl group, 1-bromonaphthalen-2-yl group, 6-bromonaphthalen-2-yl group, 7-cyanonaphthalen-2-yl group, 7-methoxynaphthalen-2-yl group, 5-bromo-6-methoxynaphthalen-2-yl group, cyclopentyl group, 1-methylcyclopentyl group, 1-ethylcyclopentyl group, 1-isopropylcyclopentyl group, 2,5-dimethylcyclopentyl group, 2,2-dimethylcyclopentyl group, cyclohexyl group, 1-methylcyclohexyl group, 1-ethylcyclohexyl group, 1-isopropylcyclohexyl group, 2,6-dimethylcyclohexyl group, cycloheptyl group, 1-methylcycloheptyl group, 1-ethylcycloheptyl group, 1-isopropylcycloheptyl group and the like can be mentioned.

The ring D for $R^1$ is preferably phenyl group, 2-fluorophenyl group, 3-fluorophenyl group, 4-fluorophenyl group, 3,4-difluorophenyl group, 2-chlorophenyl group, 3-chlorophenyl group, 4-chlorophenyl group, 3-bromophenyl group, 4-bromophenyl group, 2,3-dichlorophenyl group, 2,6-dichlorophenyl group, 3,4-dichlorophenyl group, 3,5-dichlorophenyl group, 3-chloro-2-fluorophenyl group, 4-chloro-3-fluorophenyl group, 2-chloro-6-fluorophenyl group, 3-trifluoromethylphenyl group, 3-methoxyphenyl group, 3-chloro-2-hydroxyphenyl group, 3-chloro-2-methoxyphenyl group, 3-chloro-4-methoxyphenyl group, 3-chloro-4-propyloxyphenyl group, 3-chloro-4-isopropyloxyphenyl group, 3-chloro-4-benzyloxyphenyl group, 3-chloro-5-methoxyphenyl group, 3-chloro-6-methoxyphenyl group, 4-chloro-2-methoxyphenyl group, 4-chloro-3-methoxyphenyl group, 4-chloro-2-hydroxyphenyl group, 4-chloro-2-isopropyloxyphenyl group, 4-chloro-2-propyloxyphenyl group, 4-chloro-2-benzyloxyphenyl group, 4-fluoro-3-chlorophenyl group, 4-fluoro-2-carboxyphenyl group, 4-fluoro-2-methoxycarbonylphenyl group, 4-fluoro-2-methylcarbamoylphenyl group, 4-fluoro-2-acetylaminophenyl group or 2-naphthyl group.

The "heterocyclic group optionally substituted by 1 to 3 substituent(s) selected from group B" is the above-defined "heterocyclic group", which is optionally substituted by 1 to 3 substituent(s) selected from the above-defined "group C", and includes unsubstituted heterocyclic group.

Specifically, 2-imidazolyl group, 5-methylpyrazol-3-yl group, 5-methylisoxazol-3-yl group, 2-furyl group, 2-thiazolyl group, 4-methylthiazol-2-yl group, 5-methylthiazol-2-yl group, 5-thiazolyl group, 2-oxazolyl group, 1-methylimidazol-2-yl group, 3-pyrazolyl group, 1,2,4-triazol-3-yl group, 2-methyl-1,2,4-triazol-3-yl group, 5-methyl-1,2,4-triazol-3-yl group, 5-ethyl-1,2,4-triazol-3-yl group, 1-ethyl-1,2,4-triazol-3-yl group, 1,5-dimethyl-1,2,4-triazol-3-yl group, 4-methyl-1,2,4-triazol-3-yl group, 4-ethyl-1,2,4-triazol-3-yl group, 5-tetrazolyl group, 5-ethyl-1,2,4-oxadiazol-3-yl group, 5-ethyl-1,3,4-oxadiazol-2-yl group, 3-methyl-1,2,4-thiadiazol-5-yl group, 2-pyridyl group, 3-pyridyl group, 4-pyridyl group, 4-methoxypyridin-2-yl group, 6-methylpyridin-2-yl group, 2-pyrimidinyl group, 4-pyrimidinyl group, 4-methylpyrimidin-2-yl group, 4-ethylpyrimidin-2-yl group, 4-isopropylpyrimidin-2-yl group, 4-butylpyrimidin-2-yl group, 4-sec-butylpyrimidin-2-yl group, 4-carboxypyrimidin-2-yl group, 4-methoxypyrimidin-2-yl group, 4-ethoxypyrimidin-2-yl group, 4-isopropyloxypyrimidin-2-yl group, 4-tert-butyloxypyrimidin-2-yl group, 5-methylpyrimidin-2-yl group, 5-ethylpyrimidin-2-yl group, 5-isopropylpyrimidin-2-yl group, 5-butylpyrimidin-2-yl group, 5-sec-butylpyrimidin-2-yl group, 5-carboxypyrimidin-2-yl group, 5-methoxypyrimidin-2-yl group, 5-ethoxypyrimidin-2-yl group, 5-isopropyloxypyrimidin-2-yl group, 5-tert-butyloxypyrimidin-2-yl group, 3-pyridazinyl group, 2-pyrazinyl group, 2-quinazolinyl group, 2-oxazolin-2-yl group, 5-ethyl-2-oxazolin-2-yl group, 4,4-dimethyloxazolin-2-yl group, 2-quinolyl group, 6-quinolyl group, 2-benzothiazolyl group, 1,2,4-triazin-3-yl group, 1,3,5-triazin-2-yl group, 1,2,3,4-tetrahydroquinolin-1-yl group, 5-indolyl group, 1-methylindol-2-yl group, 2-benzimidazolyl group, 2-benzofuranyl group, 1,3-benzodioxol-5-yl group, 1,2,4-benzotriazin-3-yl group, 4-piperidyl group, 4-methylpiperidin-4-yl group, 4-ethylpiperidin-4-yl group, 4-isopropylpiperidin-4-yl group, 4-tetrahydropyranyl group, 4-methyltetrahydropyran-4-yl group, 4-ethyltetrahydropyran-4-yl group, 4-isopropyltetrahydropyran-4-yl group, 3,5-dimethyltetrahydropyran-4-yl group, 4-tetrahydrothiopyranyl group, 4-methyltetrahydrothiopyran-4-yl group, 4-ethyltetrahydrothiopyran-4-yl group, 4-isopropyltetrahydrothiopyran-4-yl group and the like can be mentioned.

It is preferably 2-benzofuranyl group as ring D for $R^1$.

It is preferably 2-furyl group, 2-thiazolyl group, 4-methylthiazol-2-yl group, 5-methylthiazol-2-yl group, 5-thiazolyl group, 2-oxazolyl group, 1-methylimidazol-2-yl group, 3-pyrazolyl group, 1,2,4-triazol-3-yl group, 2-methyl-1,2,4-triazol-3-yl group, 5-tetrazolyl group, 3-methyl-1,2,4-thiadiazol-5-yl group, 2-pyridyl group, 3-pyridyl group, 4-pyridyl group, 2-pyrimidinyl group, 4-pyrimidinyl group, 2-pyrazinyl group, 3-pyridazinyl group or 2-benzofuranyl group for group C.

The "C6–14 aryl group optionally substituted by 1 to 3 substituent(s) selected from group B" is the above-defined "C6–14 aryl group", which is optionally substituted by 1 to 3 substituent(s) selected from the above-defined "group B", and includes unsubstituted C6–14 aryl group.

Specifically, phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 2,4-dichlorophenyl group, 3,4-dichlorophenyl group, 3,5-dichlorophenyl group, 3,4-dibromophenyl group, 3-chloro-2-fluorophenyl group, 2-chloro-3-fluorophenyl group, 4-chloro-3-fluorophenyl group, 3-chloro-4-fluorophenyl group, 2-methylphenyl group, 3-methylphenyl group, 4-methylphenyl group, 2,6-dimethylphenyl group, 2-ethylphenyl group, 3-ethylphenyl group, 4-ethylphenyl group, 4-propylphenyl group, 3-isopropylphenyl group, 4-isopropylphenyl group, 3-butylphenyl group, 3-isobutylphenyl group, 4-isobutylphenyl group, 3-(2-methyl-1-propenyl)phenyl group, 2-trifluoromethylphenyl group, 3-trifluoromethylphenyl group, 4-trifluoromethylphenyl group, 3,5-bistrifluoromethylphenyl group, 2-hydroxyphenyl group, 3-hydroxyphenyl group, 4-hydroxyphenyl group, 2-methoxyphenyl group, 3-methoxyphenyl group, 4-methoxyphenyl group, 2-ethoxyphenyl group, 3-ethoxyphenyl group, 4-ethoxyphenyl group, 2-isopropyloxyphenyl group, 3-isopropyloxyphenyl group, 4-isopropyloxyphenyl group, 3-phenoxyphenyl group, 4-phenoxyphenyl group, 3-methylthiophenyl group, 4-methylthiophenyl group, 3-carboxyphenyl group, 4-carboxyphenyl group, 3-cyanophenyl group, 4-cyanophenyl group, 3-acetylphenyl group, 4-acetylphenyl group, 3-isobutyrylphenyl group, 4-isobutyrylphenyl group, 3-carbamoylphenyl group, 4-carbamoylphenyl group, 3-(methylcarbamoyl)phenyl group, 4-(methylcarbamoyl)phenyl group, 3-(isopropylcarbamoyl)phenyl group, 4-(isopropylcarbamoyl)phenyl group, 3-(butylcarbamoyl)phenyl group, 3-(N-ethyl-N-methylcarbamoyl)phenyl group, 3-(dimethylcarbamoyl)phenyl group, 4-(dimethylcarbamoyl)phenyl group, 3-(diethylcarbamoyl)phenyl group, 4-(diethylcarbamoyl)phenyl group, 3-(N-methyl-N-(3-methylbutyl)carbamoyl)phenyl group, 4-(N-methyl-N-(3-methylbutyl)carbamoyl}phenyl group, 3-sulfamoylphenyl group, 4-sulfamoylphenyl group, 3-(methylsulfamoyl)phenyl group, 4-(methylsulfamoyl)phenyl group, 3-(ethylsulfamoyl)phenyl group, 4-(ethylsulfamoyl)phenyl group, 3-(isopropylsulfamoyl)phenyl group, 3-(butylsulfamoyl)phenyl group, 3-(dimethylsulfamoyl)phenyl group, 4-(dimethylsulfamoyl)phenyl group, 3-(diethylsulfamoyl)phenyl group, 4-(diethylsulfamoyl)phenyl group, 3-(N-ethyl-N-methylsulfamoyl)phenyl group, 3-(methylsulfonyl)phenyl group, 4-(methylsulfonyl)phenyl group, 3-(ethylsulfonyl)phenyl group, 4-(ethylsulfonyl)phenyl group, 3-(isopropylsulfonyl)phenyl group, 4-(isopropylsulfonyl)phenyl group, 4-chloro-3-carboxyphenyl group, 4-chloro-3-dimethylcarbamoylphenyl group, 3-chloro-4-methylphenyl group, 3-chloro-4-hydroxyphenyl group, 3-chloro-4-methoxyphenyl group, 3-chloro-4-ethoxyphenyl group, 3-chloro-4-isopropyloxyphenyl group, 3-carboxy-5-trifluoromethylphenyl group, 3-dimethylcarbamoyl-5-trifluoromethylphenyl group, 4-dimethylcarbamoyl-2-fluorophenyl group, 4-carboxy-3-chlorophenyl group, 3-chloro-4-methylcarbamoylphenyl group, 3-chloro-4-dimethylcarbamoylphenyl group, 3-chloro-4-diethylcarbamoylphenyl group, 4-carbamoyl-3-chlorophenyl group, 3-chloro-4-acetylphenyl group, 3-chloro-4-pivaloylphenyl group, 3-chloro-5-dimethylcarbamoylphenyl group, 3-hydroxy-4-dimethylcarbamoylphenyl group, 3-hydroxy-5-dimethylcarbamoylphenyl group, 3-cyano-5-dimethylcarbamoylphenyl group, 3-carboxy-5-methoxyphenyl group, 3-carboxy-5-ethoxyphenyl group, 3-carboxy-5-isopropyloxyphenyl group, 3-carboxy-5-cyanophenyl group, 3,5-dicarboxyphenyl group, 3,4-dicarboxyphenyl group, 3-carboxy-5-dimethylcarbamoylphenyl group, 3-carboxy-4-methoxyphenyl group, 3-carboxy-4-ethoxyphenyl group, 3-carboxy-4-isopropyloxyphenyl group, 3-carboxy-4-cyanophenyl group, 3-carbamoyl-5-dimethylcarbamoylphenyl group, 3-dimethylcarbamoyl-5-methylcarbamoylphenyl group, 4-carboxy-3-methoxyphenyl group, 4-carboxy-2-methoxyphenyl group, 4-carboxy-3-ethoxyphenyl group, 4-carboxy-3-isopropyloxyphenyl group, 4-carboxy-3-cyanophenyl group, 4-carbamoyl-2-methoxyphenyl group, 4-methylcarbamoyl-3-methoxyphenyl group, 4-dimethylcarbamoyl-3-methoxyphenyl group, 3,5-bis(dimethylcarbamoyl)phenyl group, 3-carbamoyl-5-cyanophenyl group, 3-carboxy-4-methylphenyl group, 3-dimethylcarbamoyl-4-methylphenyl group, 4-methyl-3-methylcarbamoylphenyl group, 3-dimethylsulfamoyl-4-methylphenyl group, 3,5-dichloro-4-hydroxyphenyl group, 3,5-dichloro-4-methoxyphenyl group, 1-naphthyl group, 2-naphthyl group, 1-bromonaphthalen-2-yl group, 6-bromonaphthalen-2-yl group, 7-cyanonaphthalen-2-yl group, 7-methoxynaphthalen-2-yl group, 5-bromo-6-methoxynaphthalen-2-yl group and the like can be mentioned.

It is preferably phenyl group, 2-fluorophenyl group, 2-ethylphenyl group, 2,6-dimethylphenyl group, 2-chlorophenyl group, 3-chlorophenyl group, 4-chlorophenyl group, 2-methoxyphenyl group, 3-methoxyphenyl group, 4-methoxyphenyl group, 2-hydroxyphenyl group, 3-hydroxyphenyl group, 4-hydroxyphenyl group or 2-trifluoromethylphenyl group for group C.

The "heteroaryl group optionally substituted by 1 to 3 substituent(s) selected from group B" is the above-defined "heteroaryl group", which is optionally substituted by 1 to 3 substituent(s) selected from the above-defined "group B", and includes unsubstituted heteroaryl group.

Specifically, 2-imidazolyl group, 5-methylpyrazol-3-yl group, 5-methylisoxazol-3-yl group, 2-thiazolyl group, 1,2,4-triazol-3-yl group, 5-methyl-1,2,4-triazol-3-yl group, 5-ethyl-1,2,4-triazol-3-yl group, 1-ethyl-1,2,4-triazol-3-yl group, 1,5-dimethyl-1,2,4-triazol-3-yl group, 4-methyl-1,2,4-triazol-3-yl group, 4-ethyl-1,2,4-triazol-3-yl group, 5-tetrazolyl group, 5-ethyl-1,2,4-oxadiazol-3-yl group, 5-ethyl-1,3,4-oxadiazol-2-yl group, 2-pyridyl group, 4-methoxypyridin-2-yl group, 6-methylpyridin-2-yl group, 2-pyrimidinyl group, 4-pyrimidinyl group, 4-methylpyrimidin-2-yl group, 4-ethylpyrimidin-2-yl group, 4-isopropylpyrimidin-2-yl group, 4-butylpyrimidin-2-yl group, 4-sec-butylpyrimidin-2-yl group, 4-carboxypyrimidin-2-yl group, 4-methoxypyrimidin-2-yl group, 4-ethoxypyrimidin-2-yl group, 4-isopropyloxypyrimidin-2-yl group, 4-tert-butyloxypyrimidin-2-yl group, 5-methylpyrimidin-2-yl group, 5-ethylpyrimidin-2-yl group, 5-isopropylpyrimidin-2-yl group, 5-butylpyrimidin-2-yl group, 5-sec-butylpyrimidin-2-yl group, 5-carboxypyrimidin-2-yl group, 5-methoxypyrimidin-2-yl group, 5-ethoxypyrimidin-2-yl group, 5-isopropyloxypyrimidin-2-yl group, 5-tert-butyloxypyrimidin-2-yl group, 3-pyridazinyl group, 2-pyrazinyl group and the like can be mentioned.

The "group C" is a group selected from the following substituent group:

(1) a hydrogen atom,
(2) the above-defined "C3–8 cycloalkyl C1–6 alkyl group",
(3) a cyano group,
(4) the above-defined "halogen atom",
(5) the above-defined "C1–6 alkyl group",
(6) the above-defined "C2–6 alkenyl group",
(7) the above-defined "C2–6 alkynyl group",
(8) the above-defined "C6–14 aryl group",
(9) a heterocyclic group which is a saturated or unsaturated 5-membered or 6-membered heteromonocycle containing at least one hetero atom selected from nitrogen atom, oxygen atom and sulfur atom, or a fused ring of such heterocycles, or a fused ring of a carbon ring selected from benzene, cyclopentane and cyclohexane and the above-defined heterocycle,
(10) the above-defined "C1–6 alkyloxy group",
(11) the above-defined "C6–14 aryl C1–6 alkyl group",
(12) the above-defined "C6–14 aryl C1–6 alkyloxy group",
(13) —$CO_2R^{c1}$ (e.g., carboxyl group, methoxycarbonyl group, ethoxycarbonyl group, isopropyloxycarbonyl group, tert-butoxycarbonyl group, 2,2-dimethylpropyloxycarbonyl group, cyclohexyloxycarbonyl etc.),
(14) —$CONR^{c2}R^{c3}$ (e.g., carbamoyl group, methylcarbamoyl group, ethylcarbamoyl group, propylcarbamoyl group, isopropylcarbamoyl group, butylcarbamoyl group, isobutylcarbamoyl group, dimethylcarbamoyl group, diethylcarbamoyl group, diisopropylcarbarnoyl group, di-tert-butylcarbamoyl group, N-ethyl-N-methylcarbamoyl group, N-isopropyl-N-methylcarbamoyl group, N-butyl-N-methylcarbamoyl group, 2-fluoroethylcarbamoyl group, 2-hydroxyethylcarbamoyl group, 2-methoxyethylcarbamoyl group, N-methyl-N-(2-methoxyethyl)carbamoyl group, 2-oxopropylcarbamoyl group, 2-hydroxypropylcarbamoyl group, carboxymethylcarbamoyl group, methoxycarbonylmethylcarbamoyl group, 2,2,2-trifluoroethylcarbamoyl group, 2-(trifluoroacetyloxy)ethylcarbamoyl group, methylcarbamoylmethylcarbamoyl group, dimethylcarbamoylmethylcarbamoyl group, 2-(methylsulfonyl)ethylcarbamoyl group, phenylcarbamoyl group, benzylcarbamoyl group, N-benzyl-N-methylcarbamoyl group, 2-fluorobenzylcarbamoyl group, 4-fluorobenzylcarbamoyl group, 4-tert-butylbenzylcarbamoyl group, 4-(dimethylamino)benzylcarbamoyl group, 4-(methylsulfonyl)benzylcarbamoyl group, 4-(acetylamino)benzylcarbamoyl group, 1-naphthylmethylcarbamoyl group, diphenylmethylcarbamoyl group, 1,2-diphenylethylcarbamoyl group, 1,3-diphenylpropylcarbamoyl group, 2-pyridylmethylcarbamoyl group, 3-pyridylmethylcarbamoyl group, 4-pyridylmethylcarbamoyl group, 2-furylmethylcarbamoyl group, 4-methoxypyrimidin-2-ylmethylcarbamoyl group, 2-(2-oxopyrrolidin-1-yl)ethylcarbamoyl group, 1-pyrrolidinylcarbonyl group, 3-hydroxypyrrolidin-1-ylcarbonyl group, 3-oxopyrrolidin-1-ylcarbonyl group, morpholinocarbonyl group etc.),
(15) —$COR^{c4}$ (e.g., formyl group, acetyl group, propionyl group, butyryl group, isobutyryl group, pivaloyl group, benzoyl group, 3-methylbutyryl group, 2,2-dimethylbutyryl group, 2,2-dimethyl-1-hydroxypropionyl group, 2,2-dimethyl-1-methoxypropionyl group, 1-acetyloxy-2,2-dimethylpropionyl group, 2-methyl-2-phenylpropionyl group etc.),
(16) —$SO_2NR^{c2}R^{c3}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group, N-isopropyl-N-methylsulfamoyl group etc.),
(17) the above-defined "C6–14 arylcarbonyl group",
(18) —$NR^{c4}R^{c5}$ (e.g., amino group, methylamino group, ethylamino group, propylamino group, isopropylamino group, butylamino group, isobutylamino group, dimethylamino group, diethylamino group, diisopropylamino group, di-tert-butylamino group, N-ethyl-N-methylamino group, N-isopropyl-N-methylamino group etc.),
(19) —$NR^{c6}COR^{c7}$ (e.g., acetylamino group, propionylamino group, butyrylamino group, isobutyrylamino group, pivaloylamino group, benzoylamino group, 4-fluorobenzoylamino group, 3-methylbutyrylamino group, 3,3-dimethylbutyrylamino group, (methoxyacetyl)amino group, 2-isopropyl-3-methylbutyrylamino group, 2,2-dimethyl-1-hydroxypropionylamino group, 2,2-dimethyl-1-methoxypropionylamino group, 1-acetyloxy-2,2-dimethylpropionylamino group, 2-methyl-2-phenylpropionylamino group, N-acetyl-N-methylamino group, N-acetyl-N-isobutylamino group, benzylcarbonylamino group, 4-fluorobenzylcarbonylamino group, 3-phenylpropionylamino group, cyclopentylcarbonylamino group, 2-pyridylcarbonylamino group, 3-pyridylcarbonylamino group, 4-pyridylcarbonylamino group, 2-furylcarbonylamino group, 2-thienylcarbonylamino group, 1-methylpyrrol-2-ylcarbonylamino group etc.)
(20) —$NR^{c8}SO_2R^{c9}$ (e.g., methylsulfonylamino group, ethylsulfonylamino group, isopropylsulfonylamino group, phenylsulfonylamino group, benzylsulfonylamino group, N-methyl-N-(methylsulfonyl)aamino group, N-methyl-N-(ethylsulfonyl)amino group, N-methyl-N-(isopropylsulfonyl)amino group, 4-pyridylsulfonylamino group, 2-furylsulfonylamino group, 2-thienylsulfonylamino group, 1-methylpyrrol-2-ylsulfonylamino group etc.)
(21) —$SR^{c10}$ (e.g., methylsulfanyl group, ethylsulfanyl group, isopropylsulfanyl group, phenylsulfanyl group etc.),
(22) —$SOR^{c11}$ (e.g., methylsulfinyl group, ethylsulfinyl group, isopropylsulfinyl group, phenylsulfinyl group etc.),
(23) —$SO_2R^{c12}$ (e.g., methylsulfonyl group, ethylsulfonyl group, isopropylsulfonyl group, phenylsulfonyl group etc.),
(24) —$NR^{c13}CONR^{c14}R^{c15}$ (e.g., methylcarbamoylamino group, dimethylcarbamoylamino group, diethylcarbamoylamino group, diisopropylcarbamoylamino group, N-ethyl-N-methylcarbamoylamino group etc.),

(25) —$NR^{c16}CO_2R^{c17}$ (e.g., methoxycarbonylamino group, ethoxycarbonylamino group, isopropyloxycarbonylamino group, phenoxycarbonylamino group etc.) and

(26) —$NR^{c18}COCOR^{c19}$ (e.g., 2-oxopropionylamino group, 2-oxobutyrylamino group, 3-methyl-2-oxobutyrylamino group, 2-oxo-2-(pyridin-2-yl) acetylamino group etc.).

Here, $R^{c1}$, $R^{c2}$, $R^{c3}$, $R^{c4}$, $R^{c5}$, $R^{c6}$, $R^{c7}$, $R^{c8}$, $R^{c9}$, $R^{c10}$, $R^{c11}$, $R^{c12}$, $R^{c13}$, $R^{c14}$, $R^{c15}$, $R^{c16}$, $R^{c17}$, $R^{c18}$ and $R^{c19}$ are each independently (1') a hydrogen atom, (2') a C1–7 alkyl group optionally substituted by 1 to 3 substituent(s) selected from.the above-mentioned group A, (3') a C6–14 aryl group optionally substituted by 1 to 3 substituent(s) selected from the above-mentioned group B, (4') a heterocyclic group optionally substituted by 1 to 3 substituent(s) selected from the above-mentioned group B, or (5') a C3–8 cycloalkyl group, wherein $R^{c2}$ and $R^{c3}$ may form, together with the adjacent nitrogen atom, a nitrogen-containing heterocycle, and the nitrogen-containing heterocycle may contain an ether moiety or a carbonyl moiety, and are optionally substituted by 1 to 3 substituent(s) selected from the above-mentioned group B.

The C1–7 alkyl group, C1–6 alkyl moiety, C2–6 alkenyl group and C2–6 alkynyl group of the above-mentioned group C are optionally substituted by 1 to 3 substituent(s) selected from the above-mentioned group A, or a nitrogen-containing heterocyclic group optionally containing a carbonyl moiety, and specifically includes the above-defined "C1–7 alkyl group optionally substituted by 1 to 3 substituent(s) selected from group A", the above-defined "C2–6 alkenyl group optionally substituted by 1 to 3 substituent(s) selected from group A", the above-defined "C2–6 alkynyl group optionally substituted by 1 to 3 substituent(s) selected from group A" and an oxy group substituted by the above-defined "C1–6 alkyl group optionally substituted by 1 to 3 substituent(s) selected from group A".

The C6–14 aryl group, C6–14 aryl moiety and heterocyclic group of the above-mentioned group C are optionally substituted by 1 to 3 substituent(s) selected from the above-mentioned group B and specifically include the above-defined "C6–14 aryl group optionally substituted by 1 to 3 substituent(s) selected from group B", the above-defined "heterocyclic group optionally substituted by 1 to 3 substituent(s) selected from group B", the above-defined "C1–6 alkyl group" substituted by the above-defined "C6–14 aryl group optionally substituted by 1 to 3 substituent(s) selected from group B", the above-defined "C1–6 alkyloxy group" substituted by the above-defined "C6–14 aryl group optionally substituted by 1 to 3 substituent(s) selected from group B", and a carbonyl group substituted by the "C6–14 aryl group optionally substituted by 1 to 3 substituent(s) selected from group B".

In addition, the "C6–14 aryl C1–6 alkyl group" of the above-mentioned group C includes a "C1–6 alkyl group" substituted by the above-defined "C6–14 aryl group optionally substituted by 1 to 3 substituent(s) selected from group B", wherein the alkyl group moiety is substituted by 1 to 3 substituent(s) selected from the above-defined "group A", and specifically, carbamoylphenylmethyl group, 1-carboxy-2-phenylethyl group, 1-hydroxymethyl-2-phenylethyl group, 1-carboxymethyl-2-phenylethyl group, 1-benzyloxycarbonyl-2-phenylethyl group and the like can be mentioned.

In addition, the "C6–14 aryl C1–6 alkyloxy group" of the above-mentioned group C includes a "C1–6 alkyloxy group" substituted by the above-defined "C6–14 aryl group optionally substituted by 1 to 3 substituent(s) selected from group B", wherein the alkyl group moiety is substituted by 1 to 3 substituent(s) selected from the above-defined "group A", and specifically, carbamoylphenylmethyloxy group, 1-carboxy-2-phenylethyloxy group, 1-hydroxymethyl-2-phenylethyloxy group, 1-carboxymethyl-2-phenylethyloxy group, 1-benzyloxycarbonyl-2-phenylethyloxy group and the like can be mentioned.

$R^{c2}$ and $R^{c3}$ may form, "together with the adjacent nitrogen atom, a nitrogen-containing heterocycle", and the "nitrogen-containing heterocycle" contains at least one nitrogen atom among the above-mentioned "heterocyclic groups", and a bond extends from the nitrogen atom. The "nitrogen-containing heterocycle" may further contain, besides nitrogen atom, a hetero atom selected from oxygen atom and sulfur atom.

Preferably, 1-pyrrolidinyl group, 3-hydroxypyrrolidin-1-yl group, 3-oxopyrrolidin-1-yl group and morpholino group can be mentioned.

When X is —$C(R^{x1})(R^{x2})$-#, —$C(R^{x1})(R^{x2})$—$C(R^{x3})(R^{x4})$-#, —$C(R^{x1})(R^{x2})$—$C(R^{x3})(R^{x4})$—$C(R^{x5})(R^{x6})$-#, —$C(R^{x1})(R^{x2})$—$C(R^{x7})$═$C(R^{x8})$-#, or —$C(R^{x7})$═$C(R^{x8})$—$C(R^{x1})(R^{x2})$-#, and when $R^{x1}$ and $R^{x2}$, $R^{x3}$ and $R^{x4}$, or $R^{x5}$ and $R^{x6}$ form a C3–8 cycloalkyl together with the adjacent carbon atom, X is, for example,

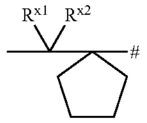

and as a cycloalkyl moiety, cyclopropyl group, cyclobutyl group, cyclopentyl group, cyclohexyl group, cycloheptyl group and cyclooctyl group can be mentioned.

The cycloalkyl moiety is preferably a cyclopentyl group or a cyclohexyl group.

$R^1$ is preferably

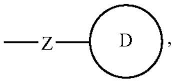

and Z is preferably the above-defined "C1–6 alkylene" or *-$(CH_2)_m$-Q-$(CH_2)_n$—, more preferably, the above-defined "C1–6 alkylene".

Ring D is preferably the above-defined "C3–10 carbon ring group optionally substituted by 1 to 3 substituent(s) selected from group B", more preferably, a phenyl group optionally substituted by 1 to 3 substituent(s) selected from the above-defined "group B", and more preferably, a phenyl group optionally substituted by 1 to 3 substituent(s) selected from a halogen atom and —$OR^{b1}$ wherein $R^{b1}$ is a hydrogen atom or a C1–6 alkyl group.

$R^1$ is preferably the above-defined "C1–6 alkyl group optionally substituted by 1 to 3 substituent(s) selected from group A", more preferably the above-defined "C1–6 alkyl group".

$R^2$ is preferably a hydrogen atom, a C6–14 aryl C1–6 alkyl group or —$SO_2R^{d1}$, more preferably a hydrogen atom.

X is preferably —$C(R^{x1})(R^{x2})$—$C(R^{x3})(R^{x4})$-#, —$C(R^{x1})(R^{x2})$—$C(R^{x3})(R^{x4})$—$C(R^{x5})(R^{x6})$-#, —$C(R^{x7})$═$C(R^{x8})$-#, —N═$C(R^{x9})$-#, or —$C(R^{x10})$═N-#, more preferably —$C(R^{x1})(R^{x2})$—$C(R^{x3})(R^{x4})$-#, or —$C(R^{x7})$═$C(R^{x8})$#.

One of the more preferable embodiments is —$C(R^{x1})(R^{x2})$—$C(R^{x3})(R^{x4})$-#, and the other is —$C(R^{x7})$═$C(R^{x8})$-#.

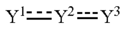

of ring B is preferably C═$C(R^{y1})$—$N(R^{y2})$, N—$C(R^{y1})$═N, N—$C(R^{y1})$═$C(R^{y2})$, or C═N—N ($R^{y2}$), more preferably N—$C(R^{y1})$═$C(R^{y2})$.

Preferable embodiments of the formula [I] include the following formulas [I]-1, [I]-2, [I]-3 and [I]-4:

[I]-1

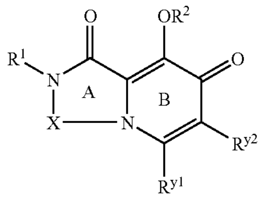

[I]-2

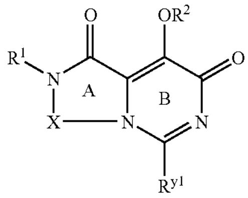

[I]-3

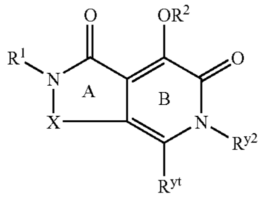

[I]-4

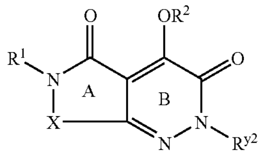

wherein each symbol is as defined above.

$R^{x1}$ to $R^{x10}$ are preferably selected from a hydrogen atom, a C3–8 cycloalkyl C1–6 alkyl group, a cyano group, a C1–7 alkyl group, a C6–14 aryl group, a C6–14 aryl C1–6 alkyl group, —$CO_2R^{c1}$, —$CONR^{c2}R^{c3}$ or —$COR^{c4}$ wherein each symbol and substituent is as defined above.

It is also preferable that $R^{x3}$ and $R^{x4}$ form a C3–8 cycloalkyl together with the adjacent carbon atom.

As $R^{x1}$ to $R^{x10}$, hydrogen atom, cyano group, methyl group, ethyl group, propyl group, isopropyl group, butyl group, isobutyl group, hydroxymethyl group, 1-hydroxyethyl group, 2-hydroxyethyl group, 1-hydroxypropyl group, 3-hydroxypropyl group, 1-hydroxy-2-methylpropyl group, methoxymethyl group, 2-methylsulfanylethyl group, 2-methylsulfonylethyl group, phenyl group, benzyl group, phenethyl group, 3-phenylpropyl group, carboxyl group, methoxycarbonyl group, formyl group, acetyl group, dimethylcarbamoyl group and the like can be mentioned, or $R^{x3}$ and $R^{x4}$ may form a cyclopentyl group or a cyclohexyl group, together with the adjacent carbon atom.

$R^{x1}$ to $R^{x10}$ are more preferably hydrogen atoms.

$R^{y1}$ is preferably selected from a hydrogen atom, a C1–7 alkyl group, a C6–14 aryl group, —$CO_2R^{c1}$, —$CONR^{c2}R^{c3}$, —$COR^{c4}$ and a C6–14 arylcarbonyl group wherein each symbol and substituent is as defined above.

$R^{y1}$ is specifically.hydrogen atom, methyl group, isopropyl group, isobutyl group, tert-butyl group, cyanomethyl group, hydroxymethyl group, 1-hydroxyethyl group, 2-hydroxyethyl group, 1-hydroxy-2-methylpropyl group, 1-hydroxy-2,2-dimethylpropyl group, methoxymethyl group, isopropyloxymethyl group, isobutyloxymethyl group, 2-hydroxy-3,3-dimethylbutyl group, methylsulfanylmethyl group, isopropylsulfanylmethyl group, methylsulfonylmethyl group, isopropylsulfonylmethyl group, pivaloylmethyl group, phenoxymethyl group, benzyloxycarbonylmethyl group, phenyl group, carboxyl group, methoxycarbonyl group, carbamoyl group, methylcarbamoyl group, dimethylcarbamoyl group, diethylcarbamoyl group, N-ethyl-N-methylcarbamoyl group, N-isopropyl-N-methylcarbamoyl group, formyl group, acetyl group, propionyl group, isobutyryl group, pivaloyl group, benzoyl group, 1-(benzyloxycarbonyl)-2-phenylethyl group and the like.

These substituents are particularly preferable when X is —$C(R^{x1})(R^{x2})$—$C(R^{x3})(R^{x4})$-#.

$R^{y1}$ is particularly preferably a hydrogen atom.

$R^{y2}$ is preferably selected from a hydrogen atom, a halogen atom, a C1–7 alkyl group, a C6–14 aryl group, a heterocyclic group, —$CO_2R^{c1}$, —$CONR^{c2}R^{c3}$, —$COR^{c4}$, —$NR^{c4}R^{c5}$, —$NR^{c6}COR^{c7}$, —$NR^{c8}SO_2R^{c9}$, —$SR^{c10}$, —$SO_2R^{c12}$, —$NR^{c13}CONR^{c14}R^{c15}$, —$NR^{c16}CO_2R^{c17}$, and —$NR^{c18}COCOR^{c19}$ wherein each symbol and substituent is as defined above.

One of the preferable embodiments of $R^{y2}$ is heterocyclic group.

More preferably, $R^{y2}$ is a heterocyclic group bonded to $Y^3$ via a carbon atom, wherein at least one of the α-position of the carbon atom is a hetero atom selected from the group consisting of nitrogen atom, oxygen atom and sulfur atom. The heterocyclic group is optionally substituted by 1 to 3 substituent(s) selected from group B, and specifically, 2-thiazolyl group, 4-methyl-thiazol-2-yl group, 5-methyl-thiazol-2-yl group, 5-thiazolyl group, 2-oxazolyl group, 1-methyl-imidazol-2-yl group, 3-pyrazolyl group, 1,2,4-triazol-3-yl group, 2-methyl-1,2,4-triazol-3-yl group, 5-tetrazolyl group, 3-methyl-1,2,4-thiadiazol-5-yl group, 2-pyridyl group, 2-pyrimidinyl group, 4-pyrimidinyl group, 2-pyrazinyl group, 3-pyridazinyl group, 2-benzofuranyl group and the like can be mentioned.

Other preferable embodiments of $R^{y2}$ include

—$CO_2R^{c1}$ (carboxyl group, methoxycarbonyl group, isopropyloxycarbonyl group, 2,2-dimethylpropyloxycarbonyl group and cyclohexyloxycarbonyl group can be specifically mentioned), —$CONR^{c2}R^{c3}$ (carbamoyl group, methylcarbamoyl group, ethylcarbamoyl group, propylcarbamoyl group, isopropylcarbamoyl group, butylcarbamoyl group, isobutylcarbamoyl group, dimethylcarbamoyl group, diethylcarbamoyl group, N-butyl-N-methylcarbamoyl group, 2-fluoroethylcarbamoyl group, 2-hydroxyethylcarbamoyl group, 2-methoxyethylcarbamoyl group, N-methyl-N-(2-methoxyethyl)carbamoyl group, 2-oxopropylcarbamoyl group, 2-hydroxypropylcarbamoyl group, carboxymethylcarbamoyl group, methoxycarbonylmethylcarbamoyl group, 2,2,2-trifluoroethylcarbamoyl group, 2-(trifluoroacetyloxy)ethylcarbamoyl group, methylcarbamoylmethylcarbamoyl group, dimethylcarbamoylmethylcarbamoyl group, 2-(methylsulfonyl)ethylcarbamoyl group, phenylcarbamoyl group, benzylcarbamoyl group, N-benzyl-N-methylcarbamoyl group, 2-fluorobenzylcarbamoyl group, 4-fluorobenzylcarbamoyl group, 4-tert-butylbenzylcarbamoyl group, 4-(dimethylamino)benzylcarbamoyl group, 4-(methylsulfonyl)benzylcarbamoyl group, 4-(acetylamino)benzylcarbamoyl group, 1-naphthylmethylcarbamoyl group, diphenylmethylcarbamoyl group, 1,2-diphenylethylcarbamoyl group, 1,3-diphenylpropylcarbamoyl group, 2-pyridylmethylcarbamoyl group, 3-pyridylmethylcarbamoyl group, 4-pyridylmethylcarbamoyl group, 2-furylmethylcarbamoyl group, 4-methoxypyrimidin-2-ylmethylcarbamoyl group, 2-(2-oxopyrrolidin-1-yl)ethylcarbamoyl group, 1-pyrrolidinylcarbonyl group, 3-hydroxypyrrolidin-1-ylcarbonyl group, 3-oxopyrrolidin-1-ylcarbonyl group and morpholinocarbonyl group can be specifically mentioned) and —$COR^{c4}$ (acetyl group, propionyl group, 2,2-dimethyl-3-hydroxypropionyl group, 2-methyl-2-phenylpropionyl group, 2,2-dimethyl-3-methoxypropionyl group, 3-acetyloxy-2,2-dimethylpropionyl group, isobutyryl group, 2,2-dimethylbutyryl group, pivaloyl group, 3-methylbutyryl group, 2,2-dimethylbutyryl group and benzoyl group can be specifically mentioned).

More preferred is —$COR^{c4}$ wherein $R^{c4}$ is more preferably an unsubstituted C1–6 alkyl group.

Still more preferable embodiment of $R^{y2}$ include

—$NR^{c4}R^{c5}$ (e.g., amino group, ethylamino group, isopropylamino group, isobutylamino group and diethylamino group), —$NR^{c6}COR^{c7}$ (e.g., acetylamino group, propionylamino group, butyrylamino group, isobutyrylamino group, pivaloylamino group, benzoylamino group, 4-fluorobenzoylamino group, 3,3-dimethylbutyrylamino group, (methoxyacetyl)amino group, 2-isopropyl-3-methylbutyrylamino group, 2-methyl-2-phenylpropionylamino group, N-acetyl-N-methylamino group, N-acetyl-N-isobutylamino group, benzylcarbonylamino group, 4-fluorobenzylcarbonylamino group, 3-phenylpropionylamino group, cyclopentylcarbonylamino group, 2-pyridylcarbonylamino group, 3-pyridylcarbonylamino group, 4-pyridylcarbonylamino group can be mentioned.), —$NR^{c8}SO_2R^{c9}$ (e.g., methylsulfonylamino group, phenylsulfonylamino group, benzylsulfonylamino group, 2-thienylsulfonylamino group and N-methyl-N-(methylsulfonyl)amino group), —$NR^{c13}CONR^{c14}R^{c15}$ (e.g., dimethylcarbamoylamino group), —$NR^{c16}CO_2R^{c17}$ (e.g., methoxycarbonylamino group) and —$NR^{c18}COCOR^{c19}$ (e.g., 2-oxopropionylamino group).

$R^{y2}$ is still more preferably —$NR^{c6}COR^{c7}$; —$NR^{c8}SO_2R^{c9}$, —$NR^{c13}CONR^{c14}R^{c15}$, —$NR^{c16}CO_2R^{c17}$ or —$NR^{c18}COCOR^{c19}$, particularly preferably —$NR^{c6}COR^{c7}$ ($R^{c6}$ is more preferably a hydrogen atom and $R^{c7}$ is more preferably an unsubstituted C1–6 alkyl group).

The "pharmaceutically acceptable salt thereof" may be any salt as long as it forms a non-toxic salt with the compounds of the above-mentioned formulas [I], [I]-1, [I]-2, [I]-3 and [I]-4, and can be obtained by a reaction with an inorganic acid such as hydrochloric acid, sulfuric acid, phosphoric acid, hydrobromic acid and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; an inorganic base such as sodium hydroxide, potassium hydroxide, calcium hydroxide, magnesium hydroxide, ammonium hydroxide and the like; an organic base such as methylamine, diethylamine, triethylamine, triethanolamine, ethylenediamine, tris(hydroxymethyl)methylamine, guanidine, choline, cinchonine and the like; or an amino acid such as lysin, arginine, alanine and the like. The present invention also encompasses hydrate and solvate of each compound.

The present invention also encompasses prodrugs and metabolites of each compound.

By the "prodrug" is meant a derivative of the compound of the present invention, which has a chemically or metabolically decomposable group and which, after administration to a body, restores to the original compound to show its inherent efficacy, including a complex and a salt free of covalent bond.

The prodrug is utilized for, for example, improving absorption by oral administration or targeting of a target site.

As the site to be modified, highly reactive functional groups in the compound of the present invention, such as hydroxyl group, carboxyl group, amino group, thiol group and the like, are mentioned.

Examples of the hydroxyl-modifying group include methyl group, benzyl group, trimethylsilyloxymethyl group, acetyl group, propionyl group, isobutyryl group, pivaloyl group, benzoyl group, 4-methylbenzoyl group, dimethylcarbamoyl group, sulfo group and the like. Examples of the carboxyl-modifying group include ethyl group, pivaloyloxymethyl group, 1-(acetyloxy)ethyl group, 1-(ethoxycarbonyloxy)ethyl group, 1-(cyclohexyloxycarbonyloxy)ethyl group, carboxylmethyl group, (5-methyl-2-oxo-1,3-dioxol-4-yl)methyl group, phenyl group, o-tolyl group and the like. Examples of the amino-modifying group include hexylcarbamoyl group, 3-methylthio-1-(acetylamino)propylcarbonyl group, 1-sulfo-1-(3-ethoky-4-hydroxyphenyl)methyl group, (5-methyl-2-oxo-1,3-dioxol-4-yl)methyl group and the like.

Preferably, prodrugs of the compounds of the formulas [I], [I]-1, [I]-2, [I]-3 and [I]-4, wherein the hydroxyl group on ring B is modified by methyl group, benzyl group or trimethylsilyloxymethyl group, can be mentioned.

The compound of the present invention can be administered to a mammal (human, mouse, rat, hamster, rabbit, cat, dog, bovine, sheep, monkey and the like) as an anti-HIV agent, an integrase inhibitor, an antiviral agent and the like.

When the compound of the present invention is used as a pharmaceutical preparation, it is admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, and other additives, that are generally known per se, such as water, vegetable oil, alcohol (e.g., ethanol or benzyl alcohol etc.), polyethylene glycol, glycerol triacetate, gelatin, carbohydrate (e.g., lactose, starch etc.), magnesium stearate, talc, lanolin, petrolatum and the like, formed into tablet, pill, powder, granule, suppository, injection, eye drop, liquid, capsule, troche, aerosol, elixir, suspension, emulsion, syrup and the like by a conventional method, and administered systemically or topically, and orally or parenterally.

While the dose varies depending on age, body weight, symptom, treatment effect, administration method and the like, it is generally 0.01 mg to 1 g per administration for an adult, which is given once to several times a day orally or in a dosage form of an injection such as intravenous injection and the like.

As a preferable embodiment of the compound of the present invention, a compound having high pharmacological activity (e.g., a compound having a strong HIV integrase-inhibitory activity, a compound having a strong anti-HIV (e.g., HIV-1 IIIB strain) activity, a compound that resists easy occurrence of drug resistant viruses, a compound effective against multiple drug resistant viruses), a compound having fine bioavailability (e.g., a compound showing high oral absorbability, a compound showing high cell membrane (e.g., Caco2) permeability, a compound stable to metabolic enzyme (e.g., S9), a compound maintained at high blood concentration for a long time (e.g., high blood concentration after 8 hours from administration), a compound showing low binding rate to a protein (e.g., human plasma protein, human serum albumin, α1-acidic glycoprotein), a highly safe compound (e.g., a compound showing low inhibitory activity against P450(CYP)) and the like can be mentioned.

An anti-HIV agent is generally required to sustain its effect for a long time, so that can be effective not only for temporal suppression of viral growth but also prohibition of viral re-growth. This means that a prolonged administration is necessary and that a high single dose may be frequently inevitable to sustain effect for a longer period through the night. Such prolonged and high dose administration increases the risk of causing side effects.

In view of this, one of the preferable modes of the nitrogen-containing fused ring compound of the present invention is such compound permitting high absorption by oral administration, and such compound capable of maintaining blood concentration of the administered compound for an extended period of time.

Furthermore, a compound that exhibits a strong anti-HIV activity, high absorbability by oral administration, and long-term sustention of blood concentration is desirable.

A compound showing less effect of addition of serum (e.g., human serum, fetal bovine serum, equine serum) in in vitro tests and capable of maintaining strong integrase inhibitory activity and strong anti-HIV activity is also one of the preferable embodiments.

By the "prophylaxis of AIDS" is meant, for example, administration of a pharmaceutical agent to an individual who tested HIV positive but has not yet developed the disease state of AIDS, administration of a pharmaceutical agent to an individual who shows an improved disease state of AIDS after treatment but who carries HIV still to be eradicated and whose relapse of AIDS is worried, and administration of a pharmaceutical agent out of a fear of possible infection.

Examples of the "other anti-HIV agents" to be used for a multiple drug combination therapy include an anti-HIV antibody, an HIV vaccine, immunostimulants such as interferon and the like, an HIV ribozyme, an HIV antisense drug, a reverse transcriptase inhibitor, a protease inhibitor, an inhibitor of bond between a bond receptor (CD4, CXCR4, CCR5 and the like) of a host cell recognized by virus and the virus, and the like.

Specific examples of the HIV reverse transcriptase inhibitor include Retrovir(R) (zidovudine), Epivir(R) (lamivudine), Zerit(R) (sanilvudine), Videx(R) (didanosine), Hivid (R) (zalcitabine), Ziagen(R) (abacavir sulfate), Viramune(R) (nevirapine), Stocrin(R) (efavirenz), Rescriptor(R) (delavirdine mesylate), Combivir(R) (zidovudine+lamivudine), Trizivir(R) (abacavir sulfate+lamivudine+zidovudine), Coactinon(R) (emivirine), Phosphonovir(R), Coviracil(R), alovudine (3'-fluoro-3'-deoxythymidine), Thiovir (thiophosphonoformic acid), Capravirin (5-[(3,5-dichlorophenyl) thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis(isopropoxycarbonyloxymethyl)ester fumarate), DPC-083 ((4S)-6-chloro-4-[(1E)-cyclopropylethenyl]-3,4-dihydro-4-trifluoromethyl-2(1H) -quinazolinone), DPC-961 ((4S)-6-chloro-4-(cyclopropylethynyl)-3,4-dihydro-4-(trifluoromethyl)-2(1H)-quinazolinone), DAPD ((−)-β-D-2,6-diaminopurine dioxolane), Immunocal, MSK-055, MSA-254, MSH-143, NV-01, TMC-120, DPC-817 and the like, wherein (R) means a registered trademark (hereinafter the same) and the names of other pharmaceutical agents are general names.

Specific examples of the HIV protease inhibitor include Crixivan(R) (indinavir sulfate ethanolate), saquinavir, Invirase(R) (saquinavir mesylate), Norvir(R) (ritonavir), Viracept(R) (nelfinavir mesylate), lopinavir, Prozei(R) (amprenavir), Kaletra(R) (ritonavir+lopinavir), mozenavir dimesylate ([4R-(4α,5α,6β)]-1,3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R) -N-tert-butyl-3-[(2S,3S) -2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy) phenylcarbonylamino]-1-oxabutyl]-4-[(2-methylphenyl)

methylamino]carbonyl-4(R)-5,5-dimethyl-1,3-thiazole), BMS-232632 ((3S,8S,9S,12S)-3,12-bis(1,1-dimethylethyl)-8-hydroxy-4,11-dioxo-9-(phenylmethyl)-6-[[4-(2-pyridinyl) phenyl]methyl]-2,5,6,10,13-pentaazatetradecanedicarboxylic acid dimethyl ester), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851 and the like.

The HIV integrase inhibitor is exemplified by S-1360 and the like, the DNA polymerase inhibitor or DNA synthesis inhibitor is exemplified by Foscavir(R), ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum album extract) and the like, the HIV antisense drug is exemplified by HGTV-43, GEM-92 and the like, the anti-HIV antibody or other antibody is exemplified by. NM-01, PRO-367, KD-247, Cytolin(R), TNX-355 (CD4 antibody), AGT-1, PRO-140 (CCR5 antibody) and the like, the HIV vaccine or other vaccine is exemplified by ALVAC (R), AIDSVAX(R), Remune(R), HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, Anti-Tat, MVA-F6 Nef vaccine, HIV rev vaccine, C4-V3 peptide, p2249f, VIR-201, HGP-30W, TBC-3B, PARTICLE-3B and the like, Antiferon (interferon-α vaccine) and the like, the interferon or interferon agonist is exemplified by Sumiferon (R), MultiFeron(R), interferon-τ, Reticulose and the like, the CCR5 antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No3, pentafuside and the like, the IL-2 agonist or antagonist is exemplified by interleukin-2, Imunace(R), Proleukin(R), Multikine(R), Ontak(R) and the like, the TNF-α antagonist is exemplified by Thalomid(R) (thalidomide), Remicade(R) (infliximab), curdlan sulfate, the α-glucosidase inhibitor is exemplified by Bucast(R) and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z(R), Panavir(R), Coenzyme Q10 (2-deca(3-methyl-2-butenylene)-5,6-dimethoxy-3-methyl-p-benzoquinone) and the like, the cholinesterase inhibitor is exemplified by Cognex(R) and the like, and the immunomodulator is exemplified by Imunox(R), Prokine(R), Met-enkephalin (6-de-L-arginine-7-de-L-arginine-8-de-L-valinamide-adrenorphin), WF-10 (10-fold dilute tetrachlorodecaoxide solution), Perthon, PRO-542 and the like.

In addition, Neurotropin(R), Lidakol(R), Ancer 20(R), Ampligen(R), Anticort(R), Inactivin(R) and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex and the like are exemplified.

As the "other anti-HIV agents" to be used for a multiple drug combination therapy with the compound of the present invention, preferred are a reverse transcriptase inhibitor and a protease inhibitor. Two or three, or even a greater number of pharmaceutical agents can be used in combination, wherein a combination of pharmaceutical agents having different action mechanisms is one of the preferable embodiments. In addition, selection of pharmaceutical agents free of side effect duplication is preferable. Specific examples of the combination of pharmaceutical agents include a combination of a group consisting of efavirenz, indinavir, nelfinavir, ritonavir+indinaviir, ritonavir+lopinavir and ritonavir+saquinavir, and a group consisting of didanosine+lamivudine, zidovudine+didanosine, stavudine+didanosine, zidovudine+lamivudine and stavudine+lamivudine (Guidelines for the Use of Antiretroviral Agents in HIV-Infected Adults and Adolescents. Aug. 13, 2001). Particularly preferred is Invirase(R) (saquinavir mesylate).

Some examples of the production method of the compound used for embodiment of the present invention are shown in the following. However, the production method of the compound of the present invention is not limited to these examples.

Even in the absence-of description in the production method, efficient production can be afforded by introducing, where necessary, a protecting group into a functional group followed by deprotection in a subsequent step, subjecting a functional group to each step as a precursor and converting the group to a desired functional group in a suitable step, exchanging the order of respective production methods and steps, and the like.

The work-up treatment in each step can be applied by a typical method, wherein isolation and purification is performed by selecting or combining conventional methods as necessary, such as crystallization, recrystallization, distillation, partitioning, column chromatography, thin layer chromatography, preparative HPLC and the like.

The abbreviations used in the present specification are as follows. Me means methyl group, Et means ethyl group, Bn means benzyl group, n-Bu (or Bu) means butyl group, t-Bu means tert-butyl group, Ac means acetyl group, Boc means tert-butoxycarbonyl group, MOM means methoxymethyl group and Ms means methanesulfonyl group.

Production Method 1

Production Method 1-1

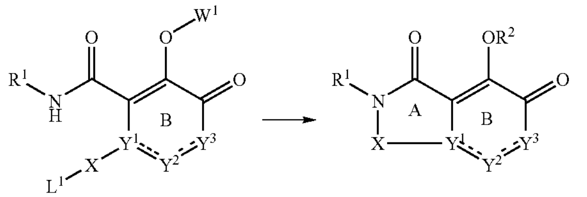

[1] [I]

wherein $L^1$ is a leaving group such as a chlorine atom, a bromine atom, a methanesulfonyloxy group, a trifluoromethanesulfonyloxy group, a toluenesulfonyloxy group and the like, $W^1$ is a protecting group such as an acetyl group, a benzoyl group, a benzyl group, a methoxyethoxymethyl group, a tert-butyldimethylsilyl group and the like, or a hydrogen atom, and other symbols are as defined above.

Compound [I] can be synthesized by reacting compound [1] in an organic solvent such as tetrahydrofuran., dioxane, dimethylformamide, dimethylacetamide, N-methylpyrrolidone, 1,3-dimethyl-2-imidazolidinone, tert-butanol, isopropanol and the like, in the presence of a base such as sodium hydride, lithium diisopropylamide, lithium bis(trimethylsilyl)amide, potassium tert-butoxide, triethylamine, diisopropylethylamine and the like at room temperature to cooling to give Compound [I].

When a compound wherein $R^2$ is a hydrogen atom is desired, the reaction only needs to be conducted by a conventional method under the conditions to make $W^1$ leave. When a compound wherein $R^2$ is a C1–6 alkyl group, a C6–14 aryl C1–6 alkyl group or $—SO_2R^{d1}$ is desired, the reaction only needs to be conducted under mild conditions under which these substituents do not leave (the same applied to the following production methods).

Production Method 1-2

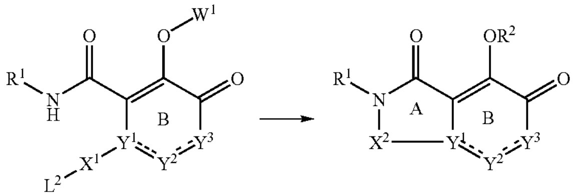

[2] [I-1]

wherein $L^2$-$X^1$— is $C(R^{x7})(OMe)_2$-$CH(R^{x8})$— or $C(R^{x7})(OMe)_2$-$CH(R^{x8})$—$C(R^{x1})(R^{x2})$— wherein each symbol is as defined above, when $L^2$-$X^1$— is $C(R^{x7})(OMe)_2$-$C(R^{x8})$—, —$X^2$— is —$C(R^{x7})$=$C(R^{x8})$-#, when $L^2$-$X^1$— is $C(R^{x7})(OMe)_2$-$CH(R^{x8})$—$C(R^{x1})(R^{x2})$—, —$X^2$— is —$C(R^{x7})$=$C(R^{x8})$—$C(R^{x1})(R^{x2})$-#, and other symbols are as defined above.

A compound represented by the formula [I-1] can be synthesized by subjecting compound [2] to a ring closure reaction under acidic conditions in a solvent or without solvent at room temperature to under heating.

As the acid to be used, inorganic acids such as hydrochloric acid, sulfuric acid, phosphoric acid, polyphosphoric acid and the like, organic acids such as acetic acid, trifluoroacetic acid, camphorsulfonic acid, p-toluenesulfonic acid, methanesulfonic acid, trifluoromethanesulfonic acid and the like, acidic salts such as pyridinium p-toluenesulfonate and the like, and the like can be mentioned, and as the solvent, ether solvents such as tetrahydrofuran, dioxane, diethyl ether and the like, benzene solvents such as benzene, toluene, chlorobenzene, dichlorobenzene and the like, alcohol solvents such as ethanol, isopropanol, tert-butanol and the like, and halogenated hydrocarbon solvents such as methylene chloride, chloroform, dichloroethane and the like can be mentioned. A combination of an organic acid and a benzene solvent often produce good results. In addition, preferable options include, for example, a reaction under the conditions of using an acid such as phosphoric acid, polyphosphoric acid, sulfuric acid and the like without using a solvent, and the conditions of using acetic acid or trifluoroacetic acid as a solvent and adding aqueous hydrochloric acid thereto.

Production Method 2

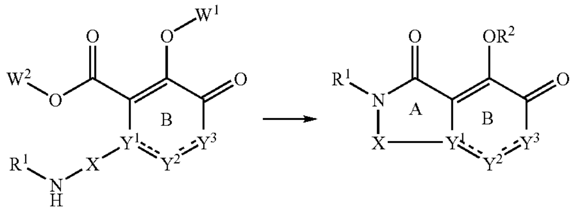

[3] [I]

wherein $W^2$ is an alkyl group such as methyl group, ethyl group and the like, or a hydrogen atom, and other symbols are as defined above.

Compound [I] can be synthesized by subjecting compound [3] to ring closure reaction under acidic or basic conditions at room temperature to under heating.

When $W^2$ is a hydrogen atom, for example, a ring closure reaction can be achieved using a condensation agent such as dicyclohexylcarbodiimide, 1-ethyl-3-(3-dimethylaminopropyl)carbodiimide, carbonyldiimidazole and the like and conducting a reaction in the presence or absence of a condensation additive such as 1-hydroxybenzotriazole, N-hydroxysuccinimide and the like in an ether solvent such as tetrahydrofuran, dioxane, diethyl ether and the like, a benzene solvent such as benzene, toluene and the like, a hydrocarbon solvent such as cyclohexane and the like, an amide solvent such as dimethylformamide, dimethylacetamide, 1,3-dimethylimidazolidinone and the like, a ketone solvent such as acetone, 2-butanone and the like or a halogenated hydrocarbon solvent such as methylene chloride, chloroform and the like.

When $W^2$ is an alkyl group, a ring closure reaction can be achieved by conducting a reaction in the presence of an acid catalyst such as camphorsulfonic acid, p-toluenesulfonic acid and the like or a base catalyst such as dimethylaminopyridine and the like in a solvent such as benzene, toluene and the like at room temperature to under heating, particularly preferably under heating.

Production Method 3

Production Method 3-1

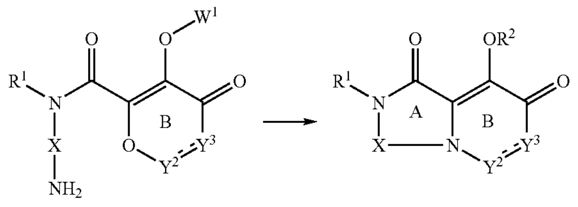

[4] [I-2]

wherein each symbol is as defined above.

Compound [I-2] can be synthesized by reacting compound [4] in an organic solvent such as tetrahydrofuran, dioxane, dimethylformamide, dimethylacetamide, N-methylpyrrolidone, 1,3-dimethyl-2-imidazolidinone, tert-butanol, isopropanol, ethanol and the like, or a mixed solvent of these with water, in the presence or absence of an organic base such as triethylamine, diisopropylethylamine and the like or a carbonate base such as sodium carbonate, potassium carbonate, sodium hydrogen carbonate and the like at room temperature to under heating.

Production Method 3-2

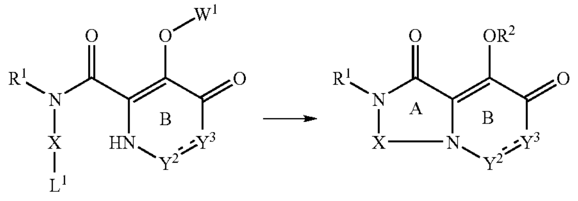

[5] [I-2]

wherein each symbol is as defined above.

Compound [I-2] can be synthesized by subjecting compound [5] to the same reaction operation as in Production method 1-1.

Production Method 3-3

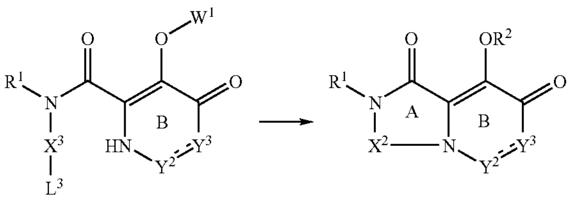

[6] [I-2]

wherein —$X^3$-$L^3$ is —CH($R^{x7}$)—C($R^{x8}$)(OMe)$_2$ or —C($R^{x1}$)($R^{x2}$)—CH($R^{x7}$)—C($R^{x8}$)(OMe)$_2$ wherein each symbol is as defined above, when —$X^3$-$L^3$ is —CH($R^{x7}$)—C($R^{x8}$)(OMe)$_2$, —$X^2$— is —C($R^{x7}$)═C($R^{x8}$)-#, when —$X^3$-$L^3$ is —C($R^{x1}$)($R^{x2}$)—CH($R^{x7}$)—C($R^{x8}$)(OMe)$_2$, —$X^2$— is —C($R^{x1}$)($R^{x2}$)—C($R^{x7}$)═C($R^{x8}$)-#, and other symbols are as defined above.

Compound [I-2] can be synthesized by subjecting compound [6] to the same reaction operation as in production method 1-2.

Production Method 3-4

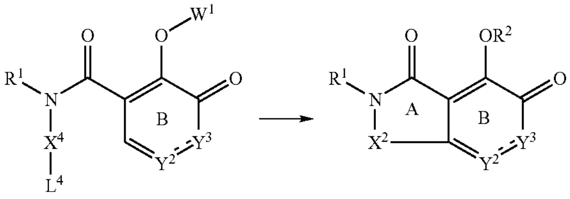

[7] [I-3]

wherein —$X^4$-$L^4$ is —CH($R^{x7}$)—C(═O)($R^{x8}$) or —C($R^{x1}$)($R^{x2}$)—CH($R^{x7}$)—C(═O)($R^{x8}$) wherein each symbol is as defined above, when —$X^4$-$L^4$ is —CH($R^{x7}$)—C(═O)($R^{x8}$), —$X^2$— is —C($R^{x7}$)═C($R^{x8}$)-#, when —$X^4$-$L^4$ is —C($R^{x1}$)($R^{x2}$)—CH($R^{x7}$)—C(═O)($R^{x8}$), —$X^2$— is —C($R^{x1}$)—($R^{x2}$)—C($R^{x7}$)═C($R^{x8}$)-#, and other symbols are as defined above.

Compound [I-3] can be-obtained by subjecting compound [7] to a ring closure reaction in the same manner as in Production method 3-3.

Production Method 4

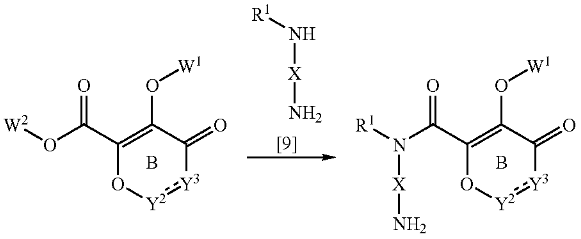

[8] [4]

-continued

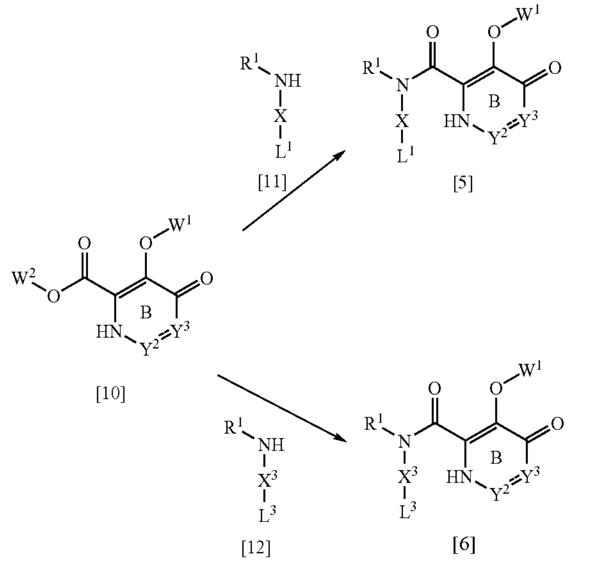

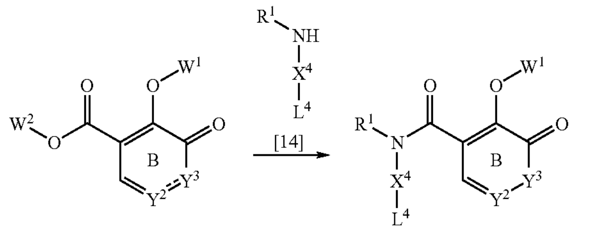

[13] [7]

wherein each symbol is as defined above.

Compound [4], compound [5], compound [6] and compound [7] can be obtained by performing a condensation amidation reaction as illustrated above in the same manner as in Production method 2.

In addition, a method comprising converting a carboxyl group to an acid halide, followed by condensation, is highly versatile, and often leads to good results. Specifically, a starting compound is reacted with thionyl chloride, oxalyl chloride and the like in a halogenated hydrocarbon solvent such as methylene chloride, chloroform and the like or a benzene solvent such as benzene, toluene and the like in the presence or absence of a catalytic amount of dimethylformamide, thereafter reacted in the presence of a base to complete the condensation reaction. Examples of the base to be used include potassium carbonate, sodium carbonate, sodium hydrogen carbonate, triethylamine, pyridine and the like, and good results are often obtained when an organic base such as triethylamine, pyridine and the like is used.

When these reactions are conducted and when other reactive moieties are present, the methods usually employed for general organic reactions often produce good results, wherein they may be protected beforehand and deprotected after the reaction, or condensation reaction is conducted in the form of a stable precursor and thereafter converted to a desired form and the like. Specifically, when two nitrogen atoms are present, a method comprising protecting the one desired to be free from reaction, a method comprising carrying out a condensation reaction using a compound wherein a leaving group moiety is a hydroxyl group, thereby avoiding a reaction between leaving groups $L^1$ to $L^3$ with a nitrogen atom, after which the hydroxyl group is converted to a leaving group and the like can be mentioned.

Compound [8], compound [10] and compound [13] can be prepared by a method described in JP-A-2-502281 (WO88/06588), WO03/016275, J. Med. Chem., 42, 4814–4823, 1999 and the like, or a method analogous thereto.

Compound [9], compound [11], compound [12] and compound [14] can be prepared as a secondary amine by a conventional method.

Production Method 5

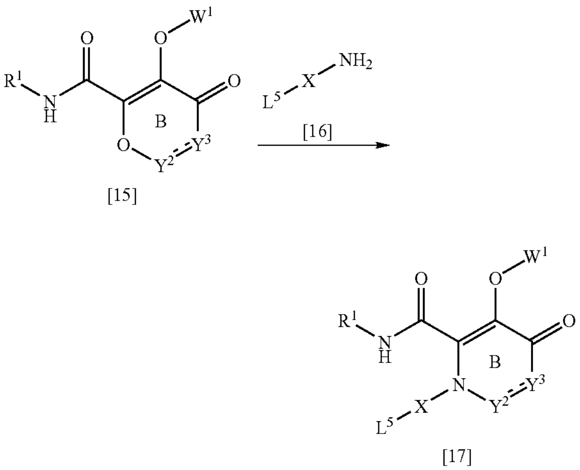

[15]

[16]

[17]

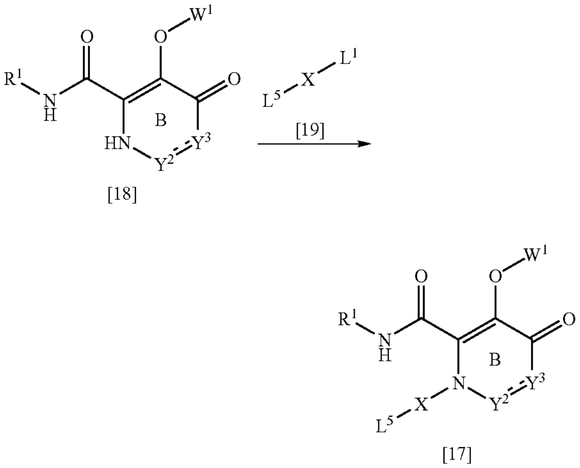

[18]

[19]

[17]

wherein $L^5$ is a leaving group such as chlorine atom, bromine atom, methanesulfonyloxy group, trifluoromethanesulfonyloxy group, toluenesulfonyloxy group and the like, and other symbols are as defined above.

Compound [17] can be obtained by reacting compound [15] or compound [18] as illustrated above in the same manner as in Production method 3. When these reactions are conducted and when other reactive moieties are present, as described in Production method 4, the methods usually employed for general organic reactions often produce good results, wherein they may be protected beforehand and deprotected after the reaction, or condensation reaction is conducted in the form of a stable precursor and thereafter converted to a desired form and the like.

When the amide moiety ($R^1$—HNCO—) of compound [15] and compound [18] is carboxylic acid or carboxylic acid ester ($W^2$—OCO—), $L^5$ may be $R^1$—NH—.

Moreover, $L^5$-X— may be $C(R^{x7})(OMe)_2$-$CH(R^{x8})$— or $C(R^{x7})(OMe)_2$-$CH(R^{x8})$—$C(R^{x1})(R^{x2})$— wherein each symbol is as defined above.

Production Method 6

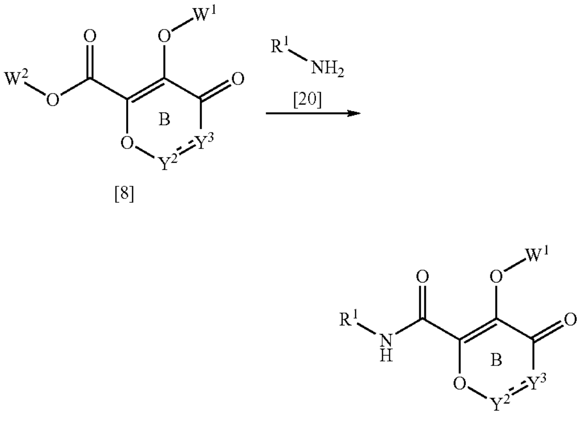

[8]

[20]

[15]

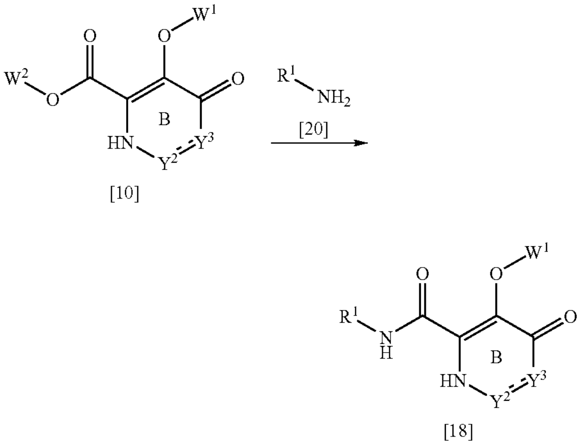

[10]

[20]

[18]

wherein each symbol is as defined above.

Compound [15] and compound [18] can be obtained by performing a condensation amidation reaction as illustrated above in the same manner as in Production method 2.

Production Method 7

Compound [I]-1 wherein, in the formula [I],

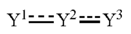

is N—$C(R^{y1})$=$C(R^{y2})$, can be synthesized by the aforementioned production methods (except Production method 3-4).

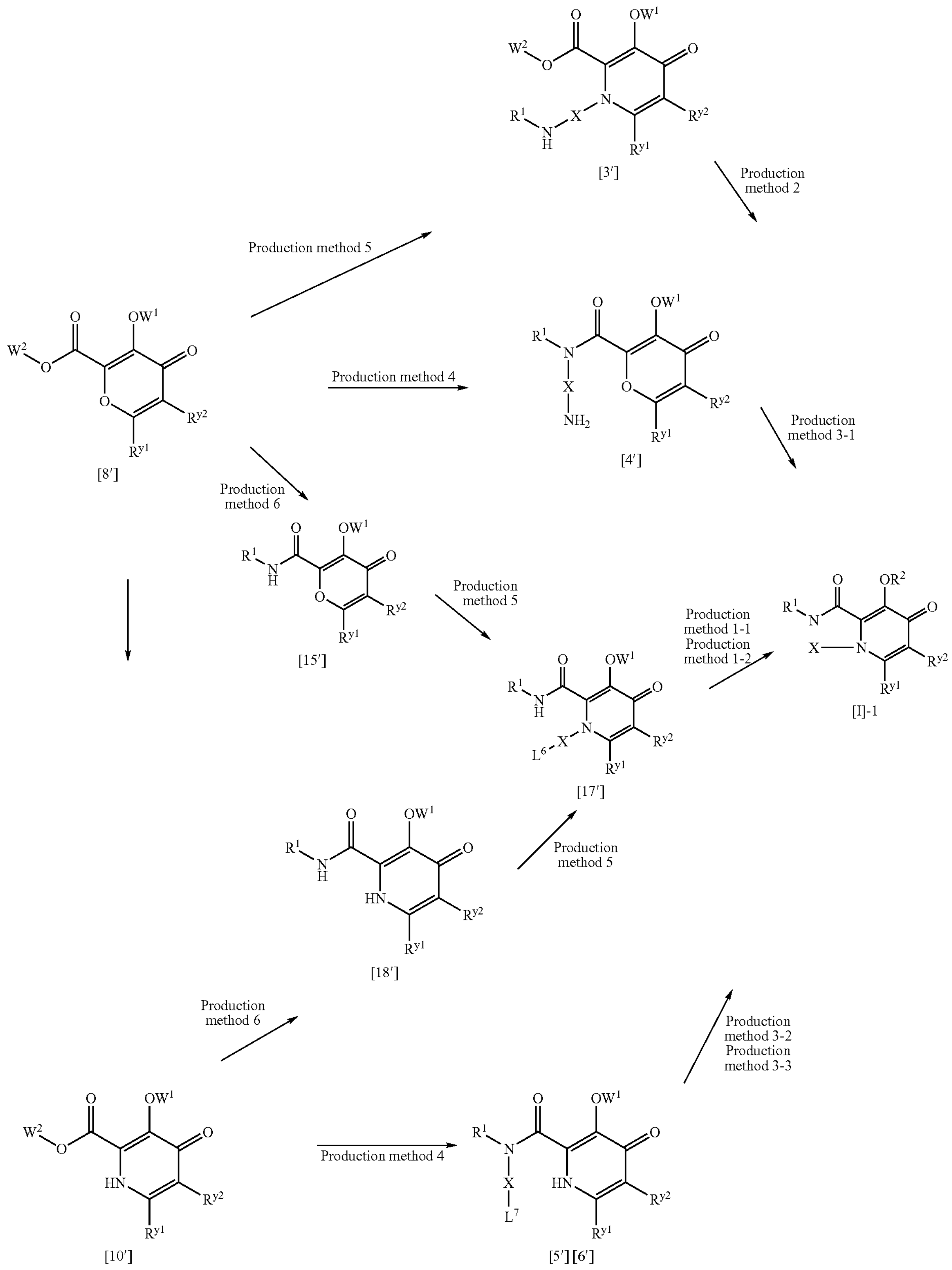
[3′] [8′] [4′] [15′] [17′] [I]-1 [18′] [10′] [5′] [6′]

wherein $L^6$ is $L^1$ or $L^2$, $L^7$ is $L^1$ or $L^3$, and other symbols are as defined above. The production method of each step may be as described for each Production method No. indicated in the scheme.

Compound [10'] can be obtained by reacting compound [8'] With $NH_3$.

When producing compound [I]-1, fine results may be achieved by using a compound wherein $R^{y2}$ is a hydrogen atom and introducing $R^{y2}$ or a precursor thereof in any of the above-mentioned steps.

Specific examples are given in the following.

Production method 7-1

Sons Inc. and the like, by subjecting compound [8'-2] to a coupling reaction using palladium as a catalyst.

More specifically, the following methods can be mentioned.

Production of compound wherein $R^{y2}$ is C6–14 aryl group or heterocyclic group.

For example, the corresponding compound [8'-3] can be obtained by heating compound [8'-2] and $R^{y2}$-$SnBu_3$ in dioxane in the presence of a catalytic amount of tetrakis (triphenylphosphine)palladium(0).

When carrying out this reaction, fine results are often obtained using $R^{y2}$—$B(OH)_2$ instead of $R^{y2}$—$SnBu_3$. While

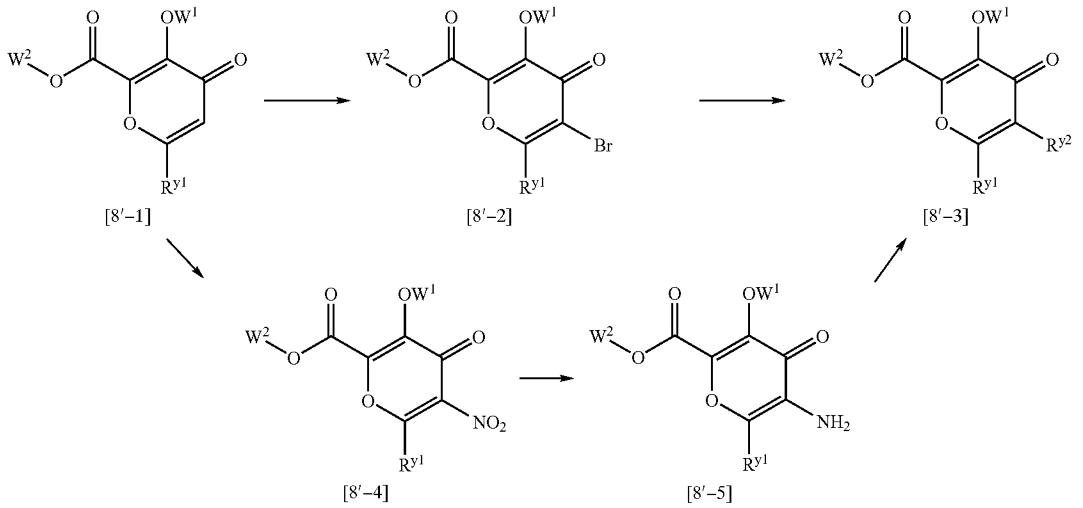

[8'-1] [8'-2] [8'-3] [8'-4] [8'-5]

wherein each symbol is as defined above.

Production of compound wherein $R^{y2}$ is a bromine atom.

Compound [8'-2] can be obtained by reacting compound [8'-1] with a brominating reagent such as bromine, phenyltrimethylammonium tribromide and the like.

As the solvent, chloroform has high versatility, but acetic acid, toluene, chlorobenzene and the like may be also used. In addition, an alcohol solvent such as methanol, ethanol and the like may be used in combination with these solvents.

Production of compound [8'-3] wherein $R^{y2}$ is C1–7 alkyl group, C3–8 cycloalkyl C1–6 alkyl group, C6–14 aryl C1–6 alkyl group, C1–6 alkyloxy group, C6–14 aryl C1–6 alkyloxy group, C6–14 aryl group, heterocyclic group, cyano group, —$CO_2R^{c1}$, —$CONR^{c2}R^{c3}$, —$SO_2NR^{c2}R^{c3}$, C6–14 arylcarbonyl group, —$NR^{c4}R^{c5}$, —$NR^{c6}COR^{c7}$, —$NR^{c8}SO_2R^{c9}$, —$NR^{c13}CONR^{c14}R^{c15}$, —$NR^{c16}CO_2R^{c17}$ or —$NR^{c18}COCOR^{c19}$, wherein each symbol is as defined above.

Synthesis is performed according to a method described in a) Handbook of Palladium—Catalysed Organic Reactions: Synthetic Aspects and Catalytic Cycles. Jean-Luc Malleron et al. (1997) Academic Pr.

b) Palladium in Heterocyclic Chemistry: A Guide for the Synthetic Chemist (Tetrahedron Organic Chemistry Series, V. 20). Jie Jack Li et al. (2000) Elsevier Science Ltd.

c) Handbook of Organopalladium Chemistry for Organic Synthesis, Ei-Ichi Negishi et al. (2002) John Wiley & many useful options of palladium catalyst are described in the above-mentioned reference literatures, one of the options is a combined use of palladium(II) acetate and 1,3-bis (diphenylphosphino)propane. The usable solvent is not limited to those mentioned above, and unless the reaction is particularly inhibited, a comparatively wide variety of solvents such as tetrahydrofuran, toluene and the like can be used. When carrying out this reaction, fine results are often obtained by carrying out the reaction in an inert gas to avoid interference by oxygen and water.

Production of compound wherein $R^{y2}$ is C1–7 alkyl group, C3–8 cycloalkyl C1–6 alkyl group or C6–14 aryl C1–6 alkyl group.

A desired compound [8'-3] can be obtained by, for example, reacting compound [8'-2] with $R^{y2}$—$SnBU_3$ in the same manner as above.

Here, in the case of a compound wherein $R^{y2}$ is $R^{y2'}$—$CX^5H$—$CY^5H$— (wherein $X^5$ and $Y^5$ are each a lower alkyl group such as methyl group, ethyl group and the like and $R^{y2'}$ is a group such as a C1–7 alkyl group, a C3–8 cycloalkyl C1–6 alkyl group and a C6–14 aryl C1–6 alkyl group, wherein the alkyl moiety is free of $CX^5H$—$CY^5H$ moiety), fine results are often obtained by using $R_{y2'}$—$CX^5$═$CY^5$—$SnBu_3$ to give compound [8'-3] wherein $R^{y2}$ is $R^{y2'}$—$CX^5$═$CY^5$—, and subjecting this compound to a catalytic reduction to give compound [8'-3] wherein $R^{y2}$ is $R^{y2'}$—$CX^5H$—$CY^5H$—.

Production of compound wherein $R^{y2}$ is C1–6 alkyloxy group or C6–14 aryl C1–6 alkyloxy group.

A desired compound [8'-3] can be obtained by, for example, reacting compound [8'-2] with $R^{y2'}ONa$ (wherein $R^{y2'}$ is a C1–6 alkyl group or C6–14 aryl C1–6 alkyl group) in toluene in the presence of bis(dibenzylideneacetone) palladium(0) or 1,1'-bis(diphenylphosphino)ferrocene.

Production of compound wherein $R^{y2}$ is cyano group.

The corresponding compound [8'-3] can be obtained by, for example, heating compound [8'-2] and zinc cyanide in the presence of a catalytic amount of tetrakis(triphenylphosphine)palladium(0) in dimethylformamide.

Production of compound wherein $R^{y2}$ is —$CO_2R^{c1}$ or —$CONR^{c2}R^{c3}$.

A compound [8'-3] wherein $R^{y2}$ is —$CO_2R^{c1}$ can be obtained by, for example, heating compound [8'-2] under a carbon monoxide atmosphere in dimethyl sulfoxide in the presence of $R^{c1}OH$, triethylamine, palladium(II) acetate and 1,3-bis(diphenylphosphino)propane.

A compound [8'-3] wherein $R^{y2}$ is —$CO_2H$ can be obtained by using methanol for $R^{c1}OH$ to give compound [8'-3], wherein $R^{y2}$ is —$CO_2CH_3$, and subjecting this compound to hydrolysis by a conventional method using aqueous sodium hydroxide solution/tetrahydrofuran and the like.

Compound [8'-3] wherein $R^{y2}$ is —$CONR^{c2}R^{c3}$ can be obtained by condensation of this compound with $NHR^{c2}R^{c3}$. As used herein, the condensation reaction can be carried out according to the aforementioned production method 2 and production method 4.

Production of compound wherein $R^{y2}$ is —$NR^{c4}R^{c5}$.

A desired compound [8'-3] can be obtained by, for example, heating compound [8'-2] and $HNR^{c4}R^{c5}$ in the presence of cesium carbonate and a catalytic amount of palladium(II) acetate and 2,2'-bis(di-tert-butylphosphino)-1,1'-binaphthyl in benzene.

Production of compound wherein $R^{y2}$ is —$NR^{c6}COR^{c7}$, —$NR^{c8}SO_2R^{c9}$, —$NR^{c13}CONR^{c14}R^{c15}$, —$NR^{c16}CO_2R^{c17}$ or —$NR^{c18}COCOR^{c19}$.

Compound (8'-3] wherein $R^{y2}$ is —$NR^{c6}COR^{c7}$ can be obtained by, for example, heating compound [8'-2] and $HNR^{c6}COR^{c7}$ in toluene in the presence of sodium tert-butoxide and a catalytic amount of palladium(II) acetate or 1,1'-bis(diphenylphosphino)ferrocene.

While compound [8'-3] wherein $R^{y2}$ is —$NR^{c8}SO_2R^{c9}$, —$NR^{c13}CONR^{c14}R^{c15}$, —$NR^{c16}CO_2R^{c17}$ and —$NR^{c18}COCOR^{c19}$ can be also synthesized in the same manner, finer results are sometimes obtained when the reaction is carried out step by step. That is, $NH_2CO_2$t-Bu and compound [8'-2] are subjected to a reaction similar to the one mentioned above, whereby compound [8'-3] wherein $R^{y2}$ is —$NHCO_2$t-Bu can be obtained. This is treated with trifluoroacetic acid, hydrochloric acid-dioxane and the like according to a conventional method to-give compound [8'-5] wherein $R^{y2}$ is —$NH_2$ can be obtained.

The corresponding compound [8'-3] can be synthesized by reacting the obtained compound [8'-5] with the corresponding. carboxylic acid (e.g., $R^{c7}CO_2H$), carboxylic acid anhydride (e.g., $R^{c7}CO_2COR^{c7}$) or acid chloride (e.g., $R^{c7}COCl$), chlorocarbonic acid ester ($R^{c17}OCOCl$), isocyanate ($R^{c14}$—NCO), chlorocarbonic acid amide ($R^{c14}R^{c15}NCOCl$), sulfonyl chloride ($R^{c9}SO_2Cl$) and the like, as described in the above-mentioned Production method 2 and Production method 4.

$R^{c6}$, $R^{c8}$, $R^{c13}$, $R^{c16}$ or $R^{c18}$ may be introduced into —$NH_2$ prior to the above-mentioned reactions or after the reactions by a conventional method.

Production of compound wherein $R^{y2}$ is amino group.

Compound [8'-4] can be obtained by reacting compound [8'-1] with nitric acid, fuming nitric acid, nitronium tetrafluoroborate and the like.

As the solvent, acetic acid, chloroform and the like are generally used and various conditions known as nitration conditions of aromatic ring may be used.

Compound [8'-5] can be obtained by subjecting [8'-4] to catalytic reduction, reduction with a metal powder such as iron, zinc and the like, or reduction with a metal ion such as tin chloride and the like.

As a solvent for reduction with a metal powder, acetic acid, hydrochloric acid-alcohol, hydrochloric acid-tetrahydrofuran and the like are generally used and for reduction using tin chloride, methanol or ethanol is generally used.

The above-mentioned introduction of Br and conversion to $R^{y2}$ are not limited by compound [8] and can be performed at a desired or suitable timing in the whole steps in the already described Production methods, wherein introduction of Br and conversion to $R^{y2}$ may be conducted in different steps. Particularly, introduction of Br sometimes provide fine results when done in compound [5], [6], [10], [17], [18], [10] or [I-1].

Production Method 7-2

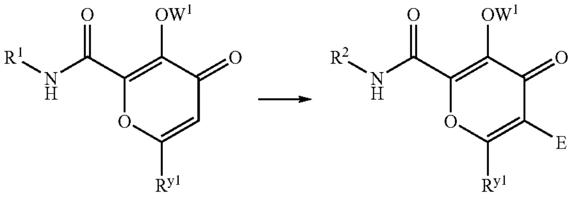

[15'-1] [15'-2]

wherein E is a functional group derived from an electrophile corresponding to $R^{y2}$ such as —$COR^{c4}$, —COOH, —$SR^{c10}$ and the like, and each symbol is as defined above.

As a different method of introducing a functional group, a method comprising reacting compound (15'-1] with a base and then reacting with an electrophile can be mentioned.

Specific examples of electrophile include esters, aldehydes, ketones, disulfides, carbon dioxide and the like.

As the base to be used, lithium diisopropylamide, potassium hexamethyldisilamide, n-butyllithium and the like can be mentioned, and as a solvent, tetrahydrofuran, diethyl ether, dimethoxyethane and the like can be mentioned. When lithium diisopropylamide is used in tetrahydrofuran, fine results are often obtained. As the reaction temperature, when a reaction is carried out at room temperature to under cooling, fine results are often obtained. In this way, the introduced functional group can be also converted to a desired and suitable $R^{y2}$ by various known reactions.

As concrete examples, the following production methods can be mentioned.

Production of compound wherein $R^{y2}$ is —$COR^{c4}$.

Compound [15'-2] wherein $R^{y2}$ is —$CH(OH)R^{c4}$ can be obtained by adding $R^{c4}$—CHO as an electrophile to compound [15'-1] treated with lithium diisopropylamide at −78° C. in tetrahydrofuran.

The obtained compound [15'-2] wherein $R^{y2}$ is —CH(OH)$R^{c4}$ can be converted to compound [15'-2] wherein $R^{y2}$ is —$COR^{c4}$ by a treatment with a sulfur trioxide pyridine complex in the presence of triethylamine and dimethyl sulfoxide in a solvent that does not itself inhibit the reaction such as chloroform. This oxidation reaction is not limited to the above-mentioned conditions, and the conditions comprising using 1,1,1-tris(acetoxy)-1,1-dihydro-1,2-benziodoxol-3-(1H)-one (Dess-Martin reagent) as an oxidant in chloroform also affords fine results. While the reaction is carried out at room temperature to under cooling under any conditions, the range of from 0° C. to room temperature is more preferable.

Production of compound wherein $R^{y2}$ is —COOH, —$SR^{c10}$, —$SOR^{c11}$ or —$SO_2R^{c12}$.

Using carbon dioxide or disulfide ($R^{c10}SSR^{c10}$ etc.) as an electrophile, compound [15'-2] wherein $R^{y2}$ is —COOH or —$SR^{c10}$ can be obtained. Compound [15'-2] wherein $R^{y2}$ is —$SR^{c10}$ is treated with a peracid such as m-chloroperbenzoic acid and the like in chloroform, whereby compound [15'-2] wherein $R^{y2}$ is —$SOR^{c11}$ or —$SO_2R^{c12}$ can be obtained.

The introduction of E by electrophile and conversion to $R^{y2}$ are not limited by compound [15] and can be performed at a desired or suitable timing in the whole steps in the already described Production methods, wherein introduction of E and conversion to $R^{y2}$ may be conducted in different steps.

However, in order to control side reaction, it is often better to not introduce E by electrophile in the presence of a base in compounds [3], [8] and [10].

Production Method 8

Production Method 8-1

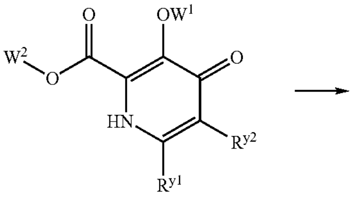

[10']

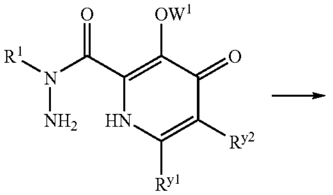

[19]

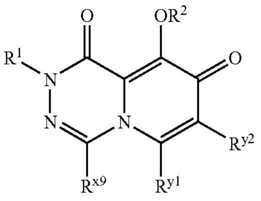

[I-5]

wherein each symbol is as defined above.

Compound [I-5] can be obtained by converting compound [10'] to compound [19] and sequentially condensing the compound with a compound represented by $R^{x9}$—$CH(OMe)_2$.

For conversion of compound [10'] to compound [19] here, $R^1$—NHNH—W (W is amino-protecting group) is used instead of $R^1$—$NH_2$, and a method according to the method described in Production method 6 is performed.

A condensation reaction of compound [19] to compound [I-5] is carried out in the presence of an acid catalyst such as hydrochloric acid, p-toluenesulfonic acid, pyridinium p-toluenesulfonate and the like in a benzene solvent such as benzene, toluene, chlorobenzene and the like or an alcohol solvent such as methanol, ethanol and the like at room temperature to under heating.

Production Method 8-2

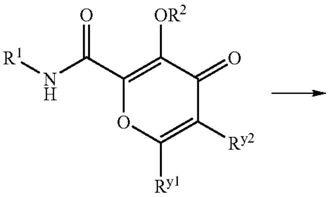

[8']

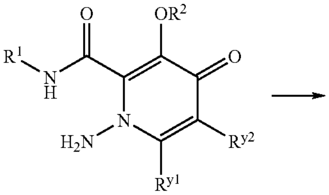

[20]

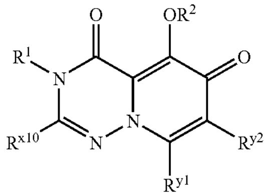

[I-6]

wherein each symbol is as defined above.

Compound [I-6] can be obtained by converting compound [8'] to compound [20] and sequentially condensing with a compound represented by $R^{x10}$—$CH(OMe)_2$.

For conversion of compound [8'] to compound [20] here, W—NH—$NH_2$ (W is amino-protecting group) is used instead of $L^5$-X—$NH_2$, and a method according to the method described in Production method 5 is performed. A condensation reaction of compound [20] to compound [I-6] is carried out under acidic conditions in the same manner as in Production method 8-1.

Production Method 3-5

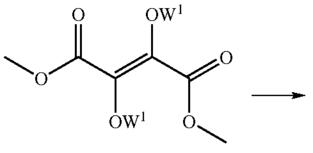

[21]

-continued

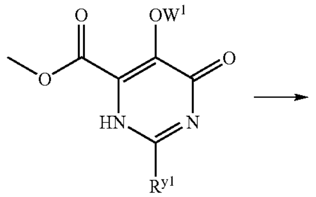

[22]

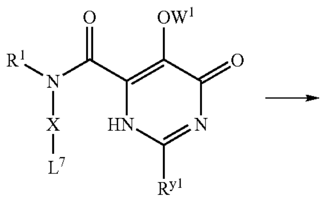

[23]

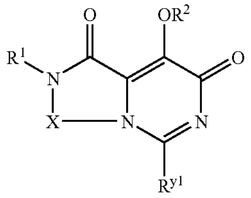

[I]-2 wherein each symbol is as defined above.

Compound [I]-2 is a part of the compound represented by the formula [I] and produced according to the aforementioned method, wherein preferable results are often obtained when the production follows this production method.

That is, compound [22] is synthesized by reacting compound [21] prepared according to the a method described in a reference (Breslow, D. S. et al., J. Am. Chem. Soc., 1946, 68, 1232) or a method analogous thereto with $R^{y1}$—$C(NH_2)$=NH under acidic conditions or basic conditions. As the acid to be used, hydrochloric acid, p-toluenesulfonic acid and the like can be mentioned, and the acid is generally applied to the reaction in the form of an amidine salt. Where necessary, the acid may be further added. As the base, sodium methoxide, potassium carbonate and the like can be mentioned, and as the solvent, methanol, ethanol, dioxane, tetrahydrofuran and the like can be mentioned. This reaction can be carried out in such a solvent that does not particularly inhibit the reaction under comparatively wide pH conditions. As a preferable method, for example, conditions under which the reaction is carried out in methanol using sodium methoxide as a base under heating can be mentioned.

The subsequent production step to produce compound [I]-2 from compound [22] via compound [23] is performed according to the aforementioned Production method 4 and Production method 3. Prior to this conversion, it is necessary to hydrolyze compound [22] into carboxylic acid in a solvent such as alcohol, tetrahydrofuran and the like using sodium hydroxide and the like.

Production Method 3-6

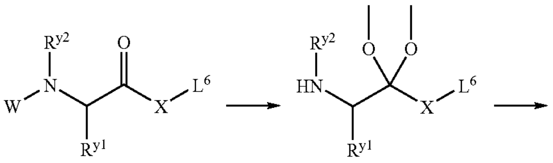

[24] [25]

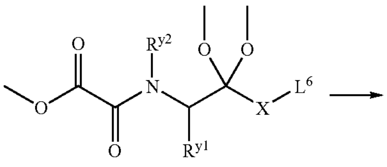

[26]

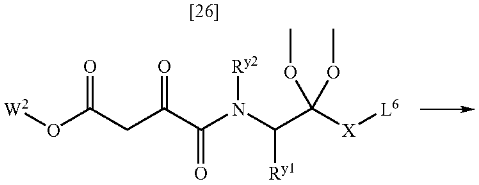

[27]

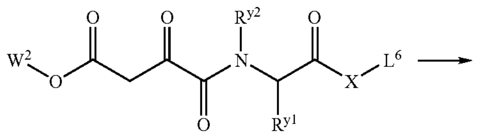

[28]

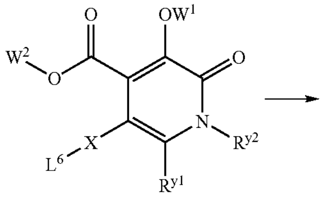

[29]

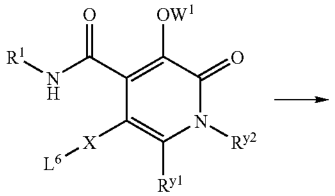

[30]

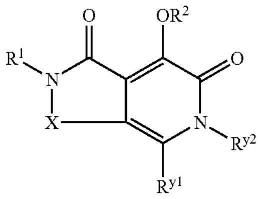

[I]-3 wherein each symbol is as defined above.

Preferable results are often obtained when the production of compound [I]-3 follows this production method.

That is, compound [24] derived from amino acid is reacted with methyl orthoformate in methanol or without solvent in the presence of an acid catalyst such as hydrochloric acid, p-toluenesulfonic acid, pyridinium p-toluenesulfonate and the like, and thereafter deprotected, whereby compound [25] can be obtained.

Compound [26] can be obtained by reacting compound [25] with methyl chloroglyoxylate in the presence of a base such as pyridine, triethylamine and the like in a solvent such as chloroform, toluene, tetrahydrofuran and the like or without solvent. Fine results are often obtained when this reaction is carried out under cooling.

Compound [27] can be obtained by reacting compound [26] with $W^2$—OAc. When performing this reaction, fine results are often obtained when $W^2$—OAc is treated with a base such as lithium diisopropylamide, lithium hexamethyldisilamide and the like in a solvent such as tetrahydrofuran and the like to give an enolate, which is then reacted with compound [26]. While the reaction is carried out at room temperature to under cooling, preferable results are often obtained when the reaction is particularly carried out at a temperature not more than 0° C.

Compound [28] can be obtained by hydrolyzing compound [27] under acidic conditions. As the acid to be used, 4N (or below) hydrochloric acid is preferable, and the reaction is carried out in tetrahydrofuran or dioxane.

Compound [29] can be obtained by treating compound [28] with a base. As the base to be used, a metal salt such as potassium carbonate, sodium carbonate and the like, a metal amide such as lithium diisopropylamide, potassium hexamethyldisilamide and the like, and an organic base such as triethylamine, ethyldiisopropylamine, pyridine and the like can be mentioned, and preferable results are often obtained when triethylamine, ethyldiisopropylamine and the like are used. There are many options of solvent, and, for example, chloroform, tetrahydrofuran, dioxane, methanol, ethanol, toluene and the like can be mentioned, which are obviously subject to limitation depending on the kind of a base to be used.

A step to produce compound [I]-3 from compound [29] via compound [30] can be performed according to the aforementioned Production method 5 and Production method 1-1 or 1-2.

Production Method 3-7

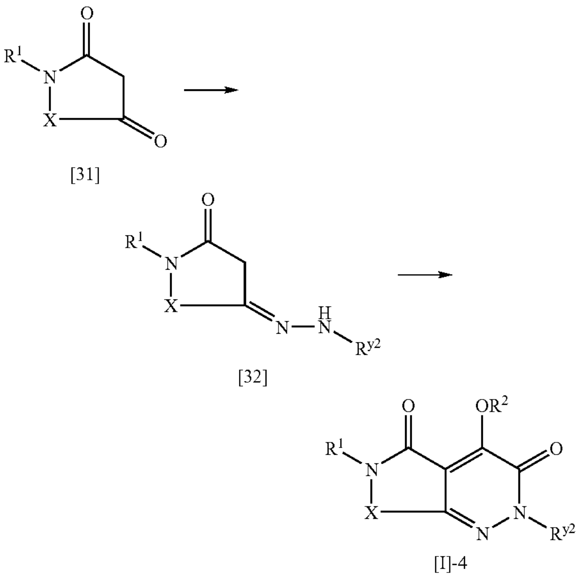

[31]

[32]

[I]-4 wherein each symbol is as defined above.

Compound [32] can be synthesized by reacting compound [31] prepared by the method described in a reference (Micovic, I. V. et al., J. Chem. Soc., Perkin Trans. 1(1996) 16, 2041) or a method analogous thereto with a compound $H^2N$—NH—$R^{y2}$ in a solvent such as methanol, ethanol, tetrahydrofuran, dioxane, toluene and the like at room temperature to under heating.

Compound [I]-4 can be obtained by reacting compound [32] with oxalyl chloride in the presence of an organic base such as triethylamine, ethyldiisopropylamine, pyridine and the like in a solvent such as chloroform, tetrahydrofuran, dioxane, toluene and the like. While the reaction temperature is subject to no limitation, preferable results are often obtained when the reaction is carried out under cooling to room temperature.

EXAMPLES

The nitrogen-containing fused ring compound represented by the formula [I] and a pharmaceutically acceptable salt thereof of the present invention and production methods thereof are now specifically explained by way of Examples. However, the present invention is not limited by these Examples.

Example 1

Synthesis of 2-(3,4-dichlorobenzyl)-9-hydroxy-3,4-dihydro-2H-pyrido[1,2-a]pyrazine-1,8-dione hydrochloride

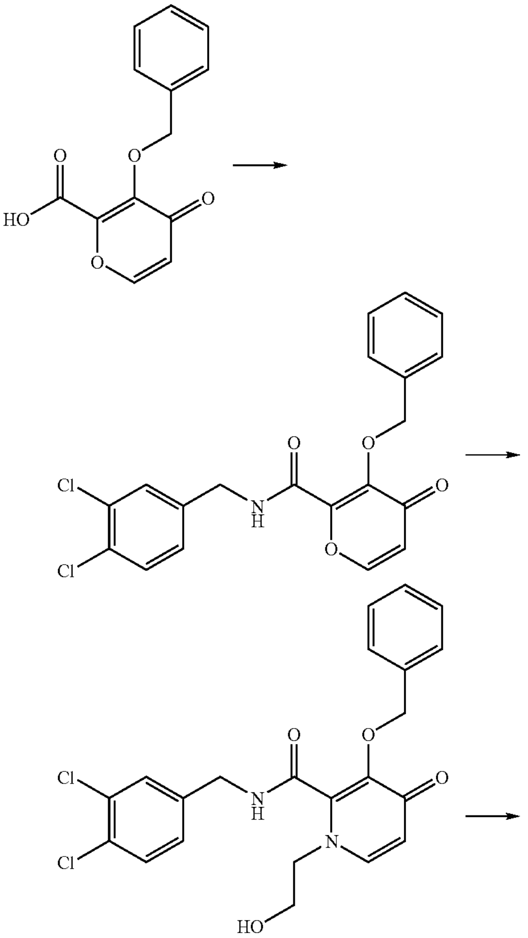

-continued

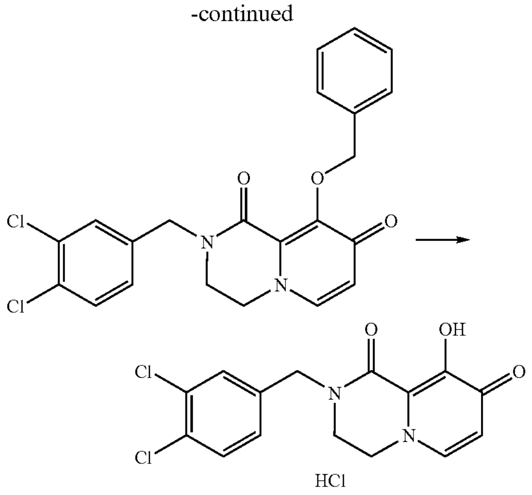

Step 1

To a solution of 3-benzyloxy-4-oxo-4H-pyran-2-carboxylic acid (0.4 g) prepared according to the method described in references (JP-A-2-502281 (WO88/06588), J. Med. Chem., 1999, 42, 4814–4823) in chloroform (30 ml) were added oxalyl chloride (0.21 ml) and dimethylformamide (0.01 ml), and the mixture was stirred at room temperature for 30 min. The reaction solvent was evaporated under reduced pressure, toluene was added, the mixture was concentrated and dissolved in chloroform (5 ml). 3,4-Dichlorobenzylamine (0.23 ml) and triethylamine (0.34 ml) were added successively under ice-cooling, and the mixture was stirred under ice-cooling for 20 min. 5% Aqueous potassium hydrogen sulfate solution was added to the obtained reaction mixture and the mixture was extracted with. chloroform. The organic layer was washed with saturated brine and dried over sodium sulfate. The solvent was evaporated and the residue was purified by silica gel column chromatography (hexane:ethyl acetate=1:1–1:8) to give N-(3,4-dichlorobenzyl)-3-benzyloxy-4-oxo-4H-pyran-2-carboxamide (0.43 g).

$^1$H-NMR ($CDCl_3$)δ 9.15(t, 1H, J=6.0 Hz), 8.19(d, 1H, J=5.8 Hz), 7.54(s, 1H), 7.53(d, 1H, J=8.4 Hz), 7.31–7.20(m, 5H), 6.51(d, 1H, J=5.8 Hz), 5.17(s, 2H), 4.46(d, 1H, J=6.0 Hz).

Step 2

To a solution of N-(3,4-dichlorobenzyl)-3-benzyloxy-4-oxo-4H-pyran-2-carboxamide obtained in the previous step in tetrahydrofuran (1 ml), ethanol (1 ml) and water (0.2 ml) were added successively ethanolamine (0.05 ml) and 2N aqueous sodium carbonate solution (0.06 ml), and the mixture was stirred at room temperature for 1 hr and at 35° C. for 4 hrs. The solvent was evaporated, and the obtained crystals were washed successively with ethyl acetate and water and dried to give N-(3,4-dichlorobenzyl)-3-benzyloxy-1-(2-hydroxyethyl)-4-oxo-1,4-dihydropyridine-2-carboxamide (0.142 g).

$^1$H-NMR (DMSO-$d_6$)δ 9.46(t, 1H, J=5.8 Hz), 7.60(d, 1H, J=7.7 Hz), 7.56(d, 1H, J=2.1 Hz), 7.32(d, 1H, J=8.3 Hz), 7.30–7.27(m, 5H), 7.25(dd, 1H, J=2.1,8.3 Hz), 6.24(d, 1H, J=7.7 Hz), 5.05(s, 2H), 5.06–5.01(m, 1H), 4.41(d, 1H, J=5.8 Hz), 3.88–3.81(m, 2H), 3.65–3.57(m, 2H).

Step 3

To N-(3,4-dichlorobenzyl)-3-benzyloxy-1-(2-hydroxyethyl)-4-oxo-1,4-dihydropyridine-2-carboxamide (0.142 g) obtained in the previous step was added dry tetrahydrofuran (2 ml), and the mixture was cooled under an argon atmosphere at 0° C. Diisopropylethylamine (0.026 ml) and methanesulfonyl chloride (0.009 ml) were successively added dropwise at the same temperature, and the mixture was stirred at room temperature for 1 hr. Diisopropylethylamine (0.053 ml) and methanesulfonyl chloride (0.019 ml) were successively added dropwise again at 0° C., and the mixture was stirred at room temperature for 1 hr. 1N Aqueous hydrochloric acid was added to the obtained reaction mixture under ice-cooling, and the mixture was extracted three times with ethyl acetate. The organic layer was washed with saturated brine and dried over sodium sulfate. The solvent was evaporated and the obtained crude product was dissolved in dry tetrahydrofuran (4 ml). Sodium hydride (60%) (8 mg) was added, and the mixture was heated at 80° C. Sodium hydride (60%) (8 mg) was added every 30 minutes, and after adding 5 times in total, 1N aqueous hydrochloric acid was added under ice-cooling, and the mixture was extracted three times with ethyl acetate. The organic layer was washed with saturated brine and dried over sodium sulfate. The solvent was evaporated and the residue was purified by thin layer chromatography (ethyl acetate:methanol=5:2) to give 9-benzyloxy-2-(3,4-dichlorobenzyl)-3,4-dihydro-2H-pyrido[1,2-a]pyrazine-1,8-dione (22 mg).

$^1$H-NMR (DMSO-$d_6$)δ 7.64(d, 1H, J=7.4 Hz), 7.62–7.56 (m, 2H), 7.51–7.46(m, 2H), 7.34–7.22(m, 4H), 6.26(d, 1H, J=7.4 Hz), 5.08(s, 2H), 4.67(s, 2H), 4.17–4.08(m, 2H), 3.63–3.55(m, 2H).

Step 4

To 9-benzyloxy-2-(3,4-dichlorobenzyl)-3,4-dihydro-2H-pyrido[1,2-a]pyrazine-1,8-dione (12 mg) obtained in the previous step were added acetic acid (0.75 ml) and conc. hydrochloric acid (0.15 ml) and the mixture was stirred at 90° C. for 20 min. The solvent was evaporated, and the obtained residue was crystallized from hexane:ethyl acetate=1:2 to give 2-(3,4-dichlorobenzyl)-9-hydroxy-3,4-dihydro-2H-pyrido[1,2-a]pyrazine-1,8-dione hydrochloride (8 mg).

$^1$H-NMR (DMSO-$d_6$)δ 7.96(d, 1H, J=7.2 Hz), 7.67(d, 1H, J=1.9 Hz), 7.62(d, 1H, J=8.4 Hz), 7.36(dd, 1H, J=1.9, 8.4 Hz), 6.73(d, 1H, J=7.2 Hz), 4.74(s, 2H), 4.42–4.36(m, 2H), 3.79–3.74(m, 2H).

Example 2

Synthesis of 2-(3,4-dichlorobenzyl)-10-hydroxy-2,3,4,5-tetrahydropyrido[1,2-a][1,4]diazepine-1,9-dione

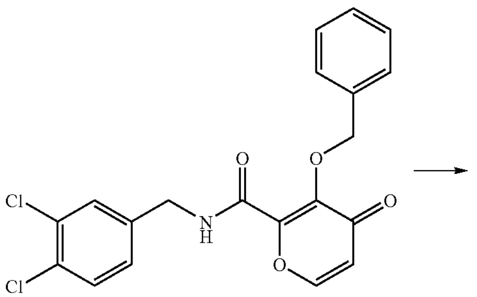

-continued

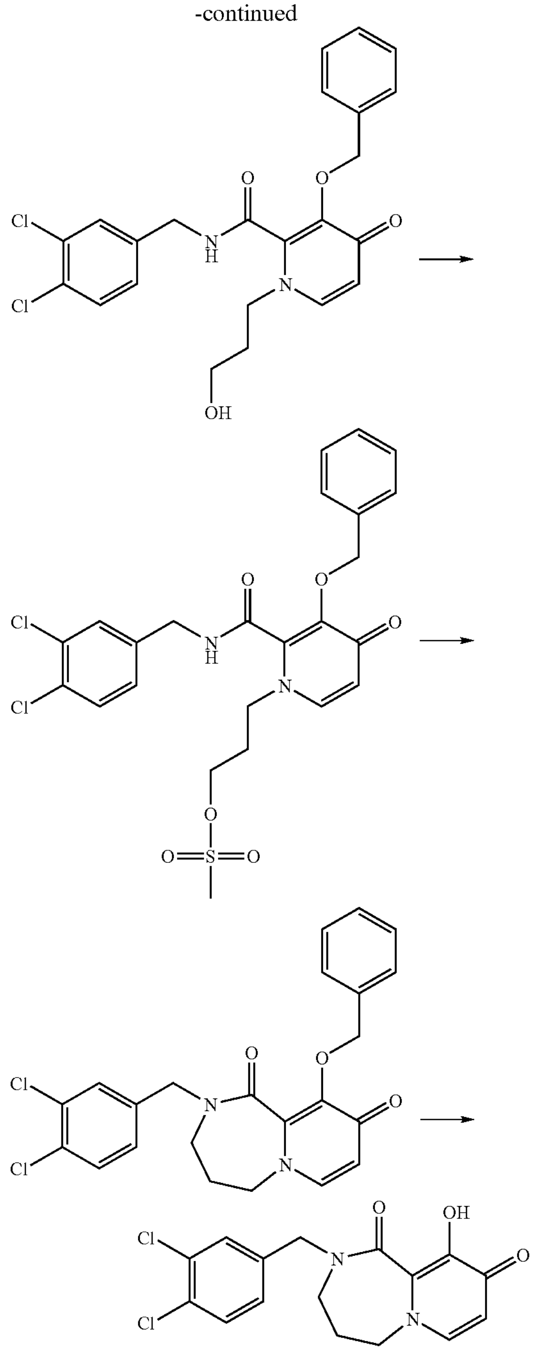

Step 1

N-(3,4-Dichlorobenzyl)-3-benzyloxy-4-oxo-4H-pyran-2-carboxamide (60 mg) obtained in the same manner as in Example 1, step 1 was dissolved in tetrahydrofuran (0.5 ml), ethanol (0.5 ml) and water (0.1 ml), and 3-amino-1-propanol (0.0226 ml) and sodium carbonate (8 mg) were successively added. The mixture was stirred at room temperature for 7 hr. The solvent was evaporated, and the obtained residue was purified by silica gel column chromatography (ethyl acetate: methanol=100:0–4:1) to give N-(3,4-dichlorobenzyl)-3-benzyloxy-1-(3-hydroxypropyl)-4-oxo-1,4-dihydropyridine-2-carboxamide (43 mg).

$^1$H-NMR (DMSO-$d_6$)δ 9.47(t, 1H, J=6.0 Hz), 7.65(d, 1H, J=7.4 Hz) 7.57(d, 1H, J=1.9 Hz), 7.34–7.25(m, 7H), 6.26(d, 1H, J=7.4 Hz), 5.05(s, 2H), 4.65(t, 1H, J=4.9 Hz), 4.42(d, 2H, J=6.0 Hz), 3.86(dd, 2H, J=7.2, 7.2 Hz), 3.35(dd, 2H, J=6.3, 10.9 Hz), 1.84–1.77(m, 2H).

Step 2

N-(3,4-Dichlorobenzyl)-3-benzyloxy-1-(3-hydroxypropyl)-4-oxo-1,4-dihydropyridine-2-carboxamide (30 mg) obtained in the previous step was dissolved in tetrahydrofuran (1.5 ml) and the mixture was cooled to 0° C. under an argon atmosphere. Diisopropylethylamine (0.034 ml) and methanesulfonyl chloride (0.0065 ml) were successively added dropwise at the same temperature and the mixture was stirred at room temperature for 2 hr. Diisopropylethylamine (0.017 ml) and methanesulfonyl chloride (0.005 ml) were successively added dropwise again at 0° C., and the mixture was stirred at room temperature for 1.5 hr. To the obtained reaction mixture was added 1N aqueous hydrochloric acid under ice-cooling, and the mixture was extracted twice with ethyl acetate. The combined organic layer was washed successively with saturated aqueous sodium hydrogen carbonate solution and saturated brine and dried over sodium sulfate. The solvent was evaporated and the obtained crude product was dissolved in tetrahydrofuran (1.5 ml). Sodium hydride (60%) (5 mg) was added at room temperature, and sodium hydride (60%) (8 mg) was added every 30 minutes. After adding 3 times in total, 1N aqueous hydrochloric acid was added under ice-cooling, and the mixture was extracted twice with ethyl acetate. The combined organic layer was washed successively with saturated aqueous sodium hydrogen carbonate solution and saturated brine and dried over sodium sulfate. The solvent was evaporated, and the obtained residue was purified by thin layer chromatography (ethyl acetate:methanol=2:1) to give 10-benzyloxy-2-(3,4-dichlorobenzyl)-2,3,4,5-tetrahydropyrido[1,2-a][1,4]diazepine-1,9-dione (23 mg).

$^1$H-NMR ($CDCl_3$)δ 7.49–7.46(m, 3H), 7.39(d, 1H, J=8.3 Hz), 7.30–7.26(m, 3H), 7.22(dd, 1H, J=2.3,8.3 Hz), 7.09(d, 1H, J=7.5 Hz), 6.46(d, 1H, J=7.5 Hz), 5.69(d, 1H, J=10.9 Hz), 5.06(d, 1H, J=10.9 Hz), 4.71(d, 1H, J=14.7 Hz), 4.48(d, 1H, J=14.7 Hz), 3.82–3.77(m, 2H), 3.07(dd, 1H, J=6.8, 15.5 Hz), 2.96–2.85(m, 1H), 1.92–1.79(m, 1H), 1.74–1.61(m, 1H).

Step 3

10-Benzyloxy-2-(3,4-dichlorobenzyl)-2,3,4,5-tetrahydropyrido[1,2-a][1,4]diazepine-1,9-dione (15 mg) obtained in the previous step was dissolved in trifluoroacetic acid (1.0 ml), and the mixture was stirred at room temperature for 30 min and then at 60° C. for 1.5 hr. The solvent was evaporated, toluene was added, and the mixture was concentrated, which operations were performed 3 times. Ethyl acetate was added and the mixture was concentrated, which operations were performed 2 times. The obtained residue was crystallized from ethyl acetate/hexane to give 2-(3,4-dichlorobenzyl)-10-hydroxy-2,3,4,5-tetrahydropyrido[1,2-a][1,4]diazepine-1,9-dione (11 mg)

$^1$H-NMR (DMSO-$d_6$)δ 7.79(brs, 1H), 7.66(d, 1H, J=8.3 Hz), 7.65(d, 1H, J=2.3 Hz), 7.38(dd, 1H, J=2.3, 8.3 Hz), 6.50(brs, 1H), 4.68(brs, 2H), 4.10(brs, 2H), 3.33(bt, 2H, J=6.4 Hz), 1.94(bt, 2H, J=6.4 Hz).

Example 3

Synthesis of 2-(3,4-dichlorobenzyl)-9-hydroxy-3-methyl-3,4-dihydro-2H-pyrido[1,2-a]pyrazine-1,8-dione

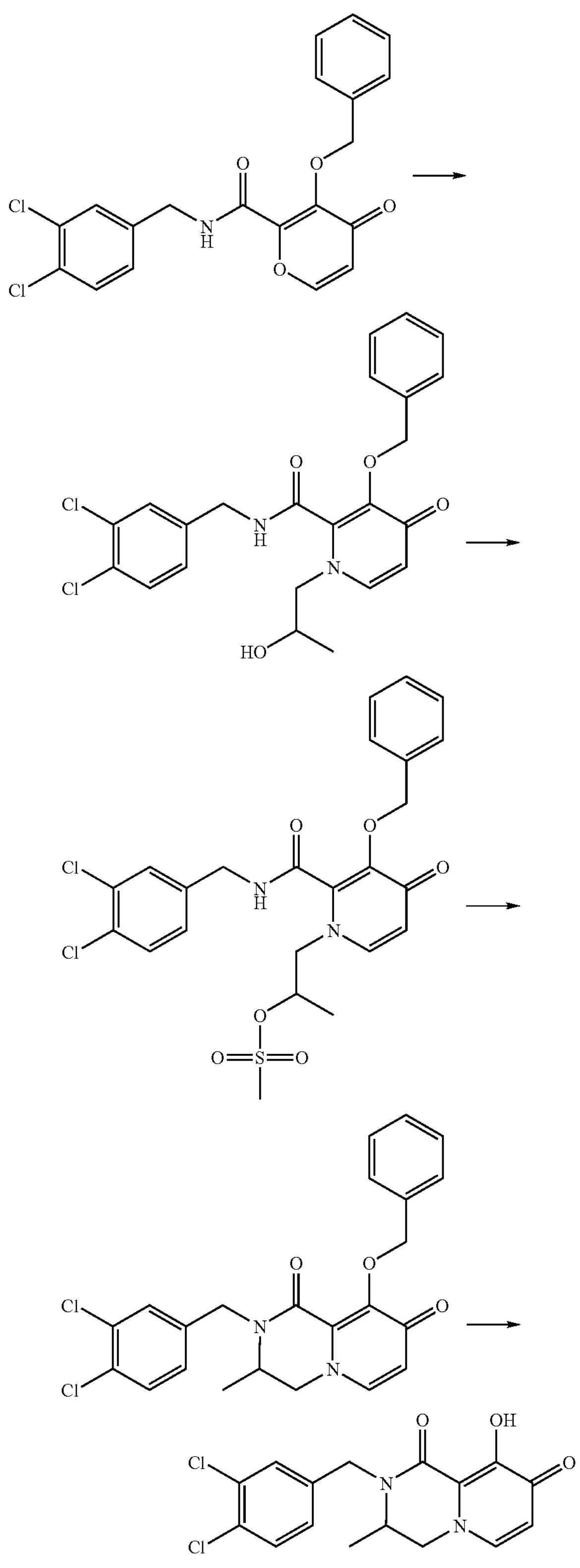

Step 1

N-(3,4-Dichlorobenzyl)-3-benzyloxy-4-oxo-4H-pyran-2-carboxamide (50 mg) obtained in the same manner as in Example 1, Step 1 was dissolved in tetrahydrofuran (0.5 ml), ethanol (0.5 ml) and water (0.1 ml). DL-1-Amino-2-propanol (0.0191 ml) and sodium carbonate (7 mg) were successively added, and the mixture was stirred overnight at room temperature. The solvent was evaporated, and the obtained residue was purified by silica gel column chromatography (ethyl acetate:methanol=100:0–4:1) to give N-(3,4-dichlorobenzyl)-3-benzyloxy-1-(2-hydroxypropyl)-4-oxo-1,4-dihydropyridine-2-carboxamide (34 mg).

$^1$H-NMR (DMSO-$d_6$)δ 9.43(t, 1H, J=6.3 Hz), 7.57(s, 1H) 7.57(d, 1H, J=7.4 Hz), 7.36(d, 1H, J=8.1 Hz), 7.31–7.26(m, 6H), 6.23(d, 1H, J=7.4 Hz), 5.08(d, 1H, J=10.9 Hz), 5.04(d, 1H, J=10.9 Hz), 5.02(d, 1H, J=6.3 Hz), 4.44(dd, 1H, J=6.3, 14.8 Hz), 4.37(dd, 1H, J=6.3,14.8 Hz), 3.81(brs, 1H), 3.69 (dd, 1H, J=3.7,14.4 Hz), 3.60(dd, 1H, J=8.8,14.4 Hz), 0.94 (d, 3H, J=6.3 Hz).

Step 2

N-(3,4-Dichlorobenzyl)-3-benzyloxy-1-(2-hydroxypropyl)-4-oxo-1,4-dihydropyridine-2-carboxamide (34 mg) obtained in the previous step was dissolved in tetrahydrofuran (1.5 ml) and the mixture was cooled to 0° C. under an argon atmosphere. Diisopropylethylamine (0.0385 ml) and methanesulfonyl chloride (0.0074 ml) were successively added dropwise at the same temperature, and the mixture was stirred at room temperature for 1 hr. Diisopropylethylamine (0.0385 ml) and methanesulfonyl chloride (0.0074 ml) were successively added dropwise at 0° C. and the mixture was stirred at room temperature for 1.5 hr. To the obtained reaction mixture was added 1N aqueous hydrochloric acid under ice-cooling, and the mixture was extracted twice with ethyl acetate. The combined organic layer was washed successively with saturated aqueous sodium hydrogen carbonate solution and saturated brine, and dried over sodium sulfate. The solvent was evaporated and the obtained crude product was dissolved in tetrahydrofuran (1.5 ml). Sodium hydride (60%) (5 mg) was added at room temperature, and sodium hydride (60%) (8 mg) was added every 30 minutes. After adding 3 times in total, 1N aqueous hydrochloric acid was added under ice-cooling, and the mixture was extracted twice with ethyl acetate. The combined organic layer was washed successively with saturated aqueous sodium hydrogen carbonate solution and saturated brine, and dried over sodium sulfate. The solvent was evaporated, and the obtained residue was purified by thin layer chromatography (ethyl acetate:methanol=2:1) to give 9-benzyloxy-2-(3,4-dichlorobenzyl)-3-methyl-3,4-dihydro-2H-pyrido[1,2-a]pyrazine-1, 8-dione (8 mg).

$^1$H-NMR ($CDCl_3$)δ 7.62–7.59(m, 2H), 7.45–7.42(m, 2H), 7.35–7.27(m, 3H), 7.20(dd, 1H, J=2.3,8.3 Hz), 7.13(d, 1H, J=7.5 Hz), 6.52(d, 1H, J=7.5 Hz), 5.58(d, 1H, J=10.2 Hz), 5.25(d, 1H, J=14.7 Hz), 5.24(d, 1H, J=10.2 Hz), 4.09(dd, 1H, J=3.8, 12.8 Hz), 3.97(d, 1H, J=14.7 Hz), 3.62–3.58(m, 2H), 1.04(d, 3H, J=6.8 Hz).

Step 3

9-Benzyloxy-2-(3,4-dichlorobenzyl)-3-methyl-3,4-dihydro-2H-pyrido[1,2-a]pyrazine-1,8-dione (8 mg) obtained in the previous step was dissolved in trifluoroacetic acid (1.0 ml) and the mixture was stirred at 60° C. for 1.5 hr. The solvent was evaporated, toluene was added, and the mixture was concentrated, which operations were performed 3 times. Ethyl acetate was added and the mixture was concentrated, which operations were performed twice. The obtained residue was crystallized from ethyl acetate/hexane to give 2-(3,4-dichlorobenzyl)-9-hydroxy-3-methyl-3,4-dihydro-2H-pyrido[1,2-a]pyrazine-1,8-dione (6 mg).

$^1$H-NMR (DMSO-$d_6$)δ 7.84(brs, 1H), 7.70(d, 1H, J=1.9 Hz), 7.63(d, 1H, J=8.4 Hz), 7.40(dd, 1H, J=1.9,8.4 Hz), 6.57(brs, 1H), 5.03(d, 1H, J=15.3 Hz), 4.45(d, 1H, J=15.3 Hz), 4.42–4.39(m, 1H), 4.22–4.19(m, 1H), 4.00(m, 1H), 1.18(d, 3H, J=6.5 Hz).

Example 4

Synthesis of 2-(3,4-dichlorobenzyl)-9-hydroxy-4,4-dimethyl-3,4-dihydro-2H-pyrido[1,2-a]pyrazine-1,8-dione

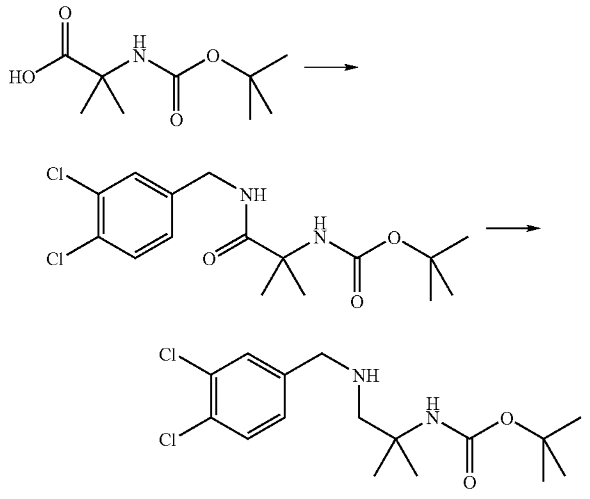

Step 1

2-tert-Butoxycarbonylamino-2-methylpropionic acid (2 g) was dissolved in tetrahydrofuran (20 ml), and 3,4-dichlorobenzylamine (1.2 ml), 1-hydroxybenzotriazole (1.81 g) and 1-ethyl-3-(3-dimethylaminopropyl)carbodiimide (2.26 g) were added. The mixture was stirred at room temperature for 1 hr. To the obtained reaction mixture was added saturated aqueous sodium hydrogen carbonate solution, and the mixture was extracted with ethyl acetate. The organic layer was washed successively with saturated aqueous sodium hydrogen carbonate solution, 5% aqueous potassium hydrogen sulfate solution and saturated brine and dried over sodium sulfate. The solvent was evaporated, and the obtained solid was washed with ethyl acetate/hexane and collected by filtration to give crude crystals (2.98 g) of tert-butyl [1-(3,4-dichlorobenzylcarbamoyl)-1-methylethyl] carbamate.

Step 2

The crude crystals (1.0 g) of tert-butyl [1-(3,4-dichlorobenzylcarbamoyl)-1-methylethyl]carbamate obtained in the previous step was dissolved in tetrahydrofuran (5 ml) and cooled to 0° C. under an argon atmosphere. A borane-tetrahydrofuran complex (1.0 M/tetrahydrofuran solution) (15 ml) was added dropwise at the same temperature, removed from an ice-bath and stirred at room temperature for 2 hr. A borane-tetrahydrofuran complex (1.0 M/tetrahydrofuran solution) (5 ml) was added every 30 minutes twice in total. To the obtained reaction mixture was added methanol (10 ml) under ice-cooling, and the solvent was evaporated. The obtained residue was dissolved in tetrahydrofuran (10 ml) and 1N aqueous sodium hydroxide solution (4 ml) and the mixture was stirred at 90° C. for 1 hr. The obtained reaction mixture was extracted twice with toluene, and the combined organic layer was washed with saturated brine and dried over sodium sulfate. The solvent was evaporated and the obtained residue was purified by silica-gel column chromatography (hexane:ethyl acetate=l:l) to give tert-butyl [2-(3,4-dichlorobenzylamino)-1,1-dimethylethyl]carbamate (290 mg).

$^1$H-NMR (DMSO-$d_6$)δ 7.59(d, 1H, J=1.9 Hz), 7.56(d, 1H, J=8.3 Hz), 7.31(dd, 1H, J=1.9, 8.3 Hz), 6.20(brs, 1H), 3.69(brs, 2H), 2.48(brs, 2H), 2.17(brs, 1H), 1.35(s, 9H), 1.16(s, 6H).

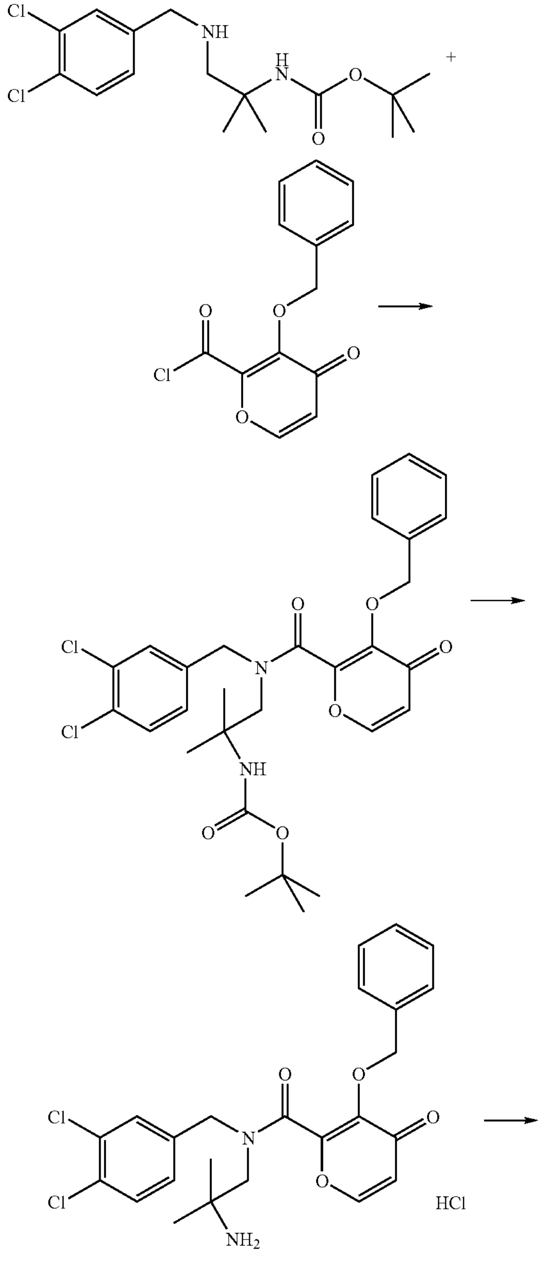

-continued

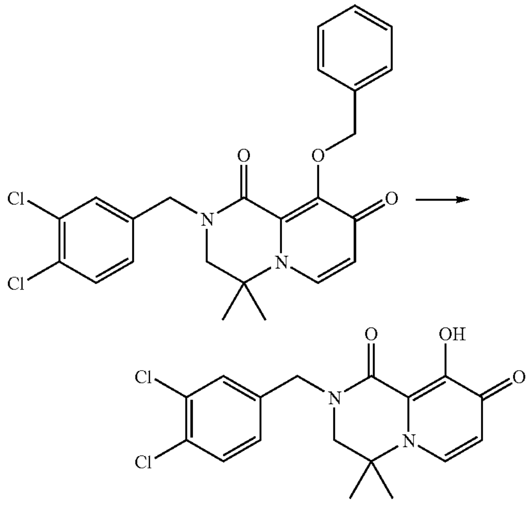

Step 3

To a solution of 3-benzyloxy-4-oxo-4H-pyran-2-carboxylic acid (150 mg) obtained in the same manner as in Example 1, Step 1 in chloroform (3 ml) were added oxalyl chloride (0.069 ml) and dimethylformamide (0.005 ml) and the mixture was stirred at room temperature for 1 hr. The reaction solvent was evaporated under reduced pressure. Toluene was added and the mixture was concentrated, which operations were performed twice and the residue was dissolved in chloroform (2 ml). This solution was added dropwise under ice-cooling to a solution of tert-butyl [2-(3, 4-dichlorobenzylamino)-1,1-dimethylethyl]carbamate (192 mg) obtained in Step 2 and triethylamine (0.11 ml) in chloroform,(3 ml), and the mixture was stirred under ice-cooling for 1 hr. 5% Aqueous potassium hydrogen sulfate solution was added to the obtained reaction mixture and the mixture was extracted with chloroform. The organic layer was washed successively with saturated aqueous sodium hydrogen carbonate solution and saturated brine and dried over sodium sulfate. The solvent was evaporated and the residue was purified by silica gel column chromatography (hexane:ethyl acetate=1:1) to give crude tert-butyl {2-[N-(3-benzyloxy-4-oxo-4H-pyran-2-carbonyl)-N-(3,4-dichlorobenzyl)amino]-1,1-dimethylethyl}carbamate (270 mg).

Step 4

Crude tert-butyl {2-[N-(3-benzyloxy-4-oxo-4H-pyran-2-carbonyl)-N-(3,4-dichlorobenzyl)amino]-1,1-dimethylethyl}carbamate (90 mg) obtained in the previous step was dissolved in 4N hydrochloric acid/dioxane solution (2 ml) and the mixture was stirred at room temperature for 30 min. The solvent was evaporated and azeotropic distillation with chloroform was performed 3 times. The obtained residue was dissolved in ethanol (3 ml) and saturated aqueous sodium carbonate solution (1.5 ml) and stirred at 50° C. for 30 min. Water was added to the obtained reaction mixture and the mixture was extracted twice with ethyl acetate. The combined organic layer was washed with saturated brine and dried over sodium sulfate. The solvent was evaporated and the obtained residue was purified by thin layer chromatography (ethyl acetate:methanol=3:2) to give 9-benzyloxy-2-(3,4-dichlorobenzyl)-4,4-dimethyl-3,4-dihydro-2H-pyrido[1,2-a]pyrazine-1,8-dione (50 mg).

$^1$H-NMR ($CDCl_3$)δ 7.65(dd, 2H, J=1.5, 7.9 Hz), 7.46(d, 1H, J=1.9 Hz), 7.45(d, 1H, J=8.3 Hz), 7.37–7.29(m, 4H), 7.22(dd, 1H, J=1.9, 8.3 Hz), 6.50(d, 1H, J=7.5 Hz), 5.37(s, 2H), 4.65(s, 2H), 3.26(s, 2H), 1.39(s, 6H).

Step 5

9-Benzyloxy-2-(3,4-dichlorobenzyl)-4,4-dimethyl-3,4-dihydro-2H-pyrido[1,2-a]pyrazine-1,8-dione (30 mg) obtained in the previous step was dissolved in trifluoroacetic acid (2.0 ml) and the mixture was stirred at 65° C. for 2 hr. The solvent was evaporated, toluene was added and the mixture was concentrated, which operations were performed 3 times. Ethyl acetate was added and the mixture was concentrated, which operations were performed twice. The obtained residue was crystallized from diisopropyl ether to give 2-(3,4-dichlorobenzyl)-9-hydroxy-4,4-dimethyl-3,4-dihydro-2H-pyrido[1,2-a]pyrazine-1,8-dione (22 mg).

$^1$H-NMR (DMSO-$d_6$)δ 7.96(bd, 1H, J=7.9 Hz), 7.68(d, 1H, J=1.9 Hz), 7.65(d, 1H, J=8.1 Hz), 7.40(dd, 1H, J=1.9, 8.1 Hz), 6.49(brs, 1H), 4.74(s, 2H), 3.67(s, 2H), 1.44(s, 6H).

Example 5

Synthesis of 2-(3,4-dichlorobenzyl)-9-hydroxy-6-hydroxymethyl-3,4-dihydro-2H-pyrido[1,2-a]pyrazine-1,8-dione

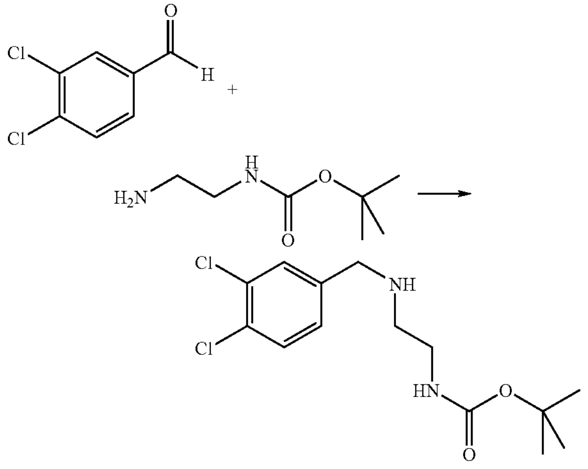

Step 1 tert-Butyl N-(2-aminoethyl)carbamate (1.51 g) was dissolved in chloroform (20 ml) and 3,4-dichlorobenzaldehyde (1.65 g), acetic acid (0.54 ml) and sodium triacetoxyborohydride (2.6 g) were added at room temperature. The mixture was stirred overnight. Saturated aqueous sodium hydrogen carbonate solution was added to the obtained reaction mixture and the mixture was stirred and extracted three times with chloroform. The combined organic layer was washed with saturated brine and dried over sodium sulfate. The solvent was evaporated and the obtained residue was purified by silica gel column chromatography (chloroform:methanol=9:1) to give tert-butyl [2-(3,4-dichlorobenzylamino)ethyl]carbamate (2.1 g).

$^1$H-NMR (DMSO-$d_6$)δ 7.59(d, 1H, J=1.9 Hz), 7.56(d, 1H, J=8.3 Hz) 7.31(dd, 1H, J=1.9, 8.3 Hz), 6.73(brs, 1H), 3.67(brs, 2H), 3.00(bdd, 2H, J=6.0, 12.4 Hz), 2.47(m, 2H), 2.27(brs, 1H), 1.37(s, 9H).

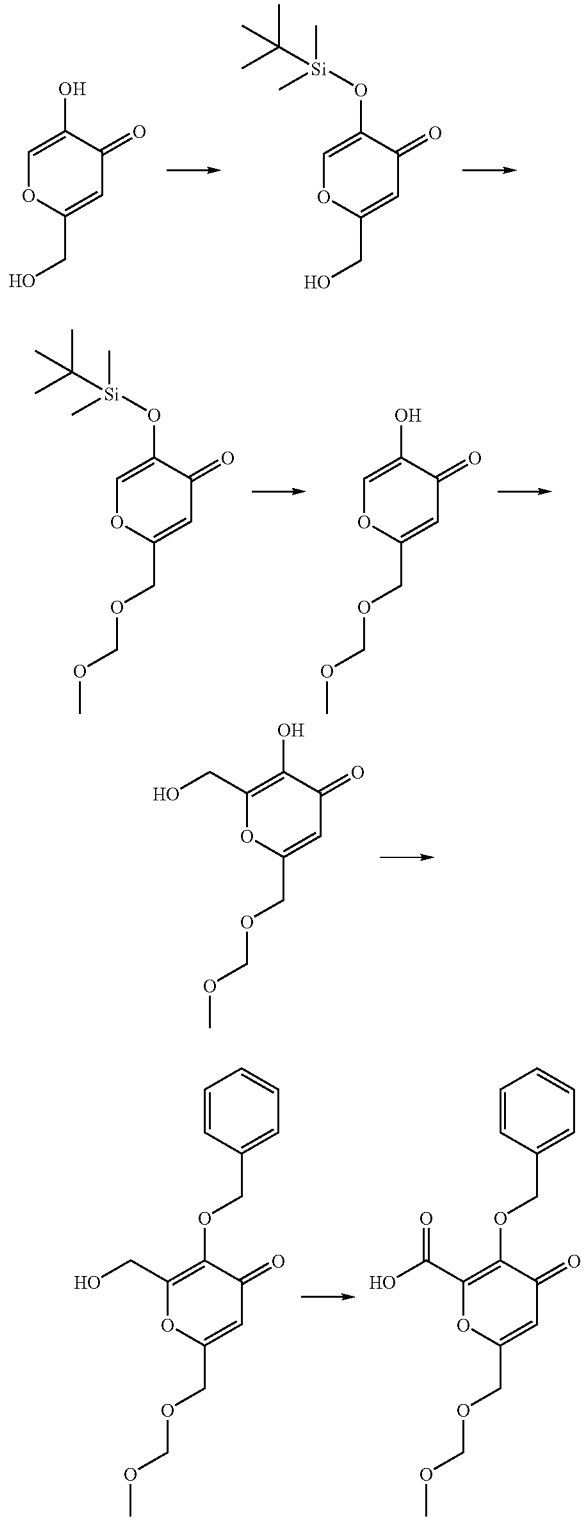

Step 2

Kojic acid (5 g) was dissolved in chloroform (50 ml) and triethylamine (7.4 ml) and dimethylaminopyridine (5 mg) were added. Then tert-butyldimethylsilyl chloride (5.3 g) was added under ice-cooling, and the mixture was stirred at the same temperature for 1 hr. To the obtained reaction mixture was added 5% aqueous potassium hydrogen sulfate solution, and the mixture was extracted with chloroform. The organic layer was washed with saturated aqueous sodium hydrogen carbonate solution and saturated brine, and dried over sodium sulfate. The solvent was evaporated and the obtained residue was dissolved in chloroform (50 ml). Diisopropylethylamine, (8.0 ml) was added and chloromethyl methyl ether (3.2 ml) was added. The mixture was stirred under ice-cooling for 30 min. The ice-bath was removed and the mixture was stirred overnight at room temperature. 5% Aqueous potassium hydrogen sulfate solution was added to the obtained reaction mixture and the mixture was extracted with chloroform. The organic layer was washed with saturated aqueous sodium hydrogen carbonate solution and saturated brine, and dried over sodium sulfate. The solvent was evaporated and the obtained residue was purified by silica gel column chromatography (hexane: ethyl acetate=4:1–2:1) to give 5-(tert-butyldimethylsilyloxy) -2-methoxymethoxymethyl-4H-pyran-4-one (5.5 g).

$^1$H-NMR (DMSO-$d_6$)δ 8.19(s, 1H), 6.41(s, 1H), 4.66(s, 2H), 4.39(s, 2H), 3.28(s, 3H), 0.92(s, 9H), 0.16(s, 6H).

Step 3

5-(tert-Butyldimethylsilyloxy)-2-methoxymethoxymethyl-4H-pyran-4-one (5.5 g) obtained in the previous step was dissolved in tetrahydrofuran (30 ml), tetra(n-butyl) ammonium fluoride (1.0 M/tetrahydrofuran solution) (19.2 ml) was added under ice-cooling and the mixture was stirred for 30 min. 5% Aqueous potassium hydrogen sulfate solution was added to the obtained reaction mixture to adjust to pH=3, and the mixture was extracted 4 times with ethyl acetate. The combined organic layer was washed with saturated brine and dried over sodium sulfate. The solvent was evaporated and the obtained solid was washed with ethyl acetate/hexane. The obtained solid (2.3 g) was dissolved in water (20 ml) and 1N aqueous sodium hydroxide solution (12.7 ml). 36% Aqueous formaldehyde solution was added at room temperature and the mixture was stirred for 6 hr. 5% Aqueous potassium hydrogen sulfate solution was added to the obtained reaction mixture to adjust to pH=3, and sodium chloride was added. The mixture was extracted 5 times with ethyl acetate, and the combined organic layer was washed with saturated brine and dried over sodium sulfate. The solvent was evaporated and the obtained residue was dissolved in dimethylformamide (10 ml). Potassium carbonate (1.97 g) was added and benzyl chloride (0.82 ml) was added at room temperature, and the mixture was stirred overnight. 5% Aqueous potassium hydrogen sulfate solution was added to the obtained reaction mixture to adjust to pH=3, and the mixture was extracted three times with ethyl acetate. The combined organic layer was washed with saturated brine and dried over sodium sulfate. The solvent was evaporated and the obtained residue was purified by silica gel column chromatography (hexane: ethyl acetate=1:1–1:4) to give 3-benzyloxy-2-hydroxymethyl-6-methoxymethoxymethyl-4H-pyran-4-one (783 mg)

$^1$H-NMR (DMSO-$d_6$)δ 7.47–7.32(m, 5H), 6.43(s, 1H), 5.48(t, 1H, J=6.0 Hz), 5.03(s, 2H), 4.68(s, 2H), 4.40(s, 2H), 4.28(d, 2H, J=6.0 Hz), 3.29(s, 3H).

Step 4

3-Benzyloxy-2-hydroxymethyl-6-methoxymethoxymethyl-4H-pyran-4-one (783 mg) obtained in the previous step was dissolved in acetone (8.0 ml) and saturated aqueous sodium hydrogen carbonate solution (8.0 ml), and potassium bromide (30 mg), 2,2,6,6-tetramethylpiperidine 1-oxyl, free radical (39 mg) were added, and 6% aqueous sodium hypochlorite solution (3.4 ml) was added dropwise under ice-cooling. The mixture was stirred for 30 min and 6% aqueous sodium hypochlorite solution (3.3 ml) was further added dropwise. The mixture was further stirred for 30 min. Water was added to the obtained reaction mixture and washed twice with ethyl acetate. 5% Aqueous potassium hydrogen sulfate solution was added to the aqueous layer to adjust to pH=3, and the mixture was extracted twice with ethyl acetate. The combined organic layer was washed with saturated brine and dried over sodium sulfate. The solvent was evaporated to give 3-benzyloxy-6-methoxymethoxymethyl-4-oxo-4H-pyran-2-carboxylic acid (710 mg).

$^1$H-NMR (DMSO-$d_6$)δ 7.44–7.30(m, 5H), 6.54(s, 1H), 5.11(s, 2H), 4.65(s, 2H), 4.43(s, 2H), 3.27(s, 3H).

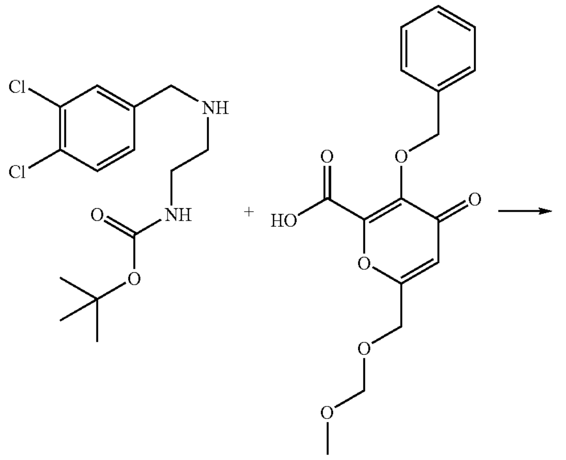

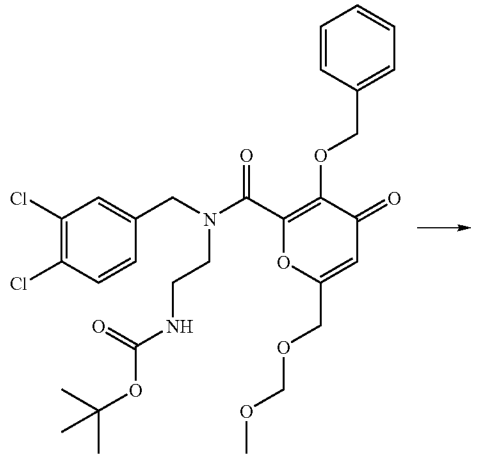

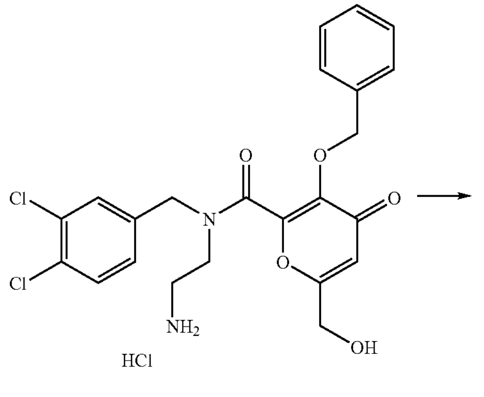

-continued

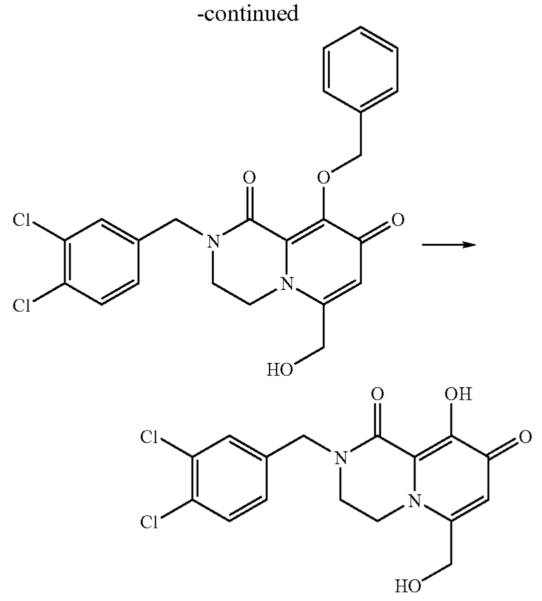

Step 5

3-Benzyloxy-6-methoxymethoxymethyl-4-oxo-4H-pyran-2-carboxylic acid (658 mg) obtained in Step 4 was dissolved in dimethylformamide (5 ml), and tert-butyl [2-(3,4-dichlorobenzylamino)ethyl]carbamate (596 mg) obtained in Step 1, 1-ethyl-3-(3-dimethylaminopropyl)carbodiimide (429 mg) and 1-hydroxybenzotriazole (343 mg) were added at room temperature, and the mixture was stirred for 1 hr. Saturated aqueous sodium hydrogen carbonate solution was added to the obtained reaction mixture and the mixture was extracted twice with ethyl acetate. The combined organic layer was washed with saturated brine and dried over sodium sulfate. The solvent was evaporated and the obtained residue was purified by silica gel column chromatography (chloroform:methanol=15:1) to give crude tert-butyl {2-[N-(3-benzyloxy-6-methoxymethoxymethyl-4-oxo-4H-pyran-2-carbonyl)-N-(3,4-dichlorobenzyl)amino]ethyl}carbamate (1.12 g).

Step 6

The crude tert-butyl {2-[N-(3-benzyloxy-6-methoxymethoxymethyl-4-oxo-4H-pyran-2-carbonyl)-N-(3,4-dichlorobenzyl)amino]ethyl}carbamate (1.12 g) obtained in the previous step was dissolved in 4N hydrochloric acid/dioxane solution (10 ml) and the mixture was stirred at room temperature for 30 min. The solvent was evaporated, toluene was added, and the mixture was concentrated, which operations were performed 3 times. The obtained residue was dissolved in ethanol (40 ml) and saturated aqueous sodium carbonate solution (10 ml), and the mixture was stirred at 50° C. for 30 min. The solvent was evaporated, and the resulting crystals were washed with 5% aqueous potassium hydrogen sulfate solution and a small amount of ethyl acetate, and collected by filtration to give. 9-benzyloxy-2-(3,4-dichlorobenzyl)-6-hydroxymethyl-3,4-dihydro-2H-pyrido[1,2-a]pyrazine-1,8-dione (433 mg).

$^1$H-NMR (DMSO-$d_6$)δ 7.64(d, 1H, J=1.5 Hz), 7.63(d, 1H, J=8.3 Hz), 7.51(dd, 2H, J=1.5,8.3 Hz), 7.37–7.29(m, 4H), 6.40(s, 1H), 5.67(t, 1H, J=5.7 Hz), 5.08(s, 2H), 4.68(s, 2H), 4.43(d, 2H, J=5.7 Hz), 4.10–4.04(m, 2H), 3.63–3.57(m, 2H).

Step 7

9-Benzyloxy-2-(3,4-dichlorobenzyl)-6-hydroxymethyl-3,4-dihydro-2H-pyrido[1,2-a]pyrazine-1,8-dione (15 mg) obtained in the previous step was dissolved in trifluoroacetic acid (1 ml) and the mixture was stirred at room temperature for 1 hr. The solvent was evaporated, toluene was added, and the mixture was concentrated, which operations were performed 3 times. Ethyl acetate was added and the mixture was concentrated, which operations were performed twice. The obtained residue was crystallized from ethyl acetate/diisopropyl ether to give 2-(3,4-dichlorobenzyl)-9-hydroxy-6-hydroxymethyl-3,4-dihydro-2H-pyrido[1,2-a]pyrazine-1,8-dione (12 mg).

$^1$H-NMR (DMSO-$d_6$)δ 12.20(brs, 1H), 7.66(d, 1H, J=1.9 Hz), 7.62(d, 1H, J=8.1 Hz), 7.36(dd, 2H, J=1.9, 8.1 Hz), 6.25(s, 1H), 5.65(t, 1H, J=5.6 Hz), 4.71(s, 2H), 4.41(d, 2H, J=5.6 Hz), 4.15–4.13(m, 2H), 3.68–3.65(m, 2H).

Example 6

Synthesis of 2-(3,4-dichlorobenzyl)-9-hydroxy-1,8-dioxo-1,3,4,8-tetrahydro-2H-pyrido[1,2-a]pyrazine-6-carboxylic acid

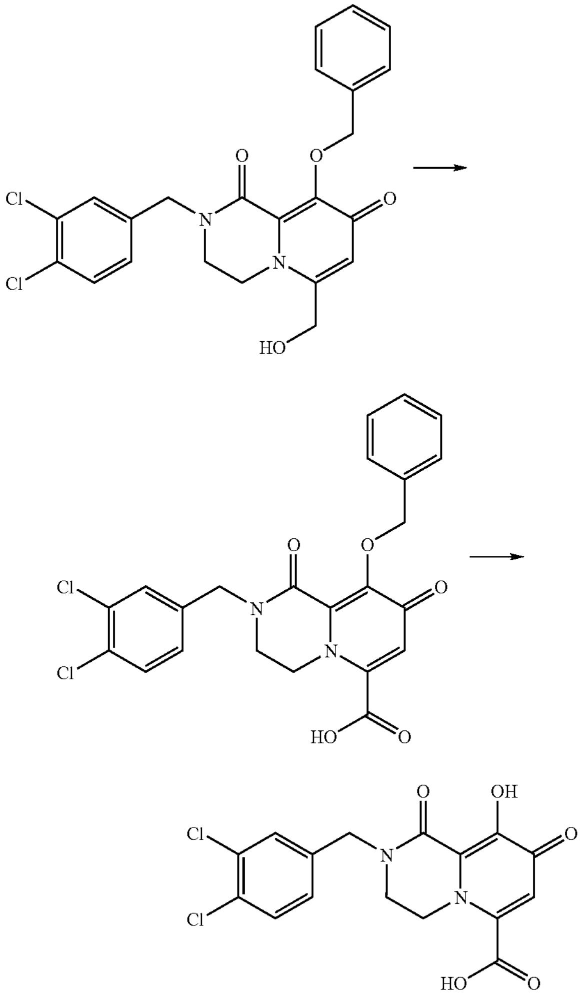

Step 1

9-Benzyloxy-2-(3,4-dichlorobenzyl)-6-hydroxymethyl-3,4-dihydro-2H-pyrido[1,2-a]pyrazine-1,8-dione (100 mg) obtained in Example 5, Step 6 was dissolved in acetone (1.6 ml) and saturated aqueous sodium hydrogen carbonate solution (1.0 ml) and potassium bromide (3 mg), 2,2,6,6-tetramethylpiperidine 1-oxyl and free radical (3 mg) were added, and 6% aqueous sodium hypochlorite solution (3.4 ml) was added dropwise under ice-cooling. After stirring for 15 min, the ice bath was removed and the mixture was stirred at room temperature for 4 hr. Furthermore, 6% aqueous sodium hypochlorite solution (0.1 ml) was added dropwise and the mixture was stirred for 1.5 hr. The obtained reaction mixture was poured into 5% aqueous potassium hydrogen sulfate solution and stirred for 30 min. The resulting crystals were collected by filtration to give 9-benzyloxy-2-(3,4-dichlorobenzyl)-1,8-dioxo-1,3,4,8-tetrahydro-2H-pyrido[1,2-a]pyrazine-6-carboxylic acid (94 mg).

$^1$H-NMR (DMSO-$d_6$)δ 7.64(d, 1H, J=1.9 Hz), 7.62(d, 1H, J=8.4 Hz), 7.49(dd, 2H, J=1.9, 8.4 Hz), 7.36–7.29(m, 4H), 6.70(s, 1H), 5.11(s, 2H), 4.67(s, 2H), 4.26–4.24(m, 2H), 3.59–3.56(m, 2H).

Step 2

9-Benzyloxy-2-(3,4-dichlorobenzyl)-1,8-dioxo-1,3,4,8-tetrahydro-2H-pyrido[1,2-a]pyrazine-6-carboxylic acid (25 mg) obtained in the previous step was dissolved in trifluoroacetic acid (2 ml) and the mixture was stirred at room temperature for 1 hr. The solvent was evaporated, toluene was added, and the mixture was concentrated, which operations were performed 3 times. Methanol was added and the mixture was concentrated. Ethyl acetate was added and the mixture was concentrated. The obtained residue was crystallized from methanol/ethyl acetate to give 2-(3,4-dichlorobenzyl)-9-hydroxy-1,8-dioxo-1,3,4,8-tetrahydro-2H-pyrido[1,2-a]pyrazine-6-carboxylic acid (20 mg).

$^1$H-NMR (DMSO-$d_6$)δ 7.69(d, 1H, J=2.2 Hz), 7.64(d, 1H, J=8.4 Hz), 7.39(dd, 2H, J=2.2, 8.4 Hz), 6.58(s, 1H), 4.73(s, 2H), 4.44–4.41(m, 2H), 3.71–3.68(m, 2H).

Example 7

Synthesis of 2-(3,4-dichlorobenzyl)-6-(2,2-dimethylpropionyl)-9-hydroxy-3,4-dihydro-2H-pyrido[1,2-a]pyrazine-1,8-dione

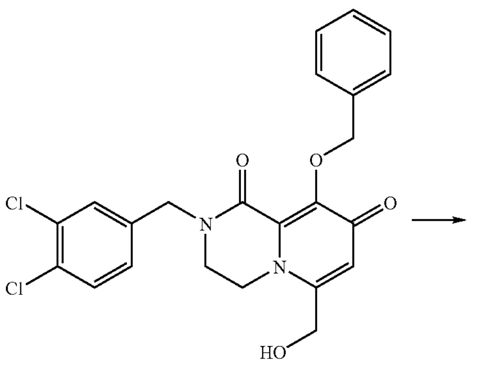

-continued

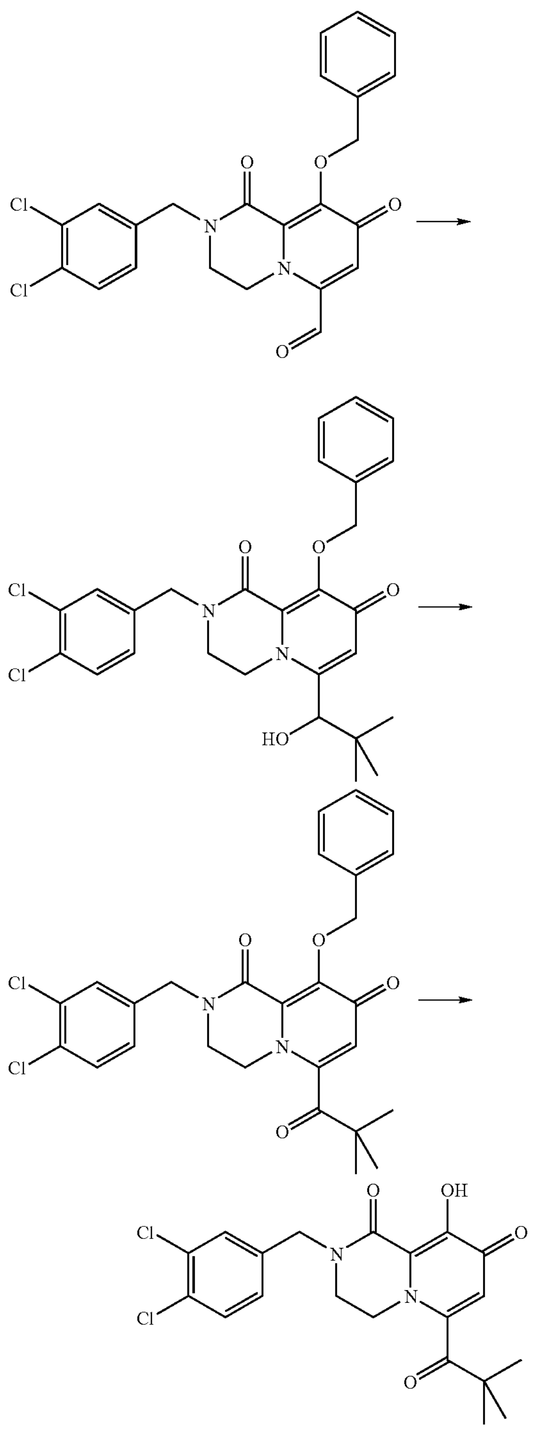

Step 1

To a solution of 9-benzyloxy-2-(3,4-dichlorobenzyl)-6-hydroxymethyl-3,4-dihydro-2H-pyrido[1,2-a]pyrazine-1,8-dione (860 mg) obtained in Example 5, Step 6 in chloroform (80 ml) was added Dess-Martin reagent (843 mg). After stirring at room temperature for 1 hr, the solvent was evaporated and chloroform (50 ml) was added to the obtained residue and a solid product was filtered off. The filtrate was concentrated and purified by silica gel column chromatography (chloroform:acetone=1:2) to give 9-benzyloxy-2-(3,4-dichlorobenzyl)-1,8-dioxo-1,3,4,8-tetrahydro-2H-pyrido[1,2-a]pyrazine-6-carbaldehyde (621 mg).

$^1$H-NMR ($CDCl_3$)δ 9.58(s, 1H), 7.62–7.55(m, 2H), 7.46–7.40(m, 2H), 7.37–7.26(m, 3H), 7.16(dd, 1H, J=2.0, 8.1 Hz), 6.97(s, 1H), 5.39(s, 2H), 4.65(s, 2H), 4.43–4.37(m, 2H), 3.43–3.36(m, 2H).

Step 2

A solution of 9-benzyloxy-2-(3,4-dichlorobenzyl)-1,8-dioxo-1,3,4,8-tetrahydro-2H-pyrido[1,2-a]pyrazine-6-carbaldehyde (205 mg) obtained in the previous step in dry tetrahydrofuran (40 ml) was cooled in a dry ice-acetone bath. tert-Butylmagnesium chloride (2.0 M/diethyl ether solution) (0.448 ml) was added dropwise at the same temperature and the mixture was stirred for 30 min. Then 5% aqueous potassium hydrogen sulfate solution was added to adjust to pH=2, and the mixture was-extracted with ethyl acetate. The organic layer was washed with saturated brine and dried over sodium sulfate. The solvent was evaporated and the residue was purified by silica gel column chromatography (chloroform:methanol=12:1) to give crude 9-benzyloxy-2-(3,4-dichlorobenzyl)-6-(1-hydroxy-2,2-dimethylpropyl)-3,4-dihydro-2H-pyrido[1,2-a]pyrazine-1,8-dione (220 mg).

To a solution of the above-mentioned crude 9-benzyloxy-2-(3,4-dichlorobenzyl)-6-(1-hydroxy-2,2-dimethylpropyl)-3,4-dihydro-2H-pyrido[1,2-a]pyrazine-1,8-dione (132 mg) in chloroform (4 ml) was added Dess-Martin reagent (65 mg) and the mixture was stirred at room temperature for 20 min. Saturated aqueous sodium hydrogen carbonate solution and sodium sulfite were added to the reaction mixture, and the mixture was extracted with ethyl acetate. The organic layer was washed with saturated brine and dried over sodium sulfate. The solvent was evaporated and the residue was purified by silica gel column chromatography (ethyl acetate:chloroform=4:1) to give 9-benzyloxy-2-(3,4-dichlorobenzyl)-6-(2,2-dimethylpropionyl)-3,4-dihydro-2H-pyrido[1,2-a]pyrazine-1,8-dione (38 mg).

$^1$H-NMR ($CDCl_3$)δ 7.63–7.57(m, 2H), 7.46–7.38(m, 2H), 7.37–7.26(m, 3H), 7.15(dd, 1H, J=2.1, 8.1 Hz), 6.42(s, 1H), 5.38(s, 2H), 4.63(s, 2H), 3.69–3.61(m, 2H), 3.43–3.36(m, 2H), 1.27(s, 9H).

Step 3

To 9-benzyloxy-2-(3,4-dichlorobenzyl)-6-(2,2-dimethylpropionyl)-3,4-dihydro-2H-pyrido[1,2-a]pyrazine-1,8-dione (36 mg) obtained in the previous step was added trifluoroacetic acid (4 ml) and the mixture was stirred at room temperature for 1 hr. The solvent was evaporated, toluene was added, and the mixture was concentrated, which operations were performed twice. The obtained residue was crystallized from ethyl acetate:diisopropyl ether=1:4 to give 2-(3,4-dichlorobenzyl)-6-(2,2-dimethylpropionyl)-9-hydroxy-3,4-dihydro-2H-pyrido[1,2-a]pyrazine-1,8-dione (26 mg).

$^1$H-NMR (DMSO-$d_6$)δ 12.40(brs, 1H), 7.68(d, 1H, J=2.1 Hz), 7.62(d, 1H, J=8.4 Hz), 7.38(dd, 1H, J=2.1, 8.4 Hz), 6.15(s, 1H), 4.71(s, 2H), 3.92–3.85(m, 2H), 3.67–3.59(m, 2H), 1.22(s, 9H).

Example 8

Synthesis of 2-(3,4-dichlorobenzyl)-9-hydroxy-2H-pyrido[1,2-a]pyrazine-1,8-dione

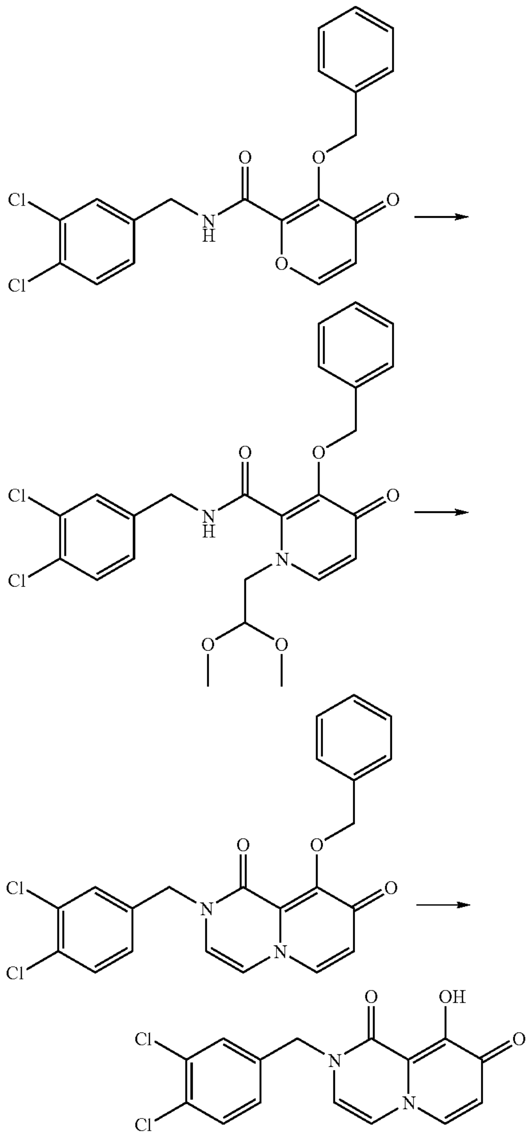

Step 1

To a solution of N-(3,4-dichlorobenzyl)-3-benzyloxy-4-oxo-4H-pyran-2-carboxamide (49 mg) obtained in the same manner as in Example 1, Step 1 in tetrahydrofuran (0.5 ml), ethanol (0.5 ml) and water (0.1 ml) were successively added aminoacetaldehyde dimethyl acetal (0.026 ml) and sodium carbonate (6.4 mg), and the mixture was stirred at room temperature for 1 hr and then at 45° C. for 4 hr, and at 60° C. for 20 hr. The solvent was evaporated and the residue was purified by silica gel column chromatography (ethyl acetate: methanol=100:0–5:1) to give N-(3,4-dichlorobenzyl)-3-benzyloxy-1-(2,2-dimethoxyethyl)-4-oxo-1,4-dihydropyridine-2-carboxamide (30 mg).

$^1$H-NMR ($CDCl_3$)δ 7.35(d, 1H, J=2.0 Hz), 7.30–7.20(m, 7H), 7.09(t, 1H, J=6.3 Hz), 7.05(dd, 1H, J=2.0,8.0 Hz), 6.33(d, 1H, J=7.4 Hz), 5.20(s, 2H), 4.51(t, 1H, J=5.1 Hz), 4.32(d, 2H, J=6.3 Hz), 3.86(d, 1H, J=5.1 Hz), 3.31(s, 6H).

Step 2

To a solution of N-(3,4-dichlorobenzyl)-3-benzyloxy-1-(2,2-dimethoxyethyl)-4-oxo-1,4-dihydropyridine-2-carboxamide (30 mg) obtained in the previous step in toluene (3 ml) was added camphorsulfonic acid (15 mg) and the mixture was stirred at 110° C. for 30 min. A saturated aqueous sodium hydrogen carbonate solution was added to the reaction mixture and the mixture was extracted twice with ethyl acetate. The organic layers were combined, washed with saturated brine, and dried over sodium sulfate. The solvent was evaporated and the residue was purified by silica gel column chromatography (ethyl acetate:methanol=5:1–4:1) to give 9-benzyloxy-2-(3,4-dichlorobenzyl)-2H-pyrido[1,2-a]pyrazine-1,8-dione (17 mg).

$^1$H-NMR ($CDCl_3$)δ 7.63(d, 1H, J=7.4 Hz), 7.43(d, 1H, J=8.4 Hz), 7.39(d, 1H, J=2.0 Hz), 7.38–7.25(m, 5H), 7.15 (dd, 1H, J=2.0,8.4 Hz), 6.70(d, 1H, J=7.4 Hz), 6.41(d, 1H, J=6.3 Hz), 6.20(d, 1H, J=6.3 Hz), 5.39(s, 2H), 4.89(s, 2H).

Step 3

To 9-benzyloxy-2-(3,4-dichlorobenzyl)-2H-pyrido[1,2-a]pyrazine-1,8-dione (16 mg) obtained in the previous step was added trifluoroacetic acid (2 ml) and the mixture was stirred at room temperature for 1 hr. The solvent was evaporated, toluene was added, and the mixture was concentrated, which operations were performed twice. The obtained residue was crystallized from-diisopropyl ether to give 2-(3,4-dichlorobenzyl)-9-hydroxy-2H-pyrido[1,2-a]pyrazine-1,8-dione (9 mg).

$^1$H-NMR (DMSO-$d_6$)δ 8.11(d, 1H, J=7.3 Hz), 7.71(d, 1H, J=1.8 Hz), 7.66(d, 1H, J=8.4 Hz), 7.40(dd, 1H, J=1.8,8.4 Hz), 7.35(d, 1H, J=6.2 Hz), 7.03(d, 1H, J=6.2 Hz), 6.76(d, 1H, J=7.3 Hz), 4.99(s, 2H).

Example 9

Synthesis of 2-(3,4-dichlorobenzyl)-9-hydroxy-3-methyl-2H-pyrido[1,2-a]pyrazine-1,8-dione

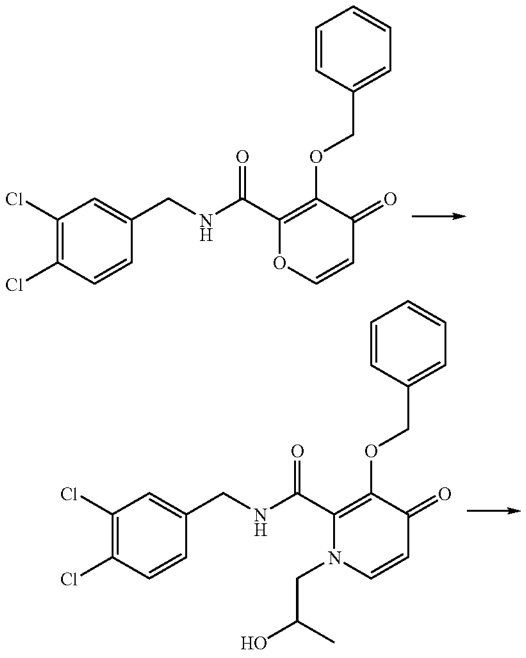

-continued

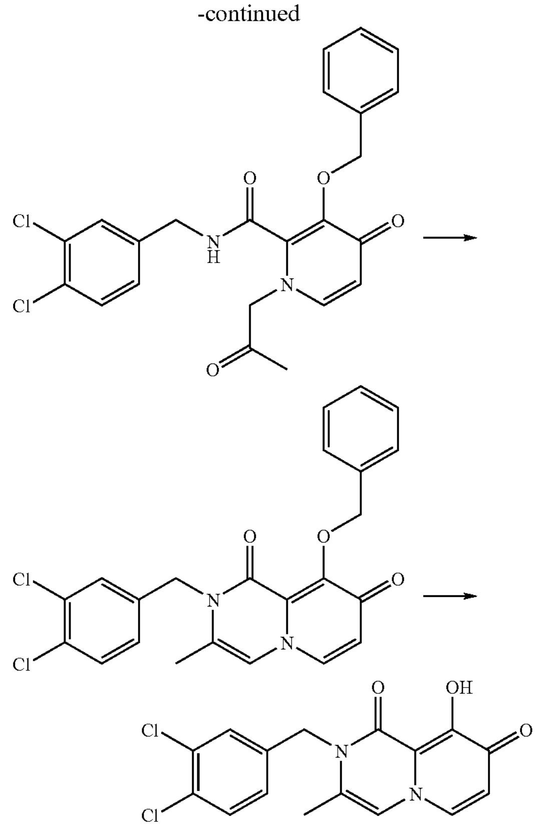

Step 1

To a solution of N-(3,4-dichlorobenzyl)-3-benzyloxy-4-oxo-4H-pyran-2-carboxamide (0.04 g) obtained in the same manner as in Example 1, Step 1 in tetrahydrofuran (3 ml) were added 1-amino-2-propanol (0.224 g) and saturated aqueous sodium hydrogen carbonate solution (1 ml), and the mixture was stirred at 60° C. for 4 hr. The reaction solvent was evaporated under reduced pressure, and ethyl acetate was added to the residue. The mixture was washed successively with 1N aqueous hydrochloric acid solution and saturated brine. After drying over magnesium sulfate, the solvent was evaporated and the residue was purified by silica gel column chromatography (chloroform:methanol=20:1) to give N-(3,4-dichlorobenzyl)-3-benzyloxy-1-(2-hydroxypropyl)-4-oxo-1,4-dihydropyridine-2-carboxamide (0.334 g).

$^1$H-NMR (DMSO-$d_6$)δ 9.45(t, 1H), 7.58–7.56(m, 2H), 7.37–7.23(m, 7H), 6.62(d, 1H, J=5.7 Hz), 5.09–5.05(m, 3H), 4.50–4.31(m, 4H), 3.81–3.42(m, 4H), 0.92(d, 3H, J=5.7 Hz).

Step 2

N-(3,4-Dichlorobenzyl)-3-benzyloxy-1-(2-hydroxypropyl)-4-oxo-1,4-dihydropyridine-2-carboxamide (0.250 g) obtained in the previous step was dissolved in chloroform (10 ml), Dess-Martin reagent (0.5 g) was added, and the mixture was stirred overnight at room temperature. The obtained reaction mixture was washed with saturated aqueous sodium hydrogen carbonate solution and dried over magnesium sulfate. The solvent was evaporated and the residue was purified by silica gel column chromatography (chloroform:methanol=10:1) to give crude crystals (0.304 g) of N-(3,4-dichlorobenzyl)-3-benzyloxy-4-oxo-1-(2-oxopropyl)-1,4-dihydropyridine-2-carboxamide. The crude crystals were dissolved in tetrahydrofuran-toluene (5:2, 7 ml), p-toluenesulfonic acid (0.03 g) was added., and the mixture was stirred at 80° C. for 10 hr. The obtained reaction mixture was purified by silica gel column chromatography (chloroform:methanol=10:1) to give 9-benzyloxy-2-(3,4-dichlorobenzyl)-3-methyl-2H-pyrido[1,2-a]pyrazine-1,8-dione (0.063 g).

$^1$H-NMR (DMSO-$d_6$)δ 7.93(d, 1H, J=5.7 Hz), 7.84–7.69 (m, 4H), 7.32–7.20(m, 4H), 7.03(s, 1H), 6.62(d, 1H, J=5.7 Hz), 5.12(s, 2H), 5.07(s, 2H), 2.01(s, 3H).

Step 3

9-Benzyloxy-2-(3,4-dichlorobenzyl)-3-methyl-2H-pyrido[1,2-a]pyrazine-1,8-dione (0.063 g) obtained in the previous step was dissolved in trifluoroacetic acid (2 ml) and the mixture was stirred at room temperature for 3 hr. Thereafter, the reaction mixture was subjected to azeotropic distillation 3 times with toluene. Crystallization from ethyl acetate-diisopropyl ether gave 2-(3,4-dichlorobenzyl)-9-hydroxy-3-methyl-2H-pyrido[1,2-a]pyrazine-1,8-dione (0.05 g).

$^1$H-NMR (DMSO-$d_6$)δ 8.19(d, 1H, J=10 Hz), 7.64–7.61 (m, 2H), 7.44(s, 1H), 7.33(dd, 1H, J=7.3,11.2 Hz), 7.05(d, 1H, J=9.6 Hz), 5.21(s, 2H), 2.12(s, 3H).

Example 10

Synthesis of 2-(3-chlorobenzyl)-9-hydroxy-4-isopropyl-2H-pyrido[1,2-a]pyrazine-1,8-dione hydrochloride

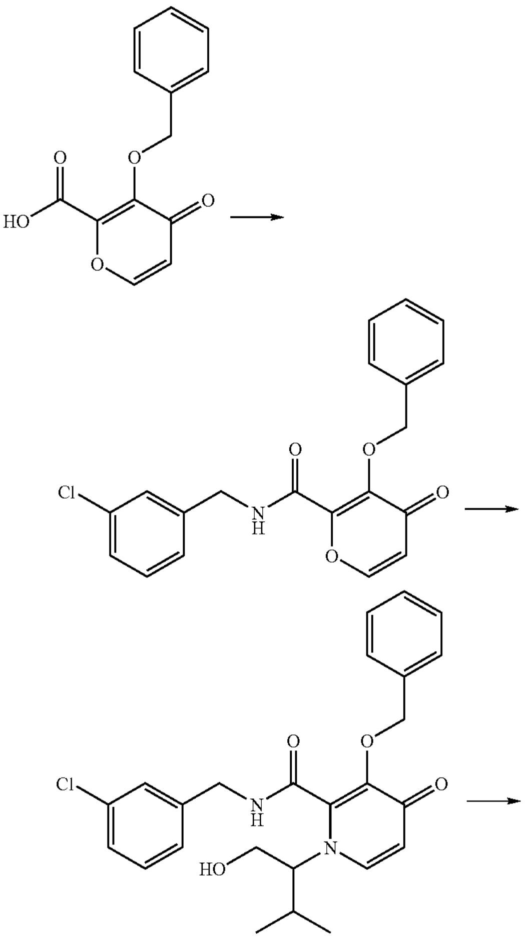

-continued

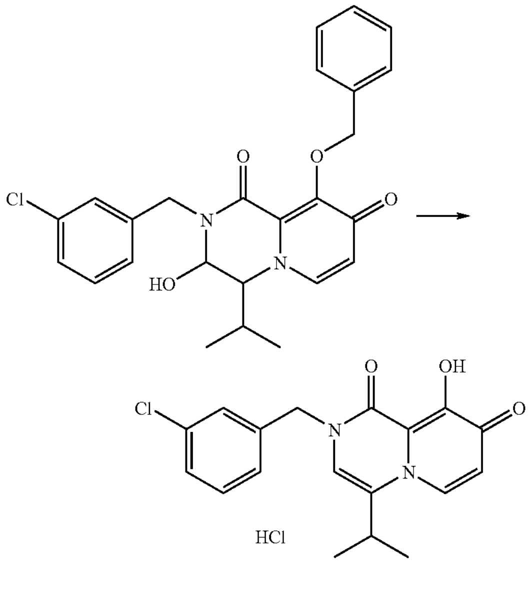

Step 1

To a solution of 3-benzyloxy-4-oxo-4H-pyran-2-carboxylic acid (3.00 g) in chloroform (30 ml) were added oxalyl chloride (2.00 g) and dimethylformamide (50 μl) and the mixture was stirred at room temperature for 30 min. The solvent was evaporated from the reaction mixture, toluene was added and the mixture was concentrated to give acid chloride. To a solution of 3-chlorobenzylamine (1.90 g) in chloroform (30 ml) was added triethylamine (1.85 g) and a solution of the above-mentioned acid chloride in chloroform (30 ml) was added dropwise with stirring the mixture at 0° C. After stirring at 0° C. for 30 min, saturated aqueous sodium hydrogen carbonate solution (40 ml) was added to the reaction mixture, and the mixture was warmed to room temperature and the organic layer was separated. The aqueous layer was extracted with chloroform. The organic layers were combined, washed with saturated brine, and dried over sodium sulfate. The solvent was evaporated and the residue was purified by silica gel column chromatography (hexane: ethyl acetate=1:1–1:2) to give 3-benzyloxy-4-oxo-4H-pyran-2-carboxylic acid 3-chlorobenzylamide (3.90 g).

$^1$H-NMR ($CDCl_3$)δ 8.08(brs, 1H), 7.84(d, 1H, J=5.5 Hz), 7.37–7.20(m, 7H), 7.15(m, 1H), 7.05(m, 1H), 5.38(s, 2H), 4.37(d, 2H, J=5.8 Hz).

Step 2

To a solution of 3-benzyloxy-4-oxo-4H-pyran-2-carboxylic acid 3-chlorobenzylamide (1.20 g) obtained in the previous step in toluene (120 ml) were added pyridinium p-toluenesulfonate (815 mg) and 2-amino-3-methylbutanol (702 mg) and the mixture was stirred at 110° C. for 15 hr. 2-Amino-3-methylbutanol (833 mg) was added and the mixture was further stirred at 110° C. for 30 hr. The solvent was evaporated from the reaction mixture, saturated aqueous sodium carbonate solution (30 ml) was added and the mixture was extracted twice with chloroform. The organic layer was washed with saturated brine and dried over sodium sulfate. The solvent was evaporated and the residue was purified by silica gel column chromatography (ethyl acetate-chloroform:methanol=10:1) to give a crude product containing N-(3-chlorobenzyl)-3-benzyloxy-1-(1-hydroxymethyl-2-methylpropyl)-4-oxo-1,4-dihydropyridine-2-carboxamide as a main component. The total amount of this crude product was used in the next step without further purification.

Step 3

To a solution of crude product of N-(3-chlorobenzyl)-3-benzyloxy-1-(1-hydroxymethyl-2-methylpropyl)-4-oxo-1,4-dihydropyridine-2-carboxamide obtained in the previous step in dimethyl sulfoxide (8.5 ml) were successively added triethylamine (1.60 g) and sulfur trioxide pyridine complex (900 mg) and the mixture was stirred at room temperature for 20 min. 1M Hydrochloric acid (50 ml) was added to the reaction mixture and the mixture was extracted twice with ethyl acetate. The organic layer was washed successively with water and saturated brine, and dried over sodium sulfate. The solvent was evaporated and the residue was purified by silica gel column chromatography (chloroform: methanol=100:1–20:1) to give 9-benzyloxy-2-(3-chlorobenzyl)-3-hydroxy-4-isopropyl-3,4-dihydro-2H-pyrido[1,2-a]pyrazine-1,8-dione (202 mg).

$^1$H-NMR (DMSO-$d_6$)δ 7.70(d, 1H, J=7.4 Hz), 7.53–7.46 (m, 3H), 7.40–7.27(m, 5H), 6.83(d, 1H, J=5.6 Hz), 29(d, 1H, J=7.4 Hz), 5.12–5.02(m, 4H), 4.31(d, 1H, J=14.6 Hz), 3.83(dd, 1H, J=10.0,1.5 Hz), 1.41(m, 1H), 0.66(d, 3H, J=6.7 Hz), 0.55(d, 3H, J=6.5 Hz).

Step 4

To 9-benzyloxy-2-(3-chlorobenzyl)-3-hydroxy-4-isopropyl-3,4-dihydro-2H-pyrido[1,2-a]pyrazine-1,8-dione (200 mg) obtained in the previous step were successively added acetic acid (5 ml) and conc. hydrochloric acid (5 ml) and the mixture was stirred at 90° C. for 15 hr. The solvent was evaporated from the reaction mixture, toluene was added and the mixture was concentrated. Crystallization from diisopropyl ether-ethyl acetate gave 2-(3-chlorobenzyl)-9-hydroxy-4-isopropyl-2H-pyrido[1,2-a]pyrazine-1,8-dione hydrochloride (164 mg).

$^1$H-NMR (DMSO-$d_6$)δ 13.0(brs, 1H), 8.52(d, 1H, J=7.4 Hz), 7.50(s, 1H), 7.43–7.35(m, 3H), 7.25(m, 1H), 7.22(s, 1H), 5.13(s, 2H), 3.25(Hept, 1H, J=6.7 Hz), 1.25(d, 6H, J=6.7 Hz).

Example 11

Synthesis of 2-[3-(2,6-dichlorophenyl)propyl]-9-hydroxy-2H-pyrido[1,2-a]pyrazine-1,8-dione

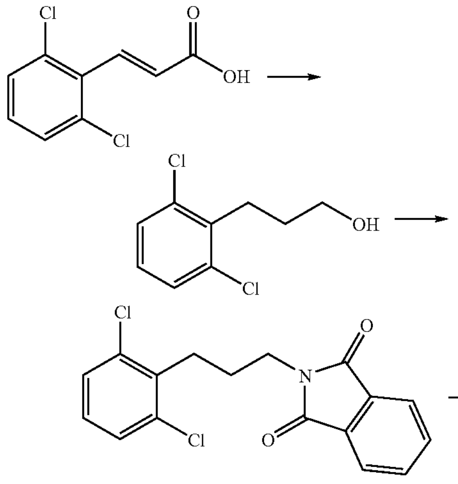

-continued

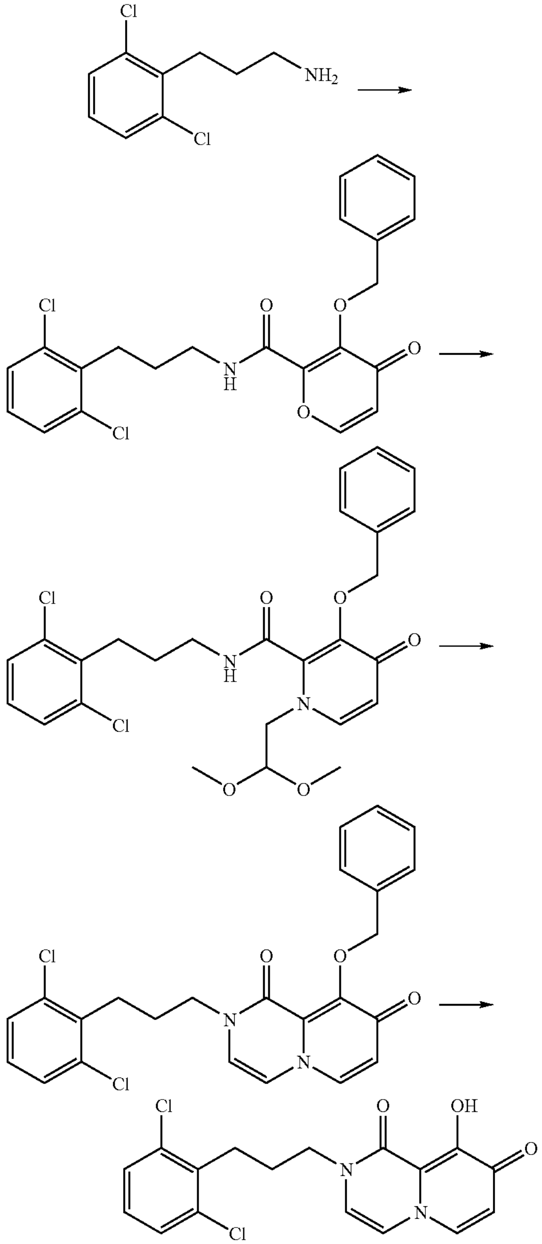

Step 1

Lithium aluminum hydride (1.31 g) was suspended in tetrahydrofuran (30 ml) and 3-(2,6-dichlorophenyl)acrylic acid (4.62 g) was added dropwise under ice-cooling over about 20 min. During the dropwise addition, tetrahydrofuran (20 ml) was added. After stirring at 0° C. for 3.5 hr, the mixture was stirred at room temperature for 18 hr. 4N Aqueous potassium hydroxide solution was added to the reaction mixture and a solid component was filtered off. The filtrate was concentrated under reduced pressure, and to the residue was added 1N aqueous hydrochloric acid solution. The mixture was extracted twice with ethyl acetate, and the organic layer was washed with saturated brine and dried over sodium sulfate. The solvent was evaporated to give a crude product (5.40 g) of 3-(2,6-dichlorophenyl)propan-1-ol.

Step 2

To a solution of triphenylphosphine (6.14 g), phthalimide (3.44 g) and 3-(2,6-dichlorophenyl)propan-1-ol (crude product:5.40 g) obtained in the previous step in tetrahydrofuran (90 ml) was added dropwise diethyl azodicarboxylate (40% toluene solution) (10.19 g) under ice-cooling. After stirring at room temperature for 2 hr, the reaction mixture was concentrated under reduced pressure. Diethyl ether was added to the residue and precipitated solid component was filtered off. The filtrate was concentrated. Diethyl ether was added again to the obtained residue and the precipitated solid component was filtered off. The filtrate was concentrated and purified by silica gel column chromatography (chloroform-hexane:ethyl acetate=4:1) to give a crude product (4.28 g) of 2-[3-(2,6-dichlorophenyl)propyl]isoindole-1,3-dione.

Step 3

To a solution of 2-[3-(2,6-dichlorophenyl)propyl]isoindole-1,3-dione (crude product:4.28 g) obtained in the previous step in ethanol (50 ml) was added hydrazine monohydrate (2.79 ml) and the mixture was heated under reflux for 1 hr. The reaction mixture was cooled to room temperature, and 10% aqueous sodium carbonate solution (90 ml) was added. The mixture was extracted with chloroform (100 ml×2). The organic layer was washed with water and dried over sodium sulfate. The solvent was evaporated to give a crude product (3.20 g) of 3-(2,6-dichlorophenyl)propylamine.

Step 4

To a suspension of 3-benzyloxy-4-oxo-4H-pyran-2-carboxylic acid (0.30 g) in chloroform (10 ml) were added oxalyl chloride (0.13 ml) and dimethylformamide (0.01 ml), and the mixture was stirred at room temperature for 30 min. The reaction solvent was evaporated under reduced pressure and toluene was added. The mixture was concentrated and chloroform (5 ml) was added. A solution of 3-(2,6-dichlorophenyl)propylamine (0.31 g) obtained in the previous step in chloroform (1 ml) and triethylamine (0.21 ml) were successively added under ice-cooling, and the mixture was stirred under ice-cooling for 10 min. 1N Aqueous hydrochloric acid solution was added to the obtained reaction mixture and the mixture was extracted with chloroform. The organic layer was dried over sodium sulfate. The solvent was evaporated and the residue was purified by silica gel column chromatography (hexane:ethyl acetate=1:1–1:2) to give N-[3-(2,6-dichlorophenyl)propyl]-3-benzyloxy-4-oxo-4H-pyran-2-carboxamide (0.24 g).

$^1$H-NMR ($CDCl_3$)δ 7.81(d, 1H, J=5.6 Hz), 7.79(br, 1H), 7.39–7.26(m, 7H), 7.08(dd, 1H, J=7.6,8.6 Hz), 6.49(d, 1H, J=5.6 Hz), 5.40(s, 2H), 3.31(dt, 2H, J=5.2,7.2 Hz), 2.82(dd, 2H, J=7.9,8.1 Hz), 1.62–1.57(m, 2H).

Step 5

To N-[3-(2,6-dichlorophenyl)propyl]-3-benzyloxy-4-oxo-4H-pyran-2-carboxamide (0.24 g) obtained in the previous step were added tetrahydrofuran (1.8 ml), ethanol (1.8 ml) and aminoacetaldehyde dimethyl acetal (0.012 ml), and the mixture was stirred at 60° C. for 46 hr. The solvent was evaporated and the residue was purified by silica gel column chromatography (chloroform:methanol=100:0–10:1) to give N-[3-(2,6-dichlorophenyl)propyl]-3-benzyloxy-1-(2,2-dimethoxyethyl)-4-oxo-1,4-dihydropyridine-2-carboxamide (0.24 g).

$^1$H-NMR ($CDCl_3$)δ 7.35–7.24(m, 8H), 7.07(dd, 1H, J=7.6,8.1 Hz), 6.42(d, 1H, J=7.5 Hz), 6.25(br, 1H), 5.28(s,

2H), 4.57(dd, 1H, J=3.1,5.1 Hz), 3.89(d, 2H, J=4.8 Hz), 3.41–3.36(m, 6H), 3.29(m, 2H), 2.85(dd, 2H, J=7.2,8.6 Hz), 1.71–1.62(m, 2H).

Step 6

To a solution of N-[3-(2,6-dichlorophenyl)propyl]-3-benzyloxy-1-(2,2-dimethoxyethyl)-4-oxo-1,4-dihydropyridine-2-carboxamide (237 mg) obtained in the previous step in toluene (20 ml) was added camphorsulfonic acid (106 mg) and the mixture was stirred at 110° C. for 5 hr. After stirring at room temperature for 15 hr, camphorsulfonic acid (21 mg) was added and the mixture was stirred at 110° C. for 3 hr. Triethylamine (1 ml) was added to the reaction mixture at room temperature and the precipitated solid was filtered off. The filtrate was concentrated and purified by silica gel column chromatography (ethyl acetate:methanol=10:1–5:1) and thin layer chromatography (ethyl acetate:methanol=5:1) to give 9-benzyloxy-2-[3-(2,6-dichlorophenyl)propyl]-2H-pyrido[1,2-a]pyrazine-1,8-dione (120 mg).

$^1$H-NMR ($CDCl_3$)δ 7.64(d, 2H, J=7.9 Hz), 7.38(d, 1H, J=7.4 Hz), 7.38–7.23(m, 5H), 7.08(dd, 1H, J=7.7,8.4 Hz), 6.71(d, 1H, J=7.4 Hz), 6.43(d, 1H, 5.8 Hz), 6.28(d, 1H, J=6.0 Hz), 5.35(s, 2H), 3.89(t, 2H, J=7.4 Hz), 2.98(dd, 2H, J=7.2,8.4 Hz), 1.99(m, 2H).

Step 7

Trifluoroacetic acid (1 ml) was added to 9-benzyloxy-2-[3-(2,6-dichlorophenyl)propyl]-2H-pyrido[1,2-a]pyrazine-1,8-dione (120 mg) obtained in the previous step and the mixture was left standing at room temperature for 1 hr. The solvent was evaporated, toluene was added, and the mixture was concentrated, which operations were performed twice. The obtained crystals were washed with diisopropyl ether to give 2-[3-(2,6-dichlorophenyl)propyl]-9-hydroxy-2H-pyrido[1,2-a]pyrazine-1,8-dione (92 mg).

$^1$H-NMR (DMSO-$d_6$)δ 8.16(d, 1H, J=7.3 Hz), 7.46(d, 2H, J=7.7 Hz), 7.41(d, 1H, J=6.2 Hz), 7.28(m, 1H), 7.11(d, 1H, J=5.9 Hz), 6.85(d, 1H, J=7.7 Hz), 4.43(br, 1H), 3.92(t, 2H, J=7.0 Hz), 2.93(dd, 2H, J=7.7,8.4 Hz), 1.92(m, 2H).

Example 12

Synthesis of 2-(3,4-dichlorobenzyl)-9-hydroxy-2H-pyrazino[1,2-a]pyrimidine-1,8-dione hydrochloride

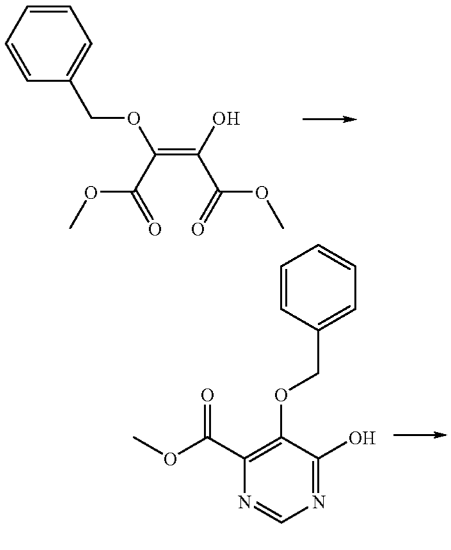

-continued

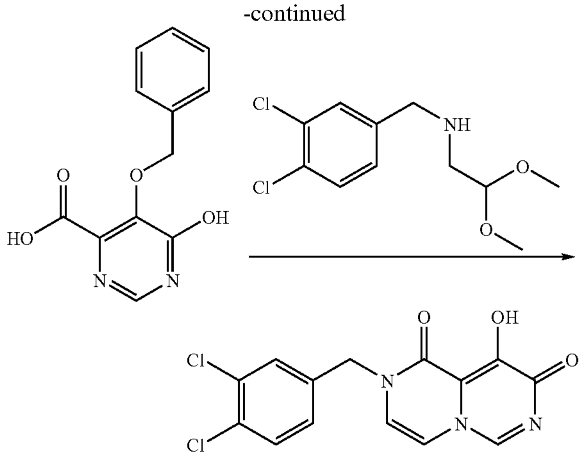

Step 1

To a solution of dimethyl 2-benzyloxy-3-hydroxy-2-butenedicarboxylate (3.0 g) in methanol (60 ml) were added sodium methoxide (1.28 g) and formamidine hydrochloride (953 mg) under ice-cooling, and the mixture was stirred at 70° C. for 1.5 hr. The reaction solvent was evaporated under reduced pressure, and water was added to dissolve the residue. 5% Aqueous potassium hydrogen sulfate solution was added, and the precipitated solid was collected by filtration, washed with water and dried to give methyl 5-benzyloxy-6-hydroxypyrimidine-4-carboxylate (1.1 g).

$^1$H-NMR (DMSO-$d_6$)δ 13.1(brs, 1H), 8.01(s, 1H), 7.2–7.5(m, 5H), 5.12(s, 2H), 3.75(s, 3H).

Step 2

Methanol (6 ml) and 1N aqueous sodium hydroxide solution (2.5 ml) were added to methyl 5-benzyloxy-6-hydroxypyrimidine-4-carboxylate (530 mg) obtained in the previous step, and the mixture was stirred at room temperature for 1 hr. 2N Hydrochloric acid (2.5 ml) was added to the reaction mixture, and methanol was evaporated under reduced pressure. The precipitate was collected by filtration, washed with water and dried to give 5-benzyloxy-6-hydroxypyrimidine-4-carboxylic acid (253 mg).

$^1$H-NMR (DMSO-$d_6$)δ 13.5(brs, 1H), 13.0(brs, 1H), 8.00 (s, 2H), 7.2–7.5(s, 2H).

Step 3

5-Benzyloxy-6-hydroxypyrimidine-4-carboxylic acid (103 mg) obtained in the previous step was dissolved in acetonitrile/tetrahydrofuran (2 ml), carbonyldiimidazole (88 mg) was added, and the mixture was stirred at room temperature for 30 min. The mixture was added to a solution of N-(3,4-dichlorobenzyl)-N-(2,2-dimethoxyethyl)amine obtained in the same manner as in Example 5, Step 1 in acetonitrile (2 ml), and the mixture was stirred overnight at room temperature. The reaction mixture was evaporated under reduced pressure, and the residue was dissolved in chloroform, washed with saturated brine and dried over magnesium sulfate. The solvent was evaporated and the residue was purified by silica gel column chromatography (hexane:ethyl acetate=1:2-ethyl acetate) to give an oil (210 mg). This oil was dissolved in dioxane (5 ml), pyridinium p-toluenesulfonate (22 mg) was added, and the mixture was heated under reflux overnight. The reaction solvent was evaporated under reduced pressure, and the residue was dissolved in chloroform, washed with saturated aqueous sodium hydrogen carbonate solution and saturated brine and dried over magnesium sulfate. The solvent was evaporated and the residue was purified by silica gel column chromatography (ethyl acetate-ethyl acetate:methanol=9:1) to give an oil (40 mg). This oil was dissolved in acetic acid (600 μl) and conc. hydrochloric acid (200 μl) and the mixture was stirred at 100° C. for 1.5 days. The reaction solvent was evaporated under reduced pressure. Toluene was added to the residue and the mixture was concentrated, which operations were performed twice, after which the residue was crystallized from methanol. The crystals were collected by filtration and dried to give 2-(3,4-dichlorobenzyl)-9-hydroxy-2H-pyrazino[1,2-c]pyrimidine-1,8-dione hydrochloride (12 mg).

$^1$H-NMR (DMSO-$d_6$)δ 1.08(brs, 1H), 8.48(s, 1H), 7.68(d, 1H, J=4 Hz), 7.63(d, 1H, J=8 Hz), 7.3–7.4(m, 2H), 7.16(d, 1H, J=8 Hz), 6.80(d, 1H, J=8 Hz), 4.90(s, 2H).

Examples 13–92

In the same manner as in Example 1–12 or by a similar method or by a conventional method, the compounds of Example 13–92 to be shown in the Tables below were obtained.

Example 118

Synthesis of 2-(3-chlorobenzyl)-9-hydroxy-7-(1-hydroxy-2,2-dimethylpropyl)-2H-pyrido[1,2-a]pyrazine-1,8-dione hydrochloride

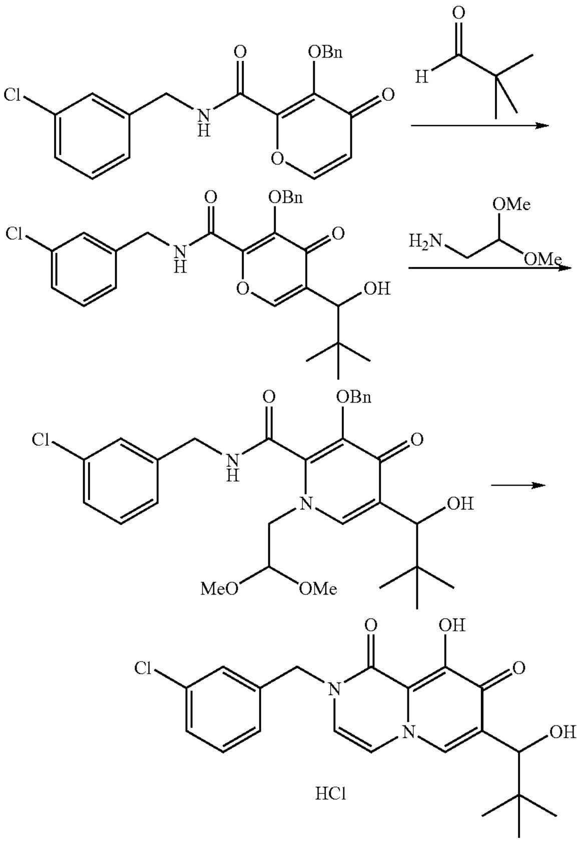

Step 1

To a solution of 3-benzyloxy-4-oxo-4H-pyran-2-carboxylic acid 3-chlorobenzylamide (300 mg) obtained in Example 10, Step 1 and 2,2-dimethylpropionaldehyde (9 ml) in tetrahydrofuran (9 ml) was added dropwise 1.5 M lithium diisopropylamide-tetrahydrofuran/cyclohexane solution (4.5 ml) under nitrogen at −78° C. After stirring at the same temperature for 2 hr, the cooling bath was removed and 1N aqueous hydrochloric acid (15 ml) and ethyl acetate (25 ml) were added, and the mixture was warmed to room temperature. The organic layer was separated from the aqueous layer and extracted with ethyl acetate (25 ml). The combined organic layer was dried, concentrated and purified by silica gel column chromatography (ethyl acetate:hexane=1:3) to give 3-benzyloxy-5-(1-hydroxy-2,2-dimethylpropyl)-4-oxo-4H-pyran-2-carboxylic acid 3-chlorobenzylamide (0.22 g).

$^1$H-NMR ($CDCl_3$)δ 8.07(brt, 1H, J=5.8 Hz), 7.82(s, 1H), 7.35–7.18(m, 7H), 7.15(s, 1H), 7.05(d, 1H, J=7.0 Hz), 5.33(s, 2H), 4.43(d, 1H, J=7.2 Hz), 4.39(d, 2H, J=5.8 Hz), 3.61(d, 1H, J=7.2 Hz), 0.96(s, 9H).

Step 2

To a solution of 3-benzyloxy-5-(1-hydroxy-2,2-dimethylpropyl)-4-oxo-4H-pyran-2-carboxylic acid 3-chlorobenzylamide (0.22 g) in tetrahydrofuran (1.5 ml)-ethanol (1.5 ml) was added aminoacetaldehyde dimethyl acetal (0.16 ml) and the mixture was stirred at 60° C. for 24 hr. The solvent was evaporated and purified by silica gel column chromatography (ethyl acetate:hexane=1:1-ethyl acetate) to give 3-benzyloxy-1-(2,2-dimethoxyethyl)-5-(1-hydroxy-2,2-dimethylpropyl)-4-oxo-1,4-dihydropyridine-2-carboxylic acid 3-chlorobenzylamide (198 mg).

$^1$H-NMR ($CDCl_3$)δ 7.73(brdd, 1H, J=6.2,5.8 Hz), 7.33–7.10(m, 10H), 5.76(brd, 1H, J=7.4 Hz), 5.17(d, 1H, J=11.0 Hz), 5.01(d, 1H, J=11.0 Hz), 4.50(t, 1H, J=5.0 Hz), 4.39(dd, 1H, J=6.2,15.1 Hz), 4.23(dd, 1H, J=5.8,15.1 Hz), 4.14(d, 1H, J=7.4 Hz), 3.29(s, 3H), 3.27(s, 3H), 0.89(s, 9H).

Step 3

To a solution of 3-benzyloxy-1-(2,2-dimethoxyethyl)-5-(1-hydroxy-2,2-dimethylpropyl)-4-oxo-1,4-dihydropyridine-2-carboxylic acid 3-chlorobenzylamide (60 mg) in dioxane (0.55 ml) was added conc. hydrochloric acid (0.55 ml) and the mixture was stirred at 90° C. for 2 hr. The solvent was evaporated, toluene was added, and the mixture was concentrated, which operations were performed twice. Crystallization from ethyl acetate-diisopropyl ether gave 2-(3-chlorobenzyl)-9-hydroxy-7-(1-hydroxy-2,2-dimethylpropyl)-2H-pyrido[1,2-a]pyrazine-1,8-dione hydrochloride (44 mg).

$^1$H-NMR (DMSO-$d_6$)δ 8.30(s, 1H), 7.70(d, 1H, J=6.2 Hz), 7.50(s), 7.44–7.34(m, 3H), 7.26(d, 1H, J=6.2 Hz), 5.09(d, 1H, J=14.9 Hz), 4.99(d, 1H, J=14.9 Hz), 4.76(s, 1H), 0.87(s, 9H).

Example 125

Synthesis of 2-(3-chlorobenzyl)-7-(2,2-dimethylpropionyl)-9-hydroxy-2H-pyrido[1,2-a]pyrazine-1,8-dione hydrochloride

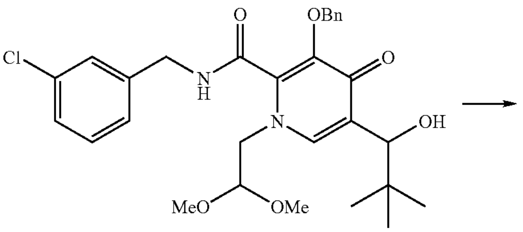

-continued

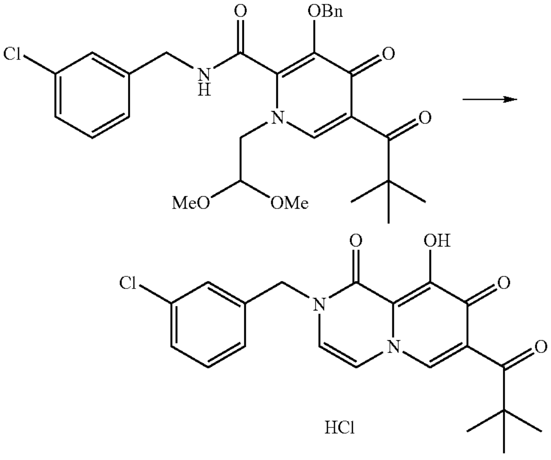

Step 1

To a solution of 3-benzyloxy-1-(2,2-dimethoxyethyl)-5-(1-hydroxy-2,2-dimethylpropyl)-4-oxo-1,4-dihydropyridine-2-carboxylic acid 3-chlorobenzylamide (120 mg) obtained in Example 118, Step 2 in dimethyl sulfoxide (5 ml) were added triethylamine (1.1 ml) and sulfur trioxide pyridine complex (450 mg) and the mixture was stirred at room temperature for 1 hr. A saturated aqueous ammonium chloride solution was added to the reaction mixture and the mixture was extracted twice with ethyl acetate (30 ml). The combined ethyl acetate layer washed with water, dried, concentrated and purified by silica gel column chromatography (ethyl acetate:hexane=1:3) to give 3-benzyloxy-1-(2,2-dimethoxyethyl)-5-(2,2-dimethylpropionyl)-4-oxo-1,4-dihydropyridine-2-carboxylic acid 3-chlorobenzylamide (104 mg).

$^1$H-NMR ($CDCl_3$)δ 8.27(brt, 1H, J=6.0 Hz), 7.26–7.14 (m, 8H), 7.06(t, 1H, J=7.7 Hz), 5.08(s, 2H), 4.54(t, 1H, J=5.1 Hz), 4.34(d, 2H, J=6.0 Hz), 3.81(d, 2H, J=5.1 Hz), 3.28(s, 6H), 1.20(s, 9H).

Step 2

To a solution of 3-benzyloxy-1-(2,2-dimethoxyethyl)-5-(2,2-dimethylpropionyl)-4-oxo-1,4-dihydropyridine-2-carboxylic acid 3-chlorobenzylamide (100 mg) in dioxane (1 ml) was added conc. hydrochloric acid (1 ml) and the mixture was stirred at 90° C. for 2 hr. The solvent was evaporated, toluene was added, and the mixture was concentrated, which operations were performed twice. Crystallization from ethyl acetate-diisopropyl ether gave 2-(3-chlorobenzyl)-7-(2,2-dimethylpropionyl)-9-hydroxy-2H-pyrido[1,2-a]pyrazine-1,8-dione hydrochloride (71 mg).

$^1$H-NMR (DMSO-$d_6$)δ 8.09(s, 1H), 7.48(s, 1H), 7.43–7.32(m, 3H), 7.22(d, 1H, J=6.2 Hz), 6.94(d, 1H, J=6.2 Hz), 4.98(s, 2H), 1.19(s, 9H).

Example 161

Synthesis of 7-amino-2-(3-chlorobenzyl)-9-hydroxy-2H-pyrido[1,2-a]pyrazine-1,8-dione hydrochloride

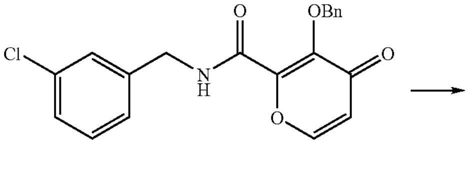

-continued

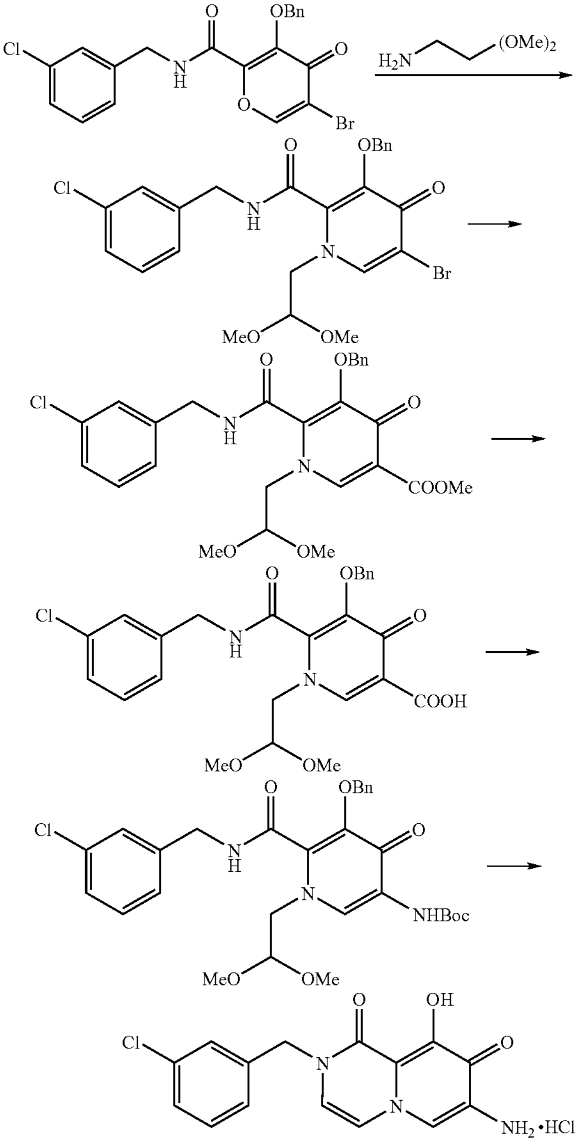

Step 1

To a solution of 3-benzyloxy-4-oxo-4H-pyran-2-carboxylic acid 3-chlorobenzylamide (5.13 g) obtained in Example 10, Step 1 in chloroform (100 ml) was added a solution of bromine (1.5 ml) in chloroform (50 ml) and the mixture was stirred with heating under reflux for 2 hr. A solution of bromine in chloroform (1.0 ml) was added, and after stirring with heating for 16 hr, the solvent was evaporated. Toluene was added to the residue and the mixture was concentrated, which operations were performed twice to give a crude product of 5-bromo-3-hydroxy-4-oxo-4H-pyran-2-carboxylic acid 3-chlorobenzylamide. The obtained crude product was dissolved in dimethylformamide (50 ml), and potassium carbonate (3.87 g) and benzyl bromide (2.75 ml) were added thereto. The reaction mixture was stirred at room temperature for 1 hr. Water (100 ml) and 1N aqueous hydrochloric acid (50 ml) were added to the reaction mixture and the mixture was extracted twice with ethyl acetate (200 ml each). The ethyl acetate layer was washed, dried, concentrated and purified by silica gel column chromatography (ethyl acetate:hexane=1:3) to give 3-benzyloxy-5-bromo-4-oxo-4H-pyran-2-carboxylic acid 3-chlorobenzylamide (3.31 g).

$^1$H-NMR ($CDCl_3$)δ 8.21(s, 1H), 8.01(brt, 1H, J=5.9 Hz), 7.41–7.20(m, 7H), 7.15(s, 1H), 7.05(d, 1H, J=7.3 Hz), 5.38(s, 2H), 4.39(d, 2H, J=5.9 Hz).

Step 2

To a solution of 3-benzyloxy-5-bromo-4-oxo-4H-pyran-2-carboxylic acid 3-chlorobenzylamide (1.50 g) in tetrahydrofuran (10 ml)-ethanol (10 ml) was added aminoacetaldehyde dimethyl acetal (0.73 ml) and the mixture was stirred at 60° C. for 1 hr. The solvent was evaporated and the residue was purified by silica gel column chromatography (ethyl acetate:hexane=1:3–1:2) to give 3-benzyloxy-5-bromo-1-(2,2-dimethoxyethyl)-4-oxo-1,4-dihydropyridine-2-carboxylic acid 3-chlorobenzylamide (1.35 g).

$^1$H-NMR ($CDCl_3$)δ 8.03(brt, 1H, J=6.2 Hz), 7.65(s, 1H), 7.33–7.11(m, 9H), 5.04(s, 2H), 4.53(t, 1H, J=5.1 Hz), 4.34 (d, 2H, J=6.2 Hz), 3.83(d, 2H, J=5.1 Hz), 3.30(s, 6H).

Step 3

To a solution of 3-benzyloxy-5-bromo-1-(2,2-dimethoxyethyl)-4-oxo-1,4-dihydropyridine-2-carboxylic acid 3-chlorobenzylamide (3.89 g) in dimethyl sulfoxide (26 ml)-methanol (13 ml) were added palladium(II) acetate (0.16 g), 1,3-bis(diphenylphosphino)propane (0.3 g) and triethylamine (2 ml) and the mixture was stirred under carbon monoxide at 70° C. for 24 hr. The reaction mixture was concentrated and water was added, and the mixture was extracted twice with ethyl acetate (200 ml each) The ethyl acetate layer was washed with water, dried and concentrated to give a crude product of methyl 5-benzyloxy-6-(3-chlorobenzylcarbamoyl)-1-(2,2-dimethoxyethyl)-4-oxo-1,4-dihydropyridine-3-carboxylate (4.12 g).

$^1$H-NMR ($CDCl_3$)δ 8.50(brs, 1H), 7.95(s, 1H), 7.29–7.12 (m, 9H), 4.97(s, 2H), 4.56(t, 1H, J=5.1 Hz), 4.46(d, 2H, J=6.3 Hz), 3.83(d, 2H, J=5.1 Hz), 3.73(s, 3H), 3.27(s, 6H).

Step 4

To a solution of methyl 5-benzyloxy-6-(3-chlorobenzylcarbamoyl)-1-(2,2-dimethoxyethyl)-4-oxo-1,4-dihydropyridine-3-carboxylate (2.0 g) in tetrahydrofuran (20 ml)-methanol (10 ml) was added 4N aqueous lithium hydroxide solution (1.5 ml) and the mixture was stirred at 70° C. for 1 hr. The precipitated solid was removed by thin layer of celite and washed with methanol. The solvent was evaporated and 1N aqueous hydrochloric acid (6.5 ml) and water (50 ml) were added. The mixture was extracted twice with ethyl acetate (75 ml each). The ethyl acetate layer was dried, concentrated and crystallized from ethyl acetate-diisopropyl ether to give 5-benzyloxy-6-(3-chlorobenzylcarbamoyl)-1-(2,2-dimethoxyethyl)-4-oxo-1,4-dihydropyridine-3-carboxylic acid (1.2 g).

$^1$H-NMR ($CDCl_3$)δ 8.35(s, 1H), 7.42–7.09(m, 9H), 6.55 (brs, 1H), 5.34(s, 2H), 4.50(t, 1H, J=4.4 Hz), 4.40(d, 2H, J=5.9 Hz), 4.10(d, 2H, J=4.4 Hz), 3.31(s, 6H).

Step 5

To a solution of 5-benzyloxy-6-(3-chlorobenzylcarbamoyl)-1-(2,2-dimethoxyethyl)-4-oxo-1,4-dihydropyridine-3-carboxylic acid (50 mg) in dimethylformamide (0.3 ml) were added triethylamine (0.07 ml) and diphenylphosphoryl azide (0.054 ml). After stirring at room temperature for 1 hr, tert-butanol (0.3 ml) was added, and the mixture was heated to 100° C. and stirred for 1 hr. After cooling to room temperature, saturated aqueous ammonium chloride solution (5 ml) and water (5 ml) were added, and the mixture was extracted twice with ethyl acetate (15 ml each). The ethyl acetate layer was washed with water, dried and concentrated. The obtained-residue was purified by silica gel column chromatography (ethyl acetate:hexane=1:2) to give tert-butyl [5-benzyloxy-6-(3-chlorobenzylcarbamoyl)-1-(2,2-dimethoxyethyl)-4-oxo-1,4-dihydropyridin-3-yl]carbamate (40 mg).

$^1$H-NMR ($CDCl_3$)δ 8.39(s, 1H), 7.70(s, 1H), 7.36–7.08 (m, 9H), 6.43(brt, 1H, J=6.2 Hz), 5.27(s, 2H), 4.52(t, 1H, J=5.1 Hz), 4.37(d, 2H, J=6.2 Hz), 4.06(d, 2H, J=5.1 Hz), 3.28(s, 6H), 1.55(s, 9H).

Step 6 tert-Butyl [5-benzyloxy-6-(3-chlorobenzylcarbamoyl)-1-(2,2-dimethoxyethyl)-4-oxo-1,4-dihydropyridin-3-yl]carbamate (40 mg) was dissolved in acetic acid (0.4 ml) and conc. hydrochloric acid (0.4 ml) was added. The mixture was stirred at 90° C. for 5 hr. The reaction mixture was concentrated, toluene was added to the residue and the mixture was concentrated, which operations were performed twice. Methanol was further added, and the mixture was concentrated, which operations were performed twice. Crystallization from ethyl acetate-methanol-diisopropyl ether gave 7-amino-2-(3-chlorobenzyl)-9-hydroxy-2H-pyrido[1,2-a]pyrazine-1,8-dione hydrochloride (23 mg).

$^1$H-NMR (DMSO-$d_6$)δ 12.29(brs, 1H), 7.99(s, 1H), 7.78 (d, 1H, J=6.0 Hz), 7.58(d, 1H, J=6.0 Hz), 7.49(s, 1H), 7.43–7.33(m, 3H), 5.10(s, 2H).

Example 165

Synthesis of N-[2-(3-chlorobenzyl)-9-hydroxy-1,8-dioxo-1,8-dihydro-2H-pyrido[1,2-a]pyrazin-7-yl]acetamide

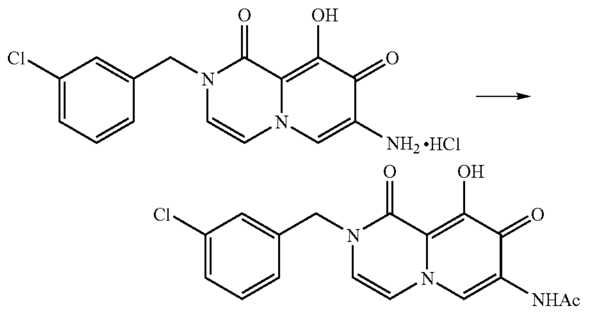

7-Amino-2-(3-chlorobenzyl)-9-hydroxy-2H-pyrido[1,2-a]pyrazine-1,8-dione hydrochloride (23 mg) obtained in Example 161 was dissolved in pyridine (0.1 ml) and acetic anhydride (0.0123 ml) was added. After stirring at room temperature for 1 hr, water (3 ml) was added to the reaction mixture, and the mixture was extracted twice with chloroform (6 ml each). The chloroform layer was dried, concentrated and crystallized from chloroform-methanol-diisopropyl ether to give 22 mg of a solid. This solid was suspended in tetrahydrofuran (0.4 ml)-methanol (1 ml)-chloroform (1 ml) and 2N aqueous sodium hydroxide solution (0.043 ml) was added. The mixture was stirred at room temperature for 30 min. The reaction mixture was concentrated, 1N aqueous hydrochloric acid (6 ml) was added, and the mixture was extracted three times with chloroform (8 ml each). The chloroform layer was dried, concentrated and crystallized from chloroform-methanol-diisopropyl ether to give N-[2-(3-chlorobenzyl)-9-hydroxy-1,8-dioxo-1,8-dihydro-2H-pyrido[1,2-a]pyrazin-7-yl]acetamide (18 mg).

$^1$H-NMR (DMSO-$d_6$)δ 11.59(bs, 1H), 9.44(s, 1H), 9.08(s, 1H), 7.49(s, 1H), 7.47(d, 1H, J=6.0 Hz), 7.42–7.32(m, 3H), 6.95(d, 1H, J=6.0 Hz), 4.97(s, 2H), 2.17(s, 3H).

Example 94

Synthesis of 7-bromo-2-(3-chlorobenzyl)-9-hydroxy-2H-pyrido[1,2-a]pyrazine-1,8-dione hydrochloride

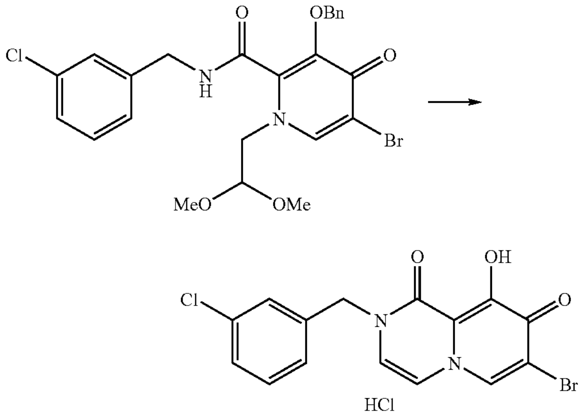

By subjecting 3-benzyloxy-5-bromo-1-(2,2-dimethoxyethyl)-4-oxo-1,4-dihydropyridine-2-carboxylic acid 3-chlorobenzylamide (50 mg) obtained in Example 161, Step 2 to a reaction operation similar to that in Example 161, Step 6 and crystallization from ethyl acetate-methanol-diisopropyl ether, 7-bromo-2-(3-chlorobenzyl)-9-hydroxy-2H-pyrido[1,2-a]pyrazine-1,8-dione hydrochloride (30 mg) was obtained.

$^1$H-NMR (DMSO-$d_6$)δ 8.63(s, 1H), 7.48(s, 1H), 7.44–7.33(m, 3H), 7.21(d, 1H, J=6.2 Hz), 6.95(d, 1H, J=6.2 Hz), 4.98(s, 2H).

Example 96

Synthesis of 2-(3-chlorobenzyl)-9-hydroxy-7-phenyl-2H-pyrido[1,2-a]pyrazine-1,8-dione hydrochloride

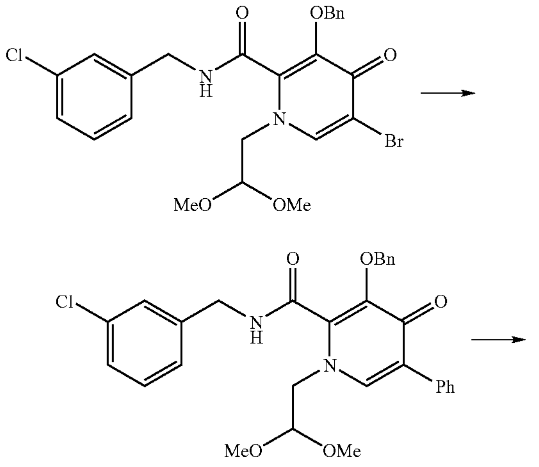

-continued

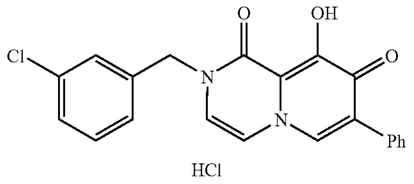

Step 1

To a solution of 3-benzyloxy-5-bromo-1-(2,2-dimethoxyethyl)-4-oxo-1,4-dihydropyridine-2-carboxylic acid 3-chlorobenzylamide (70 mg) obtained in Example 161, Step 2 in dimethoxyethane (1.4 ml)-water (0.7 ml) were successively added phenylboronic acid (32 mg), tetrakis(triphenylphosphine)palladium(0) (31 mg) and sodium carbonate (42 mg), and the mixture was stirred at 80° C. for 2 hr. After cooling to room temperature, the mixture was purified by silica gel column chromatography (ethyl acetate:hexane=1:3–1:1) to give 3-benzyloxy-1-(2,2-dimethoxyethyl)-4-oxo-5-phenyl-1,4-dihydropyridine-2-carboxylic acid 3-chlorobenzylamide (56 mg).

$^1$H-NMR ($CDCl_3$)δ 7.27(brs, 1H), 7.50(s, 1H), 7.40–7.09 (m, 14H), 5.15(s, 2H), 4.55(t, 1H, J=5.1 Hz), 4.16(d, 2H, J=6.0 Hz), 3.85(d, 2H, J=5.1 Hz), 3.28(s, 6H).

Step 2

3-Benzyloxy-1-(2,2-dimethoxyethyl)-4-oxo-5-phenyl-1,4-dihydropyridine-2-carboxylic acid 3-chlorobenzylamide (52 mg) was dissolved in acetic acid (0.5 ml) and conc. hydrochloric acid (0.5 ml) was added, and the mixture was stirred at 90° C. for 2 hr. The reaction mixture was concentrated, toluene was added to the residue and the mixture was concentrated, which operations were performed twice. Methanol was further added and the mixture was concentrated and crystallized from ethyl acetate-diisopropyl ether to give 2-(3-chlorobenzyl)-9-hydroxy-7-phenyl-2H-pyrido[1,2-a]pyrazine-1,8-dione hydrochloride (39 mg).

$^1$H-NMR (DMSO-$d_6$)δ 8.50(s, 1H), 7.73(d, 2H, J=7.0 Hz), 7.53–7.36(m, 8H), 7.10(d, 1H, J=6.2 Hz), 5.04(s, 2H).

Example 104

Synthesis of 2-(3-chlorobenzyl)-9-hydroxy-7-isopropyl-2H-pyrido[1,2-a]pyrazine-1,8-dione hydrochloride

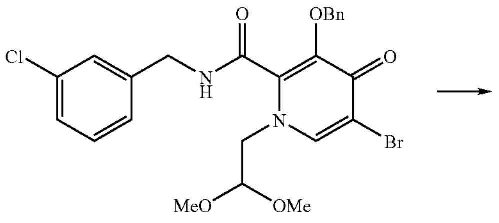

-continued

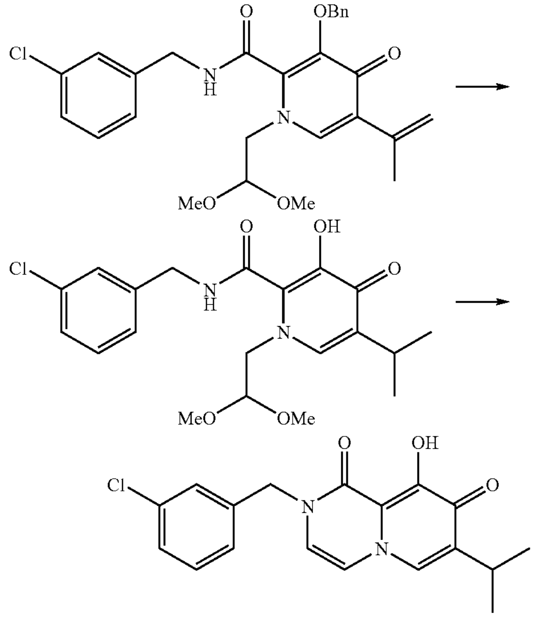

HCl

Step 1

To a solution of 3-benzyloxy-5-bromo-1-(2,2-dimethoxy-ethyl)-4-oxo-1,4-dihydropyridine-2-carboxylic acid 3-chlorobenzylamide (138 mg) obtained in Example 161, Step 2 in dioxane (2.5 ml) were added tributyl-2-propenyltin (245 mg) and tetrakis(triphenylphosphine)palladium(0) (60 mg), and the mixture was stirred at 100° C. for 4 hr. The solvent was evaporated, toluene was added, and the mixture was concentrated again. The obtained residue was purified by silica gel column chromatography (ethyl acetate:hexane=1:3) to give 3-benzyloxy-1-(2,2-dimethoxyethyl)-5-isopropenyl-4-oxo-1,4-dihydropyridine-2-carboxylic acid 3-chlorobenzylamide (89 mg).

$^1$H-NMR ($CDCl_3$)δ 7.75(brt, 1H, J=6.0 Hz), 7.31–7.09 (m, 10H), 5.80(d, 2H, J=2.3 Hz), 5.19(dq, 1H, J=2.3,1.4 Hz), 5.09(s, 2H), 4.52(t, 1H, J=5.1 Hz), 4.31(d, 2H, J=6.0 Hz), 3.82(d, 2H, J=5.1 Hz), 3.29(s, 6H), 2.05(brs, 3H).

Step 2

To a solution of 3-benzyloxy-1-(2,2-dimethoxyethyl)-5-isopropenyl-4-oxo-1,4-dihydropyridine-2-carboxylic acid 3-chlorobenzylamide (60 mg) in methanol (1 ml) was added 5% palladium-carbon (20 mg) and the mixture was stirred under an atmospheric pressure of hydrogen for 16 hr. A solid was filtered off and the filtrate was concentrated to give 1-(2,2-dimethoxyethyl)-3-hydroxy-5-isopropyl-4-oxo-1,4-dihydropyridine-2-carboxylic acid 3-chlorobenzylamide (43 mg).

$^1$H-NMR ($CDCl_3$)δ 8.89(brt, 1H, J=5.8 Hz), 7.38–7.24 (m, 5H), 4.63(d, 2H, J=5.8 Hz), 4.60(d, 1H, J=4.9 Hz), 4.51(d, 2H, J=4.9 Hz), 3.23(sep, 1H, J=6.8 Hz), 1.23(d, 6H, J=6.8 Hz).

Step 3

By subjecting 1-(2,2-dimethoxyethyl)-3-hydroxy-5-isopropyl-4-oxo-1,4-dihydropyridine-2-carboxylic acid 3-chlorobenzylamide (42 mg) to a reaction operation similar to that in Example 161, Step 6 and crystallization from ethyl acetate-methanol-diisopropyl ether, and further crystallization from ethyl acetate-methanol, 2-(3-chlorobenzyl)-9-hydroxy-7-isopropyl-2H-pyrido[1,2-a]pyrazine-1,8-dione hydrochloride (18 mg) was obtained.

$^1$H-NMR (DMSO-$d_6$)δ 8.27(s, 1H), 7.51–7.45(m, 2H), 7.42–7.31(m, 3H), 7.17(brd, 1H, J=6.2 Hz), 5.04(s, 2H), 3.23(sep, 1H, J=7.0 Hz), 1.19(d, 6H, J=7.0 Hz).

Example 187

Synthesis of methyl [2-(3-chlorobenzyl)-9-hydroxy-1,8-dioxo-1,8-dihydro-2H-pyrido[1,2-a]pyrazin-7-yl]acetate

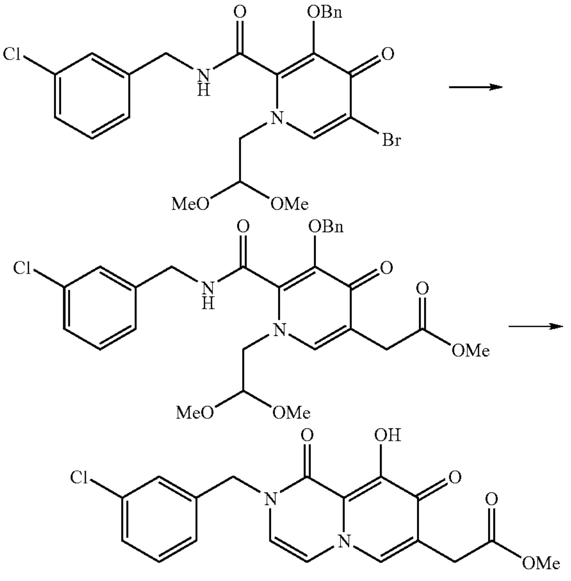

Step 1

To a solution of 3-benzyloxy-5-bromo-1-(2,2-dimethoxy-ethyl)-4-oxo-1,4-dihydropyridine-2-carboxylic acid 3-chlorobenzylamide (300 mg) obtained in Example 161, Step 2 in toluene were added under an argon stream tributyltin fluoride (518 mg), tris(dibenzylideneacetone)dipalladium(0)-chloroform adduct (58 mg), 1,1'-bis(diphenylphosphino) ferrocene (64 mg) and 1-(tert-butyldimethylsilyloxy)-1-methoxyethane (525 mg), and the mixture was stirred at 100° C. for 15 hr. After cooling to room temperature, aqueous sodium hydrogen carbonate was added to the reaction mixture and the mixture was extracted three times with ethyl acetate. The extract was dried, concentrated and purified by silica gel column chromatography (ethyl acetate) to give methyl [5-benzyloxy-6-(3-chlorobenzylcarbamoyl)-1-(2,2-dimethoxyethyl)-4-oxo-1,4-dihydropyridin-3-yl]acetate (184 mg).

$^1$H-NMR ($CDCl_3$)δ 7.38(s, 1H), 7.32–7.07(m, 9H), 6.76 (brt, 1H, J=6.0 Hz), 5.24(s, 2H), 4.52(t, 1H, J=5.1 Hz), 4.37(d, 2H, J=6.0 Hz), 3.90(d, 2H, J=5.1 Hz), 3.72(s, 3H), 3.48(s, 2H), 3.31(s, 6H).

Step 2

Methyl [5-benzyloxy-6-(3-chlorobenzylcarbamoyl)-1-(2,2-dimethoxyethyl)-4-oxo-1,4-dihydropyridin-3-yl]acetate (30 mg) was dissolved in trifluoroacetic acid (1 ml) and the mixture was stirred at 70° C. for 4 hr. The mixture was cooled and concentrated. Toluene was added to the residue and the mixture was concentrated again, which operations were performed twice. Crystallization from ethyl acetate-diisopropyl ether gave methyl [2-(3-chlorobenzyl)-9-hydroxy-1,8-dioxo-1,8-dihydro-2H-pyrido[1,2-a]pyrazin-7-yl]acetate (17 mg).

$^1$H-NMR (DMSO-$d_6$)δ 11.50(brs, 1H), 8.05(s, 1H), 7.48 (s, 1H), 7.42–7.31(m, 3H), 7.18(d, 1H, J=6.1 Hz), 6.86(d, 1H, J=6.1 Hz), 4.96(s, 2H), 3.59(s, 3H), 3.47(s, 2H).

Example 191

Synthesis of [2-(3-chlorobenzyl)-9-hydroxy-1,8-dioxo-1,8-dihydro-2H-pyrido[1,2-a]pyrazin-7-yl] acetic acid

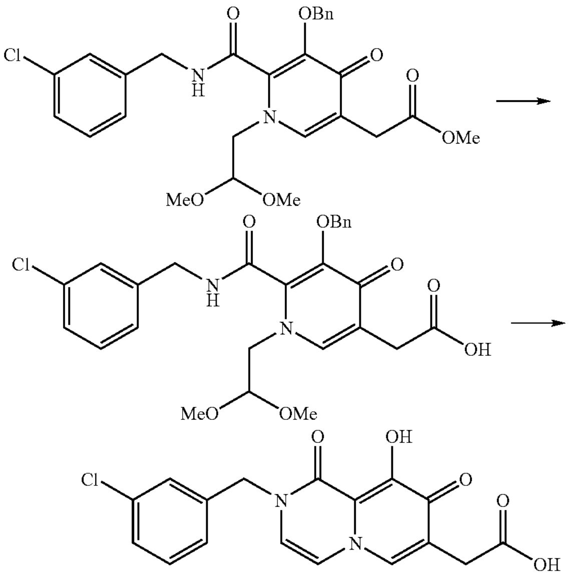

Step 1

To a solution of methyl [5-benzyloxy-6-(3-chlorobenzylcarbamoyl)-1-(2,2-dimethoxyethyl)-4-oxo-1,4-dihydropyridin-3-yl]acetate (150 mg) obtained in Example 187, Step 1 in tetrahydrofuran (1.5 ml)-methanol (1.5 ml) was added 4N aqueous sodium hydroxide solution (0.11 ml), and the mixture was stirred at 70° C. for 30 min. The reaction mixture was warmed to room temperature, 1N aqueous hydrochloric acid (0.5 ml) and water (15 ml) were added, and the mixture was extracted twice with ethyl acetate (30 ml each). The ethyl acetate layer was washed with water, dried, concentrated, and crystallized from ethyl acetate-diisopropyl ether to give [5-benzyloxy-6-(3-chlorobenzylcarbamoyl)-1-(2,2-dimethoxyethyl)-4-oxo-1,4-dihydropyridin-3-yl]acetic acid (116 mg).

$^1$H-NMR (CDCl$_3$)δ 7.42(s, 1H), 7.43–7.08(m, 9H), 6.81 (brt, 1H, J=5.8 Hz), 5.27(s, 2H), 4.51(t, 1H, J=4.6 Hz), 4.39(d, 2H, J=5.8 Hz), 4.01(d, 2H, J=4.6 Hz), 3.55(s, 2H), 3.30(s, 6H).

Step 2

By subjecting [5-benzyloxy-6-(3-chlorobenzylcarbamoyl)-1-(2,2-dimethoxyethyl)-4-oxo-1,4-dihydropyridin-3-yl]acetic acid (20 mg) to a-reaction operation similar to that in Example 187, Step 2, and crystallization from ethyl acetate-diisopropyl ether, [2-(3-chlorobenzyl)-9-hydroxy-1,8-dioxo-1,8-dihydro-2H-pyrido[1,2-a]pyrazin-7-yl]acetic acid (13 mg) was obtained.

$^1$H-NMR (DMSO-$d_6$)δ 12.40(brs, 1H), 11.52(brs, 1H), 8.05(s, 1H), 7.48(s, 1H), 7.42–7.31(m, 3H), 7.19(d, 1H, J=6.3 Hz), 6.87(d, 1H, J=6.3 Hz), 4.96(s, 2H), 3.40(s, 2H).

Example 189

Synthesis of 2-[2-(3-chlorobenzyl)-9-hydroxy-1,8-dioxo-1,8-dihydro-2H-pyrido[1,2-a]pyrazin-7-yl]-N-methylacetamide

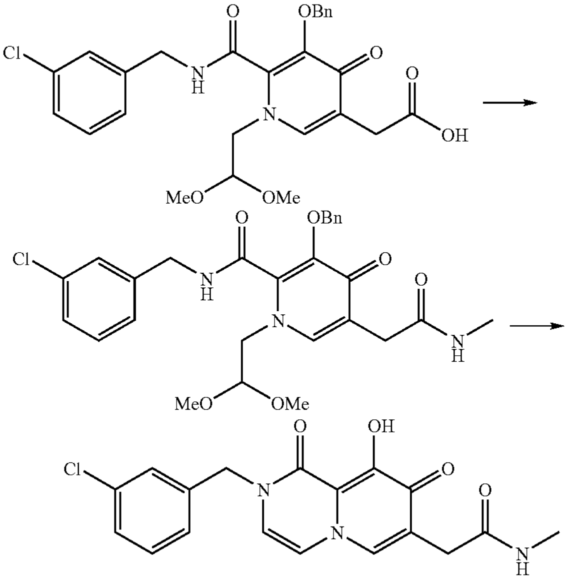

Step 1

To a solution of [5-benzyloxy-6-(3-chlorobenzylcarbamoyl)-1-(2,2-dimethoxyethyl)-4-oxo-1,4-dihydropyridin-3-yl]acetic acid (25 mg) obtained in Example 191, Step 1 in dimethylformamide (0.2 ml), were successively added 1-ethyl-3-(3-dimethylaminopropyl)carbodiimide hydrochloride (19 mg), 1-hydroxybenzotriazole hydrate (15 mg) and methylamine (2M tetrahydrofuran solution) (0.073 ml), and the mixture was stirred at room temperature for 2 hr. The obtained reaction mixture was applied as it was to silica gel thin layer chromatography (chloroform:methanol=10:1) and crystallized from ethyl acetate-diisopropyl ether to give 3-benzyloxy-1-(2,2-dimethoxyethyl)-5-methylcarbamoylmethyl-4-oxo-1,4-dihydropyridine-2-carboxylic acid 3-chlorobenzylamide (22 mg).

$^1$H-NMR (CDCl$_3$)δ 7.48(s, 1H), 7.45(brd, 1H, J=4.8 Hz), 7.34–7.05(m, 9H), 6.38(brt, 1H, J=6.0 Hz), 5.27(s, 2H), 4.49(t, 1H, J=4.8 Hz), 4.36(d, 2H, J=6.0 Hz), 3.95(d, 2H, J=4.8 Hz), 3.40(s, 2H), 3.30(s, 6H), 2.73(d, 3H, J=4.8 Hz).

Step 2

By subjecting 3-benzyloxy-1-(2,2-dimethoxyethyl)-5-methylcarbamoylmethyl-4-oxo-1,4-dihydropyridine-2-carboxylic acid 3-chlorobenzylamide (21 mg) to a reaction operation similar to that in Example 187, Step 2, and crystallization from ethyl acetate-diisopropyl ether, 2-[2-(3-chlorobenzyl)-9-hydroxy-1,8-dioxo-1,8-dihydro-2H-pyrido[1,2-a]pyrazin-7-yl]-N-methylacetamide (11 mg) was obtained.

$^1$H-NMR (DMSO-$d_6$)δ 11.44(brs, 1H), 8.01(s, 1H), 7.77 (s, 1H), 7.47(s, 1H), 7.43–7.31(m, 3H), 7.23(d, 1H, J=6.0 Hz), 6.87(d, 1H, J=6.0 Hz), 4.96(s, 2H), 3.27(s, 2H), 2.55(d, 3H, J=4.6 Hz).

Example 390

Synthesis of 9-benzyloxy-7-bromo-2-(3-chlorobenzyl)-3,4-dihydro-2H-pyrido[1,2-a]pyrazine-1,8-dione

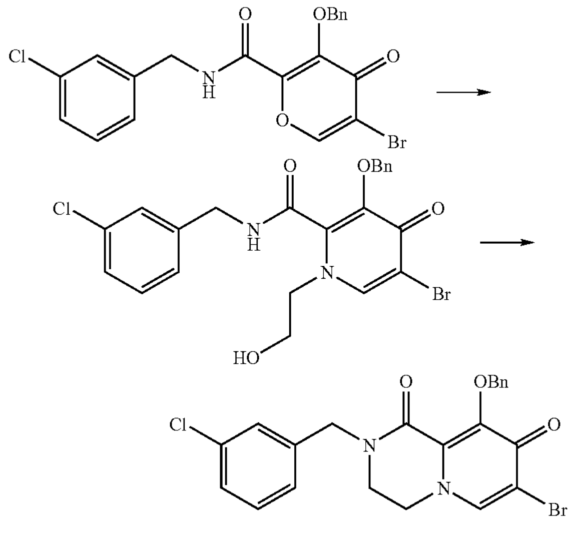

Step 1

To a solution of 3-benzyloxy-5-bromo-4-oxo-4H-pyran-2-carboxylic acid 3-chlorobenzylamide (2.0 g) obtained in Example 161, Step 1 in tetrahydrofuran (10 ml)-ethanol (10 ml) was added 2-aminoethanol (0.33 ml) and the mixture was stirred at room temperature and at 50° C. respectively for 30 min. The solvent was evaporated and the residue was crystallized from ethyl acetate-diisopropyl ether to give 3-benzyloxy-5-bromo-1-(2-hydroxyethyl)-4-oxo-1,4-dihydropyridine-2-carboxylic acid 3-chlorobenzylamide (1.95 g).

$^1$H-NMR (DMSO-$d_6$)δ 9.44(brt, 1H, J=5.8 Hz), 8.19(s, 1H), 7.39–7.16(m, 9H), 5.08(t, 1H, J=5.1 Hz), 5.05(s, 2H), 4.43(d, 2H, J=5.8 Hz), 3.92(t, 2H, J=5.1 Hz), 3.62(q, 2H, J=5.1 Hz).

Step 2

3-Benzyloxy-5-bromo-1-(2-hydroxyethyl)-4-oxo-1,4-dihydropyridine-2-carboxylic acid 3-chlorobenzylamide (1.75 g) was suspended in tetrahydrofuran (50 ml), and N,N-diisopropylethylamine (3.72 ml) and methanesulfonyl chloride (1.38 ml) were added. After stirring at room temperature for 1 hr, 0.5N aqueous hydrochloric acid (40 ml) was added, and the mixture was extracted twice with ethyl acetate (100 ml each). The ethyl acetate layer was washed with aqueous sodium hydrogen carbonate, dried and concentrated. The obtained residue was dissolved in dimethylformamide (50 ml) and 60% sodium hydride was added by small portions with stirring at room temperature. After confirming the completion of the reaction by thin layer chromatography (TLC), the reaction mixture was ice-cooled, 0.33N aqueous hydrochloric acid (300 ml) was added, and the mixture was extracted twice with ethyl acetate (250 ml each). The ethyl acetate layer was washed with water, dried, concentrated, and crystallized from ethyl acetate-hexane to give 9-benzyloxy-7-bromo-2-(3-chlorobenzyl)-3,4-dihydro-2H-pyrido[1,2-a]pyrazine-1,8-dione (1.58 g).

$^1$H-NMR ($CDCl_3$)δ 7.66(d, 2H, J=6.7 Hz), 7.56(s, 1H), 7.37–7.25(m, 6H), 7.16(m, 1H), 5.32(s, 2H), 4.62(s, 2H), 3.94–3.88(m, 2H), 3.52–3.45(m, 2H).

Example 244

Synthesis of 7-acetyl-2-(3-chloro-4-fluorobenzyl)-9-hydroxy-2H-pyrido[1,2-a]pyrazine-1,8-dione hydrochloride

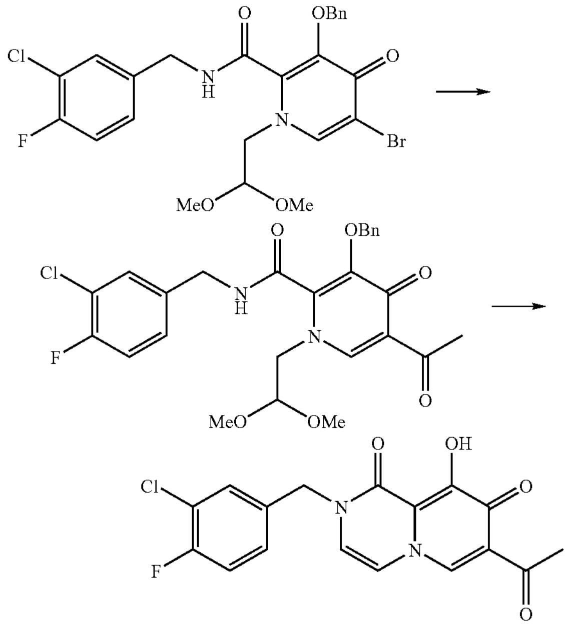

HCl

Step 1

To a solution of 3-benzyloxy-5-bromo-1-(2,2-dimethoxyethyl)-4-oxo-1,4-dihydropyridine-2-carboxylic acid 3-chloro-4-fluorobenzylamide (150 mg) produced in the same manner as for the compound described in Example 161, Step 2 in toluene (2 ml) were added tris(dibenzylideneacetone)dipalladium(0)-chloroform adduct (14 mg), 1,1'-bis(diphenylphosphino)ferrocene (15 mg) and tributyl(1-ethoxyvinyl)tin (189 mg) under an argon stream and the mixture was stirred at 90° C. for 4 hr. After cooling to room temperature, the reaction mixture was concentrated and purified by subjecting to silica gel thin layer chromatography (ethyl acetate:hexane=2:1) (toluene:acetone=3:1) twice to give 5-acetyl-3-benzyloxy-1-(2,2-dimethoxyethyl)-4-oxo-1,4-dihydropyridine-2-carboxylic acid 3-chloro-4-fluorobenzylamide (60 mg).

$^1$H-NMR ($CDCl_3$)δ 8.07(s, 1H), 7.34–7.25(m, 6H), 7.09–6.96(m, 2H), 6.67(brt, 1H, J=6.0 Hz), 5.25(s, 2H), 4.48(t, 1H, J=4.7 Hz), 4.31(d, 2H, J=6.0 Hz), 4.03(d, 2H, J=4.7 Hz), 3.31(s, 6H), 2.73(s, 3H).

Step 2

By subjecting 5-acetyl-3-benzyloxy-1-(2,2-dimethoxyethyl)-4-oxo-1,4-dihydropyridine-2-carboxylic acid 3-chloro-4-fluorobenzylamide (59 mg) to a reaction operation similar to that in Example 96, Step 2, and crystallization from ethyl acetate-diisopropyl ether, 7-acetyl-2-(3-chloro-4-fluorobenzyl)-9-hydroxy-2H-pyrido[1,2-a]pyrazine-1,8-dione hydrochloride (35 mg) was obtained.

$^1$H-NMR (DMSO-$d_6$)δ 8.48(s, 1H), 7.65(m, 1H), 7.43–7.40(m, 2H), 7.38(d, 1H, J=6.3 Hz), 6.93(d, 1H, J=6.3 Hz), 4.92(s, 2H), 2.61(s, 3H).

Example 251

Synthesis of 7-(2,2-dimethylpropionyl)-2-(4-fluorobenzyl)-9-hydroxy-2H-pyrido[1,2-a]pyrazine-1,8-dione hydrochloride

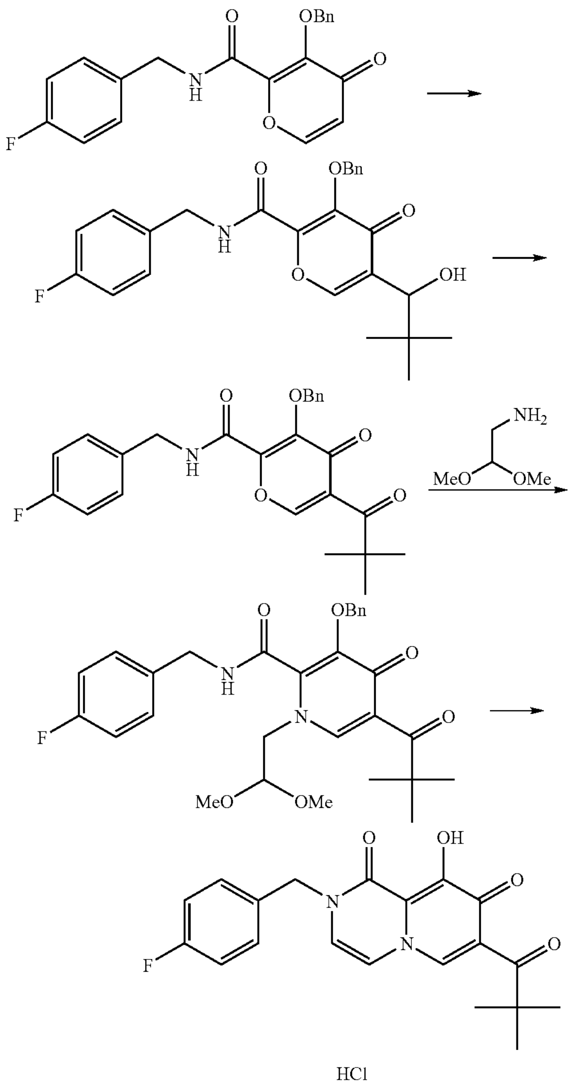

Step 1

To a solution of 3-benzyloxy-4-oxo-4H-pyran-2-carboxylic acid 4-fluorobenzylamide (0.6 g) produced in the same manner as for the compound described in Example 10, Step 1 and 2,2-dimethylpropionaldehyde (1.88 ml) in tetrahydrofuran (6 ml) was added dropwise 1.5 M lithium diisopropylamide-tetrahydrofuran/cyclohexane solution (14.9 ml) under nitrogen at −78° C. After stirring at the same temperature for 2 hr, the cooling bath was removed and 2N aqueous hydrochloric acid (15 ml) and ethyl acetate were immediately added, and the mixture was heated to room temperature. The organic layer was separated and the aqueous layer was extracted with ethyl acetate. The combined organic layer was dried, concentrated, and purified by silica gel column chromatography (ethyl acetate:hexane=1:2-ethyl acetate) to give 3-benzyloxy-5-(1-hydroxy-2,2-dimethylpropyl)-4-oxo-4H-pyran-2-carboxylic acid 4-fluorobenzylamide (0.27 g). The total amount thereof was dissolved in chloroform (3 ml) and 1,1,1-tris(acetoxy)-1,1-dihydro-1,2-benziodoxol-3-(1H)-one (Dess-Martin reagent) (291 mg) was added at room temperature, and the mixture was stirred for 2.5 hr. 2-Propanol was added and the mixture was stirred for 30 min, after which aqueous sodium hydrogen carbonate solution and aqueous sodium sulfite solution were added. The mixture was extracted with ethyl acetate. The ethyl acetate layer was washed with saturated brine, dried and concentrated. The obtained residue was purified by silica gel thin layer chromatography (ethyl acetate:hexane=1:1) to give 3-benzyloxy-5-(2,2-dimethylpropionyl)-4-oxo-4H-pyran-2-carboxylic acid 4-fluorobenzylamide (0.13 g).

$^1$H-NMR ($CDCl_3$)δ 8.00(m, 1H), 7.80(s, 1H), 7.40–6.93 (m, 9H), 5.34(s, 2H), 4.39(d, 2H, J=5.76 Hz), 1.24(s, 9H).

Step 2

To a solution of 3-benzyloxy-5-(2,2-dimethylpropionyl)-4-oxo-4H-pyran-2-carboxylic acid 4-fluorobenzylamide (0.13 g) in tetrahydrofuran (0.5 ml)-ethanol (0.5 ml) was added aminoacetaldehyde dimethyl acetal (0.033 ml) and the mixture was stirred at 70° C. for 3 days. After cooling to room temperature, the solvent was evaporated to give 3-benzyloxy-1-(2,2-dimethoxyethyl)-5-(2,2-dimethylpropionyl)-4-oxo-1,4-dihydropyridine-2-carboxylic acid 4-fluorobenzylamide (157 mg).

$^1$H-NMR ($CDCl_3$)δ 8.08(m, 1H), 7.31–7.15(m, 8H), 6.84–6.78(m, 2H), 5.06(s, 2H), 4.55(t, 1H, J=5.1 Hz), 4.35 (d, 2H, J=6.0 Hz), 3.82(d, 2H, J=5.1 Hz), 3.30(s, 6H), 1.21(s, 9H).

Step 3

3-Benzyloxy-1-(2,2-dimethoxyethyl)-5-(2,2-dimethylpropionyl)-4-oxo-1,4-dihydropyridine-2-carboxylic acid 4-fluorobenzylamide (157 mg) was dissolved in acetic acid (1.5 ml) and conc. hydrochloric acid (0.5 ml) was added. The mixture was stirred at 90° C. for 3 hr. The reaction mixture was concentrated and crystallized from ethyl acetate to give 7-(2,2-dimethylpropionyl)-2-(4-fluorobenzyl)-9-hydroxy-2H-pyrido[1,2-a]pyrazine-1,8-dione hydrochloride (92 mg).

$^1$H-NMR (DMSO-$d_6$)δ 8.07(s, 1H), 7.46–7.41(m, 2H), 7.22–7.16(m, 3H), 6.91(d, 1H, J=6.0 Hz), 4.93(s, 2H), 1.18(s, 9H).

Example 223

Synthesis of 2-(3-chlorobenzyl)-7-(2,2-dimethylpropionyl)-9-hydroxy-3,4-dihydro-2H-pyrido[1,2-a]pyrazine-1,8-dione hydrochloride

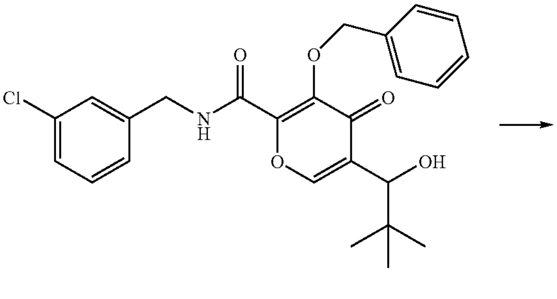

-continued

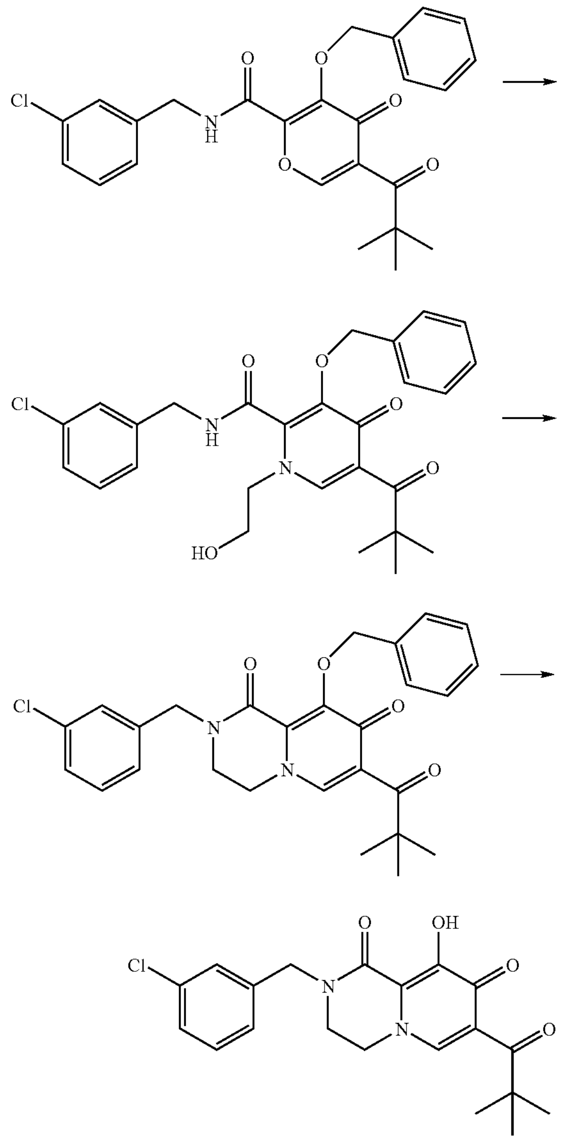

HCl

Step 1

To a solution of 3-benzyloxy-5-(1-hydroxy-2,2-dimethylpropyl)-4-oxo-4H-pyran-2-carboxylic acid 3-chlorobenzylamide (0.22 g) obtained in the same manner as in Example 118, Step 1 in chloroform (2 ml) was added 1,1,1-tris(acetoxy)-1,1-dihydro-1,2-benziodoxol-3-(1H)-one (0.23 g). The mixture was stirred at room temperature for 30 min, aqueous sodium hydrogen carbonate solution and aqueous sodium sulfite solution were added and the reaction mixture was extracted with ethyl acetate. The organic layer was washed with saturated brine, dried and concentrated to give 3-benzyloxy-5-(2,2-dimethylpropionyl)-4-oxo-4H-pyran-2-carboxylic acid 3-chlorobenzylamide (225 mg).

$^1$H-NMR ($CDCl_3$)δ 8.02(1H, t, J=6.0 Hz), 7.81(1H, s), 7.36–7.16(7H, m), 7.14(1H, s), 7.04(1H, d, J=7.0 Hz), 5.36(2H, s), 4.39(2H, d, J=6.0 Hz), 1.26(9H, s).

Step 2

To a solution of 3-benzyloxy-5-(2,2-dimethylpropionyl)-4-oxo-4H-pyran-2-carboxylic acid 3-chlorobenzylamide (113 mg) in tetrahydrofuran (0.7 ml)-ethanol (0.7 ml) was added 2-aminoethanol (0.015 ml) and the mixture was stirred at 60° C. for 11 hr. The solvent was evaporated and the obtained residue was purified by silica gel column chromatography (ethyl acetate:hexane=3:1) to give 3-benzyloxy-5-(2,2-dimethylpropionyl)-1-(2-hydroxyethyl)-4-oxo-1,4-dihydropyridine-2-carboxylic acid 3-chlorobenzylamide (91 mg).

$^1$H-NMR ($CDCl_3$)δ 8.37(1H, t, J=6.0 Hz), 7.36(1H, s), 7.30(1H, s), 7.28–7.07(8H, m), 4.94(2H, s), 4.76(1H, br s), 4.28(2H, d, J=6.0 Hz), 4.03–3.95(2H, m), 3.84–3.76(2H, m), 1.15(9H, s).

Step 3

To a solution of 3-benzyloxy-5-(2,2-dimethylpropionyl)-1-(2-hydroxyethyl)-4-oxo-1,4-dihydropyridine-2-carboxylic acid 3-chlorobenzylamide (91 mg) in tetrahydrofuran (3 ml) was added N,N-diisopropylethylamine (0.187 ml) and the mixture was ice-cooled. Methanesulfonyl chloride (0.07 ml) was added at the same temperature over 30 min with stirring. After confirmation of the completion of the reaction by thin layer chromatography, 5% aqueous potassium hydrogen sulfate solution was added to the reaction mixture and the mixture was extracted with ethyl acetate. The ethyl acetate layer was washed successively with brine, aqueous sodium hydrogen carbonate solution and brine, dried and concentrated. The obtained residue was dissolved in dimethylformamide (2 ml) and 60% sodium hydride (50 mg) was added by small portions with stirring at room temperature. After stirring for 30 min, the reaction mixture was ice-cooled and 5% aqueous potassium hydrogen sulfate solution was added, and the mixture was extracted with ethyl acetate. The ethyl acetate layer was washed with brine, dried and concentrated. The obtained residue was purified by silica gel thin layer chromatography (ethyl acetate) to give 9-benzyloxy-2-(3-chlorobenzyl)-7-(2,2-dimethylpropionyl)-3,4-dihydro-2H-pyrido[1,2-a]pyrazine-1,8-dione (44 mg).

$^1$H-NMR ($CDCl_3$)δ 7.61–7.59(2H, m), 7.29–7.22(8H, m), 5.39(2H, s), 4.68(2H, s), 3.96–3.92(2H, m), 3.52–3.46(2H, m), 1.32(9H, s).

Step 4

9-Benzyloxy-2-(3-chlorobenzyl)-7-(2,2-dimethylpropionyl)-3,4-dihydro-2H-pyrido[1,2-a]pyrazine-1,8-dione (43 mg) was dissolved in trifluoroacetic acid (2 ml) and the mixture was stirred at room temperature for 1 hr. The solvent was evaporated and toluene was added, and the mixture was concentrated again. Subsequently, a suitable amount of hydrochloric acid/ethyl acetate solution was added, and the mixture was concentrated again. Ethyl acetate (0.6 ml)-diisopropyl ether (1 ml) was added to the obtained residue and the obtained solid was collected by filtration to give 2-(3-chlorobenzyl)-7-(2,2-dimethylpropionyl)-9-hydroxy-3,4-dihydro-2H-pyrido[1,2-a]pyrazine-1,8-dione hydrochloride (25.6 mg).

$^1$H-NMR (DMSO-$d_6$)δ 7.73(1H, s), 7.45–7.30(4H, m), 4.71(2H, s), 4.25(2H, t, J=5.6 Hz), 3.72(2H, t, J=5.6 Hz), 1.20(9H, s).

Example 154

Synthesis of 2-(3-chlorobenzyl)-9-hydroxy-1,8-dioxo-1,8-dihydro-2H-pyrido[1,2-a]pyrazine-7-carboxylic acid isopropylamide

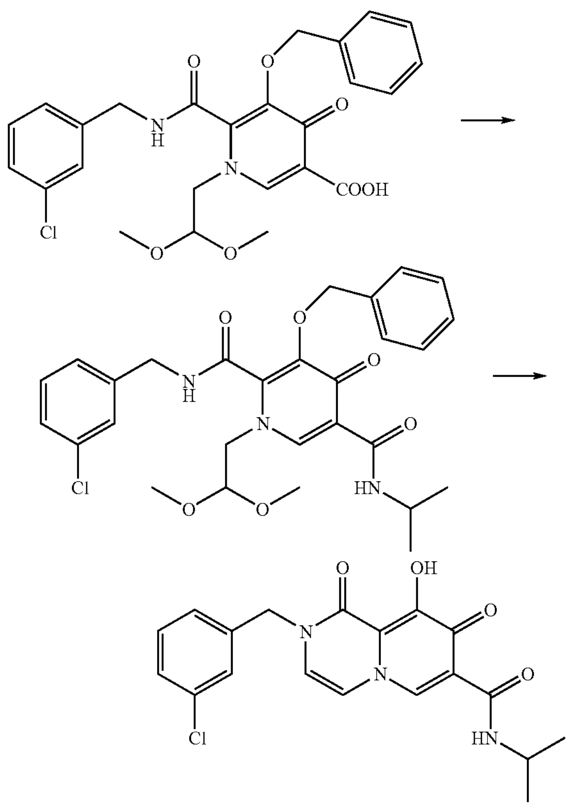

To a solution of 5-benzyloxy-6-(3-chlorobenzylcarbamoyl)-1-(2,2-dimethoxyethyl)-4-oxo-1,4-dihydropyridine-3-carboxylic acid (25.4 mg) obtained in Example 161, Step 4 in tetrahydrofuran (0.3 ml) were successively added triethylamine (0.021 ml) and thionyl chloride (0.0056 ml) at 0° C. with stirring. After stirring at room temperature for 10 min, the mixture was ice-cooled again and isopropylamine (0.0086 ml) was added. After stirring at room temperature for 30 min, 5% aqueous potassium hydrogen sulfite solution was added, and the mixture was extracted with ethyl acetate. The ethyl acetate layer was washed with brine, dried and concentrated. Trifluoroacetic acid was added to the obtained residue and the mixture was stirred at 70° C. for 5.5, hr. Trifluoroacetic acid was evaporated, toluene was added and the mixture was concentrated, which operations were performed twice. Crystallization from ethyl acetate (2 ml) gave 2-(3-chlorobenzyl)-9-hydroxy-1,8-dioxo-1,8-dihydro-2H-pyrido[1,2-a]pyrazine-7-carboxylic acid isopropylamide (13.6 mg)

$^1$H-NMR (DMSO-$d_6$)δ 11.79(1H, s), 10.10(1H, d, J=7.9 Hz), 8.74(1H, s), 7.51–7.49(2H, m), 7.40–7.34(3H, m), 7.01(1H, d, J=6.5 Hz), 4.96(2H, s), 4.05(1H, sept, J=6.5 Hz), 1.18(6H, d, J=6.5 Hz).

Example 249

Synthesis of 2-(3,4-dichlorobenzyl)-9-hydroxy-7-(thiazol-2-yl)-3,4-dihydro-2H-pyrido[1,2-a]pyrazine-1,8-dione

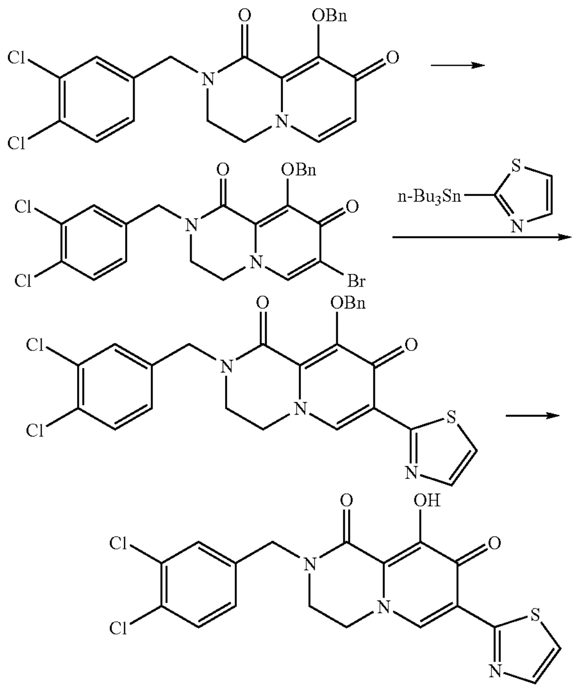

Step 1

To a solution of 9-benzyloxy-2-(3,4-dichlorobenzyl)-3,4-dihydro-2H-pyrido[1,2-a]pyrazine-1,8-dione (3.8 g) obtained in Example 1, Step 3 in chloroform (90 ml)-methanol (60 ml) was added phenyltrimethylammonium tribromide (5.0 g) and the mixture was stirred at room temperature for 13 hr. An aqueous sodium sulfite solution was added to the reaction mixture and the mixture was extracted twice with chloroform. The combined extract was washed with brine and purified as it was by silica gel column chromatography (chloroform-methanol=19:1–10:1) to give 9-benzyloxy-7-bromo-2-(3,4-dichlorobenzyl)-3,4-dihydro-2H-pyrido[1,2-a]pyrazine-1,8-dione (2.44 g).

$^1$H-NMR (DMSO-$d_6$)δ 8.36(s, 1H), 7.6–7.7(m, 2H), 7.5–7.6(m, 2H), 7.2–7.4(m, 4H), 5.08(s, 2H), 4.68(s, 2H), 4.1–4.3(m, 2H), 3.6–3.8(m, 2H).

Step 2

To a solution of 9-benzyloxy-7-bromo-2-(3,4-dichlorobenzyl)-3,4-dihydro-2H-pyrido[1,2-a]pyrazine-1,8-dione (150 mg) in dioxane (5 ml) were added tris(dibenzylideneacetone)dipalladium(0)-chloroform adduct (63 mg), tri-2-furylphosphine (57 mg) and (2-thiazolyl)tributyltin (0.285 ml) under an argon stream and a microwave at 80 W was irradiated under sealing for 1 hr. The obtained reaction mixture was concentrated, and then purified by silica gel column chromatography (chloroform:methanol=40:1) to give 9-benzyloxy-2-(3,4-dichlorobenzyl)-7-(thiazol-2-yl)-3,4-dihydro-2H-pyrido[1,2-a]pyrazine-1,8-dione (95 mg).

$^1$H-NMR ($CDCl_3$)δ 8.49(s, 1H), 7.85(d, 1H, J=3.3 Hz), 7.6–7.8(m, 2H), 7.1–7.5(m, 7H), 5.47(s, 2H), 4.64(s, 2H), 4.11(t, 2H, J=5.4 Hz), 3.56(t, 2H, J=5.4 Hz).

Step 3

9-Benzyloxy-2-(3,4-dichlorobenzyl)-7-(thiazol-2-yl)-3,4-dihydro-2H-pyrido[1,2-a]pyrazine-1,8-dione (93 mg) was dissolved in trifluoroacetic acid (2 ml). After leaving at room temperature for 1.5 hr, the mixture was concentrated. Toluene was added to the residue and the mixture was concentrated again, which operations were performed twice. Ethyl acetate was added and the solid was collected by filtration to give 2-(3,4-dichlorobenzyl)-9-hydroxy-7-(thiazol-2-yl)-3,4-dihydro-2H-pyrido[1,2-a]pyrazine-1,8-dione (53 mg).

$^1$H-NMR (DMSO-$d_6$)δ 12.25(brs, 1H), 8.71(s, 1H), 7.89 (d, 1H, J=3.2 Hz), 7.69(d, 1H, J=2 Hz), 7.6–7.65(m, 2H), 7.39(dd, 1H, J=8.4 Hz, 2 Hz), 4.74(s, 2H), 4.4–4.5(m, 2H), 3.75–3.85(m, 2H).

Example 219

Synthesis of 2-(3-chlorobenzyl)-9-hydroxy-1,8-dioxo-1,3,4,8-tetrahydro-2H-pyrido[1,2-a]pyrazine-7-carboxylic acid methylamide

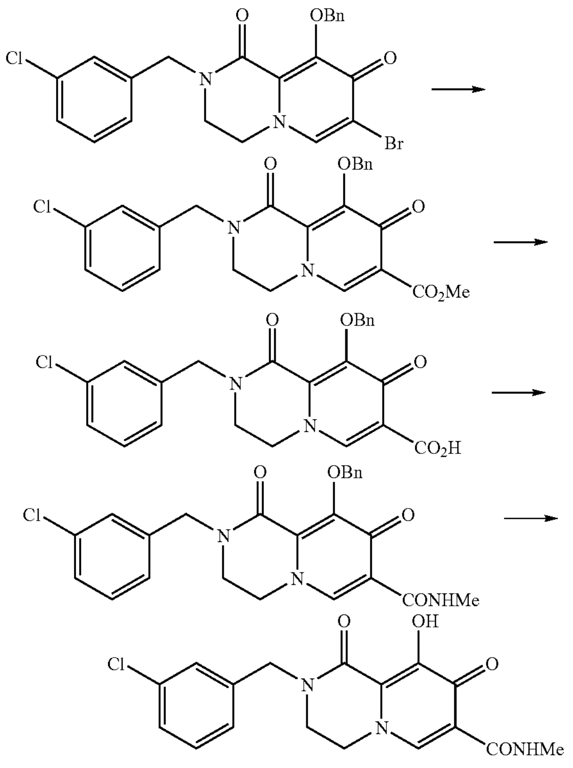

Step 1

By subjecting 9-benzyloxy-7-bromo-2-(3-chlorobenzyl)-3,4-dihydro-2H-pyrido[1,2-a]pyrazine-1,8-dione (600 mg) produced by the same method as in Example 249, Step 1 to a reaction operation similar to that in Example 161, Step 3, a mixture of methyl 9-benzyloxy-2-(3-chlorobenzyl)-1,8-dioxo-1,3,4,8-tetrahydro-2H-pyrido[1,2-a]pyrazine-7-carboxylate and methyl 2-(3-chlorobenzyl)-1,8-dioxo-9-hydroxy-1,3,4,8-tetrahydro-2H-pyrido[1,2-a]pyrazine-7-carboxylate was obtained (13 mg). This mixture was dissolved in dimethylformamide (17 ml) and treated with benzyl bromide (1.36 g) and potassium carbonate (1.75 g) and purified by silica gel column chromatography (ethyl acetate-chloroform:methanol=10:1) to give methyl 9-benzyloxy-2-(3-chlorobenzyl)-1,8-dioxo-1,3,4,8-tetrahydro-2H-pyrido[1,2-a]pyrazine-7-carboxylate (480 mg).

$^1$H-NMR ($CDCl_3$)δ 8.02(s, 1H), 7.66(d, 2H, J=6 Hz), 7.2–7.4(m, 6H), 7.1–7.2(m, 1H), 5.33(s, 2H), 4.62(s, 2H), 3.94(t, 2H, J=5.3 Hz), 3.91(s, 3H), 3.50(t, 2H, J=5.3 Hz).

Step 2

Methyl 9-benzyloxy-2-(3-chlorobenzyl)-1,8-dioxo-1,3,4,8-tetrahydro-2H-pyrido[1,2-a]pyrazine-7-carboxylate (420 mg) was dissolved in tetrahydrofuran (8 ml)-water (2 ml), and 4N aqueous lithium hydroxide solution (0.58 ml) was added with stirring. After stirring at 70° C. for 1 hr, the mixture was concentrated. Water (5 ml) and then 5% aqueous potassium hydrogen sulfate solution (15 ml) were added with stirring. The precipitated crystals were collected by filtration to give 9-benzyloxy-2-(3-chlorobenzyl)-1,8-dioxo-1,3,4,8-tetrahydro-2H-pyrido[1,2-a]pyrazine-7-carboxylic acid (352 mg).

$^1$H-NMR (DMSO-$d_6$)δ 8.70(brs, 1H), 7.2–7.6(m, 9H), 5.16(s, 2H), 4.72(s, 2H), 4.3–4.6(m, 2H), 3.6–3.8(m, 2H).

Step 3

By subjecting 9-benzyloxy-2-(3-chlorobenzyl)-1,8-dioxo-1,3,4,8-tetrahydro-2H-pyrido[1,2-a]pyrazine-7-carboxylic acid (350 mg) to a reaction operation similar to that in Example 154, 2-(3-chlorobenzyl)-9-hydroxy-1,8-dioxo-1,3,4,8-tetrahydro-2H-pyrido[1,2-a]pyrazine-7-carboxylic acid methylamide (182 mg) was obtained.

$^1$H-NMR (DMSO-$d_6$)δ 12.28(s, 1H), 9.8–10.0(m, 1H), 8.38(s, 1H), 7.46(s, 1H), 7.25–7.4(m, 3H), 4.72(s, 2H), 4.40(t, 2H, J=5.5 Hz), 3.75(t, 2H, J=5.5 Hz), 2.83(d, 3H, J=4.9 Hz).

Example 362

Synthesis of 2-(3-chlorobenzyl)-7-(2,2-dimethylbutyryl)-9-hydroxy-3,4-dihydro-2H-pyrido[1,2-a]pyrazine-1,8-dione

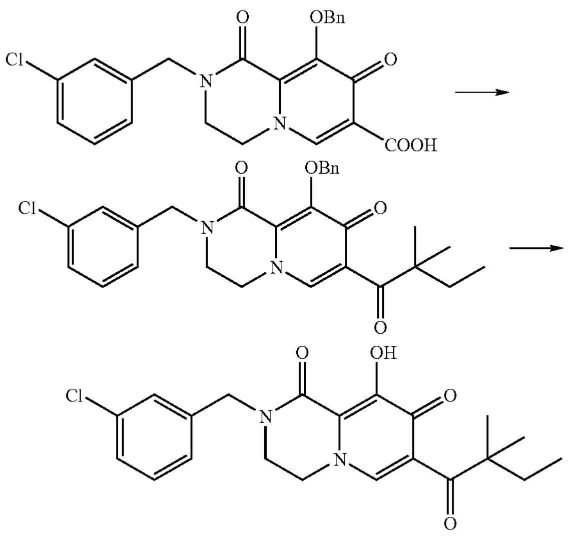

Step 1

9-Benzyloxy-2-(3-chlorobenzyl)-1,8-dioxo-1,3,4,8-tetrahydro-2H-pyrido[1,2-a]pyrazine-7-carboxylic acid (200 mg) obtained in Example 219, Step 2 was suspended in tetrahydrofuran (6 ml), and triethylamine (0.07 ml) and thionyl chloride (0.037 ml) were added at room temperature with stirring. After stirring at room temperature for 10 min, the mixture was cooled to −78° C. and 1.0 M 1,1-dimethylpropylmagnesium chloride/ether solution was added dropwise. After further stirring at the same temperature for 20 min, 5% aqueous potassium hydrogen sulfate solution (5 ml) and ethyl acetate (6 ml) were added, and water (5 ml) was further added. The mixture was extracted twice with ethyl acetate-tetrahydrofuran (1:1, 30 ml each). The organic layer was dried and concentrated, and ethyl acetate was added to the residue. The obtained solid was collected by filtration to give 9-benzyloxy-2-(3-chlorobenzyl)-7-(2,2-dimethylbutyryl)-3,4-dihydro-2H-pyrido[1,2-a]pyrazine-1,8-dione (59 mg).

$^1$H-NMR ($CDCl_3$)δ 7.63–7.59(m, 2H), 7.36–7.17(m, 8H), 5.89(s, 2H), 4.68(s, 2H), 3.97–3.91(m, 2H), 3.51–3.46(m, 2H), 1.78(q, 2H, J=7.6 Hz), 1.28(s, 6H), 0.83(t, 3H, J=7.6 Hz).

Step 2

9-Benzyloxy-2-(3-chlorobenzyl)-7-(2,2-dimethylbutyryl)-3,4-dihydro-2H-pyrido[1,2-a]pyrazine-1,8-dione (55 mg) was dissolved in trifluoroacetic acid (0.5 ml) and the mixture was stirred at room temperature for 30 min. The solvent was evaporated and toluene was added, and the mixture was concentrated, which operations were performed twice. Crystallization from chloroform-diisopropyl ether gave 2-(3-chlorobenzyl)-7-(2,2-dimethylbutyryl)-9-hydroxy-3,4-dihydro-2H-pyrido[1,2-a]pyrazine-1,8-dione (32 mg).

$^1$H-NMR (DMSO-$d_6$)δ 12.08(bs, 1H), 7.70(s, 1H), 7.46(s, 1H), 7.44–7.32(m, 3H), 4.72(s, 2H), 4.30–4.22(m, 2H), 3.76–3.69(m, 2H), 1.65(q, 2H, J=7.4 Hz), 1.16(s, 6H), 0.77(t, 3H, J=7.4 Hz).

Example 205

Synthesis of 2-(3-chlorobenzyl)-9-hydroxy-7-propionyl-2H-pyrido[1,2-a]pyrazine-1,8-dione hydrochloride

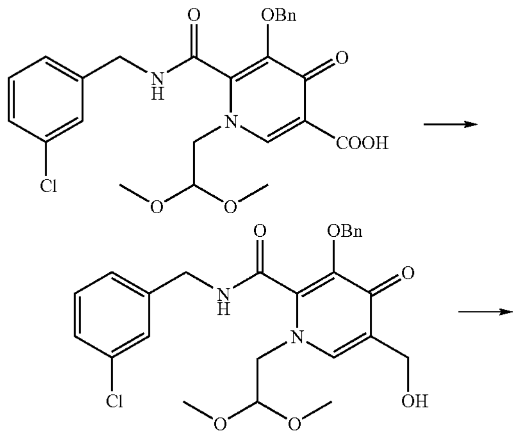

-continued

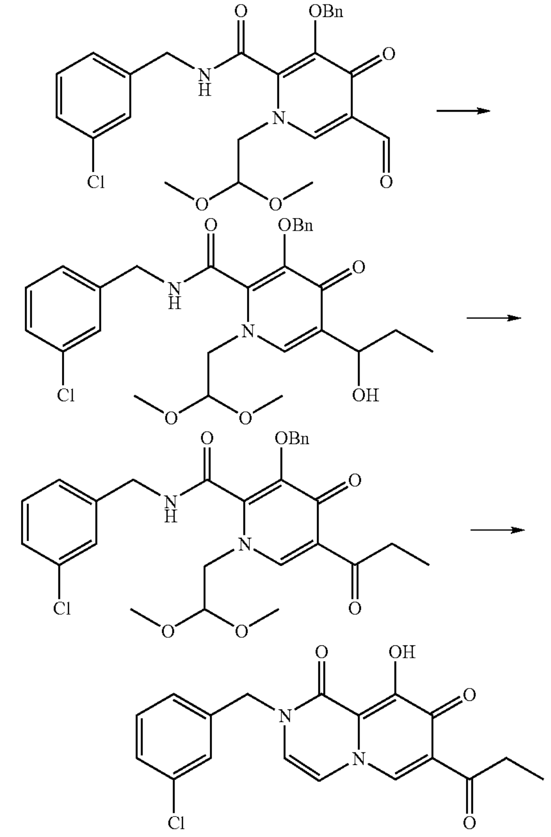

HCl

Step 1

5-Benzyloxy-6-(3-chlorobenzylcarbamoyl)-1-(2,2-dimethoxyethyl)-4-oxo-1,4-dihydropyridine-3-carboxylic acid (517 mg) obtained in Example 161, Step 4 and triethylamine (0.43 ml) were added to tetrahydrofuran (7 ml), and thionyl chloride (0.098 ml) was subsequently added at 0° C. The mixture was stirred at room temperature for 3 min and the reaction mixture was cooled to −78° C. 1M Lithium aluminum hydride/tetrahydrofuran solution (1.55 ml) was added dropwise. After stirring at the same temperature for 3 min, 5% aqueous potassium hydrogen sulfate solution was added, and the mixture was extracted with ethyl acetate. The ethyl acetate layer was dried, concentrated and purified by silica gel column chromatography (ethyl acetate-ethyl acetate:methanol=20:1) to give 3-benzyloxy-1-(2,2-dimethoxyethyl)-5-hydroxymethyl-4-oxo-1,4-dihydropyridine-2-carboxylic acid 3-chlorobenzylamide (240 mg).

$^1$H-NMR ($CDCl_3$)δ 7.33–7.15(8H, m), 7.11(1H, d, J=7.4 Hz), 6.88(1H, t, J=6.0 Hz), 5.23(2H, s), 4.54–4.35(3H, m), 4.34(2H, d, J=6.0 Hz), 3.93(2H, d, J=5.1 Hz), 3.32(6H, s).

Step 2

By subjecting 3-benzyloxy-1-(2,2-dimethoxyethyl)-5-hydroxymethyl-4-oxo-1,4-dihydropyridine-2-carboxylic acid 3-chlorobenzylamide (235 mg) to a reaction operation similar to that in Example 223, Step 1, 3-benzyloxy-1-(2,2-dimethoxyethyl)-5-formyl-4-oxo-1,4-dihydropyridine-2-carboxylic acid 3-chlorobenzylamide (197 mg) was obtained.

$^1$H-NMR ($CDCl_3$)δ 10.28(1H, s), 7.89(1H, s), 7.31–7.19 (8H, m), 7.11(1H, d, J=7.9 Hz), 6.72(1H, t, J=6.0 Hz), 5.29(2H, s), 4.49(1H, t, J=4.9 Hz), 4.37(2H, d, J=6.0 Hz), 3.99(2H, d, J=4.9 Hz), 3.30(6H, s).

Step 3

To a solution of 3-benzyloxy-1-(2,2-dimethoxyethyl)-5-formyl-4-oxo-1,4-dihydropyridine-2-carboxylic acid 3-chlorobenzylamide (168 mg) in tetrahydrofuran (6 ml) was added dropwise 0.89 M ethylmagnesium bromide (1.09 ml) with stirring at −78° C. After stirring at the same temperature for 10 min, 5% aqueous potassium hydrogen sulfate solution was added, and the mixture was extracted with ethyl acetate. The ethyl acetate layer was washed with saturated brine, dried and concentrated. The obtained residue was purified by silica gel column chromatography (ethyl acetate:hexane=2:1–4:1) to give 3-benzyloxy-1-(2,2-dimethoxyethyl)-5-(1-hydroxypropyl)-4-oxo-1,4-dihydropyridine-2-carboxylic acid 3-chlorobenzylamide (137 mg).

$^1$H-NMR ($CDCl_3$)δ 7.30–7.16(8H, m), 7.10(1H, d, J=7.4 Hz), 6.78(1H, t, J=5.1 Hz), 5.23(2H, s), 4.56(1H, d, J=7.4 Hz), 4.49(1H, t, J=4.9 Hz), 4.46(1H, dd, J=7.4,10.2 Hz), 4.35(2H, d, J=5.1 Hz), 3.92(2H, d, J=4.9 Hz), 3.30(3H, s), 3.29(3H, s), 1.83(2H, dq, J=7.2,10.2 Hz), 0.94(3H, t, J=7.2 Hz).

Step 4

By subjecting 3-benzyloxy-1-(2,2-dimethoxyethyl)-5-(1-hydroxypropyl)-4-oxo-1,4-dihydropyridine-2-carboxylic acid 3-chlorobenzylamide (102 mg) to a reaction operation similar to that in Example 223, Step 1, 3-benzyloxy-1-(2,2-dimethoxyethyl)-4-oxo-5-propionyl-1,4-dihydropyridine-2-carboxylic acid 3-chlorobenzylamide (92 mg) was obtained.

$^1$H-NMR ($CDCl_3$)δ 8.09(1H, s), 7.28–7.21(8H, m), 7.08 (1H, d, J=7.4 Hz), 6.54(1H, d, J=6.0 Hz), 5.27(2H, s), 4.47(1H, t, J=5.1 Hz), 4.34(2H, d, J=6.0 Hz), 4.04(2H, d, J=5.1 Hz), 3.29(6H, s), 3.21(2H, q, J=7.1 Hz), 1.16(3H, t, J=7.1 Hz).

Step 5

By subjecting 3-benzyloxy-1-(2,2-dimethoxyethyl)-4-oxo-5-propionyl-1,4-dihydropyridine-2-carboxylic acid 3-chlorobenzylamide (89 mg) to a reaction operation similar to that in Example 96, Step 2, 2-(3-chlorobenzyl)-9-hydroxy-7-propionyl-2H-pyrido[1,2-a]pyrazine-1,8-dione hydrochloride (56 mg) was obtained.

$^1$H-NMR (DMSO-$d_6$)δ 8.48(1H, s), 7.47(1H, s), 7.44–7.29(4H, m), 6.93(1H, d, J=6.0 Hz), 4.94(2H, s), 3.10(3H, q, J=7.2 Hz), 1.03(3H, t, J=7.2 Hz).

Example 242

Synthesis of N-[2-(3-chlorobenzyl)-9-hydroxy-1,8-dioxo-1,8-dihydro-2H-pyrido[1,2-a]pyrazin-7-yl]propionamide

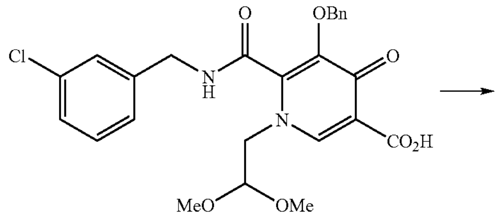

-continued

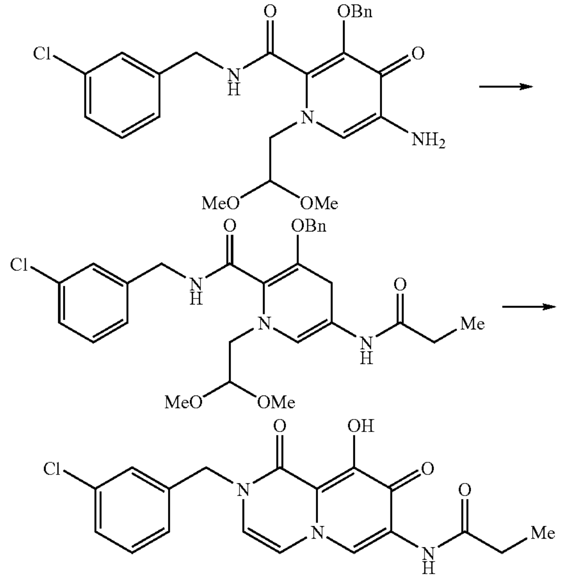

Step 1

To a solution of 5-benzyloxy-6-(3-chlorobenzylcarbamoyl)-1-(2,2-dimethoxyethyl)-4-oxo-1,4-dihydropyridine-3-carboxylic acid (1 g) obtained in Example 161, Step 4 in tetrahydrofuran (15 ml)-toluene (15 ml) were added triethylamine (0.61 ml) and diphenylphosphoryl azide (0.47 ml) and the mixture was stirred at room temperature for 30 min. The solvent was evaporated, and the residue was dissolved in tetrahydrofuran (8 ml). Triethylamine (0.61 ml) and diphenylphosphoryl azide (0.47 ml) were added again and 2 hr later, and 3 hr later, triethylamine (1.22 ml, 0.61 ml) and diphenylphosphoryl azide (0.94 ml, 0.47 ml) were respectively added, and stirring was continued. After confirmation of disappearance of the starting material, 9-fluorenylmethanol (7.7 g) and toluene (10 ml) were added, and the mixture was stirred under reflux with heating. After 20 min, triethylamine (2.5 ml) was added, and stirring was continued with heating for 1.5 hr. The mixture was concentrated, water was added to the residue and the mixture was extracted twice with ethyl acetate. The combined ethyl acetate layer was washed with brine, dried and concentrated. The residue was subjected to silica gel column chromatography (ethyl acetate:hexane=1:1-chloroform:methanol=15:1) to give 5-amino-3-benzyloxy-1-(2,2-dimethoxyethyl)-4-oxo-1,4-dihydropyridine-2-carboxylic acid 3-chlorobenzylamide (886 mg).

$^1$H-NMR ($CDCl_3$)δ 7.41–7.18(m, 8H), 7.15–7.12(m, 2H), 6.96(s, 1H), 5.15(s, 2H), 4.53(t, 1H, J=5.0 Hz), 4.32(d, 2H, J=5.8 Hz), 3.93(brs, 2H), 3.86(d, 2H, J=5.0 Hz), 3.29(s, 6H).

Step 2

To a solution of 5-amino-3-benzyloxy-1-(2,2-dimethoxyethyl)-4-oxo-1,4-dihydropyridine-2-carboxylic acid 3-chlorobenzylamide (55 mg) in chloroform (1 ml) were added, triethylamine (0.033 ml) and propanoyl chloride (0.012 ml) at 0° C. After stirring at the same temperature for 20 min, aqueous sodium hydrogen carbonate solution was added and the reaction mixture was extracted with ethyl acetate. The ethyl acetate layer was dried, concentrated and purified by silica gel thin layer chromatography (chloroform:methanol=10:1) to give N-[5-benzyloxy-6-(3-chlorobenzylcarbamoyl)-1-(2,2-dimethoxyethyl)-4-oxo-1,4-dihydropyridin-3-yl]propionamide (55 mg). By subjecting 51 mg of the obtained compound to a reaction operation similar to that in Example 187, Step 2, N-[2-(3-chlorobenzyl)-9-hydroxy-1,8-dioxo-1,8-dihydro-2H-pyrido[1,2-a]pyrazin-7-yl]propionamide (27 mg) was obtained.

$^1$H-NMR (DMSO-$d_6$)δ 11.59(s, 1H), 9.34(s, 1H), 9.12(s, 1H), 7.50–7.45(m, 2H), 7.41–7.33(m, 3H), 6.96(d, 1H, J=6.0 Hz), 4.98(s, 1H), 2.50(q, 2H, J=7.5 Hz), 1.06(t, 3H, J=7.5 Hz).

Example 382

Synthesis of 7-(2,2-dimethylbutyryl)-2-(4-fluorobenzyl)-9-hydroxy-2H-pyrido[1,2-a]pyrazine-1,8-dione hydrochloride

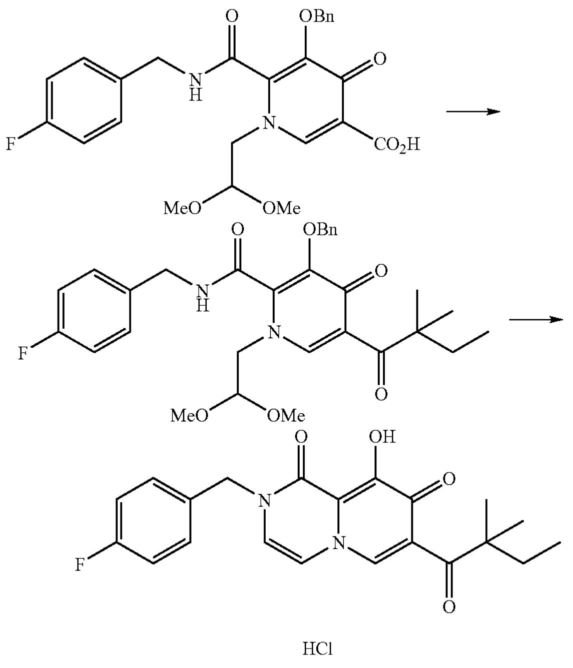

Step 1

By subjecting 5-benzyloxy-6-(4-fluorobenzylcarbamoyl)-1-(2,2-dimethoxyethyl)-4-oxo-1,4-dihydropyridine-3-carboxylic acid (100 mg) obtained by the same production method as in Example 161, Step 4 to a reaction operation similar to that in Example 362, Step 1, and purification by silica gel thin layer chromatography (chloroform:acetone=3:1), 3-benzyloxy-1-(2,2-dimethoxyethyl)-5-(2,2-dimethylbutyryl)-4-oxo-1,4-dihydropyridine-2-carboxylic acid 4-fluorobenzylamide (40 mg) was obtained.

$^1$H-NMR ($CDCl_3$)δ 7.86(br, 1H), 7.29–7.18(m, 8H), 6.84 (dd, 2H, J=8.7 Hz, 8.7 Hz), 5.10(s, 2H), 4.54(t, 1H, J=5.0 Hz), 4.35(d, 2H, J=5.8 Hz), 3.83(d, 2H, J=5.0 Hz), 3.30(s, 6H), 1.65(q, 2H, J=7.5 Hz), 1.19(s, 6H), 0.83(t, 3H, J=7.5 Hz).

Step 2

By subjecting 3-benzyloxy-1-(2,2-dimethoxyethyl)-5-(2,2-dimethylbutyryl)-4-oxo-1,4-dihydropyridine-2-carboxylic acid 4-fluorobenzylamide (40 mg) to a reaction operation similar to that in Example 161, Step 6, 7-(2,2-dimethylbutyryl)-2-(4-fluorobenzyl)-9-hydroxy-2H-pyrido[1,2-a]pyrazine-1,8-dione hydrochloride (25 mg) was obtained.

$^1$H-NMR (DMSO-$d_6$)δ 8.01(s, 1H), 7.43(dd, 2H, J=9.0 Hz, 5.5 Hz), 7.22(d, 1H, J=6.3 Hz), 7.19(dd, 2H, J=9.0 Hz, 9.0 Hz), 6.90(d, 1H, J=6.3 Hz), 1.60(q, 2H, J=7.5 Hz), 1.13(s, 6H), 0.77(t, 3H, J=7.5 Hz).

Example 283

Synthesis of 2-(3-chlorobenzyl)-9-hydroxy-7-isobutylamino-2H-pyrido[1,2-a]pyrazine-1,8-dione hydrochloride

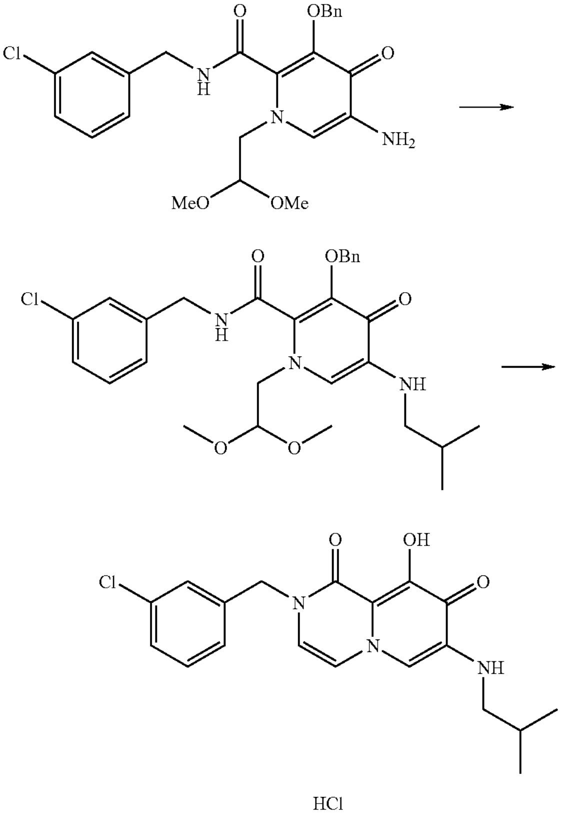

Step 1

To a solution of 5-amino-3-benzyloxy-1-(2,2-dimethoxyethyl)-4-oxo-1,4-dihydropyridine-2-carboxylic acid 3-chlorobenzylamide (65 mg) obtained in Example 242, Step 1 in chloroform (1 ml) were successively added isobutylaldehyde (0.025 ml), acetic acid (0.016 ml), sodium triacetoxyborohydride and the mixture was stirred at room temperature for 1 hr. Saturated brine (10 ml) was added to the reaction mixture and the mixture was extracted twice with chloroform (10 ml each). The organic layer was dried, concentrated and purified by silica gel thin layer chromatography (chloroform:methanol=10:1) to give 3-benzyloxy-1-(2,2-dimethoxyethyl)-5-isobutylamino-4-oxo-1,4-dihydropyridine-2-carboxylic acid 3-chlorobenzylamide (68 mg).

$^1$H-NMR ($CDCl_3$)δ 7.26–7.20(8H, m), 7.10(1H, d, J=7.4 Hz), 6.80(1H, t, J=6.0 Hz), 6.63(1H, s), 5.22(2H, s), 4.55 (1H, t, J=5.1 Hz), 4.34(2H, d, J=6.0 Hz), 3.99(2H, d, J=5.1

Hz), 3.31(6H, s), 2.82(2H, d, J=7.0 Hz), 1.93(1H, dt, J=6.5, 7.0 Hz), 1.01(6H, d, J=6.5 Hz).

Step 2

By subjecting 3-benzyloxy-1-(2,2-dimethoxyethyl)-5-isobutylamino-4-oxo-1,4-dihydropyridine-2-carboxylic acid 3-chlorobenzylamide (66 mg) to a reaction operation similar to that in Example 161, Step 6, 2-(3-chlorobenzyl)-9-hydroxy-7-isobutylamino-2H-pyrido[1,2-a]pyrazine-1,8-dione hydrochloride (43.5 mg) was obtained.

$^1$H-NMR (DMSO-$d_6$)δ 8.07(1H, s), 7.64(1H, d, J=6.0 Hz), 7.50–7.30(5H, m), 5.09(2H, s), 2.99(2H, d, J=7.0 Hz), 1.95(1H, dt, J=6.0,7.0 Hz), 0.91(6H, d, J=7.0 Hz).

Example 302

Synthesis of N-[2-(3-chlorobenzyl)-9-hydroxy-1,8-dioxo-1,8-dihydro-2H-pyrido[1,2-a]pyrazin-7-yl]-N-isobutylacetamide

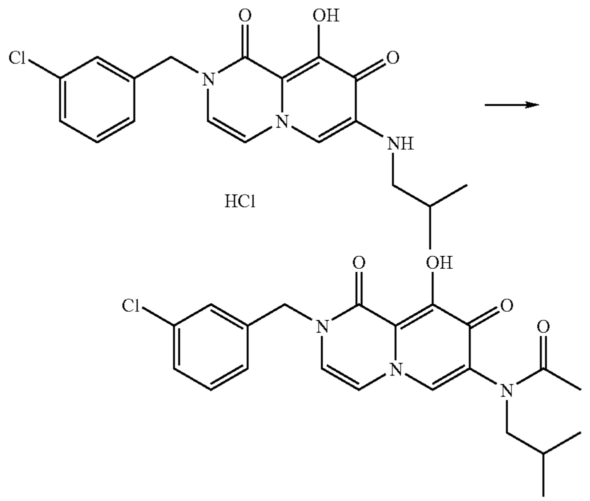

2-(3-Chlorobenzyl)-9-hydroxy-7-isobutylamino-2H-pyrido[1,2-a]pyrazine-1,8-dione hydrochloride (23 mg) was added to chloroform (2 ml), and pyridine (0.062 ml) and acetyl chloride (0.024 ml) were successively added at 0° C. The mixture was stirred at room temperature for 2 hr. 5% Aqueous potassium hydrogen sulfate solution was added to the obtained reaction mixture, and the mixture was extracted with ethyl acetate. The solvent was evaporated and the obtained residue was dissolved in tetrahydrofuran (0.5 ml)-methanol (0.1 ml), and 1N aqueous sodium hydroxide solution (0.084 ml) was added. The mixture was stirred at room temperature for 30 min. 2N Aqueous hydrochloric acid (0.056 ml) was added to the reaction mixture and the mixture was extracted with ethyl acetate. The ethyl acetate layer was washed with saturated brine, dried and concentrated. Crystallization from ethyl acetate-diisopropyl ether gave N-[2-(3-chlorobenzyl)-9-hydroxy-1,8-dioxo-1,8-dihydro-2H-pyrido[1,2-a]pyrazin-7-yl]-N-isobutylacetamide (18.2 mg).

$^1$H-NMR (DMSO-$d_6$)δ 8.27(1H, s), 7.49(1H, s), 7.39–7.32(3H, m), 7.18(1H, d, J=6.0 Hz), 6.92(1H, d, J=6.0 Hz), 4.97(2H, s), 3.53(1H, dd, J=13.7,8.6 Hz), 3.12(1H, dd, J=13.7,7.2 Hz), 1.76(3H, s), 1.62(1H, ddt, J=7.2,8.6,6.5 Hz), 0.82(6H, d, J=6.5 Hz).

Example 349

Synthesis of N-[2-(3-chloro-4-fluorobenzyl)-9-hydroxy-1,8-dioxo-1,3,4,8-tetrahydro-2H-pyrido[1,2-a]pyrazin-7-yl]isobutyramide

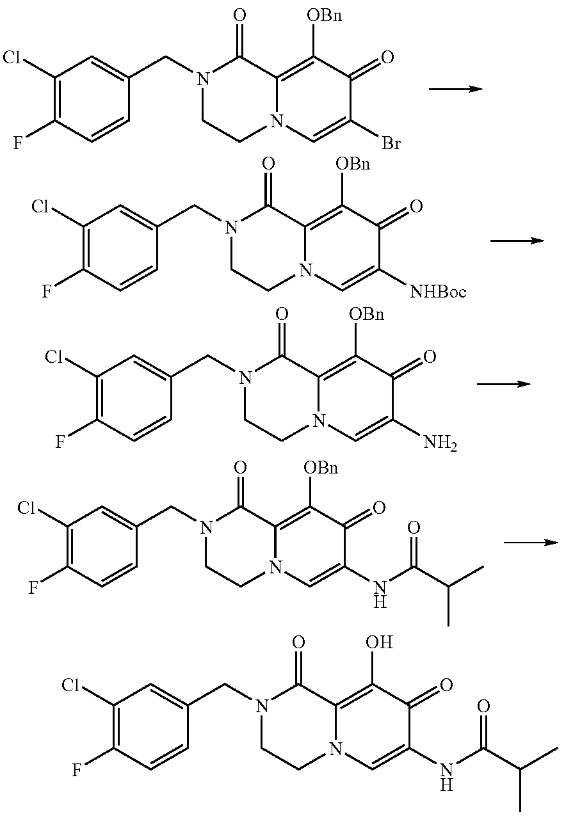

Step 1

To a solution of 9-benzyloxy-7-bromo-2-(3-chloro-4-fluorobenzyl)-3,4-dihydro-2H-pyrido[1,2-a]pyrazine-1,8-dione (170 mg) produced by the same method as in Example 249, Step 1 in dioxane (1.7 ml) were added tert-butyl carbamate (49 mg), tris(dibenzylideneacetone)dipalladium (0)-chloroform adduct (1.8 mg), 4,5-bis(diphenylphosphino)-9,9-dimethylxanthene (3 mg) and cesium carbonate (158 mg) under an argon stream and the mixture was stirred at 100° C. After 10 hr, tert-butyl carbamate (49 mg), tris(dibenzylideneacetone)dipalladium(0)-chloroform adduct (18 mg) and 4,5-bis(diphenylphosphino)-9,9-dimethylxanthene (30 mg) were added, and the mixture was continuously stirred for 18 hr with heating. After cooling to room temperature, insoluble materials were filtered off through celite. The solvent was evaporated and the residue was purified by silica gel column chromatography (chloroform:acetone=2:1) to give tert-butyl [9-benzyloxy-2-(3-chloro-4-fluorobenzyl)-1,8-dioxo-1,3,4,8-tetrahydro-2H-pyrido[1,2-a]pyrazin-7-yl]carbamate (156 mg).

$^1$H-NMR ($CDCl_3$)δ 8.31(s, 1H), 7.80(s, 1H), 7.62(m, 2H), 7.38–7.10(m, 5H), 7.12(dd, 1H, J=8.3, 8.3 Hz), 5.33(s, 2H), 4.65(s, 2H), 4.38(br, 1H), 4.02–3.98(m, 2H), 3.50–3.47(m, 2H), 1.50(s, 9H).

Step 2

To a solution of tert-butyl [9-benzyloxy-2-(3-chloro-4-fluorobenzyl)-1,8-dioxo-1,3,4,8-tetrahydro-2H-pyrido[1,2-a]pyrazin-7-yl]carbamate (179 mg) in dioxane (2 ml) was added 4N hydrochloric acid/dioxane solution (2 ml) and the mixture was stirred at room temperature for 3.5 hr. The solvent was evaporated and aqueous sodium hydrogen carbonate solution was added to the obtained residue. The mixture was extracted with chloroform. The chloroform layer was dried, concentrated and purified by silica gel column chromatography (ethyl acetate:methanol=5:1) to give 7-amino-9-benzyloxy-2-(3-chloro-4-fluorobenzyl)-3,4-dihydro-2H-pyrido[1,2-a]pyrazine-1,8-dione (88 mg).

$^1$H-NMR ($CDCl_3$)δ 7.66–7.64(m, 2H), 7.35–7.24(m, 4H), 7.19–7.15(ddd, 1H, J=1.9, 4.4, 8.6 Hz), 7.10(dd, 1H, J=8.3, 8.6 Hz), 6.96(s, 1H), 5.27(s, 2H), 4.59(s, 2H), 3.91–3.88(m, 2H), 3.45–3.42(m, 2H), 2.42(br, 2H).

Step 3

To a solution of 7-amino-9-benzyloxy-2-(3-chloro-4-fluorobenzyl)-3,4-dihydro-2H-pyrido[1,2-a]pyrazine-1,8-dione (29 mg) in chloroform (0.6 ml) were added pyridine (0.0082 ml) and isobutyryl chloride (0.01 ml) at 0° C., and the mixture was stirred at room temperature for 1.5 hr. 5% Aqueous potassium hydrogen sulfate solution was added and the mixture was extracted with ethyl acetate. The obtained ethyl acetate layer was dried, concentrated and purified by silica gel thin layer chromatography (chloroform:methanol=10:1) to give N-[9-benzyloxy-2-(3-chloro-4-fluorobenzyl)-1,8-dioxo-1,3,4,8-tetrahydro-2H-pyrido[1,2-a]pyrazin-7-yl]isobutyramide (29 mg).

$^1$H-NMR ($CDCl_3$)δ 8.80(s, 1H), 8.62(s, 1H), 7.66–7.64 (m, 2H), 7.39(dd, 1H, J=2.3, 6.7 Hz), 7.36–7.30(m, 3H), 7.21(ddd, 1H, J=2.3, 4.6, 8.4 Hz), 7.14(dd, 1H, J=8.3,8.8 Hz), 5.35(s, 2H), 4.66(s, 2H), 4.03–4.00(m, 2H), 3.52–3.50 (m, 2H), 2.63(sept, 1H, J=7.0 Hz), 1.25(d, 6H, J=7.0 Hz).

Step 4

By subjecting N-[9-benzyloxy-2-(3-chloro-4-fluorobenzyl)-1,8-dioxo-1,3,4,8-tetrahydro-2H-pyrido[1,2-a]pyrazin-7-yl]isobutyramide (27 mg) to a reaction operation similar to that in Example 223, Step 4, N-[2-(3-chloro-4-fluorobenzyl)-9-hydroxy-1,8-dioxo-1,3,4,8-tetrahydro-2H-pyrido[1,2-a]pyrazin-7-yl]isobutyramide (17 mg) was obtained.

$^1$H-NMR (DMSO-$d_6$)δ 11.91(br, 1H), 9.13(s, 1H), 8.71(s, 1H), 7.64(dd, 1H, J=1.6, 7.9 Hz), 7.43–7.39(m, 2H), 4.70(s, 2H), 4.30–4.26(m, 2H), 3.74–3.71(m, 2H), 2.88(sept, 1H, J=6.7 Hz), 1.07(d, 6H, J=6.7 Hz).

Example 353

Synthesis of N-[2-(3-chloro-4-fluorobenzyl)-9-hydroxy-1,8-dioxo-1,3,4,8-tetrahydro-2H-pyrido[1,2-a]pyrazin-7-yl]methanesulfonamide

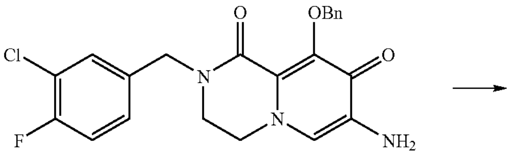

-continued

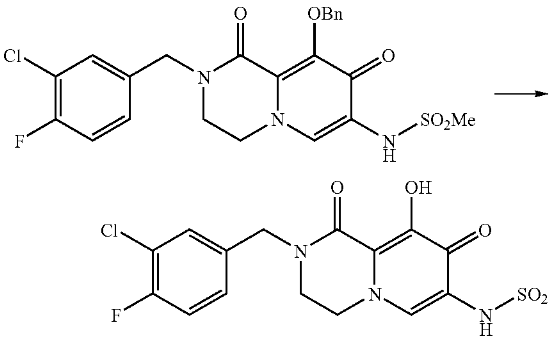

By subjecting 7-amino-9-benzyloxy-2-(3-chloro-4-fluorobenzyl)-3,4-dihydro-2H-pyrido[1,2-a]pyrazine-1,8-dione (29 mg) obtained in Example 349, Step 2 to a reaction operation similar to that in Example 349, Steps 3 and 4 except that methanesulfonyl chloride was used instead of isobutyryl chloride, N-[2-(3-chloro-4-fluorobenzyl)-9-hydroxy-1,8-dioxo-1,3,4,8-tetrahydro-2H-pyrido[1,2-a]pyrazin-7-yl]methanesulfonamide (4.7 mg) was obtained.

$^1$H-NMR (DMSO-$d_6$)δ 12.08(br, 1H), 8.83(br, 1H), 7.78 (s, 1H), 7.63(dd, 1H, J=1.7, 7.7 Hz), 7.42–7.40(m, 2H), 4.71(s, 2H), 4.30–4.27(m, 2H), 3.74–3.72(m, 2H), 2.97(s, 3H).

Example 222

Synthesis of 2-(3-chloro-4-fluorobenzyl)-9-hydroxy-4-hydroxymethyl-1,8-dioxo-1,8-dihydro-2H-pyrido[1,2-a]pyrazine-7-carboxylic acid methylamide hydrochloride

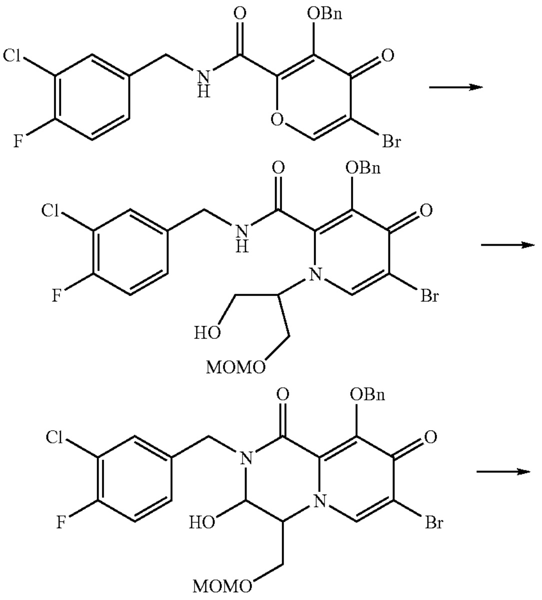

-continued

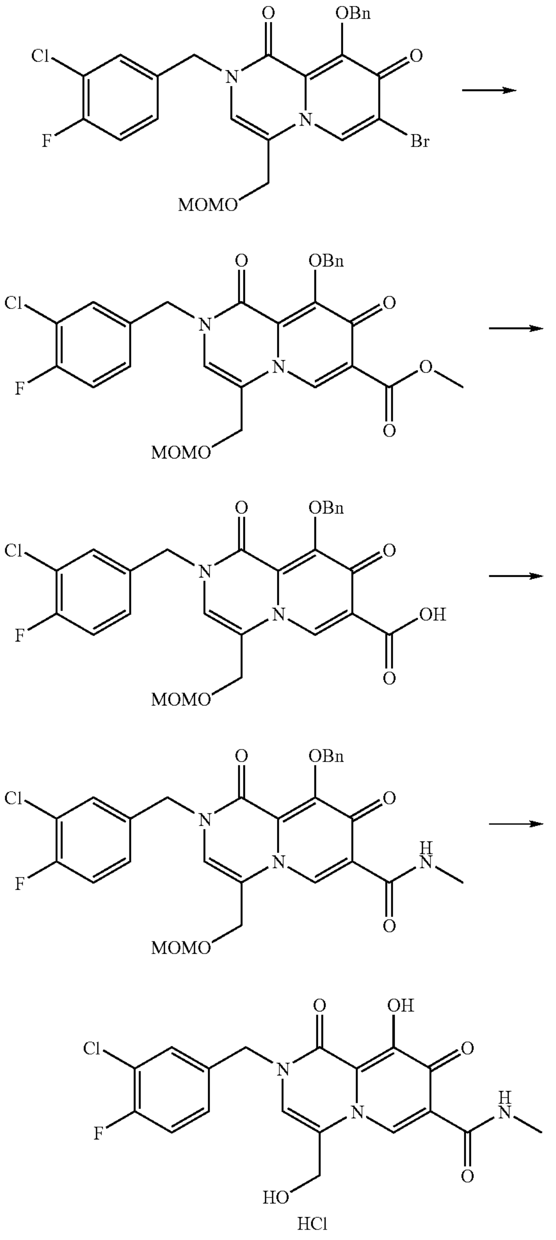

Step 1

3-Benzyloxy-5-bromo-4-oxo-4H-pyran-2-carboxylic acid 3-chloro-4-fluorobenzylamide (380 mg) obtained by the same method as in Example 161, Step 1 and 2-amino-3-methoxymethoxy-1-propanol (275 mg) were dissolved in tetrahydrofuran (2 ml)-ethanol (2 ml) and the mixture was stirred at 60° C. for 1 hr. The reaction mixture was concentrated and purified by silica gel column chromatography (chloroform:methanol=10:1) to give 3-benzyloxy-5-bromo-1-(1-hydroxy-3-methoxymethoxy-2-propyl)-4-oxo-1,4-dihydropyridine-2-carboxylic acid 3-chloro-4-fluorobenzylamide (410 mg).

Step 2

To a solution of oxalyl chloride (0.245 ml) in methylene chloride (1 ml) was added dropwise a solution of dimethyl sulfoxide (0.269 ml) in methylene chloride (1 ml) under a nitrogen stream at −78° C. and the mixture was stirred for 10 min. A solution of 3-benzyloxy-5-bromo-1-(1-hydroxy-3-methoxymethoxy-2-propyl)-4-oxo-1,4-dihydropyridine-2-carboxylic acid 3-chloro-4-fluorobenzylamide (410 mg) in methylene chloride (16 ml) was added at the same temperature over 5 min. After stirring for further 10 min after the completion of the dropwise addition, triethylamine (1.37 ml) was added and the mixture was heated to room temperature. The mixture was stirred at room temperature for 1 hr and concentrated. Water was added and the mixture was extracted twice with ethyl acetate. The combined ethyl acetate layer was washed with saturated brine, dried and concentrated. The obtained crude product was dissolved in chloroform (8 ml), and N,N-diisopropylethylamine (0.734 ml) and methanesulfonyl chloride (0.101 ml) were successively added under ice-cooling. After stirring at room temperature for 2 hr, methanesulfonyl chloride (0.05 ml) was added and the mixture was further stirred for 1 hr. The reaction mixture was concentrated, and aqueous sodium hydrogen carbonate solution was added to the residue. The mixture was extracted twice with ethyl acetate. The combined ethyl acetate layer was washed with saturated brine, dried, concentrated and purified by silica gel column chromatography (ethyl acetate:hexane=1:2-ethyl acetate) to give 9-benzyloxy-7-bromo-2-(3-chloro-4-fluorobenzyl)-4-(methoxymethoxy)methyl-2H-pyrido[1,2-a]pyrazine-1,8-dione (163 mg).

$^1$H-NMR ($CDCl_3$)δ 8.35(s, 1H), 7.69–7.65(m, 2H), 7.37–7.16(m, 5H), 7.13(dd, 1H, J=8.7 Hz, 8.7 Hz), 6.32(s, 1H), 5.37(s, 2H), 4.88(s, 2H), 4.68(s, 2H), 4.46(s, 2H), 3.42(s, 3H).

Step 3

By subjecting 9-benzyloxy-7-bromo-2-(3-chloro-4-fluorobenzyl)-4-(methoxymethoxy)methyl-2H-pyrido[1,2-a]pyrazine-1,8-dione (125 mg) to a reaction operation similar to that in Example 161, Step 3, methyl 9-benzyloxy-2-(3-chloro-4-fluorobenzyl)-4-(methoxymethoxy)methyl-1,8-dioxo-1,8-dihydro-2H-pyrido[1,2-a]pyrazine-7-carboxylate (28 mg) was obtained.

$^1$H-NMR ($CDCl_3$)δ 8.68(s, 1H), 7.69–7.65(m, 2H), 7.38–7.18(m, 5H), 7.13(dd, 1H, J=8.5 Hz, 8.5 Hz), 6.32(s, 1H), 5.39(s, 2H), 4.87(s, 2H), 4.69(s, 2H), 4.46(s, 2H), 3.96(s, 3H), 3.41(s, 3H).

Step 4

By hydrolyzing methyl 9-benzyloxy-2-(3-chloro-4-fluorobenzyl)-4-(methoxymethoxy)methyl-1,8-dioxo-1,8-dihydro-2H-pyrido[1,2-a]pyrazine-7-carboxylate (27 mg) by the same method as in Example 161, Step 4, and subsequently subjecting to a method analogous to Example 154, 2-(3-chloro-4-fluorobenzyl)-9-hydroxy-4-hydroxymethyl-1,8-dioxo-1,8-dihydro-2H-pyrido[1,2-a]pyrazine-7-carboxylic acid methylamide hydrochloride (2.2 mg) was obtained.

$^1$H-NMR (DMSO-$d_6$)δ 12.22(s, 1H), 9.97(s, 1H), 8.83(s, 1H), 7.69–7.66(m, 1H), 7.44–7.41(m, 2H), 7.16(s, 1H), 5.68(t, 1H, J=5.3 Hz), 4.96(s, 2H), 4.50(d, 2H, J=5.3 Hz), 2.85(d, 3H, J=4.6 Hz).

Example 316

Synthesis of 9-hydroxy-2-(3-phenylpropyl)-7-(thiazol-2-yl)-3,4-dihydro-2H-pyrido[1,2-a]pyrazine-1,8-dione hydrochloride

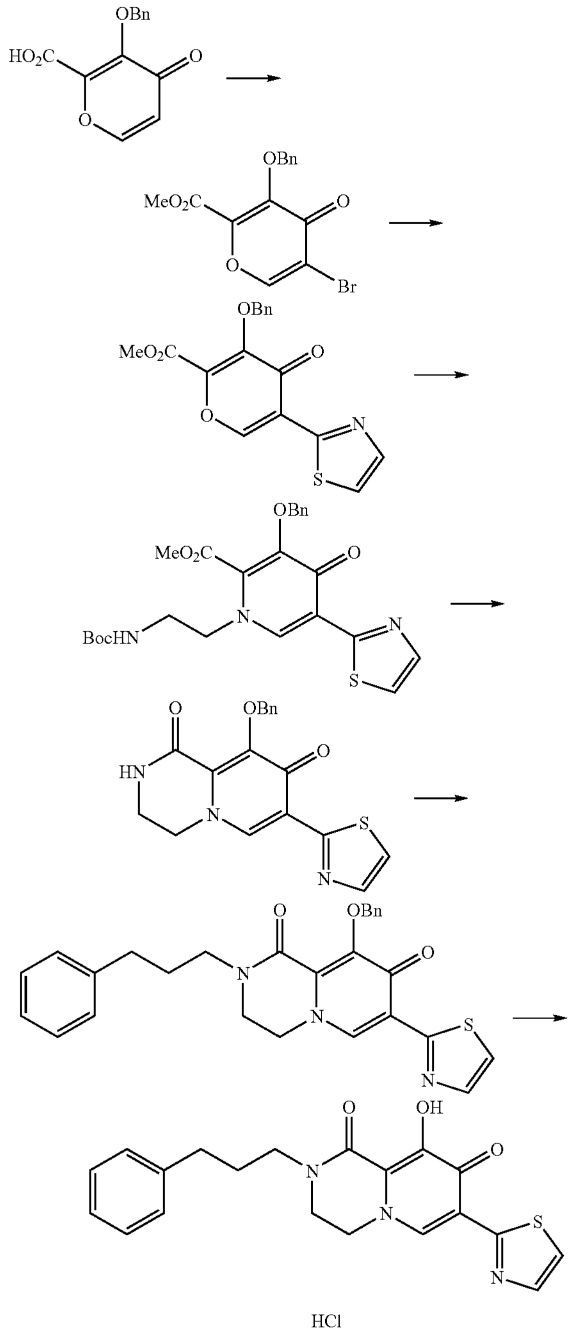

Step 1

3-Benzyloxy-4-oxo-4H-pyran-2-carboxylic acid (6.82 g) was suspended in methanol (20 ml)-tetrahydrofuran (50 ml) and 2M (trimethylsilyl)diazomethane/hexane solution (25.8 ml) was added dropwise under ice-cooling, and the mixture was stirred at room temperature for 1.5 hr. The solvent was evaporated under reduced pressure and the obtained residue was dissolved in chloroform (50 ml). Thereto was added bromine (14.2 ml) and the mixture was stirred at 75° C. for 2 days. After allowing the mixture to return to room temperature, the mixture was concentrated under reduced pressure, and hexane was added to the residue. The precipitated solid was collected by filtration. The obtained solid was dissolved in dimethylformamide (40 ml) and potassium carbonate (4.59 g) and benzyl bromide (3.62 ml) were added. The mixture was stirred at 80° C. for 40 min. The solvent was evaporated and 1N aqueous hydrochloric acid was added to the obtained residue. The mixture was extracted twice with ethyl acetate. The combined ethyl acetate layer was washed with saturated brine, dried, concentrated and purified by silica gel column chromatography (ethyl acetate:hexane=1:4–1:1) The eluate was concentrated and the precipitated crystals were collected by filtration to give methyl 3-benzyloxy-5-bromo-4-oxo-4H-pyran-2-carboxylate (4.69 g).

$^1$H-NMR ($CDCl_3$)δ 8.10(s, 1H), 7.47–7.44(m, 2H), 7.38–7.32(m, 3H), 5.32(s, 2H), 3.88(s, 3H).

Step 2

To a solution of methyl 3-benzyloxy-5-bromo-4-oxo-4H-pyran-2-carboxylate (2.3 g) in dioxane (25 ml) were added tetrakis(triphenylphosphine)palladium(0) (1.57 g) and (2-thiazolyl)tributyltin (5.08 g) under an argon stream, and the mixture was stirred at 100° C. for 1.5 hr. The obtained reaction mixture was concentrated, and subsequently purified by silica gel column chromatography (ethyl acetate: hexane=1:4–1:2) to give methyl 3-benzyloxy-4-oxo-5-(thiazol-2-yl)-4H-pyran-2-carboxylate (1.47 g).

$^1$H-NMR ($CDCl_3$)δ 8.98(s, 1H), 7.92(d, 1H, J=3.2 Hz), 7.53–7.48(m, 3H), 7.48–7.25(m, 3H), 5.41(s, 2H), 3.91(s, 3H).

Step 3

Methyl 3-benzyloxy-4-oxo-5-(thiazol-2-yl)-4H-pyran-2-carboxylate (1.47 g) was suspended in ethanol (15 ml)-dioxane (15 ml), and tert-butyl (2-aminoethyl)carbamate (0.816 ml) was added. After stirring at 70° C. for 1.5 hr, the solvent was evaporated and 4N hydrochloric acid/dioxane solution (70 ml) and chloroform (10 ml) were added to the residue. After stirring at room temperature for 2 hr, the reaction mixture was concentration under reduced pressure. Saturated aqueous sodium hydrogen carbonate solution (20 ml) and methanol (50 ml) were added to the residue and the mixture was stirred for 2 hr. The solvent was evaporated and the obtained solid was collected by filtration and washed thoroughly with water to give 9-benzyloxy-7-(thiazol-2-yl)-3,4-dihydro-2H-pyrido[1,2-a]pyrazine-1,8-dione (1.07 g)

$^1$H-NMR (DMSO-$d_6$)δ 8.84(s, 1H), 8.66(brt, 1H, J=3.7 Hz), 7.93(d, 1H, J=3.2 Hz), 7.68(d, 1H, J=3.2 Hz), 7.59(d, 2H, J=6.8 Hz), 7.40–7.30(m, 3H), 5.17(s, 2H), 4.41–4.36(m, 2H), 3.54–3.48(m, 2H).

Step 4

9-Benzyloxy-7-(thiazol-2-yl)-3,4-dihydro-2H-pyrido[1,2-a]pyrazine-1,8-dione (30 mg) and 3-phenylpropyl bromide (0.02 ml) were added to dimethyl sulfoxide (1 ml), and sodium hydride (7 mg) was added with stirring. After stirring for 20 min, 5% aqueous potassium hydrogen sulfate solution was added and the mixture was extracted twice with ethyl acetate. The ethyl acetate layer was washed with brine, dried, concentrated, and subsequently purified by silica gel thin layer chromatography (chloroform-methanol=15:1) to give 9-benzyloxy-2-(3-phenylpropyl)-7-(thiazol-2-yl)-3,4-dihydro-2H-pyrido[1,2-a]pyrazine-1,8-dione (27 mg).

$^1$H-NMR ($CDCl_3$)δ 8.50(s, 1H), 7.86(d, 1H, J=3.2 Hz), 7.69–7.65(m, 2H), 7.42(d, 1H, J=3.2 Hz), 7.36–7.16(m, 8H), 5.45(s, 2H), 4.11–4.07(m, 2H), 3.62–3.53(m, 4H), 2.70(t, 2H, J=7.5 Hz), 1.96(tt, 2H, J=7.5 Hz, 7.5 Hz).

Step 5

To a solution of 9-benzyloxy-2-(3-phenylpropyl)-7-(thiazol-2-yl)-3,4-dihydro-2H-pyrido[1,2-a]pyrazine-1,8-dione (27 mg) in acetic acid (1 ml) was added conc. aqueous hydrochloric acid (0.5 ml) and the mixture was stirred at 90° C. for 2 hr. The solvent was evaporated and ethyl acetate was added to the residue. The obtained solid was collected by filtration to give 9-hydroxy-2-(3-phenylpropyl)-7-(thiazol-2-yl)-3,4-dihydro-2H-pyrido[1,2-a]pyrazine-1,8-dione hydrochloride (25 mg).

$^1$H-NMR (DMSO-$d_6$)δ 8.72(s, 1H), 7.89(d, 1H, J=3.1 Hz), 7.63(d, 1H, J=3.1 Hz), 7.30–7.14(m, 5H), 4.45–4.40(m, 2H), 3.82–3.77(m, 2H), 3.55(t, 2H, J=7.1 Hz), 2.64(t, 2H, J=7.7 Hz), 1.91(tt, 2H, J=7.1 Hz, 7.7 Hz).

Example 291

Synthesis of 2-(3,4-difluorobenzyl)-9-hydroxy-7-(thiazol-2-yl)-3,4-dihydro-2H-pyrido[1,2-a]pyrazine-1,8-dione

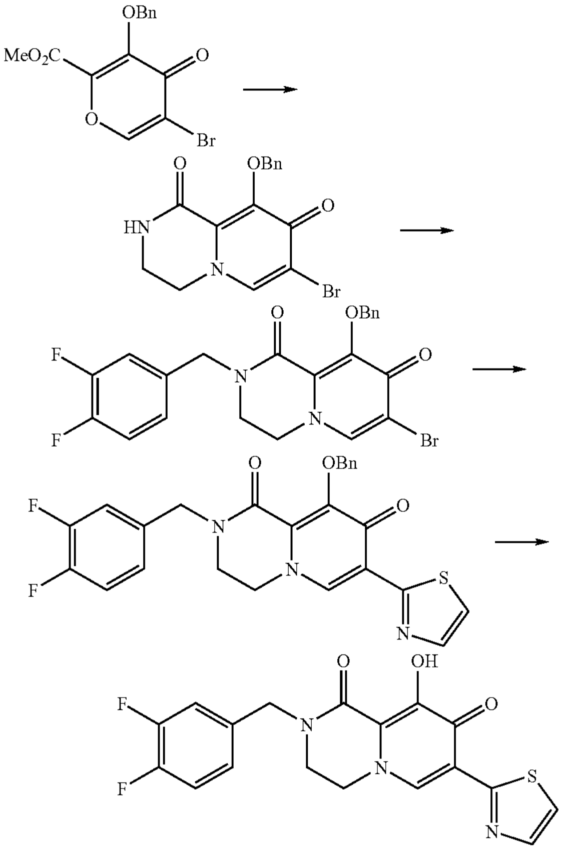

Step 1

According to a method analogous to the method described in Example 316, Step 3, 9-benzyloxy-7-bromo-3,4-dihydro-2H-pyrido[1,2-a]pyrazine-1,8-dione (1.05 g) was obtained from methyl 3-benzyloxy-5-bromo-4-oxo-4H-pyran-2-carboxylate (1.2 g) obtained in Example 316, Step 1.

$^1$H-NMR (DMSO-$d_6$)δ 8.61(brt, 1H, J=4.0 Hz), 8.37(s, 1H), 7.53(dd, 2H, J=8.4 Hz, 1.7 Hz), 7.37–7.26(m, 3H), 5.05(s, 2H), 4.20–4.15(m, 2H), 3.46–3.41(m, 2H).

Step 2

According to a method analogous to the method described in Example 316, Step 4, 9-benzyloxy-7-bromo-2-(3,4-difluorobenzyl)-3,4-dihydro-2H-pyrido[1,2-a]pyrazine-1,8-dione (60 mg) was obtained from 9-benzyloxy-7-bromo-3,4-dihydro-2H-pyrido[1,2-a]pyrazine-1,8-dione (50 mg).

$^1$H-NMR ($CDCl_3$)δ 7.67–7.64(m, 2H), 7.57(s, 1H), 7.37–7.29(m, 3H), 7.18–7.10(m, 2H), 7.04–6.99(m, 1H), 5.33(s, 2H), 4.61(s, 2H), 3.96–3.92(m, 2H), 3.53–3.48(m, 2H).

Step 3

According to a method analogous to the method described in Example 249, Step 2, 9-benzyloxy-2-(3,4-difluorobenzyl)-7-(thiazol-2-yl)-3,4-dihydro-2H-pyrido[1,2-a]pyrazine-1,8-dione (35 mg) was obtained from 9-benzyloxy-7-bromo-2-(3,4-difluorobenzyl)-3,4-dihydro-2H-pyrido[1,2-a]pyrazine-1,8-dione (60 mg).

$^1$H-NMR ($CDCl_3$)δ 8.50(s, 1H), 7.85(d, 1H, J=3.3 Hz), 7.69–7.65(m, 2H), 7.42(d, 1H, J=3.3 Hz), 7.38–7.30(m, 3H), 7.20–7.12(m, 2H), 7.07–7.02(m, 1H), 5.47(s, 2H), 4.66(s, 2H), 4.14–4.09(m, 2H), 3.59–3.54(m, 2H).

Step 4

9-Benzyloxy-2-(3,4-difluorobenzyl)-7-(thiazol-2-yl)-3,4-dihydro-2H-pyrido[1,2-a]pyrazine-1,8-dione (35 mg) was dissolved in trifluoroacetic acid (1 ml) and the mixture was stirred at room temperature for 3 hr. Trifluoroacetic acid was evaporated under reduced pressure, toluene was added to the obtained residue and the mixture was concentrated, which operations were performed twice. Ethyl acetate was further added and the obtained solid was collected by filtration to give 2-(3,4-difluorobenzyl)-9-hydroxy-7-(thiazol-2-yl)-3,4-dihydro-2H-pyrido[1,2-a]pyrazine-1,8-dione (14 mg).

$^1$H-NMR (DMSO-$d_6$)δ 12.30(s, 1H), 8.71(s, 1H), 7.89(d, 1H, J=3.2 Hz), 7.63(d, 1H, J=3.2 Hz), 7.52–7.40(m, 2H), 7.28–7.22(m, 1H), 4.72(s, 2H), 4.49–4.43(m, 2H), 3.81–3.76(m, 2H).

Example 106

Synthesis of 2-(3-chlorobenzyl)-8-hydroxy-6-methyl-2,3,4,6-tetrahydro-2,6-naphthyridine-1,7-dione Step 1

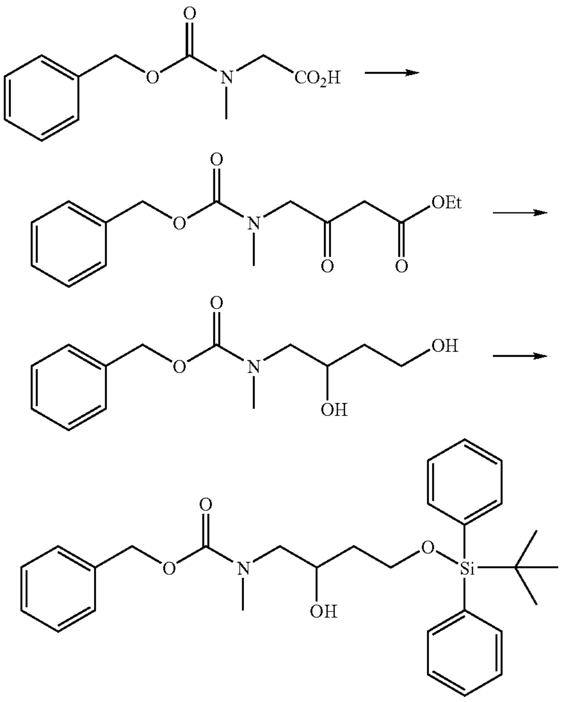

To a solution of (N-benzyloxycarbonyl-N-methylamino) acetic acid (15 g) in tetrahydrofuran (150 ml) was added carbonyldiimidazole (16.3 g) under ice-cooling, and the mixture was stirred at room temperature for 2 hr. A suspension of magnesium chloride (6.21 g) and ethyl potassium malonate (17.2 g) in tetrahydrofuran (250 ml) was separately stirred at 50° C. for 7 hr and ice-cooled. The above-mentioned solution was added dropwise thereto over 30 min with stirring. The mixture was stirred for 12 hr and the solvent was evaporated under reduced pressure. Ethyl acetate and 5% aqueous potassium hydrogen sulfate solution were added to the residue and the mixture was stirred. The organic layer was washed with saturated aqueous sodium hydrogen carbonate solution and saturated brine, dried over sodium sulfate and concentrated under reduced pressure to give an oil (16.8 g). This oil was dissolved in tetrahydrofuran (120 ml)/ethanol (180 ml) and sodium borohydride (6.5 g) was added under ice-cooling. After 20 min, calcium chloride (9.54 g) was added, and the mixture was stirred at room temperature for 1 hr. 1N Aqueous hydrochloric acid and ethyl acetate were added to the reaction mixture. The separated organic layer was washed with saturated brine, dried over sodium sulfate, and concentrated under reduced pressure to give an oil (12.48 g). This oil was dissolved in dimethylformamide (100 ml), and tert-butyldiphenylchlorosilane (12.81 ml) and imidazole (6.71 g) were added under ice-cooling, and the mixture was stirred for 1 hr. Water was added to the reaction mixture and the mixture was extracted with ethyl acetate. The organic layer was washed with saturated brine, subsequently dried over sodium sulfate, and concentrated under reduced pressure. The residue was purified by silica gel column chromatography (ethyl acetate: hexane=1:3) to give benzyl N-[4-(tert-butyldiphenylsilanyloxy)-2-hydroxybutyl]-N-methylcarbamate (12.84 g).

$^1$H-NMR ($CDCl_3$)δ 7.67(4H, d, J=7.0 Hz), 7.48–7.28 (11H, m), 5.14(2H, s), 4.14(1H, br s), 3.89(2H, br s), 3.47–3.27(2H, m), 3.04(3H, s), 1.79–1.60(2H, m), 1.07(9H, s).

Step 2

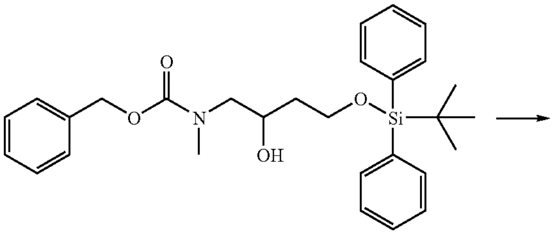

-continued

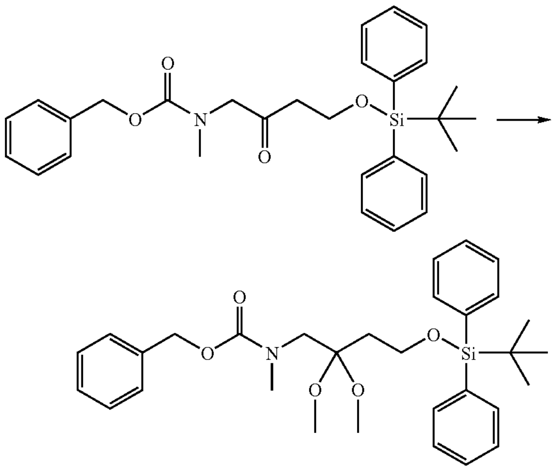

To a solution of benzyl N-[4-(tert-butyldiphenylsilanyloxy)-2-hydroxybutyl]-N-methylcarbamate (12.84 g) in chloroform (150 ml) was added 1,1,1-tris(acetoxy)-1,1-dihydro-1,2-benziodoxol-3-(1H)-one (Dess-Martin reagent) (15.50 g) under ice-cooling, and the mixture was stirred for 1 hr. The reaction mixture was washed successively with saturated aqueous sodium hydrogen carbonate solution, saturated aqueous sodium sulfite solution and saturated brine and dried over sodium sulfate. The solvent was evaporated under reduced pressure and the obtained residue was purified by silica gel column chromatography (ethyl acetate: hexane=1:4) to give benzyl N-[4-(tert-butyldiphenylsilanyloxy)-2-oxobutyl]-N-methylcarbamate (10.92 g). To a solution of the obtained compound (7.95 g) in methanol (70 ml) were added methyl orthoformate (70 ml) and pyridinium p-toluenesulfonate (4.08 g) and the mixture was stirred at 60° C. for 18 hr. The reaction mixture was concentrated, and ethyl acetate was added to the residue and the precipitated solid was filtered off. The filtrate was concentrated under reduced pressure and the residue was purified by silica gel column chromatography (ethyl acetate:hexane=1:5) to give benzyl N-[4-(tert-butyldiphenylsilanyloxy)-2,2-dimethoxybutyl]-N-methylcarbamate (2.25 g).

$^1$H-NMR ($CDCl_3$)δ 7.74–7.62(4H, m), 7.45–7.22(11H, m), 5.07(1H, br s), 4.96(1H, d, J=10.0 Hz), 3.79(2H, br s), 3.41(2H, br s), 3.12(6H, br s), 2.95(3H, s), 1.99(2H, s), 1.06(9H, s).

Step 3

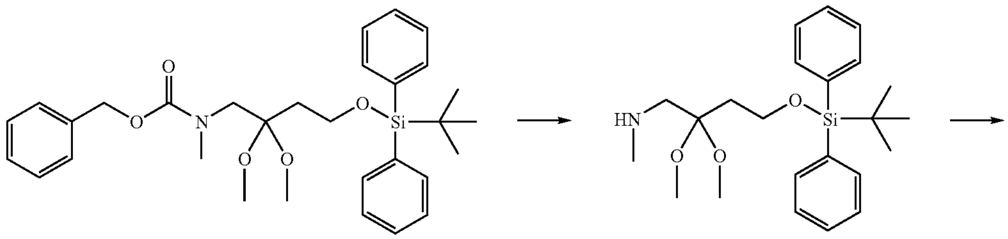

-continued

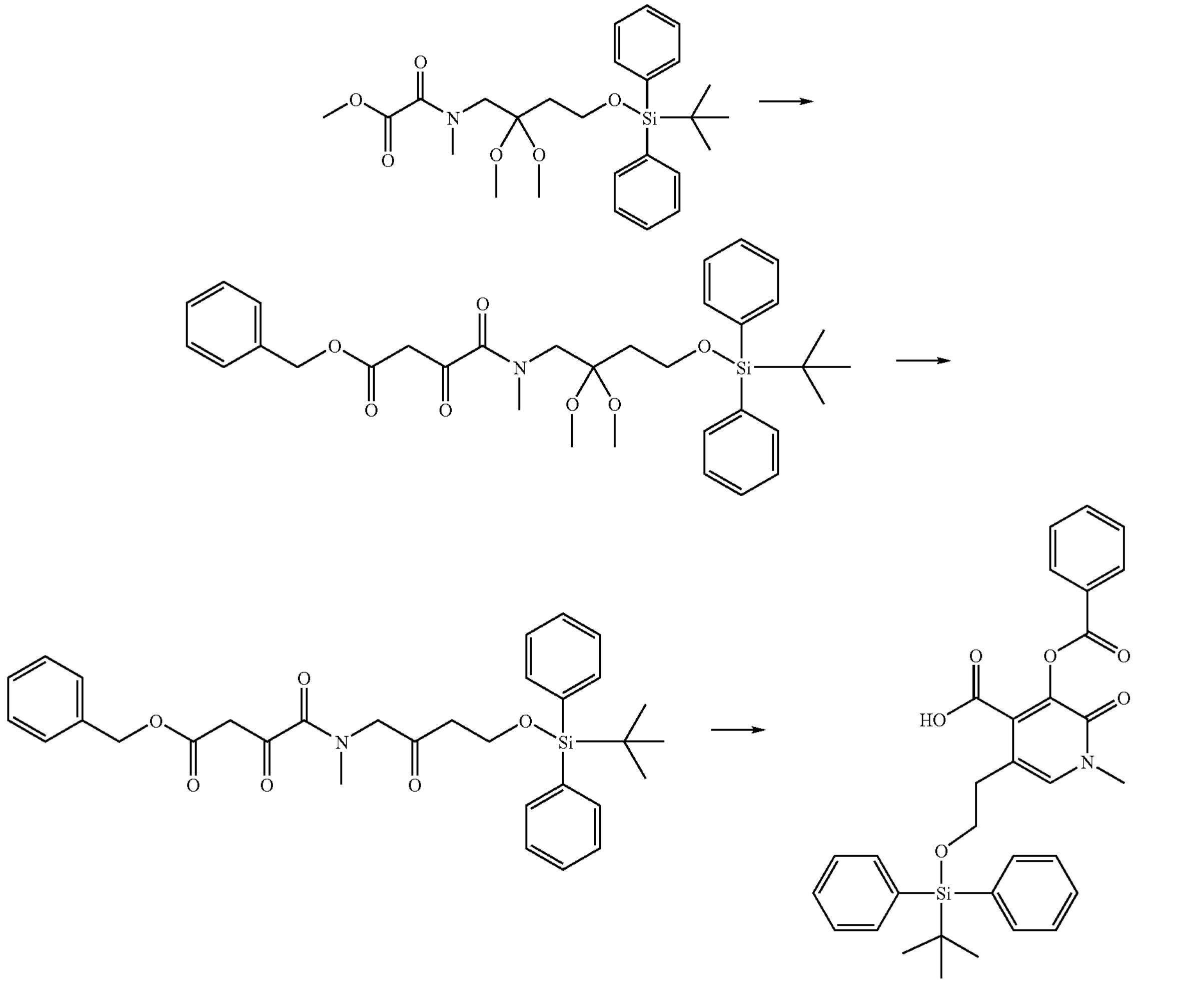

To a solution of benzyl N-[4-(tert-butyldiphenylsilanyloxy)-2, 2-dimethoxybutyl]-N-methylcarbamate (3.22 g) in methanol (60 ml) was added 10% palladium-carbon under a hydrogen atmosphere (3 atm), and the mixture was stirred for 2.5 hr. Palladium-carbon was filtered off and the filtrate was concentrated to give an oil (2.44 g). This oil was dissolved in pyridine (30 ml), methyl chloroglyoxylate (0.839 ml) was added under ice-cooling, and the mixture was stirred at the same temperature for 30 min and at room temperature for 30 min. The solvent was evaporated and saturated aqueous sodium hydrogen carbonate solution was added to the obtained residue. The mixture was extracted with ethyl acetate and the organic layer was washed with saturated brine and dried over sodium sulfate. The solvent was evaporated under reduced pressure to give an oil (2.968 g). To a solution of lithium enolate prepared from lithium bis(trimethylsilyl)amide (1M tetrahydrofuran solution, 12.14 ml) and benzyl acetate (1.753 ml) at −78° C. in tetrahydrofuran (60 ml) was added the above-mentioned oil at −78° C. and the mixture was stirred at the same temperature for 20 min. Acetic acid (1.04 ml), water and ethyl acetate were successively added to the reaction mixture and the mixture was heated to room temperature and partitioned. The aqueous layer was extracted with ethyl acetate, and the combined organic layer was washed with saturated brine, dried over sodium sulfate, and concentrated under reduced pressure. Dioxane (50 ml) and 2N aqueous hydrochloric acid solution (5 ml) were added to the residue and the mixture was stirred at room temperature for 1 hr. The solvent was evaporated and subsequently, toluene was added and concentrated again. The obtained residue was dissolved in chloroform (40 ml) and triethylamine (20 ml) and the mixture was stirred for 1 hr. The solvent was evaporated and the residue was dissolved in pyridine (60 ml), and benzoyl chloride (1.41 ml) was added under ice-cooling. After stirring for 1 hr, the solvent was evaporated. Water was added to the residue and the mixture was extracted twice with ethyl acetate. The organic layer was washed with saturated brine, dried over sodium sulfate and concentrated under reduced pressure. The residue was purified by silica gel column chromatography (ethyl acetate:hexane=1:2) to give benzyl 3-benzoyloxy-5-[2-(tert-butyldiphenylsilanyloxy)ethyl]-1-methyl-2-oxo-1,2-dihydropyridine-4-carboxylate (2.519 g). This compound was dissolved in methanol (75 ml) and 7.5% palladium-carbon was added. The mixture was stirred under a hydrogen atmosphere (1 atm) for 1 hr. Palladium-carbon was filtered off and the filtrate was concentrated. Crystallization from ethyl acetate/hexane gave 3-benzoyloxy-5-[2-(tert-butyldiphenylsilanyloxy)ethyl]-1-methyl-2-oxo-1,2-dihydropyridine-4-carboxylic acid (1.32 g).

$^1$H-NMR ($CDCl_3$)δ 8.15(2H, d, J=8.3 Hz), 7.62–7.56(5H, m), 7.49–7.36(8H, m), 7.07(1H, s), 3.83(2H, t, J=6.0 Hz), 3.52(3H, s), 2.70(2H, t, J=6.0 Hz), 1.06(9H, s).

Step 4

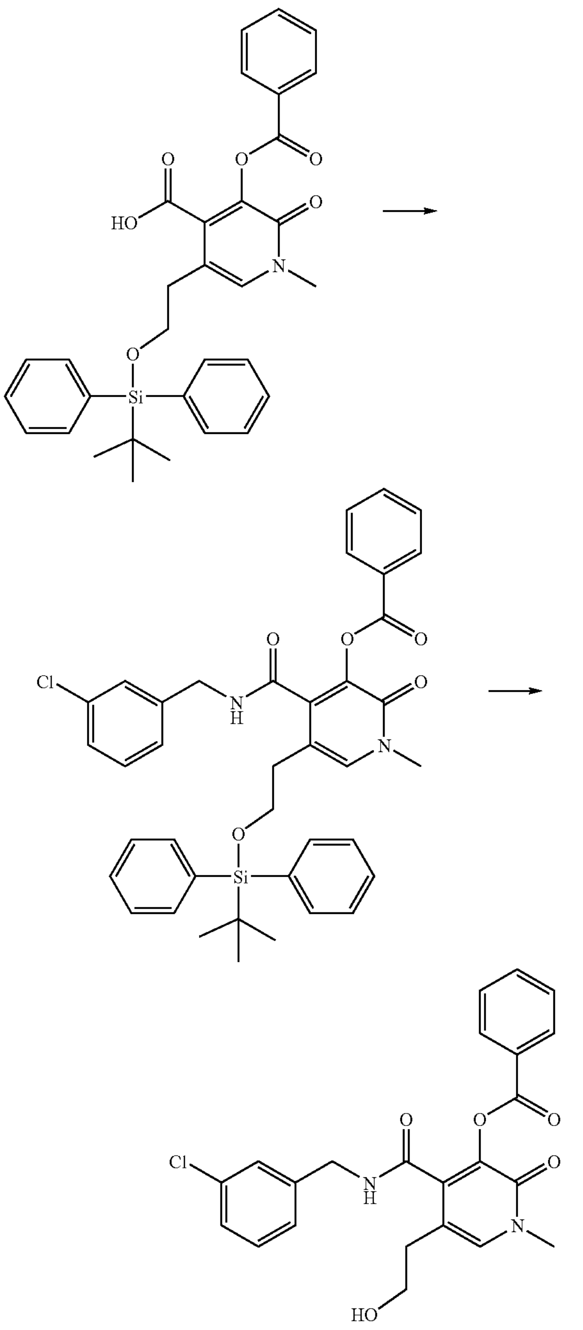

To a solution of 3-benzoyloxy-5-[2-(tert-butyldiphenylsilanyloxy)ethyl]-1-methyl-2-oxo-1,2-dihydropyridine-4-carboxylic acid (0.956 g) in dimethylformamide (10 ml) were added 1-hydroxybenzotriazole hydrate (HOBT) (0.395 g), 1-ethyl-3-(3-dimethylaminopropyl)carbodiimide hydrochloride, (WSC) (0.495 g) and 3-chlorobenzylamine (0.274 ml) and the mixture was stirred at room temperature for 2 hr. Water was added and the mixture was extracted twice with ethyl acetate. The organic layer was washed with saturated brine, dried over sodium sulfate and concentrated under, reduced pressure. The residue was purified by silica gel column chromatography (ethyl acetate:hexane=1:2) to give 5-[2-(tert-butyldiphenylsilanyloxy)ethyl]-4-(3-chlorobenzylcarbamoyl)-1-methyl-2-oxo-1,2-dihydropyridin-3-yl benzoate (0.615 g). This compound was dissolved in tetrahydrofuran (20 ml), and acetic acid (0.259 ml) and tetrabutylammonium fluoride (0.474 g) were added, and the mixture was stirred overnight at room temperature. The reaction mixture was concentrated, and the residue was purified by silica gel thin layer chromatography (chloroform:methanol=10:1) to give 4-(3-chlorobenzylcarbamoyl)-5-(2-hydroxyethyl)-1-methyl-2-oxo-1,2-dihydropyridin-3-yl benzoate (0.213 g).

$^1$H-NMR ($CDCl_3$)δ 8.04 (2H, d, J=7.4 Hz), 7.64(1H, t, J=7.4 Hz), 7.46(2H, t, J=7.9 Hz), 7.22(1H, s), 7.15(1H, s), 6.99(2H, d, J=7.9 Hz), 6.86(1H, t, J=7.9 Hz), 6.67(1H, t, J=6.5 Hz), 4.43(2H, d, J=6.0 Hz), 3.86–3.78(2H, m), 2.69 (2H, t, J=6.0 Hz), 2.67(1H, br s).

Step 5

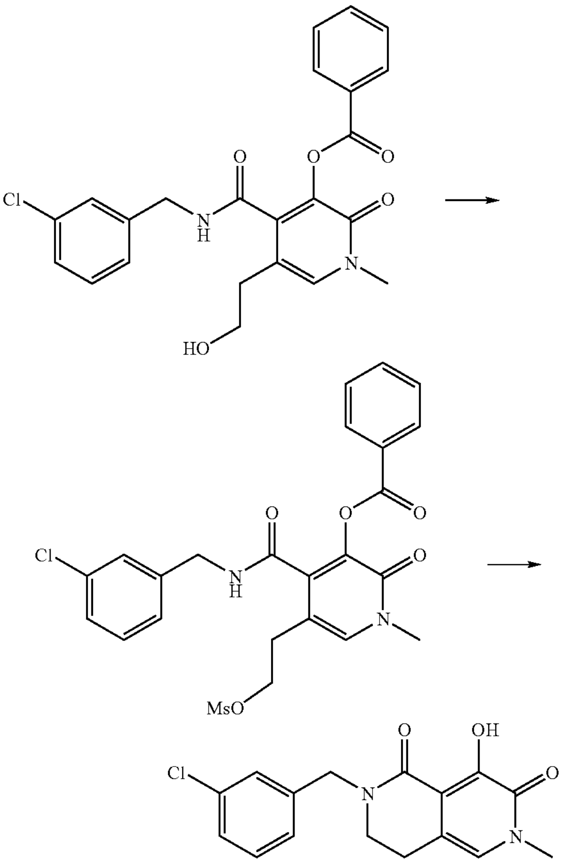

To a solution of 4-(3-chlorobenzylcarbamoyl)-5-(2-hydroxyethyl)-1-methyl-2-oxo-1,2-dihydropyridin-3-yl benzoate (0.1 g) in tetrahydrofuran (4 ml) were successively added diisopropylethylamine (0.119 ml) and methanesulfonyl chloride (0.035 ml) under ice-cooling. After 20 min, diisopropylethylamine (0.119 ml) and methanesulfonyl chloride (0.035 ml) were further added and the mixture was stirred under ice-cooling for 20 min. Water was added and the mixture was extracted twice with ethyl acetate. The organic layer was washed with saturated brine, dried over sodium sulfate, and concentrated under reduced pressure.

The residue was crystallized from ethyl acetate/hexane and the crystals were collected by filtration to give crystals (0.15 g). The crystals were dissolved in dimethylformamide (3 ml) and sodium hydride (0.09 g, 60%) was added under ice-cooling. The mixture was stirred at room temperature for 30 min. Ethyl acetate and 2N aqueous hydrochloric acid solution were added and the mixture was extracted. The organic layer was washed with saturated brine, dried over sodium sulfate, and concentrated under reduced pressure. The residue was purified by silica gel thin layer chromatography (ethyl acetate-chloroform:methanol=6:1) and crystallized from ethyl acetate/hexane and the crystals were collected by filtration to give 2-(3-chlorobenzyl)-8-hydroxy-6-methyl-2,3,4,6-tetrahydro-2,6-naphthyridine-1,7-dione (0.029 g).

$^1$H-NMR ($CDCl_3$)δ 12.75(1H, s), 7.33–7.29(3H, m), 7.24–7.19(1H, m) 6.61(1H, s), 4.71(2H, s), 3.57(3H, s), 3.46(2H, t, J=6.4 Hz), 2.73(2H, t, J=6.4 Hz).

Example 123

Synthesis of 6-(3-chlorobenzyl)-4-hydroxy-2-methyl-2,6,7,8-tetrahydropyrido[4,3-c]pyridazine-3,5-dione Step 1

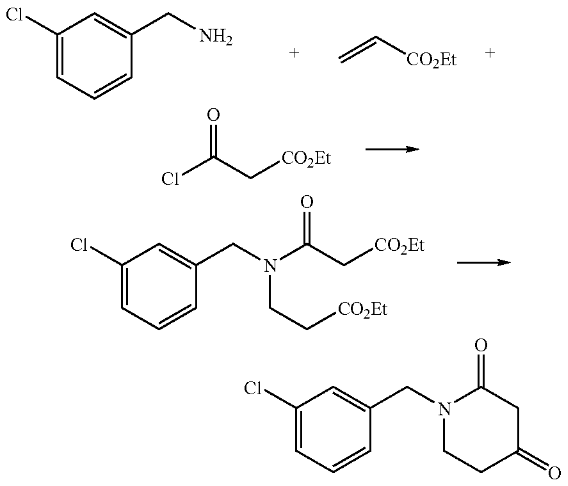

To a solution of 3-chlorobenzylamine (15 g) in ethanol (150 ml) was added dropwise a solution of ethyl acrylate (11.5 ml) in ethanol at room temperature and the mixture was stirred overnight. The reaction mixture was concentrated under reduced pressure and chloroform (500 ml), pyridine (50 ml) and 4-dimethylaminopyridine (3.9 g) were added to the residue. Ethyl malonyl chloride (13.6 ml) was added dropwise to this mixture under ice-cooling, and the mixture was stirred under ice-cooling for 1 hr, and further at room temperature for 1 hr. The reaction mixture was washed with 2N aqueous hydrochloric acid, saturated aqueous sodium hydrogen carbonate solution and saturated brine, and dried over magnesium sulfate. The mixture was concentrated under reduced pressure and the obtained residue was purified by silica gel column chromatography (n-hexane:,ethyl acetate=2:1–3:2) to give an oil (25.6 g). A solution of this oil (25.6 g) in toluene (50 ml) was added dropwise to a suspension of potassium carbonate (50 g) and 18-crown-6 (1.9 g) in toluene (250 ml) with heating under reflux and the mixture was stirred at the same temperature for 12 hr. After cooling to room temperature, the reaction mixture was poured into iced water, 6N aqueous hydrochloric acid was added to adjust the pH of the reaction mixture to not more than 1 and the mixture was extracted three times with chloroform. The chloroform layer was dried, concentrated and 10% aqueous oxalic acid solution (200 ml) was added to the obtained residue. The mixture was heated under reflux for 3 hr. The reaction mixture was cooled, extracted three times with chloroform, and dried over magnesium sulfate. The solvent was evaporated under reduced pressure and the obtained residue was purified by silica gel column chromatography (n-hexane:ethyl acetate=2:3–1:2) to give 1-(3-chlorobenzyl)piperidine-2,4-dione (6.2 g).

$^1$H-NMR ($CDCl_3$)δ 7.1–7.4(4H, m), 4.67(2H, s), 3.51 (2H, t, J=6.3 Hz), 3.44(2H, s), 2.58(2H, t, J=6.3 Hz).

Step 2

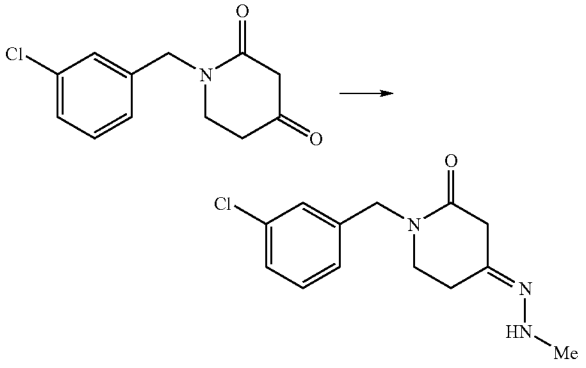

1-(3-Chlorobenzyl)piperidine-2,4-dione (1.2 g) was dissolved in ethanol (25 ml), and methylhydrazine (0.5 ml) was added. The mixture was heated under reflux for 1 hr. The reaction mixture was concentrated under reduced pressure and the obtained residue was purified by silica gel column chromatography (chloroform:methanol=95:1) to give 1-(3-chlorobenzyl)-4-(methylhydrazono)piperidin-2-one (1.05 g).

$^1$H-NMR ($CDCl_3$)δ 7.1–7.4(4H, m), 4.2–4.8(3H, m), 3.2–3.5(4H, m), 2.95(3H, s), 2.3–2.7(2H, m).

Step 3

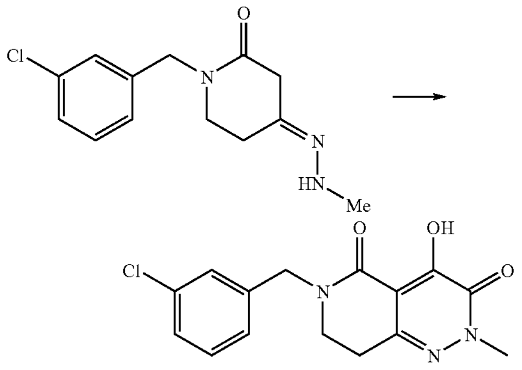

1-(3-Chlorobenzyl)-4-(methylhydrazono)piperidin-2-one (1.05 g) was dissolved in chloroform (20 ml) and triethylamine (1.2 ml) and methyl oxalyl chloride (0.735 ml) were successively added under ice-cooling. After stirring at room temperature for 2 hr, the reaction mixture was washed with saturated aqueous sodium hydrogen carbonate solution and saturated aqueous sodium chloride solution, and dried over magnesium sulfate. The mixture was concentrated under reduced pressure and the obtained residue was purified by silica gel column chromatography (n-hexane:ethyl acetate=2:3-ethyl acetate-chloroform:methanol=90:10) to give an oil (200 mg). This oil was dissolved in tetrahydrofuran (4 ml), sodium hydride (27 mg) was added under ice-cooling and the mixture was stirred at the is same temperature for 30 min. 5% Aqueous potassium hydrogen sulfate solution was added to the reaction mixture and the mixture was extracted three times with ethyl acetate. The ethyl acetate layer was washed with saturated brine and dried over magnesium sulfate. The solvent was evaporated under reduced pressure and the obtained residue was purified by silica gel column chromatography (chloroform: methanol=90:10) to give 6-(3-chlorobenzyl)-4-hydroxy-2-methyl-2,6,7,8-tetrahydropyrido[4,3-c]pyridazine-3,5-dione (92 mg).

$^1$H-NMR (DMSO-$d_6$)δ 13.41(1H, s), 7.39–7.33(4H, m), 4.70(2H, s), 3.64–3.56(5H, m), 2.85(2H, t, J=6.5 Hz).

Example 438

7-(2,2-Dimethylpropionyl)-2-(4-fluorobenzyl)-9-hydroxy-2H-pyrido[1,2-a]pyrazine-1,8-dione hydrochloride (7.5 g) obtained in the same manner as in Example 251 was suspended in ethyl acetate (1.5 L) and saturated aqueous sodium hydrogen carbonate (500 ml) was added with stirring. After the suspended substance was dissolved, the aqueous layer was separated and extracted with a small amount of ethyl acetate. The combined ethyl acetate layer was washed with saturated brine, dried over sodium sulfate, and concentrated. Acetone-ethyl acetate was added to the obtained residue and the obtained crystals were collected by filtration to give 7-(2,2-dimethylpropionyl)-2-(4-fluorobenzyl)-9-hydroxy-2H-pyrido[1,2-a]pyrazine-1,8-dione (6.38 g).

$^1$H-NMR (DMSO-$d_6$)δ 11.65(1H, br), 8.04(1H, s) 7.44 (2H, dd, J=8.8, 5.1 Hz), 7.19(2H, dd, J=8.8,8.8 Hz), 7.18 (1H, d, J=6.0 Hz), 6.88(1H, d, J=6.0 Hz), 4.92(2H, s), 1.17(9H, s).

Example 439

7-(2,2-Dimethylpropionyl)-2-(4-fluorobenzyl)-9-hydroxy-2H-pyrido[1,2-a]pyrazine-1,8-dione (100 mg) obtained in Example 438 was suspended in tetrahydrofuran-methanol (3:1) (4 ml). 1M Aqueous sodium hydroxide solution (270 μl) was added and the mixture was stirred for 24.5 hr. The precipitate was collected by filtration, washed with tetrahydrofuran and dried in vacuo at 50° C. to give 7-(2,2-dimethylpropionyl)-2-(4-fluorobenzyl)-9-hydroxy-2H-pyrido[1,2-a]pyrazine-1,8-dione sodium salt (94 mg).

$^1$H-NMR (DMSO-$d_6$)δ 7.48(1H, s), 7.37(2H, dd, J=8.8, 5.6 Hz), 7.12(2H, t, J=8.8 Hz), 6.86(1H, d, J=6.3 Hz), 6.57(1H, d, J=6.3 Hz), 4.78(2H, s), 1.21(9H, s).

Sodium salt, potassium salt, hydrochloride, trifluoroacetate, methanesulfonate, benzenesulfonate and toluenesulfonate were obtained from the compound of Example 165 by conventional methods.

N-[2-(3-chlorobenzyl)-9-hydroxy-1,8-dioxo-1,8-dihydro-2H-pyrido[1,2-a]pyrazin-7-yl]acetamide sodium salt (Example 440)

$^1$H-NMR (DMSO-$d_6$)δ 8.92(1H, brs), 8.54(1H, s), 7.41–7.26(4H, m) 6.97(1H, brs), 6.60(1H, brs), 4.83(2H, s), 2.08(3H, s).

A free compound and a sodium salt were obtained from the compound of Example 223 by conventional methods. 2-(3-chlorobenzyl)-7-(2,2-dimethylpropionyl)-9-hydroxy-3,4-dihydro-2H-pyrido[1,2-a]pyrazine-1,8-dione sodium salt (Example 441)

H-NMR (DMSO-$d_6$)δ 7.39–7.24(5H, m), 4.65(2H, s), 4.17–4.05(2H, m), 3.54–3.47(2H, m), 1.23(9H, s).

A free compound, a sodium salt, a potassium salt and a benzenesulfonic acid salt were obtained from the compound of Example 251 by conventional methods.

Examples 93–437

The compounds of Examples 93–437 other than the above-mentioned compounds were obtained by methods similar or analogous to those of Examples 1–12, 118, 125, 161, 165, 94, 96, 104, 187, 191, 189, 390, 244, 251, 223, 154, 249, 219, 362, 205, 242, 382, 283, 302, 349, 353, 222, 316, 291, 106, 123, 438 and 439 or conventional methods.

The chemical structural formulas and physicochemical data of Example compounds are shown in Tables 1–37.

TABLE 1

| Example No. | Structural formula |
|---|---|
| 1 | 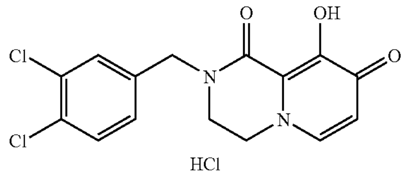 |
| 2 | 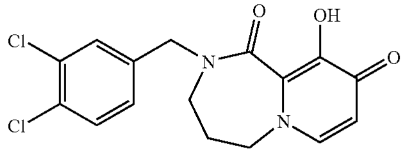 |
| 3 | 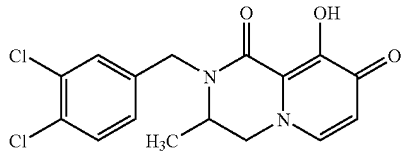 |
| 4 | 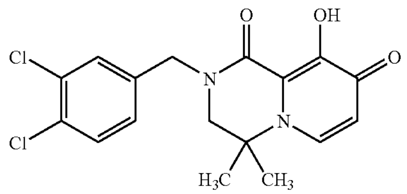 |
| 5 | 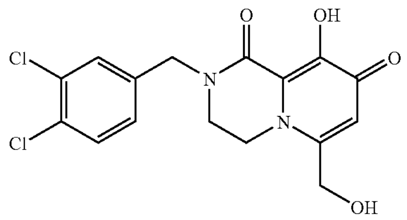 |

TABLE 1-continued
| Example No. | Structural formula |
|---|---|
| 6 | 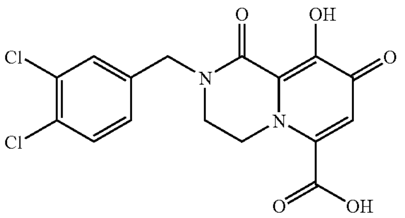 |
| 7 | 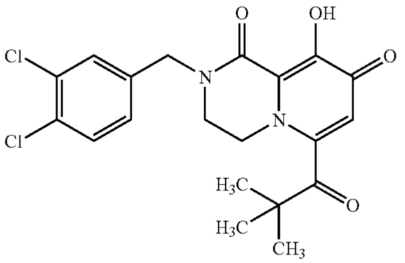 |
| 8 | 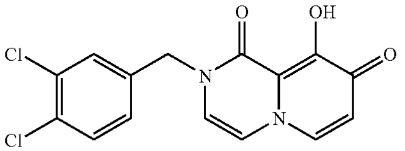 |
| 9 | 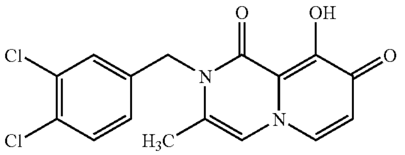 |
| 10 | 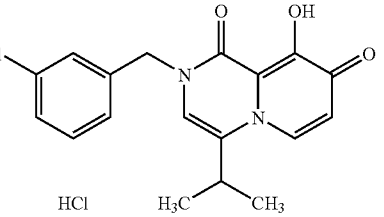 HCl |
| 11 | 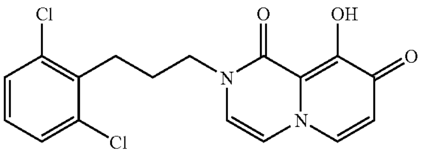 |
| 12 | 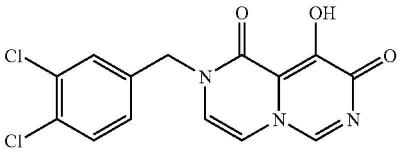 HCl |
TABLE 2
| Example No. | Structural formula |
|---|---|
| 13 | 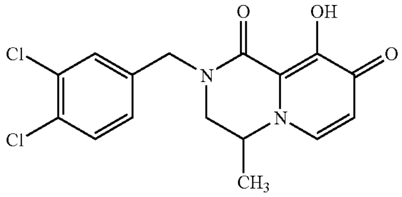 |
| 14 | 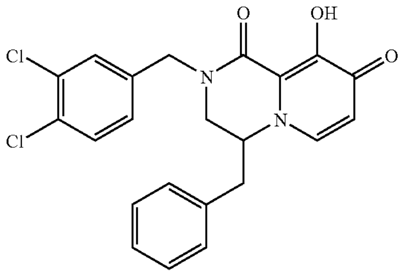 |
| 15 | 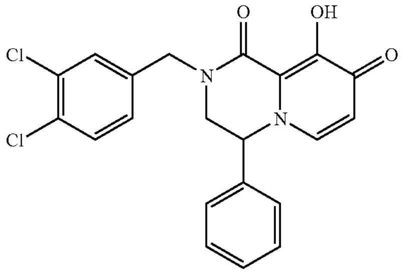 |
| 16 | 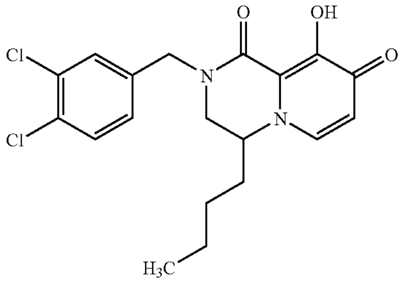 |
| 17 | 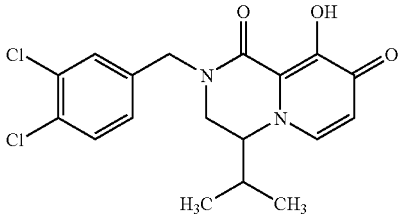 |
| 18 | 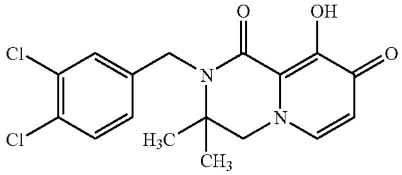 |

TABLE 2-continued
| Example No. | Structural formula |
|---|---|
| 19 | 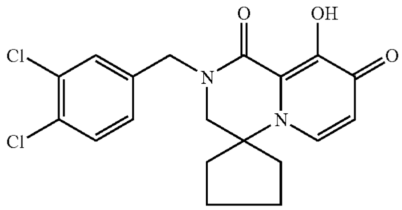 |
| 20 | 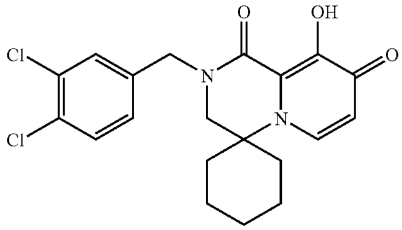 |
| 21 | 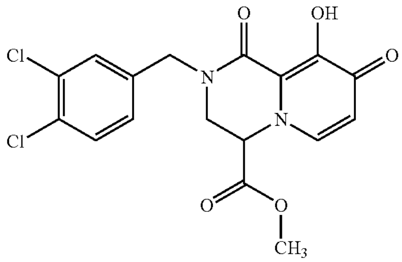 |
| 22 | 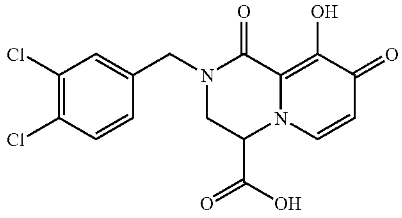 |
TABLE 3
| Example No. | Structural formula |
|---|---|
| 23 | 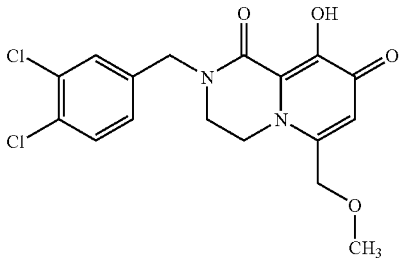 |
TABLE 3-continued
| Example No. | Structural formula |
|---|---|
| 24 | 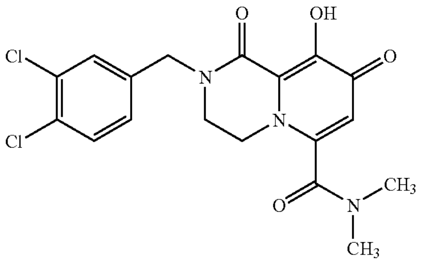 |
| 25 | 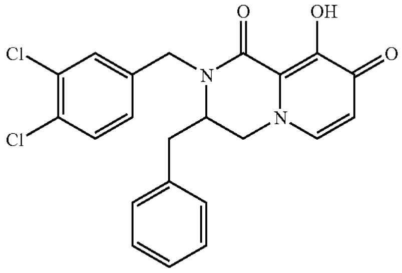 |
| 26 | 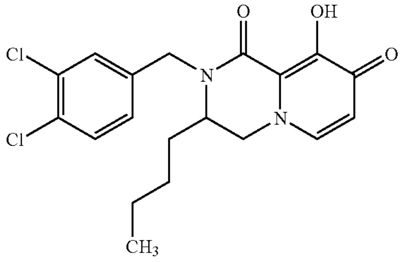 |
| 27 | 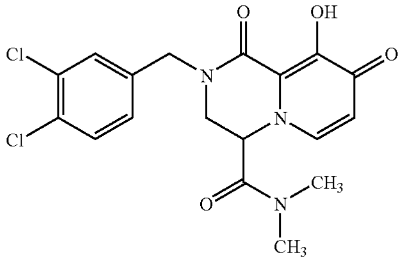 |
| 28 | 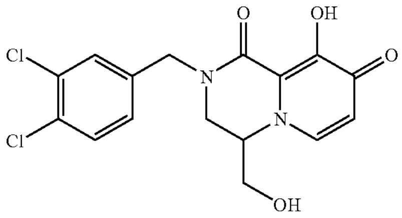 |

TABLE 3-continued
| Example No. | Structural formula |
| --- | --- |
| 29 | 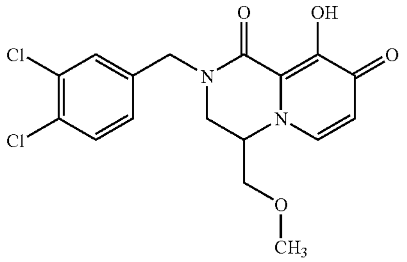 |
| 30 | 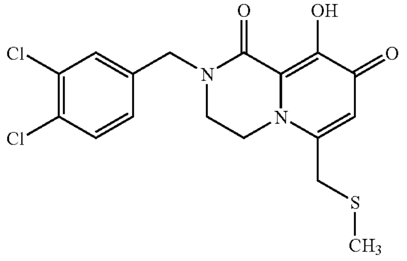 |
| 31 | 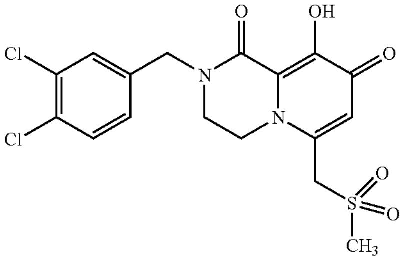 |
| 32 | 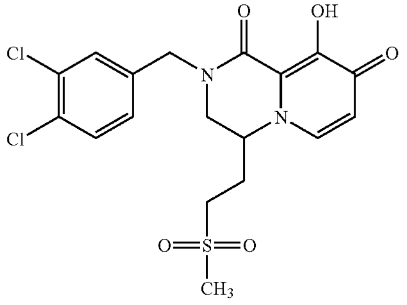 |
TABLE 4
| Example No. | Structural formula |
| --- | --- |
| 33 | 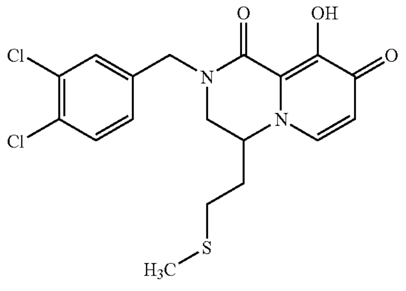 |
TABLE 4-continued
| Example No. | Structural formula |
| --- | --- |
| 34 | 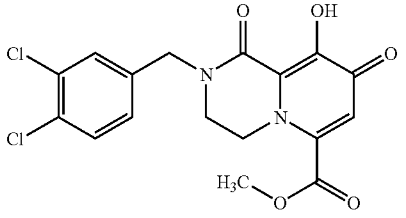 |
| 35 | 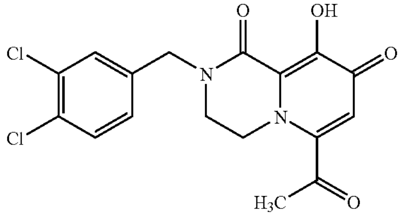 |
| 36 | 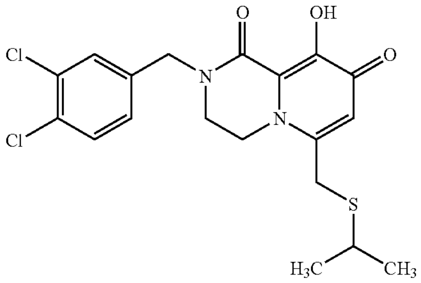 |
| 37 | 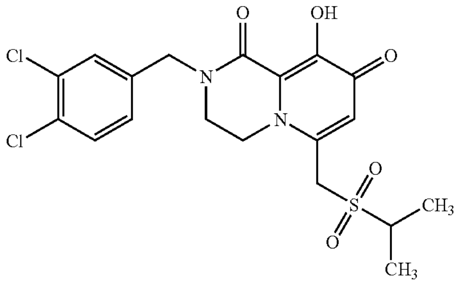 |
| 38 | 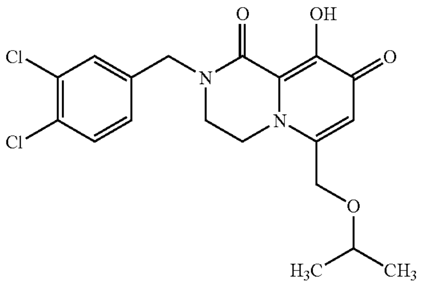 |

TABLE 4-continued
| Example No. | Structural formula |
|---|---|
| 39 | 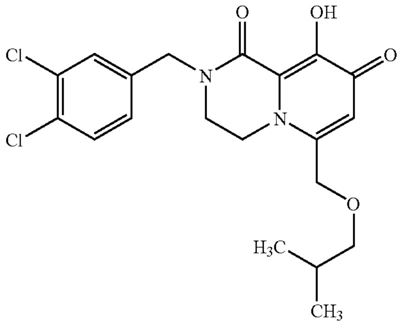 |
| 40 | 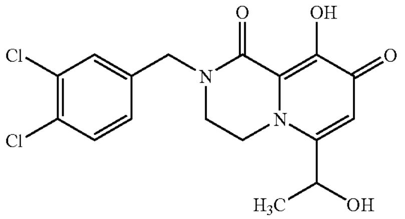 |
TABLE 5
| Example No. | Structural formula |
|---|---|
| 41 | 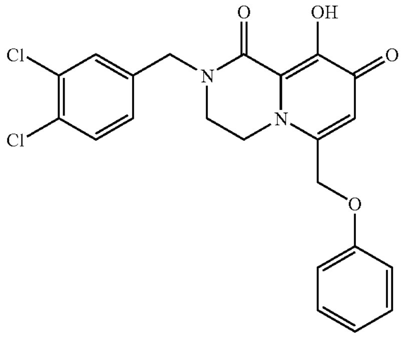 |
| 42 | 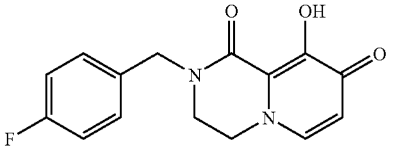 |
| 43 | 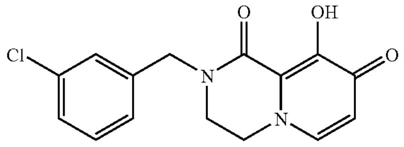 |
| 44 | 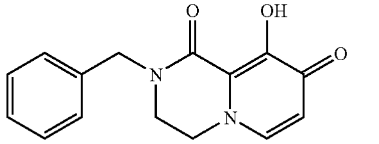 |
TABLE 5-continued
| Example No. | Structural formula |
|---|---|
| 45 | 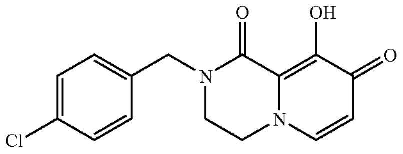 |
| 46 | 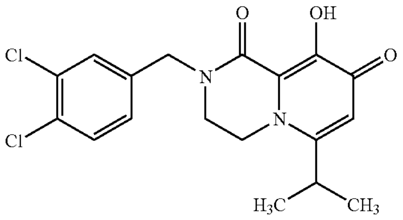 |
| 47 | 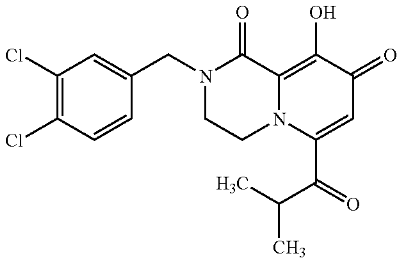 |
| 48 | 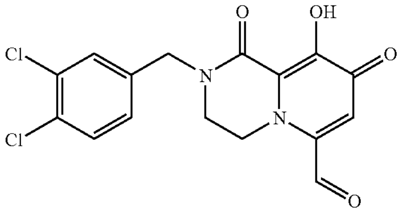 |
| 49 | 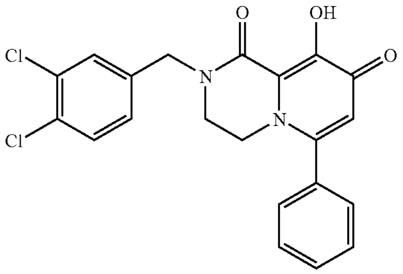 |
| 50 | 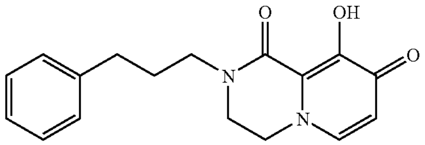 |

TABLE 6
| Example No. | Structural formula |
|---|---|
| 51 | 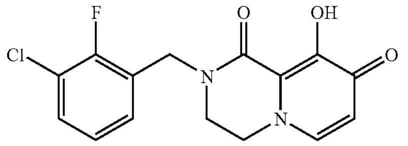 |
| 52 | 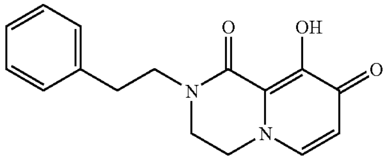 |
| 53 | 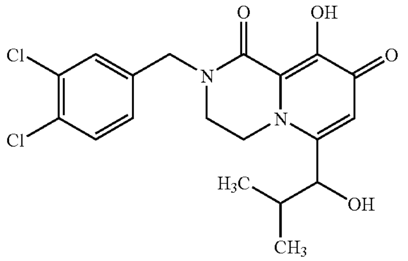 |
| 54 | 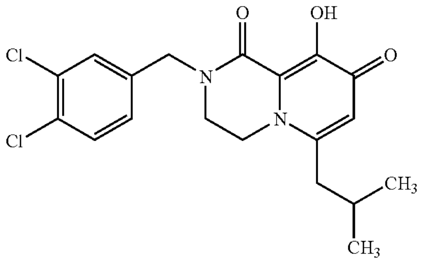 |
| 55 | 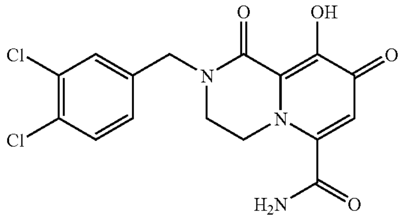 |
| 56 | 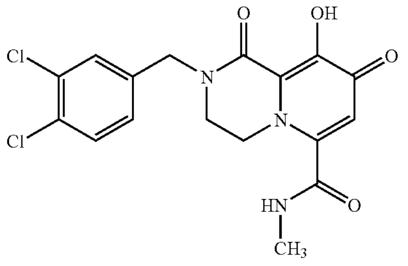 |
| 57 | 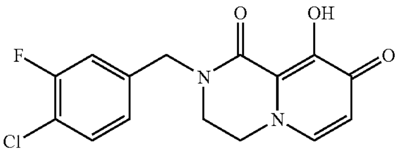 |
TABLE 6-continued
| Example No. | Structural formula |
|---|---|
| 58 | 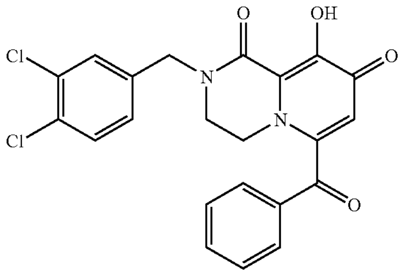 |
| 59 | 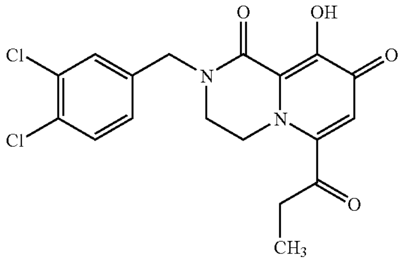 |
| 60 | 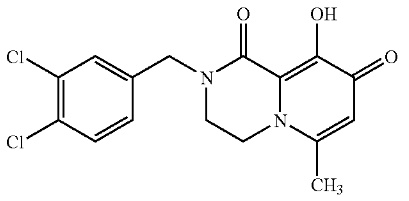 |
TABLE 7
| Example No. | Structural formula |
|---|---|
| 61 | 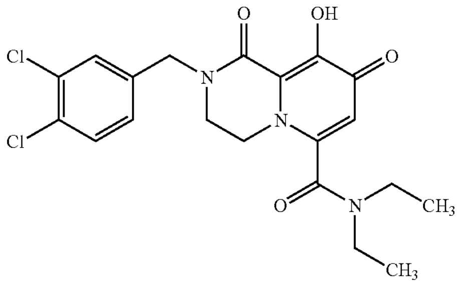 |
| 62 | 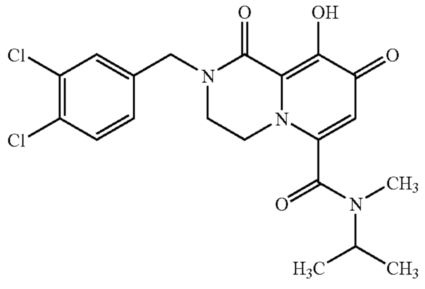 |

TABLE 7-continued
| Example No. | Structural formula |
|---|---|
| 63 | 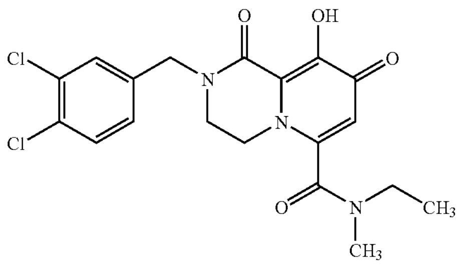 |
| 64 | 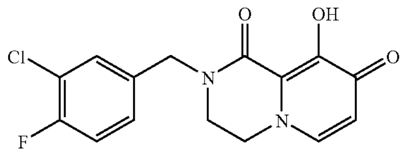 |
| 65 | 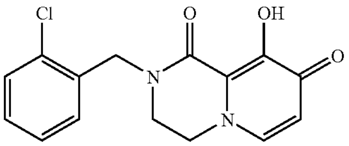 |
| 66 | 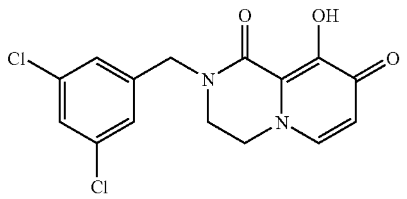 |
| 67 | 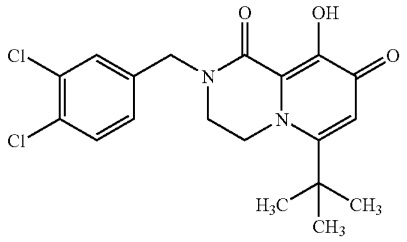 |
| 68 | 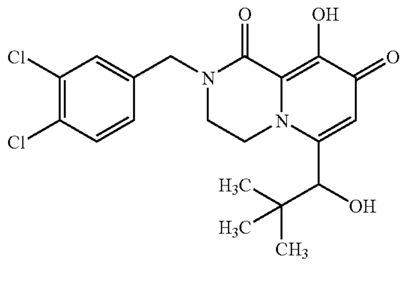 |
| 69 | 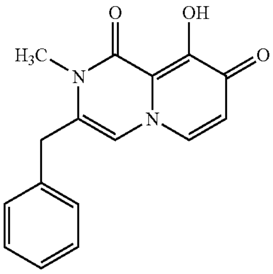 |
| 70 | 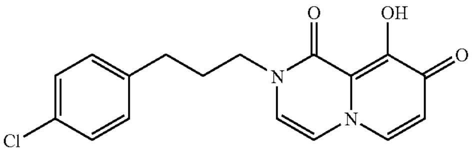 |
TABLE 8
| Example No. | Structural formula |
|---|---|
| 71 | 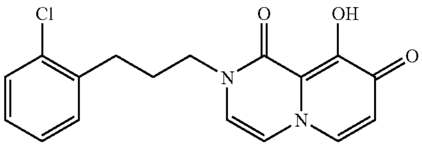 |
| 72 | 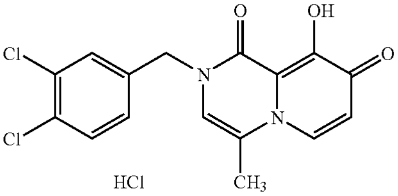 HCl |
| 73 | 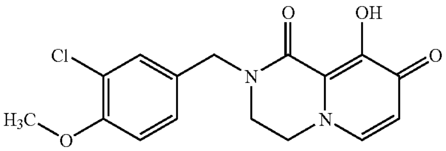 |
| 74 | 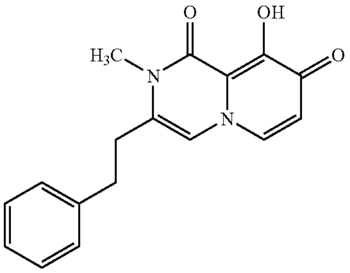 |

TABLE 8-continued
| Example No. | Structural formula |
|---|---|
| 75 | 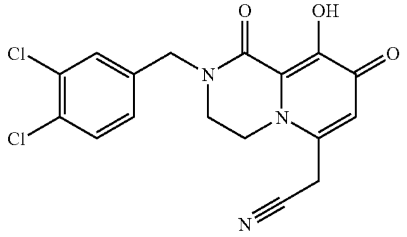 |
| 76 | 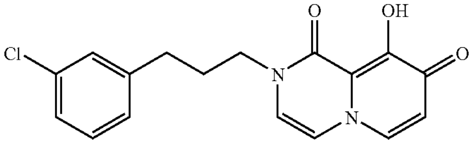 |
| 77 | 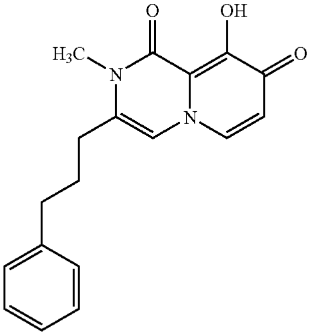 |
| 78 | 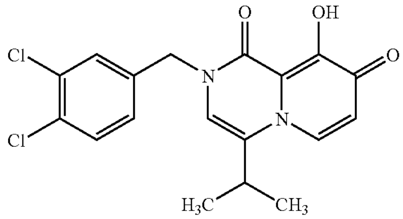 |
| 79 | 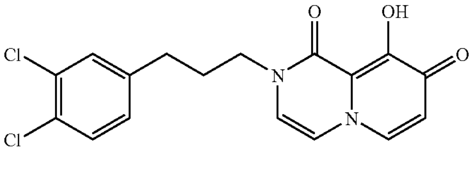 |
| 80 | 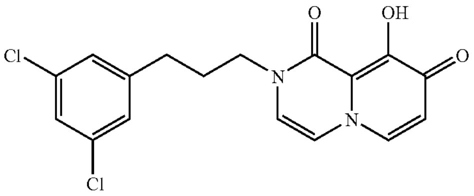 |
TABLE 9
| Example No. | Structural formula |
|---|---|
| 81 | 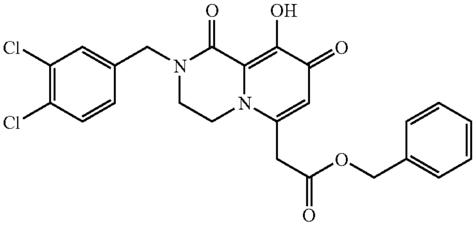 |
| 82 | 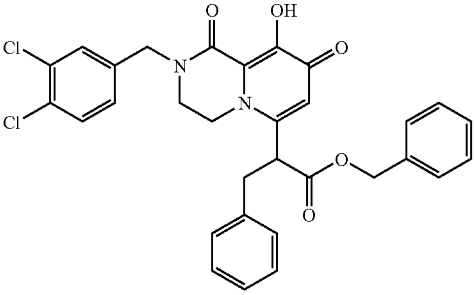 |
| 83 | 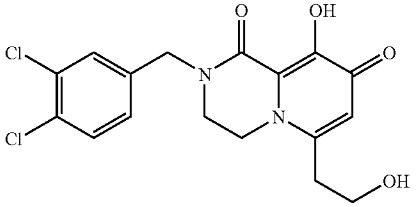 |
| 84 | 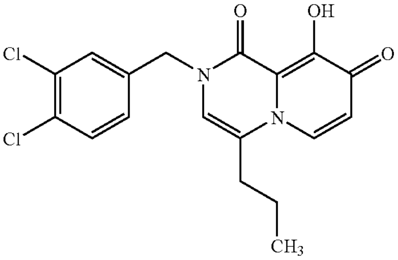 |
| 85 | 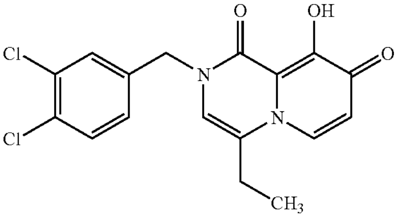 |
| 86 | 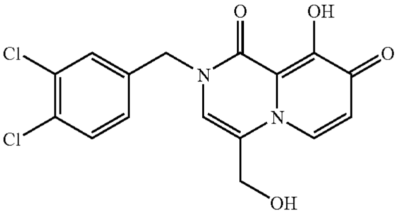 |

TABLE 9-continued
| Example No. | Structural formula |
|---|---|
| 87 | 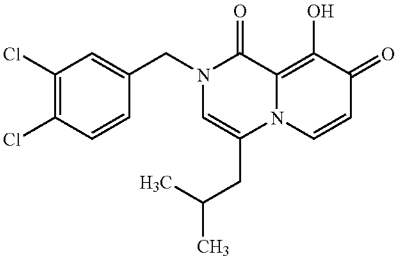 |
| 88 | 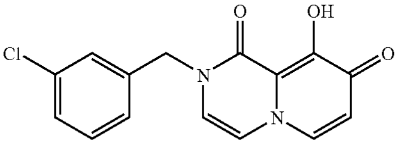 HCl |
| 89 | 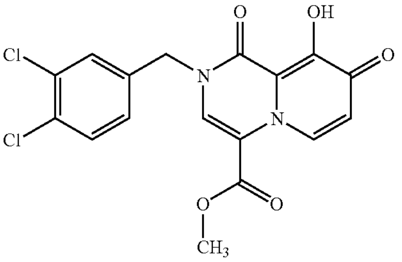 |
| 90 | 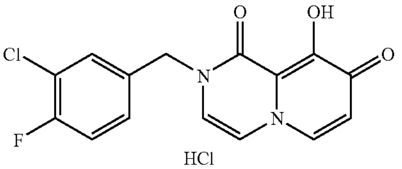 HCl |
TABLE 10
| Example No. | Structural formula |
|---|---|
| 91 | 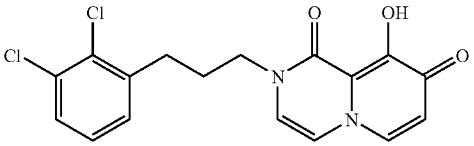 HCl |
| 92 | 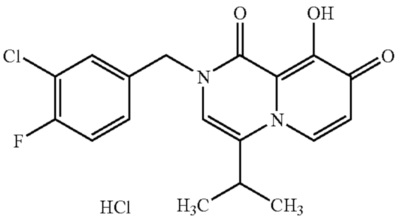 HCl |
TABLE 10-continued
| Example No. | Structural formula |
|---|---|
| 93 | 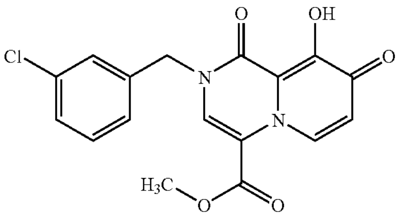 |
| 94 | 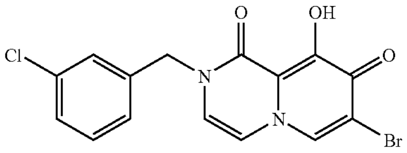 HCl |
| 95 | 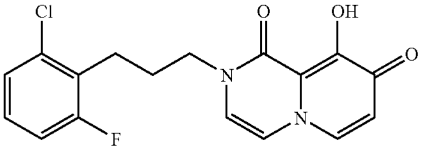 HCl |
| 96 | 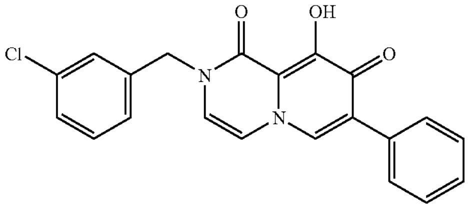 HCl |
| 97 | 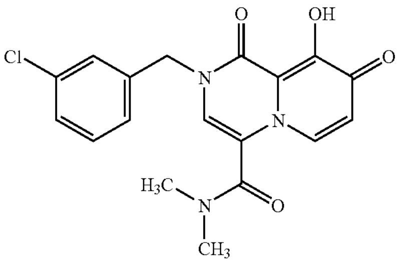 |
| 98 | 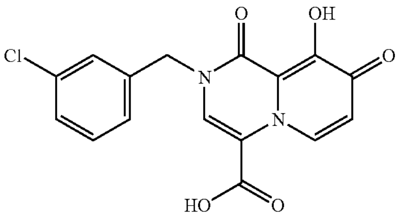 |

TABLE 10-continued
| Example No. | Structural formula |
| --- | --- |
| 99 | 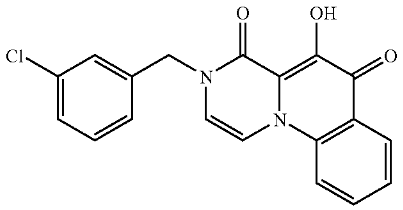 HCl |
| 100 | 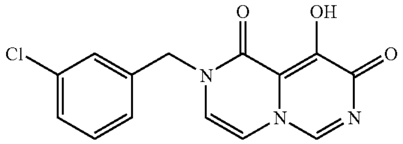 HCl |
| 101 | 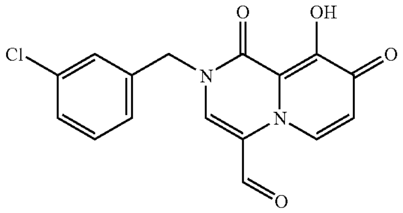 |
| 102 | 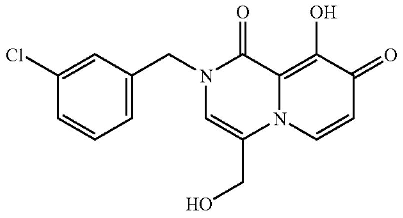 |
TABLE 11
| Example No. | Structural formula |
| --- | --- |
| 103 | 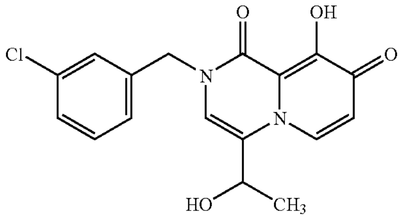 |
| 104 | 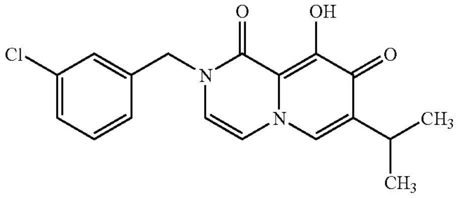 HCl |
TABLE 11-continued
| Example No. | Structural formula |
| --- | --- |
| 105 | 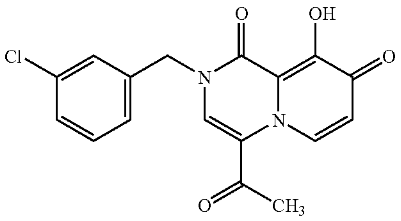 |
| 106 | 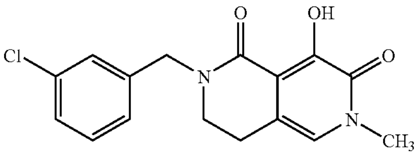 |
| 107 | 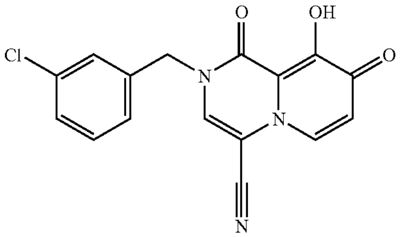 |
| 108 | 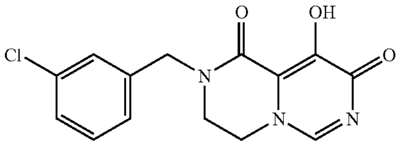 |
| 109 | 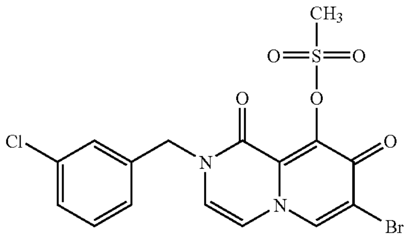 |
| 110 | 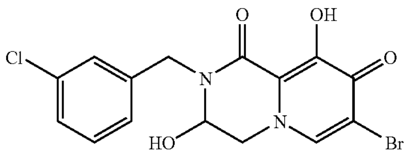 HCl |
| 111 | 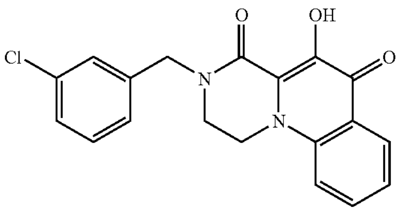 |

TABLE 11-continued
| Example No. | Structural formula |
|---|---|
| 112 | 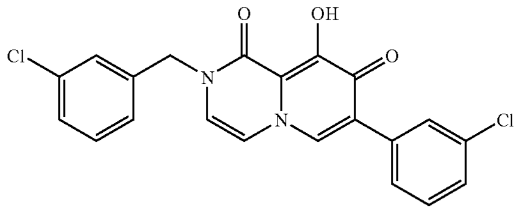 HCl |
TABLE 12
| Example No. | Structural formula |
|---|---|
| 113 | 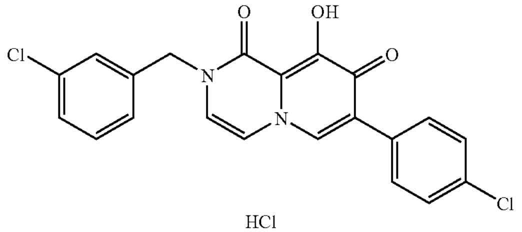 HCl |
| 114 | 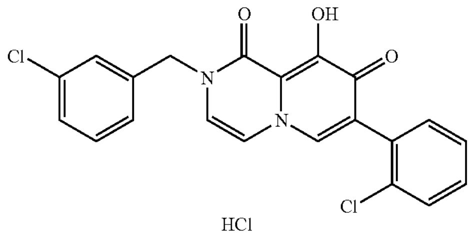 HCl |
| 115 | 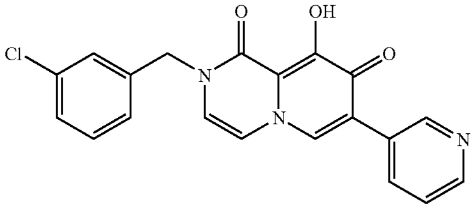 HCl |
| 116 | 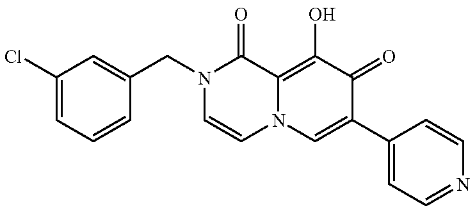 HCl |
TABLE 12-continued
| Example No. | Structural formula |
|---|---|
| 117 | 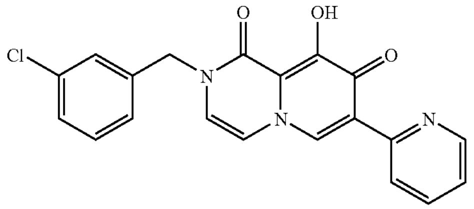 HCl |
| 118 | 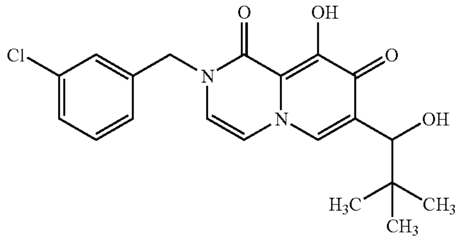 HCl |
| 119 | 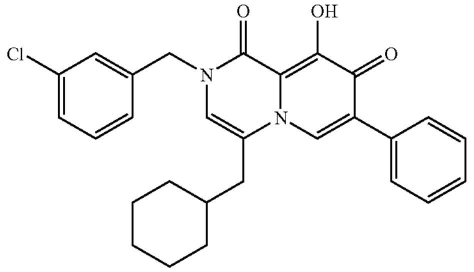 HCl |
| 120 | 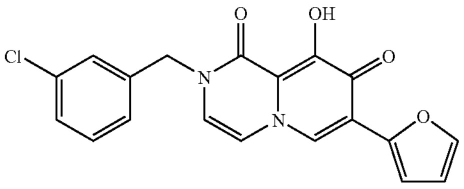 HCl |
| 121 | 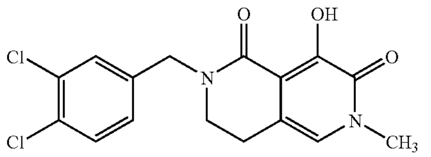 |
| 122 | 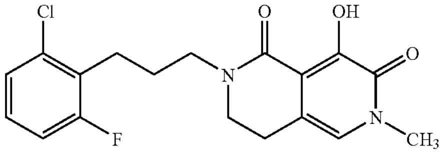 |

TABLE 12-continued
| Example No. | Structural formula |
|---|---|
| 123 | 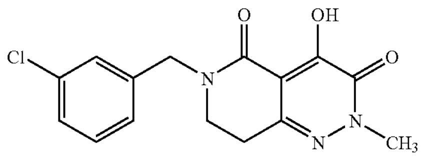 |
| 124 | 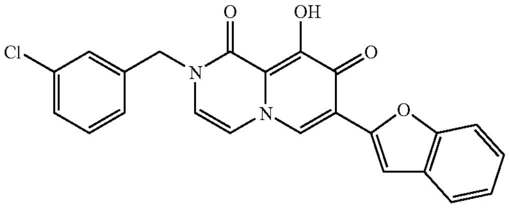 HCl |
TABLE 13
| Example No. | Structural formula |
|---|---|
| 125 | 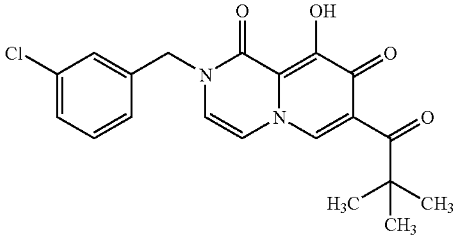 HCl |
| 126 | 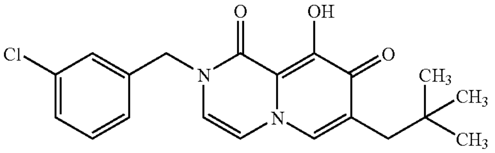 HCl |
| 127 | 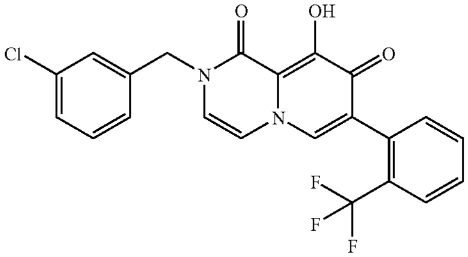 HCl |
TABLE 13-continued
| Example No. | Structural formula |
|---|---|
| 128 | 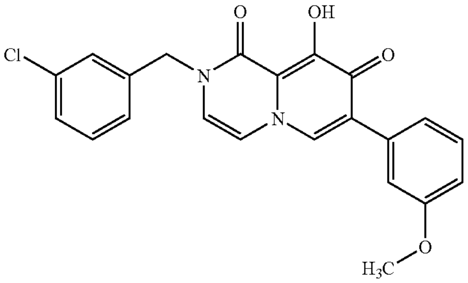 HCl |
| 129 | 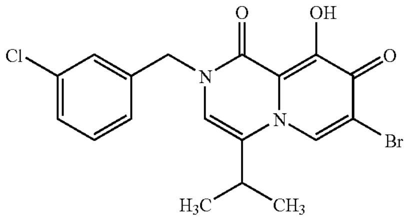 HCl |
| 130 | 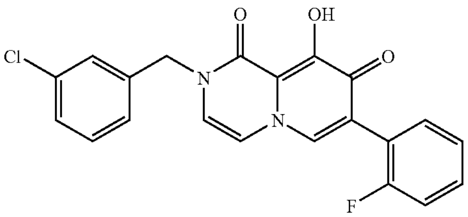 HCl |
| 131 | 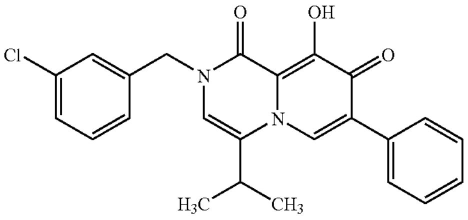 HCl |
| 132 | 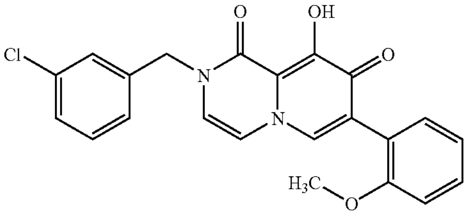 HCl |

TABLE 13-continued
| Example No. | Structural formula |
|---|---|
| 133 | 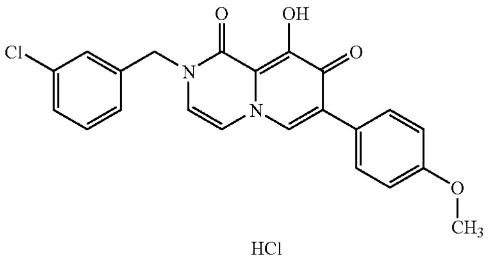 HCl |
| 134 | 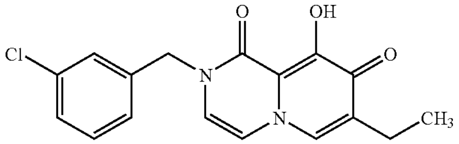 HCl |
| 135 | 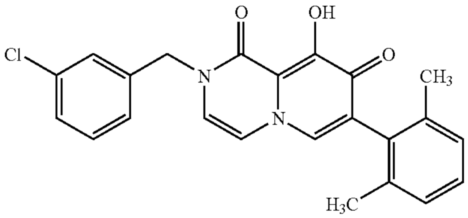 HCl |
| 136 | 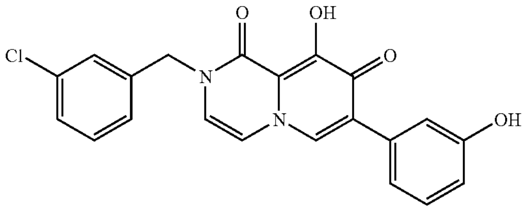 |
TABLE 14
| Example No. | Structural formula |
|---|---|
| 137 | 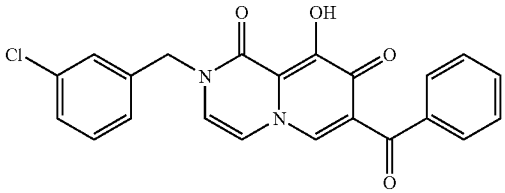 HCl |
TABLE 14-continued
| Example No. | Structural formula |
|---|---|
| 138 | 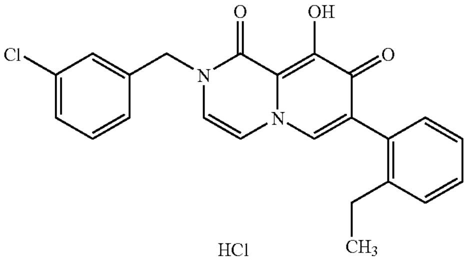 HCl |
| 139 | 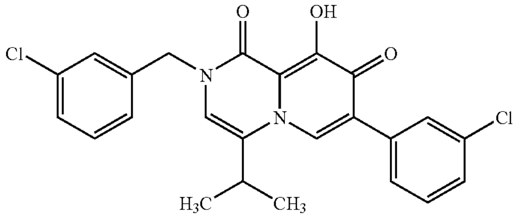 |
| 140 | 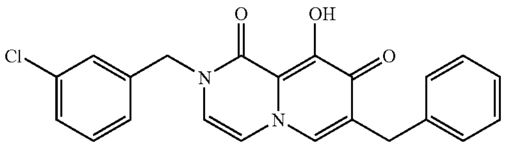 HCl |
| 141 | 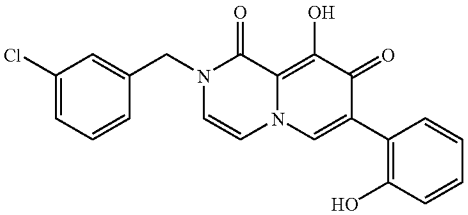 |
| 142 | 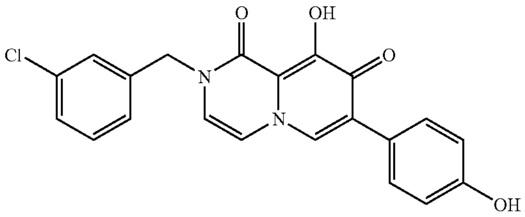 |
| 143 | 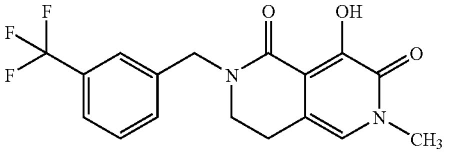 |
| 144 | 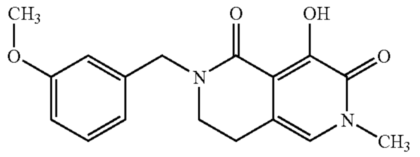 |

TABLE 14-continued
| Example No. | Structural formula |
|---|---|
| 145 | 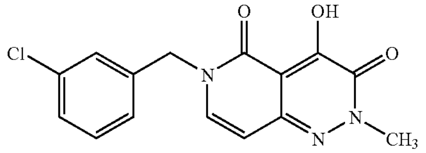 |
| 146 | 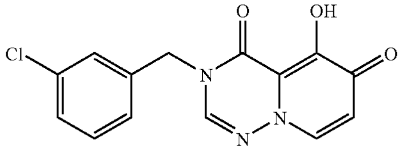 |
| 147 | 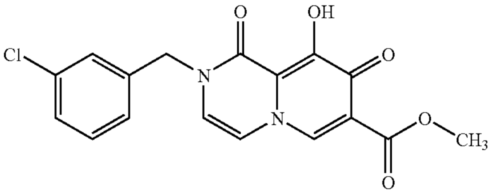 HCl |
| 148 | 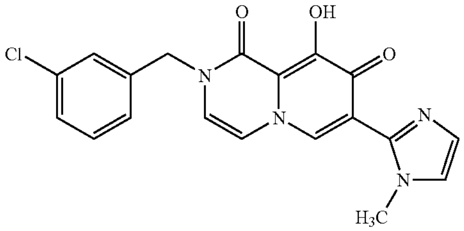 HCl |
TABLE 15
| Example No. | Structural formula |
|---|---|
| 149 | 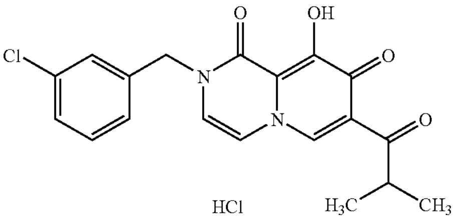 HCl |
| 150 | 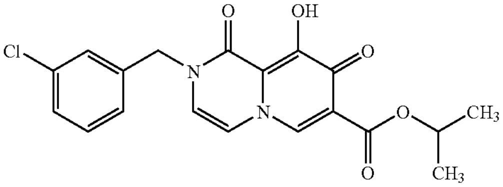 |
TABLE 15-continued
| Example No. | Structural formula |
|---|---|
| 151 | HCl 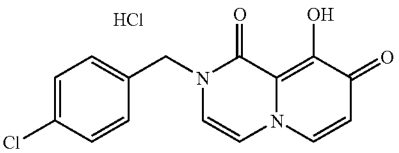 |
| 152 | 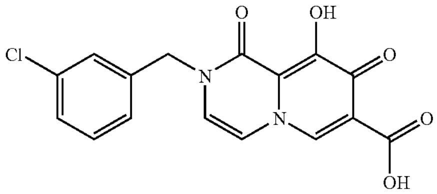 HCl |
| 153 | 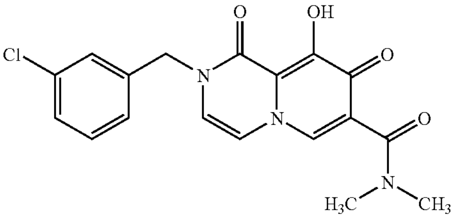 |
| 154 | 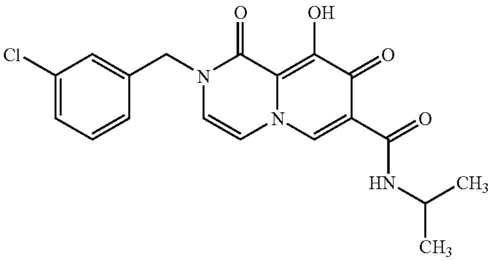 |
| 155 | 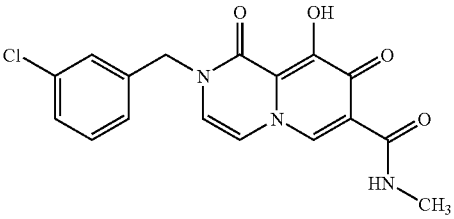 |
| 156 | 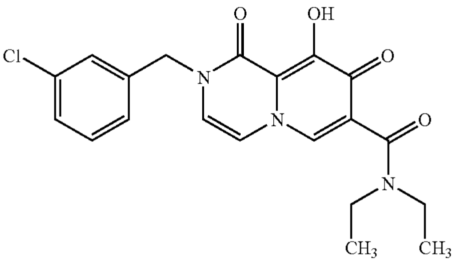 |

TABLE 15-continued
| Example No. | Structural formula |
|---|---|
| 157 | 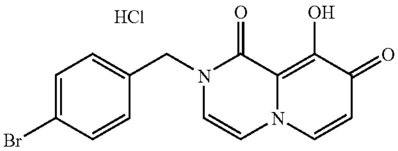 HCl |
| 158 | 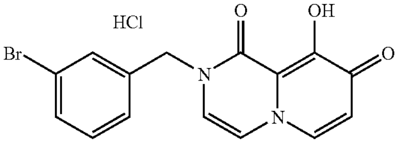 HCl |
| 159 | 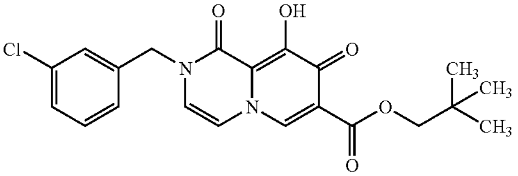 |
| 160 | 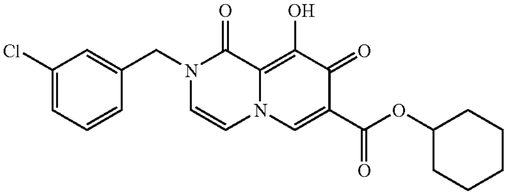 |
TABLE 16
| Example No. | Structural formula |
|---|---|
| 161 | 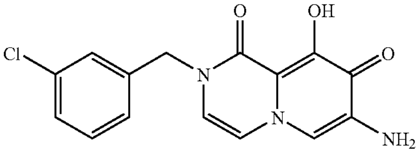 HCl |
| 162 | 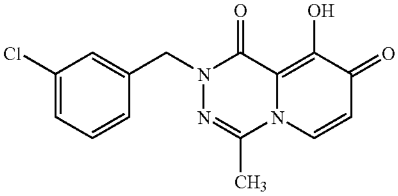 HCl |
TABLE 16-continued
| Example No. | Structural formula |
|---|---|
| 163 | 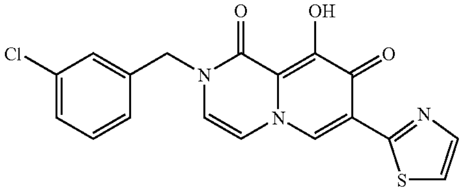 HCl |
| 164 | 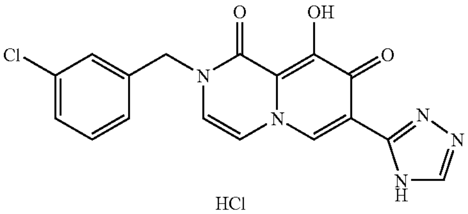 HCl |
| 165 | 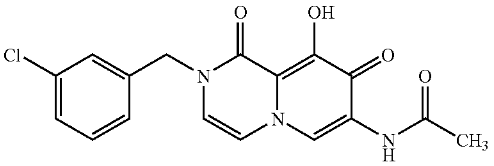 |
| 166 | 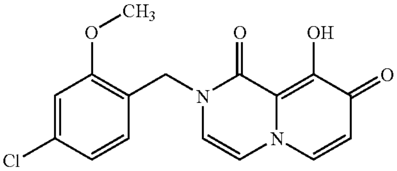 HCl |
| 167 | 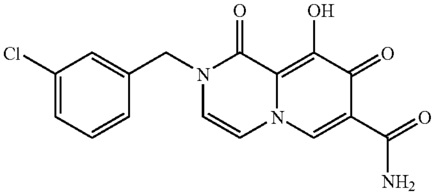 |
| 168 | 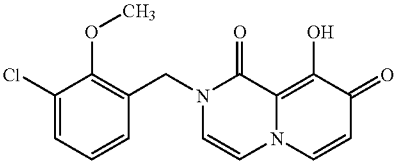 HCl |
| 169 | 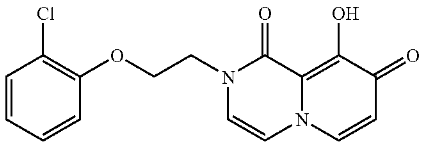 HCl |

TABLE 16-continued
| Example No. | Structural formula |
| --- | --- |
| 170 | 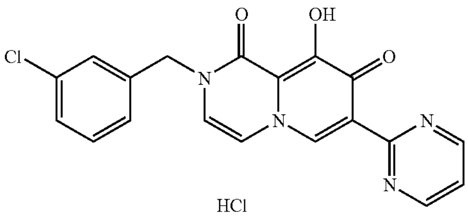 HCl |
| 171 | 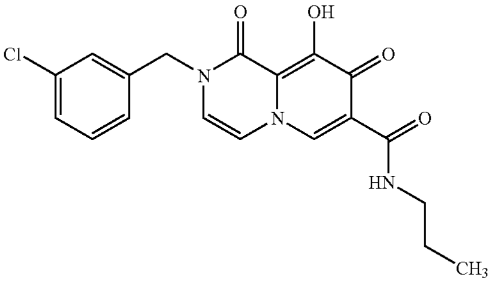 |
| 172 | 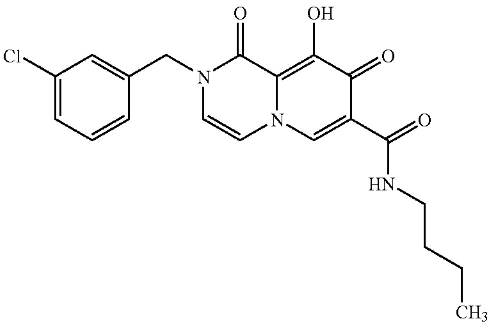 |
TABLE 17
| Example No. | Structural formula |
| --- | --- |
| 173 | 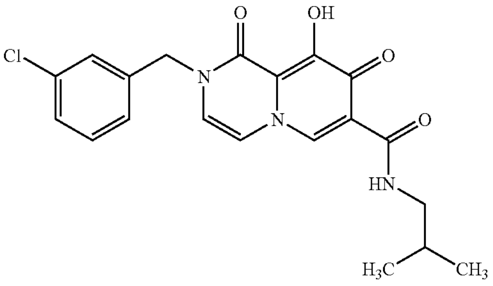 |
TABLE 17-continued
| Example No. | Structural formula |
| --- | --- |
| 174 | 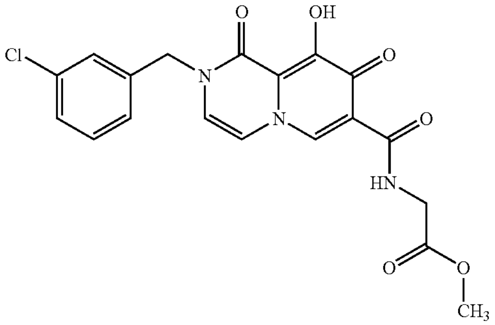 |
| 175 | 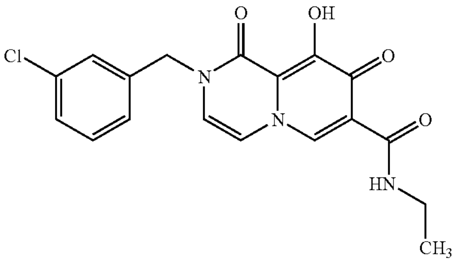 |
| 176 | 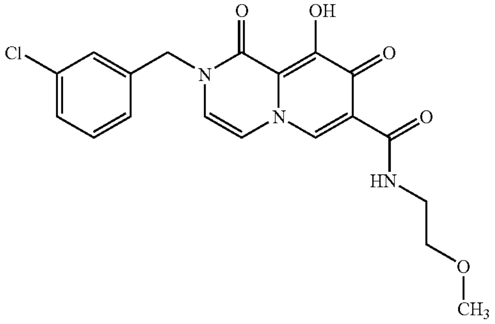 |
| 177 | 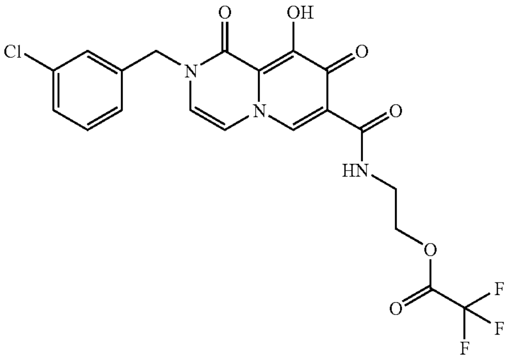 |

TABLE 17-continued
| Example No. | Structural formula |
|---|---|
| 178 | 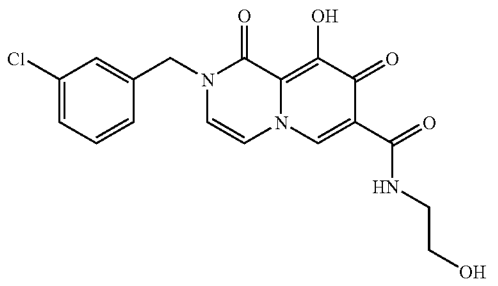 |
| 179 | 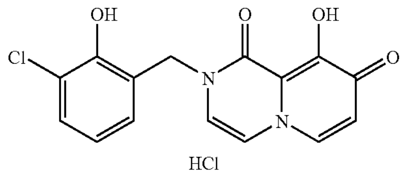 |
| 180 | 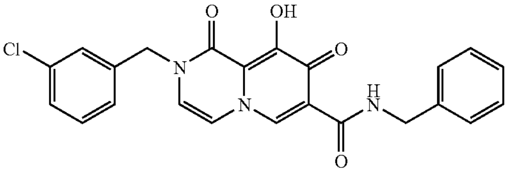 |
| 181 | 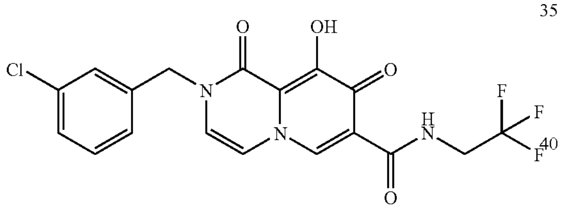 |
| 182 | 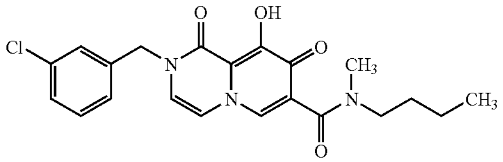 |
| 183 | 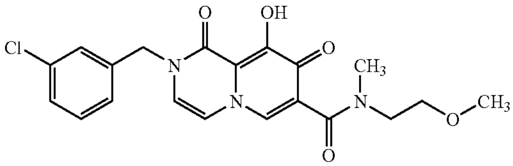 |
| 184 | 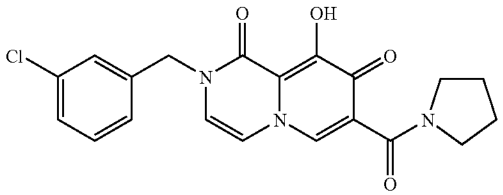 |
TABLE 18
| Example No. | Structural formula |
|---|---|
| 185 | 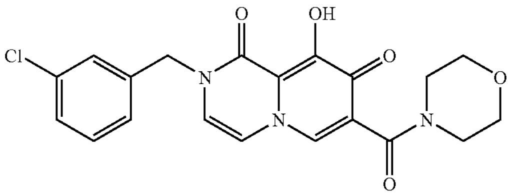 |
| 186 | 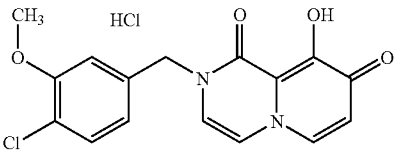 |
| 187 | 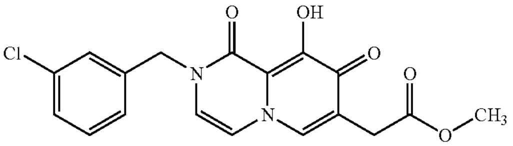 |
| 188 | 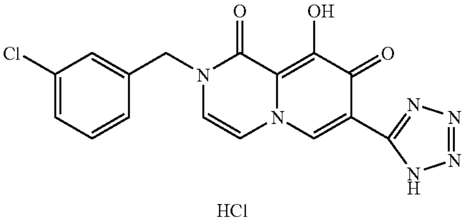 |
| 189 | 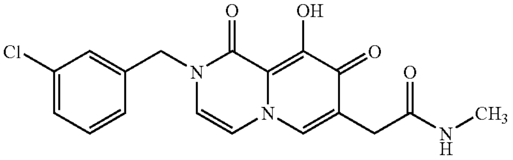 |
| 190 | 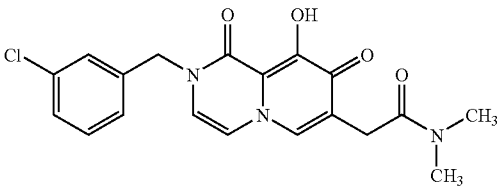 |
| 191 | 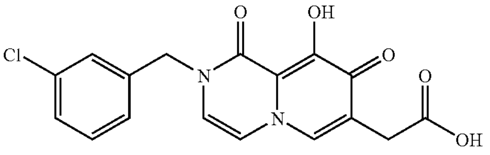 |

TABLE 18-continued
| Example No. | Structural formula |
| --- | --- |
| 192 | 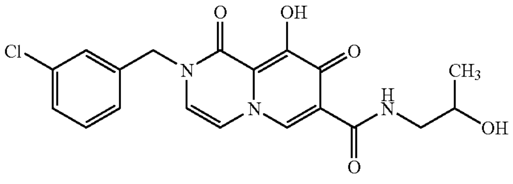 HCl |
| 193 | 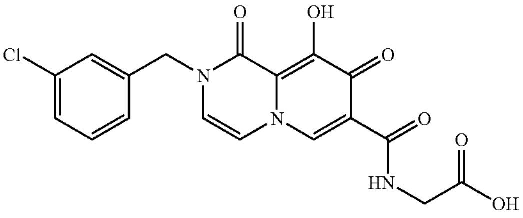 |
| 194 | 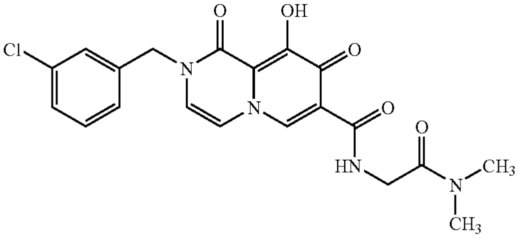 |
| 195 | 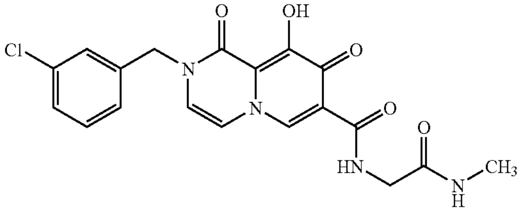 |
| 196 | 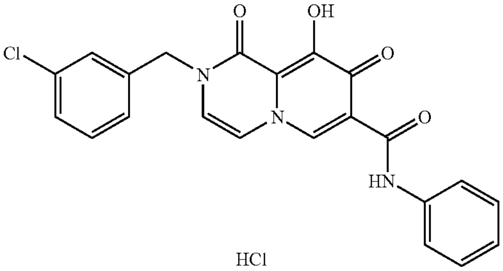 HCl |
| 197 | 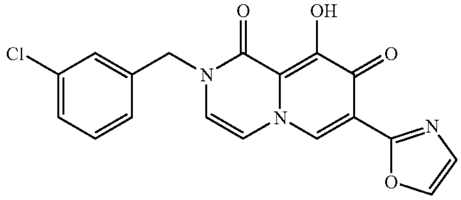 HCl |
| 198 | 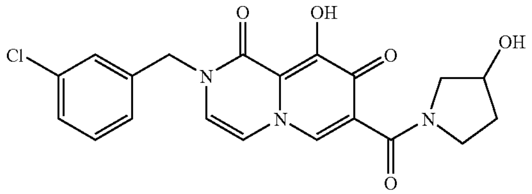 HCl |
TABLE 19
| Example No. | Structural formula |
| --- | --- |
| 199 | 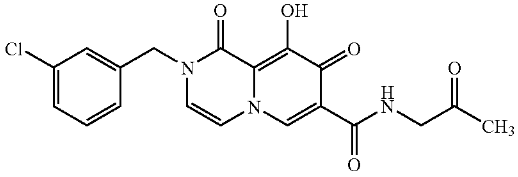 |
| 200 | 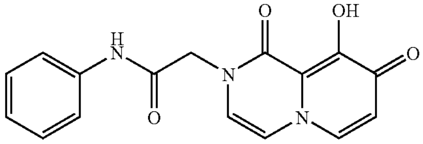 HCl |
| 201 | 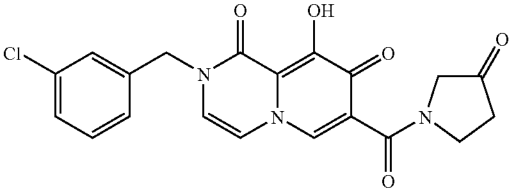 |
| 202 | 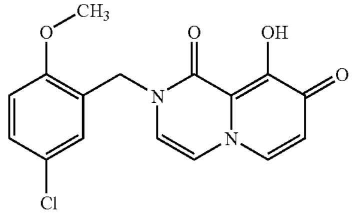 HCl |
| 203 | 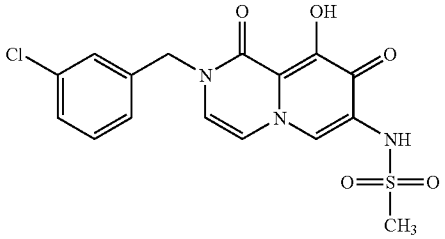 |

TABLE 19-continued
| Example No. | Structural formula |
|---|---|
| 204 | 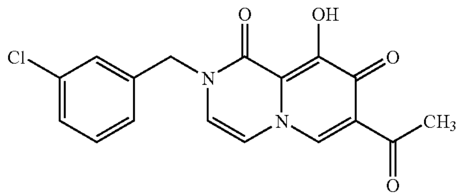 HCl |
| 205 | 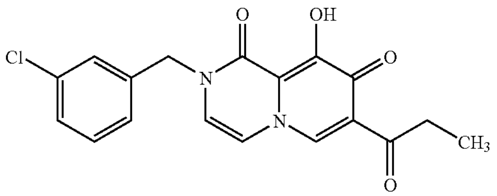 HCl |
| 206 | 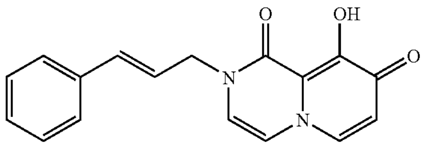 |
| 207 | 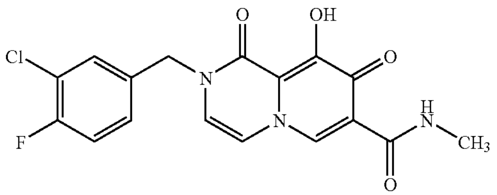 |
| 208 | 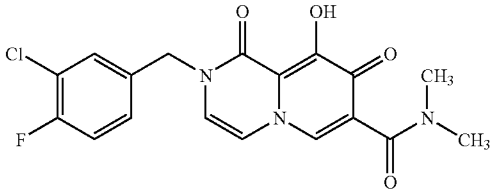 |
| 209 | 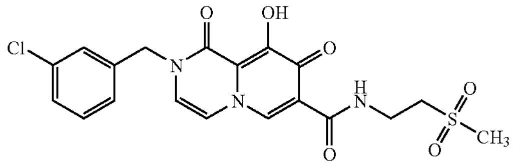 |
| 210 | 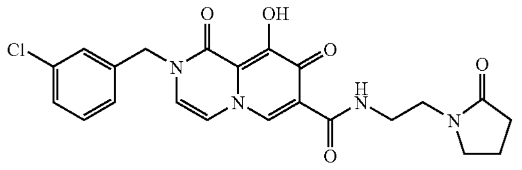 |
| 211 | 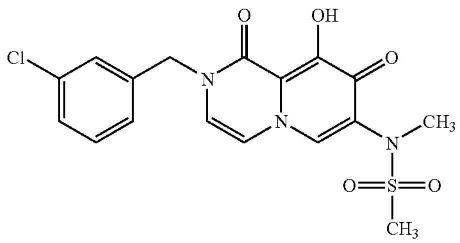 |
| 212 | 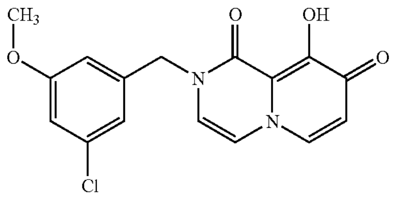 HCl |
TABLE 20
| Example No. | Structural formula |
|---|---|
| 213 | 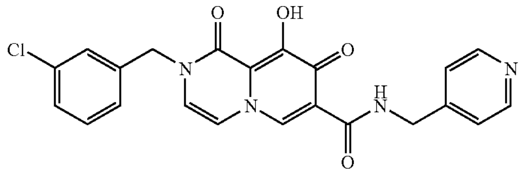 |
| 214 | 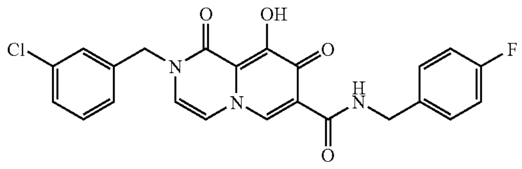 |
| 215 | 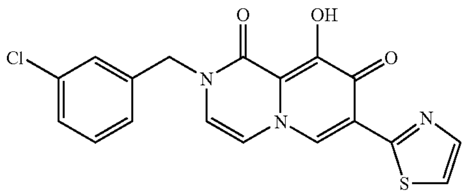 |
| 216 | 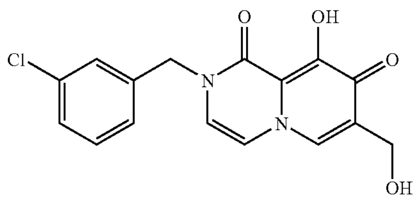 HCl |

TABLE 20-continued
| Example No. | Structural formula |
|---|---|
| 217 | 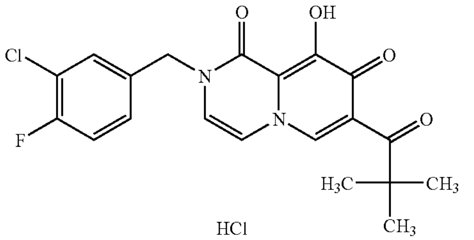 HCl |
| 218 | 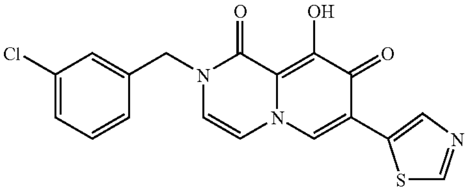 HCl |
| 219 | 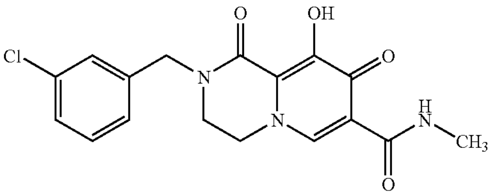 |
| 220 | 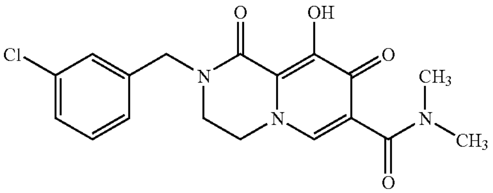 |
| 221 | 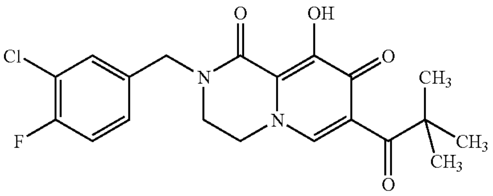 HCl |
| 222 | 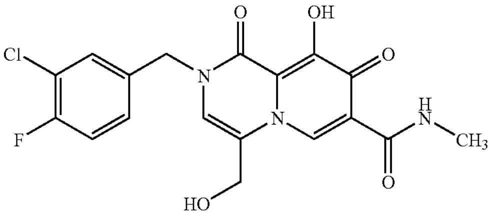 HCl |
| 223 | 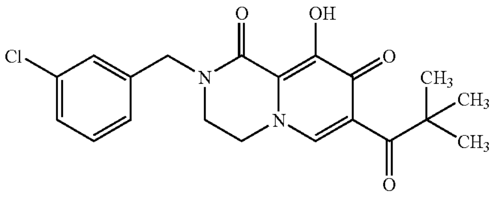 HCl |
| 224 | 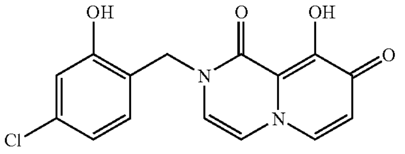 HCl |
| 225 | 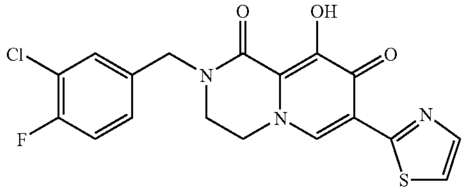 |
| 226 | 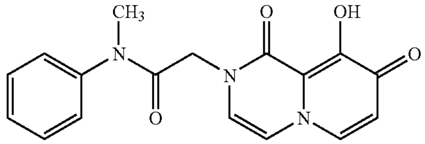 HCl |
TABLE 21
| Example No. | Structural formula |
|---|---|
| 227 | 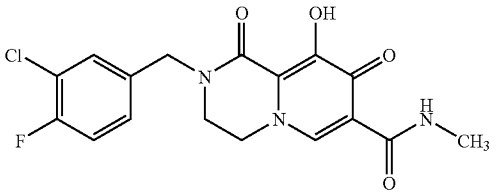 |
| 228 | 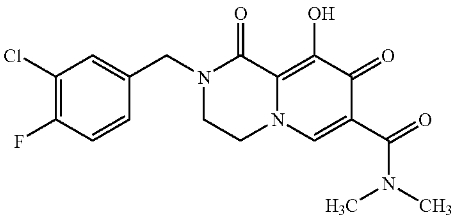 |

TABLE 21-continued
| Example No. | Structural formula |
| --- | --- |
| 229 | 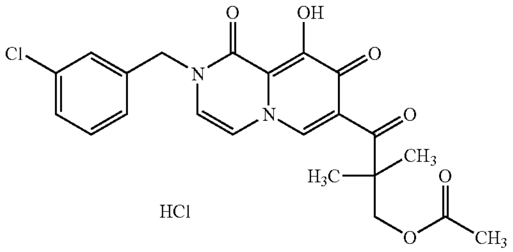 HCl |
| 230 | 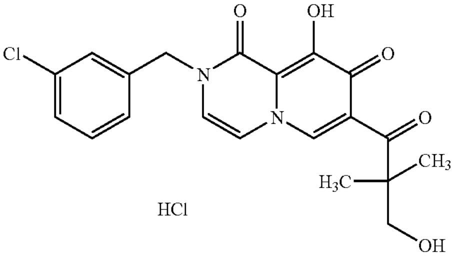 HCl |
| 231 | 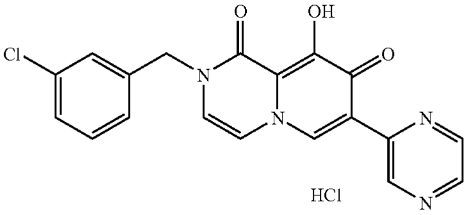 HCl |
| 232 | 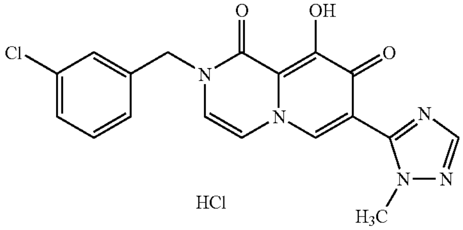 HCl |
| 233 | 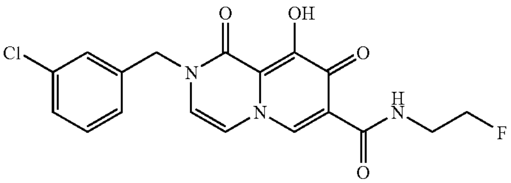 |
| 234 | 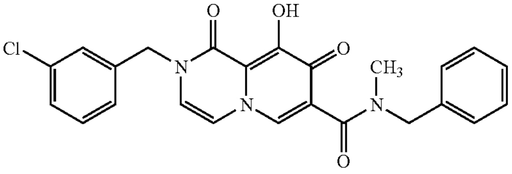 |
TABLE 21-continued
| Example No. | Structural formula |
| --- | --- |
| 235 | 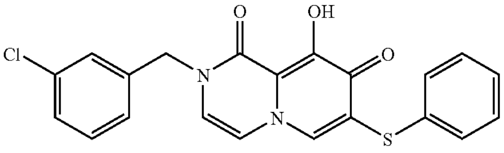 |
| 236 | 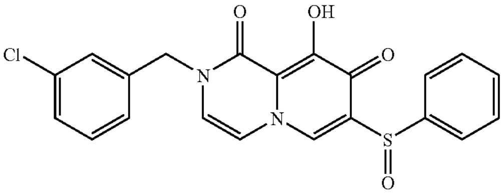 |
| 237 | 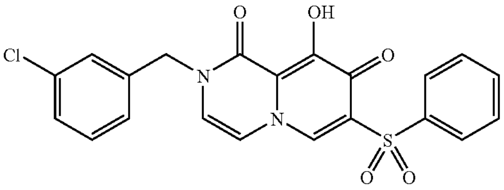 |
| 238 | 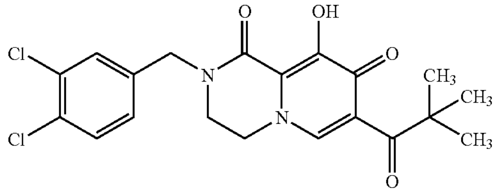 |
| 239 | 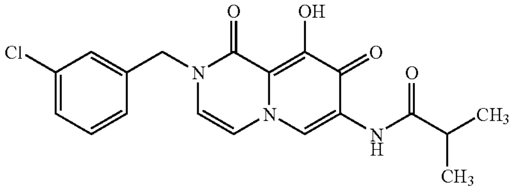 |
| 240 | 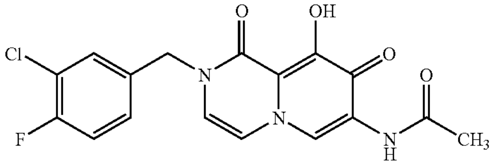 |

TABLE 22
| Example No. | Structural formula |
|---|---|
| 241 | 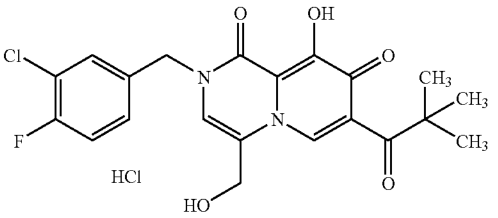 HCl |
| 242 | 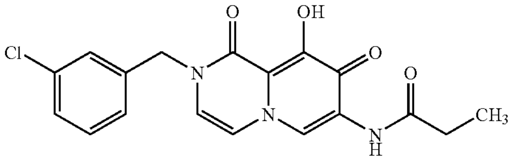 |
| 243 | 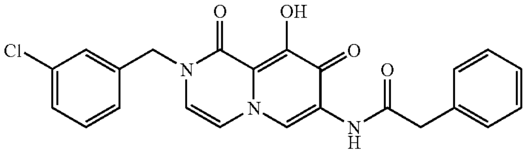 |
| 244 | 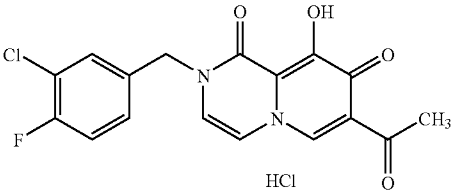 HCl |
| 245 | 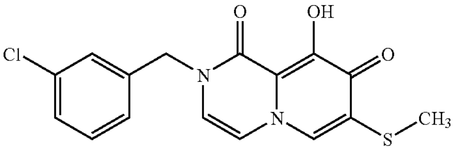 |
| 246 | 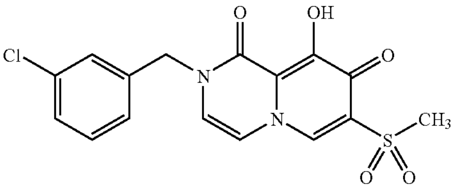 |
| 247 | 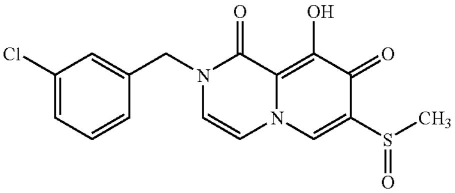 |
TABLE 22-continued
| Example No. | Structural formula |
|---|---|
| 248 | 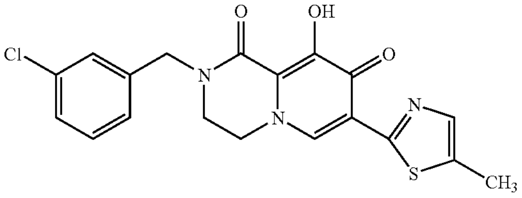 |
| 249 | 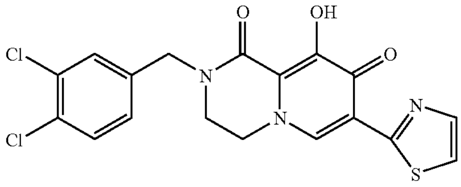 |
| 250 | HCl 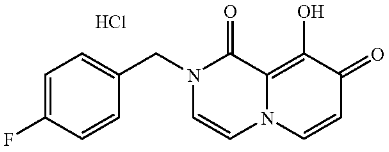 |
| 251 | 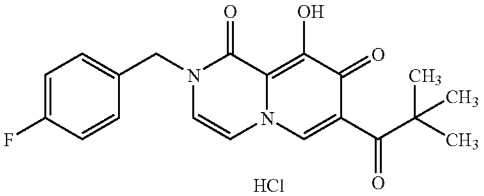 HCl |
| 252 | 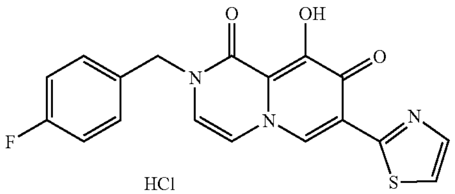 HCl |
| 253 | 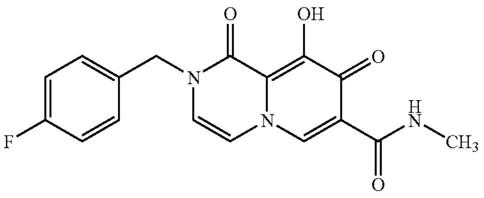 |
| 254 | 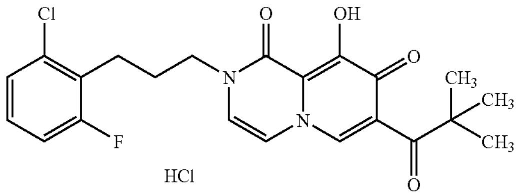 HCl |

TABLE 22-continued
| Example No. | Structural formula |
|---|---|
| 255 | 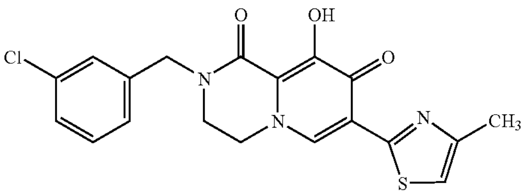 |
| 256 | 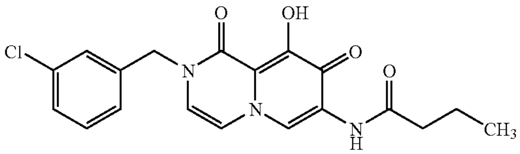 |
TABLE 23
| Example No. | Structural formula |
|---|---|
| 257 | 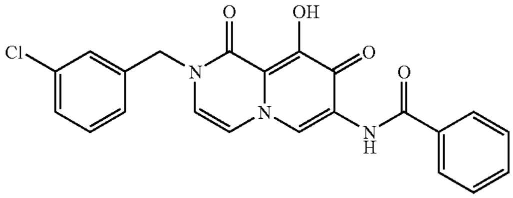 |
| 258 | 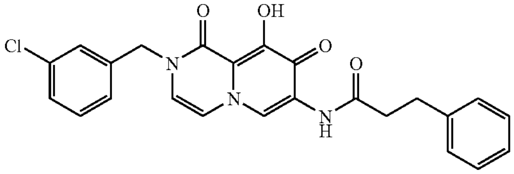 |
| 259 | 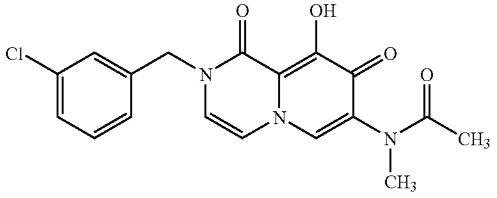 |
| 260 | 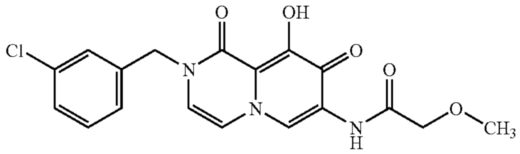 |
TABLE 23-continued
| Example No. | Structural formula |
|---|---|
| 261 | 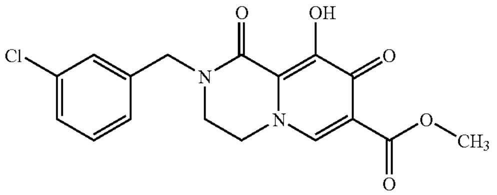 |
| 262 | 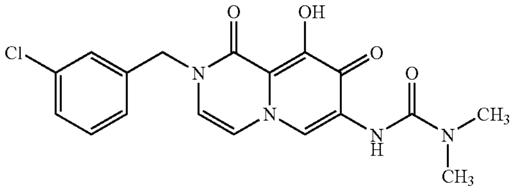 |
| 263 | 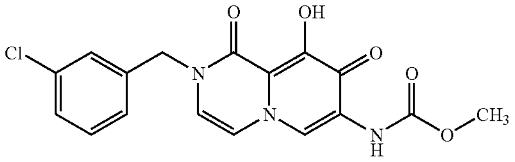 |
| 264 | 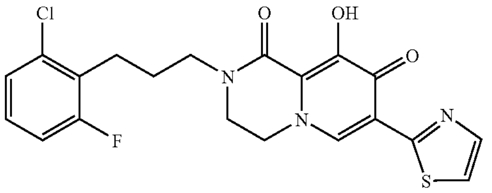 |
| 265 | 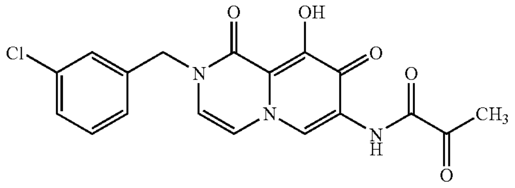 |
| 266 | 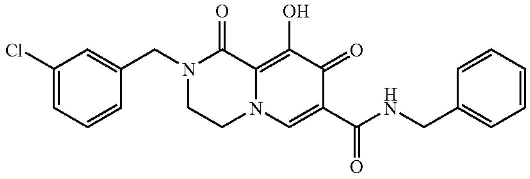 |
| 267 | 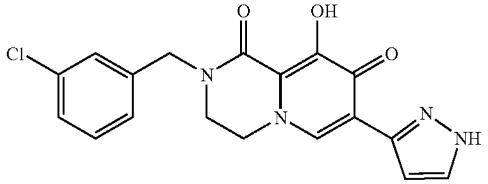 |

TABLE 23-continued
| Example No. | Structural formula |
|---|---|
| 268 | 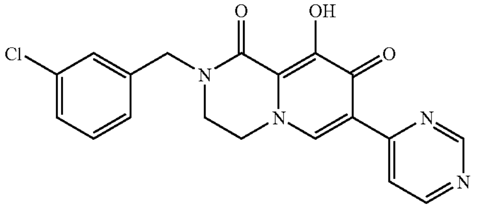 |
| 269 | 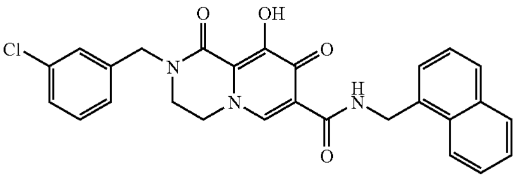 |
| 270 | 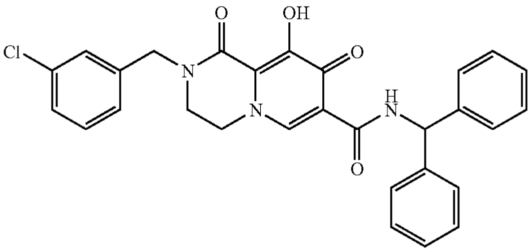 |
TABLE 24
| Example No. | Structural formula |
|---|---|
| 271 | 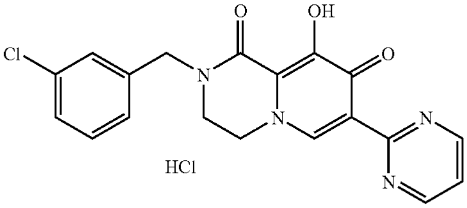 HCl |
| 272 | 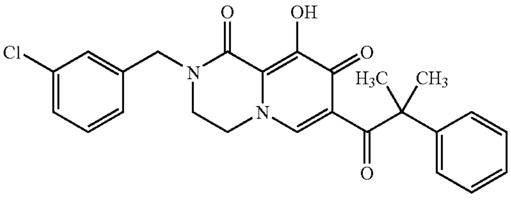 |
| 273 | 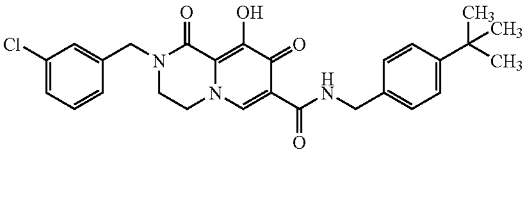 |
TABLE 24-continued
| Example No. | Structural formula |
|---|---|
| 274 | 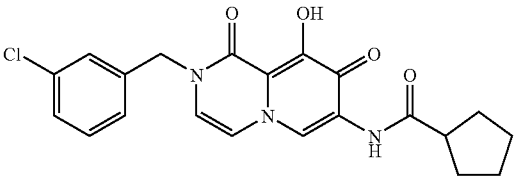 |
| 275 | 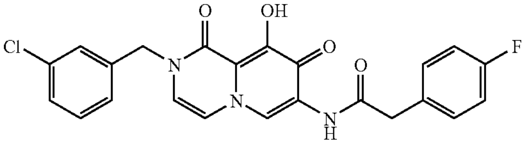 |
| 276 | 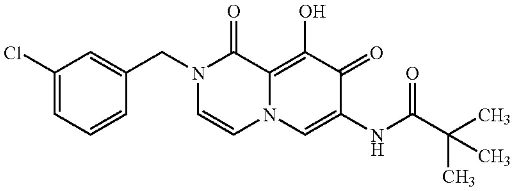 |
| 277 | 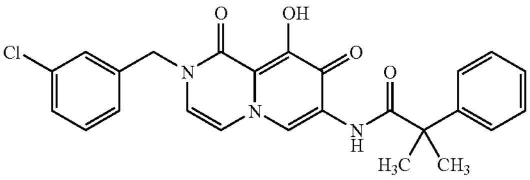 |
| 278 | 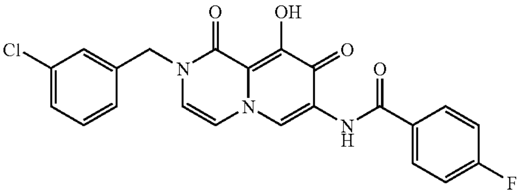 |
| 279 | 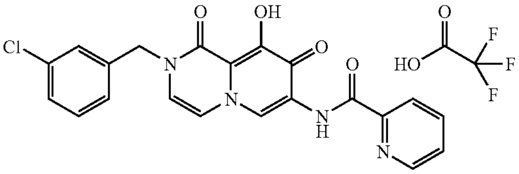 |
| 280 | 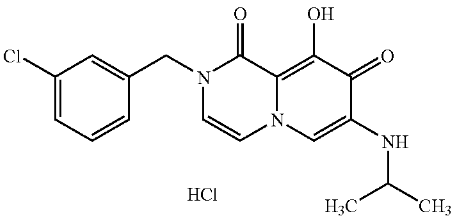 HCl |

TABLE 24-continued
| Example No. | Structural formula |
|---|---|
| 281 | 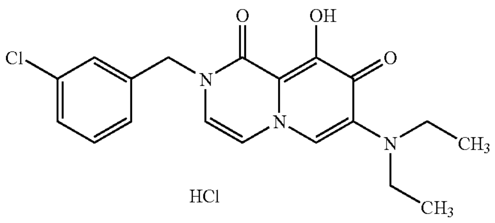 HCl |
| 282 | 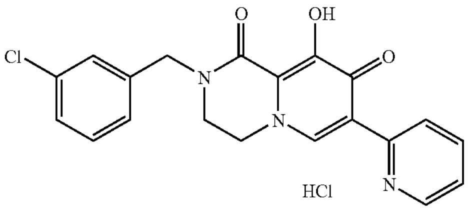 HCl |
| 283 | 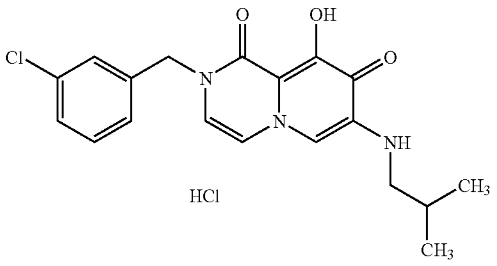 HCl |
| 284 | 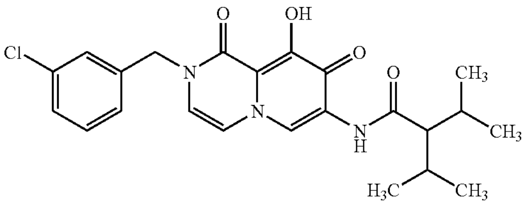 |
TABLE 25
| Example No. | Structural formula |
|---|---|
| 285 | 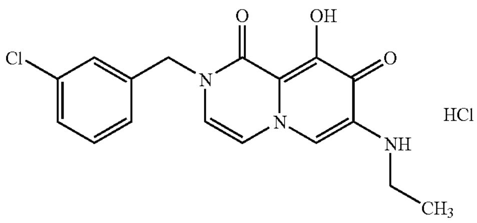 HCl |
TABLE 25-continued
| Example No. | Structural formula |
|---|---|
| 286 | 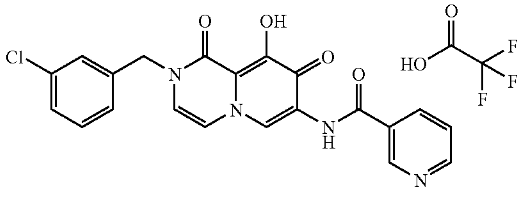 |
| 287 | 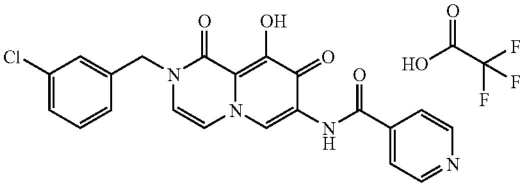 |
| 288 | 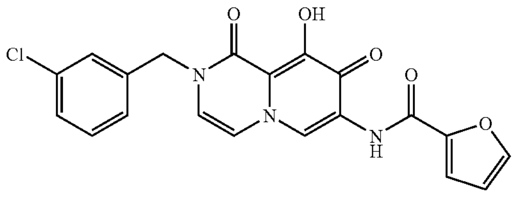 |
| 289 | 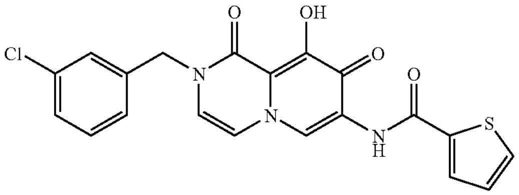 |
| 290 | 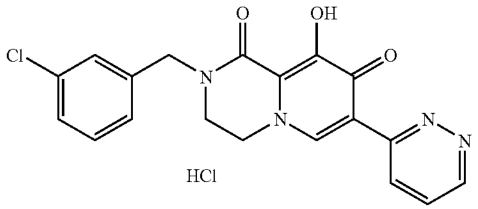 HCl |
| 291 | 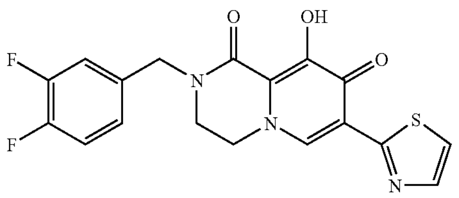 |
| 292 | 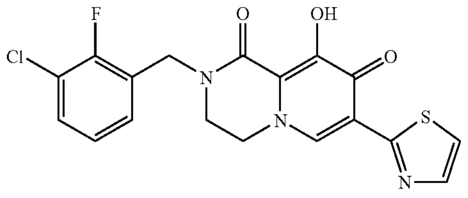 |

TABLE 25-continued
| Example No. | Structural formula |
|---|---|
| 293 | 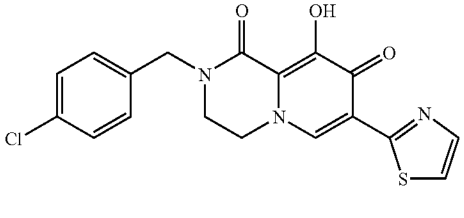 |
| 294 | 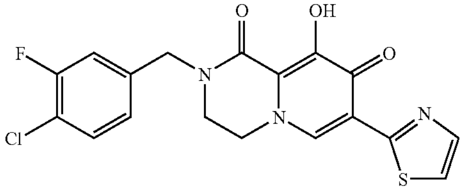 |
| 295 | 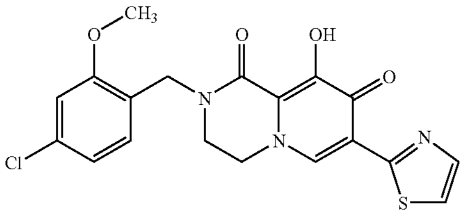 |
| 296 | 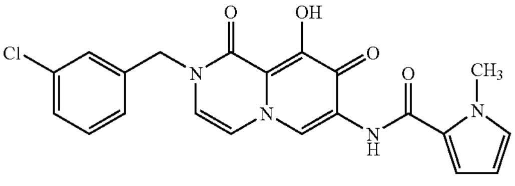 |
| 297 | 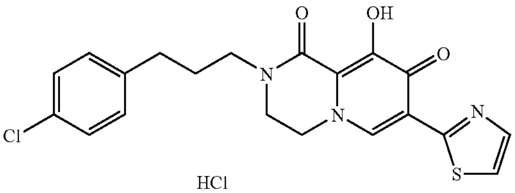 HCl |
| 298 | 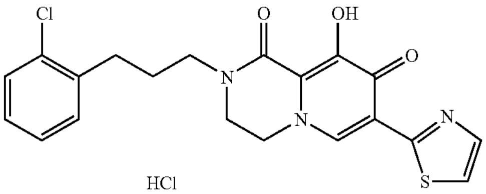 HCl |
TABLE 26
| Example No. | Structural formula |
|---|---|
| 299 | 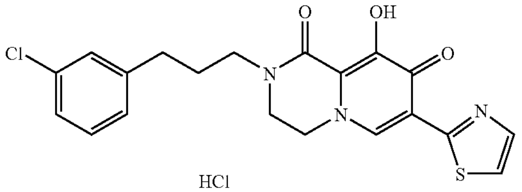 HCl |
| 300 | 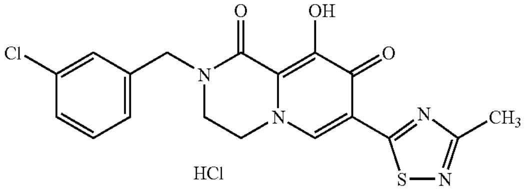 HCl |
| 301 | 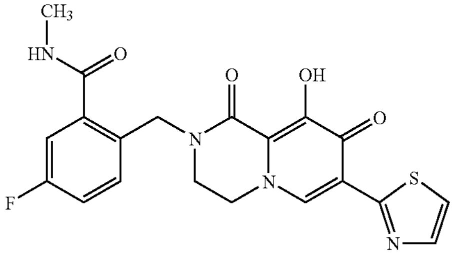 |
| 302 | 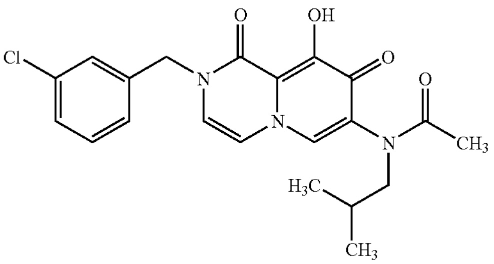 |
| 303 | 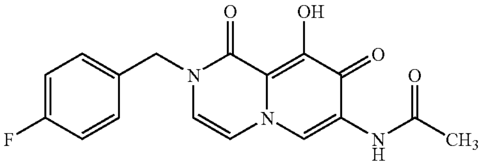 |
| 304 | 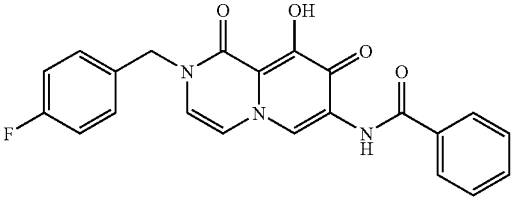 |
| 305 | 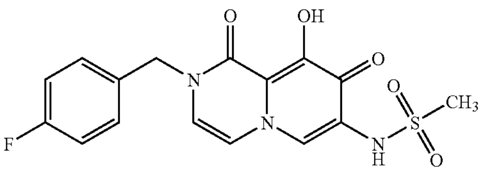 |

TABLE 26-continued
| Ex- am- ple No. | Structural formula |
|---|---|
| 306 | 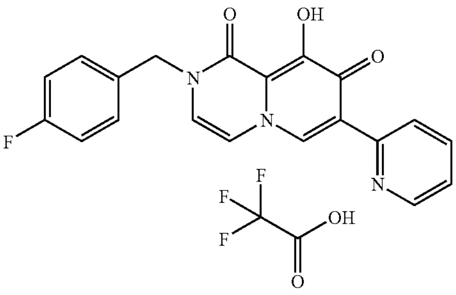 |
| 307 | 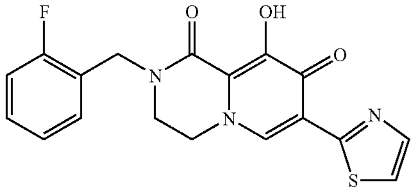 |
| 308 | 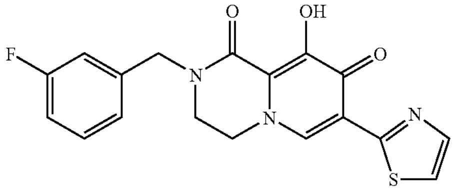 |
| 309 | 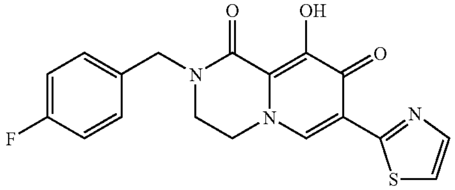 |
| 310 | 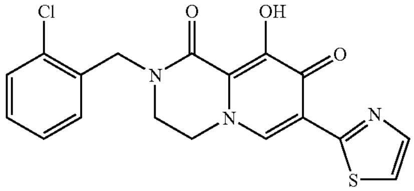 |
TABLE 27
| Ex- am- No. | ple Structural formula |
|---|---|
| 311 | 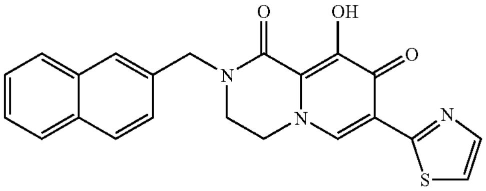 |
TABLE 27-continued
| Ex- am- No. | ple Structural formula |
|---|---|
| 312 | 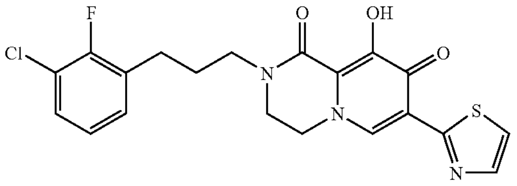 |
| 313 | 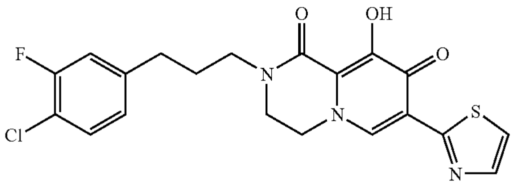 |
| 314 | 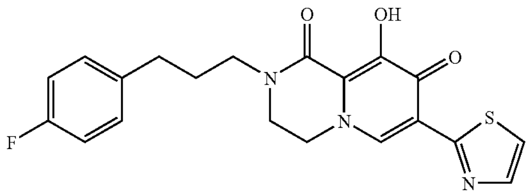 |
| 315 | 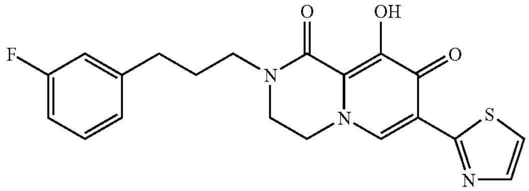 |
| 316 | 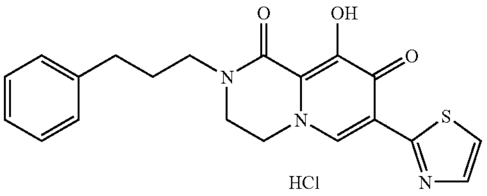 |
| 317 | 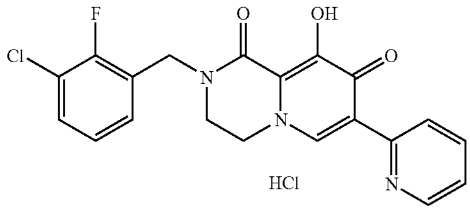 |
| 318 | 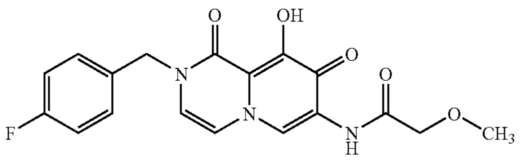 |

TABLE 27-continued
| Example No. | Structural formula |
| --- | --- |
| 319 | 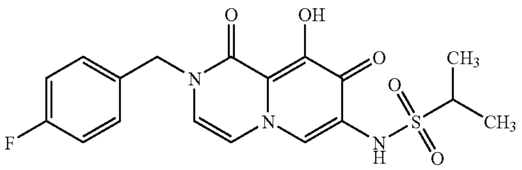 |
| 320 | 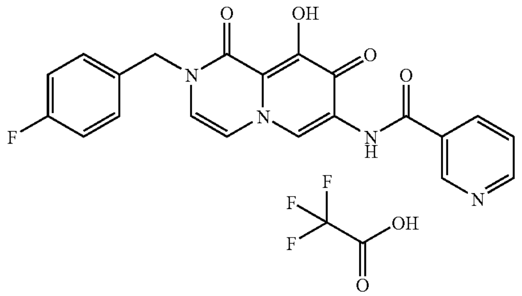 |
| 321 | 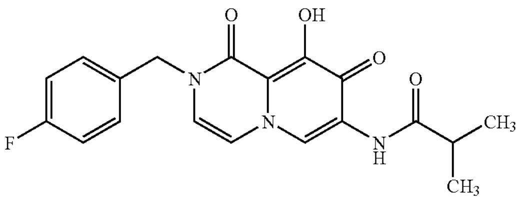 |
| 322 | 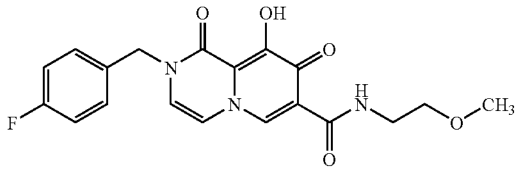 |
| 323 | 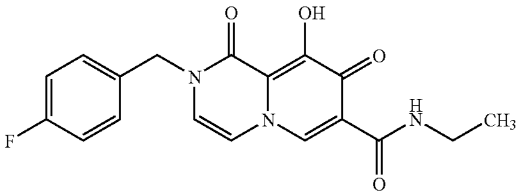 |
| 324 | 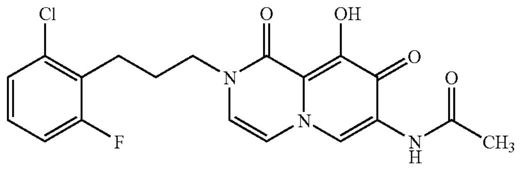 |
TABLE 28
| Example No. | Structural formula |
| --- | --- |
| 325 | 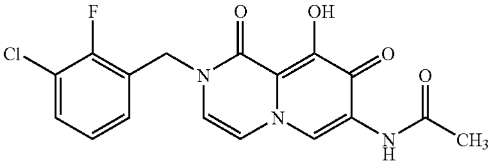 HCl |
| 326 | 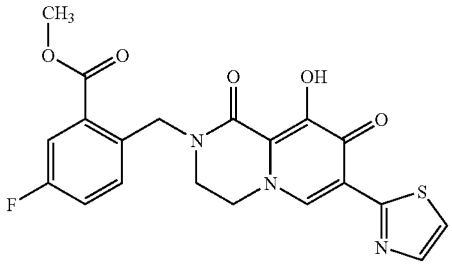 |
| 327 | 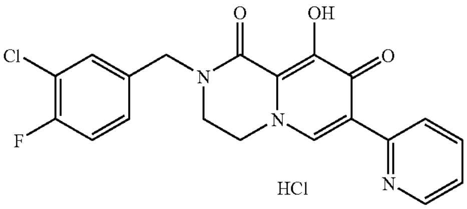 HCl |
| 328 | 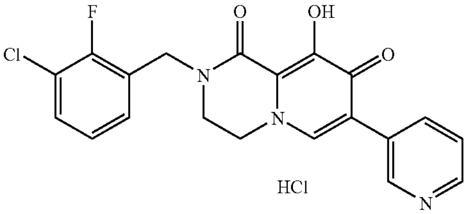 HCl |
| 329 | 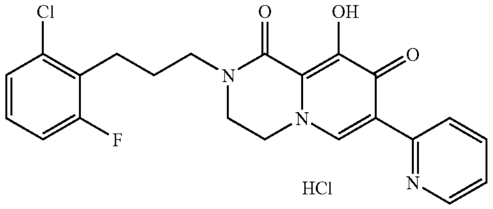 HCl |
| 330 | 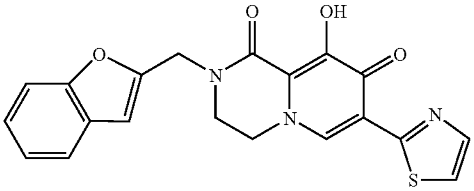 |

TABLE 28-continued
| Example No. | Structural formula |
|---|---|
| 331 | 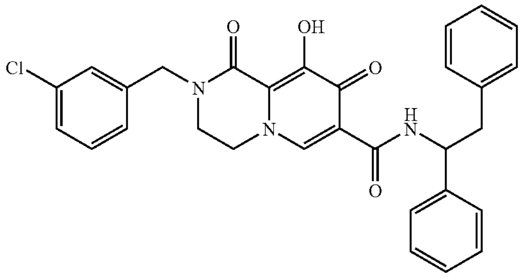 |
| 332 | 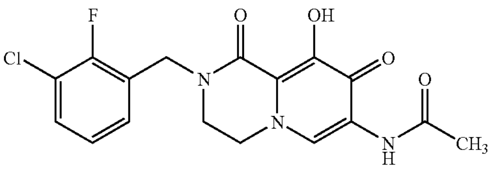 |
| 333 | 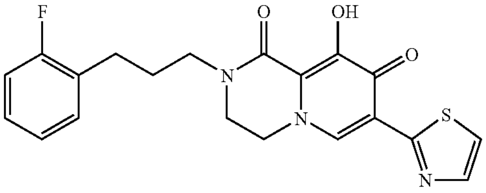 |
| 334 | 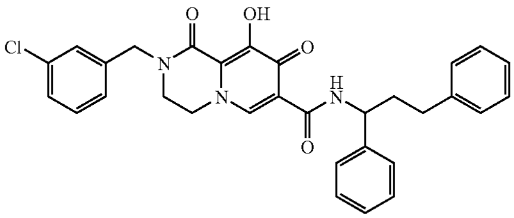 |
| 335 | 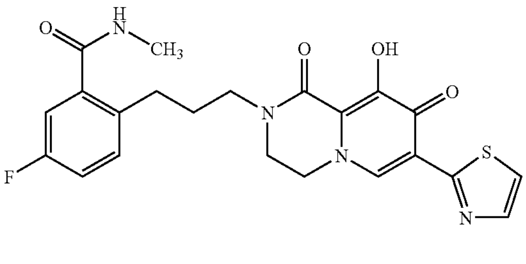 |
| 336 | 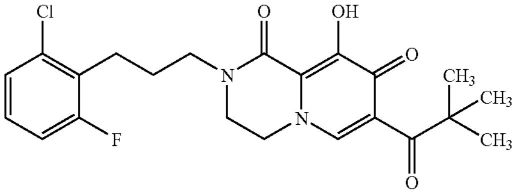 |
| 337 | 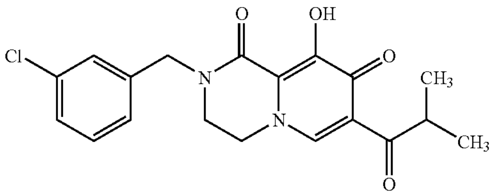 |
| 338 | 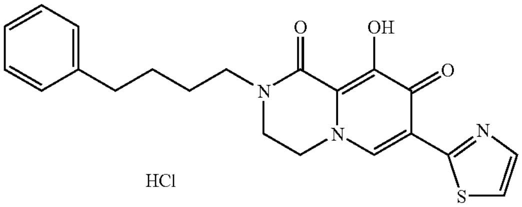 HCl |
TABLE 29
| Example No. | Structural formula |
|---|---|
| 339 | 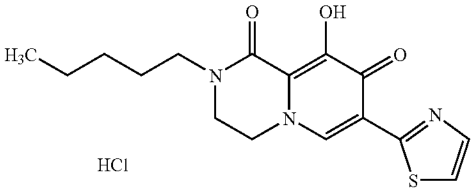 HCl |
| 340 | 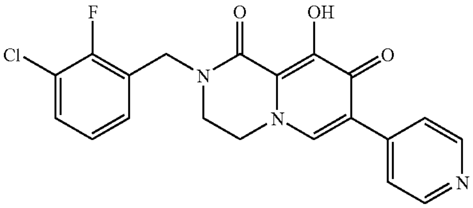 HCl |
| 341 | 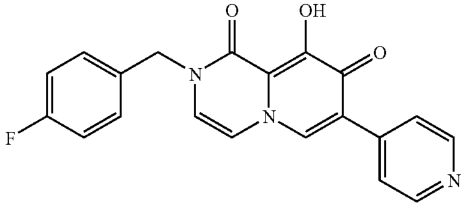 HCl |

TABLE 29-continued
| Example No. | Structural formula |
|---|---|
| 342 | 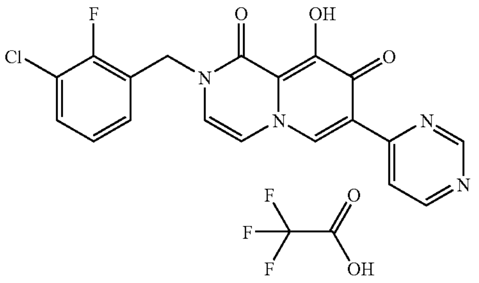 |
| 343 | 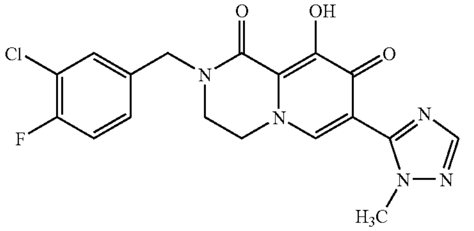 |
| 344 | 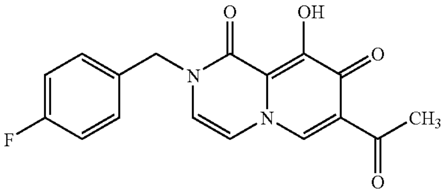 |
| 345 | 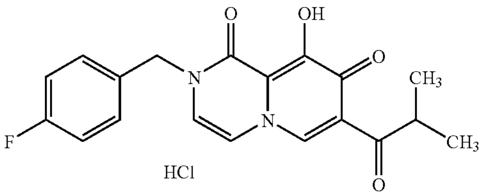 HCl |
| 346 | 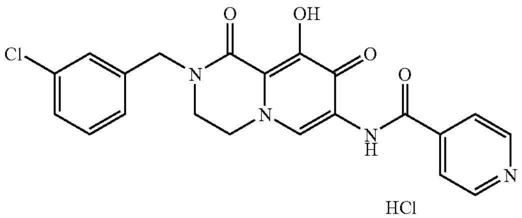 HCl |
| 347 | 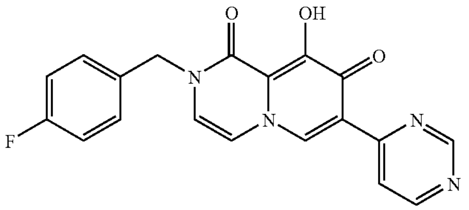 |
| 348 | 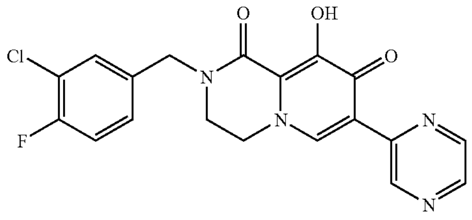 |
| 349 | 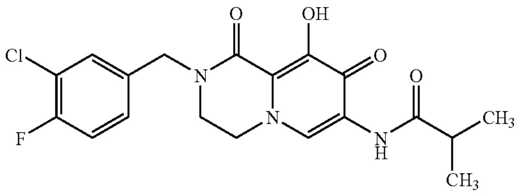 |
| 350 | 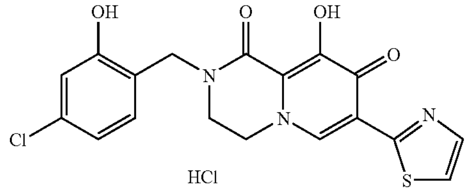 HCl |
| 351 | 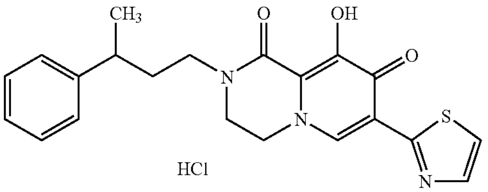 HCl |
| 352 | 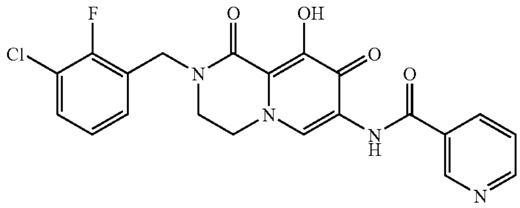 HCl |
TABLE 30
| Example No. | Structural formula |
|---|---|
| 353 | 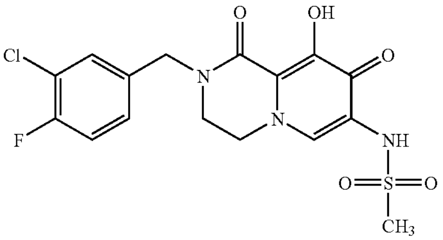 |

TABLE 30-continued
| Example No. | Structural formula |
|---|---|
| 354 | 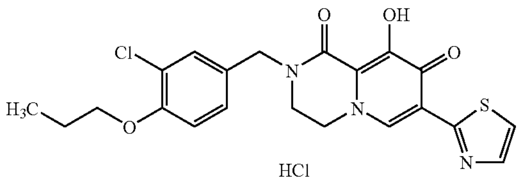 HCl |
| 355 | 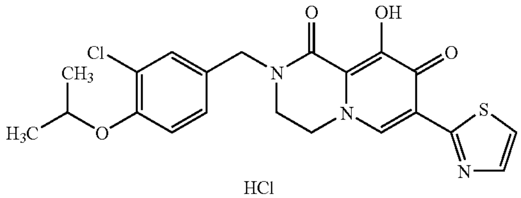 HCl |
| 356 | 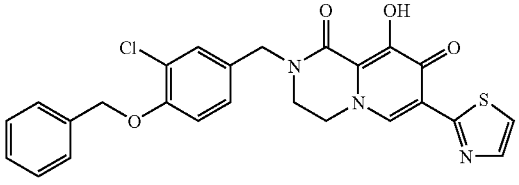 HCl |
| 357 | 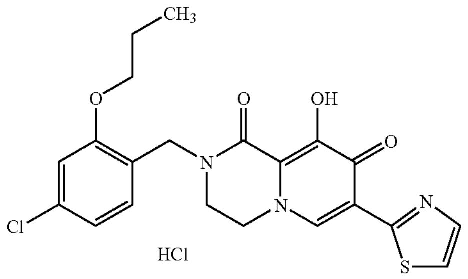 HCl |
| 358 | 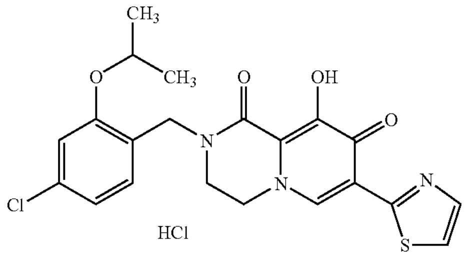 HCl |
| 359 | 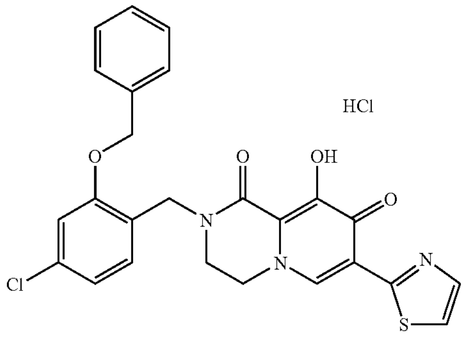 HCl |
| 360 | 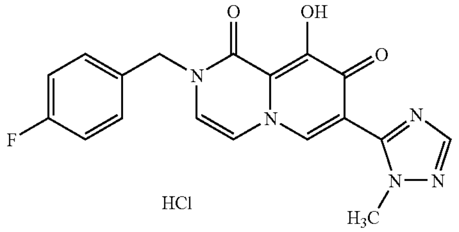 HCl |
| 361 | 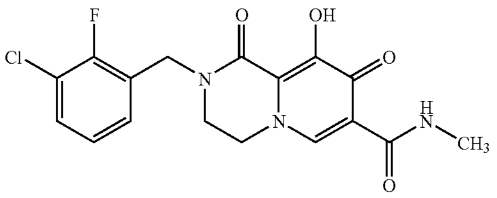 |
| 362 | 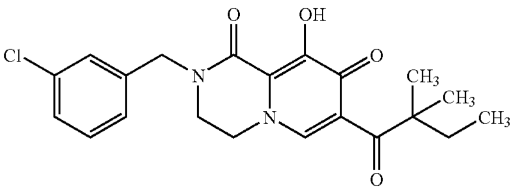 |
| 363 | 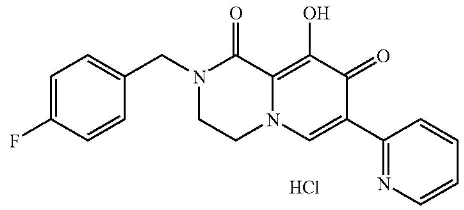 HCl |
| 364 | 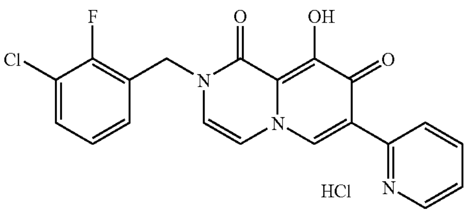 HCl |

TABLE 31
| Example No. | Structural formula |
|---|---|
| 365 | 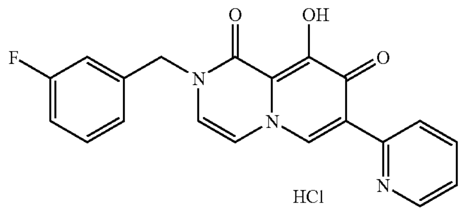 |
| 366 | 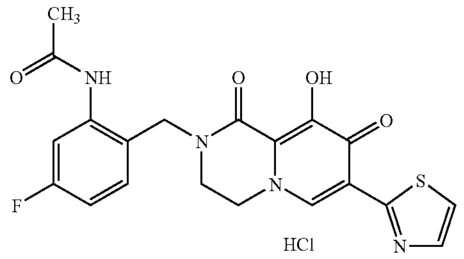 |
| 367 | 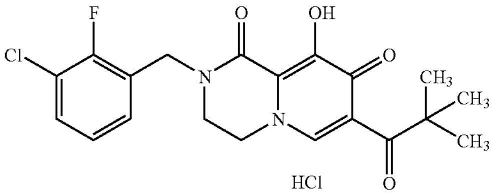 |
| 368 | 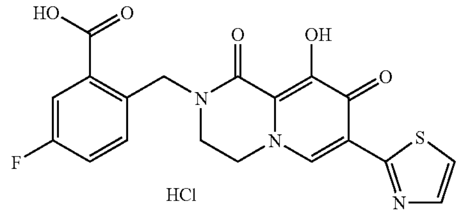 |
| 369 | 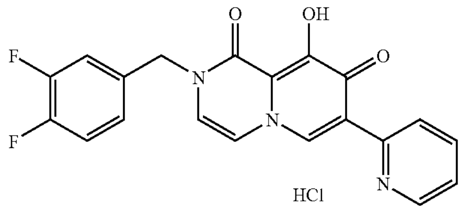 |
| 370 | 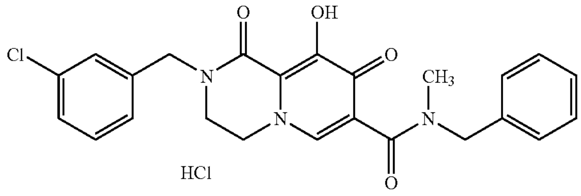 |
| 371 | 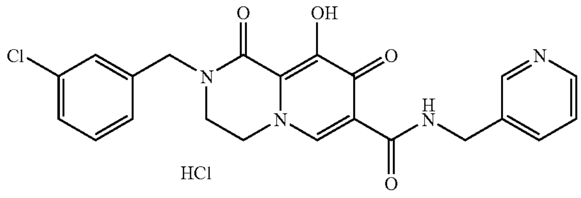 |

TABLE 31-continued
| Example No. | Structural formula |
|---|---|
| 372 | 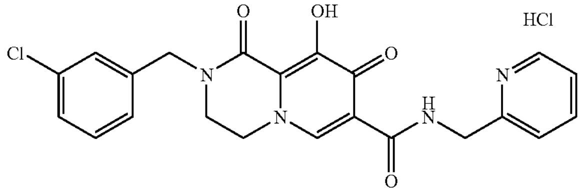 |
| 373 | 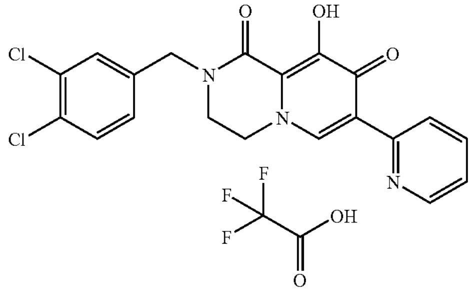 |
| 374 | 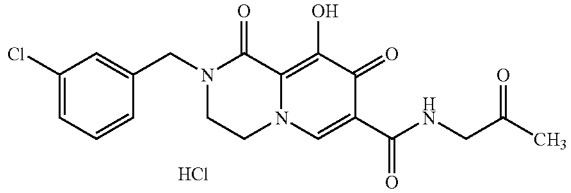 |
| 375 | 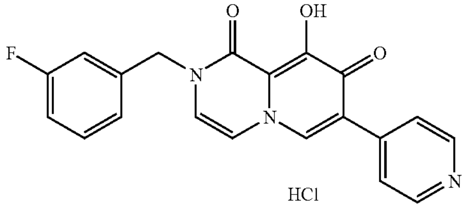 |
| 376 | 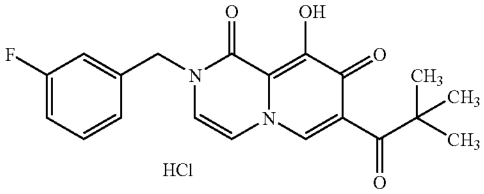 |
| 377 | 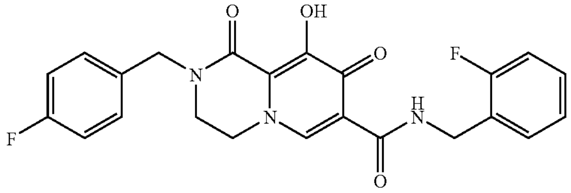 |
| 378 | 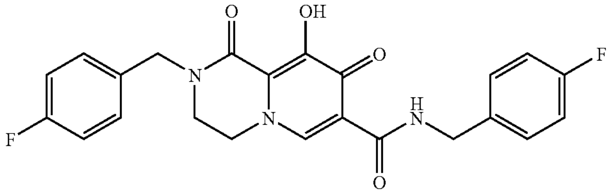 |

TABLE 32
| Example No. | Structural formula |
|---|---|
| 379 | 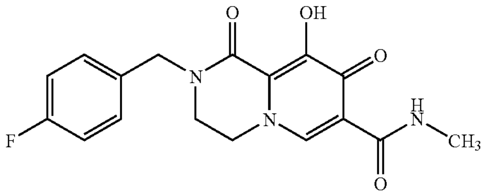 |
| 380 | 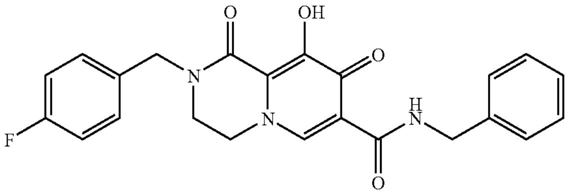 |
| 381 | 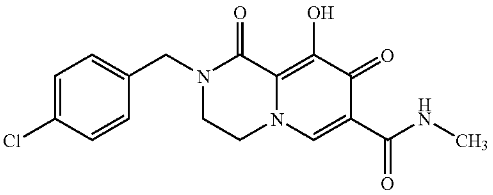 |
| 382 | 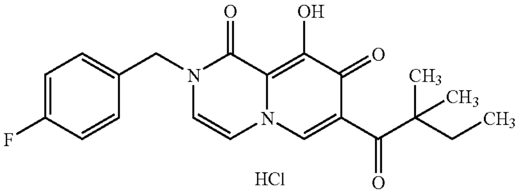 HCl |
| 383 | 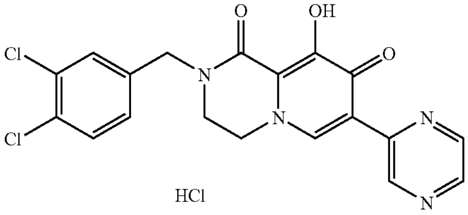 HCl |
| 384 | 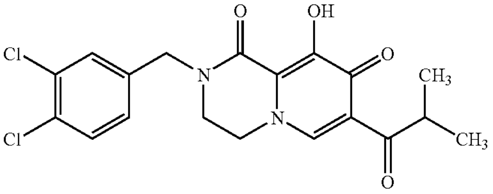 |
| 385 | 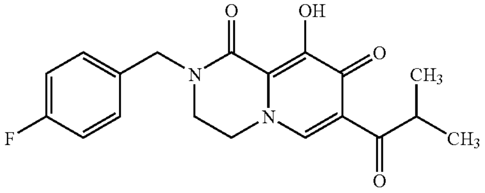 |

TABLE 32-continued
| Example No. | Structural formula |
| --- | --- |
| 386 | 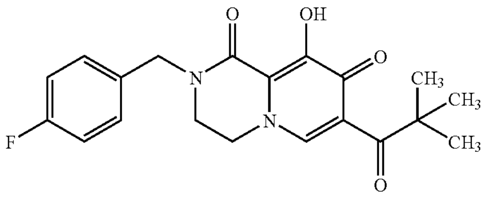 |
| 387 | 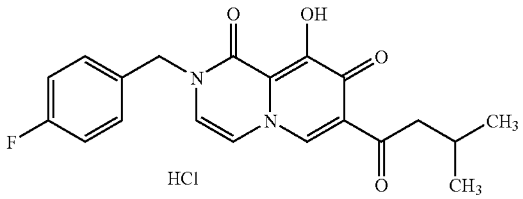 HCl |
| 388 | 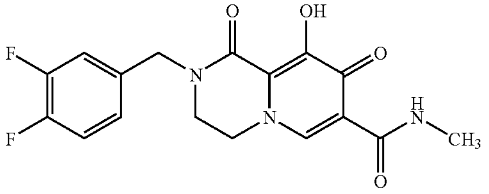 |
| 389 | 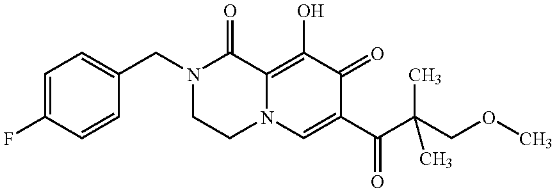 |
| 390 | 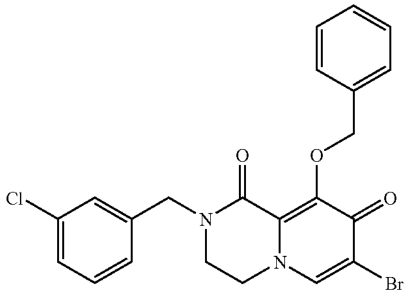 |
TABLE 33
| Example No. | Structural formula |
| --- | --- |
| 391 | 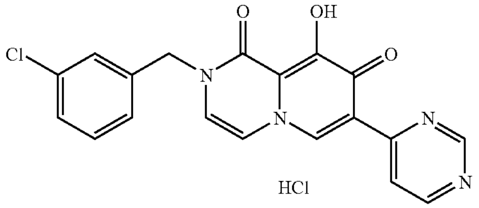 HCl |

TABLE 33-continued
| Example No. | Structural formula |
|---|---|
| 392 | 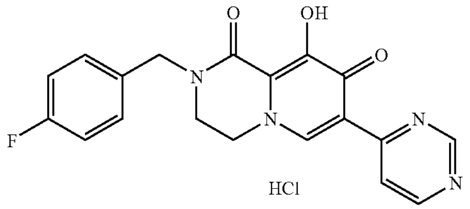 |
| 393 | 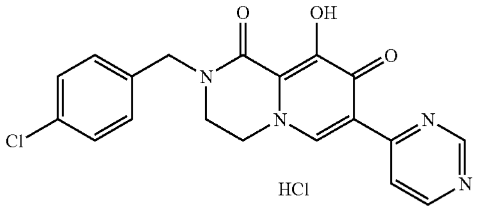 |
| 394 | 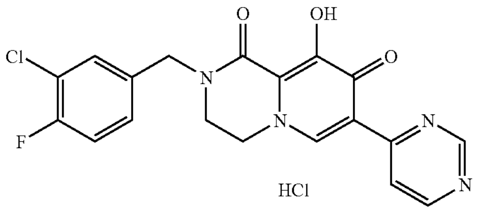 |
| 395 | 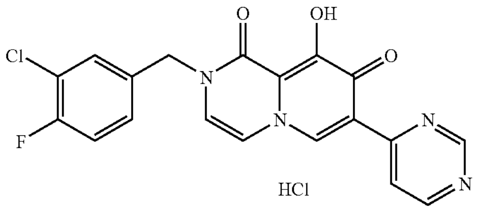 |
| 396 | 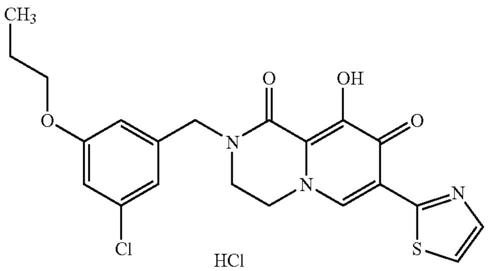 |
| 397 | 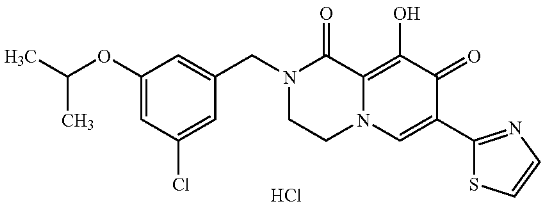 |

TABLE 33-continued
| Example No. | Structural formula |
|---|---|
| 398 | 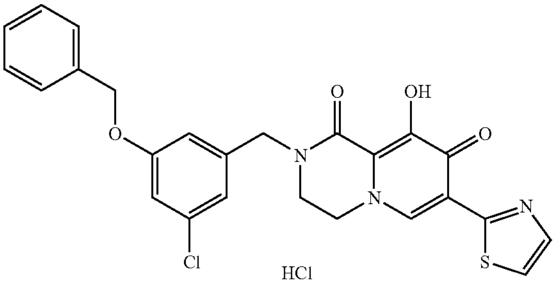 HCl |
| 399 | 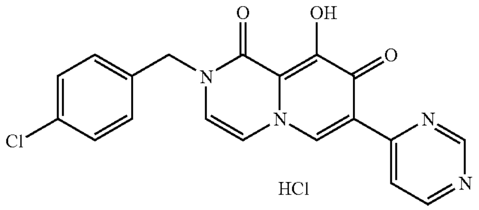 HCl |
| 400 | 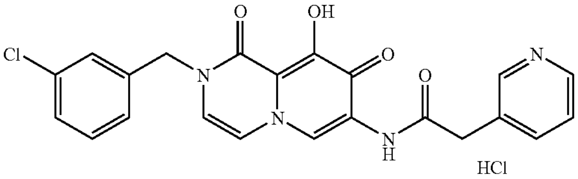 HCl |
| 401 | 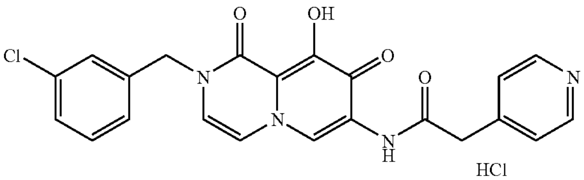 HCl |
| 402 | 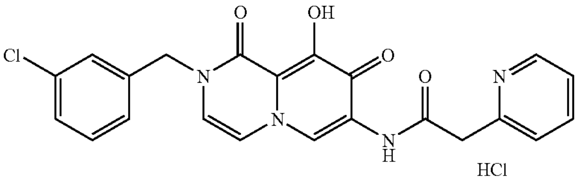 HCl |
TABLE 34
| Example No. | Structural formula |
|---|---|
| 403 | 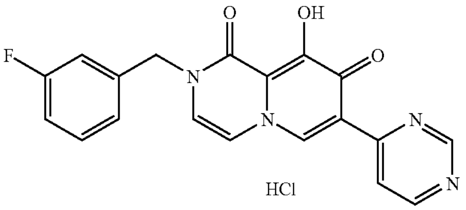 HCl |

TABLE 34-continued
| Example No. | Structural formula |
|---|---|
| 404 | 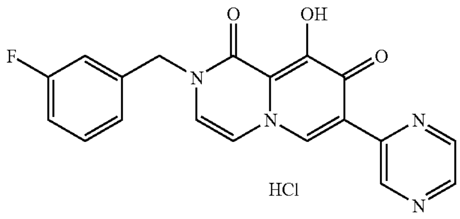 |
| 405 | 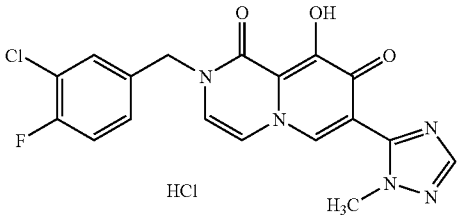 |
| 406 | 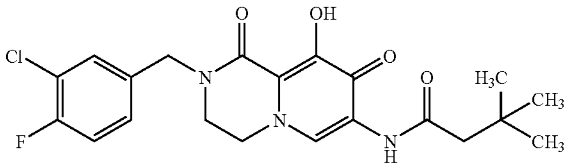 |
| 407 | 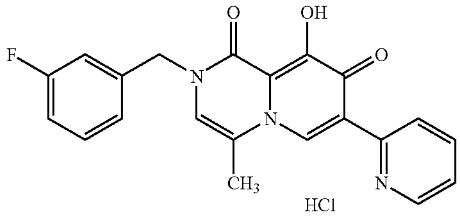 |
| 408 | 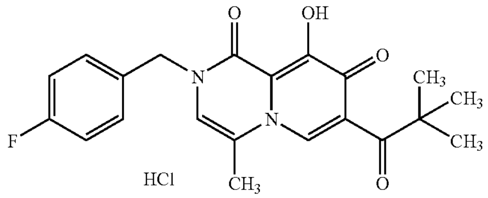 |
| 409 | 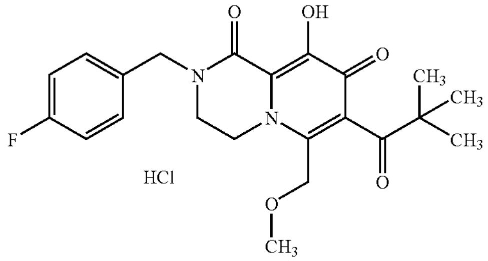 |
| 410 | 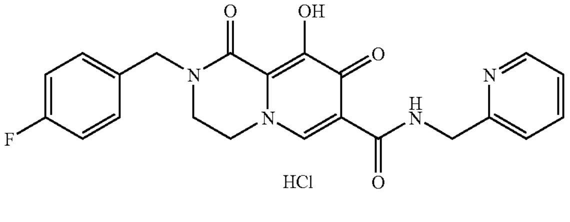 |

TABLE 34-continued
| Example No. | Structural formula |
|---|---|
| 411 | 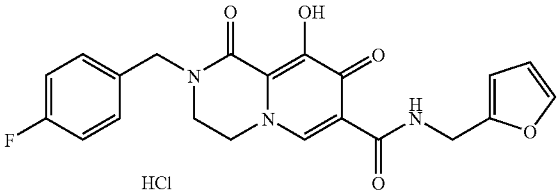 |
| 412 | 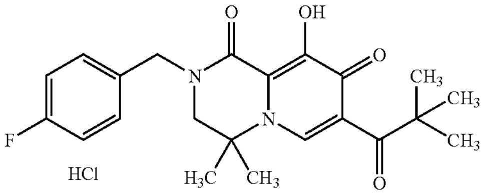 |
| 413 | 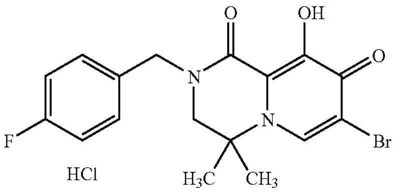 |
| 414 | 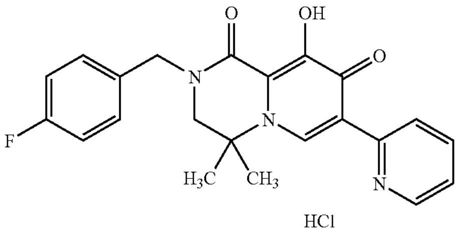 |
TABLE 35
| Example No. | Structural formula |
|---|---|
| 415 | 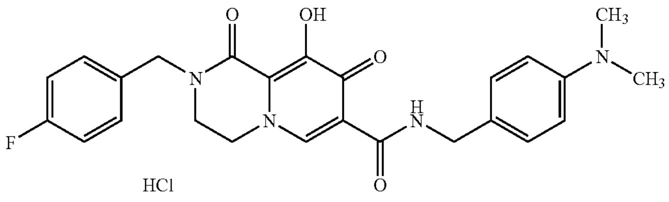 |
| 416 | 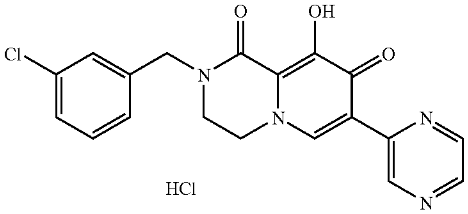 |

TABLE 35-continued
| Example No. | Structural formula |
| --- | --- |
| 417 | 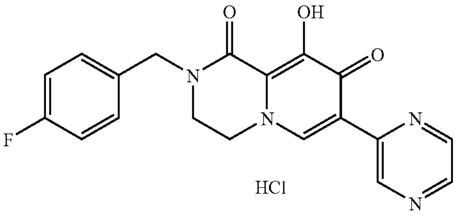 HCl |
| 418 | 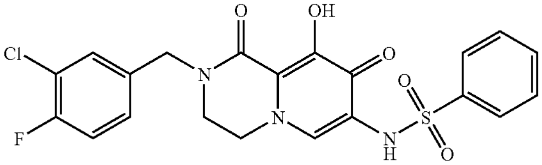 |
| 419 | 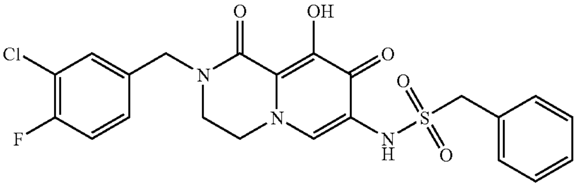 |
| 420 | 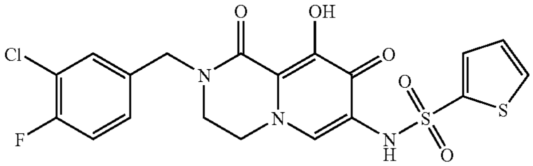 |
| 421 | 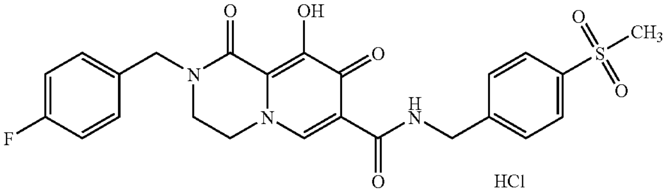 HCl |
| 422 | 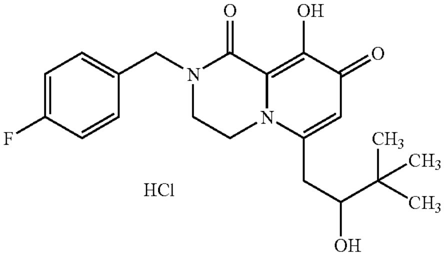 HCl |
| 423 | 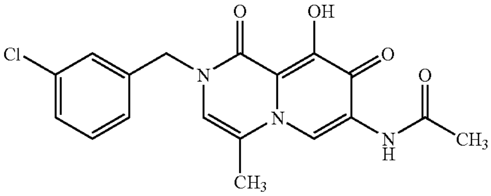 |

TABLE 35-continued
| Example No. | Structural formula |
|---|---|
| 424 | 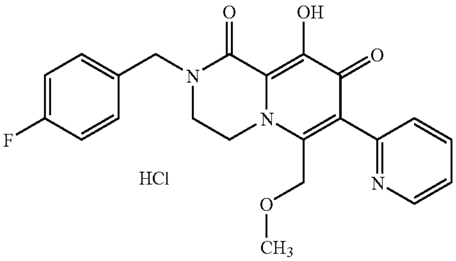 HCl |
| 425 | 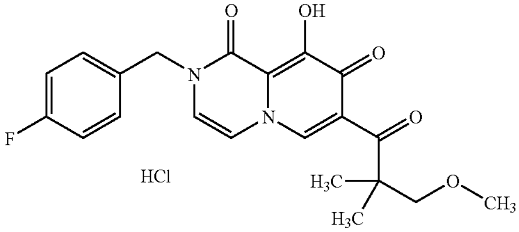 HCl |
| 426 | 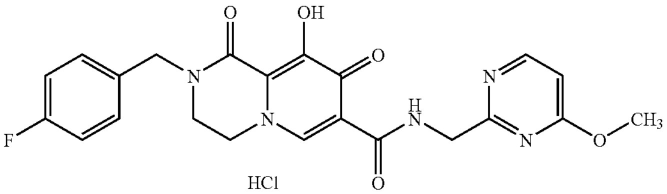 HCl |
TABLE 36
| Example No. | Structural formula |
|---|---|
| 427 | 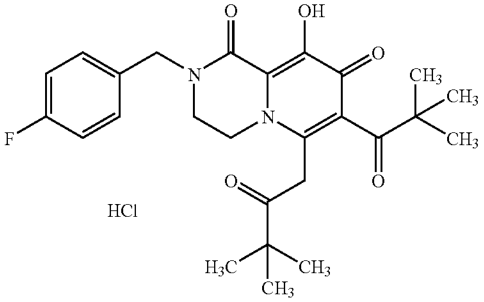 HCl |
| 428 | 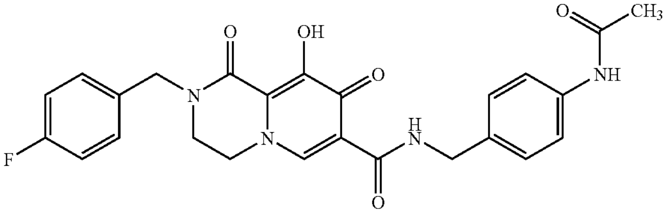 |

TABLE 36-continued
| Example No. | Structural formula |
|---|---|
| 429 | 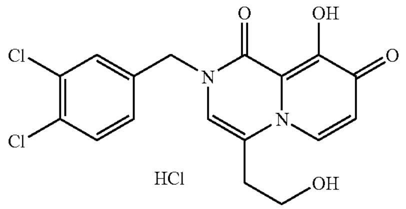 |
| 430 | 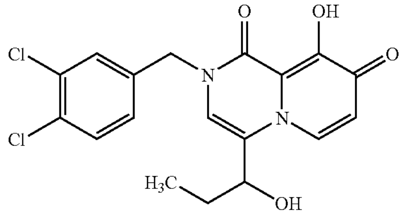 |
| 431 | 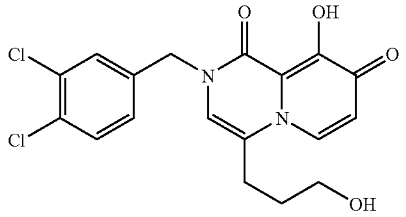 |
| 432 | 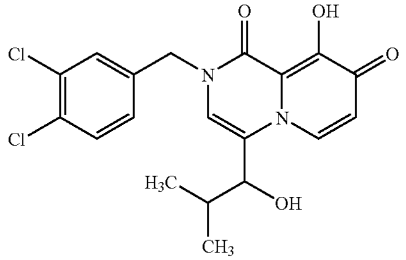 |
| 433 | 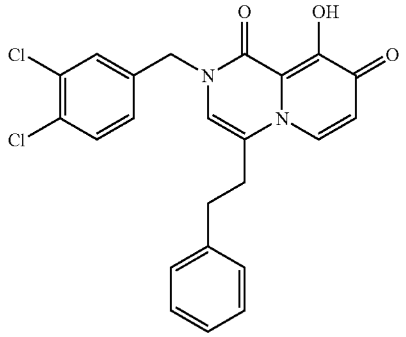 |
| 434 | 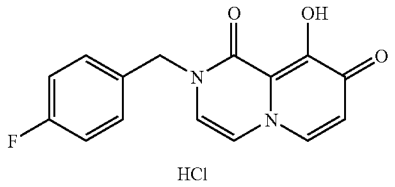 |

TABLE 36-continued

| Example No. | Structural formula |
|---|---|
| 435 | 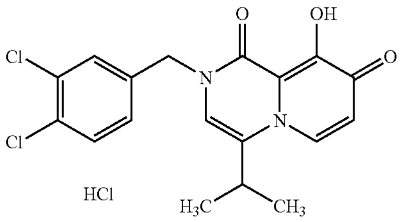 |
| 436 | 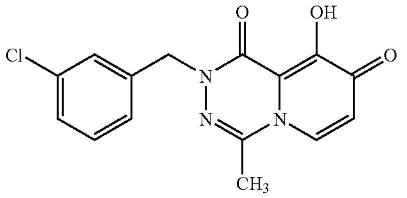 |
| 437 | 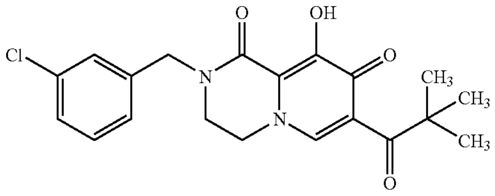 |
| 438 | 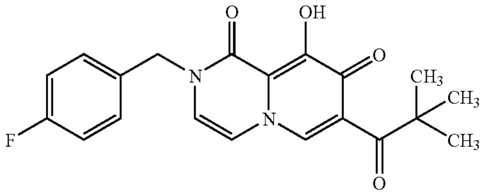 |

TABLE 37

| Example | $^{1}$H-NMR |
|---|---|
| 13 | $^{1}$H-NMR(DMSO-$d_6$) δ: 7.92(1H, d, J=7.0Hz), 7.69(2H, d, J=1.9Hz), 7.65(2H, d, J=8.3Hz), 7.39(1H, dd, J=8.3, 2.3Hz), 6.57(1H, d, J=7.4Hz), 4.81(1H, d, J=14.8Hz), 4.67(1H, d, J=14.8Hz), 3.98(1H, dd, J=13.4, 3.7Hz), 3.53(1H, dd, J=13.4, 2.8Hz), 1.29(3H, d, J=6.5Hz). |
| 14 | $^{1}$H-NMR(DMSO-$d_6$) δ: 7.69(1H, s), 7.66(1H, d, J=8.3Hz), 7.42(1H, dd, J=1.9, 8.3Hz), 7.27(1H, d, J=7.4Hz), 7.24–7.14(3H, m), 6.94–6.84(2H, m), 6.02(1H, d, J=7.4Hz), 4.87(1H, d, J=14.8Hz), 4.64–4.56(1H, m), 4.52(1H, d, J=14.8Hz), 3.97(1H, dd, J=13.4, 4.2Hz), 3.36(1H, d, J=13.4Hz), 2.90–2.80(2H, m). |
| 15 | $^{1}$H-NMR(DMSO-$d_6$) δ: 7.65(1H, d, J=7.4Hz), 7.35(1H, d, J=8.3Hz), 7.31–7.22(3H, m), 7.15(1H, d, J=2.3Hz), 6.92(1H, dd, J=8.3, 2.3Hz), 6.89–6.82(2H, m), 6.24(1H, d, J=7.4Hz), 5.68(1H, brs), 4.81(1H, d, J=15.3Hz), 4.35–4.22(2H, m), 3.91(1H, dd, J=13.7, 2.6Hz). |
| 16 | $^{1}$H-NMR(DMSO-$d_6$) δ: 7.90(1H, d, J=7.4Hz), 7.70(1H, d, J=1.9Hz), 7.66(1H, d, J=8.3Hz), 7.41(1H, dd, J=8.3, 2.3Hz), 6.57(1H, d, J=7.4Hz), 4.98(1H, d, J=14.8Hz), 4.51–4.40(1H, m), 4.45(1H, d, J=14.8Hz), 4.07–3.97(1H, m), 3.54(1H, d, J=13.9Hz), 1.55–1.42(2H, m), 1.19–0.86(4H, m), 0.74(3H, t, J=7.2Hz). |
| 17 | $^{1}$H-NMR(DMSO-$d_6$) δ: 7.72(1H, d, J=1.9Hz), 7.64(2H, dd, J=7.7, 3.9Hz), 7.41(1H, dd, J=8.3, 1.9Hz), 6.16(1H, d, J=7.5Hz), 4.82(1H, d, J=14.7Hz), 4.59(1H, d, J=14.7Hz), 3.96(2H, d, J=10.9Hz), 3.66(1H, d, J=12.4Hz), 1.82–1.79(1H, m), 0.71(3H, d, J=6.4Hz), 0.65(3H, d, J=6.8Hz). |
| 18 | $^{1}$H-NMR(DMSO-$d_6$) δ: 7.72(1H, d, J=7.1Hz), 7.66(1H, d, J=2.0Hz), 7.60(1H, d, J=8.2Hz), 7.37(1H, dd, J=8.2, 2.0Hz), 6.44(1H, d, J=7.1Hz), 4.80(2H, s), 4.24(2H, s), 1.25(6H, s). |
| 19 | $^{1}$H-NMR(DMSO-$d_6$) δ: 7.67(1H, d, J=2.2Hz), 7.66–7.63(1H, m), 7.64(1H, d, J=8.4Hz), 7.38(1H, dd, J=8.4, 2.2Hz), 6.18(1H, d, J=7.7Hz), 4.72(2H, s), 3.67(2H, s), 2.03–1.58(8H, m). |
| 20 | $^{1}$H-NMR(DMSO-$d_6$) δ: 12.44(1H, s), 7.87(1H, d, J=7.7Hz), 7.72(1H, d, J=1.5Hz), 7.64(1H, d, J=8.3Hz), 7.42(1H, dd, J=8.3, 1.7Hz), 6.15(1H, d, J=7.7Hz), 4.73(2H, s), 3.80(2H, s), 1.92–1.69(4H, m), 1.64–1.44(3H, m), 1.41–1.08(3H, m). |

TABLE 37-continued

| Example | $^1$H-NMR |
|---|---|
| 21 | $^1$H-NMR($CDCl_3$) δ: 11.70(1H, s), 7.66(1H, d, J=8.3Hz), 7.58(1H, d, J=7.4Hz), 7.55(1H, d, J=1.9Hz), 7.27(1H, dd, J=8.3, 1.9Hz), 6.20(1H, d, J=7.4Hz), 5.43–5.37(1H, m), 4.93(1H, d, J=14.8Hz), 4.34(1H, d, J=14.8Hz), 4.19(1H, dd, J=13.4, 4.2Hz), 3.87(1H, dd, J=13.4, 1.4Hz), 3.49(3H, s). |
| 22 | $^1$H-NMR(DMSO-$d_6$) δ: 13.85(1H, brs), 11.75(1H, brs), 7.63–7.57(3H, m), 7.29(1H, dd, J=8.3, 1.9Hz), 6.18(1H, d, J=7.4Hz), 5.24(1H, brs), 4.79(1H, d, J=14.8Hz), 4.51(1H, d, J=14.8Hz), 4.14(1H, dd, J=13.2, 4.4Hz), 3.93(1H, dd, J=12.5, 1.9Hz). |
| 23 | $^1$H-NMR(DMSO-$d_6$) δ: 7.68(1H, d, J=2.2Hz), 7.63(1H, d, J=8.4Hz), 7.38(1H, dd, J=8.3, 2.0Hz), 6.58(1H, s), 4.73(2H, s), 4.47(2H, s), 4.25–4.23(2H, m), 3.73–3.70(2H, m), 3.31(3H, s). |
| 24 | $^1$H-NMR(DMSO-$d_6$) δ: 7.69(1H, d, J=1.9Hz), 7.63(1H, d, J=8.3Hz), 7.39(1H, dd, J=8.3, 1.9Hz), 6.12(1H, s), 4.83(1H, d, J=15.1Hz), 4.62(1H, d, J=16.2Hz), 4.03–3.98(2H, m), 3.68(2H, t, J=5.7Hz), 2.97(3H, s), 2.90(3H, s). |
| 25 | $^1$H-NMR(DMSO-$d_6$) δ: 7.73(1H, d, J=7.1Hz), 7.70(1H, d, J=1.8Hz), 7.64(1H, d, J=8.1Hz), 7.41(1H, dd, J=8.1, 1.8Hz), 7.29–7.10(6H, m), 6.45(1H, d, J=7.1Hz), 5.14(1H, d, J=15.4Hz), 4.39–4.30(2H, m), 4.19–4.10(2H, m), 3.00(1H, dd, J=13.7, 4.4Hz), 2.87(1H, dd, J=13.7, 8.1Hz). |
| 26 | $^1$H-NMR(DMSO-$d_6$) δ: 7.88(1H, d, J=7.1Hz), 7.71(1H, d, J=2.1Hz), 7.63(1H, d, J=8.2Hz), 7.41(1H, dd, J=8.2, 2.1Hz), 6.52(1H, d, J=7.1Hz), 5.07(1H, d, J=15.2Hz), 4.42(1H, d, J=15.2Hz), 4.34(2H, s), 3.88–3.77(1H, m), 1.70–1.12(6H, m), 0.82(3H, t, J=6.7Hz). |
| 27 | $^1$H-NMR(DMSO-$d_6$) δ: 11.70(1H, brs), 7.64(1H, d, J=8.3Hz), 7.57–7.49(2H, m), 7.24(1H, d, J=6.5Hz), 6.15(1H, d, J=7.4Hz), 5.60(1H, s), 5.00(1H, d, J=15.3Hz), 4.22–4.13(1H, m), 4.22(1H, d, J=15.3Hz), 3.68(1H, d, J=13.9Hz), 2.91(3H, s), 2.61(3H, s). |
| 28 | $^1$H-NMR(DMSO-$d_6$) δ: 7.66(1H, d, J=1.9Hz), 7.63(1H, d, J=8.3Hz), 7.54(1H, d, J=7.4Hz), 7.36(1H, dd, J=8.3, 1.9Hz), 6.14(1H, d, J=7.4Hz), 5.22(1H, s), 4.71(1H, d, J=14.8Hz), 4.64(1H, d, J=14.8Hz), 4.32–4.22(1H, m), 3.96(1H, dd, J=13.2, 4.4Hz), 3.60(1H, dd, J=13.2, 1.4Hz), 3.53–3.42(2H, m). |
| 29 | $^1$H-NMR(DMSO-$d_6$) δ: 12.02(1H, brs), 7.67(1H, d, J=1.9Hz), 7.62(1H, d, J=8.3Hz), 7.62(1H, d, J=7.4Hz), 7.37(1H, dd, J=8.3, 1.9Hz), 6.15(1H, d, J=7.4Hz), 4.85(1H, d, J=15.3Hz), 4.55–4.46(1H, m), 4.50(1H, d, J=15.3Hz), 3.98(1H, dd, J=13.4, 4.6Hz), 3.57(1H, dd, J=13.4, 1.4Hz), 3.47–3.36(2H, m), 3.12(3H, s). |
| 30 | $^1$H-NMR(DMSO-$d_6$) δ: 7.69(1H, d, J=1.9Hz), 7.63(1H, d, J=8.7Hz), 7.38(1H, dd, J=8.3, 1.9Hz), 6.23(1H, s), 4.72(2H, s), 4.21–4.19(2H, m), 3.76(2H, s), 3.68–3.66(2H, m), 2.02(3H, s). |
| 31 | $^1$H-NMR(DMSO-$d_6$) δ: 7.67(1H, d, J=1.8Hz), 7.62(1H, d, J=8.4Hz), 7.36(1H, dd, J=8.3, 2.0Hz), 6.32(1H, s), 4.78(2H, s), 4.71(2H, s), 4.27–4.25(2H, m), 3.68–3.66(2H, m), 3.08(3H, s). |
| 32 | $^1$H-NMR(DMSO-$d_6$) δ: 7.72(1H, d, J=7.2Hz), 7.68(1H, d, J=1.9Hz), 7.63(1H, d, J=8.3Hz), 7.38(1H, dd, J=8.3, 1.9Hz), 6.33(1H, d, J=7.2Hz), 4.80(1H, d, J=14.8Hz), 4.68(1H, d, J=14.8Hz), 4.55–4.47(1H, m), 4.00(1H, dd, J=13.9, 4.2Hz), 3.68–3.55(1H, m), 3.20–3.10(1H, m), 3.00–2.91(1H, m), 2.93(3H, s), 2.10–1.99(2H, m). |
| 33 | $^1$H-NMR(DMSO-$d_6$) δ: 7.80(1H, d, J=7.1Hz), 7.70(1H, d, J=1.8Hz), 7.66(1H, d, J=8.4Hz), 7.41(1H, dd, J=8.4, 1.8Hz), 6.46(1H, d, J=7.1Hz), 4.84(1H, d, J=14.7Hz), 4.62(1H, d, J=14.7Hz), 4.57–4.47(1H, m), 4.02(1H, dd, J=13.8, 3.5Hz), 3.65–3.55(1H, m), 2.29–2.21(2H, m), 1.96(3H, s), 1.88–1.76(2H, m). |
| 34 | $^1$H-NMR(DMSO-$d_6$) δ: 7.69(1H, d, J=2.0Hz), 7.63(1H, d, J=8.2Hz), 7.39(1H, dd, J=8.2, 2.0Hz), 6.56(1H, s), 4.72(2H, s), 4.39–4.31(2H, m), 3.87(3H, s), 3.73–3.65(2H, m). |
| 35 | $^1$H-NMR(DMSO-$d_6$) δ: 7.68(1H, d, J=1.9Hz), 7.63(1H, d, J=8.4Hz), 7.38(1H, dd, J=8.4, 1.9Hz), 6.70(1H, s), 4.72(2H, s), 4.21–4.13(2H, m), 3.69–3.61(2H, m), 2.57(3H, s). |
| 36 | $^1$H-NMR($CDCl_3$) δ: 7.46(1H, d, J=8.0Hz), 7.43(1H, d, J=2.0Hz), 7.20(1H, dd, J=8.0, 2.0Hz), 6.25(1H, s), 4.71(2H, s), 4.24–4.14(2H, m), 3.67–3.59(2H, m), 3.56(2H, s), 2.88(1H, sept, J=6.5Hz), 1.25(6H, d, J=6.5Hz). |
| 37 | $^1$H-NMR(DMSO-$d_6$) δ: 12.48(1H, brs), 7.69(1H, d, J=2.2Hz), 7.63(1H, d, J=8.2Hz), 7.38(1H, dd, J=8.2, 2.2Hz), 6.28(1H, s), 4.76(2H, s), 4.71(2H, s), 4.30–4.18(2H, m), 3.73–3.63(2H, m), 3.43(1H, sept, J=7.0Hz), 1.31(6H, d, J=7.0Hz). |
| 38 | $^1$H-NMR(DMSO-$d_6$) δ: 7.68(1H, d, J=1.8Hz), 7.63(1H, d, J=8.4Hz), 7.38(1H, dd, J=8.4, 2.0Hz), 6.69(1H, s), 4.73(2H, s), 4.52(2H, s), 4.32–4.22(2H, m), 3.79–3.58(3H, m), 1.14(7H, d, J=6.2Hz). |
| 39 | $^1$H-NMR(DMSO-$d_6$) δ: 7.69(1H, s), 7.66(1H, d, J=8.8Hz), 7.40(1H, d, J=8.8Hz), 6.66(1H, s), 4.75(2H, s), 4.54(2H, s), 4.28(2H, s), 3.75(2H, s), 3.24(2H, d, J=6.2Hz), 1.93–1.75(1H, m), 0.87(6H, d, J=7.3Hz). |
| 40 | $^1$H-NMR(DMSO-$d_6$) δ: 7.67(1H, d, J=1.5Hz), 7.63(1H, d, J=8.2Hz), 7.38(1H, dd, J=8.2, 1.5Hz), 6.35(1H, s), 5.71–5.62(1H, m), 4.85–4.76(1H, m), 4.76(1H, d, J=15.5Hz), 4.69(1H, d, J=15.5Hz), 4.31–4.23(2H, m), 3.71–3.63(2H, m), 1.34(3H, d, J=6.2Hz). |
| 41 | $^1$H-NMR($CDCl_3$) δ: 8.25(1H, t, J=5.6Hz), 7.51–7.45(1H, m), 7.42–7.27(3H, m), 7.27–7.21(2H, m), 7.16–7.10(1H, m), 6.98(1H, dd, J=8.1, 2.1Hz), 5.47(2H, s), 5.03(2H, s), 4.37–4.30(2H, m), 3.73–3.63(2H, m). |
| 42 | $^1$H-NMR(DMSO-$d_6$) δ: 7.86(1H, d, J=7.2Hz), 7.44(2H, dd, J=8.8, 5.6Hz), 7.21(2H, t, J=8.8Hz), 6.60(1H, d, J=7.2Hz), 4.73(2H, s), 4.35(2H, t, J=5.8Hz), 3.75(2H, t, J=5.8Hz). |

TABLE 37-continued

| Example | $^{1}$H-NMR |
|---|---|
| 43 | $^{1}$H-NMR(DMSO-$d_6$) δ: 7.86(1H, d, J=6.8Hz), 7.48(1H, s), 7.41–7.37(3H, m), 6.58(1H, d, J=6.8Hz), 4.75(2H, s), 4.36(2H, t, J=5.6Hz), 3.77(2H, t, J=5.6Hz). |
| 44 | $^{1}$H-NMR(DMSO-$d_6$) δ: 7.91(1H, d, J=7.0Hz), 7.42–7.30(5H, m), 6.67(1H, d, J=7.0Hz), 4.75(2H, s), 4.38(2H, t, J=5.6Hz), 3.76(2H, t, J=5.8Hz). |
| 45 | $^{1}$H-NMR(DMSO-$d_6$) δ: 7.89(1H, d, J=7.0Hz), 7.44–7.42(4H, m), 6.64(1H, d, J=7.0Hz), 4.74(2H, s), 4.37(2H, t, J=5.6Hz), 3.76(2H, t, J=5.8Hz). |
| 46 | $^{1}$H-NMR(DMSO-$d_6$) δ: 7.67(1H, d, J=1.9Hz), 7.63(1H, d, J=8.3Hz), 7.37(1H, dd, J=8.3, 1.9Hz), 6.24(1H, s), 4.73(2H, s), 4.30–4.23(2H, m), 3.72–3.66(2H, m), 3.13(1H, sept, J=6.5Hz), 1.17(7H, d, J=6.5Hz). |
| 47 | $^{1}$H-NMR(DMSO-$d_6$) δ: 12.42(1H, brs), 7.68(1H, d, J=2.1Hz), 7.63(1H, d, J=8.3Hz), 7.38(1H, dd, J=8.3, 2.1Hz), 6.57(1H, s), 4.73(2H, s), 4.08–3.98(2H, m), 3.71–3.61(2H, m), 3.38–3.28(1H, m), 1.10(6H, d, J=7.0Hz). |
| 48 | $^{1}$H-NMR(DMSO-$d_6$) δ: 9.77(1H, s), 7.69(1H, d, J=2.1Hz), 7.64(1H, d, J=8.1Hz), 7.39(1H, dd, J=8.1, 2.1Hz), 6.84(1H, s), 4.75(2H, s), 4.66–4.58(2H, m), 3.77–3.68(2H, m). |
| 49 | $^{1}$H-NMR(DMSO-$d_6$) δ: 7.67–7.64(2H, m), 7.59–7.44(5H, m), 7.37(1H, dd, J=7.9, 1.4Hz), 6.54(1H, s), 4.75(2H, s), 4.16–4.14(2H, m), 3.72–3.63(2H, m). |
| 50 | $^{1}$H-NMR(DMSO-$d_6$) δ: 7.87(1H, d, J=7.0Hz), 7.29–7.08(5H, m), 6.62(1H, d, J=7.0Hz), 4.34(2H, t, J=5.8Hz), 3.78(2H, t, J=5.8Hz), 3.53(2H, t, J=7.2Hz), 2.62(2H, t, J=7.9Hz), 1.93–1.82(2H, m). |
| 51 | $^{1}$H-NMR(DMSO-$d_6$) δ: 7.86(1H, d, J=7.0Hz), 7.58–7.52(1H, m), 7.44(1H, t, J=7.2Hz), 7.23(1H, t, J=7.9Hz), 6.58(1H, d, J=7.0Hz), 4.80(2H, s), 4.36(2H, t, J=5.6Hz), 3.80(2H, t, J=5.6Hz). |
| 52 | $^{1}$H-NMR(DMSO-$d_6$) δ: 7.79(1H, d, J=7.0Hz), 7.32–7.16(5H, m), 6.52(1H, d, J=7.0Hz), 4.25(2H, t, J=5.8Hz), 3.75–3.67(4H, m), 2.90(2H, t, J=7.4Hz). |
| 53 | $^{1}$H-NMR(DMSO-$d_6$) δ: 12.37(1H, brs), 7.68(1H, d, J=2.1Hz), 7.63(1H, d, J=8.3Hz), 7.38(1H, dd, J=8.3, 2.1Hz), 6.27(1H, s), 5.75(1H, d, J=4.6Hz), 4.72(2H, s), 4.41–4.30(2H, m), 4.29–4.17(1H, m), 3.65(2H, t, J=5.3Hz), 1.95–1.83(1H, m), 0.87(6H, dd, J=10.0, 6.7Hz). |
| 54 | $^{1}$H-NMR(DMSO-$d_6$) δ: 7.68(1H, d, J=1.9Hz), 7.64(1H, d, J=8.1Hz), 7.39(1H, dd, J=8.1, 1.9Hz), 6.56(1H, s), 4.75(2H, s), 4.38–4.31(2H, m), 3.76–3.69(2H, m), 2.64(2H, d, J=7.0Hz), 1.93–1.80(1H, m), 0.91(9H, d, J=6.5Hz). |
| 55 | $^{1}$H-NMR(DMSO-$d_6$) δ: 12.35(0H, s), 8.31(1H, s), 8.05(1H, s), 7.67(1H, d, J=2.0Hz), 7.62(1H, d, J=8.3Hz), 7.37(1H, dd, J=8.3, 2.0Hz), 6.25(1H, s), 4.72(2H, s), 4.25–4.17(2H, m), 3.71–3.64(2H, m). |
| 56 | $^{1}$H-NMR(DMSO-$d_6$) δ: 12.34(1H, brs), 8.86–8.77(1H, m), 7.67(1H, d, J=2.3Hz), 7.62(1H, d, J=8.3Hz), 7.36(1H, dd, J=8.3, 2.3Hz), 6.22(1H, s), 4.72(2H, s), 4.20–4.12(2H, m), 3.70–3.62(2H, m), 2.74(3H, d, J=4.6Hz). |
| 57 | $^{1}$H-NMR(DMSO-$d_6$) δ: 7.93(1H, d, J=7.0Hz), 7.60(1H, t, J=7.9Hz), 7.48(1H, dd, J=10.2, 1.9Hz), 7.27(1H, d, J=8.3Hz), 6.68(1H, d, J=7.0Hz), 4.76(2H, s), 4.41(2H, t, J=5.6Hz), 3.79(2H, t, J=5.6Hz). |
| 58 | $^{1}$H-NMR(DMSO-$d_6$) δ: 12.44(1H, brs), 7.93(2H, d, J=7.4Hz), 7.79(1H, t, J=7.4Hz), 7.71–7.58(4H, m), 7.38(1H, dd, J=8.3, 1.9Hz), 6.22(1H, s), 4.73(2H, s), 4.07–3.97(2H, m), 3.68–3.60(2H, m). |
| 59 | $^{1}$H-NMR(DMSO-$d_6$) δ: 12.39(1H, s), 7.68(1H, d, J=1.9Hz), 7.63(1H, d, J=8.3Hz), 7.38(1H, dd, J=8.3, 1.9Hz), 6.63(1H, s), 4.73(2H, s), 4.15–4.06(2H, m), 3.70–3.61(2H, m), 2.98(2H, q, J=7.1Hz), 1.05(3H, t, J=7.1Hz). |
| 60 | $^{1}$H-NMR(DMSO-$d_6$) δ: 12.19(1H, s), 7.65(1H, d, J=2.1Hz), 7.62(1H, d, J=8.3Hz), 7.36(1H, dd, J=8.3, 2.1Hz), 6.10(1H, s), 4.71(2H, s), 4.14–4.07(2H, m), 3.70–3.63(2H, m), 2.26(3H, s). |
| 61 | $^{1}$H-NMR(DMSO-$d_6$) δ: 12.32(1H, brs), 7.68(1H, d, J=1.9Hz), 7.62(1H, d, J=8.1Hz), 7.38(1H, dd, J=8.1, 1.9Hz), 6.11(1H, s), 4.83(1H, d, J=15.3Hz), 4.60(1H, d, J=15.3Hz), 4.08–3.98(1H, m), 3.95–3.85(1H, m), 3.72–3.64(2H, m), 3.58–3.47(1H, m), 3.36–3.18(3H, m), 1.55–0.72(1H, m), 1.13(3H, t, J=7.0Hz), 1.06(3H, t, J=7.0Hz). |
| 62 | $^{1}$H-NMR(DMSO-$d_6$) δ: 7.68(1H, s), 7.62(1H, d, J=8.3Hz), 7.38(1H, d, J=8.3Hz), 6.25–6.19(1H, m), 4.90–4.54(2H, m), 4.14–3.89(2H, m), 3.87–3.62(3H, m), 2.86–2.71(2H, m), 1.18–1.08(7H, m). |
| 63 | $^{1}$H-NMR(DMSO-$d_6$) δ: 12.31(1H, brs), 7.68(1H, s), 7.62(1H, d, J=8.1Hz), 7.38(1H, d, J=8.1Hz), 6.12–6.08(1H, m), 4.89–4.54(2H, m), 4.09–3.87(2H, m), 3.73–3.62(2H, m), 3.52–3.15(2H, m), 2.96–2.85(3H, m), 1.16–1.02(3H, m). |
| 64 | $^{1}$H-NMR(DMSO-$d_6$) δ: 11.94(1H, s), 7.62(1H, dd, J=7.9, 1.9Hz), 7.56(1H, d, J=7.4Hz), 7.42–7.40(2H, m), 6.13(1H, d, J=7.4Hz), 4.69(2H, s), 4.20–4.15(2H, m), 3.72–3.67(2H, m). |
| 65 | $^{1}$H-NMR(DMSO-$d_6$) δ: 7.91(1H, d, J=7.2Hz), 7.48–7.35(4H, m), 6.65(1H, d, J=7.2Hz), 4.82(2H, s), 4.42(2H, t, J=5.8Hz), 3.80(2H, t, J=5.8Hz). |
| 66 | $^{1}$H-NMR(DMSO-$d_6$) δ: 7.89(1H, d, J=7.0Hz), 7.56(1H, t, J=1.9Hz), 7.48(2H, d, J=1.9Hz), 6.64(1H, d, J=7.0Hz), 4.74(2H, s), 4.39(2H, t, J=5.6Hz), 3.79(2H, t, J=5.6Hz). |
| 67 | $^{1}$H-NMR(DMSO-$d_6$) δ: 7.68(1H, d, J=2.0Hz), 7.64(1H, d, J=8.2Hz), 7.38(1H, dd, J=8.2, 2.0Hz), 6.69(1H, s), 4.76(2H, s), 4.58–4.51(2H, m), 3.75–3.67(2H, m), 1.41(9H, s). |
| 68 | $^{1}$H-NMR(DMSO-$d_6$) δ: 7.70(1H, d, J=1.9Hz), 7.64(1H, d, J=8.3Hz), 7.40(1H, dd, J=8.3, 1.9Hz), 6.74(1H, s), 4.83–4.64(3H, m), 4.61–4.45(2H, m), 3.73–3.63(2H, m), 0.91(9H, s). |
| 69 | $^{1}$H-NMR(DMSO-$d_6$) δ: 8.07(1H, d, J=7.2Hz), 7.41–7.24(6H, m), 6.77(1H, d, J=7.2Hz), 3.97(2H, s), 3.19(3H, s). |

TABLE 37-continued

| Example | $^1$H-NMR |
|---|---|
| 70 | 1H-NMR(DMSO-$d_6$) δ: 8.14(1H, d, J=7.2Hz), 7.38(1H, d, J=6Hz), 7.32(2H, d, J=8.4Hz), 7.25(2H, d, J=8.4Hz), 7.02(1H, d, J=6Hz), 6.84(1H, d, J=7.2Hz), 3.82(2H, t, J=7Hz), 2.65(2H, t, J=7.8Hz), 1.9–2.1(2H, m). |
| 71 | 1H-NMR(DMSO-$d_6$) δ: 8.08(1H, d, J=7.2Hz), 7.2–7.5(5H, m), 6.98(1H, d, J=6.3Hz), 6.73(1H, d, J=7.2Hz), 3.85(2H, t, J=7Hz), 2.76(2H, t, J=7.8Hz), 1.9–2.1(2H, m). |
| 72 | $^1$H-NMR(DMSO-$d_6$) δ: 12.14(1H, brs), 7.90(1H, d, J=7.4Hz), 7.69(1H, d, J=1.9Hz), 7.64(1H, d, J=8.3Hz), 7.38(1H, dd, J=8.3, 1.9Hz), 6.78(1H, s), 6.49(1H, d, J=7.4Hz), 4.94(2H, s), 2.20(3H, s). |
| 73 | $^1$H-NMR(DMSO-$d_6$) δ: 7.92(1H, d, J=7.0Hz), 7.47(1H, d, J=2.3Hz), 7.33(1H, dd, J=8.6, 2.3Hz), 7.14(1H, d, J=8.6Hz), 6.69(1H, d, J=7.0Hz), 4.67(2H, s), 4.37(2H, t, J=5.8Hz), 3.85(3H, s), 3.74(2H, t, J=5.8Hz). |
| 74 | $^1$H-NMR(DMSO-$d_6$) δ: 8.04(1H, d, J=7.0Hz), 7.41–7.21(6H, m), 6.76(1H, d, J=7.0Hz), 3.41(3H, s), 2.92–2.79(4H, m). |
| 75 | $^1$H-NMR(DMSO-$d_6$) δ: 7.68(1H, d, J=2.0Hz), 7.63(1H, d, J=8.0Hz), 7.38(1H, dd, J=8.0, 2.0Hz), 6.29(1H, s), 4.72(2H, s), 4.26(2H, s), 4.14(2H, t, J=5.4Hz), 3.71(2H, t, J=5.4Hz). |
| 76 | $^1$H-NMR(DMSO-$d_6$) δ: 8.13(1H, d, J=7.4Hz), 7.37(1H, d, J=6.3Hz), 7.32–7.25(2H, m), 7.23–7.16(2H, m), 7.01(1H, d, J=6.3Hz), 6.83(1H, d, J=7.4Hz), 3.82(2H, t, J=7.0Hz), 2.66(2H, t, J=7.9Hz), 1.98(2H, tt, J=7.9, 7.0Hz). |
| 77 | $^1$H-NMR(DMSO-$d_6$) δ: 8.18(1H, d, J=7.0Hz), 7.36(1H, s), 7.32–7.10(5H, m), 6.99(1H, d, J=7.0Hz), 3.37(3H, s), 2.71(2H, t, J=7.7Hz), 2.62(2H, t, J=7.4Hz), 1.87(2H, tt, J=7.7, 7.4Hz). |
| 78 | $^1$H-NMR(DMSO-$d_6$) δ: 12.26(1H, s), 8.08(1H, d, J=7.9Hz), 7.69(1H, d, J=1.9Hz), 7.62(1H, d, J=8.3Hz), 7.37(1H, dd, J=8.3, 1.9Hz), 6.70(1H, s), 6.49(1H, d, J=7.9Hz), 4.99(2H, s), 3.13(1H, sept, J=6.5Hz), 1.19(6H, d, J=6.5Hz). |
| 79 | $^1$H-NMR(DMSO-$d_6$) δ: 7.90(1H, d, J=7.4Hz), 7.51(1H, d, J=2.3Hz), 7.49(1H, d, J=7.9Hz), 7.23(1H, dd, J=8.3, 1.9Hz), 7.15(1H, d, J=6.0Hz), 6.74(1H, d, J=6.5Hz), 6.46(1H, d, J=7.4Hz), 3.76(2H, t, J=6.7Hz), 2.65(2H, t, J=7.4Hz), 2.00–1.93(2H, m). |
| 80 | $^1$H-NMR(DMSO-$d_6$) δ: 7.90(1H, d, J=7.4Hz), 7.32–7.34(1H, m), 7.31(2H, d, J=1.9Hz), 7.15(1H, d, J=6.0Hz), 6.74(1H, d, J=6.5Hz), 6.49(1H, d, J=7.4Hz), 3.76(2H, t, J=6.7Hz), 2.66(2H, t, J=7.7Hz), 2.01–1.93(2H, m). |
| 81 | $^1$H-NMR(DMSO-$d_6$) δ: 7.66(1H, d, J=2.3Hz), 7.63(1H, d, J=8.3Hz), 7.36–7.29(6H, m), 6.22(1H, s), 5.14(2H, s), 4.70(2H, s), 4.05–3.97(4H, m), 3.59–3.55(2H, m). |
| 82 | $^1$H-NMR(DMSO-$d_6$) δ: 12.44(1H, s), 7.66–7.61(2H, m), 7.34–7.13(11H, m), 6.22(1H, s), 5.11(2H, dd, J=18.1, 12.5Hz), 4.66(2H, dd, J=18.1, 14.8Hz), 4.50(1H, t, J=7.7Hz), 4.20–4.10(1H, m), 4.09–3.97(1H, m), 3.54–3.26(3H, m), 3.09(1H, dd, J=13.4, 7.4Hz). |
| 83 | $^1$H-NMR(DMSO-$d_6$) δ: 7.66(1H, d, J=2.1Hz), 7.63(1H, d, J=8.3Hz), 7.36(1H, dd, J=8.3, 2.1Hz), 6.13(1H, s), 4.85(1H, s), 4.72(2H, s), 4.20(2H, t, J=5.3Hz), 3.66–3.64(4H, m), 2.76(2H, t, J=6.5Hz). |
| 84 | $^1$H-NMR(DMSO-$d_6$) δ: 7.98(1H, d, J=7.9Hz), 7.71–7.68(1H, m), 7.63(1H, d, J=8.3Hz), 7.40–7.35(1H, m), 6.73(1H, s), 6.47(1H, d, J=7.9Hz), 4.95(2H, s), 2.57–2.52(2H, m), 1.61–1.48(2H, m), 0.94(3H, t, J=7.2Hz). |
| 85 | $^1$H-NMR(DMSO-$d_6$) δ: 8.00(1H, d, J=7.9Hz), 7.69(1H, d, J=1.9Hz), 7.63(1H, d, J=8.3Hz), 7.38(1H, dd, J=8.3, 1.9Hz), 6.75(1H, s), 6.55–6.49(1H, m), 4.97(2H, s), 2.62(3H, q, J=7.2Hz), 1.16(3H, t, J=7.2Hz). |
| 86 | $^1$H-NMR(DMSO-$d_6$) δ: 7.99(1H, d, J=7.7Hz), 7.70(1H, d, J=2.2Hz), 7.64(1H, d, J=8.3Hz), 7.38(1H, dd, J=8.3, 2.2Hz), 6.94(1H, s), 6.51(1H, d, J=7.7Hz), 5.54(1H, brs), 4.95(2H, s), 4.43(2H, d, J=4.0Hz). |
| 87 | $^1$H-NMR(DMSO-$d_6$) δ: 7.96(1H, d, J=7.9Hz), 7.69(1H, d, J=1.9Hz), 7.63(1H, d, J=8.3Hz), 7.37(1H, dd, J=8.3, 1.9Hz), 6.74(1H, s), 6.49(1H, d, J=7.9Hz), 4.95(2H, s), 2.46(2H, d, J=7.0Hz), 1.91–1.77(1H, m), 0.91(6H, d, J=6.5Hz). |
| 88 | $^1$H-NMR($CDCl_3$) δ: 8.42(1H, d, J=7.0Hz), 7.65(1H, d, J=6.5Hz), 7.50(1H, s), 7.45–7.43(4H, m), 7.31(1H, d, J=7.4Hz), 5.08(2H, s). |
| 89 | 1H-NMR(DMSO-$d_6$) δ: 8.76(1H, d, J=8.1Hz), 7.92(1H, brs), 7.73(1H s), 7.63(1H, d, J=8.4Hz), 7.3–7.5(1H, m), 6.5(1H, d, J=8.1Hz), 5.05(2H, s), 3.84(3H, s). |
| 90 | $^1$H-NMR(DMSO-$d_6$) δ: 8.42(1H, d, J=7.2Hz), 7.72–7.61(2H, m), 7.49–7.42(2H, m), 7.37(1H, d, J=6.4Hz), 7.30(1H, d, J=7.2Hz), 5.06(2H, s). |
| 91 | $^1$H-NMR(DMSO-$d_6$) δ: 8.48(1H, d, J=6.5Hz), 7.70(1H, d, J=6.5Hz), 7.49(1H, dd, J=7.4, 1.4Hz), 7.43(1H, d, J=7.4Hz), 7.41(1H, d, J=6.5Hz), 7.36(1H, dd, J=7.4, 1.4Hz), 7.30(1H, dd, J=7.9, 7.9Hz), 3.95(2H, t, J=7.2Hz), 2.84(2H, dd, J=9.3, 7.9Hz), 2.05–1.98(2H, m). |
| 92 | $^1$H-NMR(DMSO-$d_6$) δ: 8.58(1H, d, J=7.4Hz), 7.68(1H, dd, J=7.0, 1.9Hz), 7.49–7.37(3H, m), 7.29(1H, s), 5.13(2H, s), 3.27(1H, d, J=6.5Hz), 1.26(6H, d, J=6.5Hz). |
| 93 | $^1$H-NMR(DMSO-$d_6$) δ: 8.76(1H, d, J=7.9Hz), 7.91(1H, s), 7.51(1H, s), 7.43–7.34(3H, m), 6.51(1H, d, J=7.9Hz), 5.07(2H, s), 3.84(3H, s). |
| 95 | $^1$H-NMR(DMSO-$d_6$) δ: 8.50(1H, d, J=7.0Hz), 7.72(1H, d, J=6.0Hz), 7.46(1H, d, J=7.0Hz), 7.45(1H, d, J=6.0Hz), 7.33–7.28(2H, m), 7.25–7.19(1H, m), 3.95(2H, t, J=7.4Hz), 2.82(2H, td, J=7.4, 1.9Hz), 2.00–1.91(2H, m). |
| 97 | $^1$H-NMR(DMSO-$d_6$) δ: 7.76(1H, d, J=7.9Hz), 7.53(1H, s), 7.43–7.34(3H, m), 7.24(1H, s), 6.61(1H, d, J=7.9Hz), 4.98(2H, s), 3.06(3H, s), 3.01(3H, s). |
| 98 | $^1$H-NMR(DMSO-$d_6$) δ: 9.04(1H, d, J=8.1Hz), 7.94(1H, s), 7.51(1H, s), 7.43–7.33(3H, m), 6.60(1H, d, J=8.1Hz), 5.08(2H, s). |

TABLE 37-continued

| Example | $^1$H-NMR |
|---|---|
| 99 | $^1$H-NMR(DMSO-$d_6$) δ: 11.93(1H, s), 8.31(1H, dd, J=7.9, 1.9Hz), 8.23(1H, d, J=8.8Hz), 7.95(1H, d, J=6.5Hz), 7.81(1H, ddd, J=8.8, 7.0, 1.9Hz), 7.53(1H, s), 7.48(1H, dd, J=7.9, 7.0Hz), 7.42–7.37(3H, m), 6.93(1H, d, J=6.5Hz), 5.03(2H, s). |
| 100 | $^1$H-NMR(DMSO-$d_6$) δ: 8.52(1H, s), 7.47–7.18(5H, m), 6.83(1H, d, J=6.0Hz), 4.92(2H, s). |
| 101 | $^1$H-NMR(DMSO-$d_6$) δ: 9.28(1H, d, J=7.9Hz), 9.25(1H, s), 8.07(1H, s), 7.55(1H, s), 7.45–7.36(3H, m), 6.54(1H, d, J=7.9Hz), 5.08(2H, s). |
| 102 | $^1$H-NMR(DMSO-$d_6$) δ: 8.00(1H, d, J=7.9Hz), 7.49(1H, s), 7.44–7.32(3H, m), 6.96(1H, s), 6.52(1H, d, J=7.9Hz), 5.61–5.50(1H, m), 4.96(2H, s), 4.45(2H, d, J=4.2Hz). |
| 103 | $^1$H-NMR(DMSO-$d_6$) δ: 8.23(1H, d, J=7.9Hz), 7.49(1H, s), 7.41–7.34(3H, m), 6.94(1H, s), 6.56(1H, d, J=7.9Hz), 5.68(1H, s), 5.01(2H, s), 4.83(1H, d, J=6.5Hz), 1.44(3H, d, J=6.5Hz). |
| 105 | $^1$H-NMR(DMSO-$d_6$) δ: 8.78(1H, d, J=8.3Hz), 8.16(1H, s), 7.54(1H, s), 7.48–7.32(3H, m), 6.47(1H, d, J=7.9Hz), 5.07(2H, s), 2.50(3H, s). |
| 107 | $^1$H-NMR(DMSO-$d_6$) δ: 8.13(1H, s), 7.95(1H, d, J=7.4Hz), 7.52(1H, s), 7.45–7.30(3H, m), 6.54(1H, d, J=7.4Hz), 4.95(2H, s). |
| 108 | $^1$H-NMR(DMSO-$d_6$) δ: 11.62(1H, s), 8.09(1H, s), 7.47–7.28(4H, m), 4.70(2H, s), 4.22–4.13(2H, m), 3.76–3.67(2H, m). |
| 109 | $^1$H-NMR(DMSO-$d_6$) δ: 8.85(1H, s), 7.45–7.28(4H, m), 7.21(1H, d, J=6.5Hz), 7.12(1H, d, J=6.0Hz), 4.99(2H, s), 3.50(3H, s). |
| 110 | $^1$H-NMR(DMSO-$d_6$) δ: 11.92(1H, s), 8.33(1H, s), 7.46(1H, s), 7.43–7.31(4H, m), 5.28–5.22(1H, m), 5.02(1H, d, J=15.3Hz), 4.54(1H, d, J=15.3Hz), 4.38–4.20(2H, m). |
| 111 | $^1$H-NMR(DMSO-$d_6$) δ: 12.22(1H, s), 8.21(1H, dd, J=8.3, 1.4Hz), 7.78(1H, d, J=8.8Hz), 7.71(1H, ddd, J=8.3, 7.4, 1.9Hz), 7.50(1H, s), 7.45–7.35(3H, m), 7.30(1H, t, J=7.4Hz), 4.80(2H, s), 4.50–4.42(2H, m), 3.86–3.77(2H, m). |
| 112 | $^1$H-NMR(DMSO-$d_6$) δ: 8.48(1H, s), 7.87(1H, t, J=1.6Hz), 7.72(1H, dt, J=7.4, 1.6Hz), 7.52–7.24(7H, m), 7.00(1H, d, J=6.0Hz), 5.00(2H, s). |
| 113 | 1H-NMR(DMSO-$d_6$) δ: 8.47(1H, s), 7.80(2H, d, J=8.4Hz), 7.3–7.6(7H, m), 7.02(1H, d, J=6Hz), 5.01(2H, s). |
| 114 | 1H-NMR(DMSO-$d_6$) δ: 8.23(1H, s), 7.3–7.6(8H, m), 7.26(1H, d, J=6Hz), 6.98(1H, d, J=6Hz), 5.00(s, 2H). |
| 115 | $^1$H-NMR(DMSO-$d_6$) δ: 9.28(1H, s), 8.77(1H, d, J=5.5Hz), 8.73–8.63(2H, m), 7.93(1H, dd, J=8.1, 5.5Hz), 7.50(1H, s), 7.44–7.34(3H, m), 7.24(1H, dd, J=6.6, 1.7Hz), 6.98(1H, dd, J=6.2, 1.7Hz), 5.01(2H, s). |
| 116 | $^1$H-NMR(DMSO-$d_6$) δ: 8.87(2H, d, J=6.8Hz), 8.83(1H, s), 8.47(2H, d, J=6.8Hz), 7.50(1H, s), 7.45–7.34(3H, m), 7.26(1H, d, J=6.4Hz), 6.99(1H, d, J=6.4Hz), 5.00(2H, s). |
| 117 | $^1$H-NMR(DMSO-$d_6$) δ: 9.27(1H, s), 8.82(1H, d, J=5.1Hz), 8.65(1H, d, J=7.9Hz), 8.33(1H, t, J=7.9Hz), 7.72(1H, t, J=5.9Hz), 7.52(1H, s), 7.47(1H, d, J=6.2Hz), 7.44–7.35(3H, m), 7.11(1H, d, J=6.2Hz), 5.03(2H, s). |
| 119 | $^1$H-NMR($CDCl_3$) δ: 7.69(1H, s), 7.67(2H, d, J=7.2Hz), 7.48–7.30(7H, m), 7.26–7.21(1H, m), 5.99(1H, brs), 4.94(2H, s), 2.42(2H, d, J=6.8Hz), 1.81–1.63(5H, m), 1.35–0.89(6H, m). |
| 120 | $^1$H-NMR($CDCl_3$) δ: 8.60(1H, s), 7.77(1H, s), 7.50–7.49(1H, m), 7.48(1H, d, J=6.0Hz), 7.43–7.35(4H, m), 7.01(1H, d, J=6.0Hz), 6.62(1H, dd, J=1.9, 3.2Hz), 4.98(2H, s). |
| 121 | $^1$H-NMR($CDCl_3$) δ: 12.68(1H, s), 7.44(1H, d, J=8.3Hz), 7.41(1H, d, J=1.9Hz), 7.18(1H, dd, J=8.3, 1.9Hz), 6.62(1H, s), 4.68(2H, s), 3.56(3H, s), 3.46(2H, t, J=6.5Hz), 2.73(2H, t, J=6.5Hz). |
| 122 | $^1$H-NMR($CDCl_3$) δ: 12.86(1H, s), 7.19–7.08(2H, m), 7.00–6.92(1H, m), 6.60(1H, s), 3.62(2H, t, J=7.2Hz), 3.54(3H, s), 3.52(2H, t, J=6.2Hz), 2.84(2H, td, J=7.9, 2.1Hz), 2.77–2.71(2H, m), 1.97–1.85(2H, m). |
| 124 | $^1$H-NMR(DMSO-$d_6$) δ: 8.77(1H, s), 7.92(1H, s), 7.71(1H, d, J=7.2Hz), 7.57(1H, d, J=8.3Hz), 7.53(1H, d, J=6.4Hz), 7.52(1H, s), 7.43–7.24(5H, m), 7.00(1H, d, J=6.4Hz), 4.99(2H, s). |
| 126 | $^1$H-NMR(DMSO-$d_6$) δ: 8.23(1H, s), 7.52–7.47(2H, m), 7.44–7.34(3H, m), 7.20(1H, d, J=6.0Hz), 5.04(2H, s), 0.90(9H, s). |
| 127 | $^1$H-NMR(DMSO-$d_6$) δ: 8.20(1H, s), 7.83(1H, d, J=7.4Hz), 7.74(1H, t, J=7.4Hz), 7.64(1H, t, J=7.7Hz), 7.52(1H, s), 7.44–7.36(4H, m), 7.28(1H, d, J=6.5Hz), 7.02(1H, d, J=6.5Hz), 5.01(2H, s). |
| 128 | $^1$H-NMR(DMSO-$d_6$) δ: 8.49(1H, s), 7.50(1H, s), 7.44–7.34(4H, m), 7.41(1H, d, J=7.9Hz), 7.36(1H, d, J=7.9Hz), 7.30(1H, d, J=7.4Hz), 7.08(1H, d, J=6.0Hz), 6.97(1H, dd, J=7.9, 2.3Hz), 5.03(2H, s), 4.48(1H, brs), 3.80(3H, s). |
| 129 | $^1$H-NMR(DMSO-$d_6$) δ: 12.40(1H, brs), 8.43(1H, s), 7.48(1H, s), 7.43–7.30(3H, m), 6.79(1H, s), 5.03(2H, s), 3.31(1H, sept, J=5.6Hz), 1.19(6H, d, J=5.6Hz). |
| 130 | $^1$H-NMR(DMSO-$d_6$) δ: 7.68(1H, s), 7.62(1H, d, J=8.3Hz), 7.38(1H, d, J=8.3Hz), 6.25–6.19(1H, m), 4.90–4.54(2H, m), 4.14–3.89(2H, m), 3.87–3.62(3H, m), 2.86–2.71(2H, m), 1.18–1.08(7H, m). |
| 131 | $^1$H-NMR($CDCl_3$) δ: 7.94(1H, brs), 7.71–7.63(2H, m), 7.49–7.26(7H, m), 6.36(1H, brs), 5.05(2H, brs), 3.14(1H, brs), 1.36(6H, brs). |
| 132 | $^1$H-NMR(DMSO-$d_6$) δ: 8.43(1H, s), 7.51(1H, s), 7.48(1H, d, J=6.0Hz), 7.45–7.37(4H, m), 7.29(1H, dd, J=7.4, 1.4Hz), 7.23(1H, d, J=6.0Hz), 7.14(1H, d, J=7.9Hz), 7.05(1H, t, J=7.4Hz), 5.08(2H, s), 4.19(1H, brs), 3.74(3H, s). |
| 133 | $^1$H-NMR(DMSO-$d_6$) δ: 8.48(1H, s), 7.71(2H, d, J=8.3Hz), 7.49(1H, s), 7.44–7.36(4H, m), 7.10(1H, d, J=6.5Hz), 7.03(2H, d, J=8.8Hz), 5.04(2H, s), 4.02(1H, br s), 3.81(3H, s). |

TABLE 37-continued

| Example | $^1$H-NMR |
|---|---|
| 134 | $^1$H-NMR(DMSO-$d_6$) δ: 8.38(1H, brs), 7.55–7.47(2H, m), 7.44–7.33(3H, m), 7.33–7.24(1H, m), 5.07(2H, s), 2.61(2H, q, J=7.5Hz), 1.17(3H, t, J=7.5Hz). |
| 135 | $^1$H-NMR(DMSO-$d_6$) δ: 8.37(1H, s), 7.54(1H, s), 7.49–7.29(5H, m), 7.23(1H, t, J=7.7Hz), 7.14(2H, d, J=7.4Hz), 5.09(2H, s), 2.03(6H, s). |
| 136 | $^1$H-NMR(DMSO-$d_6$) δ: 9.41(1H, brs), 8.27(1H, s), 7.49(1H, s), 7.43–7.35(3H, m), 7.26(1H, d, J=6.0Hz), 7.24(1H, dd, J=2.8, 4.2Hz), 7.20(1H, d, J=7.9Hz), 7.09(1H, d, J=7.9Hz), 6.89(1H, d, J=6.0Hz), 6.74(1H, dd, J=8.1, 2.6Hz), 4.98(2H, s). |
| 137 | $^1$H-NMR(DMSO-$d_6$) δ: 8.32(1H, s), 7.76(2H, dd, J=8.3, 1.6Hz), 7.62(1H, tt, J=7.4, 1.6Hz), 7.52–7.34(6H, m), 7.27(1H, d, J=6.5Hz), 6.93(1H, d, J=6.0Hz), 4.98(2H, s). |
| 138 | $^1$H-NMR(DMSO-$d_6$) δ: 8.39(1H, s), 7.13(1H, d, J=7.3Hz), 6.84–6.84(9H, m), 5.07(2H, s), 2.44(1H, q, J=7.4Hz), 1.04(3H, t, J=7.4Hz). |
| 139 | $^1$H-NMR(DMSO-$d_6$) δ: 12.35(1H, s), 8.10(1H, s), 7.83(1H, t, J=1.9Hz), 7.64(1H, dt, J=7.5, 1.4Hz), 7.50–7.34(6H, m), 6.78(1H, s), 5.04(2H, s), 3.47–3.35(1H, m), 1.22(6H, d, J=7.0Hz). |
| 140 | $^1$H-NMR(DMSO-$d_6$) δ: 8.18(1H, brs), 7.47(1H, brs), 7.42–7.30(4H, m), 7.29–7.22(4H, m), 7.21–7.14(1H, m), 7.05(1H, brs), 5.00(2H, s), 3.86(2H, s). |
| 141 | $^1$H-NMR(DMSO-$d_6$) δ: 10.55(1H, s), 8.46(1H, brs), 7.50(1H, s), 7.44–7.33(5H, m), 7.28(1H, t, J=7.2Hz), 7.08(1H, brs), 6.95–6.85(2H, m), 5.03(2H, s). |
| 142 | $^1$H-NMR(DMSO-$d_6$) δ: 8.57(1H, s), 7.63–7.57(2H, m), 7.51(1H, d, J=6.0Hz), 7.50(1H, s), 7.44–7.36(3H, m), 7.25(1H, d, J=6.0Hz), 6.87(2H, d, J=8.8Hz), 5.07(2H, s). |
| 143 | $^1$H-NMR($CDCl_3$) δ: 12.72(1H, s), 7.63–7.48(4H, m), 6.62(1H, s), 4.80(2H, s), 3.57(3H, s), 3.47(2H, t, J=6.4Hz), 2.73(2H, t, J=6.4Hz). |
| 144 | $^1$H-NMR($CDCl_3$) δ: 12.86(1H, s), 7.31–7.25(1H, m), 6.90–6.85(3H, m), 6.60(1H, t, J=1.2Hz), 4.71(2H, s), 3.82(3H, s), 3.56(3H, s), 3.45(2H, t, J=6.5Hz), 2.70(2H, td, J=6.5, 0.9Hz). |
| 145 | 1H-NMR(DMSO-$d_6$) δ: 7.2–7.5(5H, m), 6.39(1H, d, J=8.1Hz), 5.05(2H, s), 3.74(3H, s). |
| 146 | $^1$H-NMR(DMSO-$d_6$) δ: 8.17(1H, s), 8.07(1H, d, J=7.4Hz), 7.53(1H, s), 7.42–7.35(3H, m), 6.45(1H, d, J=7.4Hz), 4.96(2H, s). |
| 147 | $^1$H-NMR(DMSO-$d_6$) δ: 11.64(1H, brs), 8.59(1H, s), 7.48(1H, brs), 7.43–7.33(3H, m), 7.31(1H, d, J=6.0Hz), 6.90(1H, d, J=6.5Hz), 4.93(2H, s), 3.77(3H, s). |
| 148 | $^1$H-NMR(DMSO-$d_6$) δ: 12.00(1H, s), 8.61(1H, s), 7.85(1H, d, J=1.9Hz), 7.81(1H, d, J=1.9Hz), 7.51(1H, s), 7.45–7.33(4H, m), 7.05(1H, d, J=6.5Hz), 5.02(2H, s), 3.79(3H, s). |
| 149 | $^1$H-NMR(DMSO-$d_6$) δ: 8.45(1H, s), 7.48(1H, brs), 7.44–7.31(4H, m), 6.93(1H, d, J=6.2Hz), 4.95(2H, s), 3.95(1H, sept, J=6.8Hz), 1.05(6H, d, J=6.8Hz). |
| 150 | $^1$H-NMR(DMSO-$d_6$) δ: 8.50(1H, s), 7.47(1H, brs), 7.42–7.32(3H, m), 7.31(3H, d, J=6.0Hz), 6.89(1H, d, J=6.0Hz), 5.06(1H, t, J=6.5Hz), 4.93(2H, s), 1.28(6H, d, J=6.5Hz). |
| 151 | $^1$H-NMR(DMSO-$d_6$) δ: 8.48(1H, d, J=7.4Hz), 7.70(1H, d, J=6.0Hz), 7.45(4H, s), 7.43(1H, d, J=6.5Hz), 7.41(1H, d, J=7.0Hz), 5.08(2H, s). |
| 152 | $^1$H-NMR(DMSO-$d_6$) δ: 15.97(1H, s), 12.21(1H, s), 8.92(1H, s), 7.58(1H, d, J=6.5Hz), 7.50(1H, s), 7.45–7.32(3H, m), 7.20(1H, d, J=6.5Hz), 5.02(2H, s). |
| 153 | $^1$H-NMR(DMSO-$d_6$) δ: 8.14(1H, s), 7.48(1H, s), 7.44–7.30(3H, m), 7.20(1H, d, J=6.0Hz), 6.91(1H, d, J=6.5Hz), 4.96(2H, s), 2.95(3H, s), 2.85(3H, s). |
| 155 | $^1$H-NMR(DMSO-$d_6$) δ: 11.83(1H, s), 10.00(1H, d, J=5.1Hz), 8.77(1H, s), 7.56–7.46(2H, m), 7.45–7.32(3H, m), 7.01(1H, d, J=6.0Hz), 4.97(2H, s), 2.86(3H, d, J=5.1Hz). |
| 156 | $^1$H-NMR(DMSO-$d_6$) δ: 8.13(1H, s), 7.49(1H, s), 7.44–7.30(3H, m), 7.18(1H, d, J=6.0Hz), 6.89(1H, d, J=6.5Hz), 4.96(2H, s), 3.40(2H, q, J=7.1Hz), 3.16(2H, q, J=7.3Hz), 1.12(3H, t, J=7.0Hz), 1.03(3H, t, J=7.2Hz). |
| 157 | $^1$H-NMR(DMSO-$d_6$) δ: 8.40(1H, d, J=7.2Hz), 7.63(1H, d, J=6.3Hz), 7.58(2H, d, J=8.6Hz), 7.38(2H, d, J=8.6Hz), 7.34(1H, d, J=6.3Hz), 7.27(1H, d, J=7.2Hz), 5.05(2H, s). |
| 158 | $^1$H-NMR(DMSO-$d_6$) δ: 8.42(1H, d, J=7.0Hz), 7.66–7.63(2H, m), 7.54(1H, d, J=7.9Hz), 7.42(1H, d, J=7.9Hz), 7.37(1H, t, J=3.0Hz), 7.34(1H, d, J=7.9Hz), 7.29(1H, d, J=7.0Hz), 5.08(2H, s). |
| 159 | $^1$H-NMR(DMSO-$d_6$) δ: 11.59(1H, brs), 8.53(1H, s), 7.48(1H, s), 7.43–7.32(4H, m), 6.91(1H, d, J=6.5Hz), 4.94(2H, s), 3.91(2H, s), 0.99(9H, s). |
| 160 | $^1$H-NMR(DMSO-$d_6$) δ: 11.58(1H, s), 8.51(1H, s), 7.48(1H, s), 7.43–7.30(4H, m), 6.91(1H, brs), 4.94(2H, s), 4.91–4.84(1H, m), 1.88–1.69(4H, m), 1.57–1.25(6H, m). |
| 162 | $^1$H-NMR(acetone-$d_6$) δ: 8.06(1H, d, J=7.9Hz), 7.50(1H, s), 7.46–7.32(3H, m), 6.67(1H, s), 6.49(1H, d, J=7.9Hz), 5.11(2H, s), 2.57(3H, s). |
| 163 | $^1$H-NMR(DMSO-$d_6$) δ: 9.10(1H, s), 7.97(1H, d, J=3.2Hz), 7.74(1H, d, J=3.2Hz), 7.58(1H, d, J=6.0Hz), 7.51(1H, s), 7.44–7.35(3H, m), 7.05(1H, d, J=6.0Hz), 5.00(2H, s). |
| 164 | $^1$H-NMR(DMSO-$d_6$) δ: 8.94(1H, s), 8.23(1H, s), 7.53(1H, d, J=6.5Hz), 7.51(1H, s), 7.44–7.35(3H, m), 7.04(1H, d, J=6.5Hz), 5.00(2H, s). |
| 166 | $^1$H-NMR(DMSO-$d_6$) δ: 8.49(1H, d, J=7.4Hz), 7.71–7.62(1H, m), 7.42–7.28(3H, m), 7.21(1H, d, J=1.9Hz), 7.06(1H, dd, J=8.3, 1.9Hz), 5.02(2H, s), 3.92(3H, s). |
| 167 | $^1$H-NMR(DMSO-$d_6$) δ: 11.80(1H, brs), 9.43(1H, d, J=4.2Hz), 8.76(1H, s), 7.68(1H, d, J=3.7Hz), 7.48(2H, d, J=6.0Hz), 7.44–7.31(3H, m), 7.00(1H, d, J=6.0Hz), 4.97(2H, s). |

TABLE 37-continued

| Example | $^1$H-NMR |
|---|---|
| 168 | $^1$H-NMR(DMSO-$d_6$) δ: 8.35(1H, d, J=7.0Hz), 7.57(1H, d, J=6.5Hz), 7.47(1H, dd, J=7.9, 1.4Hz), 7.29(1H, d, J=6.5Hz), 7.20(1H, d, J=6.0Hz), 7.18–7.13(2H, m), 5.10(2H, s), 3.87(3H, s). |
| 169 | $^1$H-NMR(DMSO-$d_6$) δ: 8.39(1H, d, J=7.0Hz), 7.63(1H, d, J=6.5Hz), 7.40(1H, dd, J=8.0, 1.3Hz), 7.32–7.24(3H, m), 7.16(1H, dd, J=8.0, 1.3Hz), 6.96(1H, td, J=7.7, 1.4Hz), 4.38–4.30(4H, m). |
| 170 | $^1$H-NMR(DMSO-$d_6$) δ: 8.93–8.92(2H, m), 8.66(1H, s), 7.52–7.47(2H, m), 7.44–7.35(4H, m), 6.97(1H, d, J=6.0Hz), 4.98(2H, s). |
| 171 | $^1$H-NMR(DMSO-$d_6$) δ: 11.81(1H, s), 10.18(1H, t, J=5.8Hz), 8.75(1H, s), 7.53–7.33(5H, m), 7.01(1H, d, J=6.0Hz), 4.97(2H, s), 3.34–3.28(2H, m), 1.59–1.46(2H, m), 0.91(3H, t, J=7.4Hz). |
| 172 | $^1$H-NMR(DMSO-$d_6$) δ: 11.80(1H, s), 10.16(1H, t, J=5.6Hz), 8.75(1H, s), 7.53–7.33(5H, m), 7.01(1H, d, J=6.0Hz), 4.97(2H, s), 3.35–3.29(2H, m), 1.55–1.28(4H, m), 0.91(3H, t, J=7.4Hz). |
| 173 | $^1$H-NMR(DMSO-$d_6$) δ: 11.81(1H, s), 10.26(1H, t, J=5.6Hz), 8.76(1H, s), 7.54–7.47(2H, m), 7.43–7.33(3H, m), 7.01(1H, d, J=6.0Hz), 4.97(2H, s), 3.18(2H, t, J=6.3Hz), 1.86–1.74(1H, m), 0.92(6H, d, J=7.0Hz). |
| 174 | 1H-NMR(DMSO-$d_6$) δ: 11.87(1H, brs), 10.44(1H, t, J=5.5Hz), 8.76(1H, s), 7.2–7.7(5H, m), 7.01(1H, d, J=6.3Hz), 5.00(2H, s), 4.17(2H, d, J=5.4Hz), 3.66(s, 3H). |
| 175 | 1H-NMR(DMSO-$d_6$) δ: 11.82(1H, s), 10.12(1H, t, J=5.7Hz), 8.76(1H, s), 7.3–7.7(5H, m), 7.01(1H, d, J=6Hz), 4.97(2H, s), 3.3–3.5(2H, m), 1.14(3H, t, J=7Hz). |
| 176 | $^1$H-NMR(DMSO-$d_6$) δ: 11.78(1H, s), 10.25(1H, d, J=5.6Hz), 8.75(1H, s), 7.56–7.44(2H, m), 7.43–7.29(3H, m), 7.01(1H, d, J=6.0Hz), 4.96(2H, s), 3.50–3.46(4H, m), 3.29(3H, s). |
| 177 | $^1$H-NMR(DMSO-$d_6$) δ: 10.35(1H, brs), 8.76(1H, s), 7.57–7.45(2H, m), 7.43–7.29(3H, m), 7.01(1H, d, J=6.5Hz), 4.97(2H, s), 4.52(2H, t, J=5.3Hz), 3.73(2H, q, J=5.6Hz). |
| 178 | $^1$H-NMR(DMSO-$d_6$) δ: 11.80(1H, s), 10.24(1H, t, J=5.6Hz), 8.75(1H, s), 7.56–7.46(2H, m), 7.45–7.30(3H, m), 7.01(1H, d, J=6.0Hz), 4.97(2H, s), 4.81(1H, t, J=5.6Hz), 3.51(2H, q, J=5.6Hz), 3.39(2H, q, J=5.6Hz). |
| 179 | $^1$H-NMR(DMSO-$d_6$) δ: 8.27(1H, d, J=7.4Hz), 7.49(1H, d, J=6.0Hz), 7.34(1H, dd, J=8.0, 1.6Hz), 7.17(1H, d, J=7.0Hz), 7.07(1H, d, J=6.0Hz), 7.01(1H, d, J=7.4Hz), 6.86(1H, t, J=7.7Hz), 5.01(2H, s). |
| 180 | $^1$H-NMR(DMSO-$d_6$) δ: 11.84(1H, brs), 10.56(1H, t, J=6.0Hz), 8.80(1H, s), 7.54–7.03(11H, m), 4.98(2H, s), 4.57(2H, d, J=6.0Hz). |
| 181 | $^1$H-NMR(DMSO-$d_6$) δ: 11.92(1H, s), 10.66(1H, t, J=6.5Hz), 8.82(1H, s), 7.53(1H, d, J=6.0Hz), 7.49(1H, s), 7.43–7.35(3H, m), 7.05(1H, d, J=6.0Hz), 4.98(2H, s), 4.34–4.14(2H, m). |
| 182 | $^1$H-NMR(DMSO-$d_6$)(mixture of two isomers)δ: 8.14(1H, s), 7.48(1H, s), 7.45–7.30(3H, m), 7.21(1H, s), 6.98–6.84(1H, m), 4.96(2H, s), 3.57–3.04(2H, m), 2.92(1.2H, s), 2.82(1.8H, s), 1.56–1.09(4H, m), 0.92(1.8H, t, J=7.2Hz), 0.77(1.2H, t, J=7.4Hz). |
| 183 | $^1$H-NMR(DMSO-$d_6$)(mixture of two isomers) δ: 8.16(0.5H, s), 8.12(0.5H, s), 7.49(1H, s), 7.44–7.29(3H, m), 7.22(1H, d, J=6.5Hz), 6.91(1H, d, J=6.0Hz), 4.96(2H, s), 3.67–3.33(4H, m), 3.29(1.5H, s), 3.17(1.5H, s), 2.96(1.5H, s), 2.89(1.5H, s). |
| 184 | $^1$H-NMR(DMSO-$d_6$) δ: 8.18(1H, s), 7.48(1H, s), 7.43–7.30(3H, m), 7.21(1H, d, J=6.0Hz), 6.91(1H, d, J=6.0Hz), 4.96(2H, s), 3.43–3.29(4H, m), 1.87–1.78(4H, m). |
| 185 | $^1$H-NMR(DMSO-$d_6$) δ: 8.18(1H, s), 7.47(1H, s), 7.44–7.29(3H, m), 7.20(1H, d, J=6.0Hz), 6.91(1H, d, J=6.5Hz), 4.96(2H, s), 3.65–3.50(6H, m), 3.26–3.17(2H, m). |
| 186 | $^1$H-NMR(DMSO-$d_6$) δ: 8.46–8.45(1H, m), 7.67–7.66(1H, m), 7.42(1H, d, J=8.3Hz), 7.39–7.36(2H, m), 7.23(1H, d, J=1.9Hz), 6.98(1H, dd, J=7.9, 1.9Hz), 5.06(2H, s), 3.86(3H, s). |
| 188 | $^1$H-NMR(DMSO-$d_6$) δ: 16.33(1H, brs), 12.00(1H, brs), 9.05(1H, s), 7.54–7.50(2H, m), 7.44–7.35(3H, m), 7.03(1H, d, J=6.5Hz), 5.00(2H, s). |
| 190 | $^1$H-NMR(DMSO-$d_6$) δ: 7.94(1H, s), 7.47(1H, brs), 7.42–7.31(3H, m), 7.25(1H, d, J=6.0Hz), 6.86(1H, d, J=6.5Hz), 4.96(2H, s), 3.49(2H, s), 3.06(3H, s), 2.82(3H, s). |
| 192 | $^1$H-NMR(DMSO-$d_6$) δ: 11.80(1H, brs), 10.26(1H, t, J=5.6Hz), 8.76(1H, s), 7.55–7.29(5H, m), 7.01(1H, d, J=6.5Hz), 4.97(2H, s), 4.83(1H, d, J=4.2Hz), 3.82–3.69(1H, m), 3.46–3.14(2H, m), 1.08(3H, d, J=6.0Hz). |
| 193 | 1H-NMR(DMSO-$d_6$) δ: 11.85(1H, brs), 10.3–10.5(1H, m), 8.76(1H, s), 7.3–7.7(5H, m), 7.01(1H, d, J=6.6Hz), 4.98(2H, s), 4.06(2H, d, J=5.1Hz). |
| 194 | 1H-NMR(DMSO-$d_6$) δ: 11.8(1H, brs), 10.4–10.6(1H, m), 8.75(1H, s), 7.3–7.6(5H, m), 6.9–7.1(1H, m), 4.96(2H, s), 4.21(2H, d, J=4Hz), 2.98(3H, s), 2.87(3H, s). |
| 195 | 1H-NMR(DMSO-$d_6$) δ: 11.8(1H, brs), 10.3–10.5(1H, m), 8.76(1H, s), 7.8–8.0(1H, m), 7.3–7.6(5H, m), 6.9–7.1(1H, m), 4.97(2H, s), 3.96(2H, d, J=5.4Hz), 2.61(3H, d, J=5Hz). |
| 196 | 1H-NMR(DMSO-$d_6$) δ: 12.64(1H, s), 11.9(1H, brs), 8.90(1H, s), 7.70(2H, d, J=7.8Hz), 7.3–7.65(7H, m), 7.0–7.2(2H, m), 5.0(2H, s). |
| 197 | $^1$H-NMR(DMSO-$d_6$) δ: 8.73(1H, s), 8.24(1H, s), 7.49(1H, s), 7.44–7.34(5H, m), 6.97(1H, d, J=6.5Hz), 4.97(2H, s). |
| 198 | $^1$H-NMR(DMSO-$d_6$)(mixture of two isomers) δ: 8.21(0.5H, s), 8.18(0.5H, s), 7.48(1H, s), 7.43–7.30(3H, m), 7.28–7.20(1H, m), 6.93(1H, d, J=6.0Hz), 4.96(2H, s), 4.31(0.5H, brs), 4.23(0.5H, brs), 3.55–3.01(2H, m), 2.02–1.71(2H, m). |
| 199 | $^1$H-NMR($CF_3COOD$) δ: 9.44(1H, s), 7.72(1H, d, J=6.0Hz), 7.57–7.33(5H, m), 5.31(2H, s), 4.80(2H, s), 2.59(3H, s). |

TABLE 37-continued

| Example | $^1$H-NMR |
|---|---|
| 200 | $^1$H-NMR(DMSO-$d_6$) δ: 10.52(1H, s), 8.44(1H, d, J=7.4Hz), 7.63(1H, d, J=6.0Hz), 7.58(2H, d, J=7.4Hz), 7.38–7.23(4H, m), 7.08(1H, t, J=7.4Hz), 4.78(2H, s). |
| 201 | $^1$H-NMR(DMSO-$d_6$) δ: 8.25–8.18(1H, m), 7.47(1H, s), 7.45–7.31(3H, m), 7.30–7.21(1H, m), 6.98–6.89(1H, m), 4.96(2H, s), 3.95–3.68(4H, m), 2.70–2.50(2H, m). |
| 202 | $^1$H-NMR(DMSO-$d_6$) δ: 8.45(1H, d, J=7.2Hz), 7.63(1H, d, J=6.4Hz), 7.37–7.30(4H, m), 7.09(1H, d, J=9.0Hz), 4.98(2H, s), 3.84(3H, s). |
| 203 | $^1$H-NMR(DMSO-$d_6$) δ: 11.65(1H, brs), 8.94(1H, brs), 8.18(1H, s), 7.48(1H, brs), 7.43–7.32(4H, m), 6.96(1H, d, J=6.5Hz), 4.98(2H, s), 3.02(3H, s). |
| 204 | $^1$H-NMR(DMSO-$d_6$) δ: 11.69(1H, brs), 8.48(1H, s), 7.47(1H, brs), 7.40–7.33(4H, m), 6.93(1H, d, J=6.0Hz), 4.94(2H, s), 2.61(3H, s). |
| 206 | $^1$H-NMR(DMSO-$d_6$) δ: 7.94(1H, d, J=7.4Hz), 7.45(2H, d, J=7.1Hz), 7.33(2H, t, J=7.4Hz), 7.26(1H, t, J=7.2Hz), 7.20(1H, d, J=6.5Hz), 6.76(1H, d, J=6.0Hz), 6.67(1H, d, J=16.2Hz), 6.48(1H, d, J=7.4Hz), 6.36(1H, dt, J=16.2, 6.0Hz), 4.53(2H, dd, J=6.0, 0.9Hz). |
| 207 | $^1$H-NMR(DMSO-$d_6$) δ: 11.82(1H, s), 10.00(1H, d, J=4.6Hz), 8.76(1H, s), 7.66(1H, d, J=7.4Hz), 7.52(1H, d, J=6.5Hz), 7.42(2H, dd, J=6.5, 1.4Hz), 7.01(1H, d, J=6.0Hz), 4.95(2H, s), 2.86(3H, d, J=4.6Hz). |
| 208 | $^1$H-NMR(DMSO-$d_6$) δ: 8.14(1H, s), 7.65(1H, d, J=7.4Hz), 7.42(2H, dd, J=6.7, 1.6Hz), 7.19(1H, d, J=6.5Hz), 6.90(1H, d, J=6.5Hz), 4.94(2H, s), 2.95(3H, s), 2.85(3H, s). |
| 209 | $^1$H-NMR(DMSO-$d_6$) δ: 11.8(1H, brs), 10.3–10.5(1H, m), 8.77(1H, s), 7.3–7.6(5H, m), 7.01(1H, d, J=6.3Hz), 4.97(2H, s), 3.75–3.9(2H, m), 3.2–3.5(2H, m), 3.02(3H, s). |
| 210 | $^1$H-NMR(DMSO-$d_6$) δ: 11.84(1H, s), 10.18(1H, t, J=6.0Hz), 8.75(1H, s), 7.54–7.46(2H, m), 7.43–7.32(3H, m), 7.01(1H, d, J=6.0Hz), 4.97(2H, s), 3.52–3.32(6H, m), 2.18(2H, t, J=8.1Hz), 1.97–1.84(2H, m). |
| 211 | $^1$H-NMR(DMSO-$d_6$) δ: 11.68(1H, brs), 8.29(1H, s), 7.47(1H, brs), 7.42–7.30(3H, m), 7.26(1H, d, J=6.5Hz), 6.93(1H, d, J=6.0Hz), 4.97(2H, s), 3.18(3H, s), 3.07(3H, s). |
| 212 | $^1$H-NMR(DMSO-$d_6$) δ: 8.45(1H, d, J=7.4Hz), 7.67(1H, d, J=6.0Hz), 7.37(2H, t, J=7.0Hz), 7.06(1H, d, J=1.4Hz), 7.01–6.97(2H, m), 5.04(2H, s), 3.78(3H, s). |
| 213 | $^1$H-NMR(DMSO-$d_6$) δ: 11.90(1H, brs), 10.70(1H, t, J=6.0Hz), 8.78(1H, s), 8.67(2H, d, J=6.0Hz), 7.61(2H, d, J=5.6Hz), 7.52(1H, d, J=6.5Hz), 7.49(1H, brs), 7.44–7.33(3H, m), 7.04(1H, d, J=6.5Hz), 4.98(2H, s), 4.73(2H, d, J=6.0Hz). |
| 214 | $^1$H-NMR(DMSO-$d_6$) δ: 11.83(1H, brs), 10.55(1H, t, J=5.9Hz), 8.79(1H, brs), 7.49(1H, brs), 7.43–7.31(6H, m), 7.15(3H, t, J=9.0Hz), 4.97(2H, s), 4.54(3H, d, J=5.9Hz). |
| 215 | $^1$H-NMR(DMSO-$d_6$) δ: 12.32(1H, brs), 8.71(1H, s), 7.90(1H, d, J=3.2Hz), 7.64(1H, d, J=3.2Hz), 7.48(1H, s), 7.45–7.33(3H, m), 4.76(2H, s), 4.47(2H, t, J=5.6Hz), 3.80(2H, t, J=5.6Hz). |
| 216 | $^1$H-NMR(DMSO-$d_6$) δ: 7.97(1H, s), 7.49(1H, s), 7.45–7.24(4H, m), 6.87(1H, d, J=6.0Hz), 5.23(1H, t, J=3.7Hz), 4.96(2H, s), 4.42(2H, d, J=3.7Hz). |
| 217 | $^1$H-NMR(DMSO-$d_6$) δ: 8.09(1H, s), 7.67(1H, d, J=7.5Hz), 7.45–7.40(2H, m), 7.23(1H, d, 6.3Hz), 6.94(1H, d, J=6.2Hz), 4.95(2H, s), 1.19(9H, s). |
| 218 | $^1$H-NMR(DMSO-$d_6$) δ: 9.09(1H, s), 8.98(1H, s), 8.51(1H, s), 7.50(1H, s), 7.44–7.34(3H, m), 7.25(1H, d, J=6.5Hz), 7.01(1H, d, J=6.5Hz), 5.00(2H, s). |
| 220 | $^1$H-NMR(DMSO-$d_6$) δ: 7.81(1H, s), 7.45(1H, brs), 7.43–7.30(3H, m), 4.72(2H, s), 4.29–4.20(2H, m), 3.77–3.69(2H, m), 2.93(3H, s), 2.85(3H, s). |
| 221 | $^1$H-NMR(DMSO-$d_6$) δ: 7.74(1H, s), 7.62(1H, dd, J=7.4, 1.4Hz), 7.43–7.38(2H, m), 4.69(2H, s), 4.25(2H, t, J=5.6Hz), 3.73(2H, t, J=5.6Hz), 1.20(9H, s). |
| 224 | $^1$H-NMR(DMSO-$d_6$) δ: 10.48(1H, brs), 8.43(1H, d, J=7.0Hz), 7.62(1H, d, J=6.0Hz), 7.30–7.19(3H, m), 6.90(1H, d, J=2.3Hz), 6.85(1H, dd, J=8.1, 2.3Hz), 4.95(2H, s). |
| 225 | $^1$H-NMR(DMSO-$d_6$) δ: 12.29(1H, brs), 8.70(1H, s), 7.89(1H, d, J=3.2Hz), 7.65(1H, s), 7.63(2H, d, J=3.2Hz), 7.41(2H, d, J=8.8Hz), 4.73(2H, s), 4.46(2H, t, J=5.6Hz), 3.79(2H, t, J=5.6Hz). |
| 226 | $^1$H-NMR(DMSO-$d_6$) δ: 8.25(1H, d, J=7.0Hz), 7.63–7.37(6H, m), 7.05–6.96(2H, m), 4.38(2H, s), 3.22(3H, s). |
| 227 | $^1$H-NMR(DMSO-$d_6$) δ: 12.25(1H, s), 9.86(1H, q, J=4.6Hz), 8.37(1H, s), 7.63(1H, d, J=7.4Hz), 7.44–7.37(2H, m), 4.70(2H, s), 4.42–4.36(2H, m), 3.79–3.71(2H, m), 2.82(3H, d, J=4.6Hz). |
| 228 | $^1$H-NMR(DMSO-$d_6$) δ: 7.81(1H, s), 7.62(1H, dd, J=6.0, 3.0Hz), 7.42–7.40(2H, m), 4.70(2H, s), 4.23(2H, t, J=6.0Hz), 3.73(2H, t, J=5.7Hz), 2.93(6H, s), 2.86(6H, s). |
| 229 | $^1$H-NMR(DMSO-$d_6$) δ: 8.05(1H, s), 7.50–7.46(1H, m), 7.43–7.31(3H, m), 7.26(1H, d, J=6.0Hz), 6.91(1H, d, J=6.0Hz), 4.95(2H, s), 4.16(2H, s), 1.97(3H, s), 1.25(6H, s). |
| 230 | $^1$H-NMR(DMSO-$d_6$) δ: 11.64(1H, brs), 7.95(1H, s), 7.50–7.46(1H, m), 7.43–7.32 (3H, m), 7.24(1H, d, J=6.0Hz), 6.91(1H, d, J=6.0Hz), 4.98–4.90(3H, m), 3.49(2H, d, J=4.6Hz), 1.13(6H, s). |
| 231 | $^1$H-NMR(DMSO-$d_6$) δ: 11.65(1H, brs), 9.89(1H, d, J=1.9Hz), 8.89(1H, s), 8.72–8.67(1H, m), 8.59(1H, d, J=2.3Hz), 7.50(2H, s), 7.44–7.33(3H, m), 6.96(1H, d, J=6.0Hz), 4.97(2H, s). |
| 232 | 1H-NMR(DMSO-$d_6$) δ: 8.39(1H, s), 8.00(1H, s), 7.50(1H, s), 7.2–7.5(4H, m), 6.95(1H, d, J=6.3Hz), 4.99(2H, s), 3.76(3H, s). |
| 233 | $^1$H-NMR(DMSO-$d_6$) δ: 10.37(1H, t, J=6.0Hz), 8.77(1H, s), 7.52(1H, d, J=6.5Hz), 7.49(1H, s), 7.42–7.33(3H, m), 7.02(1H, d, J=6.0Hz), 4.97(2H, s), 4.60(1H, t, J=5.1Hz), 4.48(1H, t, J=5.1Hz), 3.69(1H, q, J=5.1Hz), 3.62(1H, q, J=5.1Hz). |

TABLE 37-continued

| Example | $^1$H-NMR |
|---|---|
| 234 | $^1$H-NMR(DMSO-$d_6$) δ (mixture of two isomers): 8.27(0.3H, s), 8.25(0.7H, s), 7.51–7.14(10H, m), 6.92(0.7H, d, J=5.6Hz), 6.89(0.3H, d, J=6.5Hz), 4.97(1.4H, s), 4.95(0.6H, s), 4.68(1.4H, s), 4.39(0.6H, s), 2.82(2.1H, s), 2.80(0.9H, s). |
| 235 | $^1$H-NMR(DMSO-$d_6$) δ: 11.66(1H, brs), 8.20(1H, s), 7.48(1H, brs), 7.44–7.16(9H, m), 6.89(1H, d, J=6.0Hz), 4.96(2H, s). |
| 236 | $^1$H-NMR(DMSO-$d_6$) δ: 11.88(1H, brs), 8.41(1H, s), 7.83–7.76(2H, m), 7.57–7.48(4H, m), 7.46(1H, brs), 7.41–7.30(3H, m), 6.96(1H, d, J=6.0Hz), 5.00(1H, d, J=15.3Hz), 4.90(1H, d, J=15.3Hz). |
| 237 | $^1$H-NMR(DMSO-$d_6$) δ: 11.90(1H, brs), 8.85(1H, s), 7.99(2H, d, J=7.4Hz), 7.68(1H, t, J=7.4Hz), 7.59(2H, t, J=7.7Hz), 7.46(1H, d, J=6.5Hz), 7.45(1H, brs), 7.42–7.29(3H, m), 6.97(1H, d, J=6.5Hz), 4.94(2H, s). |
| 238 | $^1$H-NMR(DMSO-$d_6$) δ: 12.1(1H, brs), 7.73(1H, s), 7.6–7.7(2H, m), 7.3–7.5(1H, m), 4.71(2H, s), 4.2–4.3(2H, m), 3.7–3.8(2H, m), 1.20(9H, s). |
| 239 | $^1$H-NMR(DMSO-$d_6$) δ: 11.59(1H, brs), 9.31(1H, s), 9.13(1H, s), 7.49(1H, s), 7.45(1H, d, J=6.0Hz), 7.42–7.31(3H, m), 6.98(1H, d, J=6.0Hz), 4.98(2H, s), 3.33(4H, s), 2.94(1H, sept, J=7.0Hz), 1.09(6H, d, J=7.0Hz). |
| 240 | $^1$H-NMR(DMSO-$d_6$) δ: 11.58(1H, brs), 9.45(1H, s), 9.08(1H, s), 7.67(1H, d, J=6.0Hz), 7.47(1H, d, J=6.5Hz), 7.45–7.40(2H, m), 6.96(1H, d, J=6.0Hz), 4.96(2H, s), 2.17(3H, s). |
| 241 | $^1$H-NMR(DMSO-$d_6$) δ: 7.95(1H, s), 7.67(1H, d, J=7.9Hz), 7.43(2H, dd, J=7.9, 0.9Hz), 7.05(1H, s), 4.96(2H, s), 4.46(2H, s), 1.20(9H, s). |
| 243 | $^1$H-NMR(DMSO-$d_6$) δ: 11.60(1H, s), 9.60(1H, s), 9.09(1H, s), 7.49–7.22(10H, m), 6.96(1H, d, J=6.5Hz), 4.97(2H, s), 3.86(2H, s). |
| 245 | $^1$H-NMR(DMSO-$d_6$) δ: 7.91(1H, s), 7.48(1H, brs), 7.43–7.28(4H, m), 6.92(1H, d, J=5.9Hz), 4.98(2H, s), 2.35(3H, s). |
| 246 | $^1$H-NMR(DMSO-$d_6$) δ: 12.01(1H, brs), 8.65(1H, s), 7.50–7.44(2H, m), 7.44–7.31(3H, m), 6.99(1H, d, J=6.5Hz), 4.96(2H, s), 3.27(3H, s). |
| 247 | $^1$H-NMR(DMSO-$d_6$) δ: 11.91(1H, brs), 8.21(1H, s), 7.55(1H, d, J=6.0Hz), 7.48(1H, brs), 7.44–7.32(3H, m), 6.98(1H, d, J=6.0Hz), 5.00(1H, d, J=15.3Hz), 4.95(1H, d, J=15.3Hz), 2.82(3H, s). |
| 248 | $^1$H-NMR(DMSO-$d_6$) δ: 12.29(1H, s), 8.63(1H, s), 7.56(1H, s), 7.48(1H, s), 7.45–7.33(3H, m), 4.75(2H, s), 4.44(2H, t, J=5.6Hz), 3.79(2H, t, J=5.6Hz), 2.47(3H, s). |
| 250 | $^1$H-NMR(DMSO-$d_6$) δ: 8.46(1H, d, J=7.4Hz), 7.69(1H, d, J=6.5Hz), 7.50–7.45(2H, m), 7.42–7.38(2H, m), 7.23–7.21(2H, m), 5.07(2H, s). |
| 252 | $^1$H-NMR($CDCl_3$) δ: 9.11(1H, s), 7.97(1H, d, J=3.4Hz), 7.74(1H, d, J=3.4Hz), 7.58(1H, d, J=6.4Hz), 7.49(2H, dd, J=8.7, 5.7Hz), 7.22(2H, t, J=8.9Hz), 7.05(1H, d, J=6.4Hz), 4.98(2H, s). |
| 253 | $^1$H-NMR(DMSO-$d_6$) δ: 11.91(1H, s), 10.01(1H, d, J=4.5Hz), 8.77(1H, s), 7.53(1H, d, J=6.4Hz), 7.47(2H, dd, J=8.3, 5.7Hz), 7.21(2H, t, J=8.9Hz), 7.02(1H, d, J=6.0Hz), 4.95(2H, s), 2.86(3H, d, J=4.9Hz). |
| 254 | $^1$H-NMR(DMSO-$d_6$) δ: 8.08(1H, s), 7.35–7.25(2H, m), 7.24–7.13(2H, m), 6.94(1H, d, J=6.5Hz), 3.83(2H, t, J=7.4Hz), 2.79(2H, t, J=7.7Hz), 1.99–1.83(2H, m), 1.20(9H, s). |
| 255 | $^1$H-NMR(DMSO-$d_6$) δ: 12.30(1H, s), 8.64(1H, s), 7.48(1H, s), 7.44–7.34(3H, m), 7.18(1H, d, J=0.9Hz), 4.75(2H, s), 4.47(2H, t, J=5.6Hz), 3.79(2H, t, J=5.6Hz), 2.42(3H, s). |
| 256 | $^1$H-NMR(DMSO-$d_6$) δ: 11.60(1H, s), 9.34(1H, s), 9.13(1H, s), 7.51–7.45(2H, m), 7.43–7.34(3H, m), 6.97(1H, d, J=6.5Hz), 4.98(2H, s), 2.48(2H, q, J=10.0Hz), 1.60(2H, q, J=7.3Hz), 0.91(3H, t, J=7.4Hz). |
| 257 | $^1$H-NMR(DMSO-$d_6$) δ: 11.73(1H, s), 9.52(1H, s), 9.21(1H, s), 7.96(2H, d, J=6.8Hz), 7.67–7.56(4H, m), 7.51(1H, s), 7.44–7.36(3H, m), 7.04(1H, d, J=6.5Hz), 5.01(2H, s). |
| 258 | $^1$H-NMR(DMSO-$d_6$) δ: 11.59(1H, s), 9.47(1H, s), 9.13(1H, s), 7.50–7.46(2H, m), 7.43–7.34(3H, m), 7.29–7.24(4H, m), 7.19–7.14(1H, m), 6.97(1H, d, J=6.0Hz), 4.98(2H, s), 2.92–2.81(4H, m). |
| 259 | $^1$H-NMR(DMSO-$d_6$) δ: 11.67(1H, brs), 8.33(1H, s), 7.49(1H, s), 7.44–7.33(3H, m), 7.13(1H, d, J=6.0Hz), 6.94(1H, d, J=6.0Hz), 5.02–4.95(2H, m), 3.00(3H, br s), 1.78(3H, brs). |
| 260 | $^1$H-NMR(DMSO-$d_6$) δ: 11.70(1H, s), 9.36(1H, s), 9.11(1H, s), 7.55(1H, d, J=6.0Hz), 7.50(1H, s), 7.44–7.34(3H, m), 7.00(1H, d, J=6.0Hz), 4.99(2H, s), 4.09(2H, s), 3.43(3H, s). |
| 261 | $^1$H-NMR(DMSO-$d_6$) δ: 12.19(1H, brs), 8.26(1H, s), 7.45(1H, brs), 7.43–7.30(3H, m), 4.71(2H, s), 4.34–4.26(2H, m), 3.76–3.68(2H, m), 3.52(3H, s). |
| 262 | $^1$H-NMR(DMSO-$d_6$) δ: 11.58(1H, brs), 8.92(1H, s), 7.97(1H, s), 7.51–7.47(2H, m), 7.43–7.32(3H, m), 6.99(1H, d, J=6.0Hz), 4.98(2H, s), 2.97(6H, s). |
| 263 | $^1$H-NMR(DMSO-$d_6$) δ: 11.59(1H, brs), 8.70(1H, s), 8.44(1H, s), 7.51–7.46(2H, m), 7.43–7.31(3H, m), 6.98(1H, d, J=6.5Hz), 4.98(2H, s), 3.70(3H, s). |
| 264 | $^1$H-NMR(DMSO-$d_6$) δ: 12.45(1H, s), 8.71(1H, s), 7.89(1H, d, J=3.2Hz), 7.63(1H, d, J=3.2Hz), 7.37–7.13(3H, m), 4.45(2H, t, J=5.6Hz), 3.94(2H, t, J=5.6Hz), 3.60(2H, t, J=7.4Hz), 2.79(2H, t, J=7.4Hz), 1.94–1.78(2H, m). |
| 265 | $^1$H-NMR(DMSO-$d_6$) δ: 11.77(1H, brs), 9.68(1H, s), 9.12(1H, s), 7.58(1H, d, J=6.0Hz), 7.50(1H, s), 7.43–7.32(3H, m), 7.03(1H, d, J=6.0Hz), 4.99(2H, s), 2.44(3H, s). |
| 266 | $^1$H-NMR(DMSO-$d_6$) δ: 10.45(1H, brs), 8.41(1H, s), 7.46–7.25(9H, m), 4.73(2H, s), 4.54(2H, d, J=6.0Hz), 4.46–4.35(2H, m), 3.81–3.70(2H, m). |
| 267 | 1H-NMR(DMSO-$d_6$) δ: 8.36(1H, s), 7.64(1H, d, J=2.1Hz), 7.3–7.5(4H, m), 6.85–7.0(1H, m), 4.75(2H, s), 4.25–4.45(2H, m), 3.7–3.9(2H, m). |

TABLE 37-continued

| Example | $^1$H-NMR |
|---|---|
| 268 | 1H-NMR(DMSO-$d_6$) δ: 12.22(1H, brs), 9.14(1H, s), 8.7–9.0(3H, m), 7.3–7.6(4H, m), 4.75(2H, s), 4.4–4.6(2H, m), 3.7–3.9(2H, m). |
| 269 | $^1$H-NMR(DMSO-$d_6$) δ: 12.25(1H, s), 10.49(1H, t, J=5.8Hz), 8.47(1H, s), 8.13–8.12(1H, m), 7.97–7.96(1H, m), 7.88–7.86(1H, m), 7.57–7.55(1H, m), 7.51–7.47(3H, m), 7.43–7.33(3H, m), 7.29–7.22(1H, m), 5.01(2H, d, J=5.6Hz), 4.73(2H, s), 4.45–4.42(2H, m), 3.77–3.76(2H, m). |
| 270 | $^1$H-NMR(DMSO-$d_6$) δ: 12.30(1H, s), 11.18(1H, d, J=7.9Hz), 8.39(1H, s), 7.46(1H, s), 7.38–7.34(10H, m), 7.28–7.23(2H, m), 6.28(1H, d, J=7.9Hz), 4.74(2H, s), 4.41(2H, t, J=5.6Hz), 3.76(2H, t, J=5.6Hz). |
| 271 | $^1$H-NMR(DMSO-$d_6$) δ: 9.20(2H, d, J=5.1Hz), 9.10(1H, s), 7.86(1H, t, J=5.3Hz), 7.51(1H, s), 7.46–7.34(3H, m), 4.79(2H, s), 4.66(2H, t, J=5.6Hz), 3.87(2H, t, J=5.6Hz). |
| 272 | $^1$H-NMR(DMSO-$d_6$) δ: 11.95(1H, s), 7.60(1H, s), 7.45–7.22(8H, m), 7.21–7.11(1H, m), 4.69(2H, s), 4.22–4.12(2H, m), 3.73–3.62(2H, m), 1.54(6H, s). |
| 273 | $^1$H-NMR(DMSO-$d_6$) δ: 12.19(1H, brs), 10.39(1H, t, J=5.6Hz), 8.41(1H, s), 7.46(1H, s), 7.43–7.30(5H, m), 7.26–7.18(2H, m), 4.73(2H, s), 4.49(2H, d, J=6.0Hz), 4.41(2H, t, J=5.6Hz), 3.76(2H, t, J=5.6Hz), 1.27(9H, s). |
| 274 | $^1$H-NMR(DMSO-$d_6$) δ: 9.28(1H, s), 9.13(1H, s), 7.49(1H, s), 7.47–7.33(4H, m), 6.97(1H, d, J=6.0Hz), 4.98(2H, s), 3.19–3.06(1H, m), 1.96–1.43(8H, m). |
| 275 | $^1$H-NMR(DMSO-$d_6$) δ: 11.60(1H, brs), 9.63(1H, s), 9.08(1H, s), 7.48(1H, s), 7.43(1H, d, J=6.5Hz), 7.41–7.31(5H, m), 7.20–7.07(2H, m), 6.95(1H, d, J=6.0Hz), 4.97(2H, s), 3.85(2H, s). |
| 276 | $^1$H-NMR(DMSO-$d_6$) δ: 11.67(1H, brs), 9.11(1H, s), 8.85(1H, s), 7.52–7.46(2H, m), 7.43–7.33(3H, m), 7.01(1H, d, J=6.0Hz), 4.99(2H, s), 1.26(9H, s). |
| 277 | $^1$H-NMR(DMSO-$d_6$) δ: 11.59(1H, brs), 9.11(1H, s), 8.41(1H, s), 7.50–7.29(10H, m), 7.00(1H, d, J=6.5Hz), 4.97(2H, s), 1.61(6H, s). |
| 278 | $^1$H-NMR($CDCl_3$) δ: 11.72(1H, brs), 9.39(1H, s), 9.21(1H, s), 7.99(2H, dd, J=8.6, 5.3Hz), 7.41–7.32(3H, m), 7.29–7.15(3H, m), 6.73(1H, d, J=6.0Hz), 6.35(1H, d, J=6.0Hz), 4.98(2H, s). |
| 279 | $^1$H-NMR(DMSO-$d_6$) δ: 11.76(1H, brs), 10.85(1H, s), 9.32(1H, s), 8.79(1H, d, J=4.6Hz), 8.19(1H, d, J=7.9Hz), 8.11(1H, td, J=7.5, 1.5Hz), 7.74–7.70(1H, m), 7.59(1H, d, J=6.0Hz), 7.51(1H, s), 7.44–7.35(3H, m), 7.04(1H, d, J=6.5Hz), 5.01(2H, s). |
| 280 | $^1$H-NMR(DMSO-$d_6$) δ: 12.01(1H, brs), 8.19(1H, brs), 7.65(1H, brs), 7.54–7.32(6H, m), 5.10(2H, s), 3.67(1H, brs), 1.22(6H, d, J=6.0Hz). |
| 281 | $^1$H-NMR(DMSO-$d_6$) δ: 8.12(1H, brs), 7.47(1H, brs), 7.44–7.31(5H, m), 7.10(1H, brs), 5.01(2H, s), 3.38(4H, q, J=7.0Hz), 1.02(6H, t, J=7.0Hz). |
| 282 | $^1$H-NMR(DMSO-$d_6$) δ: 9.05(1H, s), 8.82(1H, d, J=5.6Hz), 8.58(1H, d, J=8.3Hz), 8.44(1H, t, J=7.7Hz), 7.79(1H, t, J=6.5Hz), 7.50(1H, s), 7.46–7.33(3H, m), 4.78(2H, s), 4.49(2H, t, J=5.6Hz), 3.83(2H, t, J=5.6Hz). |
| 284 | $^1$H-NMR(DMSO-$d_6$) δ: 11.60(1H, brs), 9.18(1H, s), 9.13(1H, s), 7.52–7.44(2H, m), 7.42–7.29(3H, m), 6.96(1H, d, J=6.0Hz), 4.98(2H, s), 2.41(1H, t, J=7.0Hz), 2.03–1.87(2H, m), 0.97–0.81(12H, m). |
| 285 | $^1$H-NMR(DMSO-$d_6$) δ: 8.18(1H, s), 7.69(1H, d, J=6.0Hz), 7.54(1H, d, J=6.0Hz), 7.49(1H, s), 7.45–7.33(3H, m), 5.11(2H, s), 3.23(2H, q, J=7.2Hz), 1.19(3H, t, J=7.2Hz). |
| 286 | $^1$H-NMR(DMSO-$d_6$) δ: 11.72(1H, brs), 9.82(1H, s), 9.16(1H, s), 9.11(1H, d, J=2.3Hz), 8.80(1H, dd, J=4.6, 1.4Hz), 8.35(1H, td, J=1.9, 7.9Hz), 7.61(1H, dd, J=7.9, 3.2Hz), 7.55(1H, d, J=6.0Hz), 7.52(1H, s), 7.42–7.37(3H, m), 7.03(1H, d, J=5.6Hz), 5.01(2H, s). |
| 287 | $^1$H-NMR(DMSO-$d_6$) δ: 11.74(1H, brs), 9.86(1H, s), 9.15(1H, s), 8.83(2H, dd, J=4.6, 1.4Hz), 7.92(2H, q, J=2.2Hz), 7.55(1H, d, J=6.0Hz), 7.52(1H, s), 7.44–7.36(3H, m), 7.04(1H, d, J=6.0Hz), 5.01(2H, s). |
| 288 | $^1$H-NMR(DMSO-$d_6$) δ: 11.75(1H, brs), 9.38(1H, s), 9.14(1H, s), 8.02(1H, s), 7.57(1H, d, J=6.0Hz), 7.51(1H, s), 7.44–7.34(4H, m), 7.04(1H, d, J=6.0Hz), 6.75(1H, dd, J=3.2, 2.3Hz), 5.01(2H, s). |
| 289 | $^1$H-NMR(DMSO-$d_6$) δ: 11.70(1H, brs), 9.48(1H, s), 9.04(1H, s), 7.99(1H, dd, J=3.7, 0.9Hz), 7.90(1H, dd, J=5.1, 0.9Hz), 7.51–7.49(2H, m), 7.43–7.34(3H, m), 7.23(1H, dd, J=4.6, 3.7Hz), 7.01(1H, d, J=6.0Hz), 4.99(2H, s). |
| 290 | $^1$H-NMR(DMSO-$d_6$) δ: 9.14(1H, dd, J=4.9, 1.6Hz), 8.78(1H, dd, J=8.8, 1.9Hz), 8.73(1H, s), 7.76(1H, q, J=4.5Hz), 7.48(1H, s), 7.44–7.31(3H, m), 4.75(2H, s), 4.44(2H, t, J=5.6Hz), 3.79(1H, t, J=5.6Hz). |
| 292 | $^1$H-NMR(DMSO-$d_6$) δ: 12.22(1H, s), 8.71(1H, s), 7.89(1H, d, J=3.2Hz), 7.63(1H, d, J=3.2Hz), 7.55(1H, td, J=7.9, 1.4Hz), 7.45(1H, td, J=7.9, 1.4Hz), 7.23(1H, td, J=7.9, 0.9Hz), 4.81(2H, s), 4.47(2H, t, J=5.6Hz), 3.83(2H, t, J=5.6Hz). |
| 293 | $^1$H-NMR(DMSO-$d_6$) δ: 12.34(1H, s), 8.70(1H, s), 7.89(1H, d, J=3.2Hz), 7.63(1H, d, J=3.2Hz), 7.44–7.40(4H, m), 4.73(2H, s), 4.45–4.44(2H, m), 3.77–3.76(2H, m). |
| 294 | $^1$H-NMR(DMSO-$d_6$) δ: 12.27(1H, s), 8.71(1H, s), 7.89–7.25(1H, m), 7.63(1H, d, J=3.2Hz), 7.58(1H, t, J=7.9Hz), 7.47(1H, dd, J=10.2, 1.9Hz), 7.26(1H, dd, J=4.9, 2.4Hz), 4.74(2H, s), 4.47–4.46(2H, m), 3.80–3.78(2H, m). |
| 295 | $^1$H-NMR(DMSO-$d_6$) δ: 12.36(1H, s), 8.71(1H, s), 7.89(1H, d, J=3.2Hz), 7.63(1H, d, J=3.2Hz), 7.31(1H, d, J=7.9Hz), 7.12(1H, d, J=2.6Hz), 6.99(1H, dd, J=8.1, 2.1Hz), 4.64(2H, s), 4.45(2H, t, J=5.6Hz), 3.85(3H, s), 3.77(2H, t, J=5.6Hz). |
| 296 | $^1$H-NMR(DMSO-$d_6$) δ: 11.68(1H, brs), 9.13(1H, s), 9.03(1H, s), 7.56(1H, d, J=6.0Hz), 7.50(1H, s), 7.43–7.34(3H, m), 7.09(1H, t, J=2.1Hz), 7.02(1H, d, J=6.0Hz), 6.90(1H, dd, J=1.9, 4.2Hz), 6.14(1H, dd, J=1.4, 4.2Hz), 5.00(2H, s), 3.91(3H, s). |

TABLE 37-continued

| Example | $^1$H-NMR |
|---|---|
| 297 | $^1$H-NMR(DMSO-$d_6$) δ: 8.73(1H, s), 7.90(1H, d, J=3.4Hz), 7.64(1H, d, J=3.4Hz), 7.33–7.30(4H, m), 4.45–4.43(2H, m), 3.84–3.81(2H, m), 2.65–2.62(2H, m), 1.89–1.87(2H, m). |
| 298 | $^1$H-NMR(DMSO-$d_6$) δ: 8.73(1H, s), 7.90(1H, d, J=3.2Hz), 7.64(1H, d, J=3.2Hz), 7.42–7.41(2H, m), 7.30–7.22(2H, m), 4.46(2H, t, J=5.6Hz), 3.83(2H, t, J=5.6Hz), 3.60(2H, t, J=7.2Hz), 2.75(2H, t, J=7.9Hz), 1.94–1.89(2H, m). |
| 299 | $^1$H-NMR(DMSO-$d_6$) δ: 8.73(1H, s), 7.90(1H, d, J=3.2Hz), 7.64(1H, d, J=3.2Hz), 7.34–7.31(2H, m), 7.24–7.23(2H, m), 4.45(2H, t, J=5.6Hz), 3.81(2H, t, J=5.6Hz), 3.56(2H, t, J=7.0Hz), 2.65(2H, t, J=7.9Hz), 1.95–1.87(2H, m). |
| 300 | $^1$H-NMR(DMSO-$d_6$) δ: 8.80(1H, s), 7.49(1H, s), 7.43–7.35(3H, m), 4.76(2H, s), 4.52(2H, t, J=5.6Hz), 3.82(2H, t, J=5.6Hz), 2.60(3H, s). |
| 301 | $^1$H-NMR(DMSO-$d_6$) δ: 12.35(1H, s), 8.71(1H, s), 8.49(1H, q, J=4.6Hz), 7.90(1H, d, J=3.2Hz), 7.64(1H, d, J=3.2Hz), 7.49(1H, dd, J=9.7, 5.6Hz), 7.32–7.26(2H, m), 4.84(2H, s), 4.45(2H, t, J=5.6Hz), 3.72(2H, t, J=5.6Hz), 2.75(3H, d, J=4.6Hz). |
| 303 | $^1$H-NMR(DMSO-$d_6$) δ: 11.62(1H, brs), 9.45(1H, s), 9.08(1H, s), 7.51–7.41(3H, m), 7.26–7.14(2H, m), 6.96(1H, d, J=6.0Hz), 4.96(2H, s), 2.17(3H, s). |
| 304 | $^1$H-NMR(DMSO-$d_6$) δ: 11.78(1H, brs), 9.51(1H, s), 9.20(1H, s), 7.99–7.92(2H, m), 7.69–7.41(6H, m), 7.26–7.15(2H, m), 7.03(1H, d, J=6.0Hz), 4.98(2H, s). |
| 305 | $^1$H-NMR(DMSO-$d_6$) δ: 8.18(1H, s), 7.49–7.41(2H, m), 7.39(1H, d, J=6.5Hz), 7.24–7.14(2H, m), 6.96(1H, d, J=6.5Hz), 4.96(2H, s), 3.01(3H, s). |
| 306 | $^1$H-NMR(DMSO-$d_6$) δ: 9.06(1H, s), 8.73(1H, d, J=4.6Hz), 8.64(1H, d, J=8.3Hz), 8.14(1H, t, J=7.9Hz), 7.57(1H, t, J=6.0Hz), 7.48–7.42(3H, m), 7.23–7.18(2H, m), 7.02(1H, d, J=6.0Hz), 4.97(2H, s). |
| 307 | $^1$H-NMR(DMSO-$d_6$) δ: 12.29(1H, s), 8.70(1H, s), 7.88(1H, d, J=3.2Hz), 7.62(1H, d, J=3.2Hz), 7.46(1H, td, J=7.7, 1.7Hz), 7.40–7.35(1H, m), 7.23–7.21(2H, m), 4.78(2H, s), 4.47–4.45(2H, m), 3.81–3.79(2H, m). |
| 308 | $^1$H-NMR(DMSO-$d_6$) δ: 12.31(1H, s), 8.70(1H, s), 7.88(1H, d, J=3.2Hz), 7.62(1H, d, J=3.2Hz), 7.42–7.40(1H, m), 7.24–7.21(2H, m), 7.13(1H, td, J=8.7, 2.5Hz), 4.75(2H, s), 4.46(2H, t, J=5.6Hz), 3.78(2H, t, J=5.8Hz). |
| 309 | $^1$H-NMR(DMSO-$d_6$) δ: 12.37(1H, s), 8.69(1H, s), 7.88(1H, d, J=3.2Hz), 7.62(1H, d, J=3.2Hz), 7.44–7.42(2H, m), 7.21–7.18(2H, m), 4.72(2H, s), 4.43(2H, t, J=5.6Hz), 3.75(2H, t, J=5.6Hz). |
| 310 | $^1$H-NMR(DMSO-$d_6$) δ: 12.24(1H, s), 8.72(1H, s), 7.89(1H, d, J=3.2Hz), 7.63(1H, d, J=3.2Hz), 7.52–7.44(2H, m), 7.36–7.34(2H, m), 4.81(2H, s), 4.50(2H, t, J=5.6Hz), 3.81(2H, t, J=5.6Hz). |
| 311 | $^1$H-NMR(DMSO-$d_6$) δ: 12.45(1H, s), 8.73(1H, s), 7.95–7.90(5H, m), 7.64(1H, d, J=3.0Hz), 7.53–7.52(3H, m), 4.93(2H, s), 4.49–4.47(2H, m), 3.83–3.81(2H, m). |
| 312 | $^1$H-NMR($CDCl_3$) δ: 12.24(1H, brs), 8.50(1H, s), 7.83(1H, d, J=3.2Hz), 7.40(1H, d, J=3.2Hz), 7.30–7.24(1H, m), 7.14(1H, t, J=7.2Hz), 7.02(1H, t, J=7.9Hz), 4.26(2H, t, J=5.6Hz), 3.79(2H, t, J=5.6Hz), 3.66(2H, t, J=7.4Hz), 2.77(2H, t, J=7.7Hz), 2.06–1.98(2H, m). |
| 313 | $^1$H-NMR($CDCl_3$) δ: 12.21(1H, brs), 8.41(1H, s), 7.79(1H, d, J=3.2Hz), 7.38(1H, d, J=3.2Hz), 7.32(1H, t, J=7.9Hz), 7.02(1H, dd, J=9.7, 1.9Hz), 6.95(1H, d, J=8.3Hz), 4.26(2H, t, J=5.6Hz), 3.80(2H, t, J=5.6Hz), 3.62(2H, t, J=7.4Hz), 2.71(2H, t, J=7.7Hz), 2.04–1.97(2H, m). |
| 314 | $^1$H-NMR($CDCl_3$) δ: 12.29(1H, brs), 8.43(1H, s), 7.80(1H, d, J=3.2Hz), 7.38(1H, d, J=3.2Hz), 7.17(2H, dd, J=8.6, 5.3Hz), 7.02–6.96(2H, m), 4.22(2H, t, J=5.6Hz), 3.79–3.74(2H, m), 3.62(2H, t, J=7.4Hz), 2.71(2H, t, J=7.4Hz), 2.04–1.97(2H, m). |
| 315 | $^1$H-NMR($CDCl_3$) δ: 8.52(1H, s), 7.81(1H, d, J=3.3Hz), 7.39(1H, d, J=3.3Hz), 7.30–7.18(1H, m), 7.00–6.88(3H, m), 4.22(2H, t, J=5.7Hz), 3.75(2H, t, J=5.5Hz), 3.62(2H, t, J=7.3Hz), 2.73(2H, t, J=7.5Hz), 2.07–1.97(2H, m). |
| 317 | $^1$H-NMR(DMSO-$d_6$) δ: 9.01(1H, s), 8.85–8.80(1H, m), 8.57(1H, d, J=8.3Hz), 8.43(1H, t, J=7.5Hz), 7.79(1H, t, J=7.5Hz), 7.58(1H, t, J=7.5Hz), 7.49(1H, t, J=7.2Hz), 7.26(1H, t, J=7.2Hz), 4.85(2H, s), 4.53–4.46(2H, m), 3.91–3.83(2H, m). |
| 318 | $^1$H-NMR(DMSO-$d_6$) δ: 11.74(1H, brs), 9.09(1H, s), 7.52(1H, d, J=6.0Hz), 7.48(1H, s), 7.46–7.43(2H, m), 7.23–7.14(2H, m), 6.98(1H, d, J=6.5Hz), 4.95(2H, s), 4.07(2H, s), 3.41(3H, s). |
| 319 | $^1$H-NMR(DMSO-$d_6$) δ: 8.17(1H, s), 7.48–7.33(3H, m), 7.24–7.12(2H, m), 6.94(1H, d, J=6.0Hz), 4.94(2H, s), 2.59–2.51(1H, m), 1.24(6H, d, J=7.0Hz). |
| 320 | $^1$H-NMR(DMSO-$d_6$) δ: 9.78(1H, s), 9.14(1H, s), 9.08(1H, d, J=2.3Hz), 8.77(1H, dd, J=4.9, 1.6Hz), 8.31(1H, dt, J=7.9, 2.3Hz), 7.61–7.55(1H, m), 7.52(1H, d, J=6.0Hz), 7.49–7.42(2H, m), 7.24–7.15(2H, m), 7.01(1H, d, J=6.5Hz), 4.97(2H, s). |
| 321 | $^1$H-NMR(DMSO-$d_6$) δ: 11.64(1H, brs), 9.29(1H, s), 9.11(1H, s), 7.48–7.37(3H, m), 7.24–7.13(2H, m), 6.95(1H, d, J=6.0Hz), 4.95(2H, s), 2.92(1H, sept, J=6.5Hz), 1.07(6H, d, J=6.5Hz). |
| 322 | 1H-NMR(DMSO-$d_6$) δ: 11.86(1H, brs), 10.2–10.4(1H, m), 8.76(1H, s), 7.4–7.6(3H, m), 7.21(2H, t, J=8.9Hz), 7.01(1H, d, J=6.3Hz), 4.95(2H, s), 3.4–3.65(4H, m), 3.28(3H, s). |
| 323 | $^1$H-NMR(DMSO-$d_6$) δ: 11.90(1H, s), 10.17–10.07(1H, m), 8.76(1H, s), 7.56–7.41(3H, m), 7.27–7.15(2H, m), 7.02(1H, d, J=6.4Hz), 4.95(2H, s), 3.40–3.29(2H, m), 1.13(3H, t, J=7.2Hz). |
| 324 | $^1$H-NMR(DMSO-$d_6$) δ: 9.43(1H, s), 9.07(1H, s), 7.45(1H, d, J=6.0Hz), 7.34–7.25(2H, m), 7.24–7.14(1H, m), 6.94(1H, d, J=6.0Hz), 3.84(2H, t, J=7.2Hz), 2.78(2H, t, J=7.2Hz), 2.16(3H, s), 1.98–1.82(2H, m). |

TABLE 37-continued

| Example | $^1$H-NMR |
|---|---|
| 325 | $^1$H-NMR(DMSO-$d_6$) δ: 9.45(1H, s), 9.09(1H, s), 7.60–7.44(1H, m), 7.41–7.34(1H, m), 7.25–7.18(1H, m), 6.91(1H, d, J=6.5Hz), 5.06(2H, s), 2.17(3H, s), 0.00(6H, t, J=3.5Hz). |
| 326 | $^1$H-NMR(DMSO-$d_6$) δ: 8.73(1H, s), 7.89(1H, d, J=3.2Hz), 7.68(1H, dd, J=9.3, 2.8Hz), 7.63(1H, d, J=3.2Hz), 7.55(1H, dd, J=8.3, 5.6Hz), 7.45(1H, td, J=8.3, 2.8Hz), 5.02(2H, s), 4.52–4.47(2H, m), 3.87(3H, s), 3.81–3.76(2H, m). |
| 327 | $^1$H-NMR(DMSO-$d_6$) δ: 8.99–8.94(1H, m), 8.81–8.76(1H, m), 8.57(1H, d, J=8.3Hz), 8.42–8.32(1H, m), 7.76–7.69(1H, m), 7.66(1H, d, J=7.4Hz), 7.43(2H, dd, J=6.5, 1.4Hz), 4.75(2H, s), 4.47(2H, t, J=5.3Hz), 3.82(2H, t, J=5.3Hz). |
| 328 | $^1$H-NMR(DMSO-$d_6$) δ: 9.45(1H, s), 8.90(1H, d, J=8.3Hz), 8.81(1H, d, J=5.6Hz), 8.46(1H, s), 8.08(1H, dd, J=7.9, 5.6Hz), 7.57(1H, t, J=7.4Hz), 7.46(1H, t, J=7.4Hz), 7.25(1H, t, J=7.9Hz), 4.83(2H, s), 4.36(2H, t, J=5.3Hz), 3.83(2H, t, J=5.6Hz). |
| 329 | $^1$H-NMR(DMSO-$d_6$) δ: 8.98(1H, s), 8.80(1H, d, J=4.6Hz), 8.54(1H, d, J=8.8Hz), 8.41(1H, t, J=7.7Hz), 7.76(1H, t, J=6.7Hz), 7.35–7.27(2H, m), 7.26–7.19(1H, m), 4.47(2H, t, J=5.6Hz), 3.87(2H, t, J=5.6Hz), 3.61(2H, t, J=7.4Hz), 2.80(2H, td, J=7.9, 1.9Hz), 1.88(2H, t, J=7.4Hz). |
| 330 | $^1$H-NMR($CDCl_3$) δ: 12.26(1H, s), 8.72(1H, s), 7.90(1H, d, J=3.0Hz), 7.62–7.58(3H, m), 7.33–7.22(2H, m), 7.01(1H, s), 4.94(2H, s), 4.48(2H, t, J=5.7Hz), 3.89(2H, t, J=5.7Hz). |
| 331 | $^1$H-NMR(DMSO-$d_6$) δ: 12.25(1H, s), 10.69(1H, d, J=8.3Hz), 8.26(1H, s), 7.39–7.34(8H, m), 7.22–7.15(6H, m), 5.28(1H, dd, J=13.9, 8.3Hz), 4.70(2H, s), 4.34(2H, t, J=5.6Hz), 3.11–3.03(2H, m). |
| 332 | $^1$H-NMR(DMSO-$d_6$) δ: 11.82(1H, s), 9.26(1H, s), 8.65(1H, s), 7.54(1H, td, J=7.0, 1.9Hz), 7.42(1H, td, J=7.0, 1.9Hz), 7.22(1H, t, J=7.9Hz), 4.79(2H, s), 4.29(2H, t, J=5.6Hz), 3.76(2H, t, J=5.6Hz), 2.12(3H, s). |
| 333 | $^1$H-NMR($CDCl_3$) δ: 12.26(1H, brs), 8.44(1H, s), 7.82(1H, d, J=3.2Hz), 7.39(1H, d, J=3.2Hz), 7.25–7.15(2H, m), 7.09–7.00(2H, m), 4.22(2H, t, J=5.6Hz), 3.76(2H, t, J=5.6Hz), 3.66(2H, t, J=7.2Hz), 2.76(2H, t, J=7.7Hz), 2.06–1.99(2H, m). |
| 334 | $^1$H-NMR($CDCl_3$) δ: 12.21(1H, brs), 10.69(1H, d, J=8.1Hz), 8.28(1H, s), 7.37–7.15(14H, m), 5.21–5.06(1H, m), 4.73(2H, s), 4.13(2H, t, J=5.7Hz), 3.61(2H, t, J=5.3Hz), 2.79–2.58(2H, m), 2.31–2.08(2H, m). |
| 335 | $^1$H-NMR($CDCl_3$) δ: 9.03(1H, s), 7.93(1H, d, J=3.7Hz), 7.47(1H, d, J=3.7Hz), 7.27–7.20(1H, m), 7.09–7.04(2H, m), 5.89(1H, brs), 4.47(2H, t, J=5.7Hz), 3.85(2H, t, J=5.7Hz), 3.70–3.65(2H, m), 2.92(3H, d, J=5.1Hz), 2.81–2.72(2H, m). |
| 336 | $^1$H-NMR(DMSO-$d_6$) δ: 12.24(1H, brs), 7.71(1H, s), 7.35–7.15(3H, m), 4.23(2H, t, J=5.1Hz), 3.76(2H, t, J=5.1Hz), 3.55(2H, t, J=7.4Hz), 2.76(2H, t, J=7.4Hz), 1.89–1.74(2H, m), 1.19(9H, s). |
| 337 | $^1$H-NMR(DMSO-$d_6$) δ: 12.22(1H, s), 8.14(1H, s), 7.48–7.28(4H, m), 4.71(2H, s), 4.32(2H, t, J=5.6Hz), 3.93(1H, sept, J=5.3Hz), 3.72(2H, t, J=5.6Hz), 1.02(6H, t, J=5.3Hz). |
| 338 | $^1$H-NMR(DMSO-$d_6$) δ: 8.73(1H, s), 7.91–7.91(1H, m), 7.65–7.64(1H, m), 7.30–7.14(5H, m), 4.45–4.43(2H, m), 3.80–3.78(2H, m), 3.56–3.53(2H, m), 2.64–2.61(2H, m), 1.63–1.62(4H, m). |
| 339 | $^1$H-NMR(DMSO-$d_6$) δ: 8.75–8.74(1H, m), 7.91–7.91(1H, m), 7.65–7.65(1H, m), 4.45–4.44(2H, m), 3.81–3.80(2H, m), 3.51(2H, t, J=7.3Hz), 1.61–1.59(2H, m), 1.34–1.29(4H, m), 0.89(3H, t, J=7.0Hz). |
| 340 | $^1$H-NMR(DMSO-$d_6$) δ: 8.83(2H, d, J=6.5Hz), 8.59(1H, s), 8.55(2H, d, J=6.5Hz), 7.57(1H, t, J=7.9Hz), 7.46(1H, t, J=7.4Hz), 7.25(1H, t, J=7.9Hz), 4.82(2H, s), 4.38(2H, t, J=5.1Hz), 3.82(2H, t, J=5.1Hz). |
| 341 | $^1$H-NMR(DMSO-$d_6$) δ: 8.88(2H, d, J=6.5Hz), 8.84(1H, s), 8.49(2H, d, J=6.5Hz), 7.49–7.43(2H, m), 7.27–7.18(3H, m), 6.99(1H, d, J=6.5Hz), 4.97(2H, s). |
| 342 | $^1$H-NMR(DMSO-$d_6$) δ: 11.61(1H, s), 9.23–9.19(1H, m), 9.10(1H, s), 8.89–8.82(2H, m), 7.61–7.52(2H, m), 7.45–7.38(1H, m), 7.27–7.20(1H, m), 6.95(1H, d, J=6.0Hz), 5.06(2H, s). |
| 343 | $^1$H-NMR(DMSO-$d_6$) δ: 12.27(1H, brs), 8.05(1H, s), 7.97(1H, s), 7.67–7.62(1H, m), 7.46–7.39(2H, m), 4.73(2H, s), 4.36–4.29(2H, m), 3.80–3.72(5H, m). |
| 344 | $^1$H-NMR(DMSO-$d_6$) δ: 8.49(1H, s), 7.49–7.41(2H, m), 7.37(1H, d, J=6.5Hz), 7.25–7.17(2H, m), 6.94(1H, d, J=6.5Hz), 4.92(2H, s), 2.63–2.60(3H, m). |
| 345 | $^1$H-NMR(DMSO-$d_6$) δ: 8.43(1H, s), 7.48–7.39(2H, m), 7.35(1H, d, J=6.0Hz), 7.24–7.15(2H, m), 6.92(1H, d, J=6.5Hz), 4.91(2H, s), 3.93(1H, sept, J=6.5Hz), 1.03(6H, d, J=6.5Hz). |
| 346 | $^1$H-NMR(DMSO-$d_6$) δ: 9.84(1H, s), 8.85(2H, t, J=3.2Hz), 8.67(1H, s), 7.96(2H, d, J=6.0Hz), 7.48(1H, s), 7.41–7.35(3H, m), 4.74(2H, s), 4.37(2H, t, J=5.8Hz), 3.77(2H, t, J=5.6Hz). |
| 347 | $^1$H-NMR(DMSO-$d_6$) δ: 11.78(1H, brs), 9.21(1H, d, J=0.9Hz), 9.08(1H, s), 8.91–8.81(2H, m), 7.54(1H, d, J=6.5Hz), 7.48(2H, dd, J=8.8, 5.6Hz), 7.26–7.13(2H, m), 6.98(1H, d, J=6.0Hz), 4.95(2H, s). |
| 348 | $^1$H-NMR(DMSO-$d_6$) δ: 12.15(1H, brs), 9.87(1H, d, J=1.5Hz), 8.69–8.61(1H, m), 8.58–8.49(2H, m), 7.65(1H, d, J=7.2Hz), 7.47–7.36(2H, m), 4.73(2H, s), 4.41(2H, t, J=5.3Hz), 3.77(2H, t, J=5.3Hz). |
| 350 | $^1$H-NMR(DMSO-$d_6$) δ: 10.34(1H, s), 8.70(1H, s), 7.89(1H, d, J=3.2Hz), 7.64(1H, d, J=3.2Hz), 7.24(1H, d, J=8.3Hz), 6.89(1H, d, J=2.3Hz), 6.84(1H, dd, J=8.1, 2.1Hz), 4.62(2H, s), 4.44–4.43(2H, m), 3.77–3.76(2H, m). |
| 351 | $^1$H-NMR(DMSO-$d_6$) δ: 8.69(1H, s), 7.89(1H, d, J=3.2Hz), 7.63(1H, d, J=3.2Hz), 7.32–7.25(4H, m), 7.20–7.14(1H, m), 4.39–4.34(2H, m), 3.75–3.69(2H, m), 3.46–3.37(2H, m), 2.76(1H, q, J=7.0Hz), 1.95–1.82(2H, m), 1.24(3H, d, J=7.0Hz). |

TABLE 37-continued

| Example | $^1$H-NMR |
|---|---|
| 352 | $^1$H-NMR(DMSO-$d_6$) δ: 9.97(1H, s), 9.18(1H, d, J=1.9Hz), 8.87(1H, dd, J=5.1, 1.9Hz), 8.71(1H, s), 8.52(1H, dt, J=7.9, 1.9Hz), 7.77(1H, dd, J=7.9, 5.1Hz), 7.56(1H, td, J=7.8, 1.4Hz), 7.46(1H, td, J=7.0, 1.4Hz), 7.24(1H, t, J=7.9Hz), 4.82(2H, s), 4.41(2H, t, J=5.6Hz), 3.82(2H, t, J=5.6Hz). |
| 354 | $^1$H-NMR(DMSO-$d_6$) δ: 8.71(1H, s), 7.90(1H, d, J=3.2Hz), 7.64(1H, d, J=3.2Hz), 7.47(1H, d, J=2.3Hz), 7.31(1H, dd, J=8.6, 2.1Hz), 7.13(1H, d, J=8.3Hz), 4.66(2H, s), 4.42(2H, t, J=5.6Hz), 4.00(2H, t, J=6.3Hz), 3.75(2H, t, J=5.6Hz), 1.79–1.69(2H, m), 0.98(3H, t, J=7.4Hz). |
| 355 | $^1$H-NMR(DMSO-$d_6$) δ: 8.71(1H, s), 7.90(1H, d, J=3.2Hz), 7.64(1H, d, J=3.2Hz), 7.46(1H, d, J=2.3Hz), 7.30(1H, dd, J=8.6, 2.3Hz), 7.15(1H, d, J=8.6Hz), 4.68–4.62(3H, m), 4.43(2H, t, J=5.3Hz), 3.76(2H, t, J=5.6Hz), 1.28(6H, d, J=6.0Hz). |
| 356 | $^1$H-NMR(DMSO-$d_6$) δ: 8.71(1H, s), 7.90(1H, d, J=3.2Hz), 7.64(1H, d, J=3.2Hz), 7.50(1H, d, J=2.3Hz), 7.46(2H, d, J=7.0Hz), 7.40(2H, t, J=7.2Hz), 7.35–7.30(2H, m), 7.22(1H, d, J=8.8Hz), 5.21(2H, s), 4.66(2H, s), 4.43(2H, t, J=5.6Hz), 3.75(2H, t, J=5.8Hz). |
| 357 | $^1$H-NMR(DMSO-$d_6$) δ: 8.71(1H, s), 7.90(1H, d, J=3.2Hz), 7.64(1H, d, J=3.2Hz), 7.33(1H, d, J=8.3Hz), 7.09(1H, d, J=1.9Hz), 6.99(1H, dd, J=8.1, 2.1Hz), 4.67(2H, s), 4.45–4.43(2H, m), 3.99(2H, t, J=6.5Hz), 3.73–3.72(2H, m), 1.71(2H, td, J=13.9, 7.0Hz), 0.97(3H, t, J=4.9Hz). |
| 358 | $^1$H-NMR(DMSO-$d_6$) δ: 8.70(1H, s), 7.90(1H, d, J=3.2Hz), 7.64(1H, d, J=3.2Hz), 7.34(1H, d, J=7.9Hz), 7.13(1H, d, J=1.9Hz), 6.97(1H, dd, J=7.9, 1.9Hz), 4.72(1H, sept, J=6.0Hz), 4.64(2H, s), 4.43–4.42(2H, m), 3.70–3.68(2H, m), 1.24(6H, d, J=6.0Hz). |
| 359 | $^1$H-NMR(DMSO-$d_6$) δ: 8.70(1H, s), 7.90–7.90(1H, m), 7.64(1H, dd, J=1.5, 0.8Hz), 7.47–7.46(2H, m), 7.39–7.30(4H, m), 7.25(1H, d, J=1.9Hz), 7.02(1H, dd, J=7.9, 1.9Hz), 5.19(2H, s), 4.69(2H, s), 4.39–4.38(2H, m), 3.71–3.69(2H, m). |
| 360 | $^1$H-NMR(DMSO-$d_6$) δ: 8.41(1H, s), 8.00(1H, s), 7.50–7.43(2H, m), 7.32(1H, d, J=6.0Hz), 7.25–7.18(2H, m), 6.97(1H, d, J=6.0Hz), 4.97(2H, s), 3.75(3H, s). |
| 361 | $^1$H-NMR(DMSO-$d_6$) δ: 12.20(1H, s), 9.91–9.83(1H, m), 8.40(1H, s), 7.59–7.52(1H, m), 7.44(1H, t, J=6.7Hz), 7.24(1H, t, J=7.9Hz), 4.80(2H, s), 4.42(2H, t, J=5.6Hz), 3.80(2H, t, J=5.6Hz), 2.83(3H, d, J=4.6Hz). |
| 363 | 1H-NMR(DMSO-$d_6$) δ: 12.5(1H, brs), 9.00(1H, s), 8.7–8.9(1H, m), 8.58(1H, d, J=6.9Hz), 8.3–8.5(1H, m), 7.7–7.8(1H, m), 7.4–7.5(2H, m), 7.2–7.3(2H, m), 4.76(2H, s), 4.4–4.6(2H, m), 3.6–3.9(2H, m). |
| 364 | 1H-NMR(DMSO-$d_6$) δ: 9.27(1H, s), 8.82(1H, d, J=5.4Hz), 8.65(1H, d, J=8Hz), 8.2–8.4(1H, m), 7.73(1H, t, J=6Hz), 7.59(1H, t, J=7.5Hz), 7.3–7.5(2H, m), 7.25(1H, t, J=8Hz), 7.07(1H, d, J=6Hz), 5.11(2H, s). |
| 365 | $^1$H-NMR(DMSO-$d_6$) δ: 9.21(1H, s), 8.80(1H, d, J=4.2Hz), 8.64(1H, d, J=8.3Hz), 8.28(1H, t, J=7.2Hz), 7.68(1H, t, J=6.5Hz), 7.43(1H, d, J=6.5Hz), 7.43(1H, dd, J=7.9, 6.5Hz), 7.26(2H, td, J=8.3, 1.4Hz), 7.16(1H, td, J=8.7, 2.3Hz), 7.07(1H, d, J=6.5Hz), 5.03(2H, s). |
| 366 | $^1$H-NMR(DMSO-$d_6$) δ: 9.64(1H, s), 8.71(1H, s), 7.90(1H, d, J=3.2Hz), 7.64(1H, d, J=3.2Hz), 7.47–7.41(2H, m), 7.03(1H, td, J=8.3, 2.8Hz), 4.72(2H, s), 4.46–4.40(2H, m), 3.69–3.64(2H, m), 2.07(3H, s). |
| 367 | $^1$H-NMR(DMSO-$d_6$) δ: 7.75(1H, s), 7.57–7.53(1H, m), 7.43(1H, t, J=6.5Hz), 7.23(1H, t, J=7.9Hz), 4.78(2H, s), 4.27(2H, t, J=5.6Hz), 3.77(2H, t, J=5.6Hz), 1.19(9H, s). |
| 368 | $^1$H-NMR(DMSO-$d_6$) δ: 8.75(1H, s), 7.91(1H, d, J=3.2Hz), 7.68(1H, dd, J=9.7, 2.8Hz), 7.65(1H, d, J=3.2Hz), 7.52(1H, dd, J=8.8, 5.6Hz), 7.42(1H, td, J=8.8, 2.8Hz), 5.06(2H, s), 4.54–4.48(2H, m), 3.84–3.78(2H, m). |
| 369 | $^1$H-NMR(DMSO-$d_6$) δ: 9.15(1H, s), 8.80–8.75(1H, m), 8.66(1H, d, J=8.3Hz), 8.26–8.17(1H, m), 7.60–7.44(4H, m), 7.33–7.26(1H, m), 7.04(1H, d, J=6.0Hz), 5.00(2H, s). |
| 370 | $^1$H-NMR(DMSO-$d_6$) δ: 12.15(1H, brs), 7.93(0.3H, s), 7.91(0.7H, s), 7.46–7.22(9H, m), 4.72(1.4H, s), 4.71(0.6H, s), 4.65(1.4H, s), 4.39(0.6H, s), 4.31–4.21(2H, m), 3.77–3.69(2H, m), 2.81(2.1H, s), 2.77(0.9H, s). |
| 371 | $^1$H-NMR(DMSO-$d_6$) δ: 12.34(1H, brs), 10.57(1H, t, J=6.0Hz), 8.77(1H, s), 8.73(1H, d, J=5.6Hz), 8.39(1H, s), 8.31(1H, d, J=7.4Hz), 7.87(1H, t, J=6.3Hz), 7.46(1H, s), 7.43–7.32(3H, m), 4.73(2H, s), 4.68(2H, d, J=6.0Hz), 4.39(2H, t, J=5.8Hz), 3.75(2H, t, J=5.6Hz). |
| 372 | $^1$H-NMR(DMSO-$d_6$) δ: 12.34(1H, brs), 10.66(1H, t, J=5.6Hz), 8.70(1H, d, J=4.6Hz), 8.39(1H, s), 8.20(1H, t, J=7.7Hz), 7.66(2H, d, J=7.9Hz), 7.46(1H, s), 7.43–7.33(3H, m), 4.78(2H, d, J=6.0Hz), 4.73(2H, s), 4.40(2H, t, J=5.6Hz), 3.75(2H, t, J=5.8Hz). |
| 373 | $^1$H-NMR(DMSO-$d_6$) δ: 8.93(1H, s), 8.80(1H, d, J=4.6Hz), 8.56(1H, d, J=8.3Hz), 8.38(1H, t, J=7.4Hz), 7.80–7.69(2H, m), 7.66(1H, d, J=8.3Hz), 7.42(1H, dd, J=8.3, 1.9Hz), 4.77(2H, s), 4.47(2H, t, J=5.6Hz), 3.83(2H, t, J=5.6Hz). |
| 374 | $^1$H-NMR(DMSO-$d_6$) δ: 12.30(1H, brs), 10.30(1H, t, J=5.3Hz), 8.37(1H, s), 7.46(1H, s), 7.42–7.32(3H, m), 4.73(2H, s), 4.39(2H, t, J=5.6Hz), 4.23(2H, d, J=5.1Hz), 3.75(2H, t, J=5.6Hz), 2.11(3H, s). |
| 375 | $^1$H-NMR(DMSO-$d_6$) δ: 8.92–8.86(3H, m), 8.53(2H, d, J=6.5Hz), 7.46–7.40(1H, m), 7.29–7.22(3H, m), 7.16(1H, td, J=8.6, 1.7Hz), 6.99(1H, d, J=6.0Hz), 5.01(2H, s). |
| 376 | $^1$H-NMR(DMSO-$d_6$) δ: 8.09(1H, s), 7.41(1H, td, J=7.9, 6.0Hz), 7.27–7.19(3H, m), 7.15(1H, td, J=8.7, 2.0Hz), 6.92(1H, d, J=6.5Hz), 4.98(2H, s), 1.19(9H, d, J=4.6Hz). |

TABLE 37-continued

| Example | $^1$H-NMR |
|---|---|
| 377 | $^1$H-NMR(DMSO-$d_6$) δ: 12.37(1H, s), 10.44(1H, t, J=6.0Hz), 8.40(1H, s), 7.46–7.39(2H, m), 7.38–7.29(2H, m), 7.25–7.14(4H, m), 4.71(2H, s), 4.58(2H, d, J=5.6Hz), 4.42–4.35(2H, m), 3.76–3.68(2H, m). |
| 378 | $^1$H-NMR(DMSO-$d_6$) δ: 12.35(1H, brs), 10.44(1H, t, J=6.0Hz), 8.41(1H, s), 7.46–7.39(2H, m), 7.38–7.32(2H, m), 7.25–7.12(4H, m), 4.71(2H, s), 4.52(2H, d, J=6.0Hz), 4.42–4.35(2H, m), 3.76–3.69(2H, m). |
| 379 | $^1$H-NMR(DMSO-$d_6$) δ: 12.35(1H, s), 9.8–10.0(1H, m), 8.38(1H, s), 7.4–7.5(2H, m), 7.20(2H, t, J=8.7Hz), 4.71(2H, s), 4.3–4.5(2H, m), 3.6–3.8(2H, m), 2.83(3H, d, J=4.8Hz). |
| 380 | 1H-NMR(DMSO-$d_6$) δ: 12.3(1H, brs), 10.3–10.5(1H, m), 8.41(1H, s), 7.1–7.5(9H, m), 4.71(2H, s), 4.54(2H, d, J=6Hz), 4.3–4.5(2H, m), 3.6–3.8(2H, m). |
| 381 | $^1$H-NMR(DMSO-$d_6$) δ: 12.31(1H, s), 9.87(1H, d, J=5.1Hz), 8.38(1H, s), 7.43–7.40(4H, m), 4.71(2H, s), 4.39–4.37(2H, m), 3.73–3.72(2H, m), 2.82(3H, d, J=4.6Hz). |
| 383 | $^1$H-NMR(DMSO-$d_6$) δ: 9.87(1H, d, J=1.4Hz), 8.68–8.63(1H, m), 8.57–8.51(2H, m), 7.69(1H, d, J=2.3Hz), 7.64(1H, d, J=8.3Hz), 7.40(1H, dd, J=8.3, 2.3Hz), 4.74(2H, s), 4.42(2H, t, J=5.6Hz), 3.78(2H, t, J=5.6Hz). |
| 384 | $^1$H-NMR(DMSO-$d_6$) δ: 12.18(1H, brs), 8.15(1H, s), 7.67(1H, d, J=1.9Hz), 7.63(1H, d, J=8.3Hz), 7.37(1H, dd, J=8.3, 1.9Hz), 4.71(2H, s), 4.33(2H, t, J=5.3Hz), 3.94(1H, sept, J=7.0Hz), 3.74(2H, t, J=5.3Hz), 1.03(6H, d, J=7.0Hz). |
| 385 | $^1$H-NMR(DMSO-$d_6$) δ: 12.28(1H, brs), 8.13(1H, s), 7.46–7.36(2H, m), 7.25–7.14(2H, m), 4.69(2H, s), 4.30(2H, t, J=5.6Hz), 3.92(1H, t, J=7.0Hz), 3.69(2H, sept, J=5.8Hz), 1.01(6H, d, J=7.0Hz). |
| 386 | $^1$H-NMR(DMSO-$d_6$) δ: 12.14(1H, brs), 7.72(1H, s), 7.47–7.35(2H, m), 7.26–7.13(2H, m), 4.69(2H, s), 4.22(2H, t, J=5.6Hz), 3.69(2H, t, J=5.6Hz), 1.19(9H, s). |
| 387 | $^1$H-NMR(DMSO-$d_6$) δ: 8.47(1H, s), 7.44(2H, td, J=5.9, 2.5Hz), 7.35(1H, d, J=6.5Hz), 7.20(2H, tt, J=8.8, 2.6Hz), 6.93(1H, d, J=6.5Hz), 4.92(2H, s), 2.97(2H, d, J=6.5Hz), 2.08(1H, dsept, J=6.7, 6.7Hz), 0.89(6H, d, J=7.0Hz). |
| 388 | $^1$H-NMR(DMSO-$d_6$) δ: 12.27(1H, brs), 9.93–9.82(1H, m), 8.38(1H, s), 7.52–7.37(2H, m), 7.30–7.18(1H, m), 4.70(2H, s), 4.40(2H, t, J=5.6Hz), 3.74(2H, t, J=5.6Hz), 2.82(3H, d, J=5.1Hz). |
| 389 | $^1$H-NMR(DMSO-$d_6$) δ: 7.61(1H, s), 7.43–7.41(2H, m), 7.20–7.18(2H, m), 4.69(2H, s), 4.26–4.25(2H, m), 3.70–3.68(2H, m), 3.45(2H, s), 3.17(3H, s), 1.18(6H, s). |
| 391 | $^1$H-NMR(DMSO-$d_6$) δ: 9.23(1H, s), 9.10(1H, s), 8.93–8.80(2H, m), 7.59–7.33(5H, m), 6.99(1H, d, J=6.4Hz), 4.98(2H, s). |
| 392 | $^1$H-NMR(DMSO-$d_6$) δ: 9.20(1H, d, J=1.4Hz), 8.90(1H, dd, J=5.6, 1.4Hz), 8.83(1H, d, J=5.6Hz), 8.78(1H, s), 7.44(2H, dd, J=8.7, 5.3Hz), 7.21(2H, t, J=8.7Hz), 4.73(2H, s), 4.47–4.40(2H, m), 3.79–3.72(2H, m). |
| 393 | $^1$H-NMR(DMSO-$d_6$) δ: 9.22(1H, d, J=1.4Hz), 8.92(1H, dd, J=5.6, 1.4Hz), 8.84(1H, d, J=5.6Hz), 8.80(1H, s), 7.50–7.38(4H, m), 4.80–4.69(2H, m), 4.48–4.41(2H, m), 3.81–3.71(2H, m). |
| 394 | $^1$H-NMR(DMSO-$d_6$) δ: 9.19(1H, brs), 8.92–8.87(1H, m), 8.82(1H, dd, J=5.6, 1.9Hz), 8.79(1H, d, J=1.9Hz), 7.65(1H, d, J=7.4Hz), 7.43(2H, d, J=7.4Hz), 4.73(2H, s), 4.48–4.42(2H, m), 3.82–3.74(2H, m). |
| 395 | $^1$H-NMR(DMSO-$d_6$) δ: 9.21(1H, d, J=1.4Hz), 9.09(1H, s), 8.88(1H, dd, J=5.6, 1.4Hz), 8.85(1H, d, J=5.6Hz), 7.69–7.66(1H, m), 7.54(1H, d, J=6.5Hz), 7.46–7.42(2H, m), 6.98(1H, d, J=6.5Hz), 4.95(2H, s). |
| 396 | $^1$H-NMR(DMSO-$d_6$) δ: 8.71(1H, s), 7.90(1H, d, J=3.2Hz), 7.64(1H, d, J=3.2Hz), 7.03–7.01(1H, m), 6.96–6.95(1H, m), 6.92–6.90(1H, m), 4.69(2H, s), 4.46–4.44(2H, m), 3.94(2H, t, J=6.5Hz), 3.78–3.77(2H, m), 1.73–1.66(2H, m), 0.95(3H, t, J=7.4Hz). |
| 397 | $^1$H-NMR(DMSO-$d_6$) δ: 8.72(1H, s), 7.90(1H, d, J=3.2Hz), 7.64(1H, d, J=3.2Hz), 7.01–6.98(1H, m), 6.94–6.93(1H, m), 6.88–6.88(1H, m), 4.69–4.64(3H, m), 4.46–4.44(2H, m), 3.79–3.77(2H, m), 1.24(6H, d, J=6.0Hz). |
| 398 | $^1$H-NMR(DMSO-$d_6$) δ: 8.71(1H, s), 7.90(1H, d, J=3.2Hz), 7.64(1H, d, J=3.2Hz), 7.43–7.42(2H, m), 7.35–7.31(3H, m), 7.06–7.06(2H, m), 6.99–6.96(1H, m), 5.13(2H, s), 4.69(2H, s), 4.43–4.42(2H, m), 3.75–3.74(2H, m). |
| 399 | $^1$H-NMR(DMSO-$d_6$) δ: 9.22(1H, d, J=1.4Hz), 9.09(1H, s), 8.92–8.80(2H, m), 7.54(1H, d, J=6.5Hz), 7.49–7.37(4H, m), 6.98(1H, d, J=6.0Hz), 4.96(2H, s). |
| 400 | $^1$H-NMR(DMSO-$d_6$) δ: 9.96(1H, s), 9.07(1H, s), 8.79(1H, s), 8.73(1H, d, J=5.6Hz), 8.31(1H, d, J=7.9Hz), 7.85(1H, dd, J=7.9, 5.6Hz), 7.48(1H, s), 7.42(1H, d, J=6.0Hz), 7.40–7.33(3H, m), 6.97(1H, d, J=6.0Hz), 4.97(2H, s), 4.11(2H, s). |
| 401 | $^1$H-NMR(DMSO-$d_6$) δ: 10.02(1H, s), 9.07(1H, s), 8.80(2H, dd, J=5.1, 1.0Hz), 7.89(2H, d, J=6.5Hz), 7.49(1H, s), 7.43(1H, d, J=6.5Hz), 7.41–7.33(3H, m), 6.98(1H, d, J=6.5Hz), 4.97(2H, s), 4.22(2H, s). |
| 402 | $^1$H-NMR(DMSO-$d_6$) δ: 10.14(1H, s), 9.07(1H, s), 8.79(1H, d, J=6.0Hz), 8.30(1H, t, J=7.9Hz), 7.83(1H, d, J=7.9Hz), 7.75(1H, t, J=6.5Hz), 7.49(1H, s), 7.44(1H, d, J=6.5Hz), 7.41–7.34(3H, m), 6.99(1H, d, J=6.5Hz), 4.98(2H, s), 4.32(2H, d, J=8.8Hz). |
| 403 | $^1$H-NMR(DMSO-$d_6$) δ: 9.21(1H, d, J=0.9Hz), 9.09(1H, s), 8.88(1H, dd, J=5.6, 1.4Hz), 8.84(1H, d, J=5.6Hz), 7.54(1H, d, J=6.5Hz), 7.45–7.39(1H, m), 7.29–7.21(2H, m), 7.18–7.11(1H, m), 6.97(1H, d, J=6.5Hz), 4.98(2H, s). |
| 404 | $^1$H-NMR(DMSO-$d_6$) δ: 9.89(1H, d, J=1.4Hz), 8.90(1H, s), 8.71(1H, dd, J=2.3, 1.4Hz), 8.59(1H, d, J=2.3Hz), 7.51(1H, d, J=6.0Hz), 7.42(1H, td, J=7.9, 6.5Hz), 7.29–7.22(2H, m), 7.15(1H, td, J=8.5, 2.8Hz), 6.96(1H, d, J=6.0Hz), 4.99(2H, s). |
| 405 | $^1$H-NMR(DMSO-$d_6$) δ: 8.41(1H, s), 8.01(1H, s), 7.67(1H, d, J=7.4Hz), 7.44–7.41(2H, m), 7.32(1H, d, J=6.5Hz), 6.96(1H, d, J=6.5Hz), 4.96(2H, s), 3.75(3H, s). |
| 406 | $^1$H-NMR(DMSO-$d_6$) δ: 9.03(1H, s), 8.71(1H, s), 7.63(1H, d, J=7.4Hz), 7.44–7.38(2H, m), 4.70(2H, s), 4.28(2H, t, J=5.6Hz), 3.72(2H, t, J=5.8Hz), 2.34(2H, s), 0.98(9H, s). |

TABLE 37-continued

| Example | $^1$H-NMR |
|---|---|
| 407 | $^1$H-NMR(DMSO-$d_6$) δ: 8.81–8.76(2H, m), 8.72(1H, s), 8.23(1H, t, J=7.9Hz), 7.65(1H, t, J=6.5Hz), 7.46–7.41(1H, m), 7.30–7.24(2H, m), 7.20–7.14(1H, m), 7.02(1H, s), 5.02(2H, s), 2.38(3H, s). |
| 408 | $^1$H-NMR(DMSO-$d_6$) δ: 7.74(1H, s), 7.49–7.37(2H, m), 7.27–7.12(2H, m), 6.86(1H, s), 4.92(2H, s), 2.20(3H, s), 1.18(9H, s). |
| 409 | $^1$H-NMR(DMSO-$d_6$) δ: 12.48(1H, dd, J=11.4, 4.9Hz), 7.46–7.36(2H, m), 7.24–7.11(2H, m), 4.70(2H, s), 4.17(2H, t, J=5.6Hz), 4.12(2H, s), 3.64(2H, t, J=5.6Hz), 3.24(3H, s), 1.12(9H, s). |
| 410 | 1H-NMR(DMSO-$d_6$) δ: 10.5–10.7(1H, m), 8.6–8.7(1H, m), 8.39(1H, s), 7.9–8.1(1H, m), 7.4–7.6(4H, m), 7.20(2H, t, J=8.7Hz), 4.7–4.8(4H, m), 4.4–4.5(2H, m), 3.6–3.8(2H, m). |
| 411 | $^1$H-NMR(DMSO-$d_6$) δ: 12.36(1H, brs), 10.39–10.32(1H, m), 8.41(1H, s), 7.61–7.58(1H, m), 7.46–7.39(2H, m), 7.24–7.17(2H, m), 6.42–6.39(1H, m), 6.29(1H, d, J=3.2Hz), 4.71(2H, s), 4.53(2H, d, J=5.6Hz), 4.43–4.35(2H, m), 3.76–3.69(2H, m). |
| 412 | $^1$H-NMR(DMSO-$d_6$) δ: 12.68(1H, s), 7.70(1H, s), 7.47–7.41(2H, m), 7.24–7.17(2H, m), 4.70(2H, s), 3.60(2H, s), 1.40(6H, s), 1.18(9H, s). |
| 413 | $^1$H-NMR(DMSO-$d_6$) δ: 12.75(1H, s), 8.15(1H, s), 7.44(2H, dd, J=8.8, 5.6Hz), 7.20(2H, t, J=8.8Hz), 4.70(2H, s), 3.59(2H, s), 1.41(6H, s). |
| 414 | $^1$H-NMR(DMSO-$d_6$) δ: 8.81(1H, d, J=4.6Hz), 8.70(1H, d, J=8.3Hz), 8.66(1H, s), 8.40(1H, t, J=7.9Hz), 7.78(1H, t, J=6.7Hz), 7.48(2H, dd, J=8.3, 5.6Hz), 7.23(2H, t, J=1.4Hz), 4.75(2H, s), 3.70(2H, s), 1.55(6H, s). |
| 415 | $^1$H-NMR(DMSO-$d_6$) δ: 12.36(1H, brs), 10.39(1H, brs), 8.41(1H, s), 7.52–7.14(8H, m), 4.71(2H, s), 4.50(2H, d, J=5.6Hz), 4.42–4.35(2H, m), 3.77–3.68(2H, m), 3.02(6H, s). |
| 146 | $^1$H-NMR(DMSO-$d_6$) δ: 9.86(1H, d, J=1.4Hz), 8.67–8.62(1H, m), 8.56–8.49(2H, m), 7.49–7.30(4H, m), 4.74(2H, s), 4.42(2H, t, J=5.6Hz), 3.77(2H, t, J=5.6Hz). |
| 417 | $^1$H-NMR(DMSO-$d_6$) δ: 9.85(1H, d, J=1.4Hz), 8.64(1H, t, J=2.1Hz), 8.55–8.51(2H, m), 7.47–7.39(2H, m), 7.25–7.16(2H, m), 4.72(2H, s), 4.40(2H, t, J=5.6Hz), 3.74(2H, t, J=5.6Hz). |
| 418 | $^1$H-NMR(DMSO-$d_6$) δ: 7.86–7.79(3H, m), 7.65–7.56(2H, m), 7.53–7.47(2H, m), 7.43–7.36(2H, m), 4.67(2H, s), 4.32–4.25(2H, m), 3.74–3.67(2H, m). |
| 419 | $^1$H-NMR(DMSO-$d_6$) δ: 7.67–7.61(2H, m), 7.46–7.38(4H, m), 7.37–7.31(3H, m), 4.71(2H, s), 4.50(2H, s), 4.26–4.20(2H, m), 3.75–3.69(2H, m). |
| 420 | $^1$H-NMR(DMSO-$d_6$) δ: 7.90–7.86(1H, m), 7.84(1H, s), 7.65–7.58(2H, m), 7.44–7.38(2H, m), 7.12–7.08(1H, m), 4.68(2H, s), 4.33–4.26(2H, m), 3.76–3.68(2H, m). |
| 421 | $^1$H-NMR(DMSO-$d_6$) δ: 12.39(1H, s), 10.55(1H, t, J=6.3Hz), 8.41(1H, s), 7.89(2H, d, J=8.3Hz), 7.55(2H, d, J=8.3Hz), 7.43(2H, dd, J=8.8, 5.6Hz), 7.21(2H, t, J=8.8Hz), 4.72(2H, s), 4.65(2H, d, J=6.3Hz), 4.42–4.36(2H, m), 3.77–3.69(2H, m), 3.19(3H, s). |
| 422 | $^1$H-NMR(DMSO-$d_6$) δ: 7.49–7.42(2H, m), 7.27–7.19(2H, m), 7.01(1H, brs), 4.79(1H, d, J=14.8Hz), 4.74(1H, d, J=14.8Hz), 4.63–4.52(1H, m), 4.47–4.34(1H, m), 3.80–3.68(2H, m), 3.41–3.32(1H, m), 3.06–2.96(1H, m), 2.87–2.74(1H, m), 0.91(9H, s). |
| 423 | $^1$H-NMR(DMSO-$d_6$) δ: 9.55(1H, s), 9.18(1H, s), 7.49(1H, s), 7.44–7.30(4H, m), 6.97(1H, s), 4.98(2H, s), 2.22(3H, s), 2.17(3H, s). |
| 424 | $^1$H-NMR(DMSO-$d_6$) δ: 8.79(1H, d, J=4.6Hz), 8.31–8.12(1H, m), 7.68(1H, t, J=6.3Hz), 7.59(1H, d, J=7.9Hz), 7.51–7.38(2H, m), 7.28–7.13(2H, m), 4.74(2H, d, J=7.0Hz), 4.30(2H, t, J=5.6Hz), 4.26(2H, s), 3.70(2H, t, J=5.3Hz), 3.12(3H, s). |
| 425 | $^1$H-NMR(DMSO-$d_6$) δ: 7.91(1H, s), 7.49–7.42(2H, m), 7.32–7.16(3H, m), 6.92(1H, d, J=6.0Hz), 4.94(2H, s), 3.42(2H, s), 3.17(3H, s), 1.16(6H, s). |
| 426 | $^1$H-NMR(DMSO-$d_6$) δ: 10.81–10.75(1H, m), 8.51(1H, d, J=6.0Hz), 8.40(1H, s), 7.47–7.40(2H, m), 7.24–7.16(2H, m), 6.87(1H, d, J=6.0Hz), 4.72(2H, s), 4.66(2H, d, J=5.1Hz), 4.43–4.36(2H, m), 3.98(3H, s), 3.76–3.71(2H, m). |
| 427 | $^1$H-NMR(DMSO-$d_6$) δ: 7.43(2H, dd, J=8.8, 5.6Hz), 7.20(2H, t, J=8.8Hz), 4.71(2H, s), 3.96(1H, brs), 3.84(2H, brs), 3.63–3.54(2H, m), 1.13(9H, s), 1.11(9H, s). |
| 428 | $^1$H-NMR(DMSO-$d_6$) δ: 12.36(1H, brs), 10.38(1H, t, J=5.8Hz), 9.92(1H, s), 8.41(1H, s), 7.55–7.50(2H, m), 7.46–7.39(2H, m), 7.25–7.17(4H, m), 4.71(2H, s), 4.47–4.38(4H, m), 3.76–3.70(2H, m), 2.02(3H, s). |
| 429 | $^1$H-NMR(DMSO-$d_6$) δ: 8.52–8.44(1H, m), 7.72(1H, d, J=2.1Hz), 7.66(1H, d, J=8.3Hz), 7.43(1H, dd, J=8.3, 2.1Hz), 7.29–7.14(2H, m), 5.08(2H, s), 3.67(2H, t, J=5.9Hz), 2.90(2H, t, J=5.9Hz). |
| 430 | $^1$H-NMR(DMSO-$d_6$) δ: 8.51(1H, brs), 7.72(1H, brs), 7.66(1H, dd, J=8.3, 3.7Hz), 7.41(1H, d, J=8.3Hz), 7.22(1H, brs), 6.98(1H, brs), 5.07(2H, s), 4.65–4.54(1H, m), 1.89–1.69(2H, m), 0.98–0.89(3H, m). |
| 431 | $^1$H-NMR(DMSO-$d_6$) δ: 7.76–7.68(2H, m), 7.65(1H, d, J=8.8Hz), 7.56–7.37(2H, m), 7.12–7.02(1H, m), 6.93(1H, brs), 5.03(2H, s), 3.49(2H, t, J=6.0Hz), 2.71(2H, t, J=7.4Hz), 1.75–1.64(2H, m). |
| 432 | $^1$H-NMR(DMSO-$d_6$) δ: 8.34(1H, d, J=7.6Hz), 7.70(1H, d, J=1.9Hz), 7.65(1H, d, J=8.3Hz), 7.39(1H, dd, J=8.3, 1.9Hz), 6.94(1H, s), 6.60(1H, d, J=7.6Hz), 5.94(1H, brs), 5.03(1H, d, J=14.8Hz), 4.96(1H, d, J=14.8Hz), 4.21(1H, d, J=7.9Hz), 2.13–1.99(1H, m), 0.97(3H, d, J=6.5Hz), 0.81(3H, d, J=6.5Hz). |
| 433 | $^1$H-NMR(DMSO-$d_6$) δ: 8.23(1H, d, J=7.6Hz), 7.69–7.58(2H, m), 7.32–7.13(6H, m), 6.79(1H, s), 6.72(1H, d, J=7.6Hz), 4.94(2H, s), 3.01–2.82(4H, m). |
| 434 | $^1$H-NMR(DMSO-$d_6$) δ: 8.47(1H, s), 7.44(2H, dd, J=8.6, 5.7Hz), 7.26–7.13(3H, m), 6.80(1H, d, J=6.2Hz), 4.89(2H, s). |

TABLE 37-continued

| Example | $^1$H-NMR |
|---|---|
| 435 | $^1$H-NMR(DMSO-$d_6$) δ: 8.48(1H, d, J=7.4Hz), 7.71(1H, d, J=1.9Hz), 7.64(1H, d, J=8.3Hz), 7.41(1H, dd, J=8.3, 1.9Hz), 7.17(1H, s), 5.11(2H, s), 3.24(1H, sept, J=6.5Hz), 1.24(6H, d, J=6.5Hz). |
| 436 | $^1$H-NMR(DMSO-$d_6$) δ: 11.40(1H, brs), 8.08(1H, d, J=7.9Hz), 7.46(1H, brs), 7.43–7.32(3H, m), 6.53(1H, d, J=7.9Hz), 5.04(2H, s), 2.43(3H, s). |
| 437 | $^1$H-NMR(DMSO-$d_6$) δ: 12.07(1H, brs), 7.72(1H, s), 7.45(1H, brs), 7.43–7.30(3H, m), 4.71(2H, s), 4.29–4.21(2H, m), 3.76–3.69(2H, m), 1.20(9H, s). |

Experimental Example 1

The following explains evaluation methods of the HIV integrase inhibitory activity of the compound of the present invention.

(i) Construction of Recombinant Integrase Gene Expression System

The 185th phenylalanine of HIV integrase full length gene (J. Virol., 67, 425–437 (1993)) was substituted by histidine and inserted into the restriction enzyme NdeI and XhoI sites of plasmid pET21a(+) (Novagen), whereby an integrase expression vector pET21a-INH was constructed.

(ii) Production and Purification of Integrase Protein

*Escherichia coli* recombinant BL21(DE3) transformed with plasmid pET21a-INH obtained in (i) was shake cultured at 37° C. in a liquid medium containing ampicillin. When the culture reached the logarithmic growth phase, isopropyl-β-D-thiogalactopyranoside was added to promote expression of integrase gene. The culture was continued for 3 hr to promote accumulation of the integrase protein. The recombinant *E. coli* was collected in pellets by centrifugal separation and preserved at −80° C.

The *E. coli* was suspended in Lysis buffer (20 mM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (Pharmacia Corporation) and stirred at 4° C. for 30 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was applied to a Superdex 75 (Pharmacia Corporation) column for gel filtration. The protein was eluted with Lysis buffer containing 1M sodium chloride.

The obtained fractions of the integrase protein were collected and preserved at −80° C.

(iii) Preparation of DNA Solution

The following DNA synthesized by Greiner was dissolved in TE buffer (10 mM Tris-hydrochloric acid (pH 8.0), 1 mM EDTA) and mixed with donor DNA, target DNA, and each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and preserved at 25° C. to give a double stranded DNA, which was used for the test.

Donor DNA (− strand having biotin attached to the 5' terminal)

```
                                        (SEQ ID NO:1)
Donor + strand:
5'-Biotin-ACC CTT TTA GTC AGT GTG GAA AAT CTC TAG
CA-3'

                                        (SEQ ID NO:2)
Donor - strand:
5'-ACT GCT AGA GAT TTT CCA CAC TGA CTA AAA G-3'

Target DNA (+, - strands both having digoxigenin
added at 3'terminal)
                                        (SEQ ID NO:3)
Target + strand:
5'-TGA CCA AGG GCT AAT TCA CT-Dig-3'

                                        (SEQ ID NO:4)
Target - strand:
5'-AGT GAA TTA GCC CTT GGT CA-Dig-3'
```

(iv) Determination of Enzyme (HIV Integrase) Inhibitory Activity

The donor DNA was diluted with TE buffer to 10 nM, of which 50 μl was added to each well of streptavidin-coated microtiter plate (Roche) and allowed to adsorb at 37° C. for 60 min. The DNA was washed with phosphate buffer (Dulbecco PBS, Sanko Junyaku Co., Ltd.) containing 0.1% Tween 20 and phosphate buffer. Then, a reaction mixture (70 μl) having the following composition, a test substance (10 μl) diluted with the reaction mixture and 100 μg/ml integrase protein (10 μl) were added to each well and reacted at 37° C. for 60 min.

Composition of the reaction mixture: 30 mM MOPS (3-morpholinopropanesulfonic acid), 5 mM magnesium chloride, 3 mM DTT (dithiothreitol), 0.1 mg/ml BSA (bovine serum albumin), 5% glycerol, 10% DMSO (dimethyl sulfoxide), 0.01% Tween 20.

Then, 50 nM target DNA (10 μl) was added, reacted at 37° C. for 10 min and washed with phosphate buffer containing 0.1% Tween 20 to stop the reaction.

Then, 100 mU/ml peroxidase labeled anti-digoxigenin antibody solution (Roche, 100 μl) was added, and the mixture was reacted at 30° C. for 60 min, followed by washing with phosphate buffer containing 0.1% Tween 20.

A peroxidase color solution (Bio Rad, 100 μl) was added and allowed to react at room temperature for 4 min. The color reaction was stopped by adding 1N sulfuric acid (100 μl). The absorbance at 450 nm was measured.

The HIV integrase inhibitory activity ($IC_{50}$) of the compound of the present invention was calculated from the inhibition rate according to the following formula.

$$\text{inhibition rate (\%)}=[1-(\text{Object-Blank})/(\text{Control-Blank})]\times 100$$

Object; absorbance of well in the presence of test compound

Control; absorbance of well in the absence of test compound

Blank; absorbance of well in the absence of test compound, in the absence of integrase protein The results are shown in Tables 38–46. $IC_{50}$ shows the following ranges.

| | |
|---|---|
| + | not less than 1 μM and less than 10 μM |
| ++ | not less than 0.1 μM and less than 1 μM |
| +++ | not less than 0.01 μM and less than 0.1 μM |
| ++++ | less than 0.01 μM |

Experimental Example 2

Evaluation of Antivirus Activity

The effect of combined use of the compound of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and test substance A and the like are evaluated using CEM-SS cells infected with HIV-1 IIIB by XTT method.

In addition, the effect of combined use of three agents of test substance A, zidovudine and lamivudine, or test substance A, tenofovir and lamivudine, and the like is evaluated.

Prior to the combined use test, $IC_{50}$ and $CC_{50}$ of each pharmaceutical agent alone are measured. 5 concentrations of pharmaceutical agent A and 9 concentrations of pharmaceutical agent B, determined based on these results, are combined to evaluate the effect of combined use of two agents. For combined use of three agents, a high concentration pharmaceutical agent B and a pharmaceutical agent C are mixed and pharmaceutical agent A and the concentration are combined for evaluation.

The test results of the test substance and combination drug alone or in combination thereof are analyzed based on the programs of Prichard and Shipman MacSynergy II version 2.01 and Deltagraph version 1.5d. A three-dimensional plot is drawn from % inhibition at the concentrations of each combined pharmaceutical agent, obtained from 3 times of tests, with 95% (or 68%, 99%) confidence limits, and the effect of the combined use is evaluated based on the numerical values of $\mu M^2$% calculated therefrom. The criteria of evaluation are shown in the following.

| Definition of interaction | $\mu M^2$ % |
|---|---|
| Strong synergistic action | >100 |
| Slight synergistic action | +51–+100 |
| Additive action | +50–−50 |
| Slight antagonistic action | −51–−100 |
| Strong antagonistic action | <−100 |

TABLE 38

| Example No. | $IC_{50}$ | Example No. | $IC_{50}$ |
|---|---|---|---|
| 1 | ++++ | 3 | +++ |
| 4 | +++ | 5 | +++ |

TABLE 38-continued

| Example No. | $IC_{50}$ | Example No. | $IC_{50}$ |
|---|---|---|---|
| 6 | +++ | 7 | ++++ |
| 8 | ++++ | 9 | +++ |
| 10 | +++ | 11 | ++++ |
| 12 | +++ | 13 | +++ |
| 14 | +++ | 15 | +++ |
| 16 | +++ | 17 | +++ |
| 18 | +++ | 19 | +++ |
| 20 | +++ | 21 | +++ |
| 22 | +++ | 23 | +++ |
| 24 | +++ | 25 | +++ |
| 26 | +++ | 27 | ++ |
| 28 | +++ | 29 | +++ |
| 30 | +++ | 31 | +++ |
| 32 | +++ | 33 | +++ |
| 34 | +++ | 35 | +++ |
| 36 | +++ | 37 | +++ |
| 38 | +++ | 39 | +++ |
| 40 | +++ | 41 | +++ |
| 42 | +++ | 43 | +++ |
| 44 | ++ | 45 | +++ |
| 46 | +++ | 47 | ++++ |
| 48 | +++ | 49 | +++ |

TABLE 39

| Example No. | $IC_{50}$ | Example No. | $IC_{50}$ |
|---|---|---|---|
| 50 | +++ | 51 | +++ |
| 53 | +++ | 54 | +++ |
| 55 | +++ | 56 | +++ |
| 57 | +++ | 58 | ++++ |
| 59 | ++++ | 60 | +++ |
| 61 | +++ | 62 | +++ |
| 63 | ++++ | 64 | +++ |
| 65 | ++ | 66 | +++ |
| 67 | +++ | 68 | +++ |
| 70 | +++ | 71 | +++ |
| 72 | ++++ | 73 | +++ |
| 75 | +++ | 76 | +++ |
| 78 | ++++ | 79 | +++ |
| 80 | +++ | 81 | ++++ |
| 82 | +++ | 83 | +++ |
| 84 | ++++ | 85 | +++ |
| 86 | ++++ | 87 | ++++ |
| 88 | +++ | 89 | +++ |
| 90 | ++++ | 91 | +++ |
| 92 | ++++ | 93 | +++ |
| 94 | +++ | 95 | +++ |
| 96 | ++++ | 97 | +++ |
| 98 | +++ | 99 | +++ |
| 100 | +++ | 101 | +++ |

TABLE 40

| Example No. | $IC_{50}$ | Example No. | $IC_{50}$ |
|---|---|---|---|
| 102 | +++ | 103 | +++ |
| 104 | +++ | 105 | +++ |
| 106 | +++ | 107 | +++ |
| 108 | +++ | 109 | ++ |
| 110 | ++ | 111 | +++ |
| 112 | +++ | 113 | +++ |
| 114 | ++++ | 115 | ++++ |
| 116 | ++++ | 117 | ++++ |
| 118 | +++ | 119 | ++ |
| 120 | ++++ | 121 | ++++ |
| 122 | ++++ | 123 | ++ |
| 124 | +++ | 125 | ++++ |
| 126 | +++ | 127 | ++++ |
| 128 | +++ | 129 | +++ |
| 130 | ++++ | 131 | +++ |
| 132 | +++ | 133 | ++++ |

TABLE 40-continued

| Example No. | $IC_{50}$ | Example No. | $IC_{50}$ |
|---|---|---|---|
| 134 | +++ | 135 | +++ |
| 136 | ++++ | 137 | +++ |
| 138 | +++ | 139 | +++ |
| 140 | +++ | 141 | ++++ |
| 142 | +++ | 143 | ++ |
| 144 | +++ | 145 | ++ |
| 146 | ++ | 147 | +++ |
| 148 | +++ | 149 | ++++ |

TABLE 41

| Example No. | $IC_{50}$ | Example No. | $IC_{50}$ |
|---|---|---|---|
| 150 | +++ | 151 | +++ |
| 152 | ++ | 153 | +++ |
| 154 | +++ | 155 | ++++ |
| 156 | +++ | 157 | +++ |
| 158 | +++ | 159 | +++ |
| 160 | +++ | 161 | +++ |
| 162 | +++ | 163 | ++++ |
| 164 | +++ | 165 | +++ |
| 166 | +++ | 167 | +++ |
| 168 | +++ | 169 | ++ |
| 170 | +++ | 171 | ++++ |
| 172 | ++++ | 173 | +++ |
| 174 | +++ | 175 | ++++ |
| 176 | +++ | 177 | +++ |
| 178 | +++ | 179 | +++ |
| 180 | ++++ | 181 | +++ |
| 182 | +++ | 183 | +++ |
| 184 | +++ | 185 | +++ |
| 186 | +++ | 187 | +++ |
| 188 | +++ | 189 | +++ |
| 190 | +++ | 191 | +++ |
| 192 | +++ | 193 | +++ |
| 194 | +++ | 195 | +++ |
| 196 | +++ | 197 | +++ |

TABLE 42

| Example No. | $IC_{50}$ | Example No. | $IC_{50}$ |
|---|---|---|---|
| 198 | +++ | 199 | +++ |
| 200 | ++ | 201 | +++ |
| 202 | +++ | 203 | ++++ |
| 204 | ++++ | 205 | ++++ |
| 206 | +++ | 207 | ++++ |
| 208 | ++++ | 209 | +++ |
| 210 | +++ | 211 | ++++ |
| 212 | +++ | 213 | +++ |
| 214 | ++++ | 215 | ++++ |
| 216 | +++ | 217 | ++++ |
| 218 | ++++ | 219 | +++ |
| 220 | +++ | 221 | ++++ |
| 222 | ++++ | 223 | +++ |
| 224 | +++ | 225 | ++++ |
| 226 | ++ | 227 | +++ |
| 228 | +++ | 229 | ++++ |
| 230 | ++++ | 231 | ++++ |
| 232 | ++++ | 233 | ++++ |
| 234 | ++++ | 235 | +++ |
| 236 | +++ | 237 | +++ |
| 238 | ++++ | 239 | ++++ |
| 240 | ++++ | 241 | ++++ |
| 242 | ++++ | 243 | ++++ |
| 244 | ++++ | 245 | +++ |

TABLE 43

| Example No. | $IC_{50}$ | Example No. | $IC_{50}$ |
|---|---|---|---|
| 246 | +++ | 247 | +++ |
| 248 | ++++ | 249 | ++++ |
| 250 | +++ | 251 | ++++ |
| 252 | ++++ | 253 | ++++ |
| 254 | ++++ | 255 | ++++ |
| 256 | ++++ | 257 | ++++ |
| 258 | ++++ | 259 | ++++ |
| 260 | ++++ | 261 | +++ |
| 262 | ++++ | 263 | ++++ |
| 264 | ++++ | 265 | ++++ |
| 266 | ++++ | 267 | +++ |
| 268 | ++++ | 269 | ++++ |
| 270 | +++ | 271 | +++ |
| 272 | +++ | 273 | +++ |
| 274 | +++ | 275 | ++++ |
| 276 | ++++ | 277 | ++++ |
| 278 | ++++ | 279 | ++++ |
| 280 | +++ | 281 | +++ |
| 282 | ++++ | 283 | +++ |
| 284 | +++ | 285 | +++ |
| 286 | ++++ | 287 | ++++ |
| 288 | ++++ | 289 | ++++ |
| 290 | +++ | 291 | +++ |
| 292 | ++++ | 293 | +++ |

TABLE 44

| Example No. | $IC_{50}$ | Example No. | $IC_{50}$ |
|---|---|---|---|
| 294 | ++++ | 295 | +++ |
| 296 | ++++ | 297 | +++ |
| 298 | ++++ | 299 | +++ |
| 300 | +++ | 301 | ++ |
| 302 | +++ | 303 | +++ |
| 304 | ++++ | 305 | ++++ |
| 306 | +++ | 307 | ++ |
| 308 | +++ | 309 | +++ |
| 310 | ++ | 311 | ++++ |
| 312 | +++ | 313 | +++ |
| 314 | +++ | 315 | +++ |
| 316 | +++ | 317 | +++ |
| 318 | +++ | 319 | +++ |
| 320 | ++++ | 321 | +++ |
| 322 | +++ | 323 | +++ |
| 324 | +++ | 325 | +++ |
| 326 | ++ | 327 | ++++ |
| 328 | +++ | 329 | +++ |
| 330 | ++++ | 331 | +++ |
| 332 | +++ | 333 | +++ |
| 334 | +++ | 335 | +++ |
| 336 | ++++ | 337 | ++++ |
| 338 | +++ | 339 | ++ |
| 340 | ++++ | 341 | ++++ |

TABLE 45

| Example No. | $IC_{50}$ | Example No. | $IC_{50}$ |
|---|---|---|---|
| 342 | ++++ | 343 | ++++ |
| 344 | ++++ | 345 | ++++ |
| 346 | +++ | 347 | ++++ |
| 348 | +++ | 349 | +++ |
| 350 | ++++ | 351 | +++ |
| 352 | +++ | 353 | ++++ |
| 354 | +++ | 355 | +++ |
| 356 | +++ | 357 | +++ |
| 358 | +++ | 359 | +++ |
| 360 | ++++ | 361 | +++ |
| 362 | +++ | 363 | +++ |
| 364 | ++++ | 365 | +++ |
| 366 | ++ | 367 | +++ |
| 368 | +++ | 369 | ++++ |

TABLE 45-continued

| Example No. | $IC_{50}$ | Example No. | $IC_{50}$ |
|---|---|---|---|
| 370 | ++++ | 371 | +++ |
| 372 | +++ | 373 | ++++ |
| 374 | +++ | 375 | +++ |
| 376 | +++ | 377 | ++++ |
| 378 | ++++ | 379 | ++ |
| 380 | +++ | 381 | +++ |
| 382 | +++ | 383 | +++ |
| 384 | ++++ | 385 | +++ |
| 386 | +++ | 387 | +++ |
| 388 | ++ | 389 | +++ |

TABLE 46

| Example No. | $IC_{50}$ | Example No. | $IC_{50}$ |
|---|---|---|---|
| 391 | +++ | 392 | +++ |
| 393 | +++ | 394 | +++ |
| 395 | ++++ | 396 | +++ |
| 397 | +++ | 398 | +++ |
| 399 | ++++ | 400 | ++++ |
| 401 | +++ | 402 | +++ |
| 403 | +++ | 404 | +++ |
| 405 | ++++ | 406 | +++ |
| 407 | +++ | 408 | +++ |
| 409 | +++ | 410 | +++ |
| 411 | +++ | 412 | +++ |
| 413 | ++ | 414 | ++ |
| 415 | +++ | 416 | +++ |
| 417 | +++ | 418 | +++ |
| 419 | ++++ | 420 | +++ |
| 421 | +++ | 422 | +++ |
| 423 | +++ | 424 | +++ |
| 425 | ++++ | 426 | +++ |
| 427 | +++ | 428 | +++ |
| 429 | +++ | 430 | +++ |
| 431 | +++ | 432 | ++++ |

As is clear from the above-mentioned results, the compound of the present invention shows high inhibitory activity against HIV integrase.

Therefore, these compounds can be a pharmaceutical agent effective for the prophylaxis or treatment of AIDS, as an anti-HIV agent having an HIV integrase inhibitory activity. In addition, by the combined use with other anti-HIV agents such as a protease inhibitor, a reverse transcriptase inhibitor and the like, it can be a more effective anti-HIV agent. Because it shows integrase-specific high inhibitory activity, the compound can be a pharmaceutical agent safe on human body, which causes only a fewer side effects.

While a Formulation Example is given in the following, the present invention is not limited to this example.

Formulation Example

| | |
|---|---|
| (a) Compound of Example 1 | 10 g |
| (b) Lactose | 50 g |
| (c) Cornstarch | 15 g |
| (d) Carboxymethylcellulose sodium | 44 g |
| (e) Magnesium stearate | 1 g |

The total amount of (a), (b) and (c) and 30 g of (d) are kneaded with water, and, after vacuum drying, granulated. The granules are mixed with 14 g of (d) and 1 g of (e) and applied to a tableting machine to give 1000 tablets, each containing 10 mg of (a).

INDUSTRIAL APPLICABILITY

The present invention relates to a novel nitrogen-containing fused ring compound and a pharmaceutically acceptable salt thereof, which are useful as anti-HIV agents, and novel use of a certain kind of nitrogen-containing fused ring compound and a pharmaceutically acceptable salt thereof as anti-HIV agents. More specifically, the present invention relates to an anti-HIV agent containing a nitrogen-containing fused ring compound or a pharmaceutically acceptable salt thereof showing an anti-HIV activity particularly based on an integrase inhibitory activity. They are effective for the prophylaxis or treatment of the onset of AIDS. Particularly, since they have an integrase inhibitory activity, they can be effective anti-HIV agents and the present invention can provide pharmaceutical agents having an anti-HIV activity, particularly pharmaceutical agents having an integrase inhibitory activity.

Sequence Listing Free Text

SEQ ID NO:1: Donor+strand for activity determination of HIV integrase

SEQ ID NO:2: Donor−strand for activity determination of HIV integrase

SEQ ID NO:3: Target+strand for activity determination of HIV integrate

SEQ ID NO:4: Target−strand for activity determination of HIV integrase

This application is based on patent application Nos. 2003-293117 and 2004-134896 filed in Japan, the contents of which are hereby incorporated by reference.

The invention claimed is:

1. A nitrogen-containing fused ring compound represented by the following formula or a pharmaceutically acceptable salt thereof:

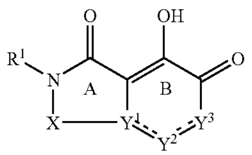

wherein $R^1$ is (1) a C1–6 alkyl group optionally substituted by 1 to 3 substituent(s) selected from the following group A, (2) a C2–6 alkenyl group optionally substituted by 1 to 3 substituent(s) selected from the following group A or (3) a group represented by the formula

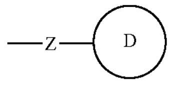

wherein Z is (1') a bond, (2') a C1–6 alkylene, (3') a C2–6 alkenylene or (4') $*—(CH_2)_m$-Q-$(CH_2)_n—$ wherein Q is (1") —O—, (2") —$NR^5$— wherein $R^5$ is a hydrogen atom or a C1–6 alkyl group, (3") —CO—, (4") —SO—, or (5") —$SO_2$— m is 0 or an integer of 1 to 4, n is 0 or an integer of 1 to 4 and

* shows the side to be bonded to a nitrogen atom of ring A, and ring D is (1') a C3–10 carbon ring group optionally substituted by 1 to 3 substituent(s) selected from the following group B or (2') a heterocyclic group optionally substituted by 1 to 3 substituent(s) selected from the following group B wherein the heterocyclic group contains at least one hetero atom selected from a nitrogen atom, oxygen atom and sulfur atom;

X is (1) —$C(R^{x1})(R^{x2})$—#, (2) —$C(R^{x1})(R^{x2})$—$C(R^{x3})(R^{x4})$—#, (3) —$C(R^{x1})(R^{x2})$—$C(R^{x3})(R^{x4})$—$C(R^{x5})(R^{x6})$—#, (4) —$C(R^{x7})$=$C(R^{x8})$—#, (5) —$C(R^{x1})(R^{x2})$—$C(R^{x7})$=$C(R^{x8})$—#, or (6) —$C(R^{x7})$=$C(R^{x8})$—$C(R^{x1})(R^{x2})$—#, wherein # shows the side to be bonded to $Y^1$ of ring B, $R^{x1}$ to $R^{x8}$ are each independently selected from the following group C, $R^{x1}$ and $R^{x2}$, $R^{x3}$ and $R^{x4}$, and $R^{x5}$ and $R^{x6}$ each independently optionally form a C3–8 cycloalkyl together with the adjacent carbon atom;

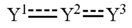

of ring B is (1) C═C($R^{y1}$)—N($R^{y2}$)

(2) N—C($R^{y1}$)═N, (3) N—C($R^{y1}$)═C($R^{y2}$)

(4) C═N—N($R^{y2}$) or (5) N—N═C($R^{y3}$)

wherein $R^{y1}$ to $R^{y3}$ are each independently selected from the following group C, when

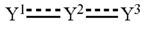

is N—C($R^{y1}$)═C($R^{y2}$), ring B is optionally condensed with a benzene ring to form a fused ring represented by

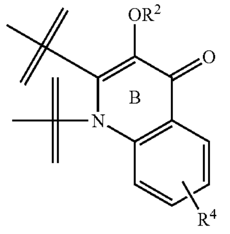

wherein $R^4$ is selected from the following group C;

group A;

(1) a halogen atom, (2) a cyano group, (3) —$OR^{a1}$, (4) —$SR^{a1}$, (5) —$CO_2R^{a1}$, (6) —$CONR^{a2}R^{a3}$, (7) —$COR^{a4}$, (8) —$SO_2NR^{a2}R^{a3}$, (9) —$SO_2R^{a4}$,

(10) a C6–14 aryloxy group, and

(11) a C6–14 aryl C1–6 alkyloxycarbonyl group, wherein $R^{a1}$, $R^{a2}$, $R^{a3}$ and $R^{a4}$ are each independently a hydrogen atom or a C1–6 alkyl group;

group B:

(1) a halogen atom, (2) a cyano group, (3) a C1–6 alkyl group, (4) a halo C1–6 alkyl group, (5) —$OR^{b1}$, (6) —$SR^{b1}$, (7) —$CO_2R^{b1}$, (8) —$CONR^{b2}R^{b3}$, (9) —$COR^{b4}$,

(10) —$SO_2NR^{b2}R^{b3}$,

(11) —$SO_2R^{b4}$,

(12) a C6–14 aryloxy group, and

(13) a C6–14 aryl C1–6 alkyloxycarbonyl group, wherein $R^{b1}$, $R^{b2}$, $R^{b3}$, and $R^{b4}$ are each independently a hydrogen atom or a C1–6 alkyl group;

group C:

(1) a hydrogen atom, (2) a cyano group, (3) a halogen atom, (4) a methyl group, ethyl group, propyl group, isopropyl group, butyl group, isobutyl group, sec-butyl group, tert-butyl group, pentyl group, isopentyl group, tert-pentyl group, or hexyl group, (5) a C2–6 alkenyl group, (6) a C2–6 alkynyl group, (7) a C6–14 aryl group, (8) a group selected from pyridyl, pyrazinyl, pyrimidinyl, pyridazinyl, 1,3,5-triazinyl, pyrrolyl, pyrazolyl, imidazoyl, 1,2,3-triazolyl, 1,2,4-triazolyl, tetrazolyl, thienyl, furyl, oxazolyl, isoxazolyl, thiazolyl, isothiazolyl, 1,2,4-oxadiazolyl, 1,3,4-oxadiazolyl, 1,2,4-thiadiazolyl, and 1,3,4-thiadiazolyl, (9) a C1–6 alkyloxy group,

(10) a C6–14 aryl C1–6 alkyl group,

(11) a C6–14 aryl C1–6 alkyloxy group,

(12) —$CO_2R^{c1}$,

(13) —$CONR^{c2}R^{c3}$,

(14) —$COR^{c4}$,

(15) —$SO_2NR^{c2}R^{c3}$, and

(16) a C6–14 arylcarbonyl group, wherein $R^{c1}$, $R^{c2}$, $R^{c3}$, and $R^{c4}$ are each independently (1') a hydrogen atom, or (2') a methyl group, ethyl group, propyl group, isopropyl group, butyl group, isobutyl group, sec-butyl group, tert-butyl group, pentyl group, isopentyl group, tert-pentyl group, or hexyl group, each of which is optionally substituted by 1 to 3 substituent(s) selected from the above-mentioned group A, the methyl group, ethyl group, propyl group, isopropyl group, butyl group, isobutyl group, sec-butyl group, tert-butyl group, pentyl group, isopentyl group, tert-pentyl group, hexyl group, C1–6 alkyl moiety, C2–6 alkenyl group and C2–6 alkynyl group of the above-mentioned group C are optionally substituted by 1 to 3 substituent(s) selected from the above-mentioned group A; and the C6–14 aryl group, C6–14 aryl moiety and the pyridyl, pyrazinyl, pyrimidinyl, pyridazinyl, 1,3,5-triazinyl, pyrrolyl, pyrazolyl, imidazoyl, 1,2,3-triazolyl, 1,2,4-triazolyl, tetrazolyl, thienyl, furyl, oxazolyl, isoxazolyl, thiazolyl, isothiazolyl, 1,2,4-oxadiazolyl, 1,3,4-oxadiazolyl, 1,2,4-thiadiazolyl, and 1,3,4-thiadiazolyl group of the above-mentioned group C are optionally substituted by 1 to 3 substituent(s) selected from the above-mentioned group B.

2. A method for the treatment of an HIV infection which comprises administering an effective amount of a nitrogen-containing fused ring compound of claim 1, or a pharmaceutically acceptable salt thereof, to a human.

* * * * *